US012435120B2

(12) United States Patent
Burleigh et al.

(10) Patent No.: US 12,435,120 B2
(45) Date of Patent: Oct. 7, 2025

(54) CELLS EXPRESSING A CHIMERIC RECEPTOR FROM A MODIFIED CD247 LOCUS, RELATED POLYNUCLEOTIDES AND METHODS

(71) Applicant: Juno Therapeutics, Inc., Seattle, WA (US)

(72) Inventors: Stephen Michael Burleigh, Seattle, WA (US); Christopher Heath Nye, Seattle, WA (US)

(73) Assignee: Juno Therapeutics, Inc., Seattle, WA (US)

(*) Notice: Subject to any disclaimer, the term of this patent is extended or adjusted under 35 U.S.C. 154(b) by 1011 days.

(21) Appl. No.: 17/607,833

(22) PCT Filed: Apr. 30, 2020

(86) PCT No.: PCT/US2020/030875
§ 371 (c)(1),
(2) Date: Oct. 29, 2021

(87) PCT Pub. No.: WO2020/223571
PCT Pub. Date: Nov. 5, 2020

(65) Prior Publication Data

US 2022/0218750 A1 Jul. 14, 2022

Related U.S. Application Data

(60) Provisional application No. 62/841,578, filed on May 1, 2019.

(51) Int. Cl.

| | |
|---|---|
| ***C07K 14/705*** | (2006.01) |
| ***A61K 38/00*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/715*** | (2006.01) |
| ***C07K 14/725*** | (2006.01) |
| ***C12N 5/0783*** | (2010.01) |
| ***C12N 9/22*** | (2006.01) |
| ***C12N 15/11*** | (2006.01) |
| ***C12N 15/62*** | (2006.01) |
| ***C12N 15/86*** | (2006.01) |
| ***C12N 15/90*** | (2006.01) |

(52) U.S. Cl.

CPC ........ *C07K 14/70521* (2013.01); *A61K 40/11* (2025.01); *A61K 40/31* (2025.01); *A61K 40/4215* (2025.01); *A61K 40/4224* (2025.01); *A61P 35/00* (2018.01); *C07K 14/7051* (2013.01); *C07K 14/7151* (2013.01); *C12N 5/0636* (2013.01); *C12N 9/22* (2013.01); *C12N 15/11* (2013.01); *C12N 15/625* (2013.01); *C12N 15/86* (2013.01); *C12N 15/907* (2013.01); *A61K 38/00* (2013.01); *A61K 2239/46* (2023.05); *A61K 2239/48* (2023.05); *C12N 2310/20* (2017.05); *C12N 2750/14143* (2013.01); *C12N 2800/80* (2013.01)

(58) Field of Classification Search

CPC .............................. C15N 5/0636; A61K 35/17
See application file for complete search history.

(56) References Cited

U.S. PATENT DOCUMENTS

| | | | |
|---|---|---|---|
| 4,452,773 | A | 6/1984 | Molday |
| 4,690,915 | A | 9/1987 | Rosenberg |
| 4,795,698 | A | 1/1989 | Owen |
| 5,033,252 | A | 7/1991 | Carter |
| 5,052,558 | A | 10/1991 | Carter |
| 5,087,616 | A | 2/1992 | Myers |
| 5,200,084 | A | 4/1993 | Liberti |
| 5,219,740 | A | 6/1993 | Miller |
| 5,323,907 | A | 6/1994 | Kalvelage |
| 5,356,802 | A | 10/1994 | Chandrasegaran |
| 5,436,150 | A | 7/1995 | Chandrasegaran |

(Continued)

FOREIGN PATENT DOCUMENTS

| | | |
|---|---|---|
| EP | 452342 | 10/1991 |
| EP | 2537416 | 11/2014 |
| EP | 3443075 | 2/2019 |
| WO | WO 1992/008796 | 5/1992 |

(Continued)

OTHER PUBLICATIONS

US 8,252,592 B2, 08/2012, Sadelain (withdrawn)

(Continued)

*Primary Examiner* — Christopher M Babic
*Assistant Examiner* — Jennifer S Spence
(74) *Attorney, Agent, or Firm* — Morrison & Foerster LLP

(57) ABSTRACT

Provided herein are engineered immune cells, e.g. T cells, expressing a chimeric receptor comprising an intracellular region comprising a CD3zeta (CD3ζ) signaling domain. In some embodiments, the engineered immune cells contain a modified CD247 locus that encodes the chimeric receptor or a portion thereof. In some embodiments, at least a portion of a CD3zeta chain encoded by CD247 genomic locus. Also provided are cell compositions containing the engineered immune cells, nucleic acids for engineering cells, and methods, kits and articles of manufacture for producing the engineered cells, such as by targeting a transgene encoding a portion of a chimeric receptor for integration into a region of a CD247 genomic locus. In some embodiments, the engineered cells, e.g. T cells, can be used in connection with cell therapy, including in connection with cancer immunotherapy comprising adoptive transfer of the engineered cells.

16 Claims, 15 Drawing Sheets

Specification includes a Sequence Listing.

(56) References Cited

U.S. PATENT DOCUMENTS

| | | | |
|---|---|---|---|
| 5,487,994 | A | 1/1996 | Chandrasegaran |
| 5,789,538 | A | 8/1998 | Rebar et al. |
| 5,925,523 | A | 7/1999 | Dove et al. |
| 6,007,988 | A | 12/1999 | Choo et al. |
| 6,013,453 | A | 1/2000 | Choo et al. |
| 6,040,177 | A | 3/2000 | Riddell |
| 6,060,273 | A | 5/2000 | Dirks et al. |
| 6,140,081 | A | 10/2000 | Barbas |
| 6,200,759 | B1 | 3/2001 | Dove et al. |
| 6,207,453 | B1 | 3/2001 | Maass |
| 6,410,319 | B1 | 6/2002 | Raubitschek |
| 6,451,995 | B1 | 9/2002 | Cheung |
| 6,453,242 | B1 | 9/2002 | Eisenberg |
| 6,503,717 | B2 | 1/2003 | Case |
| 6,534,261 | B1 | 3/2003 | Cox |
| 6,599,692 | B1 | 7/2003 | Case |
| 6,689,558 | B2 | 2/2004 | Case |
| 7,067,317 | B2 | 6/2006 | Rebar |
| 7,070,995 | B2 | 7/2006 | Jensen |
| 7,262,054 | B2 | 8/2007 | Jamieson |
| 7,265,209 | B2 | 9/2007 | Jensen |
| 7,354,762 | B2 | 4/2008 | Jensen |
| 7,446,179 | B2 | 11/2008 | Jensen |
| 7,446,190 | B2 | 11/2008 | Sadelain |
| 7,446,191 | B2 | 11/2008 | Jensen |
| 7,888,121 | B2 | 2/2011 | Urnov et al. |
| 7,914,796 | B2 | 3/2011 | Miller et al. |
| 7,951,925 | B2 | 5/2011 | Ando et al. |
| 7,972,854 | B2 | 7/2011 | Miller et al. |
| 8,008,450 | B2 | 8/2011 | Williams |
| 8,110,379 | B2 | 2/2012 | DeKelver et al. |
| 8,153,765 | B2 | 4/2012 | Park |
| 8,324,353 | B2 | 12/2012 | Jensen |
| 8,339,645 | B2 | 12/2012 | Nakawaki |
| 8,389,282 | B2 | 3/2013 | Sadelain |
| 8,409,861 | B2 | 4/2013 | Guschin et al. |
| 8,497,118 | B2 | 7/2013 | Jensen |
| 8,586,526 | B2 | 11/2013 | Gregory et al. |
| 8,603,477 | B2 | 12/2013 | Afar |
| 8,703,489 | B2 | 4/2014 | Wang |
| 8,802,374 | B2 | 8/2014 | Jensen |
| 8,911,993 | B2 | 12/2014 | June et al. |
| 8,945,868 | B2 | 2/2015 | Collingwood et al. |
| 8,956,828 | B2 | 2/2015 | Bonini et al. |
| 9,005,973 | B2 | 4/2015 | Cost et al. |
| 9,045,763 | B2 | 6/2015 | DeKelver et al. |
| 9,150,847 | B2 | 10/2015 | Rebar |
| 9,200,266 | B2 | 12/2015 | Wang |
| 9,233,125 | B2 | 1/2016 | Davila et al. |
| 9,255,250 | B2 | 2/2016 | Gregory et al. |
| 9,458,205 | B2 | 10/2016 | Gregory et al. |
| 2002/0131960 | A1 | 9/2002 | Sadelain et al. |
| 2002/0150914 | A1 | 10/2002 | Andersen et al. |
| 2003/0170238 | A1 | 9/2003 | Gruenberg et al. |
| 2003/0223994 | A1 | 12/2003 | Hoogenboom et al. |
| 2003/0232410 | A1 | 12/2003 | Liljedahl et al. |
| 2004/0191260 | A1 | 9/2004 | Reiter et al. |
| 2005/0026157 | A1 | 2/2005 | Baltimore et al. |
| 2005/0064474 | A1 | 3/2005 | Urnov |
| 2005/0208489 | A1 | 9/2005 | Carroll et al. |
| 2006/0034850 | A1 | 2/2006 | Weidanz et al. |
| 2006/0063231 | A1 | 3/2006 | Li et al. |
| 2007/0092530 | A1 | 4/2007 | Weidanz et al. |
| 2007/0116690 | A1 | 5/2007 | Yang et al. |
| 2008/0159996 | A1 | 7/2008 | Ando et al. |
| 2009/0226474 | A1 | 9/2009 | Weidanz |
| 2009/0304679 | A1 | 12/2009 | Weidanz |
| 2010/0047805 | A1 | 2/2010 | Wang |
| 2010/0218264 | A1 | 8/2010 | Cui et al. |
| 2010/0260748 | A1 | 10/2010 | Elkins et al. |
| 2011/0003380 | A1 | 1/2011 | Miltenyi |
| 2011/0207221 | A1 | 8/2011 | Cost et al. |
| 2011/0265198 | A1 | 10/2011 | Gregory et al. |
| 2011/0301073 | A1 | 12/2011 | Gregory |
| 2012/0017290 | A1 | 1/2012 | Cui et al. |
| 2012/0189622 | A1 | 7/2012 | Tesar |
| 2013/0122591 | A1 | 5/2013 | Cost et al. |
| 2013/0137104 | A1 | 5/2013 | Cost et al. |
| 2013/0149337 | A1 | 6/2013 | Cooper |
| 2013/0177983 | A1 | 7/2013 | Rebar |
| 2013/0196373 | A1 | 8/2013 | Gregory et al. |
| 2013/0287748 | A1 | 10/2013 | June |
| 2013/0326645 | A1 | 12/2013 | Cost et al. |
| 2014/0120622 | A1 | 5/2014 | Gregory |
| 2014/0286987 | A1 | 9/2014 | Spencer et al. |
| 2014/0294841 | A1 | 10/2014 | Scheinberg |
| 2015/0056705 | A1 | 2/2015 | Conway et al. |
| 2015/0266973 | A1 | 9/2015 | Jarjour et al. |
| 2015/0335708 | A1 | 11/2015 | Froelich et al. |
| 2016/0024474 | A1 | 1/2016 | Conway et al. |
| 2016/0030477 | A1 | 2/2016 | Conway et al. |
| 2016/0046700 | A1 | 2/2016 | Foster et al. |
| 2016/0152723 | A1 | 6/2016 | Chen et al. |
| 2016/0272999 | A1 | 9/2016 | Duchateau et al. |
| 2017/0016027 | A1 | 1/2017 | Lee et al. |
| 2017/0211075 | A1 | 7/2017 | Lee et al. |
| 2018/0325955 | A1 | 11/2018 | Terrett et al. |

FOREIGN PATENT DOCUMENTS

| | | |
|---|---|---|
| WO | WO 1994/028143 | 12/1994 |
| WO | WO 1995/019431 | 7/1995 |
| WO | WO 1996/006166 | 2/1996 |
| WO | WO 1998/053057 | 11/1998 |
| WO | WO 1998/053058 | 11/1998 |
| WO | WO 1998/053059 | 11/1998 |
| WO | WO 1998/053060 | 11/1998 |
| WO | WO 1998/054311 | 12/1998 |
| WO | WO 2000/014257 | 3/2000 |
| WO | WO 2000/027878 | 5/2000 |
| WO | WO 2001/060970 | 8/2001 |
| WO | WO 2001/088197 | 11/2001 |
| WO | WO 2002/016536 | 2/2002 |
| WO | WO 2002/099084 | 12/2002 |
| WO | WO 2003/016496 | 2/2003 |
| WO | WO 2003/068201 | 8/2003 |
| WO | WO 2006/099875 | 9/2006 |
| WO | WO 2009/072003 | 6/2009 |
| WO | WO 2009/080829 | 7/2009 |
| WO | WO 2010/033140 | 3/2010 |
| WO | WO 2012/092612 | 7/2012 |
| WO | WO 2012/129514 | 9/2012 |
| WO | WO 2012/138927 | 10/2012 |
| WO | WO 2013/071154 | 5/2013 |
| WO | WO 2013/123061 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2014/127261 | 8/2014 |
| WO | WO 2014/210064 | 12/2014 |
| WO | WO 2015/142675 | 9/2015 |
| WO | WO 2015/161276 | 10/2015 |
| WO | WO 2016/022994 | 2/2016 |
| WO | WO 2016/030414 | 3/2016 |
| WO | WO 2016/090312 | 6/2016 |
| WO | WO 2016/090320 | 6/2016 |
| WO | WO 2016/090327 | 6/2016 |
| WO | WO 2016/090329 | 6/2016 |
| WO | WO 2017/093969 | 6/2017 |
| WO | WO 2017/180989 | 10/2017 |
| WO | WO 2017/193107 | 11/2017 |
| WO | WO 2018/073391 | 4/2018 |
| WO | WO 2018/075541 | 4/2018 |
| WO | WO 2019/032675 | 2/2019 |
| WO | WO 2019/067805 | 4/2019 |
| WO | WO 2019/076486 | 4/2019 |

OTHER PUBLICATIONS

Abate-Daga et al., "CAR models: next-generation CAR modifications for enhanced T-cell function," Mol Ther Oncolytics. (2016) 3:16014.

(56) References Cited

OTHER PUBLICATIONS

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Altschul et al., "Basic Local Alignment Search Tool," (1990) J. Mol. Biol. 215: 403-410.
Altschul et al., "Gapped BLAST and PSI-BLAST: A New Generation of Protein Database Search Programs," (1997) Nucleic Acids Res. 25(17):3389-3402.
Anders et al. "Structural basis of PAM-dependent target DNA recognition by the Cas9 endonuclease," Nature (2014) 513(7519): 569-73. doi: 10.1038/nature13579.
Bae et al., "Cas-OFFinder: a fast and versatile algorithm that searches for potential off-target sites of Cas9 RNA-guided endonucleases," Bioinformatics. (2014) 30(10):1473-1475.
Barrett et al., "Chimeric antigen receptor therapy for cancer," Annu Rev Med. (2014); 65: 333-347.
Benson et al., "CS1-directed monoclonal antibody therapy for multiple myeloma," J Clin Oncol. (2012) 30(16): 2013-15.
Boch et al., . "Breaking The Code Of DNA Binding Specificity Of TAL-Type III Effectors," Science (2009) 326(5959):1509-1512.
Boris-Lawrie et al., "Recent advances in retrovirus vector technology," Cur. Opin. Genet. Develop. (1993) 3:102-109.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. Mar. 20, 2013;5(177):177ra38.
Briner et al., "Guide RNA functional modules direct Cas9 activity and orthogonality," Mol Cell. (2014)56(2): 333-339.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Caldecott, "Single-strand break repair and genetic disease," Nature Reviews Genetics (2008) 9: 619-631.
Carlens et al., "Ex vivo T lymphocyte expansion for retroviral transduction: influence of serum-free media on variations in cell expansion rates and lymphocyte subset distribution," Exp Hematol (2000) 28(10): 1137-1146.
Carrillo et al., The Multiple Sequence Alignment Problem in Biology, SIAM J Applied Math (1988) 48: 1073.
Cavalieri et al., "Human T lymphocytes transduced by lentiviral vectors in the absence of TCR activation maintain an intact immune competence," Blood (2003) 102(2): 497-505.
Challita et al., "Multiple Modifications in Cis Elements of the Long Terminal Repeat of Retroviral Vectors Lead to Increased Expression and Decreased DNA Methylation in Embryonic Carcinoma Cells," J Virol (1995) 69(2): 748-755.
Chang et al., "Modification of DNA ends can decrease end joining relative to homologous recombination in mammalian cells," Proc Natl Acad Sci U S A. (1987) 84(14): 4959-4963.
Cheadle et al., "Chimeric antigen receptors for T-cell based therapy," Methods Mol Biol. (2012) 907: 645-66.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.
Christian et al. "Targeting DNA Double-Strand Breaks With TAL Effector Nucleases," Genetics (2010) 186(2): 757-761.
Chu et al., "CS1-specific chimeric antigen receptor (CAR)-engineered natural killer cells enhance in vitro and in vivo antitumor activity against human multiple myeloma," Leukemia. (2014) 28(4): 917-27.
Chylinski et al., "The tracrRNA and Cas9 families of type II CRISPR-Cas immunity systems," RNA Biol. (2013) 10(5): 726-737.
Clackson et al., "Making antibody fragments using phage display libraries," Nature (1991) 352(6336):624-628.
Clackson et al., "Redesigning an FKBP-ligand interface to generate chemical dimerizers with novel specificity," Proc Natl Acad Sci USA. (1998) 95(18): 10437-42.
Clarke and Davies in: Methods in Molecular Medicine, vol. 58: Metastasis Research Protocols, vol. 2: Cell Behavior In Vitro and In Vivo, Edited by: S. A. Brooks and U. Schumacher© Humana Press Inc., Totowa, NJ (2001) pp. 17-25.
Cohen et al., "Recombinant antibodies with MHC-restricted, peptide-specific, T-cell receptor-like specificity: new tools to study antigen presentation and TCR-peptide-MHC interactions," J Mol Recg (2003) 16(5):324-332.
Cong et al., "Multiplex Genome Engineering Using CRISPR/Cas Systems," Science (2013) 339(6121): 819-823.
Cooper et al., "T-cell clones can be rendered specific for CD19: toward the selective augmentation of the graft-versus-B-lineage leukemia effect," Blood. (2003) 101:1637-1644.
"CRISPR Cas9-gRNA Design," ABM Inc., (Jan. 26, 2018), 13 pages; retrieved from https://www.abmgood.com/marketing/knowledge_base/CRISPR_Cas9_gRNA_Design.php.
"CRISPR Cas9," ABM Inc., (Jan. 26, 2018); 20 pages; retrieved from https://www.abmgood.com/marketing/knowledge_base/CRISPR_Cas9_Introduction.php.
"How to Design Your gRNA for CRISPR Genome Editing," Posted on Addgene's Blog. May 3, 2017; Retrieved Jan. 26, 2018, 10 pages; from http://blog.addgene.org/how-to-design-your-grna-for-crispr-genome-editing.
Davila et al., "CD19 CAR-targeted T cells induce long-term remission and B Cell Aplasia in an immunocompetent mouse model of B cell acute lymphoblastic leukemia," PLoS ONE (2013) 8(4): e61338.
De Felipe, "Skipping the co-expression problem: the new 2A "Chysel" technology," Genet Vaccines Ther Sep. 13, 2004;2(1):13.
De Felipe, "Targeting of proteins derived from self-processing polyproteins containing multiple signal sequences," Traffic (2004) 5(8):616-626.
Delhove et al., "Genome-Edited T Cell Therapies," Curr Stem Cell Rep. (2017) 3(2):124-136.
Deveau et al., "Phage response to CRISPR-encoded resistance in *Streptococcus thermophilus*," J Bacteriol. (2008) 190(4):1390-400.
Di Stasi et al., "Inducible apoptosis as a safety switch for adoptive cell therapy," N Engl J Med. (2011) 365(18): 1673-83.
Earhart et al., "Chemical development of intracellular protein heterodimerizers," Chem Biol. (2013) 20(4): 549-57.
Esvelt et al., "A system for the continuous directed evolution of biomolecules," Nature (2011) 472(7344): 499-503.
Eyquem et al., "Targeting a CAR to the TRAC locus with CRISPR/Cas9 enhances tumour rejection," Nature (2017) 543(7643):113-117.
Fedorov et al., "PD-1- and CTLA-4-based inhibitory chimeric antigen receptors (iCARs) divert off-target immunotherapy responses," Sci Transl Med. (2013) 5(215):215ra172.
Fesnak et al., "Engineered T Cells: The Promise and Challenges of Cancer Immunotherapy," Nat Rev Cancer (2016) 16(9):566-581.
Fu et al., "Improving CRISPR-Cas nuclease specificity using truncated guide RNAs," Nat Biotechnol. (2014) 32(3): 279-284.
Gaj et al., "ZFN, TALEN, and CRISPR/Cas-based methods for genome engineering," Trends Biotechnol. (2013) 31(7):397-405.
Galbiati et al., "N-terminal fatty acylation of the alpha-subunit of the G-protein Gi1: only the myristoylated protein is a substrate for palmitoylation," Biochem J. (1994) 303 (3): 697-700.
Garfall et al., "Immunotherapy with chimeric antigen receptors for multiple myeloma," Discov Med. (2014) 17(91): 37-46.
Gauthier-Campbell et al., "Regulation of dendritic branching and filopodia formation in hippocampal neurons by specific acylated protein motifs," Mol Biol Cell. (2004) 15(5):2205-2217.
Godin et al., "Microfluidics and photonics for Bio-System-on-a-Chip: a review of advancements in technology towards a microfluidic flow cytometry chip," J Biophoton. (2008) 1(5):355-376.

(56) References Cited

OTHER PUBLICATIONS

Haft et al., "A guild of 45 CRISPR-associated (Cas) protein families and multiple CRISPR/Cas subtypes exist in prokaryotic genomes," PLoS Computational Biol. (2005) 1(6): e60.
Heigwer et al., "E-CRISP: fast CRISPR target site identification," Nat Methods. (2014) 11(2): 122-123.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Holliger et al., "Specific killing of lymphoma cells by cytotoxic T-cells mediated by a bispecific diabody," Protein Engineering Design and Selection (1996) 9(3):299-305.
Horvath et al., "CRISPR/Cas, the immune system of bacteria and archaea," Science (2010) 327(5962):167-70.
Hou et al., "Efficient genome engineering in human pluripotent stem cells using Cas9 from Neisseria meningitidis," PNAS Sep. 24, 2013 110 (39) 15644-15649.
Hsu et al., "DNA targeting specificity of RNA-guided Cas9 nucleases," Nat Biotechnol. (2013) 31(9):827-32.
Huang et al., "DNA transposons for modification of human primary T lymphocytes," Methods Mol Biol (2009) 506: 115-126.
Hudecek et al., "Receptor Affinity and Extracellular Domain Modifications Affect Tumor Recognition by ROR1-Specific Chimeric Antigen Receptor T Cells," Clin Can Res (2013) 19(12):3153.
Hudecek et al., "The nonsignaling extracellular spacer domain of chimeric antigen receptors is decisive for in vivo antitumor activity," Cancer Immunol Res (2015) 3(2):125-135.
Jinek et al., "Structures of Cas9 endonucleases reveal RNA-mediated conformational activation," Science (2014) 343(6176): 1247997.
Jinek et al., "A Programmable Dual-RNA-Guided DNA Endonuclease In Adaptive Bacterial Immunity," Science (2012) 337(6096): 816-821.
Johnston, et al., "Biolistic transformation: microbes to mice," Nature (1990) 346: 776-777.
Kim et al., "Chimeric restriction endonuclease," Proc Natl Acad Sci U S A. (1994) 91(3):883-887.
Kim et al., "Insertion and deletion mutants of Fokl restriction endonuclease," J Biol Chem. (1994) 269(50):31978-31982.
Kindt et al. Kuby Immunology, 6th ed., W.H. Freeman and Co., p. 91 (2007).
Kipriyanov et al., "Bispecific tandem diabody for tumor therapy with improved antigen binding and pharmacokinetics," J Mol Biol (1999) 293(1):41-56.
Klebanoff et al., "Sorting through subsets: which T-cell populations mediate highly effective adoptive immunotherapy?," J Immunother. (2012) 35(9): 651-660.
Klooster et al., "Targeting and localized signalling by small GTPases," Biol Cell. (2007) 99(1):1-12.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nat Rev Clin Oncol. May 2013;10(5):267-76.
Kollmannsperger et al., "Live-Cell Protein Labelling With Nanometre Precision By Cell Squeezing," Nat Comm (2016) 7(10372):1-7.
Koste et al., "T-cell receptor transfer into human T cells with ecotropic retroviral vectors," Gene Therapy (2014) 21: 533-538.
Lee et al., "Non-Endocytic Delivery Of Functional Engineered Nanoparticles Into The Cytoplasm Of Live Cells Using A Novel, High-Throughput Microfluidic Device," Nano Lett. (2012) 12(12):6322-6327.
Li et al., "Functional domains in Fok I restriction endonuclease," Proc Natl Acad Sci U S A. (1992) 89(10):4275-4279.
Li et al., "TAL nucleases (TALNs): hybrid proteins composed of TAL effectors and Fokl DNA-cleavage domain," Nucleic Acids Res. (2011) 39(1): 359-72.
Li et al., "Alteration of the cleavage distance of Fok I restriction endonuclease by insertion mutagenesis," Proc Natl Acad Sci U S A. (1993) 90(7):2764-2768.
Li et al., "Mechanisms and functions of DNA mismatch repair," Cell Res. (2008) 18(1):85-98.
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nat Biotechnol (2016) 34(4): 430-434.
Lloyd et al., "Beyond the antigen receptor: editing the genome of T-cells for cancer adoptive cellular therapies," Front Immunol (2013) 4(221):1-7.
Lombardo et al., "Site-specific integration and tailoring of cassette design for sustainable gene transfer," Nat Methods. (2011) 8(10): 861-9.
Lupton S. D. et al., "Dominant positive and negative selection using a hygromycin phosphotransferase-thymidine kinase fusion gene," Mol. and Cell Biol. (1991) 11(6):3374-3378.
Makarova et al., "Evolution and classification of the CRISPR-Cas systems," Nat Rev Microbiol. (2011) 9(6): 467-77.
Mali et al., "RNA Guided Human Genome Engineering via Cas9," Science (2013) 339(6121): 823-826.
Manuri et al., "piggyBac transposon/transposase system to generate CD19-specific T cells for the treatment of B-lineage malignancies," Hum Gene Ther (2010) 21(4): 427-437.
Marin-Acevedo et al., "Cancer immunotherapy beyond immune checkpoint inhibitors," J Hematol Oncol. (2018) 11: 8.
Marteijn et al., "Understanding nucleotide excision repair and its roles in cancer and ageing," Nature Reviews Molecular Cell Biology, (2014) 15(7):465-481.
Meyers et al., "Optimal Alignment in Linear Space," Comput Appl Biosci. (1988) 4(1):11-17.
Miller et al., "Improved retroviral vectors for gene transfer and expression," BioTechniques (1989) 7:980-990.
Miller et al., "Retrovirus packaging cells," Human Gene Therapy (1990) 1:5-14.
Mirzaei et al., "Chimeric Antigen Receptors T Cell Therapy in Solid Tumor: Challenges and Clinical Applications," Front Immunol. (2017) 8:1850.
Miyamoto et al., "Rapid and orthogonal logic gating with a gibberellin-induced dimerization system," Nat Chem Biol. (2012) 8(5): 465-70.
Morsut et al,. "Engineering Customized Cell Sensing and Response Behaviors Using Synthetic Notch Receptors," Cell. (2016) 164(4): 780-91.
Moscou et al., "A simple cipher governs DNA recognition by TAL effectors," Science (2009) 326(5959): 1501.
Mullen et al., "Transfer of the bacterial gene for cytosine deaminase to mammalian cells confers lethal sensitivity to 5-fluorocytosine: a negative selection system," Proc. Natl. Acad. Sci. USA (1992)89(1):33-37.
Nagorsen et al., "Immunomodulatory therapy of cancer with T cell-engaging BiTE antibody blinatumomab," Exp Cell Res. (2011) 317(9): 1255-60.
Needleman et al., "A General Method Applicable to the Search for Similarities in the Amino Acid sequence of Two Proteins," J. Mol. Biol. (1970) 48: 443-453.
Nehls et al., "Two genetically separable steps in the differentiation of thymic epithelium," Science (1996) 272(5263): 886-889.
Nishimasu et al., "Crystal structure of Cas9 in complex with guide RNA and target DNA," Cell (2014) 156(5): 935-949.
Park et al., "Treating cancer with genetically engineered T cells," Trends Biotechnol. (2011) 29(11): 550-557.
Pearson et al., "Improved Tools For Biological Sequence Comparison," Proc. Natl. Acad. Sci. USA (1988) 85(8): 2444-2448.
Portolano et al., "Lack of promiscuity in autoantigen-specific H and L chain combinations as revealed by human H and L chain roulette". J Immunol (1993) 150(3):880-887.
Qin et al., "Incorporation of functional elements enhances the antitumor capacity of CAR T cells," Exp Hematol Oncol. (2017) 6: 28.
Ran et al., "Double nicking by RNA-guided CRISPR Cas9 for enhanced genome editing specificity," Cell. (2013) 154(6): 1380-1389.

(56) References Cited

OTHER PUBLICATIONS

Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Rosenberg, "Cell transfer immunotherapy for metastatic solid cancer—what clinicians need to know," Nat Rev Clin Oncol. (2011) 8(10):577-585.
Roybal et al., "Precision Tumor Recognition by T Cells With Combinatorial Antigen-Sensing Circuits," Cell. (2016) 164(4): 770-779.
Rudemiller et al., "CD247 modulates blood pressure by altering T-lymphocyte infiltration in the kidney," Hypertension. (2014) 63(3):559-64.
Sadelain et a., "Targeting CARs to the TRAC locus enhances T-cell potency," Clin Cancer Res Dec. 15, 2017 (23) (24 Supplement) Abstract IA22.
Sadelain et al., "The basic principles of chimeric antigen receptor design," Cancer Discov. (2013) 3(4): 388-398.
Sadelain, "Chimeric antigen receptors: driving immunology towards synthetic biology, Chimeric antigen receptors: driving immunology towards synthetic biology," Curr Opin Immunol. (2016) 41: 68-76.
Sander et al., "CRISPR-Cas systems for editing, regulating and targeting genomes," Nat Biotechnol. (2014) 32(4):347-355.
Sander et al., "ZiFiT (Zinc Finger Targeter): an updated zinc finger engineering tool," Nucleic Acids Res. (2010) 38: W462-468.
Sander et al., "Zinc Finger Targeter (ZiFiT): an engineered zinc finger/target site design tool," Nucleic Acids Res. (2007) 35: W599-605.
Sanjana et al., "Improved vectors and genome-wide libraries for CRISPR screening," Nat Methods. Aug. 2014;11(8):783-784.
Scarpa et al., "Characterization of recombinant helper retroviruses from Moloney-based vectors in ecotropic and amphotropic packaging cell lines," Virology (1991) 180:849-852.
Seimetz et al., "Development and approval of the trifunctional antibody catumaxomab (anti-EpCAM x anti-CD3) as a targeted cancer immunotherapy," Cancer Treat Rev. (2010) 36(6): 458-467.
Sharma et al., "Efficient sleeping beauty DNA transposition from DNA minicircles," Molec Ther Nucl Acids (2013) 2:e74.
Sheng et al., "Structure-based cleavage mechanism of Thermus thermophilus Argonaute DNA guide strand-mediated DNA target cleavage," Proc Natl Acad Sci U S A (2014) 111(2): 652-657.
Smith et al., "Comparison of biosequences," Adv. Appl Math. (1981) 2: 482-489.
Spencer et al., "Controlling signal transduction with synthetic ligands," Science. (1993) 262(5136): 1019-24.
Sternberg et al., "DNA interrogation by the CRISPR RNA-guided endonuclease Cas9," Nature (2014) 507(7490): 62-67.
Swarts et al., "DNA-Guided DNA interference By A Prokaryotic Argonaute," Nature (2104) 507(7491): 258-261, 32 pages.
Tai et al., "Antibody-based therapies in multiple myeloma," Bone Marrow Res. (2011) 2011:924058.
Tamada et al., "Redirecting gene-modified T cells toward various cancer types using tagged antibodies," Clin Cancer Res. (2012) 18(23): 6436-45.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1): 84-9.
Turtle et al., "Engineered T cells for anti-cancer therapy," Curr. Opin. Immunol. (2012) 24(5): 633-639.
Urbanska et al., "A universal strategy for adoptive immunotherapy of cancer through use of a novel T cell antigen receptor," Cancer Res. (2012) 72(7): 1844-1852.
Van Tendeloo et al., "High-level transgene expression in primary human T lymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Vincent et al., "Targeting of proteins to membranes through hedgehog auto-processing," Nat Biotechnol. (2003) 21(8): 936-40.
Wadhwa et al., "Receptor mediated glycotargeting," J. Drug Targeting (1995) 3(2):111-127.
Wang et al., "Genetic screens in human cells using the CRISPR-Cas9 system," Science. (2014) 343(6166):80-84.
Wang et al., "One-step generation of mice carrying mutations in multiple genes by CRISPR/Cas-mediated genome engineering," Cell (2013) 153(4): 910-918.
Wang et al., "Phenotypic and functional attributes of lentivirus-modified CD19-specific human CD8+ central memory T cells manufactured at clinical scale," J Immunother (2012) 35(9):689-701.
Wang, Y. et al. "New Chimeric Antigen Receptor Design for Solid Tumors," Front Immunol. (2017) 8:1934, 9 pages.
Wang et al., "Immune targets and neoantigens for cancer immunotherapy and precision medicine," Cell Res. (2017) 27(1):11-37.
White et al., "Comparison of the glycosyl-phosphatidylinositol cleavage/attachment site between mammalian cells and parasitic protozoa," J Cell Sci. (2000) 113 ( Pt 4):721-7.
Wigler et al., "Transfer of purified herpes virus thymidine kinase gene to cultured mouse cells," Cell (1997) 11: 223-232.
Wu et al., "Adoptive T-cell therapy using autologous tumor-infiltrating lymphocytes for metastatic melanoma: current status and future outlook," Cancer (2012) 18(2): 160-175.
Xiao et al., "CasOT: a genome-wide Cas9/gRNA off-target searching tool," Bioinformatics (2014) 30(8):1180-1182.
Yamano et al., "Crystal Structure of Cpf1 in Complex with Guide RNA and Target DNA," Cell (2016) 165(4): 949-962.
Yoon et al., "Incorporation of Immune Checkpoint Blockade into Chimeric Antigen Receptor T Cells (CAR-Ts): Combination or Built-In CAR-T," Int J Mol Sci. (2018) 19(2): 340.
Yu et al., "Chimeric antigen receptor T cells: a novel therapy for solid tumors," J Hematol Oncol. (2017) 10(1):78.
Zetsche et al., "Cpf1 Is A Single RNA-Guided Endonuclease Of A Class 2 CRISPR-Cas System," Cell (2015) 163: 759-771.
Zhang et al., "Prospects for chimeric antigen receptormodified T cell therapy for solid tumors," Mol Cancer. (2018) 17(1):7.
Zlatkine et al., "Retargeting of cytosolic proteins to the plasma membrane by the Lck protein tyrosine kinase dual acylation motif," J Cell Sci. (1997) 110: 673-679.
Chmielewski et al., "TRUCKs: the fourth generation of CARs," Expert Opin Biol Ther. (2015, e-pub. May 18, 2015) 15(8):1145-1154.
Hu et al., "Using TWINSCAN to Predict Gene Structures in Genomic DNA Sequences," Current Protocols in Bioinformatics (Nov. 15, 2003) 3(1):4.8.1-4.8.19.
Nakagawa et al., "Development of next-generation adoptive immunotherapy using cytotoxic T-lymphocyte (CTL) expressing chimeric antigen-receptor (CAR)," Drug Delivery System (2013) 28(1):35-44. (English abstract provided).

CELLS EXPRESSING A CHIMERIC RECEPTOR FROM A MODIFIED CD247 LOCUS, RELATED POLYNUCLEOTIDES AND METHODS

CROSS-REFERENCE TO RELATED APPLICATIONS

This application is a National Stage application under 35 U.S.C. § 371 of International Application No. PCT/US2020/030875 filed on Apr. 30, 2020 which claims priority from U.S. provisional application No. 62/841,578, filed May 1, 2019, entitled "CELLS EXPRESSING A CHIMERIC RECEPTOR FROM A MODIFIED CD247 LOCUS, RELATED POLYNUCLEOTIDES AND METHODS," the contents of each which are incorporated by reference in its entirety.

INCORPORATION BY REFERENCE OF SEQUENCE LISTING

The present application is being filed along with a Sequence Listing in electronic format. The Sequence Listing is provided as a file entitled 735042015800SeqList.txt, created Oct. 28, 2021, which is 176,879 bytes in size. The information in the electronic format of the Sequence Listing is incorporated by reference in its entirety.

FIELD

The present disclosure relates to engineered immune cells, e.g. T cells, expressing a chimeric receptor comprising an intracellular region comprising a CD3zeta (CD3ζ) signaling domain. In some embodiments, the engineered immune cells contain a modified CD247 locus that encodes the chimeric receptor or a portion thereof. In some embodiments, at least a portion of a CD3zeta chain encoded by a CD247 genomic locus. Also provided are cell compositions containing the engineered immune cells, nucleic acids for engineering cells, and methods, kits and articles of manufacture for producing the engineered cells, such as by targeting a transgene encoding a portion of a chimeric receptor for integration into a region of a CD247 genomic locus. In some embodiments, the engineered cells, e.g. T cells, can be used in connection with cell therapy, including in connection with cancer immunotherapy comprising adoptive transfer of the engineered cells.

BACKGROUND

Adoptive cell therapies that utilize chimeric receptors, such as chimeric antigen receptors (CARs), to recognize antigens associated with a disease represent an attractive therapeutic modality for the treatment of cancers and other diseases. Improved strategies are needed for engineering T cells to express chimeric receptors, such as for use in adoptive immunotherapy, e.g., in treating cancer, infectious diseases and autoimmune diseases. Provided are methods, cells, compositions and kits for use in the methods that meet such needs.

SUMMARY

Provided herein are genetically engineered T cells and compositions, methods, uses, kits, and articles of manufacture related to genetically engineered T cells. In some of any of the provided embodiments, the genetically engineered T cell comprises a modified cluster of differentiation 247 (CD247) locus. In some of any embodiments, the modified CD247 locus comprises a transgene sequence encoding a chimeric receptor or a portion thereof. In provided embodiments, the transgene sequence is in-frame with an open reading frame or a partial sequence thereof of the endogenous CD247 locus. Thus, in provided embodiments, the modified CD247 locus encodes a chimeric receptor that includes sequences encoded from the transgene sequence and sequences encoded from the endogenous CD247 locus. In particular embodiments, the chimeric receptor contains an intracellular region that comprises a CD3zeta (CD3ζ) signaling domain, in which the CD3ζ signaling domain, for example the entire CD3ζ signaling domain, or at least a portion of the CD3ζ signaling domain is encoded by the genomic sequences (e.g., an open reading frame) at the endogenous CD247 locus (the genomic locus encoding CD3ζ) of the engineered cell such as a T cell.

Provided herein are genetically engineered T cells that contain a modified CD247 locus. In some of any embodiments, the modified CD247 locus comprises a nucleic acid sequence encoding a chimeric receptor comprising an intracellular region comprising a CD3zeta (CD3ζ) signaling domain. In some of any embodiments, the nucleic acid sequence comprises a transgene sequence encoding a portion of the chimeric receptor, the transgene sequence having been integrated at the endogenous CD247 locus. In some of any embodiments, the integration occurs via homology directed repair (HDR). In some of any embodiments, all or a fragment of the CD3ζ signaling domain of the intracellular region of the chimeric receptor is encoded by an open reading frame or a partial sequence thereof of the endogenous CD247 locus. In some of any embodiments, the nucleic acid sequence comprises an in-frame fusion of (i) a transgene sequence encoding a portion of the chimeric receptor and (ii) an open reading frame or a partial sequence thereof of the endogenous CD247 locus. In particular embodiments, the modified CD247 locus encodes a chimeric receptor that contains an intracellular region that comprises a CD3zeta (CD3ζ) signaling domain, in which the CD3ζ signaling domain, for example the entire CD3ζ signaling domain, or at least a portion of the CD3ζ signaling domain is encoded by the genomic sequences at the endogenous CD247 locus (the genomic locus encoding CD3ζ) of the engineered cell such as a T cell.

Provided herein are genetically engineered T cells that contain a modified CD247 locus, said modified CD247 locus comprising a nucleic acid sequence encoding a chimeric receptor comprising an intracellular region comprising a CD3ζ signaling domain, wherein the nucleic acid sequence comprises an in-frame fusion of (i) a transgene sequence encoding a portion of the chimeric receptor and (ii) an open reading frame or a partial sequence thereof of an endogenous CD247 locus encoding the CD3ζ signaling domain. In particular embodiments, the modified CD247 locus encodes a chimeric receptor that contains an intracellular region that comprises a CD3zeta (CD3ζ) signaling domain, in which the CD3ζ signaling domain or at least a portion of the CD3ζ signaling domain is encoded by the genomic sequences at the endogenous CD247 locus (the genomic locus encoding CD3ζ) of the engineered cell such as a T cell.

In some of any embodiments, the transgene sequence is in-frame with one or more exons of the open reading frame or partial sequence thereof of the endogenous CD247 locus.

In some of any embodiments, the transgene sequence does not comprise a sequence encoding a 3' UTR. In some of any embodiments, the transgene sequence does not comprise an intron.

In some of any embodiments, the transgene sequence encodes a fragment of the CD3ζ signaling domain. For example, in particular embodiments, the CD3ζ signaling domain or a fragment thereof of the chimeric receptor is encoded together by sequences of the transgene sequence and by genomic sequences (e.g., an open reading frame) at the endogenous CD247 locus (the genomic locus encoding CD3ζ) of the engineered cell such as a T cell.

In some of any embodiments, the transgene sequence does not encode the CD3ζ signaling domain or a fragment thereof. For example, in particular embodiments the entire or full-length of the CD3ζ signaling domain or a fragment thereof of the chimeric receptor is encoded by the genomic sequences at the endogenous CD247 locus (the genomic locus encoding CD3ζ) of the engineered cell such as a T cell.

In some of any embodiments, the open reading frame or a partial sequence thereof comprises at least one intron and at least one exon of the endogenous CD247 locus. In some of any embodiments, the open reading frame or a partial sequence thereof encodes a 3' UTR of the endogenous CD247 locus.

In some of any embodiments, the transgene sequence is downstream of exon 1 and upstream of exon 8 of the open reading frame of the endogenous CD247 locus. In some of any embodiments, the transgene sequence is downstream of exon 1 and upstream of exon 3 of the open reading frame of the endogenous CD247 locus.

In some of any embodiments, at least a fragment of the CD3ζ signaling domain, such as the entire CD3ζ signaling domain, of the encoded chimeric receptor is encoded by the open reading frame of the endogenous CD247 locus or a partial sequence thereof. In some of any embodiments, the CD3ζ signaling domain is encoded by a sequence of nucleotides comprising at least a portion of exon 2 and exons 3-8 of the open reading frame of the endogenous CD247 locus. In some of any embodiments, the CD3ζ signaling domain is encoded by a sequence of nucleotides that does not comprise exon 1, does not comprise the full length of exon 1 and/or does not comprise the full length of exon 2 of the open reading frame of the endogenous CD247 locus.

In some of any embodiments, the encoded chimeric receptor is capable of signaling via the CD3ζ signaling domain.

In some of any embodiments, the encoded CD3ζ signaling domain comprises the sequence selected from any one of SEQ ID NOS:13-15, or a sequence that exhibits at least 85%, 86%, 87%, 88%, 89%, 90%, 91%, 92%, 93%, 94%, 95%, 96%, 97%, 98%, 99% or more sequence identity to any one of SEQ ID NOS: 13-15, or a fragment thereof. In some embodiments, the encoded CD3ζ signaling domain comprises the sequence set forth in SEQ ID NO:13. In some embodiments, the encoded CD3ζ signaling domain comprises the sequence set forth in SEQ ID NO:14. In some embodiments, the encoded CD3 signaling domain comprises the sequence set forth in SEQ ID NO:15, In some of any embodiments, the chimeric receptor is or comprises a functional non-T cell receptor (non-TCR) antigen receptor.

In some of any embodiments, the chimeric receptor is a chimeric antigen receptor (CAR). In some of any embodiments, the chimeric receptor further comprises an extracellular region and/or a transmembrane domain.

In some of any embodiments, the transgene sequence comprises a sequence of nucleotides encoding one or more regions of the chimeric receptor. In some of any embodiments, the transgene sequence comprises a sequence of nucleotides encoding one or more of an extracellular region, a transmembrane domain and/or a portion of the intracellular region. In some of any embodiments, the extracellular region comprises a binding domain. In some of any embodiments, the binding domain is an antibody or an antigen-binding fragment thereof. In some of any embodiments, the binding domain comprises an antibody or an antigen-binding fragment thereof.

In some of any embodiments, the binding domain is capable of binding to a target antigen that is associated with, specific to, and/or expressed on a cell or tissue of a disease, disorder or condition. In some of any embodiments, the target antigen is a tumor antigen. In some of any embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In some of any embodiments, the extracellular region comprises a spacer. In some of any embodiments, the spacer is operably linked between the binding domain and the transmembrane domain. In some of any embodiments, the spacer comprises an immunoglobulin hinge region. In some of any embodiments, the spacer comprises a $C_H2$ region and a $C_H3$ region.

In some of any embodiments, the portion of the intracellular region encoded by the transgene sequence comprises one or more costimulatory signaling domain(s). In some of any embodiments, the one or more costimulatory signaling domain comprises an intracellular signaling domain of a CD28, a 4-1BB or an ICOS or a signaling portion thereof. In some embodiments, the costimulatory signaling domain is a signaling domain of human CD28. In some embodiments, the costimulatory signaling domain is a signaling domain of human 4-1BB. In some embodiments, the costimulatory signaling domain is a signaling domain of human ICOS. In some of any embodiments, the one or more costimulatory signaling domain comprises an intracellular signaling domain of 4-1BB, such as human 4-1BB.

In some of any embodiments, the modified CD247 locus encodes a chimeric receptor that comprises, from its N to C terminus in order: the extracellular binding domain, the spacer, the transmembrane domain and an intracellular signaling region. In particular embodiments, the intracellular region contains a CD3zeta (CD3ζ) signaling domain, in which the CD3ζ signaling domain or at least a portion of the CD3ζ signaling domain is encoded by the genomic sequences at the endogenous CD247 locus (the genomic locus encoding CD3ζ) of the engineered cell such as a T cell.

In some of any embodiments, the transgene sequence comprises in order: a sequence of nucleotides encoding an extracellular binding domain; a spacer; and a transmembrane domain; a costimulatory signaling domain. In some of any embodiments, the modified CD247 locus comprises in order: a sequence of nucleotides encoding an extracellular binding domain; a spacer; and a transmembrane domain; and an intracellular region containing a costimulatory signaling domain and a CD3zeta (CD3ζ) signaling domain. In particular embodiments, the intracellular signaling region contains a costimulatory signaling domain and a CD3zeta (CD3ζ) signaling domain, in which the CD3ζ signaling domain or at least a portion of the CD3ζ signaling domain is encoded by the genomic sequences (e.g., an open reading frame) at the endogenous CD247 locus (the genomic locus encoding CD3ζ) of the engineered cell such as a T cell. In some of any embodiments, the transgene sequence comprises in order a sequence of nucleotides encoding an extracellular binding domain, that is an scFv; a spacer, that includes a sequence from a human immunoglobulin hinge, that is from IgG1, IgG2 or IgG4 or a modified version thereof, that is that also includes a $C_H2$ region and/or a $C_H3$ region; and a transmembrane domain, that is from human CD28; a costimulatory signaling domain, that is from human 4-1BB. In some of any embodiments, the modified CD247 locus comprises in order a sequence of nucleotides encoding an extracellular binding domain, that is an scFv; a spacer, that includes a sequence from a human immunoglobulin hinge, that is from IgG1, IgG2 or IgG4 or a modified version thereof, that is that also includes a $C_H2$ region and/or a $C_H3$ region; and a transmembrane domain, that is from human CD28; and an intracellular region containing a costimulatory signaling domain that is from human 4-1BB, and the CD3ζ signaling domain. In particular embodiments, the intracellular region contains a costimulatory signaling domain and a CD3zeta (CD3ζ) signaling domain, in which the CD3ζ signaling domain or at least a portion of the CD3ζ signaling domain is encoded by the genomic sequences (e.g., an open reading frame) at the endogenous CD247 locus (the genomic locus encoding CD3ζ) of the engineered cell such as a T cell.

In some of any embodiments, the chimeric receptor is a CAR that is a multi-chain CAR.

In some of any embodiments, the transgene sequence comprises a sequence of nucleotides encoding at least one further protein. For example, the at least one further protein may be another chain of the CAR. In some examples, the at least one further protein is a surrogate marker or truncated receptor for co-expression on a cell with the chimeric receptor. In some of any embodiments, the transgene sequence comprises one or more multicistronic element(s), such as separating the chimeric receptor and the one or more further proteins. In some of any embodiments, the multicistronic element(s) is positioned between the sequence of nucleotides encoding the portion of the chimeric receptor and the sequence of nucleotides encoding the at least one further protein. In some of any embodiments, the at least one further protein is a surrogate marker. In some of any embodiments, the surrogate marker is a truncated receptor. In some of any embodiments, the truncated receptor lacks an intracellular signaling domain and/or is not capable of mediating intracellular signaling when bound by its ligand. In some of any embodiments, the chimeric receptor is a multi-chain CAR, and a multicistronic element is positioned between a sequence of nucleotides encoding one chain of the multi-chain CAR and a sequence of nucleotides encoding another chain of the multi-chain CAR. In some of any embodiments, the one or more multicistronic element(s) are upstream of the sequence of nucleotides encoding the portion of the chimeric receptor. In some of any embodiments, the one or more multicistronic element is or comprises a ribosome skip sequence. In some of any embodiments, the ribosome skip sequence is a T2A, a P2A, an E2A, or an F2A element.

In some of any embodiments, the modified CD247 locus comprises the promoter and/or regulatory or control element of the endogenous CD247 locus operably linked to control expression the nucleic acid sequence encoding the chimeric receptor. In some of any embodiments, the modified locus comprises one or more heterologous regulatory or control element(s) operably linked to control expression of the nucleic acid sequence encoding the chimeric receptor. In some of any embodiments, the one or more heterologous regulatory or control element comprises a promoter, an enhancer, an intron, a polyadenylation signal, a Kozak consensus sequence, a splice acceptor sequence and/or a splice donor sequence. In some of any embodiments, the heterologous promoter is or comprises a human elongation factor 1 alpha (EF1α) promoter or an MND promoter or a variant thereof.

In some of any embodiments, the T cell is a primary T cell derived from a subject. In some of any embodiments, the subject is a human. In some of any embodiments, the T cell is a CD8+ T cell or subtypes thereof. In some of any embodiments, the T cell is a CD4+ T cell or subtypes thereof. In some of any embodiments, the T cell is derived from a multipotent or pluripotent cell. In some of any embodiments, the pluripotent cell is an iPSC. In some of any embodiments, the T cell is derived from a multipotent or pluripotent cell, which is an iPSC.

Also provided herein are polynucleotides, such as polynucleotides that can be used for integration of a transgene sequence encoding a chimeric receptor into the CD247 locus. In some of any embodiments, the polynucleotides include (a) a nucleic acid sequence encoding a chimeric receptor or a portion thereof; and (b) one or more homology arm(s) linked to the nucleic acid sequence, wherein the one or more homology arm(s) comprise a sequence homologous to one or more region(s) of an open reading frame of a CD247 locus or a partial sequence thereof. In some of any embodiments, integration of the polynucleotide into the CD247 locus encodes a chimeric receptor that comprises an intracellular region (e.g., an intracellular region comprising a CD3ζ signaling domain) and the nucleic acid sequence of (a) is a nucleic acid sequence encoding a portion of the chimeric receptor, in which said portion does not include the full intracellular region of the chimeric receptor. In some embodiments, the full intracellular region includes a CD3zeta (CD3ζ) signaling domain. In some embodiments, the full intracellular region includes a costimulatory signaling domain and a CD3zeta (CD3ζ) signaling domain. In some embodiments, the nucleic acid sequence of (a) encodes a portion of the chimeric receptor that does not include the entire or full length sequence encoding a CD3zeta (CD3ζ) signaling domain. In some embodiments, the nucleic acid sequence of (a) does not contain any sequence encoding the CD3zeta (CD3ζ) signaling domain. In some embodiments, the nucleic acid sequence of (a) encodes an intracellular region that comprises a fragment of the CD3zeta (CD3ζ) signaling domain. In any of such examples, the nucleic acid sequence of (a) may encode a costimulatory signaling domain of the intracellular region.

Also provided herein are polynucleotides that contain (a) a nucleic acid sequence encoding a portion of a chimeric receptor, said chimeric receptor comprising an intracellular region (e.g., an intracellular region comprising a CD3ζ signaling domain), wherein the portion of the chimeric receptor includes less than the full intracellular region of the chimeric receptor; and (b) one or more homology arm(s) linked to the nucleic acid sequence, wherein the one or more homology arm(s) comprise a sequence homologous to one or more region(s) of an open reading frame of a CD247 locus or a partial sequence thereof. In some embodiments, the polynucleotide can be used for integration of a transgene sequence encoding the chimeric receptor into the CD247 locus. In some embodiments, the full intracellular region includes a CD3zeta (CD3ζ) signaling domain. In some embodiments, the full intracellular region includes a costimulatory signaling domain and a CD3zeta (CD3ζ) signaling domain. In some embodiments, the nucleic acid sequence of (a) encodes a portion of the chimeric receptor that does not include the entire or full length sequence encoding a CD3zeta (CD3ζ) signaling domain. In some embodiments, the nucleic acid sequence of (a) does not contain any sequence encoding the CD3zeta (CD3ζ) signaling domain. In some embodiments, the nucleic acid sequence of (a) encodes an intracellular region that comprises a fragment of the CD3zeta (CD3ζ) signaling domain. In any of such examples, the nucleic acid sequence of (a) may encode a costimulatory signaling domain of the intracellular region.

In some of any embodiments, the full intracellular region of the chimeric receptor comprises a CD3zeta (CD3ζ) signaling domain or a fragment thereof, wherein at least a portion of the intracellular region is encoded by the open reading frame of the endogenous CD247 locus or a partial sequence thereof when the chimeric receptor is expressed from a cell introduced with the polynucleotide.

In some of any embodiments, the nucleic acid sequence encoding the portion of the chimeric receptor and the one or more homology arm(s) together comprise at least a fragment of a sequence of nucleotides encoding the intracellular region of the chimeric receptor, wherein at least a portion of the intracellular region comprises the CD3ζ signaling domain or a fragment thereof encoded by the open reading frame of the CD247 locus or a partial sequence thereof when the chimeric receptor is expressed from a cell introduced with the polynucleotide.

In some of any embodiments, the nucleic acid sequence of (a) does not comprise a sequence encoding a 3' UTR. In some of any embodiments, the nucleic acid sequence of (a) does not comprise an intron.

In some of any embodiments, the nucleic acid sequence of (a) encodes a fragment of the CD3ζ signaling domain. In such embodiments, when the chimeric receptor is expressed from a cell introduced with the polynucleotide, at least a portion of the CD3ζ signaling domain is encoded by the genomic sequences at the endogenous CD247 locus (the genomic locus encoding CD3ζ) of the engineered cell such as a T cell. For example, in particular embodiments, the CD3ζ signaling domain or a fragment thereof of the chimeric receptor is encoded together by sequences of the transgene sequence and by genomic sequences at the endogenous CD247 locus (the genomic locus encoding CD3ζ) of the engineered cell such as a T cell.

In some of any embodiments, the nucleic acid sequence of (a) does not encode the CD3 signaling domain or a fragment thereof. In such embodiments, when the chimeric receptor is expressed from a cell introduced with the polynucleotide the entire or full-length of the CD3ζ signaling domain or a fragment thereof of the chimeric receptor is encoded by the genomic sequences at the endogenous CD247 locus (the genomic locus encoding CD3ζ) of the engineered cell such as a T cell.

In some of any embodiments, the open reading frame or a partial sequence thereof of the endogenous CD247 locus comprises at least one intron and at least one exon of the endogenous CD247 locus. In some of any embodiments, the open reading frame or a partial sequence thereof encodes a 3' UTR of the endogenous CD247 locus.

In some of any embodiments, at least a fragment of the CD3ζ signaling domain, such as the entire CD3ζ signaling domain, of the encoded chimeric receptor is encoded by the open reading frame of the endogenous CD247 locus or a partial sequence thereof, when the chimeric receptor is expressed from a cell introduced with the polynucleotide.

In some of any embodiments, the nucleic acid sequence of (a) is a sequence that is exogenous or heterologous to an open reading frame of the endogenous genomic CD247 locus a T cell, such as a human T cell.

In some of any embodiments, the nucleic acid sequence of (a) comprises a sequence of nucleotides that is in-frame with one or more exons of the open reading frame or a partial sequence thereof of the CD247 locus comprised in the one or more homology arm(s).

In some of any embodiments, the one or more region(s) of the open reading frame of the endogenous CD247 locus or a partial sequence thereof is or comprises sequences that are upstream of exon 8 of the open reading frame of the CD247 locus. In some of any embodiments, the one or more region(s) of the open reading frame is or comprises sequences that are upstream of exon 3 of the open reading frame of the CD247 locus. In some of any embodiments, the one or more region(s) of the open reading frame is or comprises sequences that includes exon 3 of the open reading frame of the CD247 locus. In some of any embodiments, the one or more region(s) of the open reading frame is or comprises sequences that includes at least a portion of exon 2 of the open reading frame of the CD247 locus. In some of any embodiments, the one or more homology arm(s) does not comprise exon 1, does not comprise the full length of exon 1 and/or does not comprise the full length of exon 2 of the open reading frame of the endogenous CD247 locus.

In some of any embodiments, when expressed by a cell introduced with the polynucleotide, the encoded chimeric receptor is capable of signaling via the CD3ζ signaling domain. In some of any embodiments, the CD3ζ signaling domain of the full intracellular region encoded by the chimeric receptor comprises the sequence selected from any one of SEQ ID NOS:13-15, or a sequence that exhibits at least 85%, 86%, 87%, 88%, 89%, 90%, 91%, 92%, 93%, 94%, 95%, 96%, 97%, 98%, 99% or more sequence identity to any one of SEQ ID NOS:13-15, or a fragment thereof. In some embodiments, the CD3ζ signaling domain has the sequence set forth in SEQ ID NO: 13. In some embodiments, the CD3ζ signaling domain has the sequence set forth in SEQ ID NO: 14. In some embodiments, the CD3 signaling domain has the sequence set forth in SEQ ID NO: 15.

In some of any embodiments, the one or more homology arm comprises a 5' homology arm and a 3' homology arm. In some of any embodiments, the polynucleotide comprises the structure [5' homology arm]-[nucleic acid sequence of (a)]-[3' homology arm].

In some of any embodiments, the 5' homology arm and the 3' homology arm independently are from at or about 50 to at or about 2000 nucleotides, from at or about 100 to at or about 1000 nucleotides, from at or about 100 to at or about 750 nucleotides, from at or about 100 to at or about 600 nucleotides, from at or about 100 to at or about 400 nucleotides, from at or about 100 to at or about 300 nucleotides, from at or about 100 to at or about 200 nucleotides, from at or about 200 to at or about 1000 nucleotides, from at or about 200 to at or about 750 nucleotides, from at or about 200 to at or about 600 nucleotides, from at or about 200 to at or about 400 nucleotides, from at or about 200 to at or about 300 nucleotides, from at or about 300 to at or about 1000 nucleotides, from at or about 300 to at or about 750 nucleotides, from at or about 300 to at or about 600 nucleotides, from at or about 300 to at or about 400 nucleotides, from at or about 400 to at or about 1000 nucleotides, from at or about 400 to at or about 750 nucleotides, from at or about 400 to at or about 600 nucleotides, from at or about 600 to at or about 1000 nucleotides, from at or about 600 to at or about 750 nucleotides or from at or about 750 to at or about 1000 nucleotides in length. In some of any embodiments, the 5' homology arm and the 3' homology arm independently are at or about 200, 300, 400, 500, 600, 700 or 800 nucleotides in length, or any value between any of the foregoing. In some of any embodiments, the 5' homology arm and the 3' homology arm independently are greater than at or about 300 nucleotides in length. In some of any embodiments, the 5' homology arm and the 3' homology arm independently are at or about 400, 500 or 600 nucleotides in length, or any value between any of the foregoing.

In some of any embodiments, the 5' homology arm comprises the sequence set forth in SEQ ID NO:80, or a sequence that exhibits at least 85%, 86%, 87%, 88%, 89%, 90%, 91%, 92%, 93%, 94%, 95%, 96%, 97%, 98%, 99% or more sequence identity to SEQ ID NO:80 or a partial sequence thereof. In some embodiments, the 5' homology arm comprises the sequence set forth in SEQ ID NO:80. In some embodiments, the 5' homology arm consists or consists essentially of the sequence set forth in SEQ ID NO: 80. In some of any embodiments, the 3' homology arm comprises the sequence set forth in SEQ ID NO:81, or a sequence that exhibits at least 85%, 86%, 87%, 88%, 89%, 90%, 91%, 92%, 93%, 94%, 95%, 96%, 97%, 98%, 99% or more sequence identity to SEQ ID NO:81 or a partial sequence thereof. In some embodiments, the 3' homology arm comprises the sequence set forth in SEQ ID NO:81. In some embodiments, the 3' homology arm consists or consists essentially of the sequence set forth in SEQ ID NO: 81.

In some of any embodiments, the chimeric receptor is or comprises a functional non-T cell receptor (non-TCR) antigen receptor.

In some of any embodiments, the chimeric receptor is a chimeric antigen receptor (CAR).

In some of any embodiments, the nucleic acid sequence of (a) comprises a sequence of nucleotides encoding an extracellular region a sequence of nucleotides encoding a transmembrane domain and/or a portion of the intracellular region. In some of any embodiments, the nucleic acid sequence of (a) comprises a sequence of nucleotides encoding an extracellular region, a sequence of nucleotides encoding a transmembrane domain and a sequence of nucleotides encoding a portion of the intracellular region. In some of any embodiments, the extracellular region comprises a binding domain. In some of any embodiments, the binding domain is or comprises an antibody or an antigen-binding fragment thereof.

In some of any embodiments, the binding domain is capable of binding to a target antigen that is associated with, specific to, and/or expressed on a cell or tissue of a disease, disorder or condition. In some of any embodiments, the target antigen is a tumor antigen. In some of any embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In some of any embodiments, the extracellular region comprises a spacer. In some of any embodiments, the spacer is operably linked between the binding domain and the transmembrane domain. In some of any embodiments, the spacer comprises an immunoglobulin hinge region. In some of any embodiments, the spacer comprises a $C_H2$ region and a $C_H3$ region.

In some of any embodiments, the portion of the intracellular region encoded by the nucleic acid of a) comprises one or more costimulatory signaling domain(s). In some of any embodiments, the one or more costimulatory signaling domain comprises an intracellular signaling domain of a CD28, a 4-1BB or an ICOS or a signaling portion thereof. In some embodiments, the costimulatory signaling domain is a signaling domain of human CD28. In some embodiments, the costimulatory signaling domain is a signaling domain of human 4-1BB. In some embodiments, the costimulatory signaling domain is a signaling domain of human ICOS. In some of any embodiments, the one or more costimulatory signaling domain comprises an intracellular signaling domain of 4-1BB, such as human 4-1BB.

In some of any embodiments, the encoded chimeric receptor comprises, from its N to C terminus in order: the extracellular binding domain, the spacer, the transmembrane domain and an intracellular signaling region, when the chimeric receptor is expressed from a cell introduced with the polynucleotide. In particular embodiments, when expressed from a cell such as a T cell, the intracellular region of the encoded chimeric receptor contains a CD3zeta (CD3ζ) signaling domain, in which the entire CD3ζ signaling domain or at least a portion of the CD3ζ signaling domain is encoded by the genomic sequences at the endogenous CD247 locus (the genomic locus encoding CD3ζ).

In some of any embodiments, the sequence of (a) comprises in order: a sequence of nucleotides encoding an extracellular binding domain; a spacer; and a transmembrane domain; and a costimulatory signaling domain. In some of any embodiments, the sequence of (a) comprises in order: a sequence of nucleotides encoding an extracellular binding domain; a spacer; a transmembrane domain; and an intracellular signaling region containing a costimulatory signaling domain and a fragment of the CD3ζ signaling domain. In particular embodiments, when expressed from a cell such as a T cell, the polynucleotide encodes a chimeric receptor with an intracellular signaling region that contains a costimulatory signaling domain and a CD3zeta (CD3ζ) signaling domain, in which the CD3ζ signaling domain or at least a portion of the CD3ζ signaling domain is encoded by the genomic sequences at the endogenous CD247 locus (the genomic locus encoding CD3ζ) of the engineered cell such as a T cell.

In some of any embodiments, the nucleic acid sequence of (a) comprises in order a sequence of nucleotides encoding an extracellular binding domain, that is an scFv; a spacer, that includes a sequence from a human immunoglobulin hinge, that is from IgG1, IgG2 or IgG4 or a modified version thereof, and that also includes a $C_H2$ region and/or a $C_H3$ region; and a transmembrane domain, that is from human CD28; and a costimulatory signaling domain, that is from human 4-1BB. In some of any embodiments, the sequence of (a) comprises in order: a sequence of nucleotides encoding an extracellular binding domain, that is an scFv; a spacer, that includes a sequence from a human immunoglobulin hinge, that is from IgG1, IgG2 or IgG4 or a modified version thereof, and that also includes a $C_H2$ region and/or a $C_H3$ region; a transmembrane domain that is from human CD28; and an intracellular region that contains a costimulatory signaling domain that is from human 4-1BB, and a fragment of the CD3ζ signaling domain. In particular embodiments, when expressed from a cell such as a T cell, the polynucleotide encodes a chimeric receptor with an intracellular signaling region that contains a human 4-1BB costimulatory signaling domain and a CD3zeta (CD3ζ) signaling domain, in which the CD3ζ signaling domain or at least a portion of the CD3ζ signaling domain is encoded by the genomic sequences at the endogenous CD247 locus (the genomic locus encoding CD3ζ) of the engineered cell such as a T cell. In some of any embodiments, the modified CD247 locus, following introduction of the polynucleotide into a T cell, comprises in order a sequence of nucleotides encoding an extracellular binding domain, that is an scFv; a spacer, that includes a sequence from a human immunoglobulin hinge, that is from IgG1, IgG2 or IgG4 or a modified version thereof, and that also includes a $C_H2$ region and/or a $C_H3$ region; and a transmembrane domain, that is from human CD28; a costimulatory signaling domain, that is from human 4-1BB.

In some of any embodiments, the CAR is a multi-chain CAR. In some of any embodiments, the nucleic acid sequence of (a) comprises a sequence of nucleotides encoding at least one further protein.

In some of any embodiments, the nucleic acid sequence of (a) comprises one or more multicistronic element(s). In some of any embodiments, the multicistronic element(s) is positioned between the sequence of nucleotides encoding the portion of the chimeric receptor and the sequence of nucleotides encoding the at least one further protein. In some of any embodiments, the at least one further protein is a surrogate marker. In some of any embodiments, the surrogate marker is a truncated receptor. In some of any embodiments, the truncated receptor lacks an intracellular signaling domain and/or is not capable of mediating intracellular signaling when bound by its ligand. In some of any embodiments, the chimeric receptor is a multi-chain CAR, and a multicistronic element is positioned between a sequence of nucleotides encoding one chain of the multi-chain CAR and a sequence of nucleotides encoding another chain of the multi-chain CAR. In some of any embodiments, the one or more multicistronic element(s) are upstream of the sequence of nucleotides encoding the portion of the chimeric receptor. In some of any embodiments, the one or more multicistronic element is or comprises a ribosome skip sequence. In some of any embodiments, the ribosome skip sequence is a T2A, a P2A, an E2A, or an F2A element.

In some of any embodiments, the modified CD247 locus, following introduction of the polynucleotide into a T cell, comprises the promoter and/or regulatory or control element of the endogenous CD247 locus operably linked to control expression the nucleic acid sequence encoding the chimeric receptor. In some of any embodiments, the modified locus comprises one or more heterologous regulatory or control element(s) operably linked to control expression of the nucleic acid sequence encoding the chimeric receptor. In some of any embodiments, the one or more heterologous regulatory or control element comprises a promoter, an enhancer, an intron, a polyadenylation signal, a Kozak consensus sequence, a splice acceptor sequence and/or a splice donor sequence. In some of any embodiments, the heterologous promoter is or comprises a human elongation factor 1 alpha (EF1α) promoter or an MND promoter or a variant thereof.

In some of any embodiments, the nucleic acid sequence of (a) comprises one or more heterologous regulatory or control element(s) operably linked to control expression of the nucleic acid sequence encoding the chimeric receptor. In some of any embodiments, the one or more heterologous regulatory or control element comprises a promoter, an enhancer, an intron, a polyadenylation signal, a Kozak consensus sequence, a splice acceptor sequence and/or a splice donor sequence. In some of any embodiments, the heterologous promoter is or comprises a human elongation factor 1 alpha (EF1α) promoter or an MND promoter or a variant thereof.

In some of any embodiments, the polynucleotide is comprised in a viral vector. In some of any embodiments, the viral vector is an AAV vector. In some of any embodiments, the AAV vector is selected from among AAV1, AAV2, AAV3, AAV4, AAV5, AAV6, AAV7 or AAV8 vector. In some of any embodiments, the AAV vector is an AAV2 or AAV6 vector. In some of any embodiments, the viral vector is a retroviral vector. In some of any embodiments, the viral vector a lentiviral vector.

In some of any embodiments, the polynucleotide is a linear polynucleotide. In some of any embodiments, a double-stranded polynucleotide or a single-stranded polynucleotide.

In some of any embodiments, the polynucleotide is at least at or about 2500, 2750, 3000, 3250, 3500, 3750, 4000, 4250, 4500, 4760, 5000, 5250, 5500, 5750, 6000, 7000, 7500, 8000, 9000 or 10000 nucleotides in length, or any value between any of the foregoing. In some of any embodiments, the polynucleotide is between at or about 2500 and at or about 5000 nucleotides, at or about 3500 and at or about 4500 nucleotides, or at or about 3750 nucleotides and at or about 4250 nucleotides in length.

Also provided herein are methods of producing a genetically engineered T cell, the method involving introducing the polynucleotides of any of the embodiments provided herein into a T cell comprising a genetic disruption at a CD247 locus.

Also provided herein are methods of producing a genetically engineered T cell, the method involving: (a) introducing, into a T cell, one or more agent(s) capable of inducing a genetic disruption at a target site within an endogenous CD247 locus of the T cell; and (b) introducing any of the polynucleotides described herein into a T cell comprising a genetic disruption at a CD247 locus, wherein the method produces a modified CD247 locus, said modified CD247 locus comprising a nucleic acid sequence encoding the chimeric receptor comprising an intracellular region comprising a CD3 (CD3ζ) signaling domain.

In some of any embodiments, the polynucleotide comprises a nucleic acid sequence encoding a chimeric receptor or a portion thereof, and the nucleic acid sequence encoding a chimeric receptor or a portion thereof is integrated within the endogenous CD247 locus via homology directed repair (HDR).

Also provided herein are methods of producing a genetically engineered T cell, the method involving introducing, into a T cell, a polynucleotide comprising a nucleic acid sequence encoding a chimeric receptor or a portion thereof, said T cell having a genetic disruption within a CD247 locus of the T cell, wherein the nucleic acid sequence encoding the chimeric receptor or a portion thereof is integrated within the endogenous CD247 locus via homology directed repair (HDR).

In some of any embodiments, the genetic disruption is carried out by introducing, into a T cell, one or more agent(s) capable of inducing a genetic disruption at a target site within an endogenous CD247 locus of the T cell.

In some of any embodiments, the method produces a modified CD247 locus, said modified CD247 locus comprising a nucleic acid sequence encoding a chimeric receptor comprising an intracellular region comprising a CD3 (CD3ζ) signaling domain.

In some of any embodiments, the nucleic acid sequence encoding a chimeric receptor or a portion thereof encodes a portion of the chimeric receptor. In some of any embodiments, the polynucleotide further comprises one or more homology arm(s) linked to the nucleic acid sequence, wherein the one or more homology arm(s) comprise a sequence homologous to one or more region(s) of an open reading frame of a CD247 locus.

In some of any embodiments, the full intracellular region of the chimeric receptor comprises a CD3zeta (CD3ζ) signaling domain or a fragment thereof, wherein at least a portion of the intracellular region is encoded by the open reading frame of the endogenous CD247 locus or a partial sequence thereof in a cell generated by the method.

In some of any embodiments, the nucleic acid sequence encoding the portion of the chimeric receptor and the one or more homology arm(s) together comprise at least a fragment of a sequence of nucleotides encoding the intracellular region of the chimeric receptor, wherein at least a portion of the intracellular region comprises the CD3ζ signaling domain or a fragment thereof encoded by the open reading frame of the CD247 locus or a partial sequence thereof in a cell generated by the method.

In some of any embodiments, the nucleic acid sequence encoding a chimeric receptor or a portion thereof does not comprise a sequence encoding a 3' UTR. In some of any embodiments, the nucleic acid sequence encoding a chimeric receptor or a portion thereof encodes a fragment of the CD3ζ signaling domain, in a cell generated by the method. In some of any embodiments, the nucleic acid sequence encoding a chimeric receptor or a portion thereof does not encode the CD3ζ signaling domain or a fragment thereof, in a cell generated by the method. In some of any embodiments, at least a fragment of the CD3ζ signaling domain, such as the entire CD3ζ signaling domain, of the encoded chimeric receptor is encoded by the open reading frame of the endogenous CD247 locus or a partial sequence thereof, in a cell generated by the method.

In some of any embodiments, the nucleic acid sequence encoding a chimeric receptor or a portion thereof is a sequence that is exogenous or heterologous to an open reading frame of the endogenous genomic CD247 locus a T cell, such as a human T cell.

In some of any embodiments, the nucleic acid sequence encoding a chimeric receptor or a portion thereof comprises a sequence of nucleotides that is in-frame with one or more exons of the open reading frame or a partial sequence thereof of the CD247 locus comprised in the one or more homology arm(s).

In some of any embodiments, when expressed by a cell introduced with the polynucleotide, the chimeric receptor is capable of signaling via the CD3ζ signaling domain. In some of any embodiments, the CD3ζ signaling domain of the full intracellular region comprises the sequence selected from any one of SEQ ID NOS:13-15, or a sequence that exhibits at least 85%, 86%, 87%, 88%, 89%, 90%, 91%, 92%, 93%, 94%, 95%, 96%, 97%, 98%, 99% or more sequence identity to any one of SEQ ID NOS:13-15, or a fragment thereof. In some embodiments, the CD3ζ signaling domain comprises the sequence set forth in SEQ ID NO:13. In some embodiments, the CD3ζ signaling domain comprises the sequence set forth in SEQ ID NO:14. In some embodiments, the CD3ζ signaling domain comprises the sequence set forth in SEQ ID NO:15.

In some of any embodiments, the one or more homology arm comprises a 5' homology arm and a 3' homology arm. In some of any embodiments, the polynucleotide comprises the structure [5' homology arm]-[nucleic acid sequence encoding a chimeric receptor or a portion thereof]-[3' homology arm].

In some of any embodiments, the 5' homology arm and the 3' homology arm independently are from at or about 50 to at or about 2000 nucleotides, from at or about 100 to at or about 1000 nucleotides, from at or about 100 to at or about 750 nucleotides, from at or about 100 to at or about 600 nucleotides, from at or about 100 to at or about 400 nucleotides, from at or about 100 to at or about 300 nucleotides, from at or about 100 to at or about 200 nucleotides, from at or about 200 to at or about 1000 nucleotides, from at or about 200 to at or about 750 nucleotides, from at or about 200 to at or about 600 nucleotides, from at or about 200 to at or about 400 nucleotides, from at or about 200 to at or about 300 nucleotides, from at or about 300 to at or about 1000 nucleotides, from at or about 300 to at or about 750 nucleotides, from at or about 300 to at or about 600 nucleotides, from at or about 300 to at or about 400 nucleotides, from at or about 400 to at or about 1000 nucleotides, from at or about 400 to at or about 750 nucleotides, from at or about 400 to at or about 600 nucleotides, from at or about 600 to at or about 1000 nucleotides, from at or about 600 to at or about 750 nucleotides or from at or about 750 to at or about 1000 nucleotides in length. In some of any embodiments, the 5' homology arm and the 3' homology arm independently are at or about 200, 300, 400, 500, 600, 700 or 800 nucleotides in length, or any value between any of the foregoing. In some of any embodiments, the 5' homology arm and the 3' homology arm independently are greater than at or about 300 nucleotides in length. In some of any embodiments, the 5' homology arm and the 3' homology arm independently are at or about 400, 500 or 600 nucleotides in length, or any value between any of the foregoing.

In some of any embodiments, the 5' homology arm comprises the sequence set forth in SEQ ID NO:80, or a sequence that exhibits at least 85%, 86%, 87%, 88%, 89%, 90%, 91%, 92%, 93%, 94%, 95%, 96%, 97%, 98%, 99% or more sequence identity to SEQ ID NO:80 or a partial sequence thereof. In some embodiments, the 5' homology arm comprises the sequence set forth in SEQ ID NO:80. In some embodiments, the 5' homology arm consists or consists essentially of the sequence set forth in SEQ ID NO: 80. In some of any embodiments, the 3' homology arm comprises the sequence set forth in SEQ ID NO:81, or a sequence that exhibits at least 85%, 86%, 87%, 88%, 89%, 90%, 91%, 92%, 93%, 94%, 95%, 96%, 97%, 98%, 99% or more sequence identity to SEQ ID NO:81 or a partial sequence thereof. In some embodiments, the 3' homology arm comprises the sequence set forth in SEQ ID NO:81. In some embodiments, the 3' homology arm consists or consists essentially of the sequence set forth in SEQ ID NO: 81.

In some of any embodiments, the one or more agent(s) capable of inducing a genetic disruption comprises a DNA binding protein or DNA-binding nucleic acid that specifically binds to or hybridizes to the target site, a fusion protein comprising a DNA-targeting protein and a nuclease, or an RNA-guided nuclease. In some of any embodiments, the one or more agent(s) comprises a zinc finger nuclease (ZFN), a TAL-effector nuclease (TALEN), or and a CRISPR-Cas9 combination that specifically binds to, recognizes, or hybridizes to the target site.

In some of any embodiments, the each of the one or more agent(s) comprises a guide RNA (gRNA) having a targeting domain that is complementary to the at least one target site. In some of any embodiments, the one or more agent(s) is introduced as a ribonucleoprotein (RNP) complex comprising the gRNA and a Cas9 protein.

In some of any embodiments, the RNP is introduced via electroporation, particle gun, calcium phosphate transfection, cell compression or squeezing. In some of any embodiments, the RNP is introduced via electroporation.

In some of any embodiments, the concentration of the RNP is at or about 1, 2, 2.5, 5, 10, 20, 25, 30, 40 or 50 μM, or a range defined by any two of the foregoing values. In some of any embodiments, the concentration of the RNP is at or about 25 μM.

In some of any embodiments, the molar ratio of the gRNA and the Cas9 molecule in the RNP is at or about at or about 5:1, 4:1, 3:1, 2:1, 1:1, 1:2, 1:3, 1:4 or 1:5, or a range defined by any two of the foregoing values. In some of any embodiments, the molar ratio of the gRNA and the Cas9 molecule in the RNP is at or about 2.6:1.

In some of any embodiments, the gRNA has a targeting domain sequence selected from CACCUUCACUCUCAGGAACA (SEQ ID NO:87); GAAUGACACCAUAGAUGAAG (SEQ ID NO:88); UGAAGAGGAUUCCAUCCAGC (SEQ ID NO:89); and UCCAGCAGGUAGCAGAGUUU (SEQ ID NO:90). In some of any embodiments, the gRNA has a targeting domain sequence of CACCUUCACUCUCAGGAACA (SEQ ID NO:87). In some of any embodiments, the gRNA has a targeting domain sequence of UGAAGAGGAUUCCAUCCAGC (SEQ ID NO:89)

In some of any embodiments, the T cell is a primary T cell derived from a subject. In some of any embodiments, the subject is a human. In some of any embodiments, the T cell is a CD8+ T cell or subtypes thereof. In some of any embodiments, the T cell is a CD4+ T cell or subtypes thereof. In some of any embodiments, the T cell is derived from a multipotent or pluripotent cell. In some of any embodiments, the multipotent or pluripotent cell is an iPSC. In some of any embodiments, the T cell is derived from a multipotent or pluripotent cell, which is an iPSC.

In some of any embodiments, the polynucleotide is comprised in a viral vector. In some of any embodiments, the viral vector is an AAV vector. In some of any embodiments, the AAV vector is selected from among AAV1, AAV2, AAV3, AAV4, AAV5, AAV6, AAV7 or AAV8 vector. In some of any embodiments, the AAV vector is an AAV2 or AAV6 vector. In some of any embodiments, the viral vector is a retroviral vector. In some of any embodiments, a lentiviral vector.

In some of any embodiments, the polynucleotide is a linear polynucleotide. In some of any embodiments, the linear polynucleotide is a double-stranded polynucleotide or a single-stranded polynucleotide.

In some of any embodiments, the one or more agent(s) and the polynucleotide are introduced simultaneously or sequentially, in any order. In some of any embodiments, the polynucleotide is introduced after the introduction of the one or more agent(s).

In some of any embodiments, the polynucleotide is introduced immediately after, or within about 30 seconds, 1 minute, 2 minutes, 3 minutes, 4 minutes, 5 minutes, 6 minutes, 6 minutes, 8 minutes, 9 minutes, 10 minutes, 15 minutes, 20 minutes, 30 minutes, 40 minutes, 50 minutes, 60 minutes, 90 minutes, 2 hours, 3 hours or 4 hours after the introduction of the agent.

In some of any embodiments, prior to the introducing of the one or more agent, the method comprises incubating the cells, in vitro with a stimulatory agent(s) under conditions to stimulate or activate the one or more immune cells. In some of any embodiments, the stimulatory agent(s) comprises and anti-CD3 and/or anti-CD28 antibodies, such as anti-CD3/anti-CD28 beads. In some of any embodiments, the bead to cell ratio is or is about 1:1.

In some of any embodiments, the methods also include removing the stimulatory agent(s) from the one or more immune cells prior to the introducing with the one or more agents.

In some of any embodiments, the method also includes incubating the cells prior to, during or subsequent to the introducing of the one or more agents and/or the introducing of the polynucleotide with one or more recombinant cytokines. In some of any embodiments, the one or more recombinant cytokines are selected from the group consisting of IL-2, IL-7, and IL-15. In some of any embodiments, the one or more recombinant cytokine is added at a concentration selected from a concentration of IL-2 from at or about 10 U/mL to at or about 200 U/mL, such as at or about 50 IU/mL to at or about 100 U/mL; IL-7 at a concentration of 0.5 ng/mL to 50 ng/mL, such as at or about 5 ng/mL to at or about 10 ng/mL and/or IL-15 at a concentration of 0.1 ng/mL to 20 ng/mL, such as at or about 0.5 ng/mL to at or about 5 ng/mL.

In some of any embodiments, the incubation is carried out subsequent to the introducing of the one or more agents and the introducing of the polynucleotide for up to or approximately 24 hours, 36 hours, 48 hours, 3, 4, 5, 6, 7, 8, 9, 10, 11, 12, 13, 14, 15, 16, 17, 18, 19, 20 or 21 days, such as up to or about 7 days.

In some of any embodiments, at least or greater than 35%, 40%, 45%, 50%, 55%, 60%, 65%, 70%, 75%, 80%, or 90% of the cells, such as T cells, in a plurality of engineered cells generated by the method comprise a genetic disruption of at least one target site within a CD247 locus. In some of any embodiments, at least or greater than 35%, 40%, 45%, 50%, 55%, 60%, 65%, 70%, 75%, 80%, or 90% of the cells in a plurality of engineered cells, such as T cells, generated by the method express the chimeric receptor or antigen-binding fragment thereof. In some of any embodiments, at least or greater than 35%, 40%, 45%, 50%, 55%, 60%, 65%, 70%, 75%, 80%, or 90% of the cells in a plurality of engineered cells generated by the method express the chimeric receptor or antigen-binding fragment thereof.

In some of any embodiments, at least or greater than 35%, 40%, 45%, 50%, 55%, 60%, 65%, 70%, 75%, 80%, or 90% of the cells in a plurality of engineered cells, such as T cells, generated by the method comprise a genetic disruption of at least one target site within a CD247 locus. In some of any embodiments, at least or greater than 35%, 40%, 45%, 50%, 55%, 60%, 65%, 70%, 75%, 80%, or 90% of the cells in a plurality of engineered cells, such as T cells, generated by the method express the chimeric receptor. In some of any embodiments, at least or greater than 35%, 40%, 45%, 50%, 55%, 60%, 65%, 70%, 75%, 80%, or 90% of the cells in a plurality of engineered cells, such as T cells, generated by the method express the chimeric receptor, in which the chimeric receptor contains an intracellular region containing a CD3zeta (CD3ζ) signaling domain and in which the CD3ζ signaling domain or at least a portion of the CD3ζ signaling domain is encoded by the genomic sequences at the endogenous CD247 locus (the genomic locus encoding CD3ζ) of the engineered cell such as a T cell. In some embodiments, a least a portion of the CD3ζ signaling domain is encoded by the genomic sequences at the endogenous CD247 locus. In some embodiments, the entire or full CD3ζ signaling domain of the intracellular region of the chimeric receptor is encoded by the genomic sequences at the endogenous CD247 locus.

Also provided are engineered T cells or a plurality of engineered T cells generated using any of the methods described herein.

Also provided are compositions that include any of the engineered T cells described herein.

Also provided are compositions that include a plurality of T cells that include any of the engineered T cells described herein. In some of any embodiments, at least or greater than 35%, 40%, 45%, 50%, 55%, 60%, 65%, 70%, 75%, 80%, or 90% of the T cells in the composition comprise a genetic disruption of at least one target site within a CD247 locus. In some of any embodiments, at least or greater than 35%, 40%, 45%, 50%, 55%, 60%, 65%, 70%, 75%, 80%, or 90% of the T cells in the composition express the chimeric receptor. In some of any embodiments, at least or greater than 35%, 40%, 45%, 50%, 55%, 60%, 65%, 70%, 75%, 80%, or 90% of the T cells in the composition express the chimeric receptor, in which the chimeric receptor contains an intracellular region containing a CD3zeta (CD3ζ) signaling domain and in which the CD3ζ signaling domain or at least a portion of the CD3ζ signaling domain is encoded by the genomic sequences at the endogenous CD247 locus (the genomic locus encoding CD3ζ) of the engineered cell such as a T cell. In some embodiments, a least a portion of the CD3ζ signaling domain is encoded by the genomic sequences at the endogenous CD247 locus. In some embodiments, the entire or full CD3ζ signaling domain of the intracellular region of the chimeric receptor is encoded by the genomic sequences at the endogenous CD247 locus.

In some of any embodiments, the composition comprises CD4+ and/or CD8+ T cells. In some of any embodiments, the composition comprises CD4+ and CD8+ T cells and the ratio of CD4+ to CD8+ T cells is from or from about 1:3 to 3:1, such as 1:1.

In some of any embodiments, cells expressing the chimeric receptor make up at least 30%, 40%, 50%, 60%, 70%, 80%, 90%, 91%, 92%, 93%, 94%, 95%, 96%, 97%, 98%, 99%, or more of the total cells in the composition or of the total CD4+ or CD8+ cells in the composition.

Also provided herein are methods of treatment involving administering the engineered cell, plurality of engineered cells or composition of any of the embodiments provided herein to a subject having a disease or disorder.

Also provided herein are uses of any of the engineered cell, plurality of engineered cells or composition described herein for the treatment of a disease or disorder. In provided embodiments, the chimeric receptor expressed by the engineered cell is directed to or targets an antigen associated with or expressed on a cell or tissue of the disease or condition.

Also provided herein are uses of any of the engineered cell, plurality of engineered cells or composition described herein in the manufacture of a medicament for treating a disease or disorder. In provided embodiments, the chimeric receptor expressed by the engineered cell is directed to or targets an antigen associated with or expressed on a cell or tissue of the disease or condition.

Also provided are any of the engineered cell, plurality of engineered cells or compositions from any of the embodiments provided herein for use in the treatment of a disease or disorder. In provided embodiments, the chimeric receptor expressed by the engineered cell is directed to or targets an antigen associated with or expressed on a cell or tissue of the disease or condition.

In some of any embodiments, the disease or disorder is a cancer or a tumor. In some of any embodiments, the cancer or the tumor is a hematologic malignancy. In some of any embodiments, the hematological malignancy is a lymphoma, a leukemia, or a plasma cell malignancy. In some of any embodiments, the cancer is a lymphoma and the lymphoma is Burkitt's lymphoma, non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL). In some of any embodiments, the cancer is a leukemia and the leukemia is chronic lymphocytic leukemia (CLL), plasma cell leukemia or acute lymphocytic leukemia (ALL). In some of any embodiments, the cancer is a plasma cell malignancy and the plasma cell malignancy is multiple myeloma (MM).

In some of any embodiments, the tumor is a solid tumor. In some of any embodiments, the solid tumor is a non-small cell lung cancer (NSCLC) or a head and neck squamous cell carcinoma (HNSCC).

Also provided are kits. In some of any embodiments, the kits include one or more agent(s) capable of inducing a genetic disruption at a target site within a CD247 locus; and the polynucleotide of any of the embodiments provided herein.

Also provided are kits that include one or more agent(s) capable of inducing a genetic disruption at a target site within a CD247 locus; and a polynucleotide comprising a nucleic acid sequence encoding chimeric receptor or a portion thereof, wherein the transgene encoding the chimeric receptor or antigen-binding fragment or chain thereof is targeted for integration at or near the target site via homology directed repair (HDR); and instructions for carrying out the method of any of the embodiments provided herein.

BRIEF DESCRIPTION OF THE DRAWINGS

FIG. 4A), interleukin-2 (IL-2; FIG. 4B) and tumor necrosis factor alpha (TNF-α; FIG. 4C) using a multiplex cytokine immunoassay, after incubation of the CAR-expressing T cells engineered using AAV constructs containing one of four polynucleotides (Polynucleotides A, B, C, D; described in Table E1) and RPMI 8226 or K562 target cells at E:T ratios of 2:1, 1:1 and 1:2 E:T as described in Example 3. Mock electroporated and transduced cells (mock) and target cells cultured without CAR+ cells (target only) were assessed as controls.

FIG. 8A), interleukin-2 (IL-2; FIG. 8B) and tumor necrosis factor alpha (TNF-α; FIG. 8C), after incubation of the CAR-expressing T cells engineered using AAV constructs containing one of four polynucleotides (Polynucleotides A, B, C, D; described in Table E1) and MM.1S target cells at E:T ratios of 2:1 and 1:2 as described in Example 4. T cells engineered to express the anti-BCMA CAR by lentiviral delivery (LV), T cells subject to mock transduction and electroporation with CD247-targeting RNP only (KO) and mock electroporated and transduced cells (mock) were also assessed as controls.

DETAILED DESCRIPTION

Figure 1:
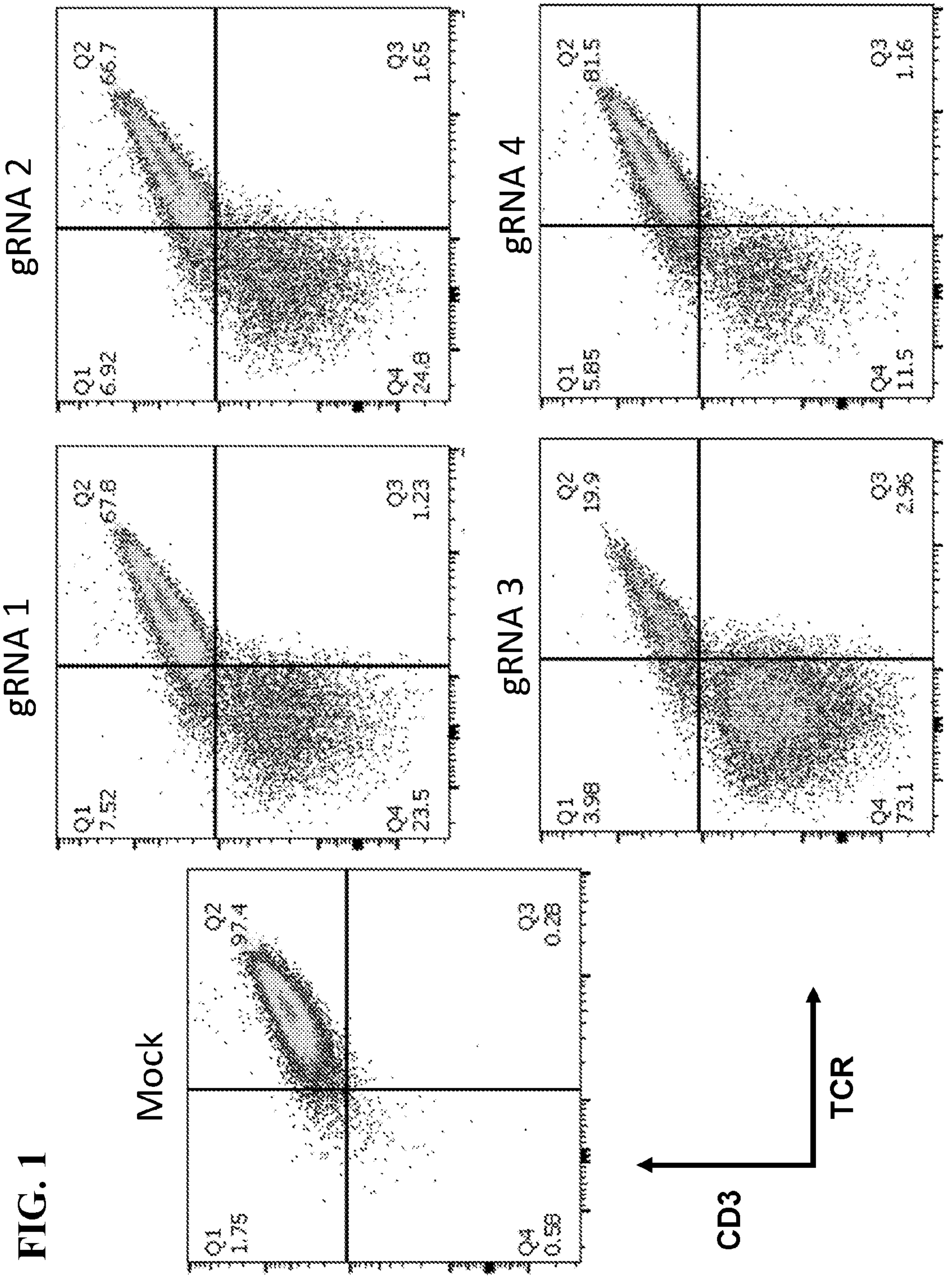
FIG. 1 depicts surface expression of CD3 and TCR, as assessed by flow cytometry, in T cells that were electroporated with ribonucleoprotein (RNP) complexes containing one of four CD247-targeting gRNAs (gRNA 1, 2, 3, 4), for introducing a genetic disruption at the endogenous CD247 locus by CRISPR/Cas9-mediated gene editing, or T cells subject to a mock electroporation that did not contain a gRNA (mock) as control.

Provided herein are genetically engineered cells such as T cells, having a modified CD247 locus that includes one or more transgene sequence (hereinafter also referred to interchangeably as "donor" sequence, for example, sequences that are exogenous or heterologous to the T cell) encoding a chimeric or a recombinant receptor, such as a chimeric antigen receptor (CAR) or a portion thereof. In some aspects, the cells are engineered to express a chimeric receptor that contains a CD3zeta (CD3ζ) chain or a fragment thereof, typically present at the C-terminus of the chimeric receptor. In some embodiments, at least a portion of the CD3ζ chain or fragment is encoded by the genomic sequences at the endogenous CD247 locus (the genomic locus encoding CD3ζ) or a partial sequence thereof, of the engineered cell such as a T cell. In some aspects, the integration of the transgene sequence into the endogenous CD247 locus, e.g., by homology-directed repair (HDR), is carried out such that nucleic acid sequences encoding a portion of the chimeric receptor is fused, e.g., fused in-frame, with an open reading frame or a partial sequence thereof, such as an exon of the open reading frame, of the endogenous CD247 locus.

Also provided are methods for producing genetically engineered cells containing a modified CD247 locus expressing a chimeric or a recombinant receptor or a portion thereof. The provided embodiments involve specifically targeting transgene sequences encoding the chimeric receptor (e.g., CAR) or a portion thereof to the endogenous CD247 locus. In some contexts, the provided embodiments involve inducing a targeted genetic disruption, e.g., generation of a DNA break, for example, using gene editing methods, and HDR for targeted integration of the chimeric receptor-encoding transgene sequences at the endogenous CD247 locus. Also provided are related cell compositions, nucleic acids and kits for use in generation of the engineered cells provided herein and/or the methods provided herein.

In some embodiments, the transgene sequence encoding a portion of the chimeric or the recombinant receptor, e.g., CAR, contains a sequence of nucleotides encoding one or more domains or regions of the chimeric receptor, for example, an extracellular region, a transmembrane domain, and an intracellular region. In some aspects, the extracellular region contains a binding domain (e.g. antigen- or ligand-binding domain) that provides specificity for a desired antigen (e.g., tumor antigen) or ligand, and/or a spacer to link the extracellular binding domain with a transmembrane domain and the intracellular region. In some aspects, the intracellular region encoded by the transgene sequence comprises one or more co-stimulatory domain and/or other domains. In some embodiments, the intracellular region encoded by the transgene sequences (i.e., introduced sequence that is exogenous to the cell) comprises less than a full length of the CD3ζ chain, or does not comprise a sequence encoding the CD3ζ chain. Upon integration of the transgene sequence into the endogenous CD247 locus, the resulting modified CD247 locus encodes a chimeric receptor, encoded by a fusion of: the transgene sequences targeted by HDR; and an open reading frame or a partial sequence thereof of an endogenous CD247 locus. The encoded chimeric receptor contains an intracellular region comprising a CD3ζ chain or a fragment thereof, e.g., a functional CD3ζ chain or a fragment thereof that is capable of mediating, activating or stimulating primary cytoplasmic or intracellular signal in a T cell. The resulting genetically engineered cells or cell compositions can be used in adoptive cell therapy methods.

T cell-based therapies, such as adoptive T cell therapies (including those involving the administration of engineered cells expressing recombinant, engineered or chimeric receptors specific for a disease or disorder of interest, such as a chimeric antigen receptor (CAR) or other recombinant, engineered or chimeric receptors) can be effective in the treatment of cancer and other diseases and disorders. In certain contexts, other approaches for generating engineered cells for adoptive cell therapy may not always be entirely satisfactory. In some contexts, optimal efficacy can depend on the ability of the administered cells to express the chimeric receptor, including with uniform, homogenous and/or consistent expression of the receptors among cells, such as a population of immune cells and/or cells in a therapeutic cell composition, and for the chimeric receptor to recognize and bind to a target, e.g., target antigen, within the subject, tumors, and environments thereof.

In some cases, available methods for introducing a chimeric receptor, such as a CAR, into a cell, include random integration of sequences encoding the chimeric receptor, such as by viral transduction. In certain respects, such methods are not entirely satisfactory. In some aspects, random integration can result in possible insertional mutagenesis and/or genetic disruption of one more random genetic loci in the cell, including those that may be important for cell function and activity. In some aspects, the efficiency of the expression of the chimeric receptor is limited among certain cells or certain cell populations that are engineered using currently available methods. In some cases, the chimeric receptor is only expressed in certain cells among a population of cells, and the level of expression of the chimeric receptor can vary widely among cells in the population. In particular aspects, the level of expression of the chimeric receptor may be difficult to predict, control and/or regulate. In some cases, semi-random or random integration of a transgene encoding the receptor into the genome of the cell may, in some cases, result in adverse and/or unwanted effects due to integration of the nucleic acid sequence into an undesired location in the genome, e.g., into an essential gene or a gene critical in regulating the activity of the cell.

In some cases, random integration may result in variable integration of the sequences encoding the recombinant or chimeric receptor, which can result in inconsistent expression, variable copy number of the nucleic acids, and/or variability of receptor expression within cells of the cell composition, such as a therapeutic cell composition. In some cases, random integration of a nucleic acid sequence encoding the receptor can result in variegated, heterogeneous, non-uniform and/or suboptimal expression or antigen binding, oncogenic transformation and transcriptional silencing of the nucleic acid sequence, depending on the site of integration and/or nucleic acid sequence copy number. In some aspects, heterogeneous and non-uniform expression in a cell population can lead to inconsistencies or instability of expression and/or antigen binding by the recombinant or chimeric receptor, unpredictability of the function or reduction in function of the engineered cells and/or a non-uniform drug product, thereby reducing the efficacy of the engineered cells. In some aspects, use of particular random integration vectors, such as certain lentiviral vectors, requires confirmation that the engineered cells do not contain replication competent virus, such as by performance of replication competent lentivirus (RCL) assay. Improved strategies are needed to achieve consistent expression levels and function of the recombinant or chimeric receptors while minimizing random integration of nucleic acids and/or heterogeneous expression in a population.

In some aspects, the size of the payload (such as transgene sequences or heterologous sequences to be inserted) in a particular polynucleotide or vector used to deliver the nucleic acid sequences encoding the chimeric receptor can be limiting. In some cases, the limited size may impact expression and/or efficiency of introduction and expression in a cell.

The provided embodiments relate to engineering a cell to have nucleic acids encoding a chimeric receptor to be integrated into the endogenous CD247 locus of a cell, e.g., T cell, by homology-directed repair (HDR). In some aspects, HDR can mediate the site specific integration of transgene sequences (such as transgene sequences encoding a recombinant receptor or a chimeric receptor or a portion, a chain or a fragment thereof), at or near a target site for genetic disruption, such as an endogenous CD247 locus. In some embodiments, the presence of a genetic disruption (for example, at a target site at the endogenous CD247 locus) and a polynucleotide, e.g., a template polynucleotide containing one or more homology arms (e.g., containing nucleic acid sequences that are homologous to sequences surrounding the genetic disruption) can induce or direct HDR, with homologous sequences acting as a template for DNA repair. Based on homology between the endogenous gene sequence surrounding the genetic disruption and the homology arms included in the polynucleotide, e.g., a template polynucleotide, cellular DNA repair machinery can use the polynucleotide, e.g., a template polynucleotide to repair the DNA break and resynthesize genetic information at the target site of the genetic disruption, thereby effectively inserting or integrating the sequences between the homology arms (such as transgene sequences encoding a chimeric receptor or a portion thereof) at or near the target site of the genetic disruption. The provided embodiments can generate cells containing a modified CD247 locus encoding a chimeric receptor or a portion thereof, where transgene sequences encoding a chimeric receptor or a portion thereof is integrated into the endogenous CD247 locus by HDR.

In some aspects, the provided embodiments offer advantages in producing engineered cells with improved and/or more efficient targeting of the nucleic acids encoding the chimeric or recombinant receptor into the cell. In some cases, the methods minimize possible semi-random or random integration and/or heterogeneous or variegated expression and/or undesired expression from unintegrated nucleic acid sequences, and result in improved, uniform, homogeneous, consistent, predictable or stable expression of the chimeric or recombinant receptor or having reduced, low or no possibility of insertional mutagenesis. In some aspects, compared to other methods of producing genetically engineered immune cells expressing a chimeric or recombinant receptor, e.g., CAR, the provided embodiments allow for a more stable, more physiological, more controllable or more uniform, consistent or homogeneous expression of the chimeric or recombinant receptor. In some cases, the methods result in the generation of more consistent and more predictable drug product, e.g. cell composition containing the engineered cells, which can result in a safer therapy for treated patients. In some aspects, the provided embodiments also allow predictable and consistent integration at a single gene locus or a multiple gene loci of interest. In some embodiments, the provided embodiments can also result in generating a cell population with consistent copy number (typically, 1 or 2) of the nucleic acids that are integrated in the cells of the population, which, in some aspects, provide consistency in chimeric or recombinant receptor expression and expression of the endogenous receptor genes within a cell population. In some cases, the provided embodiments do not involve the use of a viral vector for integration and thus can reduce the need for confirmation that the engineered cells do not contain replication competent virus, thereby improving the safety of the cell composition.

The chimeric receptors encoded from the modified CD247 locus in engineered cells provided herein can be encoded under the control of endogenous or exogenous regulatory elements. In some aspects, the provided embodiments allow the chimeric receptor to be expressed under the control of the endogenous CD247 regulatory elements, which, in some cases, can provide a more physiological level of expression. In some aspects, the provided embodiments allow the nucleic acids encoding the chimeric receptor to be expressed under the control of the endogenous regulatory or control elements, e.g., cis regulatory elements, such as the promoter, or the 5' and/or 3' untranslated regions (UTRs) of the endogenous CD247 locus. Thus, in some aspects, the provided embodiments allow the chimeric receptor, e.g., CAR, or a portion thereof, to be expressed and/or the expression is regulated at a similar level to the endogenous CD3ζ chain.

In some aspects, the provided embodiments can reduce or minimize antigen-independent signaling or activity (also known as "tonic signaling") through the chimeric receptor. In some cases, antigen-independent signaling can result from overexpression or uncontrolled activity of the expressed chimeric receptor, and can lead to undesirable effects, such as increased differentiation and/or exhaustion of T cells that express the chimeric receptor. In some embodiments, the provided engineered cells and cell compositions can reduce the effect of antigen-independent signaling by that may result from overexpression or uncontrolled activity of the expressed chimeric receptor. Thus, the provided embodiments can facilitate the production of engineered cells that exhibit improved expression, function and uniformity of expression and/or other desired feature or properties, and ultimately higher efficacy. In some embodiments, the provided polynucleotides, transgenes, and/or vectors, when delivered into immune cells, result in the expression of chimeric receptors, e.g., CARs, that can modulate T cell activity, and, in some cases, can modulate T cell differentiation or homeostasis.

In some aspects, the provided embodiments allow the chimeric receptor to be expressed under the control of exogenous or heterologous regulatory or control elements, which, in some aspects, provides a more controllable level of expression. In some aspects, the provided embodiments allow targeted and controlled expression of the chimeric receptor in various cell types, including cells in which the endogenous promoter at the endogenous CD247 locus, may not be active, such as cells that do not typically express the CD3ζ chain, e.g., a non-T cell, such as NK cells, B cells or certain induced pluripotent stem cell (iPSC)-derived cells.

In some aspects, the provided embodiments can prevent uncontrolled expression or expression from randomly integrated or unintegrated polynucleotides. In some embodiments, the introduced polynucleotide, e.g., template polynucleotide, do not contain the nucleic acid sequences encoding the full length functional receptor. In some cases, a portion of the CD3ζ chain, is not encoded by the introduced polynucleotide. In some aspects, transcription from randomly integrated or unintegrated polynucleotides would not produce a functional receptor. In some aspects, only upon integration at the target locus, e.g., the endogenous CD247 locus, a functional receptor containing all of required signaling region, can be generated. In some aspects, the provided embodiments can result in improved safety of the cell composition, for example, by preventing uncontrolled expression, e.g. from randomly integrated or unintegrated polynucleotides, such as unintegrated viral vector sequences.

In some aspects, the provided embodiments can also result in reduction and/or elimination of expression (e.g., knock-out) of the extracellular portion CD3ζ to reduce immunogenicity of the administered cells, for example, for application in allogeneic adoptive cell therapy.

The provided embodiments can also reduce the length of transgene sequences required to deliver the recombinant CAR to cells, e.g., to allow for sufficient space to package additional elements and/or transgenes within the same vector, e.g., viral vector. In some aspects, the provided embodiments also permit the use of a smaller nucleic acid sequence fragments for engineering compared to existing methods, by utilizing a portion or all of the open reading frame sequences of the endogenous gene encoding the CD3ζ chain, to encode all or a portion of the CD3ζ chain of the CAR. In some aspects, the provided embodiments provide flexibility for engineering cells to express a CAR compared to existing methods, because the methods utilize a portion or all of the open reading frame sequences of the endogenous gene encoding CD3ζ, CD247, to encode the CD3ζ or a portion thereof of the chimeric receptor. In some cases, this can reduce the payload space for sequences encoding the chimeric receptor or a portion thereof and leave space for sequences encoding other components, such as other transgene sequences, homology arms, regulatory elements, since the length requirement for nucleic acid sequences encoding the chimeric receptor or a portion thereof is reduced. In some aspects, the provided embodiments may allow accommodation of larger homology arms compared to conventional embodiments that require the entire length of the chimeric receptor, e.g., CAR, in the introduced polynucleotide, and/or allow accommodation of nucleic acid sequences encoding additional molecules, as the length requirement for nucleic acid sequences encoding a portion of the chimeric receptor, e.g., CAR, is reduced. In some aspects, generation, delivery of the nucleic acid sequences, e.g., transgene sequences, and/or targeting efficiency by homology-directed repair (HDR), may be facilitated or improved using the provided embodiments. In other aspects, the provided embodiments allow accommodation of nucleic acid sequences encoding additional molecules for expression on or in the cell.

Also provided are methods for engineering, preparing, and producing the engineered cells, and kits and devices for generating or producing the engineered cells. Also provided are cells and cell compositions generated by the methods. Provided are polynucleotides, e.g., viral vectors, that contain a nucleic acid sequence encoding a portion of the chimeric receptor, and methods for introducing such polynucleotides into the cells, such as by transduction or by physical delivery, such as electroporation. Also provided are compositions containing the engineered cells, and methods, kits, and devices for administering the cells and compositions to subjects, such as for adoptive cell therapy. In some aspects, the cells are isolated from a subject, engineered, and administered to the same subject. In other aspects, they are isolated from one subject, engineered, and administered to another subject. The resulting genetically engineered cells or cell compositions can be used in adoptive cell therapy methods.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Method for Generating Cells Expressing a Chimeric Receptor by Homology-Directed Repair Provided herein are methods of generating or producing genetically engineered cells comprising a modified CD247 locus in which the modified CD247 locus includes nucleic acid sequences encoding a chimeric or a recombinant receptor, such as a chimeric antigen receptor (CAR). In some aspects, the modified CD247 locus in the genetically engineered cell comprises a transgene sequence encoding a chimeric receptor or a portion of a chimeric receptor, integrated into an endogenous CD247 locus, which normally encodes a CD3zeta (CD3ζ) chain. In some embodiments, the methods involve inducing a targeted genetic disruption and homology-dependent repair (HDR), using polynucleotides (for example, also called "template polynucleotides") containing the transgene encoding a chimeric or a recombinant receptor or a portion of the chimeric receptor, thereby targeting integration of the transgene at the CD247 locus. Also provided are cells and cell compositions generated by the methods. In some embodiments, also provided are compositions containing a population of cells that have been engineered to express a chimeric receptor, e.g., a CAR, such that the cell population that exhibits more improved, uniform, homogeneous and/or stable expression and/or antigen binding by the chimeric receptor, including genetically engineered immune cells produced by any of the provided methods, and polynucleotides, e.g., template polynucleotides, and kits for use in the methods.

In some aspects, the expressed chimeric receptor comprises an intracellular region that contains a CD3zeta (CD3ζ) chain or a fragment thereof, such as a signaling region or signaling domain of CD3. In some embodiments, the encoded CD3ζ chain or a fragment thereof is a functional CD3ζ chain or a fragment thereof, such as the cytoplasmic signaling domain or region. In some embodiments, the CD3ζ chain or a fragment thereof is at the C-terminus of the receptor. In some aspects, after integration of the transgene sequences encoding a portion of the chimeric receptor into the CD247 locus, at least a portion of the CD3ζ chain is encoded by an open reading frame or partial sequence thereof of the CD247 locus in the genome. In some aspects, the chimeric receptor is encoded by exogenous nucleic acid sequences fused with an open reading frame or a partial sequence thereof of the endogenous CD247 locus.

In some embodiments, the methods employ HDR for targeted integration of the transgene sequences into the CD247 locus. In some cases, the methods involve introducing one or more targeted genetic disruption(s), e.g., DNA break, at the endogenous CD247 locus by gene editing techniques, combined with targeted integration of transgene sequences encoding a chimeric receptor or a portion of the chimeric receptor by HDR. In some embodiments, the HDR step entails a disruption or a break, e.g., a double-stranded break, in the DNA at the target genomic location. In some embodiments, the DNA break is induced by employing gene editing methods, e.g., targeted nucleases.

In some aspects, the provided methods involve introducing one or more agent(s) capable of inducing a genetic disruption of at a target site within a CD247 locus into a T cell; and introducing into the T cell a polynucleotide, e.g., a template polynucleotide, comprising a transgene and one or more homology arms. In some aspects, the transgene contains a sequence of nucleotides encoding a chimeric receptor or a portion thereof. In some embodiments, the nucleic acid sequence, such as the transgene, is targeted for integration within the CD247 locus via homology directed repair (HDR). In some aspects, the provided methods involve introducing a polynucleotide comprising a transgene sequence encoding a chimeric receptor or a portion thereof comprising into a T cell having a genetic disruption of within a CD247 locus, wherein the genetic disruption has been induced by one or more agents capable of inducing a genetic disruption of one or more target site within the CD247 locus, and wherein the nucleic acid sequence, such as the transgene, is targeted for integration within the CD247 locus via HDR.

In some aspects, the embodiments involve generating a targeted genomic disruption, such as a targeted DNA break, using gene editing methods and/or targeted nucleases, followed by HDR based on one or more polynucleotide(s), e.g., template polynucleotide(s) that contains homology sequences that are homologous to sequences at the endogenous CD247 locus linked to transgene sequences encoding a portion of the chimeric receptor and, in some embodiments, nucleic acid sequences encoding other molecules, to specifically target and integrate the transgene sequences at or near the DNA break. Thus, in some aspects, the methods involve a step of inducing a targeted genetic disruption (e.g., via gene editing) and introducing a polynucleotide, e.g., a template polynucleotide comprising transgene sequences, into the cell (e.g., via HDR).

In some embodiments, the targeted genetic disruption and targeted integration of the transgene sequences by HDR occurs at one or more target site(s) at the endogenous CD247 locus, which encodes a CD3zeta (CD3ζ) chain. In some aspects, the targeted integration occurs within an open reading frame sequence of the endogenous CD247 locus. In some aspects, targeted integration of the transgene sequences results in an in-frame fusion of the coding portion of the transgene with one or more exons of the open reading frame of the endogenous CD247 locus, e.g., in-frame with the adjacent exon at the integration site.

In some embodiments, a polynucleotide, e.g., template polynucleotide, is introduced into the engineered cell, prior to, simultaneously with, or subsequent to introduction of one or more agent(s) capable of inducing one or more targeted genetic disruption. In the presence of one or more targeted genetic disruption, e.g., DNA break, the polynucleotide can be used as a DNA repair template, to effectively copy and/or integrate the transgene, at or near the site of the targeted genetic disruption by HDR, based on homology between the endogenous gene sequence surrounding the genetic disruption and the one or more homology arms, such as the 5' and/or 3' homology arms, included in the template polynucleotide.

In some aspects, the two steps can be performed sequentially. In some embodiments, the gene editing and HDR steps are performed simultaneously and/or in one experimental reaction. In some embodiments, the gene editing and HDR steps are performed consecutively or sequentially, in one or consecutive experimental reaction(s). In some embodiments, the gene editing and HDR steps are performed in separate experimental reactions, simultaneously or at different times.

The immune cells can include a population of cells containing T cells. Such cells can be cells that have been obtained from a subject, such as obtained from a peripheral blood mononuclear cells (PBMC) sample, an unfractionated T cell sample, a lymphocyte sample, a white blood cell sample, an apheresis product, or a leukapheresis product. In some embodiments, the immune cells, such as the T cells are primary cells, such as primary T cells. In some embodiments, T cells can be separated or selected to enrich T cells in the population using positive or negative selection and enrichment methods. In some embodiments, the population contains CD4+, CD8+ or CD4+ and CD8+ T cells. In some embodiments, the step of introducing the polynucleotide (e.g., template polynucleotide) and the step of introducing the agent (e.g. Cas9/gRNA RNP) can occur simultaneously or sequentially in any order. In some embodiments, the polynucleotide is introduced simultaneously with the introduction of the one or more agents capable of inducing a genetic disruption (e.g. Cas9/gRNA RNP). In particular embodiments, the polynucleotide template is introduced into the immune cells after inducing the genetic disruption by the step of introducing the agent(s) (e.g. Cas9/gRNA RNP). In some embodiments, prior to, during and/or subsequent to introduction of the polynucleotide template and one or more agents (e.g. Cas9/gRNA RNP), the cells are cultured or incubated under conditions to stimulate expansion and/or proliferation of cells.

In particular embodiments of the provided methods, the introduction of the template polynucleotide is performed after the introduction of the one or more agent capable of inducing a genetic disruption. Any method for introducing the one or more agent(s) can be employed as described, depending on the particular agent(s) used for inducing the genetic disruption. In some aspects, the disruption is carried out by gene editing, such as using an RNA-guided nuclease such as a clustered regularly interspersed short palindromic nucleic acid (CRISPR)-Cas system, such as CRISPR-Cas9 system, specific for the CD247 locus being disrupted. In some aspects, the disruption is carried out using a CRISPR-Cas9 system specific for the CD247 locus. In some embodiments, an agent containing a Cas9 and a guide RNA (gRNA) containing a targeting domain, which targets a region of the CD247 locus, is introduced into the cell. In some embodiments, the agent is or comprises a ribonucleoprotein (RNP) complex of Cas9 and gRNA containing the CD247-targeted targeting domain (Cas9/gRNA RNP). In some embodiment, the introduction includes contacting the agent or portion thereof with the cells, in vitro, which can include cultivating or incubating the cell and agent for up to 24, 36 or 48 hours or 3, 4, 5, 6, 7, or 8 days. In some embodiments, the introduction further can include effecting delivery of the agent into the cells. In various embodiments, the methods, compositions and cells according to the present disclosure utilize direct delivery of ribonucleoprotein (RNP) complexes of Cas9 and gRNA to cells, for example by electroporation. In some embodiments, the RNP complexes include a gRNA that has been modified to include a 3' poly-A tail and a 5' Anti-Reverse Cap Analog (ARCA) cap. In some cases, electroporation of the cells to be modified includes cold-shocking the cells, e.g. at 32° C. following electroporation of the cells and prior to plating.

In such aspects of the provided methods, the polynucleotide, e.g., template polynucleotide, is introduced into the cells after introduction with the one or more agent(s), such as Cas9/gRNA RNP, e.g. that has been introduced via electroporation. In some embodiments, the polynucleotide, e.g., template polynucleotide, is introduced immediately after the introduction of the one or more agents capable of inducing a genetic disruption. In some embodiments, the polynucleotide, e.g., template polynucleotide, is introduced into the cells within at or about 30 seconds, within at or about 1 minute, within at or about 2 minutes, within at or about 3 minutes, within at or about 4 minutes, within at or about 5 minutes, within at or about 6 minutes, within at or about 6 minutes, within at or about 8 minutes, within at or about 9 minutes, within at or about 10 minutes, within at or about 15 minutes, within at or about 20 minutes, within at or about 30 minutes, within at or about 40 minutes, within at or about 50 minutes, within at or about 60 minutes, within at or about 90 minutes, within at or about 2 hours, within at or about 3 hours or within at or about 4 hours after the introduction of one or more agents capable of inducing a genetic disruption. In some embodiments, the polynucleotide, e.g., template polynucleotide, is introduced into cells at time between at or about 15 minutes and at or about 4 hours after introducing the one or more agent(s), such as between at or about 15 minutes and at or about 3 hours, between at or about 15 minutes and at or about 2 hours, between at or about 15 minutes and at or about 1 hour, between at or about 15 minutes and at or about 30 minutes, between at or about 30 minutes and at or about 4 hours, between at or about 30 minutes and at or about 3 hours, between at or about 30 minutes and at or about 2 hours, between at or about 30 minutes and at or about 1 hour, between at or about 1 hour and at or about 4 hours, between at or about 1 hour and at or about 3 hours, between at or about 1 hour and at or about 2 hours, between at or about 2 hours and at or about 4 hours, between at or about 2 hours and at or about 3 hours or between at or about 3 hours and at or about 4 hours. In some embodiments, the polynucleotide, e.g., template polynucleotide, is introduced into cells at or about 2 hours after the introduction of the one or more agents, such as Cas9/gRNA RNP, e.g. that has been introduced via electroporation.

Any method for introducing the polynucleotide, e.g., template polynucleotide, can be employed as described, depending on the particular methods used for delivery of the polynucleotide, e.g., template polynucleotide, to cells. Exemplary methods include those for transfer of nucleic acids encoding the receptors, including via viral, e.g., retroviral or lentiviral, transduction, transposons, and electroporation. In particular embodiments, viral transduction methods are employed. In some embodiments, the polynucleotides can be transferred or introduced into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557. In particular embodiments, the viral vector is an AAV such as an AAV2 or an AAV6.

In some embodiments, prior to, during or subsequent to contacting the agent with the cells and/or prior to, during or subsequent to effecting delivery (e.g. electroporation), the provided methods include incubating the cells in the presence of a cytokine, a stimulating agent and/or an agent that is capable of inducing proliferation, stimulation or activation of the immune cells (e.g. T cells). In some embodiments, at least a portion of the incubation is in the presence of a stimulating agent that is or comprises an antibody specific for CD3 an antibody specific for CD28 and/or a cytokine, such as anti-CD3/anti-CD28 beads. In some embodiments, at least a portion of the incubation is in the presence of a cytokine, such as one or more of recombinant IL-2, recombinant IL-7 and/or recombinant IL-15. In some embodiments, the incubation is for up to 8 days before or after the introduction with the one or more agent(s), such as Cas9/gRNA RNP, e.g. via electroporation, and the polynucleotide, e.g. template polynucleotide, such as up to 24 hours, 36 hours or 48 hours or 3, 4, 5, 6, 7 or 8 days.

In some embodiments, the method includes activating or stimulating cells with a stimulating agent (e.g. anti-CD3/anti-CD28 antibodies) prior to introducing the agent, e.g. Cas9/gRNA RNP, and the polynucleotide template. In some embodiments, the incubation in the presence of a stimulating agent (e.g. anti-CD3/anti-CD28) is for 6 hours to 96 hours, such as 24 to 48 hours or 24 to 36 hours prior to the introduction with the one or more agent(s), such as Cas9/gRNA RNP, e.g. via electroporation. In some embodiments, the incubation with the stimulating agents can further include the presence of a cytokine, such as one or more of recombinant IL-2, recombinant IL-7 and/or recombinant IL-15. In some embodiments, the incubation is carried out in the presence of a recombinant cytokine, such as IL-2 (e.g. 1 U/mL to 500 U/mL, such as 10 U/mL to 200 U/mL, for example at least or about 50 U/mL or 100 U/mL), IL-7 (e.g. 0.5 ng/mL to 50 ng/mL, such as 1 ng/mL to 20 ng/mL, for example, at least or about 5 ng/mL or 10 ng/mL) or IL-15 (e.g. 0.1 ng/mL to 50 ng/mL, such as 0.5 ng/mL to 25 ng/mL, for example, at least or about 1 ng/mL or 5 ng/mL). In some embodiments the stimulating agent(s) (e.g. anti-CD3/anti-CD28 antibodies) is washed or removed from the cells prior to introducing or delivering into the cells the agent(s) capable of inducing a genetic disruption Cas9/gRNA RNP and/or the polynucleotide template. In some embodiments, prior to the introducing of the agent(s), the cells are rested, e.g. by removal of any stimulating or activating agent. In some embodiments, prior to introducing the agent(s), the stimulating or activating agent and/or cytokines are not removed.

In some embodiments, subsequent to the introduction of the agent(s), e.g. Cas9/gRNA, and/or the polynucleotide template the cells are incubated, cultivated or cultured in the presence of a recombinant cytokine, such as one or more of recombinant IL-2, recombinant IL-7 and/or recombinant IL-15. In some embodiments, the incubation is carried out in the presence of a recombinant cytokine, such as IL-2 (e.g. 1 U/mL to 500 U/mL, such as 10 U/mL to 200 U/mL, for example at least or about 50 U/mL or 100 U/mL), IL-7 (e.g. 0.5 ng/mL to 50 ng/mL, such as 1 ng/mL to 20 ng/mL, for example, at least or about 5 ng/mL or 10 ng/mL) or IL-15 (e.g. 0.1 ng/mL to 50 ng/mL, such as 0.5 ng/mL to 25 ng/mL, for example, at least or about 1 ng/mL or 5 ng/mL). The cells can be incubated or cultivated under conditions to induce proliferation or expansion of the cells. In some embodiments, the cells can be incubated or cultivated until a threshold number of cells is achieved for harvest, e.g. a therapeutically effective dose.

In some embodiments, the incubation during any portion of the process or all of the process can be at a temperature of 30° C.±2° C. to 39° C.±2° C., such as at least or about at least 30° C.±2° C., 32° C.±2° C., 34° C.±2° C. or 37° C.±2° C. In some embodiments, at least a portion of the incubation is at 30° C.±2° C. and at least a portion of the incubation is at 37° C.±2° C.

In some embodiments, upon targeted integration, the nucleic acid sequence present at the modified CD247 locus comprises a fusion of a transgene (e.g. a portion of a chimeric receptor, such as a CAR, as described herein), targeted by HDR, with an open reading frame or a partial sequence thereof of an endogenous CD247 locus. In some aspects, the nucleic acid sequence present at the modified CD247 locus comprises a transgene, e.g. a portion of a chimeric receptor, such as a CAR, as described herein, that is integrated at an endogenous CD247 locus comprising an open reading frame encoding a CD3 chain. In some aspects, upon targeted integration or fusion, e.g., in-frame fusion, a portion of the exogenous sequence of the transgene and a portion of the open reading frame at the endogenous CD247 locus together encodes a chimeric receptor, e.g. CAR, containing a CD3ζ signaling domain or a fragment thereof. Thus, the provided embodiments utilize a portion or all of the open reading frame sequences of the endogenous CD247 locus to encode the CD3ζ signaling domain or a portion thereof of the chimeric receptor. In some embodiments, upon targeted, in-frame integration of the transgene sequence, the modified CD247 locus contains a sequence encoding a whole, complete or full-length chimeric receptor, e.g. CAR, containing a CD3ζ signaling domain.

Exemplary methods for carrying out genetic disruption at the endogenous CD247 locus and/or for carrying out HDR for targeted integration of the transgene sequences, such as a portion of a chimeric receptor, e.g. a portion of a CAR, into the CD247 locus are described in the following subsections.

A. Genetic Disruption

In some embodiments, one or more targeted genetic disruption is induced at the endogenous CD247 locus. In some embodiments, one or more targeted genetic disruption is induced at one or more target sites at or near the endogenous CD247 locus. In some embodiments, the targeted genetic disruption is induced in an intron of the endogenous CD247 locus. In some embodiments, the targeted genetic disruption is induced in an exon of the endogenous CD247 locus. In some aspects, the presence of the one or more targeted genetic disruption and a polynucleotide, e.g., a template polynucleotide that contains transgene sequences encoding a chimeric receptor or a portion thereof, can result in targeted integration of the transgene sequences at or near the one or more genetic disruption (e.g., target site) at the endogenous CD247 locus.

In some embodiments, genetic disruption results in a DNA break, such as a double-strand break (DSB) or a cleavage, or a nick, such as a single-strand break (SSB), at one or more target site in the genome. In some embodiments, at the site of the genetic disruption, e.g., DNA break or nick, action of cellular DNA repair mechanisms can result in knock-out, insertion, missense or frameshift mutation, such as a biallelic frameshift mutation, deletion of all or part of the gene; or, in the presence of a repair template, e.g., a template polynucleotide, can alter the DNA sequence based on the repair template, such as integration or insertion of the nucleic acid sequences, such as a transgene encoding all or a portion of a recombinant receptor, contained in the template. In some embodiments, the genetic disruption can be targeted to one or more exon of a gene or portion thereof. In some embodiments, the genetic disruption can be targeted near a desired site of targeted integration of exogenous sequences, e.g., transgene sequences encoding a chimeric receptor.

In some embodiments, a DNA binding protein or DNA-binding nucleic acid, which specifically binds to or hybridizes to the sequences at a region near one of the at least one target site(s), is used for targeted disruption. In some embodiments, template polynucleotides, e.g., template polynucleotides that include nucleic acid sequences, such as a transgene encoding a portion of a chimeric receptor, and homology sequences, can be introduced for targeted integration by HDR of the chimeric receptor-encoding sequences at or near the site of the genetic disruption, such as described herein, for example, in Section I.B.

In some embodiments, the genetic disruption is carried by introducing one or more agent(s) capable of inducing a genetic disruption. In some embodiments, such agents comprise a DNA binding protein or DNA-binding nucleic acid that specifically binds to or hybridizes to the gene. In some embodiments, the agent comprises various components, such as a fusion protein comprising a DNA-targeting protein and a nuclease or an RNA-guided nuclease. In some embodiments, the agents can target one or more target sites or target locations. In some aspects, a pair of single stranded breaks (e.g., nicks) on each side of the target site can be generated.

In provided embodiments, the term "introducing" encompasses a variety of methods of introducing a nucleic acid and/or a protein, such as DNA into a cell, either in vitro or in vivo, such methods including transformation, transduction, transfection (e.g. electroporation), and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors. Methods, such as electroporation, also can be used to introduce or deliver proteins or ribonucleoprotein (RNP), e.g. containing the Cas9 protein in complex with a targeting gRNA, to cells of interest.

In some embodiments, the genetic disruption occurs at a target site (also known as "target position," "target DNA sequence" or "target location"), for example, at the endogenous CD247 locus. In some embodiments, the target site includes a site on a target DNA (e.g., genomic DNA) that is modified by the one or more agent(s) capable of inducing a genetic disruption, e.g., a Cas9 molecule complexed with a gRNA that specifies the target site. For example, the target site can include locations in the DNA at a endogenous CD247 locus, where cleavage or DNA breaks occur. In some aspects, integration of nucleic acid sequences, such as a transgene encoding a recombinant receptor or a portion thereof, by HDR can occur at or near the target site or target sequence. In some embodiments, a target site can be a site between two nucleotides, e.g., adjacent nucleotides, on the DNA into which one or more nucleotides is added. The target site may comprise one or more nucleotides that are altered by a template polynucleotide. In some embodiments, the target site is within a target sequence (e.g., the sequence to which the gRNA binds). In some embodiments, a target site is upstream or downstream of a target sequence.

1. Target Site at an Endogenous CD247 Locus

In some embodiments, the genetic disruption, and/or integration of the transgene encoding a portion of a chimeric receptor, via homology-directed repair (HDR), are targeted at an endogenous or genomic locus that encodes the T-cell surface glycoprotein CD3-zeta chain (also known as CD3zeta; CD3ζ; T-cell receptor T3 zeta chain; CD3Z; T3Z; TCRZ; cluster of differentiation 247; CD247; IMD25). In humans, CD3ζ is encoded by the cluster of differentiation 247 (CD247) gene. In some embodiments, the genetic disruption, and integration of the transgene encoding a portion of a chimeric receptor, via homology-directed repair (HDR), are targeted at the human CD247 locus. In some aspects, the genetic disruption is targeted at a target site within the CD247 locus containing an open reading frame encoding CD3ζ, such that targeted integration, fusion or insertion of transgene sequences occurs at or near the site of genetic disruption at the CD247 locus. In some aspects, the genetic disruption is targeted at or near an exon of the open reading frame encoding CD3ζ. In some aspects, the genetic disruption is targeted at or near an intron of the open reading frame encoding CD3ζ.

CD3ζ is a part of the TCR-CD3 complex present on the surface of the T cell which is involved in adaptive immune response. CD3, together with T cell receptor (TCR) alpha/beta (TCRαβ) or TCR gamma/delta (TCRγδ) heterodimers, CD3-gamma (CD3γ), CD3-delta (CD3δ) and CD3-epsilon (CD3ε), form the TCR-CD3 complex. The CD3ζ contains immunoreceptor tyrosine-based activation motifs (ITAMs) in its intracellular or cytoplasmic domain. The CD3ζ chain can couple antigen recognition to intracellular signal transduction pathways, by stimulating or activating primary cytoplasmic or intracellular signaling, e.g., via the ITAMs. Upon engagement of the TCR with its ligand (e.g., a peptide in the context of an MHC molecule; MHC-peptide complex), the ITAM motifs can be phosphorylated by kinases including Src family protein tyrosine kinases LCK and FYN, resulting in the stimulation of downstream signaling pathways. In some aspects, the phosphorylation of CD3ζ ITAM creates docking sites for the protein kinase ZAP70, leading to phosphorylation and activation of ZAP70.

Exemplary human CD3ζ precursor polypeptide sequence is set forth in SEQ ID NO:73 (isoform 1; mature polypeptide includes residues 22-164 of SEQ ID NO:73; see Uniprot Accession No. P20963; NCBI Reference Sequence: NP_932170.1; mRNA sequence set forth in SEQ ID NO:74, NCBI Reference Sequence: NM_198053.2) or SEQ ID NO:75 (isoform 2; mature polypeptide includes residues 22-163 of SEQ ID NO:75; see NCBI Reference Sequence: NP_000725.1; mRNA sequence set forth in SEQ ID NO:76, NCBI Reference Sequence: NM_000734.3). Exemplary mature CD3ζ chain contains an extracellular region (including amino acid residues 22-30 of the human CD3ζ chain precursor sequence set forth in SEQ ID NO:73 or 75), a transmembrane region (including amino acid residues 31-51 of the human CD3ζ chain precursor sequence set forth in SEQ ID NO:73 or 75), and an intracellular region (including amino acid residues 52-164 of the human CD3ζ chain precursor sequence set forth in SEQ ID NO:73 or amino acid residues 52-163 of the human CD3ζ chain precursor sequence set forth in SEQ ID NO:75). The CD3ζ chain contains three immunoreceptor tyrosine-based activation motif (ITAM) domains, at amino acid residues 61-89, 100-128 or 131-159 of the human CD3ζ chain precursor sequence set forth in SEQ ID NO:73 or at amino acid residues 61-89, 100-127 or 130-158 of the human CD3ζ chain precursor sequence set forth in SEQ ID NO:75.

In humans, an exemplary genomic locus of CD247 comprises an open reading frame that contains 8 exons and 7 introns. An exemplary mRNA transcript of CD247 can span the sequence corresponding to Chromosome 1: 167,430,640-167,518,610, on the reverse strand, with reference to human genome version GRCh38 (UCSC Genome Browser on Human December 2013 (GRCh38/hg38) Assembly). Table 1 sets forth the coordinates of the exons and introns of the open reading frames and the untranslated regions of the transcript of an exemplary human CD247 locus.

TABLE 1

Coordinates of exons and introns of exemplary human CD247 locus (GRCh38, Chromosome 1, reverse strand).

| | Start (GrCh38) | End (GrCh38) | Length |
|---|---|---|---|
| 5' UTR and Exon 1 | 167,518,610 | 167,518,408 | 203 |
| Intron 1-2 | 167,518,407 | 167,440,768 | 77,640 |
| Exon 2 | 167,440,767 | 167,440,664 | 104 |
| Intron 2-3 | 167,440,663 | 167,439,401 | 1,263 |
| Exon 3 | 167,439,400 | 167,439,344 | 57 |
| Intron 3-4 | 167,439,343 | 167,438,651 | 693 |
| Exon 4 | 167,438,650 | 167,438,570 | 81 |
| Intron 4-5 | 167,438,569 | 167,435,432 | 3,138 |
| Exon 5 | 167,435,431 | 167,435,399 | 33 |
| Intron 5-6 | 167,435,398 | 167,434,077 | 1,322 |
| Exon 6 | 167,434,076 | 167,434,020 | 57 |
| Intron 6-7 | 167,434,019 | 167,433,060 | 960 |
| Exon 7 | 167,433,059 | 167,433,024 | 36 |
| Intron 7-8 | 167,433,023 | 167,431,747 | 1,277 |
| Exon 8 and 3' UTR | 167,431,746 | 167,430,640 | 1,107 |

In some aspects, the transgene (e.g., exogenous nucleic acid sequences) within the template polynucleotide can be used to guide the location of target sites and/or homology arms. In some aspects, the target site of genetic disruption can be used as a guide to design template polynucleotides and/or homology arms used for HDR. In some embodiments, the genetic disruption can be targeted near a desired site of targeted integration of transgene sequences (e.g., encoding a chimeric receptor or a portion thereof). In some aspects, the genetic disruption is targeted based on the amount of sequences encoding the CD3ζ chain contained within the transgene sequences for integration. In some aspects, the target site is within an exon of the open reading frame of the endogenous CD247 locus. In some aspects, the target site is within an intron of the open reading frame of the CD247 locus.

In some embodiments, the target site for a genetic disruption is selected such that after integration of the transgene sequences, the chimeric receptor encoded by the modified CD247 locus contains a functional CD3zeta chain or a fragment thereof such that itis capable of signaling via the CD3zeta chain or a fragment thereof. In some embodiments, the one or more homology arm sequences of the template polynucleotide is designed to surround the site of genetic disruption. In some aspects, the target site is placed within or near an exon of the endogenous CD247 locus, so that the transgene encoding a portion of the chimeric receptor can be integrated in-frame with the coding sequence of the CD247 locus.

In some embodiments, the target site is selected such that targeted integration of the transgene generates a gene fusion of transgene and endogenous sequences of the CD247 locus, which together encode a functional CD3ζ chain. The endogenous sequence can, in some aspects, encode a functional CD3ζ chain that is a portion of a CD3ζ chain capable of mediating, activating or stimulating primary cytoplasmic or intracellular signal, e.g., a cytoplasmic domain of the CD3ζ chain, such as a portion of the CD3ζ chain that includes the immunoreceptor tyrosine-based activation motif (ITAM). In some aspects, the target site is placed at or near the beginning of the endogenous open reading frame sequences encoding the intracellular regions of the CD3ζ chain, e.g., amino acid residues 52-164 of the human CD3ζ chain precursor sequence set forth in SEQ ID NO:73 or amino acid residues 52-163 of the human CD3ζ chain precursor sequence set forth in SEQ ID NO:75; or at or near exon 2 or exon 3 (e.g., sequences at or near nucleotides 167,440,767-167,440,664 or nucleotides 167,439,400-167,439,344 in GrCh38 as described in Table 1 herein). In some aspects, the target site is placed before, or upstream of, the endogenous open reading frame sequences encoding the ITAM domains of the CD3ζ chain, e.g., amino acid residues 61-89, 100-128 or 131-159 of the human CD3ζ chain precursor sequence set forth in SEQ ID NO:73 or amino acid residues 61-89, 100-127 or 130-158 of the human CD3ζ chain precursor sequence set forth in SEQ ID NO:75.

In some aspects, the target site is within an exon of the endogenous CD247 locus. In some aspects, the target site is within an intron of the endogenous CD247 locus. In some aspects, the target site is within a regulatory or control element, e.g., a promoter, 5' untranslated region (UTR) or 3' UTR, of the CD247 locus. In some embodiments, the target site is within the CD247 genomic region sequence described in Table 1 herein or any exon or intron of the CD247 genomic region sequence contained therein.

In some aspects, the target site is within an exon, such as exons corresponding to early coding regions. In some embodiments, the target site is within or in close proximity to exons corresponding to early coding region, e.g., exon 1, 2 or 3 of the open reading frame of the endogenous CD247 locus (such as described in Table 1 herein), or including sequence immediately following a transcription start site, within exon 1, 2, or 3, or within less than 500, 450, 400, 350, 300, 250, 200, 150, 100 or 50 bp of exon 1, 2, or 3. In some aspects, the target site is at or near exon 1 of the endogenous CD247 locus, e.g., within less than 500, 450, 400, 350, 300, 250, 200, 150, 100 or 50 bp of exon 1. In some embodiments, the target site is at or near exon 2 of the endogenous CD247 locus, or within less than 500, 450, 400, 350, 300, 250, 200, 150, 100 or 50 bp of exon 2. In some aspects, the target site is at or near exon 3 of the endogenous CD247 locus, e.g., within less than 500, 450, 400, 350, 300, 250, 200, 150, 100 or 50 bp of exon 3. In some aspects, the target site is within a regulatory or control element, e.g., a promoter, of the CD247 locus.

In certain embodiments, a genetic disruption is targeted at, near, or within a CD247 locus. In particular embodiments, the genetic disruption is targeted at, near, or within an open reading frame of the CD247 locus (such as described in Table 1 herein). In certain embodiments, the genetic disruption is targeted at, near, or within an open reading frame that encodes a CD3ζ chain. In some embodiments, the genetic disruption is targeted at, near, or within the CD247 locus (such as described in Table 1 herein), or a sequence having at or at least 70%, 75%, 80%, 85%, 90%, 95%, 97%, 98%, 99%, 99.5%, or 99.9% sequence identity to all or a portion, e.g., at or at least 500, 1,000, 1,500, 2,000, 2,500, 3,000, 3,500, or 4,000 contiguous nucleotides, of the CD247 locus (such as described in Table 1 herein).

In some embodiments, a genetic disruption, e.g., DNA break, is targeted within an exon of the CD247 locus or open reading frame thereof. In certain embodiments, the genetic disruption is within the first exon, second exon, third exon, or forth exon of the CD247 locus or open reading frame thereof. In particular embodiments, the genetic disruption is within the first exon of the CD247 locus or open reading frame thereof. In some embodiments, the genetic disruption is within 500 base pairs (bp) downstream from the 5' end of the first exon in the CD247 locus or open reading frame thereof. In particular embodiments, the genetic disruption is between the 5' nucleotide of exon 1 and upstream of the 3' nucleotide of exon 1. In certain embodiments, the genetic disruption is within 400 bp, 350 bp, 300 bp, 250 bp, 200 bp, 150 bp, 100 bp, or 50 bp downstream from the 5' end of the first exon in the CD247 locus or open reading frame thereof. In particular embodiments, the genetic disruption is between 1 bp and 400 bp, between 50 and 300 bp, between 100 bp and 200 bp, or between 100 bp and 150 bp downstream from the 5' end of the first exon in the CD247 locus or open reading frame thereof, each inclusive. In certain embodiments, the genetic disruption is between 100 bp and 150 bp downstream from the 5' end of the first exon in the CD247 locus or open reading frame thereof, inclusive.

2. Methods of Genetic Disruption

In some aspects, the methods for generating the genetically engineered cells involve introducing a genetic disruption at one or more target site(s), e.g., one or more target sites at a CD247 locus encoding CD3zeta (CD3ζ). Methods for generating a genetic disruption, including those described herein, can involve the use of one or more agent(s) capable of inducing a genetic disruption, such as engineered systems to induce a genetic disruption, a cleavage and/or a double strand break (DSB) or a nick (e.g., a single strand break (SSB)) at a target site or target position in the endogenous or genomic DNA such that repair of the break by an error born process such as non-homologous end joining (NHEJ) or repair by HDR using repair template can result in the insertion of a sequence of interest (e.g., exogenous nucleic acid sequences or transgene encoding a portion of a chimeric receptor) at or near the target site or position. Also provided are one or more agent(s) capable of inducing a genetic disruption, for use in the methods provided herein. In some aspects, the one or more agent(s) can be used in combination with the template nucleotides provided herein, for homology directed repair (HDR) mediated targeted integration of the transgene sequences.

In some embodiments, the one or more agent(s) capable of inducing a genetic disruption comprises a DNA binding protein or DNA-binding nucleic acid that specifically binds to or hybridizes to a particular site or position in the genome, e.g., a target site or target position. In some aspects, the targeted genetic disruption, e.g., DNA break or cleavage, at the endogenous CD247 locus is achieved using a protein or a nucleic acid is coupled to or complexed with a gene editing nuclease, such as in a chimeric or fusion protein. In some embodiments, the one or more agent(s). capable of inducing a genetic disruption comprises an RNA-guided nuclease, or a fusion protein comprising a DNA-targeting protein and a nuclease.

In some embodiments, the agent comprises various components, such as an RNA-guided nuclease, or a fusion protein comprising a DNA-targeting protein and a nuclease. In some embodiments, the targeted genetic disruption is carried out using a DNA-targeting molecule that includes a DNA-binding protein such as one or more zinc finger protein (ZFP) or transcription activator-like effectors (TALEs), fused to a nuclease, such as an endonuclease. In some embodiments, the targeted genetic disruption is carried out using RNA-guided nucleases such as a clustered regularly interspaced short palindromic nucleic acid (CRISPR)-associated nuclease (Cas) system (including Cas and/or Cfp1). In some embodiments, the targeted genetic disruption is carried using agents capable of inducing a genetic disruption, such as sequence-specific or targeted nucleases, including DNA-binding targeted nucleases and gene editing nucleases such as zinc finger nucleases (ZFN) and transcription activator-like effector nucleases (TALENs), and RNA-guided nucleases such as a CRISPR-associated nuclease (Cas) system, specifically designed to be targeted to the at least one target site(s), sequence of a gene or a portion thereof. Exemplary ZFNs, TALEs, and TALENs are described in, e.g., Lloyd et al., Frontiers in Immunology, 4(221): 1-7 (2013).

Zinc finger proteins (ZFPs), transcription activator-like effectors (TALEs), and CRISPR system binding domains can be "engineered" to bind to a predetermined nucleotide sequence, for example via engineering (altering one or more amino acids) of the recognition helix region of a naturally occurring ZFP or TALE protein. Engineered DNA binding proteins (ZFPs or TALEs) are proteins that are non-naturally occurring. Rational criteria for design include application of substitution rules and computerized algorithms for processing information in a database storing information of existing ZFP and/or TALE designs and binding data. See, e.g., U.S. Pat. Nos. 6,140,081; 6,453,242; and 6,534,261; see also WO 98/53058; WO 98/53059; WO 98/53060; WO 02/016536 and WO 03/016496 and U.S. Pub. No. 20110301073.

In some embodiments, the one or more agent(s) specifically targets the at least one target site(s) at or near a CD247 locus. In some embodiments, the agent comprises a ZFN, TALEN or a CRISPR/Cas9 combination that specifically binds to, recognizes, or hybridizes to the target site(s). In some embodiments, the CRISPR/Cas9 system includes an engineered crRNA/tracr RNA ("single guide RNA") to guide specific cleavage. In some embodiments, the agent comprises nucleases based on the Argonaute system (e.g., from *T. thermophilus*, known as 'TtAgo' (Swarts et al., (2014) Nature 507(7491): 258-261). Targeted cleavage using any of the nuclease systems described herein can be exploited to insert the nucleic acid sequences, e.g., transgene sequences encoding a portion of a chimeric receptor, into a specific target location at an endogenous CD247 locus, using either HDR or NHEJ-mediated processes.

In some embodiments, a "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Among the ZFPs are artificial ZFP domains targeting specific DNA sequences, typically 9-18 nucleotides long, generated by assembly of individual fingers. ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3, and 6) on a zinc finger recognition helix. Thus, for example, the ZFP or ZFP-containing molecule is non-naturally occurring, e.g., is engineered to bind to a target site of choice.

In some cases, the DNA-targeting molecule is or comprises a zinc-finger DNA binding domain fused to a DNA cleavage domain to form a zinc-finger nuclease (ZFN). For example, fusion proteins comprise the cleavage domain (or cleavage half-domain) from at least one Type IIS restriction enzyme and one or more zinc finger binding domains, which may or may not be engineered. In some cases, the cleavage domain is from the Type IIS restriction endonuclease Fold, which generally catalyzes double-stranded cleavage of DNA, at 9 nucleotides from its recognition site on one strand and 13 nucleotides from its recognition site on the other. See, e.g., U.S. Pat. Nos. 5,356,802; 5,436,150 and 5,487,994; Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269: 978-982. Some gene-specific engineered zinc fingers are available commercially. For example, a platform called CompoZr, for zinc-finger construction is available that provides specifically targeted zinc fingers for thousands of targets. See, e.g., Gaj et al., *Trends in Biotechnology,* 2013, 31(7), 397-405. In some cases, commercially available zinc fingers are used or are custom designed.

In some embodiments, the one or more target site(s), e.g., within the CD247 locus can be targeted for genetic disruption by engineered ZFNs. Exemplary ZFN that target the endogenous CD247 locus include those described in, e.g., Rudemiller et al., (2014) Hypertension. 63(3):559-64 the disclosures of which are incorporated by reference in their entireties.

Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from different bacterial species. The new modular proteins have the advantage of displaying more sequence variability than TAL repeats. In some embodiments, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In some embodiments, critical amino acids 12 and 13 can be mutated towards other amino acid residues in order: to modulate their specificity towards nucleotides A, T, C and G and in particular to enhance this specificity.

In some embodiments, a "TALE DNA binding domain" or "TALE" is a polypeptide comprising one or more TALE repeat domains/units. The repeat domains, each comprising a repeat variable diresidue (RVD), are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TALE proteins may be designed to bind to a target site using canonical or non-canonical RVDs within the repeat units. See, e.g., U.S. Pat. Nos. 8,586,526 and 9,458,205.

In some embodiments, a "TALE-nuclease" (TALEN) is a fusion protein comprising a nucleic acid binding domain typically derived from a Transcription Activator Like Effector (TALE) and a nuclease catalytic domain that cleaves a nucleic acid target sequence. The catalytic domain comprises a nuclease domain or a domain having endonuclease activity, like for instance I-TevI, ColE7, NucA and Fok-I. In a particular embodiment, the TALE domain can be fused to a meganuclease like for instance I-CreI and I-OnuI or functional variant thereof. In some embodiments, the TALEN is a monomeric TALEN. A monomeric TALEN is a TALEN that does not require dimerization for specific recognition and cleavage, such as the fusions of engineered TAL repeats with the catalytic domain of I-TevI described in WO2012138927. TALENs have been described and used for gene targeting and gene modifications (see, e.g., Boch et al. (2009) Science 326(5959): 1509-12; Moscou and Bogdanove (2009) Science 326(5959): 1501; Christian et al. (2010) Genetics 186(2): 757-61; Li et al. (2011) Nucleic Acids Res 39(1): 359-72). In some embodiments, one or more sites in the CD247 locus can be targeted for genetic disruption by engineered TALENs.

In some embodiments, a "TtAgo" is a prokaryotic Argonaute protein thought to be involved in gene silencing. TtAgo is derived from the bacteria *Thermus thermophilus*. See, e.g. Swarts et al., (2014) Nature 507(7491): 258-261, G. Sheng et al., (2013) Proc. Natl. Acad. Sci. U.S.A. 111, 652). A "TtAgo system" is all the components required including e.g. guide DNAs for cleavage by a TtAgo enzyme.

In some embodiments, an engineered zinc finger protein, TALE protein or CRISPR/Cas system is not found in nature and whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970; WO 01/88197 and WO 02/099084.

Zinc finger and TALE DNA-binding domains can be engineered to bind to a predetermined nucleotide sequence, for example via engineering (altering one or more amino acids) of the recognition helix region of a naturally occurring zinc finger protein or by engineering of the amino acids involved in DNA binding (the repeat variable diresidue or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs (canonical and non-canonical RVDs) and binding data. See, for example, U.S. Pat. Nos. 9,458,205; 8,586,526; 6,140,081; 6,453,242; and 6,534,261; see also WO 98/53058; WO 98/53059; WO 98/53060; WO 02/016536 and WO 03/016496.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130196373; 20140120622; 20150056705; 20150335708; 20160030477 and 20160024474, the disclosures of which are incorporated by reference in their entireties.

a. CRISPR/Cas9

In some embodiments, the targeted genetic disruption, e.g., DNA break, at the endogenous genes encoding CD3zeta (CD3ζ), such as CD247 in humans is carried out using clustered regularly interspaced short palindromic repeats (CRISPR) and CRISPR-associated (Cas) proteins. See Sander and Joung (2014) *Nature Biotechnology,* 32(4): 347-355.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracr RNA or an active partial tracr RNA), a tracr-mate sequence (encompassing a "direct repeat" and a tracr RNA-processed partial direct repeat in the context of an endogenous CRISPR system), a guide sequence (also referred to as a "spacer" in the context of an endogenous CRISPR system), and/or other sequences and transcripts from a CRISPR locus.

In some aspects, the CRISPR/Cas nuclease or CRISPR/Cas nuclease system includes a non-coding guide RNA (gRNA), which sequence-specifically binds to DNA, and a Cas protein (e.g., Cas9), with nuclease functionality.

Also provided are one or more agents capable of introducing a genetic disruption. Also provided are polynucleotides (e.g., nucleic acid molecules) encoding one or more components of the one or more agent(s) capable of inducing a genetic disruption.

(i) Guide RNA (gRNA)

In some embodiments, the one or more agent(s) capable of inducing a genetic disruption comprises at least one of: a guide RNA (gRNA) having a targeting domain that is complementary with a target site at the CD247 locus or at least one nucleic acid encoding the gRNA.

In some aspects, a "gRNA molecule" is a nucleic acid that promotes the specific targeting or homing of a gRNA molecule/Cas9 molecule complex to a target nucleic acid, such as a locus on the genomic DNA of a cell. gRNA molecules can be unimolecular (having a single RNA molecule), sometimes referred to herein as "chimeric" gRNAs, or modular (comprising more than one, and typically two, separate RNA molecules). In general, a guide sequence, e.g., guide RNA, is any polynucleotide sequences comprising at least a sequence portion that has sufficient complementarity with a target polynucleotide sequence, such as the at the CD247 locus in humans, to hybridize with the target sequence at the target site and direct sequence-specific binding of the CRISPR complex to the target sequence. In some embodiments, in the context of formation of a CRISPR complex, "target sequence" is to a sequence to which a guide sequence is designed to have complementarity, where hybridization between the target sequence and a domain, e.g., targeting domain, of the guide RNA promotes the formation of a CRISPR complex. Full complementarity is not necessarily required, provided there is sufficient complementarity to cause hybridization and promote formation of a CRISPR complex. Generally, a guide sequence is selected to reduce the degree of secondary structure within the guide sequence. Secondary structure may be determined by any suitable polynucleotide folding algorithm.

In some embodiments, a guide RNA (gRNA) specific to a target locus of interest (e.g. at the CD247 locus in humans) is used to RNA-guided nucleases, e.g., Cas, to induce a DNA break at the target site or target position. Methods for designing gRNAs and exemplary targeting domains can include those described in, e.g., International PCT Pub. Nos. WO2015/161276, WO2017/193107 and WO2017/093969.

Several exemplary gRNA structures, with domains indicated thereon, are described in WO2015/161276, e.g., in FIGS. 1A-1G therein. While not wishing to be bound by theory, with regard to the three dimensional form, or intra- or inter-strand interactions of an active form of a gRNA, regions of high complementarity are sometimes shown as duplexes in WO2015/161276, e.g., in FIGS. 1A-1G therein and other depictions provided herein.

In some cases, the gRNA is a unimolecular or chimeric gRNA comprising, from 5' to 3': a targeting domain which is complementary to a target nucleic acid, such as a sequence from the CD247 gene (coding sequence set forth in SEQ ID NO:74); a first complementarity domain; a linking domain; a second complementarity domain (which is complementary to the first complementarity domain); a proximal domain; and optionally, a tail domain.

In other cases, the gRNA is a modular gRNA comprising first and second strands. In these cases, the first strand preferably includes, from 5' to 3': a targeting domain (which is complementary to a target nucleic acid, such as a sequence from the CD247 gene, coding sequence set forth in SEQ ID NO:74 or 76) and a first complementarity domain. The second strand generally includes, from 5' to 3': optionally, a 5' extension domain; a second complementarity domain; a proximal domain; and optionally, a tail domain.

(a) Targeting Domain

The targeting domain comprises a nucleotide sequence that is complementary, e.g., at least 80, 85, 90, 95, 98 or 99% complementary, e.g., fully complementary, to the target sequence on the target nucleic acid. The strand of the target nucleic acid comprising the target sequence is referred to herein as the "complementary strand" of the target nucleic acid. Guidance on the selection of targeting domains can be found, e.g., in Fu Y et al., Nat Biotechnol 2014 (doi: 10.1038/nbt.2808) and Sternberg S H et al., Nature 2014 (doi: 10.1038/nature13011). Examples of the placement of targeting domains include those described in WO2015/161276, e.g., in FIGS. 1A-1G therein.

The targeting domain is part of an RNA molecule and will therefore comprise the base uracil (U), while any DNA encoding the gRNA molecule will comprise the base thymine (T). While not wishing to be bound by theory, In some embodiments, it is believed that the complementarity of the targeting domain with the target sequence contributes to specificity of the interaction of the gRNA molecule/Cas9 molecule complex with a target nucleic acid. It is understood that in a targeting domain and target sequence pair, the uracil bases in the targeting domain will pair with the adenine bases in the target sequence. In some embodiments, the target domain itself comprises in the 5' to 3' direction, an optional secondary domain, and a core domain. In some embodiments, the core domain is fully complementary with the target sequence. In some embodiments, the targeting domain is 5 to 50 nucleotides in length. The strand of the target nucleic acid with which the targeting domain is complementary is referred to herein as the complementary strand. Some or all of the nucleotides of the domain can have a modification, e.g., to render it less susceptible to degradation, improve bio-compatibility, etc. By way of non-limiting example, the backbone of the target domain can be modified with a phosphorothioate, or other modification(s). In some cases, a nucleotide of the targeting domain can comprise a 2' modification, e.g., a 2-acetylation, e.g., a 2' methylation, or other modification(s).

In various embodiments, the targeting domain is 16-26 nucleotides in length (i.e. it is 16 nucleotides in length, or 17 nucleotides in length, or 18, 19, 20, 21, 22, 23, 24, 25 or 26 nucleotides in length.

(b) Exemplary Targeting Domains

In some embodiments, gRNA sequences that is or comprises a targeting domain sequence targeting the target site in a particular gene, such as the CD247 locus, designed or identified. A genome-wide gRNA database for CRISPR genome editing is publicly available, which contains exemplary single guide RNA (sgRNA) sequences targeting constitutive exons of genes in the human genome or mouse genome (see e.g., genescript.com/gRNA-database.html; see also, Sanjana et al. (2014) Nat. Methods, 11:783-4). In some aspects, the gRNA sequence is or comprises a sequence with minimal off-target binding to a non-target site or position.

In some embodiments, the target sequence (target domain) is at or near the CD247 locus, such as any part of the CD247 coding sequence set forth in SEQ ID NO: 74 or 76. In some embodiments, the target nucleic acid complementary to the targeting domain is located at an early coding region of a gene of interest, such as CD247. Targeting of the early coding region can be used to genetic disruption (i.e., eliminate expression of) the gene of interest. In some embodiments, the early coding region of a gene of interest includes sequence immediately following a start codon (e.g., ATG), or within 500 bp of the start codon (e.g., less than 500, 450, 400, 350, 300, 250, 200, 150, 100, 50 bp, 40 bp, 30 bp, 20 bp, or 10 bp). In particular examples, the target nucleic acid is within 200 bp, 150 bp, 100 bp, 50 bp, 40 bp, 30 bp, 20 bp or 10 bp of the start codon. In some examples, the targeting domain of the gRNA is complementary, e.g., at least 80, 85, 90, 95, 98 or 99% complementary, e.g., fully complementary, to the target sequence on the target nucleic acid, such as the target nucleic acid in the CD247 locus.

In some embodiments, the gRNA can target a site at the CD247 locus near a desired site of targeted integration of transgene sequences, e.g., encoding a chimeric receptor. In some aspects, the gRNA can target a site based on the amount of sequences encoding the CD3zeta chain contained within the transgene sequences for integration. In some aspects, the gRNA can target a site within an exon of the open reading frame of the endogenous CD247 locus. In some aspects, the gRNA can target a site within an intron of the open reading frame of the CD247 locus. In some aspects, the gRNA can target a site within a regulatory or control element, e.g., a promoter, of the CD247 locus. In some aspects, the target site at the CD247 locus that is targeted by the gRNA can be any target sites described herein, e.g., in Section I.A.1. In some embodiments, the gRNA can target a site within or in close proximity to exons corresponding to early coding region, e.g., exon 1, 2 or 3 of the open reading frame of the endogenous CD247 locus, or including sequence immediately following a transcription start site, within exon 1, 2, or 3, or within less than 500, 450, 400, 350, 300, 250, 200, 150, 100 or 50 bp of exon 1, 2, or 3. In some embodiments, the gRNA can target a site at or near exon 2 of the endogenous CD247 locus, or within less than 500, 450, 400, 350, 300, 250, 200, 150, 100 or 50 bp of exon 2.

Exemplary target site sequences for disruption of the human at the CD247 locus using Cas9 can include any set forth in SEQ ID NOS: 59-62 and 67-72. In some aspects, exemplary target site sequences, including the NGG PAM, include any set forth in SEQ ID NOS: 63-66. Exemplary gRNAs can include a sequence of ribonucleic acids that can bind to or target the target site sequences set forth in any of SEQ ID NOS: 59-62 and 67-72. Exemplary gRNA targeting domain sequence include: CACCUUCACUCUCAGGAACA (SEQ ID NO:87); GAAUGACACCAUAGAUGAAG (SEQ ID NO:88); UGAAGAGGAUUCCAUCCAGC (SEQ ID NO:89); UCCAGCAGGUAGCAGAGUUU (SEQ ID NO:90); AGACGCCCCCGCGUACCAGC (SEQ ID NO:91); GCUGACUUACGUUAUAGAGC (SEQ ID NO:92); UUUCACCGCGGCCAUCCUGC (SEQ ID NO:93); UAAUCGGCAACUGUGCCUGC (SEQ ID NO:94); CGGAGGCCUACAGUGAGAUU (SEQ ID NO:95); or UGGUACCCACCUUCACUCUC (SEQ ID NO:96). Exemplary gRNA sequences to generate a genetic disruption of the endogenous CD247 locus (encoding CD3zeta) are described, e.g., in International PCT Pub. No. WO2017093969. Exemplary methods for gene editing of the endogenous CD247 locus (encoding CD3zeta) include those described in, e.g. WO2017093969. Any of the known methods can be used to target and generate a genetic disruption of the endogenous CD247 locus can be used in the embodiments provided herein.

In some embodiments, targeting domains include those for introducing a genetic disruption at the CD247 gene using *S. pyogenes* Cas9 or using *N. meningitidis* Cas9.

In some embodiments, targeting domains include those for introducing a genetic disruption at the CD247 gene using *S. pyogenes* Cas9. Any of the targeting domains can be used with a *S. pyogenes* Cas9 molecule that generates a double stranded break (Cas9 nuclease) or a single-stranded break (Cas9 nickase).

In some embodiments, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired with any gRNA comprising a plus strand targeting domain. In some embodiments, the two gRNAs are oriented on the DNA such that PAMs face outward and the distance between the 5' ends of the gRNAs is 0-50 bp. In some embodiments, two gRNAs are used to target two Cas9 nucleases or two Cas9 nickases, for example, using a pair of Cas9 molecule/gRNA molecule complex guided by two different gRNA molecules to cleave the target domain with two single stranded breaks on opposing strands of the target domain. In some embodiments, the two Cas9 nickases can include a molecule having HNH activity, e.g., a Cas9 molecule having the RuvC activity inactivated, e.g., a Cas9 molecule having a mutation at D10, e.g., the D10A mutation, a molecule having RuvC activity, e.g., a Cas9 molecule having the HNH activity inactivated, e.g., a Cas9 molecule having a mutation at H840, e.g., a H840A, or a molecule having RuvC activity, e.g., a Cas9 molecule having the HNH activity inactivated, e.g., a Cas9 molecule having a mutation at N863, e.g., N863A. In some embodiments, each of the two gRNAs are complexed with a D10A Cas9 nickase (c) The First Complementarity Domain The first complementarity domain is complementary with the second complementarity domain described herein, and generally has sufficient complementarity to the second complementarity domain to form a duplexed region under at least some physiological conditions. The first complementarity domain is typically 5 to 30 nucleotides in length, and may be 5 to 25 nucleotides in length, 7 to 25 nucleotides in length, 7 to 22 nucleotides in length, 7 to 18 nucleotides in length, or 7 to 15 nucleotides in length. In various embodiments, the first complementary domain is 5, 6, 7, 8, 9, 10, 11, 12, 13, 14, 15, 16, 17, 18, 19, 20, 21, 22, 23, 24, or 25 nucleotides in length. Examples of first complementarity domains include those described in WO2015/161276, e.g., in FIGS. 1A-1G therein.

Typically, the first complementarity domain does not have exact complementarity with the second complementarity domain target. In some embodiments, the first complementarity domain can have 1, 2, 3, 4 or 5 nucleotides that are not complementary with the corresponding nucleotide of the second complementarity domain. In some embodiments, a segment of 1, 2, 3, 4, 5 or 6, (e.g., 3) nucleotides of the first complementarity domain may not pair in the duplex, and may form a non-duplexed or looped-out region. In some instances, an unpaired, or loop-out, region, e.g., a loop-out of 3 nucleotides, is present on the second complementarity domain. This unpaired region optionally begins 1, 2, 3, 4, 5, or 6, e.g., 4, nucleotides from the 5' end of the second complementarity domain.

The first complementarity domain can include 3 subdomains, which, in the 5' to 3' direction are: a 5' subdomain, a central subdomain, and a 3' subdomain. In some embodiments, the 5' subdomain is 4-9, e.g., 4, 5, 6, 7, 8 or 9 nucleotides in length. In some embodiments, the central subdomain is 1, 2, or 3, e.g., 1, nucleotide in length. In some embodiments, the 3' subdomain is 3 to 25, e.g., 4-22, 4-18, or 4 to 10, or 3, 4, 5, 6, 7, 8, 9, 10, 11, 12, 13, 14, 15, 16, 17, 18, 19, 20, 21, 22, 23, 24, or 25, nucleotides in length.

In some embodiments, the first and second complementarity domains, when duplexed, comprise 11 paired nucleotides, for example, in the gRNA sequence (one paired strand underlined, one bolded):

(SEQ ID NO: 97)
NNNNNNNNNNNNNNNNNNNNGUUUUAGAGCUAGAAAUAGCAAGUUAAAAUAAGGCUAGUCCGUUAUCAACUUGAAAAAGUGGCACCGAGUCGGUGC.

In some embodiments, the first and second complementarity domains, when duplexed, comprise 15 paired nucleotides, for example in the gRNA sequence (one paired strand underlined, one bolded):

(SEQ ID NO: 98)
NNNNNNNNNNNNNNNNNNNNGUUUUAGAGCUAUGCUGAAAAGCAUAGCAAGUUAAAAUAAGGCUAGUCCGUUAUCAACUUGAAAAAGUGGCACCGAGUCGGUGC.

In some embodiments the first and second complementarity domains, when duplexed, comprise 16 paired nucleotides, for example in the gRNA sequence (one paired strand underlined, one bolded):

(SEQ ID NO: 99)
NNNNNNNNNNNNNNNNNNNNGUUUUAGAGCUAUGCUGGAAACAGCAUAGCAAGUUAAAAUAAGGCUAGUCCGUUAUCAACUUGAAAAAGUGGCACCGAGUCGGUGC.

In some embodiments the first and second complementarity domains, when duplexed, comprise 21 paired nucleotides, for example in the gRNA sequence (one paired strand underlined, one bolded):

(SEQ ID NO: 100)
NNNNNNNNNNNNNNNNNNNNGUUUUAGAGCUAUGCUGUUUUGGAAACAAACAGCAUAGCAAGUUAAAAUAAGGCUAGUCCGUUAUCAACUUGAAAAAGUGGCACCGAGUCGGUGC.

In some embodiments, nucleotides are exchanged to remove poly-U tracts, for example in the gRNA sequences (exchanged nucleotides underlined):

(SEQ ID NO: 101)
NNNNNNNNNNNNNNNNNNNNGUAUUAGAGCUAGAAAUAGCAAGUUAAUAUAAGGCUAGUCCGUUAUCAACUUGAAAAAGUGGCACCGAGUCGGUGC;

(SEQ ID NO: 102)
NNNNNNNNNNNNNNNNNNNNGUUUAAGAGCUAGAAAUAGCAAGUUUAAAUAAGGCUAGUCCGUUAUCAACUUGAAAAAGUGGCACCGAGUCGGUGC;
and (SEQ ID NO: 103)
NNNNNNNNNNNNNNNNNNNNGUAUUAGAGCUAUGCUGUAUUGGAAACAAUACAGCAUAGCAAGUUAAUAUAAGGCUAGUCCGUUAUCAACUUGAAAAAGUGGCACCGAGUCGGUGC.

The first complementarity domain can share homology with, or be derived from, a naturally occurring first complementarity domain. In some embodiments, it has at least 50% homology with a first complementarity domain disclosed herein, e.g., an *S. pyogenes, S. aureus, N. meningtidis*, or *S. thermophilus*, first complementarity domain It should be noted that one or more, or even all of the nucleotides of the first complementarity domain, can have a modification along the lines discussed herein for the targeting domain.

(d) The Linking Domain

In a unimolecular or chimeric gRNA, the linking domain serves to link the first complementarity domain with the second complementarity domain of a unimolecular gRNA. The linking domain can link the first and second complementarity domains covalently or non-covalently. In some embodiments, the linkage is covalent. In some embodiments, the linking domain covalently couples the first and second complementarity domains, see, e.g., WO2015/161276, e.g., in FIGS. 1B-1E therein. In some embodiments, the linking domain is, or comprises, a covalent bond interposed between the first complementarity domain and the second complementarity domain. Typically the linking domain comprises one or more, e.g., 2, 3, 4, 5, 6, 7, 8, 9, or 10 nucleotides, but in various embodiments the linker can be 20, 30, 40, 50 or even 100 nucleotides in length. Examples of linking domains include those described in WO2015/161276, e.g., in FIGS. 1A-1G therein.

In modular gRNA molecules, the two molecules are associated by virtue of the hybridization of the complementarity domains and a linking domain may not be present. See e.g., WO2015/161276, e.g., in FIG. 1A therein.

A wide variety of linking domains are suitable for use in unimolecular gRNA molecules. Linking domains can consist of a covalent bond, or be as short as one or a few nucleotides, e.g., 1, 2, 3, 4, or 5 nucleotides in length. In some embodiments, a linking domain is 2, 3, 4, 5, 6, 7, 8, 9, 10, 15, 20, or 25 or more nucleotides in length. In some embodiments, a linking domain is 2 to 50, 2 to 40, 2 to 30, 2 to 20, 2 to 10, or 2 to 5 nucleotides in length. In some embodiments, a linking domain shares homology with, or is derived from, a naturally occurring sequence, e.g., the sequence of a tracrRNA that is 5' to the second complementarity domain. In some embodiments, the linking domain has at least 50% homology with a linking domain disclosed herein.

As discussed herein in connection with the first complementarity domain, some or all of the nucleotides of the linking domain can include a modification.

(e) The 5' Extension Domain

In some cases, a modular gRNA can comprise additional sequence, 5' to the second complementarity domain, referred to herein as the 5' extension domain. In some embodiments, the 5' extension domain is, 2-10, 2-9, 2-8, 2-7, 2-6, 2-5, or 2-4 nucleotides in length. In some embodiments, the 5' extension domain is 2, 3, 4, 5, 6, 7, 8, 9, or 10 or more nucleotides in length. In some embodiments, examples of a 5' extension domain include those described in WO2015/161276, e.g., in FIG. 1A therein.

(f) The Second Complementarity Domain

The second complementarity domain is complementary with the first complementarity domain, and generally has sufficient complementarity to the second complementarity domain to form a duplexed region under at least some physiological conditions. In some cases, e.g., as shown in WO2015/161276, e.g., in FIG. 1A-1B therein, the second complementarity domain can include sequence that lacks complementarity with the first complementarity domain, e.g., sequence that loops out from the duplexed region. Examples of second complementarity domains include those described in WO2015/161276, e.g., in FIGS. 1A-1G therein.

The second complementarity domain may be 5 to 27 nucleotides in length, and in some cases may be longer than the first complementarity region. In some embodiments, the second complementary domain can be 7 to 27 nucleotides in length, 7 to 25 nucleotides in length, 7 to 20 nucleotides in length, or 7 to 17 nucleotides in length. More generally, the complementary domain may be 5, 6, 7, 8, 9, 10, 11, 12, 13, 14, 15, 16, 17, 18, 19, 20, 21, 22, 23, 24, 25, or 26 nucleotides in length.

In some embodiments, the second complementarity domain comprises 3 subdomains, which, in the 5' to 3' direction are: a 5' subdomain, a central subdomain, and a 3' subdomain. In some embodiments, the 5' subdomain is 3 to 25, e.g., 4 to 22, 4 to 18, or 4 to 10, or 3, 4, 5, 6, 7, 8, 9, 10, 11, 12, 13, 14, 15, 16, 17, 18, 19, 20, 21, 22, 23, 24, or 25 nucleotides in length. In some embodiments, the central subdomain is 1, 2, 3, 4 or 5, e.g., 3, nucleotides in length. In some embodiments, the 3' subdomain is 4 to 9, e.g., 4, 5, 6, 7, 8 or 9 nucleotides in length.

In some embodiments, the 5' subdomain and the 3' subdomain of the first complementarity domain, are respectively, complementary, e.g., fully complementary, with the 3' subdomain and the 5' subdomain of the second complementarity domain.

The second complementarity domain can share homology with or be derived from a naturally occurring second complementarity domain. In some embodiments, it has at least 50% homology with a second complementarity domain disclosed herein, e.g., an *S. pyogenes, S. aureus, N. meningtidis*, or *S. thermophilus*, first complementarity domain Some or all of the nucleotides of the second complementarity domain can have a modification, e.g., a modification described herein.

(g) The Proximal Domain

Examples of proximal domains include those described in WO2015/161276, e.g., in FIGS. 1A-1G therein. In some embodiments, the proximal domain is 5 to 20 nucleotides in length. In some embodiments, the proximal domain can share homology with or be derived from a naturally occurring proximal domain. In some embodiments, it has at least 50% homology with a proximal domain disclosed herein, e.g., an *S. pyogenes, S. aureus, N. meningtidis*, or *S. thermophilus*, proximal domain Some or all of the nucleotides of the proximal domain can have a modification along the lines described herein.

(h) The Tail Domain

As can be seen by inspection of the tail domains in WO2015/161276, e.g., in FIG. 1A and FIGS. 1B-1F therein, a broad spectrum of tail domains are suitable for use in gRNA molecules. In various embodiments, the tail domain is 0 (absent), 1, 2, 3, 4, 5, 6, 7, 8, 9, or 10 nucleotides in length. In certain embodiments, the tail domain nucleotides are from or share homology with sequence from the 5' end of a naturally occurring tail domain, see e.g., WO2015/161276, e.g., in FIG. 1D or 1E therein. The tail domain also optionally includes sequences that are complementary to each other and which, under at least some physiological conditions, form a duplexed region. Examples of tail domains include those described in WO2015/161276, e.g., in FIGS. 1A-1G therein.

Tail domains can share homology with or be derived from naturally occurring proximal tail domains. By way of non-limiting example, a given tail domain according to various embodiments of the present disclosure may share at least 50% homology with a naturally occurring tail domain disclosed herein, e.g., an *S. pyogenes, S. aureus, N. meningtidis*, or *S. thermophilus*, tail domain.

In certain cases, the tail domain includes nucleotides at the 3' end that are related to the method of in vitro or in vivo transcription. When a T7 promoter is used for in vitro transcription of the gRNA, these nucleotides may be any nucleotides present before the 3' end of the DNA template. When a U6 promoter is used for in vivo transcription, these nucleotides may be the sequence UUUUUU. When alternate pol-III promoters are used, these nucleotides may be various numbers or uracil bases or may include alternate bases.

As a non-limiting example, in various embodiments the proximal and tail domain, taken together comprise the following sequences:

```
                                         (SEQ ID NO: 104)
AAGGCUAGUCCGUUAUCAACUUGAAAAAGUGGCACCGAGUCGGUGCU,

                                         (SEQ ID NO: 105)
AAGGCUAGUCCGUUAUCAACUUGAAAAAGUGGCACCGAGUCGGUGGUGC,

                                         (SEQ ID NO: 106)
AAGGCUAGUCCGUUAUCAACUUGAAAAAGUGGCACCGAGUCGGUGCGGA

UC,

                                         (SEQ ID NO: 107)
AAGGCUAGUCCGUUAUCAACUUGAAAAAGUG,

                                         (SEQ ID NO: 108)
AAGGCUAGUCCGUUAUCA,
or

                                         (SEQ ID NO: 109)
AAGGCUAGUCCG.
```

In some embodiments, the tail domain comprises the 3' sequence UUUUUU, e.g., if a U6 promoter is used for transcription. In some embodiments, the tail domain comprises the 3' sequence UUUU, e.g., if an H1 promoter is used for transcription. In some embodiments, tail domain comprises variable numbers of 3' Us depending, e.g., on the termination signal of the pol-III promoter used. In some embodiments, the tail domain comprises variable 3' sequence derived from the DNA template if a T7 promoter is used. In some embodiments, the tail domain comprises variable 3' sequence derived from the DNA template, e.g., if in vitro transcription is used to generate the RNA molecule. In some embodiments, the tail domain comprises variable 3' sequence derived from the DNA template, e.g., if a pol-II promoter is used to drive transcription.

In some embodiments a gRNA has the following structure: 5' [targeting domain]-[first complementarity domain]-[linking domain]-[second complementarity domain]-[proximal domain]-[tail domain]-3', wherein, the targeting domain comprises a core domain and optionally a secondary domain, and is 10 to 50 nucleotides in length; the first complementarity domain is 5 to 25 nucleotides in length and, In some embodiments has at least 50, 60, 70, 80, 85, 90, 95, 98 or 99% homology with a reference first complementarity domain disclosed herein; the linking domain is 1 to 5 nucleotides in length; the proximal domain is 5 to 20 nucleotides in length and, In some embodiments has at least 50, 60, 70, 80, 85, 90, 95, 98 or 99% homology with a reference proximal domain disclosed herein; and the tail domain is absent or a nucleotide sequence is 1 to 50 nucleotides in length and, In some embodiments has at least 50, 60, 70, 80, 85, 90, 95, 98 or 99% homology with a reference tail domain disclosed herein.

(i) Exemplary Chimeric gRNAs

In some embodiments, a unimolecular, or chimeric, gRNA comprises, preferably from 5' to 3': a targeting domain, e.g., comprising 15, 16, 17, 18, 19, 20, 21, 22, 23, 24, 25, or 26 nucleotides (which is complementary to a target nucleic acid); a first complementarity domain; a linking domain; a second complementarity domain (which is complementary to the first complementarity domain); a proximal domain; and a tail domain, wherein, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In some embodiments, the sequence from (a), (b), or (c), has at least 60, 75, 80, 85, 90, 95, or 99% homology with the corresponding sequence of a naturally occurring gRNA, or with a gRNA described herein. In some embodiments, the proximal and tail domain, when taken together, comprise at least 15, 18, 20, 25, 30, 31, 35, 40, 45, 49, 50, or 53 nucleotides. In some embodiments, there are at least 15, 18, 20, 25, 30, 31, 35, 40, 45, 49, 50, or 53 nucleotides 3' to the last nucleotide of the second complementarity domain. In some embodiments, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain. In some embodiments, the targeting domain comprises, has, or consists of, 16, 17, 18, 19, 20, 21, 22, 23, 24, 25 or 26 nucleotides (e.g., 16, 17, 18, 19, 20, 21, 22, 23, 24, 25 or 26 consecutive nucleotides) having complementarity with the target domain, e.g., the targeting domain is 16, 17, 18, 19, 20, 21, 22, 23, 24, 25 or 26 nucleotides in length.

In some embodiments, the unimolecular, or chimeric, gRNA molecule (comprising a targeting domain, a first complementary domain, a linking domain, a second complementary domain, a proximal domain and, optionally, a tail domain) comprises the following sequence in which the targeting domain is depicted as 20 Ns but could be any sequence and range in length from 16 to 26 nucleotides and in which the gRNA sequence is followed by 6 Us, which serve as a termination signal for the U6 promoter, but which could be either absent or fewer in number: NNNNNNNNNNNNNNNNNNNNGUUUUAGAGCUAGAAAUAGCAAGUUAAAAUAAGGCUAG UCCGUUAUCAACUUGAAAAAGUGGCACCGAGUCGGUGCUUUUUU (SEQ ID NO:110). In some embodiments, the unimolecular, or chimeric, gRNA molecule is a *S. pyogenes* gRNA molecule.

In some embodiments, the unimolecular, or chimeric, gRNA molecule (comprising a targeting domain, a first complementary domain, a linking domain, a second complementary domain, a proximal domain and, optionally, a tail domain) comprises the following sequence in which the targeting domain is depicted as 20 Ns but could be any sequence and range in length from 16 to 26 nucleotides and in which the gRNA sequence is followed by 6 Us, which serve as a termination signal for the U6 promoter, but which could be either absent or fewer in number: NNNNNNNNNNNNNNNNNNNNGUUUUAGUACUCUGGAAACAGAAUCUACUAAAACAAGGC AAAAUGCCGUGUUUAUCUCGUCAACUUGUUGGCGAGAUUUUUU (SEQ ID NO:111). In some embodiments, the unimolecular, or chimeric, gRNA molecule is a *S. aureus* gRNA molecule. The sequences and structures of exemplary chimeric gRNAs are also shown in WO2015/161276, e.g., in FIGS. 10A-10B therein.

Any of the gRNA molecules as described herein can be used with any Cas9 molecules that generate a double strand break or a single strand break to alter the sequence of a target nucleic acid, e.g., a target position or target genetic signature. In some examples, the target nucleic acid is at or near the CD247 locus, such as any as described. In some embodiments, a ribonucleic acid molecule, such as a gRNA molecule, and a protein, such as a Cas9 protein or variants thereof, are introduced to any of the engineered cells provided herein. gRNA molecules useful in these methods are described below.

In some embodiments, the gRNA, e.g., a chimeric gRNA, is configured such that it comprises one or more of the following properties;

a) it can position, e.g., when targeting a Cas9 molecule that makes double strand breaks, a double strand break (i) within 50, 100, 150, 200, 250, 300, 350, 400, 450, or 500 nucleotides of a target position, or (ii) sufficiently close that the target position is within the region of end resection;
b) it has a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides; and
c) (i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. thermophilus, S. aureus*, or *N. meningitidis* tail and proximal domain, or a sequence that differs by no more than 1, 2, 3, 4, 5, 6, 7, 8, 9 or 10 nucleotides therefrom;
(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;
(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;
(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. thermophilus, S. aureus*, or *N. meningitidis* tail domain, or a sequence that differs by no more than 1, 2, 3, 4, 5; 6, 7, 8, 9 or 10 nucleotides therefrom; or
(v) the tail domain comprises 15, 20, 25, 30, 35, 40 nucleotides or all of the corresponding portions of a naturally occurring tail domain, e.g., a naturally occurring *S. pyogenes, S. thermophilus, S. aureus*, or *N. meningitidis* tail domain.

In some embodiments, the gRNA is configured such that it comprises properties: a and b(i). In some embodiments, the gRNA is configured such that it comprises properties: a and b(ii). In some embodiments, the gRNA is configured such that it comprises properties: a and b(iii). In some embodiments, the gRNA is configured such that it comprises properties: a and b(iv). In some embodiments, the gRNA is configured such that it comprises properties: a and b(v). In some embodiments, the gRNA is configured such that it comprises properties: a and b(vi). In some embodiments, the gRNA is configured such that it comprises properties: a and b(vii). In some embodiments, the gRNA is configured such that it comprises properties: a and b(viii). In some embodiments, the gRNA is configured such that it comprises properties: a and b(ix). In some embodiments, the gRNA is configured such that it comprises properties: a and b(x). In some embodiments, the gRNA is configured such that it comprises properties: a and b(xi). In some embodiments, the gRNA is configured such that it comprises properties: a and c. In some embodiments, the gRNA is configured such that in comprises properties: a, b, and c. In some embodiments, the gRNA is configured such that in comprises properties: a(i), b(i), and c(i). In some embodiments, the gRNA is configured such that in comprises properties: a(i), b(i), and c(ii). In some embodiments, the gRNA is configured such that in comprises properties: a(i), b(ii), and c(i). In some embodiments, the gRNA is configured such that in comprises properties: a(i), b(ii), and c(ii). In some embodiments, the gRNA is configured such that in comprises properties: a(i), b(iii), and c(i). In some embodiments, the gRNA is configured such that in comprises properties: a(i), b(iii), and c(ii). In some embodiments, the gRNA is configured such that in comprises properties: a(i), b(iv), and c(i). In some embodiments, the gRNA is configured such that in comprises properties: a(i), b(iv), and c(ii). In some embodiments, the gRNA is configured such that in comprises properties: a(i), b(v), and c(i). In some embodiments, the gRNA is configured such that in comprises properties: a(i), b(v), and c(ii). In some embodiments, the gRNA is configured such that in comprises properties: a(i), b(vi), and c(i). In some embodiments, the gRNA is configured such that in comprises properties: a(i), b(vi), and c(ii). In some embodiments, the gRNA is configured such that in comprises properties: a(i), b(vii), and c(i). In some embodiments, the gRNA is configured such that in comprises properties: a(i), b(vii), and c(ii). In some embodiments, the gRNA is configured such that in comprises properties: a(i), b(viii), and c(i). In some embodiments, the gRNA is configured such that in comprises properties: a(i), b(viii), and c(ii). In some embodiments, the gRNA is configured such that in comprises properties: a(i), b(ix), and c(i). In some embodiments, the gRNA is configured such that in comprises properties: a(i), b(ix), and c(ii). In some embodiments, the gRNA is configured such that in comprises properties: a(i), b(x), and c(i). In some embodiments, the gRNA is configured such that in comprises properties: a(i), b(x), and c(ii). In some embodiments, the gRNA is configured such that in comprises properties: a(i), b(xi), and c(i). In some embodiments, the gRNA is configured such that in comprises properties: a(i), b(xi), and c(ii).

In some embodiments, the gRNA, e.g., a chimeric gRNA, is configured such that it comprises one or more of the following properties;

a) one or both of the gRNAs can position, e.g., when targeting a Cas9 molecule that makes single strand breaks, a single strand break within (i) 50, 100, 150, 200, 250, 300, 350, 400, 450, or 500 nucleotides of a target position, or (ii) sufficiently close that the target position is within the region of end resection;

b) one or both have a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides; and c) (i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. thermophilus, S. aureus*, or *N. meningitidis* tail and proximal domain, or a sequence that differs by no more than 1, 2, 3, 4, 5; 6, 7, 8, 9 or 10 nucleotides therefrom;

(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;

(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;

(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. thermophilus, S. aureus*, or *N. meningitidis* tail domain, or a sequence that differs by no more than 1, 2, 3, 4, 5; 6, 7, 8, 9 or 10 nucleotides therefrom; or (v) the tail domain comprises 15, 20, 25, 30, 35, 40 nucleotides or all of the corresponding portions of a naturally occurring tail domain, e.g., a naturally occurring *S. pyogenes, S. thermophilus, S. aureus*, or *N. meningitidis* tail domain In some embodiments, the gRNA is configured such that it comprises properties: a and b(i). In some embodiments, the gRNA is configured such that it comprises properties: a and b(ii). In some embodiments, the gRNA is configured such that it comprises properties: a and b(iii). In some embodiments, the gRNA is configured such that it comprises properties: a and b(iv). In some embodiments, the gRNA is configured such that it comprises properties: a and b(v). In some embodiments, the gRNA is configured such that it comprises properties: a and b(vi). In some embodiments, the gRNA is configured such that it comprises properties: a and b(vii). In some embodiments, the gRNA is configured such that it comprises properties: a and b(viii). In some embodiments, the gRNA is configured such that it comprises properties: a and b(ix). In some embodiments, the gRNA is configured such that it comprises properties: a and b(x). In some embodiments, the gRNA is configured such that it comprises properties: a and b(xi). In some embodiments, the gRNA is configured such that it comprises properties: a and c. In some embodiments, the gRNA is configured such that in comprises properties: a, b, and c. In some embodiments, the gRNA is configured such that in comprises properties: a(i), b(i), and c(i). In some embodiments, the gRNA is configured such that in comprises properties: a(i), b(i), and c(ii). In some embodiments, the gRNA is configured such that in comprises properties: a(i), b(ii), and c(i). In some embodiments, the gRNA is configured such that in comprises properties: a(i), b(ii), and c(ii). In some embodiments, the gRNA is configured such that in comprises properties: a(i), b(iii), and c(i). In some embodiments, the gRNA is configured such that in comprises properties: a(i), b(iii), and c(ii). In some embodiments, the gRNA is configured such that in comprises properties: a(i), b(iv), and c(i). In some embodiments, the gRNA is configured such that in comprises properties: a(i), b(iv), and c(ii). In some embodiments, the gRNA is configured such that in comprises properties: a(i), b(v), and c(i). In some embodiments, the gRNA is configured such that in comprises properties: a(i), b(v), and c(ii). In some embodiments, the gRNA is configured such that in comprises properties: a(i), b(vi), and c(i). In some embodiments, the gRNA is configured such that in comprises properties: a(i), b(vi), and c(ii). In some embodiments, the gRNA is configured such that in comprises properties: a(i), b(vii), and c(i). In some embodiments, the gRNA is configured such that in comprises properties: a(i), b(vii), and c(ii). In some embodiments, the gRNA is configured such that in comprises properties: a(i), b(viii), and c(i). In some embodiments, the gRNA is configured such that in comprises properties: a(i), b(viii), and c(ii). In some embodiments, the gRNA is configured such that in comprises properties: a(i), b(ix), and c(i). In some embodiments, the gRNA is configured such that in comprises properties: a(i), b(ix), and c(ii). In some embodiments, the gRNA is configured such that in comprises properties: a(i), b(x), and c(i). In some embodiments, the gRNA is configured such that in comprises properties: a(i), b(x), and c(ii). In some embodiments, the gRNA is configured such that in comprises properties: a(i), b(xi), and c(i). In some embodiments, the gRNA is configured such that in comprises properties: a(i), b(xi), and c(ii).

In some embodiments, the gRNA is used with a Cas9 nickase molecule having HNH activity, e.g., a Cas9 molecule having the RuvC activity inactivated, e.g., a Cas9 molecule having a mutation at D10, e.g., the D10A mutation.

In some embodiments, the gRNA is used with a Cas9 nickase molecule having RuvC activity, e.g., a Cas9 molecule having the HNH activity inactivated, e.g., a Cas9 molecule having a mutation at H840, e.g., a H840A.

In some embodiments, a pair of gRNAs, e.g., a pair of chimeric gRNAs, comprising a first and a second gRNA, is configured such that they comprises one or more of the following properties;

a) one or both of the gRNAs can position, e.g., when targeting a Cas9 molecule that makes single strand breaks, a single strand break within (i) 50, 100, 150, 200, 250, 300, 350, 400, 450, or 500 nucleotides of a target position, or (ii) sufficiently close that the target position is within the region of end resection;

b) one or both have a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides;

c) for one or both:

(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. thermophilus, S. aureus*, or *N. meningitidis* tail and proximal domain, or a sequence that differs by no more than 1, 2, 3, 4, 5; 6, 7, 8, 9 or 10 nucleotides therefrom;

(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;

(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;

(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. thermophilus, S. aureus*, or *N. meningitidis* tail domain; or, or a sequence that differs by no more than 1, 2, 3, 4, 5; 6, 7, 8, 9 or 10 nucleotides therefrom; or (v) the tail domain comprises 15, 20, 25, 30, 35, 40 nucleotides or all of the corresponding portions of a naturally occurring tail domain, e.g., a naturally occurring *S. pyogenes, S. thermophilus, S. aureus*, or *N. meningitidis* tail domain;

d) the gRNAs are configured such that, when hybridized to target nucleic acid, they are separated by 0-50, 0-100, 0-200, at least 10, at least 20, at least 30 or at least 50 nucleotides;

e) the breaks made by the first gRNA and second gRNA are on different strands; and f) the PAMs are facing outwards.

In some embodiments, one or both of the gRNAs is configured such that it comprises properties: a and b(i). In some embodiments, one or both of the gRNAs is configured such that it comprises properties: a and b(ii). In some embodiments, one or both of the gRNAs is configured such that it comprises properties: a and b(iii). In some embodiments, one or both of the gRNAs is configured such that it comprises properties: a and b(iv). In some embodiments, one or both of the gRNAs is configured such that it comprises properties: a and b(v). In some embodiments, one or both of the gRNAs is configured such that it comprises properties: a and b(vi). In some embodiments, one or both of the gRNAs is configured such that it comprises properties: a and b(vii). In some embodiments, one or both of the gRNAs is configured such that it comprises properties: a and b(viii). In some embodiments, one or both of the gRNAs is configured such that it comprises properties: a and b(ix). In some embodiments, one or both of the gRNAs is configured such that it comprises properties: a and b(x). In some embodiments, one or both of the gRNAs is configured such that it comprises properties: a and b(xi). In some embodiments, one or both of the gRNAs configured such that it comprises properties: a and c. In some embodiments, one or both of the gRNAs is configured such that it comprises properties: a, b, and c. In some embodiments, one or both of the gRNAs is configured such that it comprises properties: a(i), b(i), and c(i). In some embodiments, one or both of the gRNAs is configured such that it comprises properties: a(i), b(i), and c(ii). In some embodiments, one or both of the gRNAs is configured such that it comprises properties: a(i), b(i), c, and d. In some embodiments, one or both of the gRNAs is configured such that it comprises properties: a(i), b(i), c, and e. In some embodiments, one or both of the gRNAs is configured such that it comprises properties: a(i), b(i), c, d, and e. In some embodiments, one or both of the gRNAs is configured such that it comprises properties: a(i), b(ii), and c(i). In some embodiments, one or both of the gRNAs is configured such that it comprises properties: a(i), b(ii), and c(ii). In some embodiments, one or both of the gRNAs is configured such that it comprises properties: a(i), b(ii), c, and d. In some embodiments, one or both of the gRNAs is configured such that it comprises properties: a(i), b(ii), c, and e. In some embodiments, one or both of the gRNAs is configured such that it comprises properties: a(i), b(ii), c, d, and e. In some embodiments, one or both of the gRNAs is configured such that it comprises properties: a(i), b(iii), and c(i). In some embodiments, one or both of the gRNAs is configured such that it comprises properties: a(i), b(iii), and c(ii). In some embodiments, one or both of the gRNAs is configured such that it comprises properties: a(i), b(iii), c, and d. In some embodiments, one or both of the gRNAs is configured such that it comprises properties: a(i), b(iii), c, and e. In some embodiments, one or both of the gRNAs is configured such that it comprises properties: a(i), b(iii), c, d, and e. In some embodiments, one or both of the gRNAs is configured such that it comprises properties: a(i), b(iv), and c(i). In some embodiments, one or both of the gRNAs is configured such that it comprises properties: a(i), b(iv), and c(ii). In some embodiments, one or both of the gRNAs is configured such that it comprises properties: a(i), b(iv), c, and d. In some embodiments, one or both of the gRNAs is configured such that it comprises properties: a(i), b(iv), c, and e. In some embodiments, one or both of the gRNAs is configured such that it comprises properties: a(i), b(iv), c, d, and e. In some embodiments, one or both of the gRNAs is configured such that it comprises properties: a(i), b(v), and c(i). In some embodiments, one or both of the gRNAs is configured such that it comprises properties: a(i), b(v), and c(ii). In some embodiments, one or both of the gRNAs is configured such that it comprises properties: a(i), b(v), c, and d. In some embodiments, one or both of the gRNAs is configured such that it comprises properties: a(i), b(v), c, and e. In some embodiments, one or both of the gRNAs is configured such that it comprises properties: a(i), b(v), c, d, and e. In some embodiments, one or both of the gRNAs is configured such that it comprises properties: a(i), b(vi), and c(i). In some embodiments, one or both of the gRNAs is configured such that it comprises properties: a(i), b(vi), and c(ii). In some embodiments, one or both of the gRNAs is configured such that it comprises properties: a(i), b(vi), c, and d. In some embodiments, one or both of the gRNAs is configured such that it comprises properties: a(i), b(vi), c, and e. In some embodiments, one or both of the gRNAs is configured such that it comprises properties: a(i), b(vi), c, d, and e. In some embodiments, one or both of the gRNAs is configured such that it comprises properties: a(i), b(vii), and c(i). In some embodiments, one or both of the gRNAs is configured such that it comprises properties: a(i), b(vii), and c(ii). In some embodiments, one or both of the gRNAs is configured such that it comprises properties: a(i), b(vii), c, and d. In some embodiments, one or both of the gRNAs is configured such that it comprises properties: a(i), b(vii), c, and e. In some embodiments, one or both of the gRNAs is configured such that it comprises properties: a(i), b(vii), c, d, and e. In some embodiments, one or both of the gRNAs is configured such that it comprises properties: a(i), b(viii), and c(i). In some embodiments, one or both of the gRNAs is configured such that it comprises properties: a(i), b(viii), and c(ii). In some embodiments, one or both of the gRNAs is configured such that it comprises properties: a(i), b(viii), c, and d. In some embodiments, one or both of the gRNAs is configured such that it comprises properties: a(i), b(viii), c, and e. In some embodiments, one or both of the gRNAs is configured such that it comprises properties: a(i), b(viii), c, d, and e. In some embodiments, one or both of the gRNAs is configured such that it comprises properties: a(i), b(ix), and c(i). In some embodiments, one or both of the gRNAs is configured such that it comprises properties: a(i), b(ix), and c(ii). In some embodiments, one or both of the gRNAs is configured such that it comprises properties: a(i), b(ix), c, and d. In some embodiments, one or both of the gRNAs is configured such that it comprises properties: a(i), b(ix), c, and e. In some embodiments, one or both of the gRNAs is configured such that it comprises properties: a(i), b(ix), c, d, and e. In some embodiments, one or both of the gRNAs is configured such that it comprises properties: a(i), b(x), and c(i). In some embodiments, one or both of the gRNAs is configured such that it comprises properties: a(i), b(x), and c(ii). In some embodiments, one or both of the gRNAs is configured such that it comprises properties: a(i), b(x), c, and d. In some embodiments, one or both of the gRNAs is configured such that it comprises properties: a(i), b(x), c, and e. In some embodiments, one or both of the gRNAs is configured such that it comprises properties: a(i), b(x), c, d, and e. In some embodiments, one or both of the gRNAs is configured such that it comprises properties: a(i), b(xi), and c(i). In some embodiments, one or both of the gRNAs is configured such that it comprises properties: a(i), b(xi), and c(ii). In some embodiments, one or both of the gRNAs is configured such that it comprises properties: a(i), b(xi), c, and d. In some embodiments, one or both of the gRNAs is configured such that it comprises properties: a(i), b(xi), c, and e. In some embodiments, one or both of the gRNAs is configured such that it comprises properties: a(i), b(xi), c, d, and e.

In some embodiments, the gRNAs are used with a Cas9 nickase molecule having HNH activity, e.g., a Cas9 molecule having the RuvC activity inactivated, e.g., a Cas9 molecule having a mutation at D10, e.g., the D10A mutation.

In some embodiments, the gRNAs are used with a Cas9 nickase molecule having RuvC activity, e.g., a Cas9 molecule having the HNH activity inactivated, e.g., a Cas9 molecule having a mutation at H840, e.g., a H840A. In some embodiments, the gRNAs are used with a Cas9 nickase molecule having RuvC activity, e.g., a Cas9 molecule having the HNH activity inactivated, e.g., a Cas9 molecule having a mutation at N863, e.g., N863A.

(j) Exemplary Modular gRNAs

In some embodiments, a modular gRNA comprises first and second strands. The first strand comprises, preferably from 5' to 3'; a targeting domain, e.g., comprising 15, 16, 17, 18, 19, 20, 21, 22, 23, 24, 25, or 26 nucleotides; a first complementarity domain. The second strand comprises, preferably from 5' to 3': optionally a 5' extension domain; a second complementarity domain; a proximal domain; and a tail domain, wherein: (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In some embodiments, the sequence from (a), (b), or (c), has at least 60, 75, 80, 85, 90, 95, or 99% homology with the corresponding sequence of a naturally occurring gRNA, or with a gRNA described herein. In some embodiments, the proximal and tail domain, when taken together, comprise at least 15, 18, 20, 25, 30, 31, 35, 40, 45, 49, 50, or 53 nucleotides. In some embodiments there are at least 15, 18, 20, 25, 30, 31, 35, 40, 45, 49, 50, or 53 nucleotides 3' to the last nucleotide of the second complementarity domain.

In some embodiments, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In some embodiments, the targeting domain has, or consists of, 16, 17, 18, 19, 20, 21, 22, 23, 24, 25 or 26 nucleotides (e.g., 16, 17, 18, 19, 20, 21, 22, 23, 24, 25 or 26 consecutive nucleotides) having complementarity with the target domain, e.g., the targeting domain is 16, 17, 18, 19, 20, 21, 22, 23, 24, 25 or 26 nucleotides in length.

(k) Methods for Designing gRNAs

Methods for designing gRNAs are described herein, including methods for selecting, designing and validating targeting domains. Exemplary targeting domains are also provided herein. Targeting domains discussed herein can be incorporated into the gRNAs described herein.

Methods for selection and validation of target sequences as well as off-target analyses are described, e.g., in Mali et al., 2013 Science 339(6121): 823-826; Hsu et al. Nat Biotechnol, 31(9): 827-32; Fu et al., 2014 Nat Biotechnol, doi: 10.1038/nbt.2808. PubMed PMID: 24463574; Heigwer et al., 2014 Nat Methods 11(2):122-3. doi: 10.1038/nmeth.2812. PubMed PMID: 24481216; Bae et al., 2014 Bioinformatics PubMed PMID: 24463181; Xiao A et al., 2014 Bioinformatics PubMed PMID: 24389662.

In some embodiments, a software tool can be used to optimize the choice of gRNA within a user's target sequence, e.g., to minimize total off-target activity across the genome. Off target activity may be other than cleavage. For example, for each possible gRNA choice using *S. pyogenes* Cas9, software tools can identify all potential off-target sequences (preceding either NAG or NGG PAMs) across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA can then be ranked according to its total predicted off-target cleavage; the top-ranked gRNAs represent those that are likely to have the greatest on-target and the least off-target cleavage. Other functions, e.g., automated reagent design for gRNA vector construction, primer design for the on-target Surveyor assay, and primer design for high-throughput detection and quantification of off-target cleavage via next-generation sequencing, can also be included in the tool. Candidate gRNA molecules can be evaluated by art-known methods or as described herein.

In some embodiments, gRNAs for use with *S. pyogenes, S. aureus*, and *N. meningitidis* Cas9s are identified using a DNA sequence searching algorithm, e.g., using a custom gRNA design software based on the public tool cas-offinder (Bae et al. Bioinformatics. 2014; 30(10): 1473-1475). The custom gRNA design software scores guides after calculating their genome-wide off-target propensity. Typically matches ranging from perfect matches to 7 mismatches are considered for guides ranging in length from 17 to 24. In some aspects, once the off-target sites are computationally determined, an aggregate score is calculated for each guide and summarized in a tabular output using a web-interface. In addition to identifying potential gRNA sites adjacent to PAM sequences, the software also can identify all PAM adjacent sequences that differ by 1, 2, 3 or more nucleotides from the selected gRNA sites. In some embodiments, Genomic DNA sequences for each gene are obtained from the UCSC Genome browser and sequences can be screened for repeat elements using the publicly available RepeatMasker program. RepeatMasker searches input DNA sequences for repeated elements and regions of low complexity. The output is a detailed annotation of the repeats present in a given query sequence.

Following identification, gRNAs can be ranked into tiers based on one or more of their distance to the target site, their orthogonality and presence of a 5' G (based on identification of close matches in the human genome containing a relevant PAM, e.g., in the case of *S. pyogenes*, a NGG PAM, in the case of *S. aureus*, NNGRR (e.g., a NNGRRT or NNGRRV) PAM, and in the case of *N. meningtidis*, a NNNNGATT or NNNNGCTT PAM). Orthogonality refers to the number of sequences in the human genome that contain a minimum number of mismatches to the target sequence. A "high level of orthogonality" or "good orthogonality" may, for example, refer to 20-mer targeting domains that have no identical sequences in the human genome besides the intended target, nor any sequences that contain one or two mismatches in the target sequence. Targeting domains with good orthogonality are selected to minimize off-target DNA cleavage. It is to be understood that this is a non-limiting example and that a variety of strategies could be utilized to identify gRNAs for use with *S. pyogenes, S. aureus* and *N. meningitidis* or other Cas9 enzymes.

In some embodiments, gRNAs for use with the *S. pyogenes* Cas9 can be identified using the publicly available web-based ZiFiT server (Fu et al., Improving CRISPR-Cas nuclease specificity using truncated guide RNAs. Nat Biotechnol. 2014 Jan. 26. doi: 10.1038/nbt.2808. PubMed PMID: 24463574, for the original references see Sander et al., 2007, NAR 35:W599-605; Sander et al., 2010, NAR 38: W462-8). In addition to identifying potential gRNA sites adjacent to PAM sequences, the software also identifies all PAM adjacent sequences that differ by 1, 2, 3 or more nucleotides from the selected gRNA sites. In some aspects, genomic DNA sequences for each gene can be obtained from the UCSC Genome browser and sequences can be screened for repeat elements using the publicly available Repeat-Masker program. RepeatMasker searches input DNA sequences for repeated elements and regions of low complexity. The output is a detailed annotation of the repeats present in a given query sequence.

Following identification, gRNAs for use with a *S. pyogenes* Cas9 can be ranked into tiers, e.g. into 5 tiers. In some embodiments, the targeting domains for first tier gRNA molecules are selected based on their distance to the target site, their orthogonality and presence of a 5' G (based on the ZiFiT identification of close matches in the human genome containing an NGG PAM). In some embodiments, both 17-mer and 20-mer gRNAs are designed for targets. In some aspects, gRNAs are also selected both for single-gRNA nuclease cutting and for the dual gRNA nickase strategy. Criteria for selecting gRNAs and the determination for which gRNAs can be used for which strategy can be based on several considerations. In some embodiments, gRNAs for both single-gRNA nuclease cleavage and for a dual-gRNA paired "nickase" strategy are identified. In some embodiments for selecting gRNAs, including the determination for which gRNAs can be used for the dual-gRNA paired "nickase" strategy, gRNA pairs should be oriented on the DNA such that PAMs are facing out and cutting with the D10A Cas9 nickase will result in 5' overhangs. In some aspects, it can be assumed that cleaving with dual nickase pairs will result in deletion of the entire intervening sequence at a reasonable frequency. However, cleaving with dual nickase pairs can also often result in indel mutations at the site of only one of the gRNAs. Candidate pair members can be tested for how efficiently they remove the entire sequence versus just causing indel mutations at the site of one gRNA.

In some embodiments, the targeting domains for first tier gRNA molecules can be selected based on (1) a reasonable distance to the target position, e.g., within the first 500 bp of coding sequence downstream of start codon, (2) a high level of orthogonality, and (3) the presence of a 5' G. In some embodiments, for selection of second tier gRNAs, the requirement for a 5'G can be removed, but the distance restriction is required and a high level of orthogonality was required. In some embodiments, third tier selection uses the same distance restriction and the requirement for a 5'G, but removes the requirement of good orthogonality. In some embodiments, fourth tier selection uses the same distance restriction but removes the requirement of good orthogonality and start with a 5'G. In some embodiments, fifth tier selection removes the requirement of good orthogonality and a 5'G, and a longer sequence (e.g., the rest of the coding sequence, e.g., additional 500 bp upstream or downstream to the transcription target site) is scanned. In certain instances, no gRNA is identified based on the criteria of the particular tier.

In some embodiments, gRNAs are identified for single-gRNA nuclease cleavage as well as for a dual-gRNA paired "nickase" strategy.

In some aspects, gRNAs for use with the *N. meningitidis* and *S. aureus* Cas9s can be identified manually by scanning genomic DNA sequence for the presence of PAM sequences. These gRNAs can be separated into two tiers. In some embodiments, for first tier gRNAs, targeting domains are selected within the first 500 bp of coding sequence downstream of start codon. In some embodiments, for second tier gRNAs, targeting domains are selected within the remaining coding sequence (downstream of the first 500 bp). In certain instances, no gRNA is identified based on the criteria of the particular tier.

In some embodiments, another strategy for identifying guide RNAs (gRNAs) for use with *S. pyogenes, S. aureus* and *N. meningtidis* Cas9s can use a DNA sequence searching algorithm. In some aspects, guide RNA design is carried out using a custom guide RNA design software based on the public tool cas-offinder (Bae et al. Bioinformatics. 2014; 30(10): 1473-1475). Said custom guide RNA design software scores guides after calculating their genome wide off-target propensity. Typically matches ranging from perfect matches to 7 mismatches are considered for guides ranging in length from 17 to 24. Once the off-target sites are computationally determined, an aggregate score is calculated for each guide and summarized in a tabular output using a web-interface. In addition to identifying potential gRNA sites adjacent to PAM sequences, the software also identifies all PAM adjacent sequences that differ by 1, 2, 3 or more nucleotides from the selected gRNA sites. In some embodiments, genomic DNA sequence for each gene is obtained from the UCSC Genome browser and sequences are screened for repeat elements using the publically available RepeatMasker program. RepeatMasker searches input DNA sequences for repeated elements and regions of low complexity. The output is a detailed annotation of the repeats present in a given query sequence.

In some embodiments, following identification, gRNAs are ranked into tiers based on their distance to the target site or their orthogonality (based on identification of close matches in the human genome containing a relevant PAM, e.g., in the case of *S. pyogenes*, a NGG PAM, in the case of *S. aureus*, NNGRR (e.g., a NNGRRT or NNGRRV) PAM, and in the case of *N. meningtidis*, a NNNNGATT or NNNNGCTT PAM. In some aspects, targeting domains with good orthogonality are selected to minimize off-target DNA cleavage.

As an example, for *S. pyogenes* and *N. meningtidis* targets, 17-mer, or 20-mer gRNAs can be designed. As another example, for *S. aureus* targets, 18-mer, 19-mer, 20-mer, 21-mer, 22-mer, 23-mer and 24-mer gRNAs can be designed.

In some embodiments, gRNAs for both single-gRNA nuclease cleavage and for a dual-gRNA paired "nickase" strategy are identified. In some embodiments for selecting gRNAs, including the determination for which gRNAs can be used for the dual-gRNA paired "nickase" strategy, gRNA pairs should be oriented on the DNA such that PAMs are facing out and cutting with the D10A Cas9 nickase will result in 5' overhangs. In some aspects, it can be assumed that cleaving with dual nickase pairs will result in deletion of the entire intervening sequence at a reasonable frequency. However, cleaving with dual nickase pairs can also often result in indel mutations at the site of only one of the gRNAs. Candidate pair members can be tested for how efficiently they remove the entire sequence versus just causing indel mutations at the site of one gRNA.

For designing strategies for genetic disruption, in some embodiments, the targeting domains for tier 1 gRNA molecules for *S. pyogenes* are selected based on their distance to the target site and their orthogonality (PAM is NGG). In some cases, the targeting domains for tier 1 gRNA molecules are selected based on (1) a reasonable distance to the target position, e.g., within the first 500 bp of coding sequence downstream of start codon and (2) a high level of orthogonality. In some aspects, for selection of tier 2 gRNAs, a high level of orthogonality is not required. In some cases, tier 3 gRNAs remove the requirement of good orthogonality and a longer sequence (e.g., the rest of the coding sequence) can be scanned. In certain instances, no gRNA is identified based on the criteria of the particular tier.

For designing strategies for genetic disruption, in some embodiments, the targeting domain for tier 1 gRNA molecules for *N. meningtidis* were selected within the first 500 bp of the coding sequence and had a high level of orthogonality. The targeting domain for tier 2 gRNA molecules for *N. meningtidis* were selected within the first 500 bp of the coding sequence and did not require high orthogonality. The targeting domain for tier 3 gRNA molecules for *N. meningtidis* were selected within a remainder of coding sequence downstream of the 500 bp. Note that tiers are non-inclusive (each gRNA is listed only once). In certain instances, no gRNA was identified based on the criteria of the particular tier.

For designing strategies for genetic disruption, in some embodiments, the targeting domain for tier 1 gRNA molecules for *S. aureus* is selected within the first 500 bp of the coding sequence, has a high level of orthogonality, and contains a NNGRRT PAM. In some embodiments, the targeting domain for tier 2 gRNA molecules for *S. aureus* is selected within the first 500 bp of the coding sequence, no level of orthogonality is required, and contains a NNGRRT PAM. In some embodiments, the targeting domain for tier 3 gRNA molecules for *S. aureus* are selected within the remainder of the coding sequence downstream and contain a NNGRRT PAM. In some embodiments, the targeting domain for tier 4 gRNA molecules for *S. aureus* are selected within the first 500 bp of the coding sequence and contain a NNGRRV PAM. In some embodiments, the targeting domain for tier 5 gRNA molecules for *S. aureus* are selected within the remainder of the coding sequence downstream and contain a NNGRRV PAM. In certain instances, no gRNA is identified based on the criteria of the particular tier.

(ii) Cas9

Cas9 molecules of a variety of species can be used in the methods and compositions described herein. While the *S. pyogenes, S. aureus, N. meningitidis*, and *S. thermophilus* Cas9 molecules are the subject of much of the disclosure herein, Cas9 molecules of, derived from, or based on the Cas9 proteins of other species listed herein can be used as well. In other words, while the much of the description herein uses *S. pyogenes, S. aureus, N. meningitidis*, and *S. thermophilus* Cas9 molecules, Cas9 molecules from the other species can replace them. Such species include: *Acidovorax avenae, Actinobacillus pleuropneumoniae, Actinobacillus succinogenes, Actinobacillus suis, Actinomyces* sp., *Cycliphilusdenitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., or *Verminephrobacter eiseniae*. Examples of Cas9 molecules can include those described in, e.g., WO2015/161276, WO2017/193107, WO2017/093969, US2016/272999 and US2015/056705.

A Cas9 molecule, or Cas9 polypeptide, as that term is used herein, refers to a molecule or polypeptide that can interact with a gRNA molecule and, in concert with the gRNA molecule, homes or localizes to a site which comprises a target domain and PAM sequence. Cas9 molecule and Cas9 polypeptide, as those terms are used herein, refer to naturally occurring Cas9 molecules and to engineered, altered, or modified Cas9 molecules or Cas9 polypeptides that differ, e.g., by at least one amino acid residue, from a reference sequence, e.g., the most similar naturally occurring Cas9 molecule.

Crystal structures have been determined for two different naturally occurring bacterial Cas9 molecules (Jinek et al., Science, 343(6176):1247997, 2014) and for *S. pyogenes* Cas9 with a guide RNA (e.g., a synthetic fusion of crRNA and tracrRNA) (Nishimasu et al., Cell, 156:935-949, 2014; and Anders et al., Nature, 2014, doi: 10.1038/nature13579).

A naturally occurring Cas9 molecule comprises two lobes: a recognition (REC) lobe and a nuclease (NUC) lobe; each of which further comprises domains described herein. An exemplary schematic of the organization of important Cas9 domains in the primary structure is described in WO2015/161276, e.g., in FIGS. 8A-8B therein. The domain nomenclature and the numbering of the amino acid residues encompassed by each domain used throughout this disclosure is as described in Nishimasu et al. The numbering of the amino acid residues is with reference to Cas9 from *S. pyogenes.*

The REC lobe comprises the arginine-rich bridge helix (BH), the REC1 domain, and the REC2 domain. The REC lobe does not share structural similarity with other known proteins, indicating that it is a Cas9-specific functional domain. The BH domain is a long α-helix and arginine rich region and comprises amino acids 60-93 of the sequence of *S. pyogenes* Cas9. The REC1 domain is important for recognition of the repeat:anti-repeat duplex, e.g., of a gRNA or a tracrRNA, and is therefore critical for Cas9 activity by recognizing the target sequence. The REC1 domain comprises two REC1 motifs at amino acids 94 to 179 and 308 to 717 of the sequence of *S. pyogenes* Cas9. These two REC1 domains, though separated by the REC2 domain in the linear primary structure, assemble in the tertiary structure to form the REC1 domain. The REC2 domain, or parts thereof, may also play a role in the recognition of the repeat:anti-repeat duplex. The REC2 domain comprises amino acids 180-307 of the sequence of *S. pyogenes* Cas9.

The NUC lobe comprises the RuvC domain (also referred to herein as RuvC-like domain), the HNH domain (also referred to herein as HNH-like domain), and the PAM-interacting (PI) domain. The RuvC domain shares structural similarity to retroviral integrase superfamily members and cleaves a single strand, e.g., the non-complementary strand of the target nucleic acid molecule. The RuvC domain is assembled from the three split RuvC motifs (RuvC I, RuvCII, and RuvCIII, which are often commonly referred to as RuvCI domain, or N-terminal RuvC domain, RuvCII domain, and RuvCIII domain) at amino acids 1-59, 718-769, and 909-1098, respectively, of the sequence of *S. pyogenes* Cas9. Similar to the REC1 domain, the three RuvC motifs are linearly separated by other domains in the primary structure, however in the tertiary structure, the three RuvC motifs assemble and form the RuvC domain. The HNH domain shares structural similarity with HNH endonucleases, and cleaves a single strand, e.g., the complementary strand of the target nucleic acid molecule. The HNH domain lies between the RuvC II-III motifs and comprises amino acids 775-908 of the sequence of *S. pyogenes* Cas9. The PI domain interacts with the PAM of the target nucleic acid molecule, and comprises amino acids 1099-1368 of the sequence of *S. pyogenes* Cas9.

(a) A RuvC-Like Domain and an HNH-Like Domain

In some embodiments, a Cas9 molecule or Cas9 polypeptide comprises an HNH-like domain and a RuvC-like domain. In some embodiments, cleavage activity is dependent on a RuvC-like domain and an HNH-like domain A Cas9 molecule or Cas9 polypeptide, e.g., an eaCas9 molecule or eaCas9 polypeptide, can comprise one or more of the following domains: a RuvC-like domain and an HNH-like domain. In some embodiments, a Cas9 molecule or Cas9 polypeptide is an eaCas9 molecule or eaCas9 polypeptide and the eaCas9 molecule or eaCas9 polypeptide comprises a RuvC-like domain, e.g., a RuvC-like domain described herein, and/or an HNH-like domain, e.g., an HNH-like domain described herein.

(b) RuvC-Like Domains

In some embodiments, a RuvC-like domain cleaves, a single strand, e.g., the non-complementary strand of the target nucleic acid molecule. The Cas9 molecule or Cas9 polypeptide can include more than one RuvC-like domain (e.g., one, two, three or more RuvC-like domains). In some embodiments, a RuvC-like domain is at least 5, 6, 7, 8 amino acids in length but not more than 20, 19, 18, 17, 16 or 15 amino acids in length. In some embodiments, the Cas9 molecule or Cas9 polypeptide comprises an N-terminal RuvC-like domain of about 10 to 20 amino acids, e.g., about 15 amino acids in length.

(c) N-Terminal RuvC-Like Domains

Some naturally occurring Cas9 molecules comprise more than one RuvC-like domain with cleavage being dependent on the N-terminal RuvC-like domain. Accordingly, Cas9 molecules or Cas9 polypeptide can comprise an N-terminal RuvC-like domain In embodiment, the N-terminal RuvC-like domain is cleavage competent.

In embodiment, the N-terminal RuvC-like domain is cleavage incompetent.

In some embodiments, the N-terminal RuvC-like domain differs from a sequence of an N-terminal RuvC like domain disclosed herein, e.g., in WO2015/161276, e.g., in FIGS. 3A-3B or FIGS. 7A-7B therein, as many as 1 but no more than 2, 3, 4, or 5 residues. In some embodiments, 1, 2, or all 3 of the highly conserved residues identified WO2015/161276, e.g., in FIGS. 3A-3B or FIGS. 7A-7B therein are present.

In some embodiments, the N-terminal RuvC-like domain differs from a sequence of an N-terminal RuvC-like domain disclosed herein, e.g., in WO2015/161276, e.g., in FIGS. 4A-4B or FIGS. 7A-7B therein, as many as 1 but no more than 2, 3, 4, or 5 residues. In some embodiments, 1, 2, 3 or all 4 of the highly conserved residues identified in WO2015/161276, e.g., in FIGS. 4A-4B or FIGS. 7A-7B therein are present.

(d) Additional RuvC-Like Domains

In addition to the N-terminal RuvC-like domain, the Cas9 molecule or Cas9 polypeptide, e.g., an eaCas9 molecule or eaCas9 polypeptide, can comprise one or more additional RuvC-like domains. In some embodiments, the Cas9 molecule or Cas9 polypeptide can comprise two additional RuvC-like domains. Preferably, the additional RuvC-like domain is at least 5 amino acids in length and, e.g., less than 15 amino acids in length, e.g., 5 to 10 amino acids in length, e.g., 8 amino acids in length.

(e) HNH-Like Domains

In some embodiments, an HNH-like domain cleaves a single stranded complementary domain, e.g., a complementary strand of a double stranded nucleic acid molecule. In some embodiments, an HNH-like domain is at least 15, 20, 25 amino acids in length but not more than 40, 35 or 30 amino acids in length, e.g., 20 to 35 amino acids in length, e.g., 25 to 30 amino acids in length. Exemplary HNH-like domains are described herein.

In some embodiments, the HNH-like domain is cleavage competent.

In some embodiments, the HNH-like domain is cleavage incompetent.

In some embodiments, the HNH-like domain differs from a sequence of an HNH-like domain disclosed herein, e.g., in WO2015/161276, e.g., in FIGS. 5A-5C or FIGS. 7A-7B therein, as many as 1 but no more than 2, 3, 4, or 5 residues. In some embodiments, 1 or both of the highly conserved residues identified in WO2015/161276, e.g., in FIGS. 5A-5C or FIGS. 7A-7B therein are present.

In some embodiments, the HNH-like domain differs from a sequence of an HNH-like domain disclosed herein, e.g., in WO2015/161276, e.g., in FIGS. 6A-6B or FIGS. 7A-7B therein, as many as 1 but no more than 2, 3, 4, or 5 residues. In some embodiments, 1, 2, all 3 of the highly conserved residues identified in WO2015/161276, e.g., in FIGS. 6A-6B or FIGS. 7A-7B therein are present.

(f) Nuclease and Helicase Activities

In some embodiments, the Cas9 molecule or Cas9 polypeptide is capable of cleaving a target nucleic acid molecule. Typically wild type Cas9 molecules cleave both strands of a target nucleic acid molecule. Cas9 molecules and Cas9 polypeptides can be engineered to alter nuclease cleavage (or other properties), e.g., to provide a Cas9 molecule or Cas9 polypeptide which is a nickase, or which lacks the ability to cleave target nucleic acid. A Cas9 molecule or Cas9 polypeptide that is capable of cleaving a target nucleic acid molecule is referred to herein as an eaCas9 molecule or eaCas9 polypeptide.

In some embodiments, an eaCas9 molecule or eaCas9 polypeptide comprises one or more of the following activities: a nickase activity, i.e., the ability to cleave a single strand, e.g., the non-complementary strand or the complementary strand, of a nucleic acid molecule; a double stranded nuclease activity, i.e., the ability to cleave both strands of a double stranded nucleic acid and create a double stranded break, which In some embodiments is the presence of two nickase activities; an endonuclease activity; an exonuclease activity; and a helicase activity, i.e., the ability to unwind the helical structure of a double stranded nucleic acid.

In some embodiments, an enzymatically active or eaCas9 molecule or eaCas9 polypeptide cleaves both strands and results in a double stranded break. In some embodiments, an eaCas9 molecule cleaves only one strand, e.g., the strand to which the gRNA hybridizes to, or the strand complementary to the strand the gRNA hybridizes with. In some embodiments, an eaCas9 molecule or eaCas9 polypeptide comprises cleavage activity associated with an HNH-like domain. In some embodiments, an eaCas9 molecule or eaCas9 polypeptide comprises cleavage activity associated with an N-terminal RuvC-like domain. In some embodiments, an eaCas9 molecule or eaCas9 polypeptide comprises cleavage activity associated with an HNH-like domain and cleavage activity associated with an N-terminal RuvC-like domain. In some embodiments, an eaCas9 molecule or eaCas9 polypeptide comprises an active, or cleavage competent, HNH-like domain and an inactive, or cleavage incompetent, N-terminal RuvC-like domain. In some embodiments, an eaCas9 molecule or eaCas9 polypeptide comprises an inactive, or cleavage incompetent, HNH-like domain and an active, or cleavage competent, N-terminal RuvC-like domain.

Some Cas9 molecules or Cas9 polypeptides have the ability to interact with a gRNA molecule, and in conjunction with the gRNA molecule localize to a core target domain, but are incapable of cleaving the target nucleic acid, or incapable of cleaving at efficient rates. Cas9 molecules having no, or no substantial, cleavage activity are referred to herein as an eiCas9 molecule or eiCas9 polypeptide. For example, an eiCas9 molecule or eiCas9 polypeptide can lack cleavage activity or have substantially less, e.g., less than 20, 10, 5, 1 or 0.1% of the cleavage activity of a reference Cas9 molecule or eiCas9 polypeptide, as measured by an assay described herein.

(g) Targeting and PAMs

A Cas9 molecule or Cas9 polypeptide, is a polypeptide that can interact with a guide RNA (gRNA) molecule and, in concert with the gRNA molecule, localizes to a site which comprises a target domain and a PAM sequence.

In some embodiments, the ability of an eaCas9 molecule or eaCas9 polypeptide to interact with and cleave a target nucleic acid is PAM sequence dependent. A PAM sequence is a sequence in the target nucleic acid. In some embodiments, cleavage of the target nucleic acid occurs upstream from the PAM sequence. EaCas9 molecules from different bacterial species can recognize different sequence motifs (e.g., PAM sequences). In some embodiments, an eaCas9 molecule of *S. pyogenes* recognizes the sequence motif NGG, NAG, NGA and directs cleavage of a target nucleic acid sequence 1 to 10, e.g., 3 to 5, base pairs upstream from that sequence. See, e.g., Mali et al., Science 2013; 339 (6121): 823-826. In some embodiments, an eaCas9 molecule of *S. thermophilus* recognizes the sequence motif NGGNG and/or NNAGAAW (W=A or T) and directs cleavage of a target nucleic acid sequence 1 to 10, e.g., 3 to 5, base pairs upstream from these sequences. See, e.g., Horvath et al., Science 2010; 327(5962):167-170, and Deveau et al., J Bacteriol 2008; 190(4): 1390-1400. In some embodiments, an eaCas9 molecule of *S. mutans* recognizes the sequence motif NGG and/or NAAR (R=A or G)) and directs cleavage of a core target nucleic acid sequence 1 to 10, e.g., 3 to 5 base pairs, upstream from this sequence. See, e.g., Deveau et al., J Bacteriol 2008; 190(4): 1390-1400. In some embodiments, an eaCas9 molecule of *S. aureus* recognizes the sequence motif NNGRR (R=A or G) and directs cleavage of a target nucleic acid sequence 1 to 10, e.g., 3 to 5, base pairs upstream from that sequence. In some embodiments, an eaCas9 molecule of *S. aureus* recognizes the sequence motif NNGRRT (R=A or G) and directs cleavage of a target nucleic acid sequence 1 to 10, e.g., 3 to 5, base pairs upstream from that sequence. In some embodiments, an eaCas9 molecule of *S. aureus* recognizes the sequence motif NNGRRV (R=A or G) and directs cleavage of a target nucleic acid sequence 1 to 10, e.g., 3 to 5, base pairs upstream from that sequence. In some embodiments, an eaCas9 molecule of *N. meningitidis* recognizes the sequence motif NNNNGATT or NNNGCTT (R=A or G, V=A, G or C and directs cleavage of a target nucleic acid sequence 1 to 10, e.g., 3 to 5, base pairs upstream from that sequence. See, e.g., Hou et al., PNAS Early Edition 2013, 1-6. The ability of a Cas9 molecule to recognize a PAM sequence can be determined, e.g., using a transformation assay described in Jinek et al., Science 2012 337:816. In the aforementioned embodiments, N can be any nucleotide residue, e.g., any of A, G, C or T.

As is discussed herein, Cas9 molecules can be engineered to alter the PAM specificity of the Cas9 molecule.

Exemplary naturally occurring Cas9 molecules are described in Chylinski et al., RNA Biology 2013 10:5, 727-737. Such Cas9 molecules include Cas9 molecules of a cluster 1-78 bacterial family.

Exemplary naturally occurring Cas9 molecules include a Cas9 molecule of a cluster 1 bacterial family. Examples include a Cas9 molecule of: *S. pyogenes* (e.g., strain SF370, MGAS10270, MGAS10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA159, NN2025), *S. macacae* (e.g., strain NCTC11558), *S. gallolyticus* (e.g., strain UCN34, ATCC BAA-2069), *S. equines* (e.g., strain ATCC 9812, MGCS 124), *S. dysdalactiae* (e.g., strain GGS 124), *S. bovis* (e.g., strain ATCC 700338), *S. anginosus* (e.g., strain F0211), *S. agalactiae* (e.g., strain NEM316, A909), *Listeria monocytogenes* (e.g., strain F6854), *Listeria innocua* (*L. innocua*, e.g., strain Clip11262), *Enterococcus italicus* (e.g., strain DSM 15952), or *Enterococcus faecium* (e.g., strain 1,231,408). Another exemplary Cas9 molecule is a Cas9 molecule of *Neisseria meningitidis* (Hou et al., PNAS Early Edition 2013, 1-6).

In some embodiments, a Cas9 molecule or Cas9 polypeptide, e.g., an eaCas9 molecule or eaCas9 polypeptide, comprises an amino acid sequence: having 60%, 65%, 70%, 75%, 80%, 85%, 90%, 95%, 96%, 97%, 98% or 99% homology with; differs at no more than, 2, 5, 10, 15, 20, 30, or 40% of the amino acid residues when compared with; differs by at least 1, 2, 5, 10 or 20 amino acids but by no more than 100, 80, 70, 60, 50, 40 or 30 amino acids from; or is identical to any Cas9 molecule sequence described herein, or a naturally occurring Cas9 molecule sequence, e.g., a Cas9 molecule from a species listed herein (e.g., SEQ ID NOS:112-115) or described in Chylinski et al., RNA Biology 2013 10:5, 727-737; Hou et al., PNAS Early Edition 2013, 1-6. In some embodiments, the Cas9 molecule or Cas9 polypeptide comprises one or more of the following activities: a nickase activity; a double stranded cleavage activity (e.g., an endonuclease and/or exonuclease activity); a helicase activity; or the ability, together with a gRNA molecule, to home to a target nucleic acid.

In some embodiments, a Cas9 molecule or Cas9 polypeptide comprises the amino acid sequence of the consensus sequence of WO2015/161276, e.g., in FIGS. 2A-2G therein, wherein "*" indicates any amino acid found in the corresponding position in the amino acid sequence of a Cas9 molecule of *S. pyogenes, S. thermophilus, S. mutans* and *L. innocua*, and "-" indicates any amino acid. In some embodiments, a Cas9 molecule or Cas9 polypeptide differs from the sequence of the consensus sequence of SEQ ID NOS:112-117 or the consensus sequence disclosed in WO2015/161276, e.g., in FIGS. 2A-2G therein by at least 1, but no more than 2, 3, 4, 5, 6, 7, 8, 9, or 10 amino acid residues. In some embodiments, a Cas9 molecule or Cas9 polypeptide comprises the amino acid sequence of SEQ ID NO:117 or as described in WO2015/161276, e.g., in FIGS. 7A-7B therein, wherein "*" indicates any amino acid found in the corresponding position in the amino acid sequence of a Cas9 molecule of *S. pyogenes*, or *N. meningitidis*, "-" indicates any amino acid, and "-" indicates any amino acid or absent. In some embodiments, a Cas9 molecule or Cas9 polypeptide differs from the sequence of SEQ ID NO:116 or 117 or as described in WO2015/161276, e.g., in FIGS. 7A-7B therein by at least 1, but no more than 2, 3, 4, 5, 6, 7, 8, 9, or 10 amino acid residues.

A comparison of the sequence of a number of Cas9 molecules indicate that certain regions are conserved. These are identified as: region 1 (residues 1 to 180, or in the case of region 1'residues 120 to 180); region 2 (residues 360 to 480); region 3 (residues 660 to 720); region 4 (residues 817 to 900); and region 5 (residues 900 to 960).

In some embodiments, a Cas9 molecule or Cas9 polypeptide comprises regions 1-5, together with sufficient additional Cas9 molecule sequence to provide a biologically active molecule, e.g., a Cas9 molecule having at least one activity described herein. In some embodiments, each of regions 1-6, independently, have, 50%, 60%, 70%, or 80% homology with the corresponding residues of a Cas9 molecule or Cas9 polypeptide described herein, e.g., set forth in SEQ ID NOS:112-117 or a sequence disclosed in WO2015/161276, e.g., from FIGS. 2A-2G or from FIGS. 7A-7B therein.

In some embodiments, a Cas9 molecule or Cas9 polypeptide, e.g., an eaCas9 molecule or eaCas9 polypeptide, comprises an amino acid sequence referred to as region 1, having 50%, 60%, 70%, 80%, 85%, 90%, 95%, 96%, 97%, 98% or 99% homology with amino acids 1-180 (the numbering is according to the motif sequence in FIGS. 2A-2G of WO 2015/161276; 52% of residues in the four Cas9 sequences in FIGS. 2A-2G of WO 2015/161276 are conserved) of the amino acid sequence of Cas9 of *S. pyogenes*; differs by at least 1, 2, 5, 10 or 20 amino acids but by no more than 90, 80, 70, 60, 50, 40 or 30 amino acids from amino acids 1-180 of the amino acid sequence of Cas9 of *S. pyogenes, S. thermophilus, S. mutans* or *L. innocua*; or, is identical to 1-180 of the amino acid sequence of Cas9 of *S. pyogenes, S. thermophilus, S. mutans* or *L. innocua.*

In some embodiments, a Cas9 molecule or Cas9 polypeptide, e.g., an eaCas9 molecule or eaCas9 polypeptide, comprises an amino acid sequence referred to as region 1', having 55%, 60%, 65%, 70%, 75%, 80%, 85%, 90%, 95%, 96%, 97%, 98% or 99% homology with amino acids 120-180 (55% of residues in the four Cas9 sequences in FIGS. 2A-2G of WO 2015/161276 are conserved) of the amino acid sequence of Cas9 of *S. pyogenes, S. thermophilus, S. mutans* or *L. innocua*; differs by at least 1, 2, or 5 amino acids but by no more than 35, 30, 25, 20 or 10 amino acids from amino acids 120-180 of the amino acid sequence of Cas9 of *S. pyogenes, S. thermophilus, S. mutans* or *L. innocua*; or, is identical to 120-180 of the amino acid sequence of Cas9 of *S. pyogenes, S. thermophilus, S. mutans* or *L. innocua.*

In some embodiments, a Cas9 molecule or Cas9 polypeptide, e.g., an eaCas9 molecule or eaCas9 polypeptide, comprises an amino acid sequence referred to as region 2, having 50%, 55%, 60%, 65%, 70%, 75%, 80%, 85%, 90%, 95%, 96%, 97%, 98% or 99% homology with amino acids 360-480 (52% of residues in the four Cas9 sequences in FIGS. 2A-2G of WO 2015/161276 are conserved) of the amino acid sequence of Cas9 of *S. pyogenes, S. thermophilus, S. mutans* or *L. innocua*; differs by at least 1, 2, or 5 amino acids but by no more than 35, 30, 25, 20 or 10 amino acids from amino acids 360-480 of the amino acid sequence of Cas9 of *S. pyogenes, S. thermophilus, S. mutans* or *L. innocua*; or, is identical to 360-480 of the amino acid sequence of Cas9 of *S. pyogenes, S. thermophilus, S. mutans* or *L. innocua.*

In some embodiments, a Cas9 molecule or Cas9 polypeptide, e.g., an eaCas9 molecule or eaCas9 polypeptide, comprises an amino acid sequence referred to as region 3, having 55%, 60%, 65%, 70%, 75%, 80%, 85%, 90%, 95%, 96%, 97%, 98%, or 99% homology with amino acids 660-720 (56% of residues in the four Cas9 sequences in FIGS. 2A-2G of WO 2015/161276 are conserved) of the amino acid sequence of Cas9 of *S. pyogenes, S. thermophilus, S. mutans* or *L. innocua*; differs by at least 1, 2, or 5 amino acids but by no more than 35, 30, 25, 20 or 10 amino acids from amino acids 660-720 of the amino acid sequence of Cas9 of *S. pyogenes, S. thermophilus, S. mutans* or *L. innocua*; or, is identical to 660-720 of the amino acid sequence of Cas9 of *S. pyogenes, S. thermophilus, S. mutans* or *L. innocua.*

In some embodiments, a Cas9 molecule or Cas9 polypeptide, e.g., an eaCas9 molecule or eaCas9 polypeptide, comprises an amino acid sequence referred to as region 4, having 50%, 55%, 60%, 65%, 70%, 75%, 80%, 85%, 90%, 95%, 96%, 97%, 98%, or 99% homology with amino acids 817-900 (55% of residues in the four Cas9 sequences in FIGS. 2A-2G of WO 2015/161276 are conserved) of the amino acid sequence of Cas9 of *S. pyogenes, S. thermophilus, S. mutans* or *L. innocua*; differs by at least 1, 2, or 5 amino acids but by no more than 35, 30, 25, 20 or 10 amino acids from amino acids 817-900 of the amino acid sequence of Cas9 of *S. pyogenes, S. thermophilus, S. mutans* or *L. innocua*; or, is identical to 817-900 of the amino acid sequence of Cas9 of *S. pyogenes, S. thermophilus, S. mutans* or *L. innocua.*

In some embodiments, a Cas9 molecule or Cas9 polypeptide, e.g., an eaCas9 molecule or eaCas9 polypeptide, comprises an amino acid sequence referred to as region 5, having 50%, 55%, 60%, 65%, 70%, 75%, 80%, 85%, 90%, 95%, 96%, 97%, 98%, or 99% homology with amino acids 900-960 (60% of residues in the four Cas9 sequences in FIGS. 2A-2G of WO 2015/161276 are conserved) of the amino acid sequence of Cas9 of *S. pyogenes, S. thermophilus, S. mutans* or *L. innocua*; differs by at least 1, 2, or 5 amino acids but by no more than 35, 30, 25, 20 or 10 amino acids from amino acids 900-960 of the amino acid sequence of Cas9 of *S. pyogenes, S. thermophilus, S. mutans* or *L. innocua*; or, is identical to 900-960 of the amino acid sequence of Cas9 of *S. pyogenes, S. thermophilus, S. mutans* or *L. innocua.*

(h) Engineered or Altered Cas9 Molecules and Cas9 Polypeptides

Cas9 molecules and Cas9 polypeptides described herein, e.g., naturally occurring Cas9 molecules, can possess any of a number of properties, including: nickase activity, nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In some embodiments, a Cas9 molecule or Cas9 polypeptide can include all or a subset of these properties. In typical embodiments, a Cas9 molecule or Cas9 polypeptide has the ability to interact with a gRNA molecule and, in concert with the gRNA molecule, localize to a site in a nucleic acid. Other activities, e.g., PAM specificity, cleavage activity, or helicase activity can vary more widely in Cas9 molecules and Cas9 polypeptides.

Cas9 molecules include engineered Cas9 molecules and engineered Cas9 polypeptides ("engineered," as used in this context, means merely that the Cas9 molecule or Cas9 polypeptide differs from a reference sequences, and implies no process or origin limitation). An engineered Cas9 molecule or Cas9 polypeptide can comprise altered enzymatic properties, e.g., altered nuclease activity, (as compared with a naturally occurring or other reference Cas9 molecule) or altered helicase activity. As discussed herein, an engineered Cas9 molecule or Cas9 polypeptide can have nickase activity (as opposed to double strand nuclease activity). In some embodiments an engineered Cas9 molecule or Cas9 polypeptide can have an alteration that alters its size, e.g., a deletion of amino acid sequence that reduces its size, e.g., without significant effect on one or more, or any Cas9 activity. In some embodiments, an engineered Cas9 molecule or Cas9 polypeptide can comprise an alteration that affects PAM recognition. E.g., an engineered Cas9 molecule can be altered to recognize a PAM sequence other than that recognized by the endogenous wild-type PI domain. In some embodiments a Cas9 molecule or Cas9 polypeptide can differ in sequence from a naturally occurring Cas9 molecule but not have significant alteration in one or more Cas9 activities.

Cas9 molecules or Cas9 polypeptides with desired properties can be made in a number of ways, e.g., by alteration of a parental, e.g., naturally occurring, Cas9 molecules or Cas9 polypeptides, to provide an altered Cas9 molecule or Cas9 polypeptide having a desired property. For example, one or more mutations or differences relative to a parental Cas9 molecule, e.g., a naturally occurring or engineered Cas9 molecule, can be introduced. Such mutations and differences comprise: substitutions (e.g., conservative substitutions or substitutions of non-essential amino acids); insertions; or deletions. In some embodiments, a Cas9 molecule or Cas9 polypeptide can comprises one or more mutations or differences, e.g., at least 1, 2, 3, 4, 5, 10, 15, 20, 30, 40 or 50 mutations but less than 200, 100, or 80 mutations relative to a reference, e.g., a parental, Cas9 molecule.

In some embodiments, a mutation or mutations do not have a substantial effect on a Cas9 activity, e.g. a Cas9 activity described herein. In some embodiments, a mutation or mutations have a substantial effect on a Cas9 activity, e.g. a Cas9 activity described herein.

(i) Non-Cleaving and Modified-Cleavage Cas9 Molecules and Cas9 Polypeptides

In some embodiments, a Cas9 molecule or Cas9 polypeptide comprises a cleavage property that differs from naturally occurring Cas9 molecules, e.g., that differs from the naturally occurring Cas9 molecule having the closest homology. For example, a Cas9 molecule or Cas9 polypeptide can differ from naturally occurring Cas9 molecules, e.g., a Cas9 molecule of *S. pyogenes*, as follows: its ability to modulate, e.g., decreased or increased, cleavage of a double stranded nucleic acid (endonuclease and/or exonuclease activity), e.g., as compared to a naturally occurring Cas9 molecule (e.g., a Cas9 molecule of *S. pyogenes*); its ability to modulate, e.g., decreased or increased, cleavage of a single strand of a nucleic acid, e.g., a non-complementary strand of a nucleic acid molecule or a complementary strand of a nucleic acid molecule (nickase activity), e.g., as compared to a naturally occurring Cas9 molecule (e.g., a Cas9 molecule of *S. pyogenes*); or the ability to cleave a nucleic acid molecule, e.g., a double stranded or single stranded nucleic acid molecule, can be eliminated.

(j) Modified Cleavage eaCas9 Molecules and eaCas9 Polypeptides

In some embodiments, an eaCas9 molecule or eaCas9 polypeptide comprises one or more of the following activities: cleavage activity associated with an N-terminal RuvC-like domain; cleavage activity associated with an HNH-like domain; cleavage activity associated with an HNH-like domain and cleavage activity associated with an N-terminal RuvC-like domain In some embodiments, an eaCas9 molecule or eaCas9 polypeptide comprises an active, or cleavage competent, HNH-like domain and an inactive, or cleavage incompetent, N-terminal RuvC-like domain. An exemplary inactive, or cleavage incompetent N-terminal RuvC-like domain can have a mutation of an aspartic acid in an N-terminal RuvC-like domain, e.g., an aspartic acid at position 9 of the consensus sequence of SEQ ID NOS:112-117 or the consensus sequence disclosed in WO2015/161276, e.g., in FIGS. 2A-2G therein or an aspartic acid at position 10 of SEQ ID NO:117, e.g., can be substituted with an alanine. In some embodiments, the eaCas9 molecule or eaCas9 polypeptide differs from wild type in the N-terminal RuvC-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes*, or *S. thermophilus*. In some embodiments, the reference Cas9 molecule is the naturally occurring Cas9 molecule having the closest sequence identity or homology.

In some embodiments, an eaCas9 molecule or eaCas9 polypeptide comprises an inactive, or cleavage incompetent, HNH domain and an active, or cleavage competent, N-terminal RuvC-like domain Exemplary inactive, or cleavage incompetent HNH-like domains can have a mutation at one or more of: a histidine in an HNH-like domain, e.g., a histidine shown at position 856 of the consensus sequence of SEQ ID NOS:112-117 or the consensus sequence disclosed in WO2015/161276, e.g., in FIGS. 2A-2G therein, e.g., can be substituted with an alanine; and one or more asparagines in an HNH-like domain, e.g., an asparagine shown at position 870 of the consensus sequence of SEQ ID NOS: 112-117 or the consensus sequence disclosed in WO2015/161276, e.g., in FIGS. 2A-2G therein and/or at position 879 of the consensus sequence of SEQ ID NOS:112-117 or the consensus sequence disclosed in WO2015/161276, e.g., in FIGS. 2A-2G therein, e.g., can be substituted with an alanine. In some embodiments, the eaCas9 differs from wild type in the HNH-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes*, or *S. thermophilus*. In some embodiments, the reference Cas9 molecule is the naturally occurring Cas9 molecule having the closest sequence identity or homology.

In some embodiments, an eaCas9 molecule or eaCas9 polypeptide comprises an inactive, or cleavage incompetent, HNH domain and an active, or cleavage competent, N-terminal RuvC-like domain Exemplary inactive, or cleavage incompetent HNH-like domains can have a mutation at one or more of: a histidine in an HNH-like domain, e.g., a histidine shown at position 856 of the consensus sequence of SEQ ID NOS:112-117 or the consensus sequence disclosed in WO2015/161276, e.g., in FIGS. 2A-2G therein, e.g., can be substituted with an alanine; and one or more asparagines in an HNH-like domain, e.g., an asparagine shown at position 870 of the consensus sequence of SEQ ID NOS: 112-117 or the consensus sequence disclosed in WO2015/161276, e.g., in FIGS. 2A-2G therein and/or at position 879 of the consensus sequence of SEQ ID NOS:112-117 or the consensus sequence disclosed in WO2015/161276, e.g., in FIGS. 2A-2G therein, e.g., can be substituted with an alanine. In some embodiments, the eaCas9 differs from wild type in the HNH-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes*, or *S. thermophilus*. In some embodiments, the reference Cas9 molecule is the naturally occurring Cas9 molecule having the closest sequence identity or homology.

(k) Alterations in the Ability to Cleave One or Both Strands of a Target Nucleic Acid In some embodiments, exemplary Cas9 activities comprise one or more of PAM specificity, cleavage activity, and helicase activity. A mutation(s) can be present, e.g., in: one or more RuvC-like domain, e.g., an N-terminal RuvC-like domain; an HNH-like domain; a region outside the RuvC-like domains and the HNH-like domain. In some embodiments, a mutation(s) is present in a RuvC-like domain, e.g., an N-terminal RuvC-like. In some embodiments, a mutation(s) is present in an HNH-like domain. In some embodiments, mutations are present in both a RuvC-like domain, e.g., an N-terminal RuvC-like domain, and an HNH-like domain.

Exemplary mutations that may be made in the RuvC domain or HNH domain with reference to the *S. pyogenes* sequence include: D10A, E762A, H840A, N854A, N863A and/or D986A.

In some embodiments, a Cas9 molecule or Cas9 polypeptide is an eiCas9 molecule or eiCas9 polypeptide comprising one or more differences in a RuvC domain and/or in an HNH domain as compared to a reference Cas9 molecule, and the eiCas9 molecule or eiCas9 polypeptide does not cleave a nucleic acid, or cleaves with significantly less efficiency than does wild type, e.g., when compared with wild type in a cleavage assay, e.g., as described herein, cuts with less than 50, 25, 10, or 1% of a reference Cas9 molecule, as measured by an assay described herein.

Whether or not a particular sequence, e.g., a substitution, may affect one or more activity, such as targeting activity, cleavage activity, etc., can be evaluated or predicted, e.g., by evaluating whether the mutation is conservative. In some embodiments, a "non-essential" amino acid residue, as used in the context of a Cas9 molecule, is a residue that can be altered from the wild-type sequence of a Cas9 molecule, e.g., a naturally occurring Cas9 molecule, e.g., an eaCas9 molecule, without abolishing or more preferably, without substantially altering a Cas9 activity (e.g., cleavage activity), whereas changing an "essential" amino acid residue results in a substantial loss of activity (e.g., cleavage activity).

In some embodiments, a Cas9 molecule or Cas9 polypeptide comprises a cleavage property that differs from naturally occurring Cas9 molecules, e.g., that differs from the naturally occurring Cas9 molecule having the closest homology. For example, a Cas9 molecule or Cas9 polypeptide can differ from naturally occurring Cas9 molecules, e.g., a Cas9 molecule of *S aureus, S. pyogenes*, or *C. jejuni* as follows: its ability to modulate, e.g., decreased or increased, cleavage of a double stranded break (endonuclease and/or exonuclease activity), e.g., as compared to a naturally occurring Cas9 molecule (e.g., a Cas9 molecule of *S aureus, S. pyogenes*, or *C. jejuni*); its ability to modulate, e.g., decreased or increased, cleavage of a single strand of a nucleic acid, e.g., a non-complementary strand of a nucleic acid molecule or a complementary strand of a nucleic acid molecule (nickase activity), e.g., as compared to a naturally occurring Cas9 molecule (e.g., a Cas9 molecule of *S aureus, S. pyogenes*, or *C. jejuni*); or the ability to cleave a nucleic acid molecule, e.g., a double stranded or single stranded nucleic acid molecule, can be eliminated.

In some embodiments, the altered Cas9 molecule or Cas9 polypeptide is an eaCas9 molecule or eaCas9 polypeptide comprising one or more of the following activities: cleavage activity associated with a RuvC domain; cleavage activity associated with an HNH domain; cleavage activity associated with an HNH domain and cleavage activity associated with a RuvC domain.

In some embodiments, the altered Cas9 molecule or Cas9 polypeptide is an eiCas9 molecule or eaCas9 polypeptide which does not cleave a nucleic acid molecule (either double stranded or single stranded nucleic acid molecules) or cleaves a nucleic acid molecule with significantly less efficiency, e.g., less than 20, 10, 5, 1 or 0.1% of the cleavage activity of a reference Cas9 molecule, e.g., as measured by an assay described herein. The reference Cas9 molecule can be a naturally occurring unmodified Cas9 molecule, e.g., a naturally occurring Cas9 molecule such as a Cas9 molecule of *S. pyogenes, S. thermophilus, S. aureus, C. jejuni* or *N. meningitidis*. In some embodiments, the reference Cas9 molecule is the naturally occurring Cas9 molecule having the closest sequence identity or homology. In some embodiments, the eiCas9 molecule or eiCas9 polypeptide lacks substantial cleavage activity associated with a RuvC domain and cleavage activity associated with an HNH domain.

In some embodiments, the altered Cas9 molecule or Cas9 polypeptide is an eaCas9 molecule or eaCas9 polypeptide comprising the fixed amino acid residues of *S. pyogenes* shown in the consensus sequence disclosed in WO2015/161276, e.g., in FIGS. 2A-2G therein, and has one or more amino acids that differ from the amino acid sequence of *S. pyogenes* (e.g., has a substitution) at one or more residue (e.g., 2, 3, 5, 10, 15, 20, 30, 50, 70, 80, 90, 100, 200 amino acid residues) in SEQ ID NO:117 or residue represented by an "-" in the consensus sequence disclosed in WO2015/161276, e.g., in FIGS. 2A-2G therein.

In some embodiments, the altered Cas9 molecule or Cas9 polypeptide comprises a sequence in which: the sequence corresponding to the fixed sequence of the consensus sequence disclosed in FIGS. 2A-2G of WO2015/161276 differs at no more than 1, 2, 3, 4, 5, 10, 15, or 20% of the fixed residues in the consensus sequence disclosed in FIGS. 2A-2G of WO2015/161276, the sequence corresponding to the residues identified by "*" in the consensus sequence disclosed in FIGS. 2A-2G of WO2015/161276 differ at no more than 1, 2, 3, 4, 5, 10, 15, 20, 25, 30, 35, or 40% of the "*" residues from the corresponding sequence of naturally occurring Cas9 molecule, e.g., an *S. pyogenes* Cas9 molecule; and, the sequence corresponding to the residues identified by "-" in the consensus sequence disclosed in FIGS. 2A-2G of WO2015/161276 differ at no more than 5, 10, 15, 20, 25, 30, 35, 40, 45, 55, or 60% of the "-" residues from the corresponding sequence of naturally occurring Cas9 molecule, e.g., an *S. pyogenes* Cas9 molecule.

In some embodiments, the altered Cas9 molecule or Cas9 polypeptide is an eaCas9 molecule or eaCas9 polypeptide comprising the fixed amino acid residues of *S. thermophilus* shown in the consensus sequence disclosed in FIGS. 2A-2G of WO2015/161276, and has one or more amino acids that differ from the amino acid sequence of *S. thermophilus* (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIGS. 2A-2G of WO2015/161276.

In some embodiments the altered Cas9 molecule or Cas9 polypeptide comprises a sequence in which: the sequence corresponding to the fixed sequence of the consensus sequence disclosed in FIGS. 2A-2G of WO2015/161276 differs at no more than 1, 2, 3, 4, 5, 10, 15, or 20% of the fixed residues in the consensus sequence disclosed in FIGS. 2A-2G of WO2015/161276, the sequence corresponding to the residues identified by "*" in the consensus sequence disclosed in FIGS. 2A-2G of WO2015/161276 differ at no more than 1, 2, 3, 4, 5, 10, 15, 20, 25, 30, 35, or 40% of the "*" residues from the corresponding sequence of naturally occurring Cas9 molecule, e.g., an *S. thermophilus* Cas9 molecule; and the sequence corresponding to the residues identified by "-" in the consensus sequence disclosed in FIGS. 2A-2G of WO2015/161276 differ at no more than 5, 10, 15, 20, 25, 30, 35, 40, 45, 55, or 60% of the "-" residues from the corresponding sequence of naturally occurring Cas9 molecule, e.g., an *S. thermophilus* Cas9 molecule.

In some embodiments, the altered Cas9 molecule or Cas9 polypeptide is an eaCas9 molecule or eaCas9 polypeptide comprising the fixed amino acid residues of *S. mutans* shown in the consensus sequence disclosed in FIGS. 2A-2G of WO2015/161276, and has one or more amino acids that differ from the amino acid sequence of *S. mutans* (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIGS. 2A-2G of WO2015/161276.

In some embodiments, the altered Cas9 molecule or Cas9 polypeptide comprises a sequence in which: the sequence corresponding to the fixed sequence of the consensus sequence disclosed in FIGS. 2A-2G of WO2015/161276 differs at no more than 1, 2, 3, 4, 5, 10, 15, or 20% of the fixed residues in the consensus sequence disclosed in FIGS. 2A-2G of WO2015/161276, the sequence corresponding to the residues identified by "*" in the consensus sequence disclosed in FIGS. 2A-2G of WO2015/161276 differ at no more than 1, 2, 3, 4, 5, 10, 15, 20, 25, 30, 35, or 40% of the "*" residues from the corresponding sequence of naturally occurring Cas9 molecule, e.g., an *S. mutans* Cas9 molecule; and, the sequence corresponding to the residues identified by "-" in the consensus sequence disclosed in FIGS. 2A-2G of WO2015/161276 differ at no more than 5, 10, 15, 20, 25, 30, 35, 40, 45, 55, or 60% of the "-" residues from the corresponding sequence of naturally occurring Cas9 molecule, e.g., an *S. mutans* Cas9 molecule.

In some embodiments, the altered Cas9 molecule or Cas9 polypeptide is an eaCas9 molecule or eaCas9 polypeptide comprising the fixed amino acid residues of L. innocula shown in the consensus sequence disclosed in FIGS. 2A-2G of WO2015/161276, and has one or more amino acids that differ from the amino acid sequence of L. innocula (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIGS. 2A-2G of WO2015/161276. In some embodiments, the altered Cas9 molecule or Cas9 polypeptide comprises a sequence in which: the sequence corresponding to the fixed sequence of the consensus sequence disclosed in FIGS. 2A-2G of WO2015/161276 differs at no more than 1, 2, 3, 4, 5, 10, 15, or 20% of the fixed residues in the consensus sequence disclosed in FIGS. 2A-2G of WO2015/161276, the sequence corresponding to the residues identified by "*" in the consensus sequence disclosed in FIGS. 2A-2G of WO2015/161276 differ at no more than 1, 2, 3, 4, 5, 10, 15, 20, 25, 30, 35, or 40% of the "*" residues from the corresponding sequence of naturally occurring Cas9 molecule, e.g., an L. innocula Cas9 molecule; and, the sequence corresponding to the residues identified by "-" in the consensus sequence disclosed in FIGS. 2A-2G of WO2015/161276 differ at no more than 5, 10, 15, 20, 25, 30, 35, 40, 45, 55, or 60% of the "-" residues from the corresponding sequence of naturally occurring Cas9 molecule, e.g., an L. innocula Cas9 molecule.

In some embodiments, the altered Cas9 molecule or Cas9 polypeptide, e.g., an eaCas9 molecule, can be a fusion, e.g., of two of more different Cas9 molecules or Cas9 polypeptides, e.g., of two or more naturally occurring Cas9 molecules of different species. For example, a fragment of a naturally occurring Cas9 molecule of one species can be fused to a fragment of a Cas9 molecule of a second species. As an example, a fragment of Cas9 molecule of *S. pyogenes* comprising an N-terminal RuvC-like domain can be fused to a fragment of Cas9 molecule of a species other than *S. pyogenes* (e.g., *S. thermophilus*) comprising an HNH-like domain.

(l) Cas9 Molecules with Altered PAM Recognition or No PAM Recognition

Naturally occurring Cas9 molecules can recognize specific PAM sequences, for example the PAM recognition sequences described herein for, e.g., *S. pyogenes, S. thermophilus, S. mutans, S. aureus* and *N. meningitidis.*

In some embodiments, a Cas9 molecule or Cas9 polypeptide has the same PAM specificities as a naturally occurring Cas9 molecule. In other embodiments, a Cas9 molecule or Cas9 polypeptide has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule or Cas9 polypeptide recognizes to decrease off target sites and/or improve specificity; or eliminate a PAM recognition requirement. In some embodiments, a Cas9 molecule can be altered, e.g., to increase length of PAM recognition sequence and/or improve Cas9 specificity to high level of identity, e.g., to decrease off target sites and increase specificity. In some embodiments, the length of the PAM recognition sequence is at least 4, 5, 6, 7, 8, 9, 10 or 15 amino acids in length.

Cas9 molecules or Cas9 polypeptides that recognize different PAM sequences and/or have reduced off-target activity can be generated using directed evolution. Exemplary methods and systems that can be used for directed evolution of Cas9 molecules are described, e.g., in Esvelt et al. Nature 2011, 472(7344): 499-503. Candidate Cas9 molecules can be evaluated, e.g., by methods described herein.

Alterations of the PI domain, which mediates PAM recognition, are discussed herein.

(m) Synthetic Cas9 Molecules and Cas9 Polypeptides with Altered PI Domains

Current genome-editing methods are limited in the diversity of target sequences that can be targeted by the PAM sequence that is recognized by the Cas9 molecule utilized. A synthetic Cas9 molecule (or Syn-Cas9 molecule), or synthetic Cas9 polypeptide (or Syn-Cas9 polypeptide), as that term is used herein, refers to a Cas9 molecule or Cas9 polypeptide that comprises a Cas9 core domain from one bacterial species and a functional altered PI domain, i.e., a PI domain other than that naturally associated with the Cas9 core domain, e.g., from a different bacterial species.

In some embodiments, the altered PI domain recognizes a PAM sequence that is different from the PAM sequence recognized by the naturally-occurring Cas9 from which the Cas9 core domain is derived. In some embodiments, the altered PI domain recognizes the same PAM sequence recognized by the naturally-occurring Cas9 from which the Cas9 core domain is derived, but with different affinity or specificity. A Syn-Cas9 molecule or Syn-Cas9 polypeptide can be, respectively, a Syn-eaCas9 molecule or Syn-eaCas9 polypeptide or a Syn-eiCas9 molecule Syn-eiCas9 polypeptide.

An exemplary Syn-Cas9 molecule or Syn-Cas9 polypeptide comprises: a) a Cas9 core domain, e.g., a Cas9 core domain, e.g., a *S. aureus, S. pyogenes*, or *C. jejuni* Cas9 core domain; and b) an altered PI domain from a species X Cas9 sequence.

In some embodiments, the RKR motif (the PAM binding motif) of said altered PI domain comprises: differences at 1, 2, or 3 amino acid residues; a difference in amino acid sequence at the first, second, or third position; differences in amino acid sequence at the first and second positions, the first and third positions, or the second and third positions; as compared with the sequence of the RKR motif of the native or endogenous PI domain associated with the Cas9 core domain In some embodiments, a Syn-Cas9 molecule or Syn-Cas9 polypeptide may also be size-optimized, e.g., the Syn-Cas9 molecule or Syn-Cas9 polypeptide comprises one or more deletions, and optionally one or more linkers disposed between the amino acid residues flanking the deletions. In some embodiments, a Syn-Cas9 molecule or Syn-Cas9 polypeptide comprises a REC deletion.

(n) Size-Optimized Cas9 Molecules and Cas9 Polypeptides

Engineered Cas9 molecules and engineered Cas9 polypeptides described herein include a Cas9 molecule or Cas9 polypeptide comprising a deletion that reduces the size of the molecule while still retaining desired Cas9 properties, e.g., essentially native conformation, Cas9 nuclease activity, and/or target nucleic acid molecule recognition. The Cas9 molecules or Cas9 polypeptides used in the context of the provided embodiments can comprise one or more deletions and optionally one or more linkers, wherein a linker is disposed between the amino acid residues that flank the deletion.

A Cas9 molecule, e.g., a *S. aureus, S. pyogenes*, or *C. jejuni*, Cas9 molecule, having a deletion is smaller, e.g., has reduced number of amino acids, than the corresponding naturally-occurring Cas9 molecule. The smaller size of the Cas9 molecules allows increased flexibility for delivery methods, and thereby increases utility for genome-editing. A Cas9 molecule or Cas9 polypeptide can comprise one or more deletions that do not substantially affect or decrease the activity of the resultant Cas9 molecules or Cas9 polypeptides described herein. Activities that are retained in the Cas9 molecules or Cas9 polypeptides comprising a deletion as described herein include one or more of the following: a nickase activity, i.e., the ability to cleave a single strand, e.g., the non-complementary strand or the complementary strand, of a nucleic acid molecule; a double stranded nuclease activity, i.e., the ability to cleave both strands of a double stranded nucleic acid and create a double stranded break, which In some embodiments is the presence of two nickase activities; an endonuclease activity; an exonuclease activity; a helicase activity, i.e., the ability to unwind the helical structure of a double stranded nucleic acid; and recognition activity of a nucleic acid molecule, e.g., a target nucleic acid or a gRNA.

Activity of the Cas9 molecules or Cas9 polypeptides described herein can be assessed using the activity assays described herein or are known.

(o) Identifying Regions Suitable for Deletion

Suitable regions of Cas9 molecules for deletion can be identified by a variety of methods. Naturally-occurring orthologous Cas9 molecules from various bacterial species, can be modeled onto the crystal structure of *S. pyogenes* Cas9 (Nishimasu et al., Cell, 156:935-949, 2014) to examine the level of conservation across the selected Cas9 orthologs with respect to the three-dimensional conformation of the protein. Less conserved or unconserved regions that are spatially located distant from regions involved in Cas9 activity, e.g., interface with the target nucleic acid molecule and/or gRNA, represent regions or domains are candidates for deletion without substantially affecting or decreasing Cas9 activity.

(p) REC-Optimized Cas9 Molecules and Cas9 Polypeptides

A REC-optimized Cas9 molecule, or a REC-optimized Cas9 polypeptide, as that term is used herein, refers to a Cas9 molecule or Cas9 polypeptide that comprises a deletion in one or both of the REC2 domain and the RE $1_{CT}$ domain (collectively a REC deletion), wherein the deletion comprises at least 10% of the amino acid residues in the cognate domain A REC-optimized Cas9 molecule or Cas9 polypeptide can be an eaCas9 molecule or eaCas9 polypeptide, or an eiCas9 molecule or eiCas9 polypeptide. An exemplary REC-optimized Cas9 molecule or REC-optimized Cas9 polypeptide comprises: a) a deletion selected from: i) a REC2 deletion; ii) a REC1 CT deletion; or iii) a $REC1_{SUB}$ deletion.

Optionally, a linker is disposed between the amino acid residues that flank the deletion. In some embodiments a Cas9 molecule or Cas9 polypeptide includes only one deletion, or only two deletions. A Cas9 molecule or Cas9 polypeptide can comprise a REC2 deletion and a $REC1_{CT}$ deletion. A Cas9 molecule or Cas9 polypeptide can comprise a REC2 deletion and a REC1 SUB deletion.

Generally, the deletion will contain at least 10% of the amino acids in the cognate domain, e.g., a REC2 deletion will include at least 10% of the amino acids in the REC2 domain A deletion can comprise: at least 10, 20, 30, 40, 50, 60, 70, 80, or 90% of the amino acid residues of its cognate domain; all of the amino acid residues of its cognate domain; an amino acid residue outside its cognate domain; a plurality of amino acid residues outside its cognate domain; the amino acid residue immediately N terminal to its cognate domain; the amino acid residue immediately C terminal to its cognate domain; the amino acid residue immediately N terminal to its cognate and the amino acid residue immediately C terminal to its cognate domain; a plurality of, e.g., up to 5, 10, 15, or 20, amino acid residues N terminal to its cognate domain; a plurality of, e.g., up to 5, 10, 15, or 20, amino acid residues C terminal to its cognate domain; a plurality of, e.g., up to 5, 10, 15, or 20, amino acid residues N terminal to its cognate domain and a plurality of e.g., up to 5, 10, 15, or 20, amino acid residues C terminal to its cognate domain.

In some embodiments, a deletion does not extend beyond: its cognate domain; the N terminal amino acid residue of its cognate domain; the C terminal amino acid residue of its cognate domain.

A REC-optimized Cas9 molecule or REC-optimized Cas9 polypeptide can include a linker disposed between the amino acid residues that flank the deletion. Suitable linkers for use between the amino acid resides that flank a REC deletion in a REC-optimized Cas9 molecule is described herein.

In some embodiments, a REC-optimized Cas9 molecule or REC-optimized Cas9 polypeptide comprises an amino acid sequence that, other than any REC deletion and associated linker, has at least 50, 55, 60, 65, 70, 75, 80, 85, 90, 95, 99, or 100% homology with the amino acid sequence of a naturally occurring Cas9, e.g., a *S. aureus* Cas9 molecule, a *S. pyogenes* Cas9 molecule, or a *C. jejuni* Cas9 molecule.

In some embodiments, a REC-optimized Cas9 molecule or REC-optimized Cas9 polypeptide comprises an amino acid sequence that, other than any REC deletion and associated linker, differs by no more than 1, 2, 3, 4, 5, 6, 7, 8, 9, 10, 15, 20, or 25, amino acid residues from the amino acid sequence of a naturally occurring Cas9, e.g., a *S. aureus* Cas9 molecule, a *S. pyogenes* Cas9 molecule, or a *C. jejuni* Cas9 molecule.

In some embodiments, a REC-optimized Cas9 molecule or REC-optimized Cas9 polypeptide comprises an amino acid sequence that, other than any REC deletion and associate linker, differs by no more than 1, 2, 3, 4, 5, 6, 7, 8, 9, 10, 15, 20, or 25% of the, amino acid residues from the amino acid sequence of a naturally occurring Cas9, e.g., a *S. aureus* Cas9 molecule, a *S. pyogenes* Cas9 molecule, or a *C. jejuni* Cas9 molecule.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at gcg.com), using either a Blossom 62 matrix or a PAM250 matrix, and a gap weight of 16, 14, 12, 10, 8, 6, or 4 and a length weight of 1, 2, 3, 4, 5, or 6.

Sequence information for exemplary REC deletions are provided for 83 naturally-occurring Cas9 orthologs described in, e.g., International PCT Pub. Nos. WO2015/161276, WO2017/193107 and WO2017/093969.

(q) Nucleic Acids Encoding Cas9 Molecules

Nucleic acids encoding the Cas9 molecules or Cas9 polypeptides, e.g., an eaCas9 molecule or eaCas9 polypeptide, can be used in connection with any of the embodiments provided herein.

Exemplary nucleic acids encoding Cas9 molecules or Cas9 polypeptides are described in Cong et al., Science 2013, 399(6121):819-823; Wang et al., Cell 2013, 153(4): 910-918; Mali et al., Science 2013, 399(6121):823-826; Jinek et al., Science 2012, 337(6096):816-821, and WO2015/161276, e.g., in FIG. 8 therein.

In some embodiments, a nucleic acid encoding a Cas9 molecule or Cas9 polypeptide can be a synthetic nucleic acid sequence. For example, the synthetic nucleic acid molecule can be chemically modified. In some embodiments, the Cas9 mRNA has one or more (e.g., all of the following properties: it is capped, polyadenylated, substituted with 5-methylcytidine and/or pseudouridine.

In addition, or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

In addition, or alternatively, a nucleic acid encoding a Cas9 molecule or Cas9 polypeptide may comprise a nuclear localization sequence (NLS). Nuclear localization sequences are known.

In some embodiments, the Cas9 molecule is encoded by a sequence that is or comprises any of SEQ ID NOS: 121, 123 or 125 or a sequence that exhibits at least 85%, 86%, 87%, 88%, 89%, 90%, 91%, 92%, 92%, 94%, 95%, 96%, 97%, 98%, 99% or more sequence identity to any of SEQ ID NOS: 121, 123 or 125. In some embodiments, the Cas9 molecule is or comprises any of SEQ ID NOs: 122, 124 or 125 or a sequence that exhibits at least 85%, 86%, 87%, 88%, 89%, 90%, 91%, 92%, 92%, 94%, 95%, 96%, 97%, 98%, 99% or more sequence identity to any of SEQ ID NOS: 122, 123 or 125. SEQ ID NO:121 is an exemplary codon optimized nucleic acid sequence encoding a Cas9 molecule of *S. pyogenes*. SEQ ID NO:122 is the corresponding amino acid sequence of a *S. pyogenes* Cas9 molecule. SEQ ID NO:123 is an exemplary codon optimized nucleic acid sequence encoding a Cas9 molecule of *N. meningitidis*. SEQ ID NO:124 is the corresponding amino acid sequence of a *N. meningitidis* Cas9 molecule. SEQ ID NO:125 is an exemplary codon optimized nucleic acid sequence encoding a Cas9 molecule of *S. aureus* Cas9. SEQ ID NO:126 is an amino acid sequence of a *S. aureus* Cas9 molecule.

If any of the foregoing Cas9 sequences are fused with a peptide or polypeptide at the C-terminus, it is understood that the stop codon will be removed.

(r) Other Cas Molecules and Cas Polypeptides

Various types of Cas molecules or Cas polypeptides can be used to practice the inventions disclosed herein. In some embodiments, Cas molecules of Type II Cas systems are used. In other embodiments, Cas molecules of other Cas systems are used. For example, Type I or Type III Cas molecules may be used. Exemplary Cas molecules (and Cas systems) are described, e.g., in Haft et al., PLoS Computational Biology 2005, 1(6): e60 and Makarova et al., Nature Review Microbiology 2011, 9:467-477, the contents of both references are incorporated herein by reference in their entirety. Exemplary Cas molecules (and Cas systems) are also shown in Table 2.

TABLE 2

| Cas Systems | | | | | |
|---|---|---|---|---|---|
| Gene name[‡] | System type or subtype | Name from Haft et al.[§] | Structure of encoded protein (PDB accessions)[¶] | Families (and superfamily) of encoded protein[#**] | Representatives |
| cas1 | Type I<br>Type II<br>Type III | cas1 | 3GOD, 3LFX and 2YZS | COG1518 | SERP2463, SPy1047 and ygbT |
| cas2 | Type I<br>Type II<br>Type III | cas2 | 2IVY, 2I8E and 3EXC | COG1343 and COG3512 | SERP2462, SPy1048, SPy1723 (N-terminal domain) and ygbF |
| cas3' | Type I[‡‡] | cas3 | NA | COG1203 | APE1232 and ygcB |
| cas3" | Subtype I-A<br>Subtype I-B | NA | NA | COG2254 | APE1231 and BH0336 |
| cas4 | Subtype I-A<br>Subtype I-B<br>Subtype I-C<br>Subtype I-D<br>Subtype II-B | cas4 and csa1 | NA | COG1468 | APE1239 and BH0340 |
| cas5 | Subtype I-A<br>Subtype I-B<br>Subtype I-C<br>Subtype I-E | cas5a, cas5d, cas5e, cas5h, cas5p, cas5t and cmx5 | 3KG4 | COG1688 (RAMP) | APE1234, BH0337, devS and ygcI |
| cas6 | Subtype I-A<br>Subtype I-B<br>Subtype I-D<br>Subtype III-A<br>Subtype III-B | cas6 and cmx6 | 3I4H | COG1583 and COG5551 (RAMP) | PF1131 and slr7014 |
| cas6e | Subtype I-E | cse3 | 1WJ9 | (RAMP) | ygcH |
| cas6f | Subtype I-F | csy4 | 2XLJ | (RAMP) | y1727 |
| cas7 | Subtype I-A<br>Subtype I-B<br>Subtype I-C<br>Subtype I-E | csa2, csd2, cse4, csh2, csp1 and cst2 | NA | COG1857 and COG3649 (RAMP) | devR and ygcJ |
| cas8a1 | Subtype I-A[‡‡] | cmx1, cst1, csx8, csx13 and CXXC-CXXC | NA | BH0338-like | LA3191[§§] and PG2018[§§] |
| cas8a2 | Subtype I-A[‡‡] | csa4 and csx9 | NA | PH0918 | AF0070, AF1873, MJ0385, PF0637, PH0918 and SSO1401 |
| cas8b | Subtype I-B[‡‡] | csh1 and TM1802 | NA | BH0338-like | MTH1090 and TM1802 |
| cas8c | Subtype I-C[‡‡] | csd1 and csp2 | NA | BH0338-like | BH0338 |
| cas9 | Type II[‡‡] | csn1 and csx12 | NA | COG3513 | FTN_0757 and SPy1046 |
| cas10 | Type III[‡‡] | cmr2, csm1 and csx11 | NA | COG1353 | MTH326, Rv2823c[§§] and TM1794[§§] |
| cas10d | Subtype I-D[‡‡] | csc3 | NA | COG1353 | slr7011 |
| csy1 | Subtype I-F[‡‡] | csy1 | NA | y1724-like | y1724 |
| csy2 | Subtype I-F | csy2 | NA | (RAMP) | y1725 |
| csy3 | Subtype I-F | csy3 | NA | (RAMP) | y1726 |
| cse1 | Subtype I-E[‡‡] | cse1 | NA | YgcL-like | ygcL |
| cse2 | Subtype I-E | cse2 | 2ZCA | YgcK-like | ygcK |
| csc1 | Subtype I-D | csc1 | NA | alr1563-like (RAMP) | alr1563 |
| csc2 | Subtype I-D | csc1 and csc2 | NA | COG1337 (RAMP) | slr7012 |
| csa5 | Subtype I-A | csa5 | NA | AF1870 | AF1870, MJ0380, PF0643 and SSO1398 |
| csn2 | Subtype II-A | csn2 | NA | SPy1049-like | SPy1049 |
| csm2 | Subtype III-A[‡‡] | csm2 | NA | COG1421 | MTH1081 and SERP2460 |
| csm3 | Subtype III-A | csc2 and csm3 | NA | COG1337 (RAMP) | MTH1080 and SERP2459 |
| csm4 | Subtype III-A | csm4 | NA | COG1567 (RAMP) | MTH1079 and SERP2458 |
| csm5 | Subtype III-A | csm5 | NA | COG1332 (RAMP) | MTH1078 and SERP2457 |
| csm6 | Subtype III-A | APE2256 and csm6 | 2WTE | COG1517 | APE2256 and SSO1445 |
| cmr1 | Subtype III-B | cmr1 | NA | COG1367 (RAMP) | PF1130 |
| cmr3 | Subtype III-B | cmr3 | NA | COG1769 (RAMP) | PF1128 |
| cmr4 | Subtype III-B | cmr4 | NA | COG1336 (RAMP) | PF1126 |
| cmr5 | Subtype III-B[‡‡] | cmr5 | 2ZOP and 2OEB | COG3337 | MTH324 and PF1125 |
| cmr6 | Subtype III-B | cmr6 | NA | COG1604 (RAMP) | PF1124 |
| csb1 | Subtype I-U | GSU0053 | NA | (RAMP) | Balac_1306 and GSU0053 |
| csb2 | Subtype I-U[§§] | NA | NA | (RAMP) | Balac_1305 and GSU0054 |
| csb3 | Subtype I-U | NA | NA | (RAMP) | Balac_1303[§§] |
| csx17 | Subtype I-U | NA | NA | NA | Btus_2683 |
| csx14 | Subtype I-U | NA | NA | NA | GSU0052 |
| csx10 | Subtype I-U | csx10 | NA | (RAMP) | Caur_2274 |
| csx16 | Subtype III-U | VVA1548 | NA | NA | VVA1548 |
| csaX | Subtype III-U | csaX | NA | NA | SSO1438 |
| csx3 | Subtype III-U | csx3 | NA | NA | AF1864 |

TABLE 2-continued

| Cas Systems | | | | | |
|---|---|---|---|---|---|
| Gene name‡ | System type or subtype | Name from Haft et al.§ | Structure of encoded protein (PDB accessions)¶ | Families (and superfamily) of encoded protein#** | Representatives |
| csx1 | Subtype III-U | csa3, csx1, csx2, DXTHG, NE0113 and TIGR02710 | 1XMX and 2I71 | COG1517 and COG4006 | MJ1666, NE0113, PF1127 and TM1812 |
| csx15 | Unknown | NA | NA | TTE2665 | TTE2665 |
| csf1 | Type U | csf1 | NA | NA | AFE_1038 |
| csf2 | Type U | csf2 | NA | (RAMP) | AFE_1039 |
| csf3 | Type U | csf3 | NA | (RAMP) | AFE_1040 |
| csf4 | Type U | csf4 | NA | NA | AFE_1037 |

(iii) Cpf1

In some embodiments, the guide RNA or gRNA promotes the specific association targeting of an RNA-guided nuclease such as a Cas9 or a Cpf1 to a target sequence such as a genomic or episomal sequence in a cell. In general, gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, in some embodiments by duplexing). gRNAs and their component parts are described throughout the literature, in some embodiments in Briner et al. (Molecular Cell 56(2), 333-339, Oct. 23, 2014 (Briner), which is incorporated by reference), and in Cotta-Ramusino.

Guide RNAs, whether unimolecular or modular, generally include a targeting domain that is fully or partially complementary to a target, and are typically 10-30 nucleotides in length, and in certain embodiments are 16-24 nucleotides in length (in some embodiments, 16, 17, 18, 19, 20, 21, 22, 23 or 24 nucleotides in length). In some aspects, the targeting domains are at or near the 5' terminus of the gRNA in the case of a Cas9 gRNA, and at or near the 3' terminus in the case of a Cpf1 gRNA. While the foregoing description has focused on gRNAs for use with Cas9, it should be appreciated that other RNA-guided nucleases have been (or may in the future be) discovered or invented which utilize gRNAs that differ in some ways from those described to this point. In some embodiments, Cpf1 ("CRISPR from Prevotella and Franciscella 1") is a recently discovered RNA-guided nuclease that does not require a tracrRNA to function. (Zetsche et al., 2015, Cell 163, 759-771 Oct. 22, 2015 (Zetsche I), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, in some aspects in this disclosure, gRNAs may be described solely in terms of their targeting domain sequences.

More generally, some aspects of the present disclosure relate to systems, methods and compositions that can be implemented using multiple RNA-guided nucleases. Unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

RNA-guided nucleases include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g. Cas9 vs. Cpf1), species (e.g. *S. pyogenes* vs. *S. aureus*) or variation (e.g full-length vs. truncated or split; naturally-occurring PAM specificity vs. engineered PAM specificity, etc.) of RNA-guided nuclease.

In addition to recognizing specific sequential orientations of PAMs and protospacers, RNA-guided nucleases in some embodiments can also recognize specific PAM sequences. *S. aureus* Cas9, in some embodiments, generally recognizes a PAM sequence of NNGRRT or NNGRRV, wherein the N residues are immediately 3' of the region recognized by the gRNA targeting domain *S. pyogenes* Cas9 generally recognizes NGG PAM sequences. And *F. novicida* Cpf1 generally recognizes a TTN PAM sequence.

The crystal structure of *Acidaminococcus* sp. Cpf1 in complex with crRNA and a double-stranded (ds) DNA target including a TTTN PAM sequence has been solved by Yamano et al. (Cell. 2016 May 5; 165(4): 949-962 (Yamano), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. In some embodiments, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong 2013; Wang 2013; Mali 2013; Jinek 2012).

b. Genome Editing Approaches

In general, it is to be understood that the alteration of any gene according to the methods described herein can be mediated by any mechanism and that any methods are not limited to a particular mechanism. Exemplary mechanisms that can be associated with the alteration of a gene include, but are not limited to, non-homologous end joining (e.g., classical or alternative), microhomology-mediated end joining (MMEJ), homology-directed repair (e.g., endogenous donor template mediated), synthesis dependent strand annealing (SDSA), single strand annealing, single strand invasion, single strand break repair (SSBR), mismatch repair (MMR), base excision repair (BER), Interstrand Crosslink (ICL) Translesion synthesis (TLS), or Error-free post-replication repair (PRR). Described herein are exemplary methods for targeted knockout of one or both alleles of one or all of the CD247 locus.

1) NHEJ Approaches for Gene Targeting

As described herein, nuclease-induced non-homologous end-joining (NHEJ) can be used to target gene-specific knockouts. Nuclease-induced NHEJ can also be used to remove (e.g., delete) sequence insertions in a gene of interest.

While not wishing to be bound by theory, it is believed that, in some embodiments, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. In some embodiments, a pair of gRNAs can be used to introduce two double-strand breaks, resulting in a deletion of intervening sequences between the two breaks.

Both of these approaches can be used to delete specific DNA sequences; however, the error-prone nature of NHEJ may still produce indel mutations at the site of repair.

Both double strand cleaving eaCas9 molecules and single strand, or nickase, eaCas9 molecules can be used in the methods and compositions described herein to generate NHEJ-mediated indels. NHEJ-mediated indels targeted to the gene, e.g., a coding region, e.g., an early coding region of a gene, of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In some embodiments, NHEJ-mediated indels are introduced into one or more T-cell expressed genes, such as the CD247 locus. Individual gRNAs or gRNA pairs targeting the gene are provided together with the Cas9 double-stranded nuclease or single-stranded nickase.

(1) Placement of Double Strand or Single Strand Breaks Relative to the Target Position In some embodiments, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In some embodiments, the cleavage site is between 0-30 bp away from the target position (e.g., less than 30, 25, 20, 15, 10, 9, 8, 7, 6, 5, 4, 3, 2 or 1 bp from the target position).

In some embodiments, in which two gRNAs complexing with Cas9 nickases induce two single strand breaks for the purpose of inducing NHEJ-mediated indels, two gRNAs, e.g., independently, unimolecular (or chimeric) or modular gRNA, are configured to position two single-strand breaks to provide for NHEJ repair a nucleotide of the target position. In some embodiments, the gRNAs are configured to position cuts at the same position, or within a few nucleotides of one another, on different strands, essentially mimicking a double strand break. In some embodiments, the closer nick is between 0-30 bp away from the target position (e.g., less than 30, 25, 20, 15, 10, 9, 8, 7, 6, 5, 4, 3, 2 or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp). In some embodiments, the gRNAs are configured to place a single strand break on either side of a nucleotide of the target position.

Both double strand cleaving eaCas9 molecules and single strand, or nickase, eaCas9 molecules can be used in the methods and compositions described herein to generate breaks both sides of a target position. Double strand or paired single strand breaks may be generated on both sides of a target position to remove the nucleic acid sequence between the two cuts (e.g., the region between the two breaks in deleted). In some embodiments, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position. In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position. The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

2) Targeted Knockdown

Unlike CRISPR/Cas-mediated gene knockout, which permanently eliminates or reduces expression by mutating the gene at the DNA level, CRISPR/Cas knockdown allows for temporary reduction of gene expression through the use of artificial transcription factors. Mutating key residues in both DNA cleavage domains of the Cas9 protein (e.g., the D10A and H840A mutations) results in the generation of a catalytically inactive Cas9 (eiCas9 which is also known as dead Cas9 or dCas9). A catalytically inactive Cas9 complexes with a gRNA and localizes to the DNA sequence specified by that gRNA's targeting domain, however, it does not cleave the target DNA. Fusion of the dCas9 to an effector domain, e.g., a transcription repression domain, enables recruitment of the effector to any DNA site specified by the gRNA. While it has been shown that the eiCas9 itself can block transcription when recruited to early regions in the coding sequence, more robust repression can be achieved by fusing a transcriptional repression domain (for example KRAB, SID or ERD) to the Cas9 and recruiting it to the promoter region of a gene. It is likely that targeting DNase I hypersensitive regions of the promoter may yield more efficient gene repression or activation because these regions are more likely to be accessible to the Cas9 protein and are also more likely to harbor sites for endogenous transcription factors. Especially for gene repression, it is contemplated herein that blocking the binding site of an endogenous transcription factor would aid in downregulating gene expression. In another embodiment, an eiCas9 can be fused to a chromatin modifying protein. Altering chromatin status can result in decreased expression of the target gene.

In some embodiments, a gRNA molecule can be targeted to a known transcription response elements (e.g., promoters, enhancers, etc.), a known upstream activating sequences (UAS), and/or sequences of unknown or known function that are suspected of being able to control expression of the target DNA.

In some embodiments, CRISPR/Cas-mediated gene knockdown can be used to reduce expression one or more T-cell expressed genes. In some embodiments, in which a eiCas9 or an eiCas9 fusion protein described herein is used to knockdown the CD247 locus, individual gRNAs or gRNA pairs targeting both or all genes are provided together with the eiCas9 or eiCas9 fusion protein.

3) Single-Strand Annealing

Single strand annealing (SSA) is another DNA repair process that repairs a double-strand break between two repeat sequences present in a target nucleic acid. Repeat sequences utilized by the SSA pathway are generally greater than 30 nucleotides in length. Resection at the break ends occurs to reveal repeat sequences on both strands of the target nucleic acid. After resection, single strand overhangs containing the repeat sequences are coated with RPA protein to prevent the repeats sequences from inappropriate annealing, e.g., to themselves. RAD52 binds to and each of the repeat sequences on the overhangs and aligns the sequences to enable the annealing of the complementary repeat sequences. After annealing, the single-strand flaps of the overhangs are cleaved. New DNA synthesis fills in any gaps, and ligation restores the DNA duplex. As a result of the processing, the DNA sequence between the two repeats is deleted. The length of the deletion can depend on many factors including the location of the two repeats utilized, and the pathway or processivity of the resection.

In contrast to HDR pathways, SSA does not require a template nucleic acid to alter or correct a target nucleic acid sequence. Instead, the complementary repeat sequence is utilized.

4) Other DNA Repair Pathways

A) SSBR (Single Strand Break Repair)

Single-stranded breaks (SSB) in the genome are repaired by the SSBR pathway, which is a distinct mechanism from the DSB repair mechanisms discussed above. The SSBR pathway has four major stages: SSB detection, DNA end processing, DNA gap filling, and DNA ligation. A more detailed explanation is given in Caldecott, Nature Reviews Genetics 9, 619-631 (August 2008), and a summary is given here.

In the first stage, when a SSB forms, PARP1 and/or PARP2 recognize the break and recruit repair machinery. The binding and activity of PARP1 at DNA breaks is transient and it seems to accelerate SSBr by promoting the focal accumulation or stability of SSBr protein complexes at the lesion. Arguably the most important of these SSBr proteins is XRCC1, which functions as a molecular scaffold that interacts with, stabilizes, and stimulates multiple enzymatic components of the SSBr process including the protein responsible for cleaning the DNA 3' and 5' ends. In some embodiments, XRCC1 interacts with several proteins (DNA polymerase beta, PNK, and three nucleases, APE1, APTX, and APLF) that promote end processing. APE1 has endonuclease activity. APLF exhibits endonuclease and 3' to 5' exonuclease activities. APTX has endonuclease and 3' to 5' exonuclease activity.

This end processing is an important stage of SSBR since the 3'- and/or 5'-termini of most, if not all, SSBs are 'damaged'. End processing generally involves restoring a damaged 3'-end to a hydroxylated state and and/or a damaged 5' end to a phosphate moiety, so that the ends become ligation-competent. Enzymes that can process damaged 3' termini include PNKP, APE1, and TDP1. Enzymes that can process damaged 5' termini include PNKP, DNA polymerase beta, and APTX. LIG3 (DNA ligase III) can also participate in end processing. Once the ends are cleaned, gap filling can occur.

At the DNA gap filling stage, the proteins typically present are PARP1, DNA polymerase beta, XRCC1, FEN1 (flap endonuclease 1), DNA polymerase delta/epsilon, PCNA, and LIG1. There are two ways of gap filling, the short patch repair and the long patch repair. Short patch repair involves the insertion of a single nucleotide that is missing. At some SSBs, "gap filling" might continue displacing two or more nucleotides (displacement of up to 12 bases have been reported). FEN1 is an endonuclease that removes the displaced 5'-residues. Multiple DNA polymerases, including Pol β, are involved in the repair of SSBs, with the choice of DNA polymerase influenced by the source and type of SSB.

In the fourth stage, a DNA ligase such as LIG1 (Ligase I) or LIG3 (Ligase III) catalyzes joining of the ends. Short patch repair uses Ligase III and long patch repair uses Ligase I.

Sometimes, SSBR is replication-coupled. This pathway can involve one or more of CtIP, MRN, ERCC1, and FEN1. Additional factors that may promote SSBR include: aPARP, PARP1, PARP2, PARG, XRCC1, DNA polymerase b, DNA polymerase d, DNA polymerase e, PCNA, LIG1, PNK, PNKP, APE1, APTX, APLF, TDP1, LIG3, FEN1, CtIP, MRN, and ERCC1.

B) MMR (Mismatch Repair)

Cells contain three excision repair pathways: MMR, BER, and NER. The excision repair pathways have a common feature in that they typically recognize a lesion on one strand of the DNA, then exo/endonucleases remove the lesion and leave a 1-30 nucleotide gap that is sub-sequentially filled in by DNA polymerase and finally sealed with ligase. A more complete picture is given in Li, Cell Research (2008) 18:85-98, and a summary is provided here. Mismatch repair (MMR) operates on mispaired DNA bases.

The MSH2/6 or MSH2/3 complexes both have ATPases activity that plays an important role in mismatch recognition and the initiation of repair. MSH2/6 preferentially recognizes base-base mismatches and identifies mispairs of 1 or 2 nucleotides, while MSH2/3 preferentially recognizes larger ID mispairs.

hMLH1 heterodimerizes with hPMS2 to form hMutLα which possesses an ATPase activity and is important for multiple steps of MMR. It possesses a PCNA/replication factor C (RFC)-dependent endonuclease activity which plays an important role in 3' nick-directed MMR involving EXO1. (EXO1 is a participant in both HR and MMR.) It regulates termination of mismatch-provoked excision. Ligase I is the relevant ligase for this pathway. Additional factors that may promote MMR include: EXO1, MSH2, MSH3, MSH6, MLH1, PMS2, MLH3, DNA Pol d, RPA, HMGB1, RFC, and DNA ligase I.

C) Base Excision Repair (BER)

The base excision repair (BER) pathway is active throughout the cell cycle; it is responsible primarily for removing small, non-helix-distorting base lesions from the genome. In contrast, the related Nucleotide Excision Repair pathway (discussed in the next section) repairs bulky helix-distorting lesions. A more detailed explanation is given in Caldecott, Nature Reviews Genetics 9, 619-631 (August 2008), and a summary is given here.

Upon DNA base damage, base excision repair (BER) is initiated and the process can be simplified into five major steps: (a) removal of the damaged DNA base; (b) incision of the subsequent a basic site; (c) clean-up of the DNA ends; (d) insertion of the correct nucleotide into the repair gap; and (e) ligation of the remaining nick in the DNA backbone. These last steps are similar to the SSBR.

In the first step, a damage-specific DNA glycosylase excises the damaged base through cleavage of the N-glycosidic bond linking the base to the sugar phosphate backbone. Then AP endonuclease-1 (APE1) or bifunctional DNA glycosylases with an associated lyase activity incised the phosphodiester backbone to create a DNA single strand break (SSB). The third step of BER involves cleaning-up of the DNA ends. The fourth step in BER is conducted by Pol β that adds a new complementary nucleotide into the repair gap and in the final step XRCC1/Ligase III seals the remaining nick in the DNA backbone. This completes the short-patch BER pathway in which the majority (~80%) of damaged DNA bases are repaired. However, if the 5'-ends in step 3 are resistant to end processing activity, following one nucleotide insertion by Pol β there is then a polymerase switch to the replicative DNA polymerases, Pol δ/ε, which then add ~2-8 more nucleotides into the DNA repair gap. This creates a 5'-flap structure, which is recognized and excised by flap endonuclease-1 (FEN-1) in association with the processivity factor proliferating cell nuclear antigen (PCNA). DNA ligase I then seals the remaining nick in the DNA backbone and completes long-patch BER. Additional factors that may promote the BER pathway include: DNA glycosylase, APE1, Polb, Pold, Pole, XRCC1, Ligase III, FEN-1, PCNA, RECQL4, WRN, MYH, PNKP, and APTX.

D) Nucleotide Excision Repair (NER)

Nucleotide excision repair (NER) is an important excision mechanism that removes bulky helix-distorting lesions from DNA. Additional details about NER are given in Marteijn et al., Nature Reviews Molecular Cell Biology 15, 465-481 (2014), and a summary is given here. NER a broad pathway encompassing two smaller pathways: global genomic NER (GG-NER) and transcription coupled repair NER (TC-NER). GG-NER and TC-NER use different factors for recognizing DNA damage. However, they utilize the same machinery for lesion incision, repair, and ligation.

Once damage is recognized, the cell removes a short single-stranded DNA segment that contains the lesion. Endonucleases XPF/ERCC1 and XPG (encoded by ERCC5) remove the lesion by cutting the damaged strand on either side of the lesion, resulting in a single-strand gap of 22-30 nucleotides. Next, the cell performs DNA gap filling synthesis and ligation. Involved in this process are: PCNA, RFC, DNA Pol δ, DNA Pol ε or DNA Pol κ, and DNA ligase I or XRCC1/Ligase III. Replicating cells tend to use DNA pol ε and DNA ligase I, while non-replicating cells tend to use DNA Pol δ, DNA Pol κ, and the XRCC1/Ligase III complex to perform the ligation step.

NER can involve the following factors: XPA-G, POLH, XPF, ERCC1, XPA-G, and LIG1. Transcription-coupled NER (TC-NER) can involve the following factors: CSA, CSB, XPB, XPD, XPG, ERCC1, and TTDA. Additional factors that may promote the NER repair pathway include XPA-G, POLH, XPF, ERCC1, XPA-G, LIG1, CSA, CSB, XPA, XPB, XPC, XPD, XPF, XPG, TTDA, UVSSA, USP7, CETN2, RAD23B, UV-DDB, CAK subcomplex, RPA, and PCNA.

E) Interstrand Crosslink (ICL)

A dedicated pathway called the ICL repair pathway repairs interstrand crosslinks Interstrand crosslinks, or covalent crosslinks between bases in different DNA strand, can occur during replication or transcription. ICL repair involves the coordination of multiple repair processes, in particular, nucleolytic activity, translesion synthesis (TLS), and HDR. Nucleases are recruited to excise the ICL on either side of the crosslinked bases, while TLS and HDR are coordinated to repair the cut strands. ICL repair can involve the following factors: endonucleases, e.g., XPF and RAD51C, endonucleases such as RAD51, translesion polymerases, e.g., DNA polymerase zeta and Rev1), and the Fanconi anemia (FA) proteins, e.g., FancJ.

F) Other Pathways

Several other DNA repair pathways exist in mammals Translesion synthesis (TLS) is a pathway for repairing a single stranded break left after a defective replication event and involves translesion polymerases, e.g., DNA polζ and Rev1. Error-free post replication repair (PRR) is another pathway for repairing a single stranded break left after a defective replication event.

(2) Functional Analysis of Agents for Gene Editing

Any of the Cas9 molecules, gRNA molecules, Cas9 molecule/gRNA molecule complexes, can be evaluated by art-known methods or as described herein. For example, exemplary methods for evaluating the endonuclease activity of Cas9 molecule are described, e.g., in Jinek et al., Science 2012, 337(6096):816-821.

(a) Binding and Cleavage Assay: Testing the Endonuclease Activity of Cas9 Molecule The ability of a Cas9 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cas9 protein molecule (50-500 nM) and gRNA (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions are stopped with 5×DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cas9 molecule cleaves both DNA strands, or only one of the two strands. For example, linear DNA products indicate the cleavage of both DNA strands. Nicked open circular products indicate that only one of the two strands is cleaved.

Alternatively, the ability of a Cas9 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 5 units T4 polynucleotide kinase and ~3-6 pmol (~20-40 mCi) [γ-$^{32}$P]-ATP in 1×T4 polynucleotide kinase reaction buffer at 37° C. for 30 min, in a 50 μL reaction. After heat inactivation (65° C. for 20 min), reactions are purified through a column to remove unincorporated label. Duplex substrates (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cas9 (500 nM final concentration) is pre-incubated with the annealed gRNA molecules (500 nM) in cleavage assay buffer (20 mM HEPES pH 7.5, 100 mM KCl, 5 mM $MgCl_2$, 1 mM DTT, 5% glycerol) in a total volume of 9 μl. Reactions are initiated by the addition of 1 μl target DNA (10 nM) and incubated for 1 h at 37° C. Reactions are quenched by the addition of 20 μl of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of any of the gRNA molecule or Cas9 molecule provided.

G) Binding Assay: Testing the Binding of Cas9 Molecule to Target DNA

Exemplary methods for evaluating the binding of Cas9 molecule to target DNA are described, e.g., in Jinek et al., SCIENCE 2012; 337(6096):816-821.

For example, in an electrophoretic mobility shift assay, target DNA duplexes are formed by mixing of each strand (10 nmol) in deionized water, heating to 95° C. for 3 min and slow cooling to room temperature. All DNAs are purified on 8% native gels containing 1×TBE. DNA bands are visualized by UV shadowing, excised, and eluted by soaking gel pieces in DEPC-treated $H_2O$. Eluted DNA is ethanol precipitated and dissolved in DEPC-treated $H_2O$. DNA samples are 5' end labeled with [γ-32P]-ATP using T4 polynucleotide kinase for 30 min at 37° C. Polynucleotide kinase is heat denatured at 65° C. for 20 min, and unincorporated radiolabel is removed using a column. Binding assays are performed in buffer containing 20 mM HEPES pH 7.5, 100 mM KCl, 5 mM $MgCl_2$, 1 mM DTT and 10% glycerol in a total volume of 10 μl. Cas9 protein molecule is programmed with equimolar amounts of pre-annealed gRNA molecule and titrated from 100 pM to 1 μM. Radiolabeled DNA is added to a final concentration of 20 pM. Samples are incubated for 1 h at 37° C. and resolved at 4° C. on an 8% native polyacrylamide gel containing 1×TBE and 5 mM $MgCl_2$. Gels are dried and DNA visualized by phosphorimaging.

H) Techniques for Measuring Thermostability of Cas9/gRNA Complexes

The thermostability of Cas9-gRNA ribonucleoprotein (RNP) complexes can be detected by differential scanning fluorimetry (DSF) and other techniques. The thermostability of a protein can increase under favorable conditions such as the addition of a binding RNA molecule, e.g., a gRNA. Thus, information regarding the thermostability of a Cas9/gRNA complex is useful for determining whether the complex is stable.

I) Differential Scanning Fluorimetry (DSF)

The thermostability of Cas9-gRNA ribonucleoprotein (RNP) complexes can be measured via DSF. RNP complexes, as described below, include a sequence of ribonucleotides, such as an RNA or a gRNA, and a protein, such as a Cas9 protein or variant thereof. This technique measures the thermostability of a protein, which can increase under favorable conditions such as the addition of a binding RNA molecule, e.g., a gRNA.

The assay can be applied in a number of ways. Exemplary protocols include, but are not limited to, a protocol to determine the desired solution conditions for RNP formation (assay 1, see below), a protocol to test the desired stoichiometric ratio of gRNA:Cas9 protein (assay 2, see below), a protocol to screen for effective gRNA molecules for Cas9 molecules, e.g., wild-type or mutant Cas9 molecules (assay 3, see below), and a protocol to examine RNP formation in the presence of target DNA (assay 4). In some embodiments, the assay is performed using two different protocols, one to test the best stoichiometric ratio of gRNA:Cas9 protein and another to determine the best solution conditions for RNP formation.

To determine the best solution to form RNP complexes, a 2 μM solution of Cas9 in water+10×SYPRO Orange® (Life Technologies cat #S-6650) and dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° increase in temperature every 10 seconds.

The second assay consists of mixing various concentrations of gRNA with 2 μM Cas9 in optimal buffer from assay 1 above and incubating at RT for 10' in a 384 well plate. An equal volume of optimal buffer+10×SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° increase in temperature every 10 seconds.

In the third assay, a Cas9 molecule (e.g., a Cas9 protein, e.g., a Cas9 variant protein) of interest is purified. A library of variant gRNA molecules is synthesized and resuspended to a concentration of 20 μM. The Cas9 molecule is incubated with the gRNA molecule at a final concentration of 1 μM each in a predetermined buffer in the presence of 5×SYPRO Orange® (Life Technologies cat #S-6650). After incubating at room temperature for 10 minutes and centrifugation at 2000 rpm for 2 minutes to remove any bubbles, a Bio-Rad CFX384™ Real-Time System C1000 Touch™ Thermal Cycler with the Bio-Rad CFX Manager software is used to run a gradient from 20° C. to 90° C. with an increase of 1° C. in temperature every 10 seconds.

In the fourth assay, a DSF experiment is performed with the following samples: Cas9 protein alone, Cas9 protein with gRNA, Cas9 protein with gRNA and target DNA, and Cas9 protein with target DNA. The order of mixing components is: reaction solution, Cas9 protein, gRNA, DNA, and SYPRO Orange. The reaction solution contains 10 mM HEPES pH 7.5, 100 mM NaCl, in the absence or presence of MgCl2. Following centrifugation at 2000 rpm for 2 minutes to remove any bubbles, a Bio-Rad CFX384™ Real-Time System C1000 Touch™ Thermal Cycler with the Bio-Rad CFX Manager software is used to run a gradient from 20° C. to 90° C. with a 1° increase in temperature every 10 seconds.

3. Delivery of Agents for Genetic Disruption

In some embodiments, the targeted genetic disruption, e.g., DNA break, of the endogenous CD247 locus (encoding CD3zeta) in humans is carried out by delivering or introducing one or more agent(s) capable of inducing a genetic disruption, e.g., Cas9 and/or gRNA components, to a cell, using any of a number of known delivery method or vehicle for introduction or transfer to cells, for example, using viral, e.g., lentiviral, delivery vectors, or any of the known methods or vehicles for delivering Cas9 molecules and gRNAs. Exemplary methods are described in, e.g., Wang et al. (2012) *J. Immunother.* 35(9): 689-701; Cooper et al. (2003) *Blood.* 101:1637-1644; Verhoeyen et al. (2009) *Methods Mol Biol.* 506: 97-114; and Cavalieri et al. (2003) Blood. 102(2): 497-505. In some embodiments, nucleic acid sequences encoding one or more components of one or more agent(s) capable of inducing a genetic disruption, e.g., DNA break, is introduced into the cells, e.g., by any methods for introducing nucleic acids into a cell described herein or known. In some embodiments, a vector encoding components of one or more agent(s) capable of inducing a genetic disruption such as a CRISPR guide RNA and/or a Cas9 enzyme can be delivered into the cell.

In some embodiments, the one or more agent(s) capable of inducing a genetic disruption, e.g., one or more agent(s) that is a Cas9/gRNA, is introduced into the cell as a ribonucleoprotein (RNP) complex. RNP complexes include a sequence of ribonucleotides, such as an RNA or a gRNA molecule, and a protein, such as a Cas9 protein or variant thereof. For example, the Cas9 protein is delivered as RNP complex that comprises a Cas9 protein and a gRNA molecule targeting the target sequence, e.g., using electroporation or other physical delivery method. In some embodiments, the RNP is delivered into the cell via electroporation or other physical means, e.g., particle gun, Calcium Phosphate transfection, cell compression or squeezing. In some embodiments, the RNP can cross the plasma membrane of a cell without the need for additional delivery agents (e.g., small molecule agents, lipids, etc.). In some embodiments, delivery of the one or more agent(s) capable of inducing genetic disruption, e.g., CRISPR/Cas9, as an RNP offers an advantage that the targeted disruption occurs transiently, e.g., in cells to which the RNP is introduced, without propagation of the agent to cell progenies. For example, delivery by RNP minimizes the agent from being inherited to its progenies, thereby reducing the chance of off-target genetic disruption in the progenies. In such cases, the genetic disruption and the integration of transgene can be inherited by the progeny cells, but without the agent itself, which may further introduce off-target genetic disruptions, being passed on to the progeny cells.

Agent(s) and components capable of inducing a genetic disruption, e.g., a Cas9 molecule and gRNA molecule, can be introduced into target cells in a variety of forms using a variety of delivery methods and formulations, as set forth in Tables 3 and 4, or methods described in, e.g., WO 2015/161276; US 2015/0056705, US 2016/0272999, US 2017/0211075; or US 2017/0016027. As described further herein, the delivery methods and formulations can be used to deliver template polynucleotides and/or other agents to the cell (such as those required for engineering the cells) in prior or subsequent steps of the methods described herein. When a Cas9 or gRNA component is encoded as DNA for delivery, the DNA may typically but not necessarily include a control region, e.g., comprising a promoter, to effect expression. Useful promoters for Cas9 molecule sequences include, e.g., CMV, EF-1α, EFS, MSCV, PGK, or CAG promoters. Useful promoters for gRNAs include, e.g., H1, EF-1α, tRNA or U6 promoters. Promoters with similar or dissimilar strengths can be selected to tune the expression of components. Sequences encoding a Cas9 molecule may comprise a nuclear localization signal (NLS), e.g., an SV40 NLS. In some embodiments a promoter for a Cas9 molecule or a gRNA molecule may be, independently, inducible, tissue specific, or cell specific. In some embodiments, an agent capable of inducing a genetic disruption is introduced RNP complexes. In some embodiments, the gRNA contains a modification, such as an Alt-R modification (IDT Technologies; Coralville, IA).

TABLE 3

| Exemplary Delivery Methods | | |
|---|---|---|
| Elements | | |
| Cas9 Molecule(s) | gRNA molecule(s) | Comments |
| DNA | DNA | In this embodiment, a Cas9 molecule and a gRNA are transcribed from DNA. In this embodiment, they are encoded on separate molecules. |
| DNA | | In this embodiment, a Cas9 molecule and a gRNA are transcribed from DNA, here from a single molecule. |
| DNA | RNA | In this embodiment, a Cas9 molecule is transcribed from DNA, and a gRNA is provided as in vitro transcribed or synthesized RNA |
| mRNA | RNA | In this embodiment, a Cas9 molecule is translated from in vitro transcribed mRNA, and a gRNA is provided as in vitro transcribed or synthesized RNA. |
| mRNA | DNA | In this embodiment, a Cas9 molecule is translated from in vitro transcribed mRNA, and a gRNA is transcribed from DNA. |
| Protein | DNA | In this embodiment, a Cas9 molecule is provided as a protein, and a gRNA is transcribed from DNA. |
| Protein | RNA | In this embodiment, a Cas9 molecule is provided as a protein, and a gRNA is provided as transcribed or synthesized RNA. |

TABLE 4

| Comparison of Exemplary Delivery Methods | | | | | |
|---|---|---|---|---|---|
| Delivery Vector/Mode | | Delivery into Non-Dividing Cells | Duration of Expression | Genome Integration | Type of Molecule Delivered |
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

In some embodiments, DNA encoding Cas9 molecules and/or gRNA molecules, or RNP complexes comprising a Cas9 molecule and/or gRNA molecules, can be delivered into cells by known methods or as described herein. For example, Cas9-encoding and/or gRNA-encoding DNA can be delivered, e.g., by vectors (e.g., viral or non-viral vectors), non-vector based methods (e.g., using naked DNA or DNA complexes), or a combination thereof. In some embodiments, the polynucleotide containing the agent(s) and/or components thereof is delivered by a vector (e.g., viral vector/virus or plasmid). The vector may be any described herein.

In some aspects, a CRISPR enzyme (e.g. Cas9 nuclease) in combination with (and optionally complexed with) a guide sequence is delivered to the cell. For example, one or more elements of a CRISPR system is derived from a type I, type II, or type III CRISPR system. For example, one or more elements of a CRISPR system are derived from a particular organism comprising an endogenous CRISPR system, such as *Streptococcus pyogenes, Staphylococcus aureus* or *Neisseria meningitides.*

In some embodiments, a Cas9 nuclease (e.g., that encoded by mRNA from Staphylococcus aureus or from Streptococcus pyogenes, e.g. pCW-Cas9, Addgene #50661, Wang et al. (2014) Science, 3:343-80-4; or nuclease or nickase lentiviral vectors available from Applied Biological Materials (ABM; Canada) as Cat. No. K002, K003, K005 or K006) and a guide RNA specific to the target gene (e.g. CD247 locus in humans) are introduced into cells.

In some embodiments, the polynucleotide containing the agent(s) and/or components thereof or RNP complex is delivered by a non-vector based method (e.g., using naked DNA or DNA complexes). For example, the DNA or RNA or proteins or combination thereof, e.g., ribonucleoprotein (RNP) complexes, can be delivered, e.g., by organically modified silica or silicate (Ormosil), electroporation, transient cell compression or squeezing (such as described in Lee, et al. (2012) *Nano Lett* 12: 6322-27, Kollmannsperger et al (2016) Nat Comm 7, 10372), gene gun, sonoporation, magnetofection, lipid-mediated transfection, dendrimers, inorganic nanoparticles, calcium phosphates, or a combination thereof.

In some embodiments, delivery via electroporation comprises mixing the cells with the Cas9- and/or gRNA-encoding DNA or RNP complex in a cartridge, chamber or cuvette and applying one or more electrical impulses of defined duration and amplitude. In some embodiments, delivery via electroporation is performed using a system in which cells are mixed with the Cas9- and/or gRNA-encoding DNA in a vessel connected to a device (e.g., a pump) which feeds the mixture into a cartridge, chamber or cuvette wherein one or more electrical impulses of defined duration and amplitude are applied, after which the cells are delivered to a second vessel.

In some embodiments, the delivery vehicle is a non-viral vector. In some embodiments, the non-viral vector is an inorganic nanoparticle. Exemplary inorganic nanoparticles include, e.g., magnetic nanoparticles (e.g., $Fe_3MnO_2$) and silica. The outer surface of the nanoparticle can be conjugated with a positively charged polymer (e.g., polyethylenimine, polylysine, polyserine) which allows for attachment (e.g., conjugation or entrapment) of payload. In some embodiments, the non-viral vector is an organic nanoparticle. Exemplary organic nanoparticles include, e.g., SNALP liposomes that contain cationic lipids together with neutral helper lipids which are coated with polyethylene glycol (PEG), and protamine-nucleic acid complexes coated with lipid. Exemplary lipids for gene transfer are shown below in Table 5.

TABLE 5

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)prophyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl] cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl] trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3- dimethylaminopropane | DLinDMA | Cationic |
| 2,2-dilinoleyl-4-dimethylaminoethyl-[1,3]- dioxolane | DLin-KC2-DMA | Cationic |
| dilinoleyl- methyl-4-dimethylaminobutyrate | DLin-MC3-DMA | Cationic |

Exemplary polymers for gene transfer are shown below in Table 6.

TABLE 6

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

In some embodiments, the vehicle has targeting modifications to increase target cell update of nanoparticles and liposomes, e.g., cell specific antigens, monoclonal antibodies, single chain antibodies, aptamers, polymers, sugars, and cell penetrating peptides. In some embodiments, the vehicle uses fusogenic and endosome-destabilizing peptides/polymers. In some embodiments, the vehicle undergoes acid-triggered conformational changes (e.g., to accelerate endosomal escape of the cargo). In some embodiments, a stimulus-cleavable polymer is used, e.g., for release in a cellular compartment. For example, disulfide-based cationic polymers that are cleaved in the reducing cellular environment can be used.

In some embodiments, the delivery vehicle is a biological non-viral delivery vehicle. In some embodiments, the vehicle is an attenuated bacterium (e.g., naturally or artificially engineered to be invasive but attenuated to prevent pathogenesis and expressing the transgene (e.g., *Listeria monocytogenes*, certain *Salmonella strains, Bifidobacterium longum*, and modified *Escherichia coli*), bacteria having nutritional and tissue-specific tropism to target specific cells, bacteria having modified surface proteins to alter target cell specificity). In some embodiments, the vehicle is a genetically modified bacteriophage (e.g., engineered phages having large packaging capacity, less immunogenicity, containing mammalian plasmid maintenance sequences and having incorporated targeting ligands). In some embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue-specificity. In some embodiments, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes-subject-derived membrane-bound nanovesicles (30-100 nm) of endocytic origin (e.g., can be produced from various cell types and can therefore be taken up by cells without the need for targeting ligands).

In some embodiments, RNA encoding Cas9 molecules and/or gRNA molecules, can be delivered into cells, e.g., target cells described herein, by known methods or as described herein. For example, Cas9-encoding and/or gRNA-encoding RNA can be delivered, e.g., by microinjection, electroporation, transient cell compression or squeezing (such as described in Lee, et al. (2012) *Nano Lett* 12: 6322-27), lipid-mediated transfection, peptide-mediated delivery, e.g., cell-penetrating peptides, or a combination thereof.

In some embodiments, delivery via electroporation comprises mixing the cells with the RNA encoding Cas9 molecules and/or gRNA molecules in a cartridge, chamber or cuvette and applying one or more electrical impulses of defined duration and amplitude. In some embodiments, delivery via electroporation is performed using a system in which cells are mixed with the RNA encoding Cas9 molecules and/or gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel.

In some embodiments, Cas9 molecules can be delivered into cells by known methods or as described herein. For example, Cas9 protein molecules can be delivered, e.g., by microinjection, electroporation, transient cell compression or squeezing (such as described in Lee, et al. (2012) *Nano Lett* 12: 6322-27), lipid-mediated transfection, peptide-mediated delivery, or a combination thereof. Delivery can be accompanied by DNA encoding a gRNA or by a gRNA.

In some embodiments, the one or more agent(s) capable of introducing a cleavage, e.g., a Cas9/gRNA system, is introduced into the cell as a ribonucleoprotein (RNP) complex. RNP complexes include a sequence of ribonucleotides, such as an RNA or a gRNA molecule, and a protein, such as a Cas9 protein or variant thereof. For example, the Cas9 protein is delivered as RNP complex that comprises a Cas9 protein and a gRNA molecule targeting the target sequence, e.g., using electroporation or other physical delivery method. In some embodiments, the RNP is delivered into the cell via electroporation or other physical means, e.g., particle gun, calcium phosphate transfection, cell compression or squeezing.

In some embodiments, the one or more agent(s) is or comprises a ribonucleoprotein (RNP) complex. In some embodiments, the concentration of the RNP incubated with, added to or contacted with the cells for engineering is at a concentration of at or about 0.1, 0.2, 0.3, 0.4, 0.5, 0.6, 0.7, 0.8, 0.9, 1, 2, 2.2, 2.5, 3, 4, 5, 6, 7, 7.5, 8, 9, 10, 11, 12, 13, 14, 15, 16, 17, 18, 19, 20, 21, 22, 23, 24, 25, 26, 27, 28, 29, 30, 40 or 50 μM, or a range defined by any two of the foregoing values. In some embodiments, the concentration of the RNP incubated with, added to or contacted with the cells for engineering is at a concentration of at or about 1, 2, 2.5, 5, 10, 20, 25, 30, 40 or 50 μM, or a range defined by any two of the foregoing values. In some embodiments, the concentration of RNPs is 2 μM. In some embodiments, the concentration of RNPs is 25 μM. In some embodiments, in the RNP complex, the ratio, e.g. the molar ratio, of the gRNA and the Cas9 molecule or other nucleases is at or about 5:1, 4:1, 3:1, 2:1, 1:1, 1:2, 1:3, 1:4 or 1:5, or a range defined by any two of the foregoing values. In some embodiments, in the RNP complex, the ratio, e.g., molar ratio, of the gRNA and the Cas9 molecule or other nucleases is at or about 3:1, 2.9:1, 2.8:1, 2.7:1, 2.6:1, 2.5:1, 2.4:1, 2.3:1, 2.2:1, 2.1:1, 2:1 or 1:1, or a range defined by any two of the foregoing values. In some embodiments, in the RNP complex, the molar ratio of the gRNA and the Cas9 molecule or other nucleases is at or about 2.6:1.

In some embodiments, delivery via electroporation comprises mixing the cells with the Cas9 molecules with or without gRNA molecules in a cartridge, chamber or cuvette and applying one or more electrical impulses of defined duration and amplitude. In some embodiments, delivery via electroporation is performed using a system in which cells are mixed with the Cas9 molecules with or without gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel.

In some embodiments, delivery via electroporation comprises mixing the cells with the Cas9 molecules (e.g., eaCas9 molecules, eiCas9 molecules or eiCas9 fusion proteins) with or without gRNA molecules in a cartridge, chamber or cuvette and applying one or more electrical impulses of defined duration and amplitude. In some embodiments, delivery via electroporation is performed using a system in which cells are mixed with the Cas9 molecules (e.g., eaCas9 molecules, eiCas9 molecules or eiCas9 fusion proteins)

In some embodiments, the polynucleotide containing the agent(s) and/or components thereof is delivered by a combination of a vector and a non-vector based method. For example, a virosome comprises a liposome combined with an inactivated virus (e.g., HIV or influenza virus), which can result in more efficient gene transfer than either a viral or a liposomal method alone.

In some embodiments, more than one agent(s) or components thereof are delivered to the cell. For example, in some embodiments, agent(s) capable of inducing a genetic disruption of two or more locations in the genome, such as at two or more sites within a CD247 locus (encoding CD3zeta), are delivered to the cell. In some embodiments, agent(s) and components thereof are delivered using one method. For example, in some embodiments, agent(s) for inducing a genetic disruption of the CD247 locus are delivered as polynucleotides encoding the components for genetic disruption. In some embodiments, one polynucleotide can encode agents that target the CD247 locus. In some embodiments, two or more different polynucleotides can encode the agents that target the CD247 locus. In some embodiments, the agents capable of inducing a genetic disruption can be delivered as ribonucleoprotein (RNP) complexes, and two or more different RNP complexes can be delivered together as a mixture, or separately.

In some embodiments, one or more nucleic acid molecules other than the one or more agent(s) capable of inducing a genetic disruption and/or component thereof, e.g., the Cas9 molecule component and/or the gRNA molecule component, such as a template polynucleotide for HDR-directed integration (such as any template polynucleotide described herein, e.g., in Section I.B.2), are delivered. In some embodiments, the nucleic acid molecule, e.g., template polynucleotide, is delivered at the same time as one or more of the components of the Cas system. In some embodiments, the nucleic acid molecule is delivered before or after (e.g., less than about 1 minute, 5 minutes, 10 minutes, 15 minutes, 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In some embodiments, the nucleic acid molecule, e.g., template polynucleotide, is delivered by a different means from one or more of the components of the Cas system, e.g., the Cas9 molecule component and/or the gRNA molecule component. The nucleic acid molecule, e.g., template polynucleotide, can be delivered by any of the delivery methods described herein. For example, the nucleic acid molecule, e.g., template polynucleotide, can be delivered by a viral vector, e.g., a retrovirus or a lentivirus, and the Cas9 molecule component and/or the gRNA molecule component can be delivered by electroporation. In some embodiments, the nucleic acid molecule, e.g., template polynucleotide, includes one or more exogenous sequences, e.g., sequences that encode a chimeric receptor or a portion thereof and/or other exogenous gene nucleic acid sequences.

B. Targeted Integration Via Homology-Directed Repair (HDR)

In some aspects, the provided embodiments involve targeted integration of a specific part of a polynucleotide, such as the part of a template polynucleotide containing transgene sequences encoding a chimeric receptor or a portion thereof, at a particular location (such as target site or target location) in the genome at the endogenous CD247 locus encoding CD3zeta (CD3ζ). In some aspects, homology-directed repair (HDR) can mediate the site specific integration of the transgene sequences at the target site. In some embodiments, the presence of a genetic disruption (e.g., a DNA break, such as described in Section I.A) and a template polynucleotide containing one or more homology arms (e.g., containing nucleic acid sequences homologous sequences surrounding the genetic disruption) can induce or direct HDR, with homologous sequences acting as a template for DNA repair. Based on homology between the endogenous gene sequence surrounding the genetic disruption and the 5' and/or 3' homology arms included in the template polynucleotide, cellular DNA repair machinery can use the template polynucleotide to repair the DNA break and resynthesize (e.g., copy) genetic information at the site of the genetic disruption, thereby effectively inserting or integrating the transgene sequences in the template polynucleotide at or near the site of the genetic disruption. In some embodiments, the genetic disruption at an endogenous CD247 locus encoding CD3, can be generated by any of the methods for generating a targeted genetic disruption described herein, for example, in Section I.A.

Also provided are polynucleotides, e.g., template polynucleotides described herein, and kits that include such polynucleotides. In some embodiments, the provided polynucleotides and/or kits can be employed in the methods described herein, e.g., involving HDR, to target transgene sequences encoding a portion of a chimeric receptor at the endogenous CD247 locus encoding CD3zeta.

In some embodiments, the template polynucleotide is or comprises a polynucleotide containing a transgene, such as exogenous or heterologous nucleic acid sequences, encoding a chimeric receptor or a portion thereof (e.g., one or more region(s) or domain(s) of the chimeric receptor), and homology sequences (e.g., homology arms) that are homologous to sequences at or near the endogenous genomic site at the endogenous CD247 locus encoding CD3. In some aspects, the transgene sequences in the template polynucleotide comprise sequence of nucleotides encoding a portion of a chimeric receptor. In some aspects, upon targeted integration of the transgene sequences encoding a portion of a chimeric receptor, the CD247 locus in the engineered cell is modified such that the modified CD247 locus contains a fusion of the transgene sequences and sequences of the endogenous CD247 locus, said fusion encoding a chimeric receptor, e.g., a chimeric antigen receptor (CAR).

In some aspects, the template polynucleotide is introduced as a linear DNA fragment or comprised in a vector. In some aspects, the step for inducing genetic disruption and the step for targeted integration (e.g., by introduction of the template polynucleotide) are performed simultaneously or sequentially.

1. Homology-Directed Repair (HDR)

In some embodiments, homology-directed repair (HDR) can be utilized for targeted integration or insertion of one or more nucleic acid sequences, e.g., transgene sequences encoding a chimeric receptor or a portion thereof, at one or more target site(s) in the genome at a CD247 locus. In some embodiments, the nuclease-induced HDR can be used to alter a target sequence, integrate transgene sequences at a particular target location, and/or to edit or repair a mutation in a particular target gene.

Alteration of nucleic acid sequences at the target site can occur by HDR with an exogenously provided polynucleotide, e.g., template polynucleotide (also referred to as "donor polynucleotide" or "template sequence"). For example, the template polynucleotide provides for alteration of the target sequence, such as insertion of the transgene sequences contained within the template polynucleotide. In some embodiments, a plasmid or a vector can be used as a template for homologous recombination. In some embodiments, a linear DNA fragment can be used as a template for homologous recombination. In some embodiments, a single stranded template polynucleotide can be used as a template for alteration of the target sequence by alternate methods of homology directed repair (e.g., single strand annealing) between the target sequence and the template polynucleotide. Template polynucleotide-effected alteration of a target sequence depends on cleavage by a nuclease, e.g., a targeted nuclease such as CRISPR/Cas9. Cleavage by the nuclease can comprise a double strand break or two single strand breaks.

In some embodiments, "recombination" includes a process of exchange of genetic information between two polynucleotides. In some embodiments, "homologous recombination (HR)" includes a specialized form of such exchange that takes place, for example, during repair of double-strand breaks in cells via homology-directed repair mechanisms. This process requires nucleotide sequence homology, uses a template polynucleotide to template repair of a target DNA (i.e., the one that experienced the double-strand break, such as target site in the endogenous gene), and is variously known as "non-crossover gene conversion" or "short tract gene conversion," because it leads to the transfer of genetic information from the template polynucleotide to the target. In some embodiments, such transfer can involve mismatch correction of heteroduplex DNA that forms between the broken target and the template polynucleotide, and/or "synthesis-dependent strand annealing," in which the template polynucleotide is used to resynthesize genetic information that will become part of the target, and/or related processes. Such specialized HR often results in an alteration of the sequence of the target molecule such that part or all of the sequence of the template polynucleotide is incorporated into the target polynucleotide.

In some embodiments, a portion of the polynucleotide, such as the template polynucleotide, e.g., polynucleotide containing transgene, is integrated into the genome of a cell via homology-independent mechanisms. The methods comprise creating a double-stranded break (DSB) in the genome of a cell and cleaving the template polynucleotide molecule using a nuclease, such that the template polynucleotide is integrated at the site of the DSB. In some embodiments, the template polynucleotide is integrated via non-homology dependent methods (e.g., NHEJ). Upon in vivo cleavage the template polynucleotides can be integrated in a targeted manner into the genome of a cell at the location of a DSB. The template polynucleotide can include one or more of the same target sites for one or more of the nucleases used to create the DSB. Thus, the template polynucleotide may be cleaved by one or more of the same nucleases used to cleave the endogenous gene into which integration is desired. In some embodiments, the template polynucleotide includes different nuclease target sites from the nucleases used to induce the DSB. As described herein, the genetic disruption of the target site or target position can be created by any know methods or any methods described herein, such as ZFNs, TALENs, CRISPR/Cas9 system, or TtAgo nucleases.

In some embodiments, DNA repair mechanisms can be induced by a nuclease after (1) a single double-strand break, (2) two single strand breaks, (3) two double stranded breaks with a break occurring on each side of the target site, (4) one double stranded break and two single strand breaks with the double strand break and two single strand breaks occurring on each side of the target site (5) four single stranded breaks with a pair of single stranded breaks occurring on each side of the target site, or (6) one single stranded break. In some embodiments, a single-stranded template polynucleotide is used and the target site can be altered by alternative HDR.

Template polynucleotide-effected alteration of a target site depends on cleavage by a nuclease molecule. Cleavage by the nuclease can comprise a nick, a double strand break, or two single strand breaks, e.g., one on each strand of the DNA at the target site. After introduction of the breaks on the target site, resection occurs at the break ends resulting in single stranded overhanging DNA regions.

In canonical HDR, a double-stranded template polynucleotide is introduced, comprising homologous sequence to the target site that will either be directly incorporated into the target site or used as a template to insert the transgene or correct the sequence of the target site. After resection at the break, repair can progress by different pathways, e.g., by the double Holliday junction model (or double strand break repair, DSBR, pathway) or the synthesis-dependent strand annealing (SDSA) pathway.

In the double Holliday junction model, strand invasion by the two single stranded overhangs of the target site to the homologous sequences in the template polynucleotide occurs, resulting in the formation of an intermediate with two Holliday junctions. The junctions migrate as new DNA is synthesized from the ends of the invading strand to fill the gap resulting from the resection. The end of the newly synthesized DNA is ligated to the resected end, and the junctions are resolved, resulting in the insertion at the target site, e.g., insertion of the transgene in template polynucleotide. Crossover with the template polynucleotide may occur upon resolution of the junctions.

In the SDSA pathway, only one single stranded overhang invades the template polynucleotide and new DNA is synthesized from the end of the invading strand to fill the gap resulting from resection. The newly synthesized DNA then anneals to the remaining single stranded overhang, new DNA is synthesized to fill in the gap, and the strands are ligated to produce the modified DNA duplex.

In alternative HDR, a single strand template polynucleotide, e.g., template polynucleotide, is introduced. A nick, single strand break, or double strand break at the target site, for altering a desired target site, is mediated by a nuclease molecule, and resection at the break occurs to reveal single stranded overhangs. Incorporation of the sequence of the template polynucleotide to correct or alter the target site of the DNA typically occurs by the SDSA pathway, as described herein.

"Alternative HDR", or alternative homology-directed repair, in some embodiments, refers to the process of repairing DNA damage using a homologous nucleic acid (e.g., an endogenous homologous sequence, e.g., a sister chromatid, or an exogenous nucleic acid, e.g., a template polynucleotide). Alternative HDR is distinct from canonical HDR in that the process utilizes different pathways from canonical HDR, and can be inhibited by the canonical HDR mediators, RAD51 and BRCA2. Also, alternative HDR uses a single-stranded or nicked homologous nucleic acid for repair of the break. "Canonical HDR", or canonical homology-directed repair, in some embodiments, refers to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA In a normal cell, HDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2 and the homologous nucleic acid is typically double-stranded. Unless indicated otherwise, the term "HDR" in some embodiments encompasses canonical HDR and alternative HDR.

In some embodiments, double strand cleavage is effected by a nuclease, e.g., a Cas9 molecule having cleavage activity associated with an HNH-like domain and cleavage activity associated with a RuvC-like domain, e.g., an N-terminal RuvC-like domain, e.g., a wild type Cas9. Such embodiments require only a single gRNA.

In some embodiments, one single strand break, or nick, is effected by a nuclease molecule having nickase activity, e.g., a Cas9 nickase. A nicked DNA at the target site can be a substrate for alternative HDR.

In some embodiments, two single strand breaks, or nicks, are effected by a nuclease, e.g., Cas9 molecule, having nickase activity, e.g., cleavage activity associated with an HNH-like domain or cleavage activity associated with an N-terminal RuvC-like domain Such embodiments usually require two gRNAs, one for placement of each single strand break. In some embodiments, the Cas9 molecule having nickase activity cleaves the strand to which the gRNA hybridizes, but not the strand that is complementary to the strand to which the gRNA hybridizes. In some embodiments, the Cas9 molecule having nickase activity does not cleave the strand to which the gRNA hybridizes, but rather cleaves the strand that is complementary to the strand to which the gRNA hybridizes. In some embodiments, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HNH activity and will cut on the strand to which the gRNA hybridizes (e.g., the complementary strand, which does not have the NGG PAM on it). In some embodiments, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA). In some embodiments, the Cas9 molecule is an N-terminal RuvC-like domain nickase, e.g., the Cas9 molecule comprises a mutation at N863, e.g., N863A.

In some embodiments, in which a nickase and two gRNAs are used to position two single strand nicks, one nick is on the + strand and one nick is on the − strand of the target DNA. The PAMs are outwardly facing. The gRNAs can be selected such that the gRNAs are separated by, from about 0-50, 0-100, or 0-200 nucleotides. In some embodiments, there is no overlap between the target sequences that are complementary to the targeting domains of the two gRNAs. In some embodiments, the gRNAs do not overlap and are separated by as much as 50, 100, or 200 nucleotides. In some embodiments, the use of two gRNAs can increase specificity, e.g., by decreasing off-target binding (Ran et al., Cell 2013).

In some embodiments, a single nick can be used to induce HDR, e.g., alternative HDR. It is contemplated herein that a single nick can be used to increase the ratio of HR to NHEJ at a given cleavage site, such as target site. In some embodiments, a single strand break is formed in the strand of the DNA at the target site to which the targeting domain of said gRNA is complementary. In some embodiments, a single strand break is formed in the strand of the DNA at the target site other than the strand to which the targeting domain of said gRNA is complementary.

In some embodiments, other DNA repair pathways such as single strand annealing (SSA), single-stranded break repair (SSBR), mismatch repair (MMR), base excision repair (BER), nucleotide excision repair (NER), interstrand cross-link (ICL), translesion synthesis (TLS), error-free post replication repair (PRR) can be employed by the cell to repair a double-stranded or single-stranded break created by the nucleases.

Targeted integration results in the transgene, e.g., sequences between the homology arms, being integrated into a CD247 locus in the genome. The transgene may be integrated anywhere at or near one of the at least one target site(s) or site in the genome. In some embodiments, the transgene is integrated at or near one of the at least one target site(s), for example, within 300, 250, 200, 150, 100, 50, 10, 5, 4, 3, 2, 1 or fewer base pairs upstream or downstream of the site of cleavage, such as within 100, 50, 10, 5, 4, 3, 2, 1 base pairs of either side of the target site, such as within 50, 10, 5, 4, 3, 2, 1 base pairs of either side of the target site. In some embodiments, the integrated sequence comprising the transgene does not include any vector sequences (e.g., viral vector sequences). In some embodiments, the integrated sequence includes a portion of the vector sequences (e.g., viral vector sequences).

The double strand break or single strand break (such as target site) in one of the strands should be sufficiently close to the target integration site, e.g., site for targeted integration, such that an alteration is produced in the desired region, such as insertion of transgene or correction of a mutation occurs. In some embodiments, the distance is not more than 10, 25, 50, 100, 200, 300, 350, 400 or 500 nucleotides. In some embodiments, it is believed that the break should be sufficiently close to the target integration site such that the break is within the region that is subject to exonuclease-mediated removal during end resection. In some embodiments, the targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150, 200, 300, 350, 400 or 500 nucleotides of the region desired to be altered, e.g., site for targeted insertion. The break, e.g., a double strand or single strand break, can be positioned upstream or downstream of the region desired to be altered, e.g., site for targeted insertion. In some embodiments, a break is positioned within the region desired to be altered, e.g., within a region defined by at least two mutant nucleotides. In some embodiments, a break is positioned immediately adjacent to the region desired to be altered, e.g., immediately upstream or downstream of target integration site.

In some embodiments, a single strand break is accompanied by an additional single strand break, positioned by a second gRNA molecule. For example, the targeting domains are configured such that a cleavage event, e.g., the two single strand breaks, are positioned within 1, 2, 3, 4, 5, 10, 15, 20, 25, 30, 35, 40, 45, 50, 60, 70, 80, 90, 100, 150, 200, 300, 350, 400 or 500 nucleotides of a target integration site. In some embodiments, the first and second gRNA molecules are configured such, that when guiding a Cas9 nickase, a single strand break will be accompanied by an additional single strand break, positioned by a second gRNA, sufficiently close to one another to result in alteration of the desired region. In some embodiments, the first and second gRNA molecules are configured such that a single strand break positioned by said second gRNA is within 10, 20, 30, 40, or 50 nucleotides of the break positioned by said first gRNA molecule, e.g., when the Cas9 is a nickase. In some embodiments, the two gRNA molecules are configured to position cuts at the same position, or within a few nucleotides of one another, on different strands, e.g., essentially mimicking a double strand break.

In some embodiments, in which a gRNA (unimolecular (or chimeric) or modular gRNA) and Cas9 nuclease induce a double strand break for the purpose of inducing HDR to mediated insertion of transgene or correction, the cleavage site, such as target site, is between 0 to 200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target integration site. In some embodiments, the cleavage site, such as target site, is between 0 to 100 bp (e.g., 0 to 75, 0 to 50, 0 to 25, 25 to 100, 25 to 75, 25 to 50, 50 to 100, 50 to 75 or 75 to 100 bp) away from the site for targeted integration.

In some embodiments, one can promote HDR by using nickases to generate a break with overhangs. In some embodiments, the single stranded nature of the overhangs can enhance the cell's likelihood of repairing the break by HDR as opposed to, e.g., NHEJ.

Specifically, in some embodiments, HDR is promoted by selecting a first gRNA that targets a first nickase to a first target site, and a second gRNA that targets a second nickase to a second target site which is on the opposite DNA strand from the first target site and offset from the first nick. In some embodiments, the targeting domain of a gRNA molecule is configured to position a cleavage event sufficiently far from a preselected nucleotide, e.g., the nucleotide of a coding region, such that the nucleotide is not altered. In some embodiments, the targeting domain of a gRNA molecule is configured to position an intronic cleavage event sufficiently far from an intron/exon border, or naturally occurring splice signal, to avoid alteration of the exonic sequence or unwanted splicing events. In some embodiments, the targeting domain of a gRNA molecule is configured to position in an early exon, to allow in-frame integration of the transgene sequence at or near one of the at least one target site(s).

In some embodiments, a double strand break can be accompanied by an additional double strand break, positioned by a second gRNA molecule. In some embodiments, a double strand break can be accompanied by two additional single strand breaks, positioned by a second gRNA molecule and a third gRNA molecule.

In some embodiments, two gRNAs, e.g., independently, unimolecular (or chimeric) or modular gRNA, are configured to position a double-strand break on both sides of a target integration site, e.g., site for targeted integration.

2. Template Polynucleotide

In some embodiments, a template polynucleotide, e.g., a polynucleotide containing a transgene, such as exogenous or heterologous nucleic acid sequences, that includes a sequence of nucleotides encoding one or more chains of a chimeric receptor, a recombinant receptor, or a portion thereof, and homology sequences (e.g., homology arms) that are homologous to sequences at or near the endogenous genomic site for targeted integration, can be employed molecules and machinery involved in cellular DNA repair processes, such as homologous recombination, as a repair template. In some aspects, a template polynucleotide having homology with sequences at or near one or more target site(s) in the endogenous DNA can be used to alter the structure of a target DNA, such as target site at the endogenous CD247 locus, for targeted insertion of the transgenic or exogenous sequences, e.g., exogenous nucleic acid sequences encoding the chimeric receptor or portion thereof. Also provided are polynucleotides, e.g., template polynucleotides, for use in the methods provided herein, e.g., as templates for homology directed repair (HDR) mediated targeted integration of the transgene sequences. In some embodiments, the polynucleotide includes a nucleic acid sequence, such as a transgene, encoding one or more chains of a chimeric receptor or a portion thereof; and one or more homology arm(s) linked to the nucleic acid sequence, wherein the one or more homology arm(s) comprise a sequence homologous to one or more region(s) of an open reading frame of a CD247 locus. In some embodiments, the polynucleotide includes a nucleic acid sequence encoding a portion of a chimeric receptor, said chimeric receptor comprising an intracellular region, wherein the portion of the chimeric receptor includes less than the full intracellular region of the chimeric receptor (for example, less than the entire CD3ζ signaling domain); and one or more homology arm(s) linked to the nucleic acid sequence, wherein the one or more homology arm(s) comprise a sequence homologous to one or more region(s) of an open reading frame of a CD247 locus.

In some embodiments, the template polynucleotide contains one or more homology sequences (e.g., homology arms) linked to and/or flanking the transgene (exogenous or heterologous nucleic acids sequences) that includes a sequence of nucleotides encoding the one or more chains of a chimeric receptor or portion thereof. In some embodiments, the homology sequences are used to target the exogenous sequences at the endogenous CD247 locus. In some embodiments, the template polynucleotide includes nucleic acid sequences, such as transgene sequences, between the homology arms, for insertion or integration into the genome of a cell. The transgene in the template polynucleotide may comprise one or more sequences encoding a functional polypeptide (e.g., a cDNA), with or without a promoter or other regulatory elements.

In some embodiments, a template polynucleotide is a nucleic acid sequence which can be used in conjunction with one or more agent(s) capable of introducing a genetic disruption, to alter the structure of a target site. In some embodiments, the template polynucleotide alters the structure of the target site, e.g., insertion of transgene, by a homology directed repair event.

In some embodiments, the template polynucleotide alters the sequence of the target site, e.g., results in insertion or integration of the transgene sequences between the homology arms, into the genome of the cell. In some aspects, targeted integration results in an in-frame integration of the coding portion of the transgene sequences with one or more exons of the open reading frame of the endogenous CD247 locus, e.g., in-frame with the adjacent exon at the integration site. For example, in some cases, the in-frame integration results in a portion of the endogenous open reading frame and the portion of the chimeric receptor encoded by the transgene to be expressed.

In some embodiments, the template polynucleotide includes sequences that correspond to or is homologous to a site on the target sequence that is cleaved, e.g., by one or more agent(s) capable of introducing a genetic disruption. In some embodiments, the template polynucleotide includes sequences that correspond to or is homologous to both, a first site on the target sequence that is cleaved in a first agent capable of introducing a genetic disruption, and a second site on the target sequence that is cleaved in a second agent capable of introducing a genetic disruption.

In some embodiments, a template polynucleotide comprises the following components: [5' homology arm]-[transgene sequences (exogenous or heterologous nucleic acid sequences, e.g., encoding one or more chains of a chimeric receptor or a portion thereof)]-[3' homology arm]. In some embodiments, the nucleic acid sequence encoding the chimeric receptor comprise transgene sequences encoding a portion of the chimeric receptor. The homology arms provide for recombination into the chromosome, thus effectively inserting or integrating the transgene, e.g., that encodes a the chimeric receptor or portion thereof, into the genomic DNA at or near the cleavage site, such as target site(s). In some embodiments, the homology arms flank the sequences at the target site of genetic disruption.

In some embodiments, the template polynucleotide is double stranded. In some embodiments, the template polynucleotide is single stranded. In some embodiments, the template polynucleotide comprises a single stranded portion and a double stranded portion. In some embodiments, the template polynucleotide is comprised in a vector. In some embodiments, the template polynucleotide is DNA. In some embodiments, the template polynucleotide is RNA. In some embodiments, the template polynucleotide is double stranded DNA. In some embodiments, the template polynucleotide is single stranded DNA. In some embodiments, the template polynucleotide is double stranded RNA. In some embodiments, the template polynucleotide is single stranded RNA. In some embodiments, the template polynucleotide comprises a single stranded portion and a double stranded portion. In some embodiments, the template polynucleotide is comprised in a vector.

In certain embodiments, the polynucleotide, e.g., template polynucleotide contains and/or includes a transgene encoding a portion and/or a fragment of one or more chains of a chimeric receptor, e.g., a CAR or a portion thereof. In particular embodiments, the transgene is targeted at a target site(s) that is within an endogenous gene, locus, or open reading frame that encodes the CD3zeta (CD3ζ) chain or a fragment thereof. In some embodiments, the transgene is targeted for in-frame integration within the endogenous CD247 open reading frame, such as to result in a coding sequence that encodes a complete, whole, and/or full length CAR that contains a CD3zeta (CD3ζ) chain.

Polynucleotides for insertion can also be referred to as "transgene" or "exogenous sequences" or "donor" polynucleotides or molecules. The template polynucleotide can be DNA, single-stranded and/or double-stranded and can be introduced into a cell in linear or circular form.

The template polynucleotide can be DNA, single-stranded and/or double-stranded and can be introduced into a cell in linear or circular form. The template polynucleotide can be RNA single-stranded and/or double-stranded and can be introduced as a RNA molecule (e.g., part of an RNA virus). See also, U.S. Patent Pub. Nos. 20100047805 and 20110207221. The template polynucleotide can also be introduced in DNA form, which may be introduced into the cell in circular or linear form. If introduced in linear form, the ends of the template polynucleotide can be protected (e.g., from exonucleolytic degradation) by known methods. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. If introduced in double-stranded form, the template polynucleotide may include one or more nuclease target site(s), for example, nuclease target sites flanking the transgene to be integrated into the cell's genome. See, e.g., U.S. Patent Pub. No. 20130326645.

In some embodiments, the double-stranded template polynucleotide includes sequences (also referred to as transgene) greater than 1 kb in length, for example between 2 and 200 kb, between 2 and 10 kb (or any value therebetween). The double-stranded template polynucleotide also includes at least one nuclease target site, for example. In some embodiments, the template polynucleotide includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s), such as target sites(s), may be for any nuclease(s). In some embodiments, the nuclease target site(s) contained in the double-stranded template polynucleotide are for the same nuclease(s) used to cleave the endogenous target into which the cleaved template polynucleotide is integrated via homology-independent methods.

In some embodiments, the template polynucleotide is a single stranded nucleic acid. In some embodiments, the template polynucleotide is a double stranded nucleic acid. In some embodiments, the template polynucleotide comprises a nucleotide sequence, e.g., of one or more nucleotides, that will be added to or will template a change in the target DNA. In some embodiments, the template polynucleotide comprises a nucleotide sequence that may be used to modify the target site. In some embodiments, the template polynucleotide comprises a nucleotide sequence, e.g., of one or more nucleotides, that corresponds to wild type sequence of the target DNA, e.g., of the target site.

In some embodiments, the template polynucleotide is linear double stranded DNA. The length may be, e.g., about 200 to about 5000 base pairs, e.g., about 200, 300, 400, 500, 600, 700, 800, 900, 1000, 1200, 1400, 1600, 1800, 2000, 2500, 3000, 4000 or 5000 base pairs. The length may be, e.g., at least 200, 300, 400, 500, 600, 700, 800, 900, 1000, 1200, 1400, 1600, 1800, 2000, 2500, 3000, 4000 or 5000 base pairs. In some embodiments, the length is no greater than 200, 300, 400, 500, 600, 700, 800, 900, 1000, 1200, 1400, 1600, 1800, 2000, 2500, 3000, 4000 or 5000 base pairs. In some embodiments, a double stranded template polynucleotide has a length of about 160 base pairs, e.g., about 200 to 4000, 300 to 3500, 400 to 3000, 500 to 2500, 600 to 2000, 700 to 1900, 800 to 1800, 900 to 1700, 1000 to 1600, 1100 to 1500 or 1200 to 1400 base pairs.

The transgene contained on the template polynucleotide described herein may be isolated from plasmids, cells or other sources using known standard techniques such as PCR. Template polynucleotide for use can include varying types of topology, including circular supercoiled, circular relaxed, linear and the like. Alternatively, they may be chemically synthesized using standard oligonucleotide synthesis techniques. In addition, template polynucleotides may be methylated or lack methylation. Template polynucleotides may be in the form of bacterial or yeast artificial chromosomes (BACs or YACs).

The template polynucleotide can be linear single stranded DNA In some embodiments, the template polynucleotide is (i) linear single stranded DNA that can anneal to the nicked strand of the target DNA, (ii) linear single stranded DNA that can anneal to the intact strand of the target DNA, (iii) linear single stranded DNA that can anneal to the transcribed strand of the target DNA, (iv) linear single stranded DNA that can anneal to the non-transcribed strand of the target DNA, or more than one of the preceding.

The length may be, e.g., about 200 to 5000 nucleotides, e.g., about 200, 300, 400, 500, 600, 700, 800, 900, 1000, 1200, 1400, 1600, 1800, 2000, 2500, 3000, 4000 or 5000 nucleotides. The length may be, e.g., at least 200, 300, 400, 500, 600, 700, 800, 900, 1000, 1200, 1400, 1600, 1800, 2000, 2500, 3000, 4000 or 5000 nucleotides. In some embodiments, the length is no greater than 200, 300, 400, 500, 600, 700, 800, 900, 1000, 1200, 1400, 1600, 1800, 2000, 2500, 3000, 4000 or 5000 nucleotides. In some embodiments, a single stranded template polynucleotide has a length of about 160 nucleotides, e.g., about 200 to 4000, 300 to 3500, 400 to 3000, 500 to 2500, 600 to 2000, 700 to 1900, 800 to 1800, 900 to 1700, 1000 to 1600, 1100 to 1500 or 1200 to 1400 nucleotides.

In some embodiments, the template polynucleotide is circular double stranded DNA, e.g., a plasmid. In some embodiments, the template polynucleotide comprises about 500 to 1000 base pairs of homology on either side of the transgene and/or the target site. In some embodiments, the template polynucleotide comprises about 10, 20, 30, 40, 50, 100, 200, 300, 400, 500, 600, 700, 800, 900, 1000, 1500, or 2000 base pairs of homology 5' of the target site or transgene, 3' of the target site or transgene, or both 5' and 3' of the target site or transgene. In some embodiments, the template polynucleotide comprises at least 10, 20, 30, 40, 50, 100, 200, 300, 400, 500, 600, 700, 800, 900, 1000, 1500, or 2000 base pairs of homology 5' of the target site or transgene, 3' of the target site or transgene, or both 5' and 3' of the target site or transgene. In some embodiments, the template polynucleotide comprises no more than 10, 20, 30, 40, 50, 100, 200, 300, 400, 500, 600, 700, 800, 900, 1000, 1500, or 2000 base pairs of homology 5' of the target site or transgene, 3' of the target site or transgene, or both 5' and 3' of the target site or transgene.

In some embodiments, the transgene sequence in the template polynucleotide comprises a sequence of nucleotides that is in-frame with one or more exons of the open reading frame of the CD247 locus comprised in the one or more homology arm(s). In some embodiments, the one or more region(s) of the open reading frame is or comprises sequences that are upstream of exon 8 of the open reading frame of the CD247 locus. In some embodiments, the one or more region(s) of the open reading frame is or comprises sequences that are upstream of exon 3 of the open reading frame of the CD247 locus. In some embodiments, the one or more region(s) of the open reading frame is or comprises sequences that includes exon 3 of the open reading frame of the CD247 locus. In some embodiments, the one or more region(s) of the open reading frame is or comprises sequences that includes at least a portion of exon 2 of the open reading frame of the CD247 locus.

In some embodiments, the one or more homology arm(s) in the template polynucleotide does not comprise the full length of exon 1 of the open reading frame of the CD247 locus. In some embodiments, the one or more homology arm(s) does not comprise does not comprise exon 1 and/or does not comprise the full length of exon 2 of the open reading frame of the CD247 locus.

a. Transgene Sequences

In some embodiments, the template polynucleotide contains a transgene sequence or an exogenous sequence encoding one or more chains of a chimeric receptor or a portion thereof, such as one or more regions or domains of a chimeric receptor, such as any chimeric receptor described herein, e.g., in Section III.B, or one or more regions or domains or chains of such chimeric receptor. In some aspects, HDR in the presence of a template polynucleotide containing transgene sequences linked to one or more homology arm(s) that are homologous to sequences near a target site at an endogenous CD247 locus, results in a modified CD247 locus encoding a chimeric receptor. In some embodiments, the transgene sequence encodes a chimeric receptor or a portion thereof, such as one or more domains, regions or chains of a chimeric receptor, including an extracellular binding region, transmembrane domain and/or a portion of the intracellular region. In some embodiments, the transgene sequence does not comprise an intron. In some aspects, the transgene sequence is a sequence that is exogenous or heterologous to an open reading frame of the endogenous genomic CD247 locus a T cell, optionally a human T cell.

In some aspects, the chimeric receptor encoded by the transgene sequences is or comprises a functional non-T cell receptor (non-TCR) antigen receptor. In some embodiments, the chimeric receptor is a chimeric antigen receptor (CAR). In some embodiments, the transgene sequence encodes any chimeric receptor described herein, for example in Section III.B, or a portion thereof. In some aspects, upon integration of the transgene sequence into the endogenous CD247 locus, the resulting modified CD247 locus encodes a chimeric receptor, such as any chimeric receptor described herein, for example, in Section III.B. In some embodiments, the transgene sequence encodes a portion of a chimeric receptor described herein, e.g., in Section III.B, such as a portion of a chimeric receptor that contain an intracellular region comprising a CD3ζ chain or a fragment thereof (e.g., intracellular region of the CD3ζ chain). In some embodiments, the transgene sequence encodes a portion of a chain of a chimeric receptor that is a multi-chain CAR, such as a multi-chain CAR described herein in Section III.B.2, such as a chain of a multi-chain CAR that contains a CD3ζ chain or a fragment thereof.

In some embodiments, the chimeric receptor encoded by the modified CD247 locus comprises an intracellular region, for example, comprising a CD3ζ signaling domain, and the transgene sequence encodes a portion of the chimeric receptor, said portion does not include the full intracellular region of the chimeric receptor. In some embodiments, the chimeric receptor encoded by the modified CD247 locus comprises a CD3ζ signaling domain, and the transgene sequence does not encode the entire CD3ζ signaling domain. In some embodiments, upon integration of the transgene sequence into the endogenous CD247 locus, at least a portion of the CD3ζ chain, such as a fragment of or the entire CD3ζ signaling domain, is encoded by the open reading frame sequences of the endogenous CD247 locus or a partial sequence thereof. In some aspects, the template polynucleotide, which contains nucleic acid sequence encoding a portion of the chimeric receptor and one or more homology arm(s), together comprise at least a fragment of a sequence of nucleotides encoding the intracellular region (e.g., comprising a CD3ζ signaling domain) of the chimeric receptor, wherein at least a portion of the intracellular region comprises the CD3zeta signaling domain or a fragment thereof encoded by the open reading frame of the CD247 locus or a partial sequence thereof when the chimeric receptor is expressed from a cell introduced with the polynucleotide.

In some aspects, transgene sequences, which are nucleic acid sequences of interest encoding one or more chains of a chimeric receptor or a portion thereof, including coding and/or non-coding sequences and/or partial coding sequences thereof, that are inserted or integrated at the target location in the genome can also be referred to as "transgene," "transgene sequences," "exogenous nucleic acids sequences," "heterologous sequences" or "donor sequences." In some aspects, the transgene is a nucleic acid sequence that is exogenous or heterologous to an endogenous genomic sequences, such as the endogenous genomic sequences at a specific target locus or target location in the genome, of a T cell, e.g., a human T cell. In some aspects, the transgene is a sequence that is modified or different compared to an endogenous genomic sequence at a target locus or target location of a T cell, e.g., a human T cell. In some aspects, the transgene is a nucleic acid sequence that originates from or is modified compared to nucleic acid sequences from different genes, species and/or origins. In some aspects, the transgene is a sequence that is derived from a sequence from a different locus, e.g., a different genomic region or a different gene, of the same species. In some aspects, exemplary chimeric receptors include any described herein, e.g., in Section III.B.

In some embodiments, nuclease-induced HDR results in an insertion of a transgene (also called "exogenous sequence" or "transgene sequence") for expression of a transgene for targeted insertion. The template polynucleotide sequence is typically not identical to the genomic sequence where it is placed. A template polynucleotide sequence can contain a non-homologous sequence flanked by two regions of homology to allow for efficient HDR at the location of interest. Additionally, template polynucleotide sequence can comprise a vector molecule containing sequences that are not homologous to the region of interest in cellular chromatin. A template polynucleotide sequence can contain several, discontinuous regions of homology to cellular chromatin. For example, for targeted insertion of sequences not normally present in a region of interest, said sequences can be present in a transgene and flanked by regions of homology to sequence in the region of interest.

In some aspects, the transgene is a chimeric sequence, comprising a sequence generated by joining different nucleic acid sequences from different genes, species and/or origins. In some aspects, the transgene contains sequence of nucleotides encoding different regions or domains or portions thereof, from different genes, coding sequences or exons or portions thereof, that are joined or linked. In some aspects the transgene sequences for targeted integration encode a polypeptide, e.g., a fusion polypeptide, or a fragment thereof.

In some aspects, the polypeptide encoded by the transgene is a chimeric polypeptide. In some aspects, the transgene also contains non-coding, regulatory or control sequences, e.g., sequences required for permitting, modulating and/or regulating expression of the encoded polypeptide or fragment thereof or sequences required to modify a polypeptide. In some embodiments, the transgene does not comprise an intron or lacks one or more introns as compared to a corresponding nucleic acid in the genome if the transgene is derived from a genomic sequence. In some embodiments, the transgene sequence does not comprise an intron. In some of embodiments, the transgene contains sequences encoding a chimeric receptor or a portion thereof, wherein all or a portion of the transgene sequences are codon-optimized, e.g., for expression in human cells.

In some embodiments, the length of the transgene sequences, including coding and non-coding regions, is between or between about 100 to about 10,000 base pairs, such as about 100, 200, 300, 400, 500, 600, 700, 800, 900, 1000, 1500, 2000, 2500, 3000, 3500, 4000, 4500, 5000, 6000, 7000, 8000, 9000 or 10000 base pairs. In some embodiments, the length of the transgene sequence is limited by the maximum length of polynucleotide that can be prepared, synthesized or assembled and/or introduced into the cell or the capacity of the viral vector. In some aspects, the length of the transgene sequence can vary depending on the maximum length of the template polynucleotide and/or the length of the one or more homology arm(s) required.

In some embodiments, genetic disruption-induced HDR results in an insertion or integration of transgene sequences at a target location in the genome. The template polynucleotide sequence is typically not identical to the genomic sequence where it is targeted. A template polynucleotide sequence can contain transgene sequences flanked by two regions of homology to allow for efficient HDR at the location of interest. A template polynucleotide sequence can contain several, discontinuous regions of homology to the genomic DNA. For example, for targeted insertion of sequences not normally present in a region of interest, said sequences can be present in a transgene and flanked by regions of homology to sequence in the region of interest. In some embodiments, the transgene sequences encode a chimeric receptor or a portion thereof, e.g., one or more of an extracellular binding region, transmembrane domain and/or a portion of the intracellular region.

In some aspects, upon targeted integration of the transgene by HDR, the genome of the cell contains modified CD247 locus, comprising a nucleic acid sequence encoding a chimeric receptor or a portion thereof. In some embodiments, upon targeted integration, the modified CD247 locus contains a fusion, e.g., gene fusion, of the transgene and an open reading frame or a partial sequence thereof of an endogenous CD247 locus. In some aspects, the fusion is with reference to fusion of two or more molecules of nucleic acids from different origin: e.g., fusion of a transgene sequence and genomic DNA, that occurs as a result of HDR-mediated targeted integration. In some embodiments, upon targeted integration, the modified CD247 locus contains the transgene integrated into a site within the open reading frame of the endogenous CD247 locus. In some embodiments, upon targeted integration, the modified CD247 locus that contains a fusion, e.g., gene fusion, of the transgene sequences and sequences of the endogenous CD247 locus, encodes a chimeric receptor, e.g., a chimeric antigen receptor (CAR). In some aspects, certain portions of the chimeric receptor are encoded by the transgene, and other portions of the chimeric receptor are encoded by an open reading frame of the endogenous CD247 locus or a partial sequence thereof. In some embodiments, the transgene sequence comprises a sequence of nucleotides that is in-frame with one or more exons of the open reading frame of the CD247 locus comprised in the one or more homology arm(s). In some aspects, the entire chimeric receptor is encoded by the transgene sequences. In some aspects, the transgene sequences also contain sequence of nucleotides encoding other molecules or other chains of a multi-chain chimeric receptor, and/or regulatory or control elements, e.g., exogenous promoter, and/or multicistronic elements. In some aspects, exemplary chimeric receptors include any described herein, e.g., in Section III.B.

In some aspects the transgene sequences for targeted integration include sequences encoding a chimeric receptor that is a chimeric receptor, such as a chimeric antigen receptor (CAR) or a chimeric auto antibody receptor (CAAR). In some aspects, the transgene contains sequence of nucleotides encoding different regions or domains or portions of the chimeric receptor, that can be from different genes, coding sequences or exons or portions thereof, that are joined or linked.

In some embodiments, the transgene sequence encodes all or some or a portion of the various regions, domains or chains of a chimeric receptor, such as a chimeric receptor or various regions, domains or chain described in Section III.B. In some embodiments, the transgene sequence encodes a portion of the various regions, domains or chains of the chimeric receptor. In some embodiments, the transgene sequence encodes a polypeptide chain of a multi-chain chimeric receptor, or a portion thereof. In some embodiments, the encoded chimeric receptor contains various regions or domains of the CAR. In some embodiments, the encoded chimeric receptor contains one or more regions or domains, such as one or more of extracellular region (e.g., containing one or more extracellular binding domain(s) and/or spacers), transmembrane domain and/or intracellular region (e.g., containing primary signaling region or domain and/or one or more costimulatory signaling domains). In some aspects, the encoded CAR further contains other domains, such multimerization domains or linkers.

In some embodiments, the transgene includes a sequence of nucleotides encoding an intracellular region. In some embodiments, the transgene also includes a sequence of nucleotides encoding a transmembrane region or a membrane association region. In some embodiments, the transgene also includes a sequence of nucleotides encoding an extracellular region. In some embodiments, the chimeric receptor comprises an extracellular region, and/or a transmembrane domain. In some embodiments, the transgene sequence comprises a sequence of nucleotides encoding one or more regions of the chimeric receptor, optionally wherein the transgene sequence comprises a sequence of nucleotides encoding one or more of an extracellular region, a transmembrane domain, and/or a portion of the intracellular region.

In some aspects, in the transgene, the sequence of nucleotides encoding the extracellular region is placed between the signal sequence and the nucleotides encoding the spacer. In some aspects, in the transgene, the sequence of nucleotides encoding the extracellular multimerization domain is placed between the sequence of nucleotides encoding the binding domain and the sequence of nucleotides encoding the spacer. In some aspects, the sequence of nucleotides encoding the spacer is placed between the sequence of nucleotides encoding the binding domain and the sequence of nucleotides encoding the transmembrane domain.

In some embodiments, the transgene includes, in 5' to 3' order, a sequence of nucleotides encoding an extracellular region, a sequence of nucleotides a transmembrane domain (or a membrane association domain) and a sequence of nucleotides an intracellular region. In some embodiments, the transgene includes, in 5' to 3' order, a sequence of nucleotides a transmembrane domain (or a membrane association domain) and a sequence of nucleotides an intracellular region. In some embodiments, the transgene includes, in 5' to 3' order, a sequence of nucleotides encoding an extracellular region, a sequence of nucleotides a transmembrane domain and a sequence of nucleotides an intracellular region.

In some aspects, some of the regions or domains of the chimeric receptor is encoded by sequences of the transgene (i.e., heterologous or exogenous sequences). For example, the transgene sequences can include sequence of nucleotides encoding one or more of extracellular regions, transmembrane domains, and intracellular regions that can comprise costimulatory signaling domains, and other domains or portions thereof. In some aspects, some of the regions or domains of the chimeric receptor is encoded by sequences of the endogenous sequences of the CD247 locus. For example, all or a portion of the CD3ζ chain or a fragment thereof, can be encoded by the open reading frame sequence of the endogenous CD247 locus or a partial sequence thereof and/or a portion of the CD3ζ chain can be encoded by the transgene. Thus, upon targeted integration of the transgene, the encoded chimeric receptor is encoded by a gene fusion comprising the integrated transgene and the endogenous sequences at the CD247 locus.

In some aspects, the extracellular region can include a binding domain and/or a spacer. In some embodiments, the extracellular region can include an extracellular multimerization domain. In some aspects, the intracellular region encoded by the transgene comprises one or more co-stimulatory domain and/or a multimerization domain and other domains. In some embodiments, the intracellular region encoded by the transgene sequences comprises less than a full length of the CD3ζ chain or a portion of the CD3ζ chain. In some aspects, the transgene does not contain a sequence of nucleotides encoding a CD3ζ chain or a fragment thereof. In some embodiments, the transgene sequences also includes a signal sequence encoding a signal peptide, a regulatory or control elements, such as a promoter, and/or one or more multicistronic elements, e.g., a ribosome skip element or an internal ribosome entry site (IRES). In some embodiments, the signal sequence can be placed 5' of the sequence of nucleotides encoding the extracellular region. In some embodiments, the transgene also comprises one or more multicistronic element(s), e.g., a ribosome skip sequence and/or an internal ribosome entry site (IRES). In some aspects, the transgene also includes regulatory or control elements, such as a promoter, typically at the most 5' portion of the transgene sequence, e.g., 5' of the signal sequence. In some aspects, sequence of nucleotides encoding one or more additional molecule(s) can be included in the transgene portion of the polynucleotide. In some aspects, the sequence of nucleotides encoding one or more additional molecule(s) is placed 5' of the sequence of nucleotides encoding one or more region(s) or domain(s) or chain(s) of the chimeric receptor. In some aspects, the sequence of nucleotides encoding the one or more additional molecule(s) or additional domains, regions or chains is upstream of the sequence of nucleotides encoding one or more regions of the chimeric receptor.

Exemplary regions or domains encoded by the transgene sequence are set forth below, and also include any region or domain described in Section III.B herein. In particular embodiments, the transgene sequence includes a sequence of nucleotides encoding a signal peptide, a binding domain (e.g. antigen binding domain, such as an scFv), a spacer, a transmembrane domain and an intracellular signaling region containing a costimulatory signaling domain and a CD3ζ Chain or a portion of a CD3ζ chain.

(i) Signal Sequence

In some embodiments, the transgene includes a signal sequence that encodes a signal peptide. In some aspects, the signal sequence may encode a heterologous or non-native signal peptide, e.g., a signal peptide from a different gene or species or a signal peptide that is different from the signal peptide of the endogenous CD247 locus. In some aspects, exemplary signal sequence includes signal sequence of the GMCSFR alpha chain set forth in SEQ ID NO:24 and encoding the signal peptide set forth in SEQ ID NO:25 or the CD8 alpha signal peptide set forth in SEQ ID NO:26. In the mature form of an expressed chimeric receptor, the signal sequence is cleaved from the remaining portions of the polypeptide. In some aspects, the signal sequence is placed 3' of a regulatory or control element, e.g., a promoter, such as a heterologous promoter, e.g., a promoter not derived from the CD247 locus. In some aspects, the signal sequence is placed 3' of one or more multicistronic element(s), e.g., a sequence of nucleotides encoding a ribosome skip sequence and/or an internal ribosome entry site (IRES). In some aspects, the signal sequence can be placed 5' of the sequence of nucleotides encoding the one or more components of the extracellular region in the transgene. In some embodiments, the signal sequence the most 5' region present in the transgene, and is linked to one of the homology arms. In some aspects, the signal sequence encoded by the transgene sequence include any signal sequence described herein, for example, in Section III.B.

(ii) Binding Domain

In some embodiments, the transgene encodes a portion of a chimeric receptor, such as a CAR with specificity for a particular antigen (or ligand), such as an antigen expressed on the surface of a particular cell type. In some embodiments, the antigen is selectively expressed or overexpressed on cells of the disease or condition, e.g., the tumor or pathogenic cells, as compared to normal or non-targeted cells or tissues, e.g., in healthy cells or tissues.

In some aspects, the transgene encodes an extracellular region of a chimeric receptor. In some embodiments, the transgene sequences encode extracellular binding domain, such as a binding domain that specifically binds an antigen or a ligand.

In some embodiments, the binding domain is or comprises a polypeptide, a ligand, a receptor, a ligand-binding domain, a receptor-binding domain, an antigen, an epitope, an antibody, an antigen-binding domain, an epitope-binding domain, an antibody-binding domain, a tag-binding domain or a fragment of any of the foregoing. In other embodiments, the antigen is expressed on normal cells and/or is expressed on the engineered cells. In some aspects, the antigen is recognized by a binding domain, such as a ligand binding domain or an antigen binding domain. In some aspects, the transgene encodes an extracellular region containing one or more binding domain(s). In some embodiments, exemplary binding domain encoded by the transgene include antibodies and antigen-binding fragments thereof, including scFv or sdAb. In some embodiments, an antigen-binding fragment comprises antibody variable regions joined by a flexible linker.

In some embodiments, the binding domain is or comprises a single chain variable fragment (scFv). In some embodiments, the binding domain is or comprises a single domain antibody (sdAb). In some embodiments, the binding domain is capable of binding to a target antigen that is associated with, specific to, and/or expressed on a cell or tissue of a disease, disorder or condition. In some embodiments, the disease, disorder or condition is an infectious disease or disorder, an autoimmune disease, an inflammatory disease, or a tumor or a cancer. In some embodiments, the target antigen is a tumor antigen.

Exemplary antigens and antigen- or ligand-binding domains encoded by the transgene sequences include those described in Section III.B.1 herein. In some aspects, the encoded chimeric receptor contains a binding domain that is or comprises a TCR-like antibody or a fragment thereof, such as an scFv that specifically recognizes an intracellular antigen, such as a tumor-associated antigen, presented on the cell surface as a major histocompatibility complex (MHC)-peptide complex. In some aspects, the transgene sequences can encode a binding domain that is a TCR-like antibody or fragment thereof. Thus, the encoded chimeric receptor is a TCR-like CAR, such as any described herein in Section III.B.1. In some embodiments, the binding domain is a multi-specific, such as a bi-specific, binding domain. In some embodiments, the encoded chimeric receptor contains a binding domain that is an antigen that binds to an autoantibody. In some embodiments, the chimeric receptor is a chimeric auto antibody receptor (CAAR), such as any described herein in Section III.B.3.

In some aspects, sequence of nucleotides encoding the one or more binding domain(s) can be placed 3' of a signal sequence, if present, in the transgene. In some aspects, sequence of nucleotides encoding the one or more binding domain(s) can be placed 3' of the sequence of nucleotides encoding one or more regulatory or control element(s), in the transgene. In some aspects, sequence of nucleotides encoding the one or more binding domain(s) can be placed 5' of the sequence of nucleotides encoding the spacer, if present, in the transgene. In some aspects, sequence of nucleotides encoding the one or more binding domain(s) can be placed 5' of the sequence of nucleotides encoding transmembrane domain, in the transgene.

(iii) Spacer and Transmembrane Domain

In some embodiments, the transgene includes sequences encoding a spacer and/or sequences encoding a transmembrane domain or portion thereof. In some embodiments, the extracellular region of the encoded chimeric receptor comprises a spacer, optionally wherein the spacer is operably linked between the binding domain and the transmembrane domain. In some aspects, the spacer and/or transmembrane domain can link the extracellular portion containing the ligand- (e.g., antigen-) binding domain and other regions or domains of the chimeric receptor, such as the intracellular region (e.g., containing one or more costimulatory signaling domain(s), intracellular multimerization domain and/or a CD3ζ chain or a fragment thereof).

In some embodiments, the transgene further includes sequence of nucleotides encoding a spacer and/or a hinge region that separates the antigen-binding domain and transmembrane domain. In some aspects, the spacer may be or include at least a portion of an immunoglobulin constant region or variant or modified version thereof, such as a hinge region, e.g., an IgG4 hinge region, and/or a $C_H1/C_L$ and/or Fc region. In some embodiments, the constant region or portion is of a human IgG, such as IgG4 or IgG1. In some aspects, the portion of the constant region serves as a spacer region between a binding domain, e.g., scFv, and a transmembrane domain Exemplary spacers that can be encoded by the transgene include IgG4 hinge alone, IgG4 hinge linked to $C_H2$ and $C_H3$ domains, or IgG4 hinge linked to the $C_H3$ domain, and those described in Hudecek et al. (2013) *Clin. Cancer Res.,* 19:3153, Hudecek et al. (2015) Cancer Immunol Res. 3(2): 125-135 or International Pat. App. Pub. No. WO2014031687, or any described in Section III.B.1 herein.

In some aspects, the sequence of nucleotides encoding the spacer can be placed 3' of the sequence of nucleotides encoding the one or more binding domains, in the transgene. In some aspects, the sequence of nucleotides encoding the spacer can be placed 5' of the sequence of nucleotides encoding the transmembrane domain, in the transgene. In some embodiments, the sequence of nucleotides encoding the spacer is placed between the sequence of nucleotides encoding one or more binding domains and the sequence of nucleotides encoding the transmembrane domain.

In some embodiments, the transgene encodes a transmembrane domain, which can link the extracellular region, e.g., containing one or more binding domains and/or spacers, with the intracellular region, e.g., containing one or more costimulatory signaling domain(s), intracellular multimerization domain and/or a CD3ζ chain or a fragment thereof. In some embodiments, the transgene comprises a sequence of nucleotides encoding a transmembrane domain, optionally wherein the transmembrane domain is human or comprises a sequence from a human protein. In some embodiments, the transmembrane domain is or comprises a transmembrane domain derived from CD4, CD28, or CD8, optionally derived from human CD4, human CD28 or human CD8. In some embodiments, the transmembrane domain is or comprises a transmembrane domain derived from a CD28, optionally derived from human CD28.

In some embodiments, the sequence of nucleotides encoding transmembrane domain is fused to the sequence of nucleotides encoding the extracellular region. In some embodiments, the sequence of nucleotides encoding transmembrane domain is fused to the sequence of nucleotides encoding the intracellular region. In some aspects, sequence of nucleotides encoding the transmembrane domain can be placed 3' of the sequence of nucleotides encoding the one or more binding domains and/or the spacer in the transgene. In some aspects, the sequence of nucleotides encoding the transmembrane domain can be placed 5' of the sequence of nucleotides encoding the intracellular region, e.g., containing one or more costimulatory signaling domain(s), intracellular multimerization domain and/or a CD3ζ chain or a fragment thereof, in the transgene. In some aspects, the transmembrane domain encoded by the transgene sequence include any transmembrane domain described herein, for example, in Section III.B.1.

In some embodiments, in cases where the encoded chimeric receptor comprises an intracellular region comprising a CD3ζ chain but does not comprise a transmembrane domain and/or an extracellular region, the transgene can include a sequence of nucleotides encoding a membrane association domain, such as any described herein, e.g., in Section III.B.

(iv) Intracellular Region

In some embodiments, the transgene includes a sequence of nucleotides encoding an intracellular region. In some aspects, the intracellular region comprises one or more secondary or co-stimulatory signaling region. In some aspects, the sequence of nucleotides encoding the transmembrane domain can be placed 3' of the sequence of nucleotides encoding the one or more binding domains and/or the spacer in the transgene, in the transgene. In some aspects, the sequence of nucleotides encoding the one or more costimulatory signaling domain can be placed 5' of the sequence of nucleotides encoding a portion of the CD3ζ chain. In some aspects, the sequence of nucleotides encoding the one or more costimulatory signaling domain is the most 3' region in the transgene, which is then linked to one of the homology arm sequences, e.g., the 3' homology arm sequence. For example, in some cases, the transgene does not include a sequence of nucleotides encoding a CD3ζ chain or a fragment thereof, and thus the most 3' region in the transgene, linked to the homology arm, is sequence of nucleotides encoding the one or more costimulatory signaling domains. In some aspects, the sequence of nucleotides encoding the one or more costimulatory signaling domain can be placed 3' of the sequence of nucleotides encoding the transmembrane domain, in the transgene. In some aspects, the costimulatory signaling region or a CD3ζ or a portion thereof encoded by the transgene sequence include any costimulatory signaling region or a CD3ζ or a portion thereof described herein, for example, in Section III.B.1.

(a) Costimulatory Signaling Domain

In some embodiments, the transgene comprises a sequence of nucleotides encoding a portion of the intracellular region, which can include one or more costimulatory signaling domain(s). In some embodiments, the one or more costimulatory signaling domain comprises an intracellular signaling domain of a T cell costimulatory molecule or a signaling portion thereof, optionally wherein the T cell costimulatory molecule or a signaling portion thereof is human.

In some embodiments, the one or more costimulatory signaling domain comprises an intracellular signaling domain of a T cell costimulatory molecule or a signaling portion thereof. In some embodiments, the T cell costimulatory molecule or a signaling portion thereof is human. In some embodiments, exemplary costimulatory signaling domain encoded by the transgene include signaling regions or domains from one or more costimulatory receptor such as CD28, CD137 (4-1BB), OX40 (CD134), CD27, DAP10, DAP12, NKG2D, ICOS and/or other costimulatory receptors, such as any described herein in Section III.B herein. In some embodiments, the one or more costimulatory signaling domain comprises an intracellular signaling domain of a CD28, a 4-1BB or an ICOS or a signaling portion thereof. In some embodiments, the one or more costimulatory signaling domain comprises a signaling domain of human CD28, human 4-1BB, human ICOS or a signaling portion thereof. In some embodiments, the one or more costimulatory signaling domain comprises an intracellular signaling domain of human 4-1BB.

(b) CD3ζ Chain or a Portion of a CD3ζ Chain

In some embodiments, the transgene includes a sequence of nucleotides encoding a CD3ζ chain or a fragment thereof, such as the cytoplasmic domain of CD3ζ or a portion thereof. In some embodiments, the transgene encodes only a portion of a CD3ζ chain. In some aspects, upon integration of the transgene into the endogenous CD247 locus, the resulting modified CD247 locus encodes a chimeric receptor, e.g., CAR, that contains a CD3ζ chain or a fragment thereof, such as an intracellular region of CD3ζ. In some embodiments, when expressed by a cell introduced with the polynucleotide, the chimeric receptor is capable of signaling via the CD3ζ signaling domain. In some embodiments, the encoded chimeric receptor is any describe herein, for example, in Section III.B.

In some aspects, the transgene sequence portion of the polynucleotide does not contain sequence of nucleotides encoding a full length of a CD3ζ chain. Thus, in some aspects, at least a portion of the CD3ζ chain in the encoded chimeric receptor is encoded by sequences present in the endogenous CD247 locus. In some embodiments, the transgene sequence does not include nucleic acid sequences encoding any portion of a CD3ζ chain. In some embodiments, the transgene encodes only a portion of no more than 1, 2, 3, 4, 5, 6, 7, 8, 9, 10, 11, 12, 13, 14, 15, 16, 17, 18, 19 or 20 amino acids of a CD3ζ chain. In some aspects, upon integration of the transgene sequence, some or all of the nucleic acid sequences encoding the CD3ζ chain or a fragment thereof, of the chimeric receptor, is derived from, or originates from, the open reading frame sequence of the endogenous CD247 locus or a partial sequence thereof. In some embodiments, the transgene does not include a sequence of nucleotides encoding a CD3ζ chain or a fragment thereof, or only includes a sequence of nucleotides encoding a part or a portion of the intracellular region excluding the CD3ζ chain or a fragment thereof.

In some embodiments, the transgene includes a sequence of nucleotides encoding less than a full length of a CD3ζ chain or a portion of a CD3ζ chain. In some aspects, the transgene includes a sequence of nucleotides encoding the intracellular region of the CD3ζ chain, or a partial sequence thereof. In some embodiments, the transgene does not comprise an intron in the sequences encoding the portion of the CD3ζ chain, e.g., intracellular region of the CD3ζ chain.

In some embodiments, targeted integration of the transgene generates a gene fusion of transgene and endogenous sequences of the CD247 locus, which together encode a functional CD3ζ chain, e.g., a portion of a CD3ζ chain that is capable of mediating, activating or stimulating primary cytoplasmic or intracellular signal, e.g., a cytoplasmic domain of the CD3ζ chain or a portion of the CD3ζ chain that includes the immunoreceptor tyrosine-based activation motif (ITAM).

In some aspects, exemplary CD3ζ chain or a fragment thereof encoded by the gene fusion of the transgene and endogenous sequences of the CD247 locus include all or a portion of the intracellular region of the CD3ζ chain, e.g., amino acid residues 52-164 of the human CD3ζ chain precursor sequence set forth in SEQ ID NO:73 or amino acid residues 52-163 of the human CD3ζ chain precursor sequence set forth in SEQ ID NO:75, or a sequence of amino acids that exhibits at least or at least about 85%, 86%, 87%, 88%, 89%, 90%, 91%, 92%, 93%, 94%, 95%, 96%, 97%, 98%, 99% or more sequence identity to amino acid residues 52-164 of the human CD3ζ chain precursor sequence set forth in SEQ ID NO:73 or amino acid residues 52-163 of the human CD3ζ chain precursor sequence set forth in SEQ ID NO:75, or a partial sequence thereof. In some aspects, exemplary CD3ζ chain or a fragment thereof encoded by the gene fusion of the transgene and endogenous sequences of the CD247 locus include the sequence of amino acids set forth in SEQ ID NO: 13, 14 or 15 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 13, 14 or 15, or a partial sequence thereof. Exemplary CD3ζ chain or a fragment thereof encoded by the gene fusion of the transgene and endogenous sequences of the CD247 locus include one or more of the ITAM domains of the CD3ζ chain, e.g., amino acid residues 61-89, 100-128 or 131-159 of the human CD3ζ chain precursor sequence set forth in SEQ ID NO:73 or at amino acid residues 61-89, 100-127 or 130-158 of the human CD3ζ chain precursor sequence set forth in SEQ ID NO:75 or a sequence of amino acids that containing one or more ITAM domains from the CD3ζ chain and exhibits at least or at least about 85%, 86%, 87%, 88%, 89%, 90%, 91%, 92%, 93%, 94%, 95%, 96%, 97%, 98%, 99% or more sequence identity to SEQ ID NO: 73 or at amino acid residues 61-89, 100-127 or 130-158 of the human CD3ζ chain precursor sequence set forth in SEQ ID NO:75.

In some embodiments, when expressed by a cell introduced with the polynucleotide, the chimeric receptor is capable of signaling via the CD3zeta signaling domain. In some of any embodiments, the encoded chimeric receptor, e.g., the chimeric receptor encoded by the modified CD247 locus, comprises a CD3ζ signaling domain that is capable of signaling or signal transduction, such as the entire CD3ζ signaling domain. In some of any embodiments, the entire CD3ζ signaling domain comprises the sequence selected from any one of SEQ ID NOS:13-15, or a sequence that exhibits at least 85%, 86%, 87%, 88%, 89%, 90%, 91%, 92%, 93%, 94%, 95%, 96%, 97%, 98%, 99% or more sequence identity to any one of SEQ ID NOS: 13-15. In some aspects, all or the full CD3ζ signaling domain (e.g., the entire CD3ζ signaling domain) or a portion of the CD3ζ signaling domain (e.g., a fragment of the CD3ζ signaling domain) is encoded by the open reading frame of the endogenous CD247 locus of the cell (e.g., T cell) in the provided engineered cells. In some embodiments, the CD3ζ signaling domain of the full intracellular signaling domain (e.g., an entire CD3ζ signaling domain) encoded by the modified CD247 locus encoding the chimeric receptor, comprises the sequence selected from any one of SEQ ID NOS:13-15, or a sequence that exhibits at least 85%, 86%, 87%, 88%, 89%, 90%, 91%, 92%, 93%, 94%, 95%, 96%, 97%, 98%, 99% or more sequence identity to any one of SEQ ID NOS:13-15, or a fragment thereof. In any of such examples, the CD3ζ signaling domain comprises the sequence set forth in SEQ ID NO:13. In any of such examples, the CD3ζ signaling domain consists or consists essentially of the sequence set forth in SEQ ID NO:13. In any of such examples, the CD3ζ signaling domain comprises the sequence set forth in SEQ ID NO:14. In any of such examples, the CD3ζ signaling domain consists or consists essentially of the sequence set forth in SEQ ID NO:14. In any of such examples, the CD3ζ signaling domain comprises the sequence set forth in SEQ ID NO:15. In any of such examples, the CD3ζ signaling domain consists or consists essentially of the sequence set forth in SEQ ID NO:15.

In particular embodiments, the transgene is or contains a sequence of nucleotides that encodes less than a full length of a CD3ζ chain, for example less than the entire CD3ζ signaling domain. In certain embodiments, the transgene contains a sequence of nucleotides encoding a portion of a CD3ζ chain that is or includes less than 4 exons, 3 full exons, less than 3 exons, 2 full exons, less than 2 exons, 1 exon, or less than one exon of the CD247 open reading frame. In particular embodiments, the transgene contains a sequence of nucleotides a portion of a CD3ζ chain that is or is less than 100, 90, 80, 70, 60, 50, 40, 30, 20, 10, 9, 8, 7, 6, 5, 4, 3 or 2 nucleotides in length. In some embodiment, the transgene contains a sequence of nucleotides encoding a portion of a CD3ζ chain that is at, about, or less than 100, 90, 80, 70, 60, 50, 40, 30, 20, 10, 9, 8, 7, 6, 5, 4, 3 or 2 contiguous nucleotides of a sequence having at or at least 70%, 75%, 80%, 85%, 90%, 95%, 97%, 98%, 99%, 99.5%, or 99.9% sequence identity to all or a portion of the nucleic acid sequence set forth in SEQ ID NOS: 74 or 76.

In some aspects, the portion of the CD3ζ chain encoded by the transgene includes a portion encoded by one or more exons selected from exon 1, 2, 3, 4 or 5, or a portion encoded by a partial sequence of the contiguous sequence comprising exons 1-5 or 2-5 (e.g., without intronic sequences). In some aspects, the portion of the CD3ζ chain encoded by the transgene includes a portion encoded by one or more exons selected from exon 1, 2 or 3, or a portion encoded by a partial sequence of the contiguous sequence comprising exons 1-3 or 2-3 (e.g., without intronic sequences). In some aspects, the portion of the CD3ζ chain encoded by the transgene includes a portion encoded by exon 2 or partial sequence thereof. In some aspects, the transgene includes the last 3, 6, 9, 12, 15 or 18 nucleotides of exon 2 of the open reading frame sequence of the endogenous CD247 locus. In some embodiments, the transgene includes sequences encoding the last 1, 2, 3, 4, 5 or 6 amino acid residues encoded by exon 2 of the open reading frame of the endogenous CD247 locus. In some aspects, the transgene includes the last 9 nucleotides of exon 2 and/or the sequences encoding the last 3 amino acid residues encoded by exon 2 of the open reading frame sequence of the endogenous CD247 locus. In some aspects, the transgene includes the first 3, 6, 9, 12, 15 or 18 nucleotides of exon 3 and/or the sequences encoding the first 1, 2, 3, 4, 5 or 6 amino acid residues encoded by exon 3 of the open reading frame of the endogenous CD247 locus.

In particular embodiments, the transgene does not contain any introns. In particular embodiments, the sequence of nucleotides encoding the portion of the CD3ζ chain in the transgene does not contain any introns or portions thereof.

In some aspects, the transgene does not comprise nucleic acid sequences encoding any portion of a CD3ζ chain. In some aspects, the sequence of nucleotides encoding the portion of a CD3ζ chain, if present within the transgene, is typically linked to one of the homology arm sequences, e.g., the 3' homology arm sequence. In some aspects, if present within the transgene, is the most 3' region in the transgene, which is then linked to one of the homology arm sequences, e.g., the 3' homology arm sequence.

(v) Additional Domains, e.g., Multimerization Domains

In some embodiments, the transgene also includes a sequence of nucleotides encoding one or more multimerization domain(s), e.g., a dimerization domain. In some aspects, the encoded multimerization domain can be extracellular or intracellular. In some embodiments, the encoded multimerization domain is extracellular. In some embodiments, the encoded multimerization domain is intracellular. In some embodiments, the portion of the intracellular region encoded by the transgene sequences comprises a multimerization domain, optionally a dimerization domain. In some embodiments, the transgene comprises a sequence of nucleotides encoding an extracellular region. In some embodiments, the extracellular region comprises a multimerization domain, optionally a dimerization domain. In some embodiments, the multimerization domain is capable of dimerization upon binding to an inducer.

In some aspects, the chimeric receptor is a multi-chain chimeric receptor, such as a multi-chain CAR. In some embodiments, one or more chains of the multi-chain chimeric receptor or a portion thereof is encoded by the transgene sequence. In some embodiments, one or more chains of the multi-chain chimeric receptor can together form a functional or active chimeric receptor, by virtue of multimerization of the multimerization domain included in each chain of the chimeric receptor.

In some aspects, the sequence of nucleotides encoding a multimerization domain is 5' or 3' of other domains. For example, in some embodiments, the encoded multimerization domain is extracellular, and the sequence encoding the multimerization domain is 5' of the sequence encoding the spacer. In some embodiments, the encoded multimerization domain is intracellular, and the sequence encoding the multimerization domain is 5' of the sequence encoding the CD3ζ chain or a fragment thereof. In some embodiments, the multimerization domain is intracellular, and the sequence encoding the multimerization domain is 5' or 3' of the sequence encoding one or more costimulatory signaling domain(s). In some embodiments, the encoded multimerization domain can multimerize (e.g., dimerize), upon binding of an inducer. Exemplary encoded multimerization domain includes any multimerization domain described herein, e.g., in Section III.B herein.

(vi) Additional Molecules, e.g., Markers

In some embodiments, the transgene also includes a sequence of nucleotides encoding one or more additional molecules, such as an antibody, an antigen, an additional chimeric or additional polypeptide chains of a multi-chain chimeric receptor (e.g., multi-chain CAR, chimeric costimulatory receptor, inhibitory receptor, regulatable chimeric antigen receptor or other components of multi-chain chimeric receptor systems described herein, for example, in Section III.B.2; or a recombinant T cell receptor (TCR)), a transduction marker or a surrogate marker (e.g., truncated cell surface marker), an enzyme, an factors, a transcription factor, an inhibitory peptide, a growth factor, a nuclear receptor, a hormone, a lymphokine, a cytokine, a chemokine, a soluble receptor, a soluble cytokine receptor, a soluble chemokine receptor, a reporter, functional fragments or functional variants of any of the foregoing and combinations of the foregoing. In some aspects, such sequence of nucleotides encoding one or more additional molecules can be placed 5' of the sequence of nucleotides encoding regions or domains of the chimeric receptor. In some aspects, the sequences encoding one or more other molecules and the sequence of nucleotides encoding regions or domains of the chimeric receptor are separated by regulatory sequences, such as a 2A ribosome skipping element and/or promoter sequences.

In some embodiments, the transgene also includes a sequence of nucleotides encoding one or more additional molecules. In some aspects, one or more additional molecules include one or more marker(s). In some embodiments, the one or more marker(s) includes a transduction marker, a surrogate marker and/or a selection marker. In some embodiments, the transgene also includes nucleic acid sequences that can improve the efficacy of therapy, such as by promoting viability and/or function of transferred cells;

nucleic acid sequences to provide a genetic marker for selection and/or evaluation of the cells, such as to assess in vivo survival or localization; nucleic acid sequences to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also WO 1992008796 and WO 1994028143 describing the use of bifunctional selectable fusion genes derived from fusing a dominant positive selectable marker with a negative selectable marker, and U.S. Pat. No. 6,040,177. In some aspects, the markers include any markers described herein, for example, in this section or Sections II or III.B, or any additional molecules and/or receptor polypeptides described herein, for example, in Section III.B.2. In some embodiments, the additional molecule is a surrogate marker, optionally a truncated receptor, optionally wherein the truncated receptor lacks an intracellular signaling domain and/or is not capable of mediating intracellular signaling when bound by its ligand.

In some embodiments, the marker is a transduction marker or a surrogate marker. A transduction marker or a surrogate marker can be used to detect cells that have been introduced with the polynucleotide, e.g., a polynucleotide encoding a chimeric receptor or a portion thereof. In some embodiments, the transduction marker can indicate or confirm modification of a cell. In some embodiments, the surrogate marker is a protein that is made to be co-expressed on the cell surface with the chimeric receptor or a portion thereof, e.g. CAR. In particular embodiments, such a surrogate marker is a surface protein that has been modified to have little or no activity. In certain embodiments, the surrogate marker is encoded on the same polynucleotide that encodes the chimeric receptor or a portion thereof. In some embodiments, the nucleic acid sequence encoding the chimeric receptor or a portion thereof is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, an E2A or an F2A. Extrinsic marker genes may in some cases be utilized in connection with engineered cell to permit detection or selection of cells and, in some cases, also to promote cell elimination and/or cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO:7 or 16) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR).

In some embodiments, the marker is or comprises a detectable protein, such as a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, codon-optimized, stabilized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof. In some aspects, expression of the enzyme can be detected by addition of a substrate that can be detected upon the expression and functional activity of the enzyme.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a variant thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some embodiments, the transgene includes sequences encoding one or more additional molecule that is an immunomodulatory agent. In some embodiments, the immunomodulatory molecule is selected from an immune checkpoint modulator, an immune checkpoint inhibitor, a cytokine or a chemokine. In some embodiments, the immunomodulatory agent is an immune checkpoint inhibitor capable of inhibiting or blocking a function of an immune checkpoint molecule or a signaling pathway involving an immune checkpoint molecule. In some embodiments, the immune checkpoint molecule is selected from among PD-1, PD-L1, PD-L2, CTLA-4, LAG-3, TIM3, VISTA, an adenosine receptor or extracellular adenosine, optionally an adenosine 2A Receptor (AZAR) or adenosine 2B receptor (A2BR), or adenosine or a pathway involving any of the foregoing. Other exemplary additional molecules include epitope tags, detectable molecules such as fluorescent or luminescent proteins, or molecules that mediate enhanced cell growth and/or gene amplification (e.g., dihydrofolate reductase). Epitope tags include, for example, one or more copies of FLAG, His, myc, Tap, HA or any detectable amino acid sequence. In some embodiments, additional molecules can include non-coding sequences, inhibitory nucleic acid sequences, such as antisense RNAs, RNAi, shRNAs and micro RNAs (miRNAs), or nuclease recognition sequences.

In some aspects, the additional molecule can include any additional receptor polypeptides described herein, such as any additional receptor polypeptide chain of a multi-chain chimeric receptor, such as described in Section III.B.2.

(vii) Multicistronic Elements and Regulatory or Control Elements

In some embodiments, the transgene (e.g., exogenous nucleic acid sequences) also contains one or more heterologous or exogenous regulatory or control elements, e.g., cis-regulatory elements, that are not, or are different from the regulatory or control elements of the endogenous CD247 locus. In some aspects, the heterologous regulatory or control elements include such as a promoter, an enhancer, an intron, an insulator, a polyadenylation signal, a transcription termination sequence, a Kozak consensus sequence, a multicistronic element (e.g., internal ribosome entry sites (IRES), a 2A sequence), sequences corresponding to untranslated regions (UTR) of a messenger RNA (mRNA), and splice acceptor or donor sequences, such as those that are not, or are different from the regulatory or control element at the CD247 locus. In some embodiments, the heterologous regulatory or control elements include a promoter, an enhancer, an intron, a polyadenylation signal, a Kozak consensus sequence, a splice acceptor sequence and/or a splice donor sequence. In some embodiments, the transgene comprises a promoter that is heterologous and/or not typically present at or near the target site. In some aspects, the regulatory or control element includes elements required to regulate or control the expression of the chimeric receptor, when integrated at the CD247 locus. In some embodiments, the transgene sequences include sequences corresponding to 5' and/or 3' untranslated regions (UTRs) of a heterologous gene or locus. In some aspects, the transgene sequence can include any regulatory or control elements described herein, including those described in this section and Section II.

The transgene, including the transgene encoding the chimeric receptor or a portion thereof, can be inserted so that its expression is driven by the endogenous promoter at the integration site, namely the promoter that drives expression of the endogenous CD247 gene. In some embodiments in which the polypeptide encoding sequences are promoterless, expression of the integrated transgene is then ensured by transcription driven by an endogenous promoter or other control element in the region of interest. For example, the transgene encoding a portion of the chimeric receptor can be inserted without a promoter, but in-frame with the coding sequence of the endogenous CD247 locus, such that expression of the integrated transgene is controlled by the transcription of the endogenous promoter and/or other regulatory elements at the integration site. In some embodiments, a multicistronic element such as a ribosome skipping element/self-cleavage element (e.g., a 2A element or an internal ribosome entry site (IRES)), is placed upstream of the transgene encoding a portion of the chimeric receptor, such that the multicistronic element is placed in-frame with one or more exons of the endogenous open reading frame at the CD247 locus, such that the expression of the transgene encoding the chimeric receptor is operably linked to the endogenous CD247 promoter. In some embodiments, the transgene sequence does not comprise a sequence encoding a 3' UTR. In some embodiments, upon integration of the transgene into the endogenous CD247 locus, the transgene is integrated upstream of the 3' UTR of the endogenous CD247 locus, such that the message encoding the chimeric receptor contains a 3' UTR of the endogenous CD247 locus, e.g., from the open reading frame or partial sequence thereof of the endogenous CD247 locus. In some embodiments, the open reading frame or a partial sequence thereof encoding the remaining portion of the chimeric receptor comprises a 3' UTR of the endogenous CD247 locus.

In some embodiments, a "tandem" cassette is integrated into the selected site. In some embodiments, one or more of the "tandem" cassettes encode one or more polypeptide or factors, each independently controlled by a regulatory element or all controlled as a multi-cistronic expression system. In some embodiments, such as those where the polynucleotide contains a first and second nucleic acid sequence, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). In some embodiments, transcription units can be engineered as a bicistronic unit containing an IRES (internal ribosome entry site), which allows coexpression of gene products by a message from a single promoter. Alternatively, in some cases, a single promoter may direct expression of an RNA that contains, in a single open reading frame (ORF), two or three polypeptides separated from one another by sequences encoding a self-cleavage peptide (e.g., 2A sequences) or a protease recognition site (e.g., furin), as described herein. The ORF thus encodes a single polypeptide, which, either during (in the case of 2A) or after translation, is processed into the individual proteins. In some embodiments, the "tandem cassette" includes the first component of the cassette comprising a promoterless sequence, followed by a transcription termination sequence, and a second sequence, encoding an autonomous expression cassette or a multi-cistronic expression sequence. In some embodiments, the tandem cassette encodes two or more different polypeptides or factors, e.g., two or more chains or domains of a chimeric receptor. In some embodiments, nucleic acid sequences encoding two or more chains or domains of the chimeric receptor are introduced as tandem expression cassettes or bi- or multi-cistronic cassettes, into one target DNA integration site.

In some cases, the multicistronic element, such as a T2A, can cause the ribosome to skip (ribosome skipping) synthesis of a peptide bond at the C-terminus of a 2A element, leading to separation between the end of the 2A sequence and the next peptide downstream (see, for example, de Felipe, *Genetic Vaccines and Ther.* 2:13 (2004) and de Felipe et al. *Traffic* 5:616-626 (2004); also referred to as a self-cleavage element). This allows the inserted transgene to be controlled by the transcription of the endogenous promoter at the integration site, such as a CD247 promoter. Exemplary multicistronic element include 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Pub. No. 20070116690. In some embodiments, the template polynucleotide includes a P2A ribosome skipping element (sequence set forth in SEQ ID NO: 18 or 19) upstream of the transgene, e.g., nucleic acids encoding the chimeric receptor or portion thereof.

In some embodiments, the transgene encoding the one or more chains of a chimeric receptor or portion thereof and/or the sequences encoding an additional molecule independently comprises one or more multicistronic element(s). In some embodiments, the one or more multicistronic element(s) are upstream of the nucleic acid sequence encoding the chimeric receptor portion thereof and/or the sequences encoding an additional molecule. In some embodiments, the multicistronic element(s) is positioned between the nucleic acid sequence encoding the chimeric receptor portion thereof and/or the sequences encoding an additional molecule. In some embodiments, the multicistronic element(s) is positioned between the nucleic acid sequence encoding portions or chains of the chimeric receptor.

In some embodiments, the heterologous regulatory or control element comprises a heterologous promoter. In some embodiments, the heterologous promoter is selected from among a constitutive promoter, an inducible promoter, a repressible promoter, and/or a tissue-specific promoter. In some embodiments, regulatory or control element is a promoter and/or enhancer, for example a constitutive promoter or an inducible or tissue-specific promoter. In some embodiments, the promoter is selected from among an RNA pol I, pol II or pol III promoter. In some embodiments, the promoter is recognized by RNA polymerase II (e.g., a CMV, SV40 early region or adenovirus major late promoter). In some embodiments, the promoter is recognized by RNA polymerase III (e.g., a U6 or H1 promoter). In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1α promoter (EF1α), mouse phosphoglycerate kinase 1 promoter (PGK), and chicken β-Actin promoter coupled with CMV early enhancer (CAGG). In some embodiments, the heterologous promoter is or comprises a human elongation factor 1 alpha (EF1α) promoter or an MND promoter or a variant thereof.

In some embodiments, the promoter is a regulated promoter (e.g., inducible promoter). In some embodiments, the promoter is an inducible promoter or a repressible promoter. In some embodiments, the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof. In some embodiments, the promoter is a tissue-specific promoter. In some instances, the promoter is only expressed in a specific cell type (e.g., a T cell or B cell or NK cell specific promoter).

In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1α promoter (EF1α), mouse phosphoglycerate kinase 1 promoter (PGK), and chicken β-Actin promoter coupled with CMV early enhancer (CAGG). In some embodiments, the constitutive promoter is a synthetic or modified promoter. In some embodiments, the promoter is or comprises an MND promoter, a synthetic promoter that contains the U3 region of a modified MoMuLV LTR with myeloproliferative sarcoma virus enhancer (see Challita et al. (1995) J. Virol. 69(2):748-755). In some embodiments, the promoter is a tissue-specific promoter. In some instances, the promoter drives expression only in a specific cell type (e.g., a T cell or B cell or NK cell specific promoter).

In some embodiments, the promoter is a viral promoter. In some embodiments, the promoter is a non-viral promoter. In some cases, the promoter is selected from among human elongation factor 1 alpha (EF1α) promoter (such as set forth in SEQ ID NO:77 or 118) or a modified form thereof (EF1α promoter with HTLV1 enhancer; such as set forth in SEQ ID NO:119) or the MND promoter (such as set forth in SEQ ID NO:131). In some embodiments, the polynucleotide does not include a heterologous or exogenous regulatory element, e.g., a promoter. In some embodiments, the promoter is a bidirectional promoter (see, e.g., WO2016/022994).

In some embodiments, transgene sequences may also include splice acceptor sequences. Exemplary known splice acceptor site sequences include, e.g., CTGACCTCTTCTCTTCCTCCCACAG (SEQ ID NO:78) (from the human HBB gene) and TTTCTCTCCACAG (SEQ ID NO:79) (from the human IgG gene).

In some embodiments, the transgene sequences may also include sequences required for transcription termination and/or polyadenylation signal. In some aspects, exemplary polyadenylation signal is selected from SV40, hGH, BGH, and rbGlob transcription termination sequence and/or polyadenylation signal. In some embodiments, the transgene includes an SV40 polyadenylation signal. In some embodiments, if present within the transgene, the transcription termination sequence and/or polyadenylation signal is typically the most 3' sequence within the transgene, and is linked to one of the homology arm. In some aspects, the transgene sequence does not comprise a sequence encoding a 3' UTR or a transcription terminator. In some embodiments, upon integration of the transgene into the endogenous CD247 locus, the transgene is integrated upstream of the 3' UTR and/or the transcription terminator of the endogenous CD247 locus, such that the message encoding the chimeric receptor contains a 3' UTR of the endogenous CD247 locus, e.g., from the open reading frame or partial sequence thereof of the endogenous CD247 locus. Thus, in some embodiments, upon integration of the transgene sequences encoding a portion of the chimeric receptor, the nucleic acid sequences encoding the chimeric receptor is operably linked to be under the control of 3' UTR, transcription terminator and/or other regulatory elements of the endogenous CD247 locus.

(viii) Exemplary Transgene Sequences

In some embodiments, an exemplary transgene includes, in 5' to 3' order, sequence of nucleotides encoding each encoding: a transmembrane domain (or a membrane association domain) and an intracellular region. In some embodiments, an exemplary transgene includes, in 5' to 3' order, sequence of nucleotides encoding each encoding: an extracellular region, a transmembrane domain and an intracellular region.

In some embodiments, an exemplary transgene that encodes an extracellular region includes, in 5' to 3' order, a sequence of nucleotides encoding an extracellular binding domain and a sequence of nucleotides encoding a spacer. In some embodiments, an exemplary transgene also includes a sequence of nucleotides encoding one or more extracellular multimerization domain(s), which can be placed 5' or 3' of any of the sequence of nucleotides encoding binding domains and/or spacers, and/or 5' of the sequence of nucleotides encoding a transmembrane domain. In some aspects, an exemplary transgene sequence also includes a signal sequence, typically placed 5' of the sequence of nucleotides encoding the extracellular region.

In some aspects, in an exemplary transgene, the sequence of nucleotides encoding the binding domain is placed between the signal sequence and the nucleotides encoding the spacer. In some aspects, in an exemplary transgene, the sequence of nucleotides encoding the extracellular multimerization domain is placed between the sequence of nucleotides encoding the binding domain and the sequence of nucleotides encoding the spacer. In some aspects, the sequence of nucleotides encoding the spacer is placed between the sequence of nucleotides encoding the binding domain and the sequence of nucleotides encoding the transmembrane domain In some embodiments, an exemplary transgene contains a sequence of nucleotides encoding an intracellular region, which can include, in 5' to 3' order, sequence of nucleotides encoding one or more costimulatory signaling domain(s) and optionally, a sequence of nucleotides encoding a portion of an CD3ζ chain. In some embodiments, an exemplary transgene also includes a sequence of nucleotides encoding one or more intracellular multimerization domain(s), which can be placed 5' or 3' of any of the one or more costimulatory domains, and/or 5' of the sequence of nucleotides encoding a portion of an CD3ζ chain, if present, or the 3' homology arm sequence, which is adjacent to an exemplary transgene in the polynucleotide. In some embodiments, an exemplary transgene contains a sequence of nucleotides encoding an intracellular region, which can include, in 5' to 3' order, sequence of nucleotides encoding an intracellular multimerization domain, a sequence of nucleotides encoding one or more costimulatory signaling domain(s) and optionally, a sequence of nucleotides encoding a portion of a CD3ζ chain. In some aspects, in an exemplary transgene, the sequence of nucleotides encoding one or more costimulatory signaling domain is placed between the sequence of nucleotides encoding the transmembrane domain and the sequence of nucleotides encoding a portion of an CD3ζ chain, if present, or the 3' homology arm sequence, which is adjacent to an exemplary transgene in the polynucleotide. In some aspects, in an exemplary transgene, the sequence of nucleotides encoding the intracellular multimerization domain is placed between the sequence of nucleotides encoding the transmembrane domain and the sequence of nucleotides encoding the one or more costimulatory signaling domains; or between the sequence of nucleotides encoding the one or more costimulatory signaling domains and the sequence of nucleotides encoding a portion of an CD3ζ chain, if present, or the 3' homology arm sequence, which is adjacent to an exemplary transgene in the polynucleotide.

In some embodiments, an exemplary transgene sequence comprises, in 5' to 3' direction, sequence of nucleotides each encoding: a signal peptide, an extracellular binding domain, a spacer, a transmembrane domain and an intracellular region comprising a portion of the CD3ζ chain. In some embodiments, an exemplary transgene sequence comprises, in 5' to 3' direction, sequence of nucleotides each encoding: a signal peptide, an extracellular binding domain, a spacer, a transmembrane domain and a costimulatory signaling domain. In some embodiments, an exemplary transgene sequence comprises, in 5' to 3' direction, sequence of nucleotides each encoding: a signal peptide, an extracellular binding domain, a spacer, a transmembrane domain and two costimulatory signaling domains. In some embodiments, an exemplary transgene sequence comprises, in 5' to 3' direction, sequence of nucleotides each encoding: a signal peptide, an extracellular binding domain, a spacer, a transmembrane domain and three costimulatory signaling domains. In some embodiments, an exemplary transgene sequence comprises, in 5' to 3' direction, sequence of nucleotides each encoding: a signal peptide, an extracellular binding domain, a spacer, a transmembrane domain and a costimulatory signaling domain and a portion of the CD3ζ chain. In some embodiments, an exemplary transgene sequence comprises, in 5' to 3' direction, sequence of nucleotides each encoding: a signal peptide, an extracellular binding domain, a spacer, a transmembrane domain and two costimulatory signaling domains and a portion of the CD3ζ chain. In some embodiments, an exemplary transgene sequence comprises, in 5' to 3' direction, sequence of nucleotides each encoding: a signal peptide, an extracellular binding domain, a spacer, a transmembrane domain and three costimulatory signaling domains and a portion of the CD3ζ chain.

In some embodiments, an exemplary transgene sequence comprises, in 5' to 3' direction, sequence of nucleotides each encoding: a transmembrane domain (or a membrane association domain), an intracellular multimerization domain, optionally one or more costimulatory signaling domain(s), and optionally a portion of the CD3ζ chain. In some embodiments, an exemplary transgene sequence comprises, in 5' to 3' direction, sequence of nucleotides each encoding: an extracellular multimerization domain, a transmembrane domain, optionally one or more costimulatory signaling domain(s), and optionally a portion of the CD3ζ chain.

In some embodiments, the exemplary transgene sequences can also comprise a multicistronic element, e.g., a 2A element or an internal ribosome entry site (IRES), and/or a regulatory or control element, e.g., a promoter, placed 5' of the sequences encoding the signal peptide and/or the extracellular region. In some embodiments, the exemplary transgene sequences can also comprise additional sequences, e.g., sequence of nucleotides encoding one or more additional molecules, such as a marker, an additional chimeric receptor, an antibody or an antigen-binding fragment thereof, an immunomodulatory molecule, a ligand, a cytokine or a chemokine. In some aspects, the sequences encoding one or more other molecules and the sequence of nucleotides encoding regions or domains of the chimeric receptor are separated by regulatory sequences, such as a 2A ribosome skipping element and/or promoter sequences. In some aspects, in the exemplary transgene, the sequence of nucleotides encoding one or more additional molecules is placed 5' of the sequences encoding the signal peptide and/or the extracellular region. In some embodiments, the sequence of nucleotides encoding one or more additional molecules is placed between the multicistronic element and/or regulatory or control element, and the sequence of nucleotides encoding regions or domains of the chimeric receptor. In some embodiments, the sequence of nucleotides encoding one or more additional molecules is placed between two elements and/or regulatory or control elements. In some embodiments, an exemplary transgene sequence comprises, in 5' to 3' direction: a multicistronic element and/or a regulatory element, a sequence of nucleotides encoding an additional molecule, a multicistronic element and/or a regulatory element, a signal peptide, nucleic acid sequence encoding regions or domains of the chimeric receptor (e.g., extracellular region, transmembrane domain, intracellular region).

In some embodiments, the transgene sequence comprises, in order: a sequence of nucleotides encoding an extracellular binding domain, optionally an scFv; a spacer, optionally comprising a sequence from a human immunoglobulin hinge, optionally from IgG1, IgG2 or IgG4 or a modified version thereof, optionally further comprising a $C_H2$ region and/or a $C_H3$ region; and a transmembrane domain, optionally from human CD28; an intracellular region comprising a costimulatory signaling domain, optionally from human 4-1BB; and optionally a portion of the CD3zeta signaling domain. In some embodiments, the encoded intracellular region of the chimeric receptor comprises, from its N to C terminus in order: the one or more costimulatory signaling domain(s) and the CD3zeta chain or a fragment thereof.

b. Homology Arms

In some embodiments, the template polynucleotide contains one or more homology sequences (also called "homology arms") on the 5' and/or 3' ends, linked to, flanking or surrounding the transgene sequences encoding one or more chains of a chimeric receptor or a portion thereof. In some embodiments, the one or more homology arms include the 5' and/or 3' homology arms. The homology arms allow the DNA repair mechanisms, e.g., homologous recombination machinery, to recognize the homology and use the template polynucleotide as a template for repair, and the nucleic acid sequence between the homology arms are copied into the DNA being repaired, effectively inserting or integrating the transgene sequences into the target site of integration in the genome between the location of the homology.

In some aspects, upon integration of the transgene sequences, the transgene sequence comprises a sequence of nucleotides that is in-frame with one or more exons of the open reading frame of the CD247 locus comprised in the one or more homology arm(s). In some aspects, a portion of the chimeric receptor is encoded by the transgene sequences, and the remaining portion of the chimeric receptor, e.g., a portion of the CD3ζ signaling domain or the entire CD3ζ signaling domain, is encoded by one or more exons of the endogenous CD247 locus.

In some embodiments, the homology arm sequences include sequences that are homologous to the genomic sequences surrounding the genetic disruption, e.g., a target site within the CD247 locus. In some embodiments, the template polynucleotide comprises the following components: [5' homology arm]-[transgene sequences (exogenous or heterologous nucleic acid sequences, e.g., encoding one or more chains of a chimeric receptor)]-[3' homology arm]. In some embodiments, the 5' homology arm sequences include contiguous sequences that are homologous to sequences located near the genetic disruption on the 5' side. In some embodiments, the 3' homology arm sequences include contiguous sequences that are homologous to sequences located near the genetic disruption on the 3' side. In some aspects, the target site is determined by targeting of the one or more agent(s) capable of introducing a genetic disruption, e.g., Cas9 and gRNA targeting a specific site within the CD247 locus.

In some aspects, the transgene sequences within the template polynucleotide can be used to guide the location of target sites and/or homology arms. In some aspects, the target site of genetic disruption can be used as a guide to design template polynucleotides and/or homology arms used for HDR. In some embodiments, the genetic disruption can be targeted near a desired site of targeted integration of transgene sequences. In some aspects, the homology arms are designed to target integration within an exon of the open reading frame of the endogenous CD247 locus, and the homology arm sequences are determined based on the desired location of integration surrounding the genetic disruption, including exon and intron sequences surrounding the genetic disruption. In some embodiments, the location of the target site, relative location of the one or more homology arm(s), and the transgene (exogenous nucleic acid sequence) for insertion can be designed depending on the requirement for efficient targeting and the length of the template polynucleotide or vector that can be used. In some aspects, the homology arms are designed to target integration within an intron of the open reading frame of the CD247 locus. In some aspects, the homology arms are designed to target integration within an exon of the open reading frame of the CD247 locus.

In some aspects, the target integration site (site for targeted integration) within the CD247 locus is located within an open reading frame at the endogenous CD247 locus that encodes a CD3ζ chain. In some embodiments, the target integration site is at or near any of the target sites described herein, e.g., in Section I.A. In some aspects, the target location for integration is at or around the target site for genetic disruption, e.g., within less than 500, 450, 400, 350, 300, 250, 200, 150, 100 or 50 bp of the target site for genetic disruption.

In some aspects, the target integration site is within an exon of the open reading frame of the endogenous CD247 locus. In some aspects, the target integration site is within an intron of the open reading frame of the CD247 locus. In some aspects, the target integration site is within a regulatory or control element, e.g., a promoter, of the CD247 locus. In some embodiments, the target integration site is within or in close proximity to exons corresponding to early coding region, e.g., exon 1, 2 or 3 of the open reading frame of the endogenous CD247 locus, or including sequence immediately following a transcription start site, within exon 1, 2, or 3 (such as described in Table 1 herein), or within less than 500, 450, 400, 350, 300, 250, 200, 150, 100 or 50 bp of exon 1, 2, or 3. In some embodiments, the integration is targeted at or near exon 2 of the endogenous CD247 locus, or within less than 500, 450, 400, 350, 300, 250, 200, 150, 100 or 50 bp of exon 2. In some aspects, the target integration site is at or near exon 1 of the endogenous CD247 locus, e.g., within less than 500, 450, 400, 350, 300, 250, 200, 150, 100 or 50 bp of exon 1. In some embodiments, the target integration site is at or near exon 2 of the endogenous CD247 locus, or within less than 500, 450, 400, 350, 300, 250, 200, 150, 100 or 50 bp of exon 2. In some aspects, the target integration site is at or near exon 3 of the endogenous CD247 locus, e.g., within less than 500, 450, 400, 350, 300, 250, 200, 150, 100 or 50 bp of exon 3.

In some embodiments, the 5' homology arm sequences include contiguous sequences of approximately 10, 20, 30, 40, 50, 100, 200, 300, 400, 500, 600, 700, 800, 900, 1000, 1500, 2000, 3000, 4000, or 5000 base pairs 5' of the target site for genetic disruption, starting near the target site at the endogenous CD247 locus. In some embodiments, the 3' homology arm sequences include contiguous sequences of approximately 10, 20, 30, 40, 50, 100, 200, 300, 400, 500, 600, 700, 800, 900, 1000, 1500, 2000, 3000, 4000, or 5000 base pairs 3' of the target site for genetic disruption, starting near the target site at the endogenous CD247 locus. Thus, upon integration via HDR, the transgene sequence is targeted for integration at or near the target site for genetic disruption, e.g., a target site within an exon or intron of the endogenous CD247 locus.

In some aspects, the homology arms contain sequences that are homologous to a portion of an open reading frame sequence at the endogenous CD247 locus. In some aspects, the homology arm sequences contain sequences homologous to contiguous portion of an open reading frame sequence, including exons and introns, at the endogenous CD247 locus. In some aspects, the homology arm contains sequences that are identical to a contiguous portion of an open reading frame sequence, including exons and introns, at the endogenous CD247 locus.

In some embodiments, the template polynucleotide contains homology arms for targeting integration of the transgene sequences at the endogenous CD247 locus (exemplary genomic locus sequence described in Table 1 herein; exemplary mRNA sequence set forth in SEQ ID NO:74, NCBI Reference Sequence: NM_198053.2 and SEQ ID NO:76, NCBI Reference Sequence: NM_000734.3). In some embodiments, the genetic disruption is introduced using any of the agents for genetic disruption, e.g., targeted nucleases and/or gRNAs described herein. In some embodiments, the template polynucleotide comprises about 500 to 1000, e.g., 500 to 900 or 600 to 700, base pairs of homology on either side of the genetic disruption introduced by the targeted nucleases and/or gRNAs. In some embodiments, the template polynucleotide comprises about 500, 600, 700, 800, 900 or 1000 base pairs of 5' homology arm sequences, which is homologous to 500, 600, 700, 800, 900 or 1000 base pairs of sequences 5' of the genetic disruption at a CD247 locus, the transgene, and about 500, 600, 700, 800, 900 or 1000 base pairs of 3' homology arm sequences, which is homologous to 500, 600, 700, 800, 900 or 1000 base pairs of sequences 3' of the genetic disruption at a CD247 locus.

In some aspects, the boundary between the transgene and the one or more homology arm sequences, is designed such that upon HDR and targeted integration of the transgene sequences, the sequences within the transgene that encode one or more polypeptide, e.g., chain(s), domain(s) or region(s) of a chimeric receptor, is integrated in-frame with one or more exons of the open reading frame sequence at the endogenous CD247 locus, and/or generates an in-frame fusion of the transgene that encode a polypeptide and one or more exons of the open reading frame sequence at the endogenous CD247 locus.

In some embodiments, the one or more homology arm sequences include sequences that are homologous, substantially identical or identical to sequences that surround or flank the target site that are within an open reading frame sequence at the endogenous CD247 locus. In some embodiments, the one or more homology arm(s) comprise at least one intron and at least one exon of the open reading frame of the CD247 locus. In some aspects, the one or more homology arm sequences contain introns and exons of a partial sequence of an open reading frame at the endogenous CD247 locus. In some aspects, the boundary of the 5' homology arm sequence and the transgene is such that, in a case of a transgene that does not contain a heterologous promoter, the coding portion of the transgene sequence is fused in-frame with an upstream exon or a portion thereof, e.g., exon 1, 2, or 3, depending on the location of targeted integration, of the open reading frame of the endogenous CD247 locus. In some aspects, the boundary of the 3' homology arm sequence and the transgene is such that, the downstream exons or a portion thereof, e.g., exons 2, 3, 4, 5, 6, 7 or 8, of the open reading frame of the endogenous CD247 locus, is fused in-frame with the coding portions of the transgene sequence. Thus, upon targeted integration, transcription and translation, the encoded chimeric receptor that is a contiguous polypeptide is produced, from a fusion DNA sequence of the transgene and an open reading frame sequence of the endogenous CD247 locus. In some aspects, the portion of the encoded chimeric receptor produced by the fusion DNA sequence is a CD3ζ chain or a fragment thereof. In some aspects, the encoded chimeric receptor is capable of signaling via the CD3ζ chain or portion thereof. In some embodiments, the one or more homology arm(s) does not comprise the full length of exon 1 of the open reading frame of the CD247 locus. In some embodiments, the one or more homology arm(s) does not comprise does not comprise exon 1 and/or does not comprise the full length of exon 2 of the open reading frame of the CD247 locus.

In some embodiments, exemplary 5' homology arm for targeting integration at the endogenous CD247 locus comprises the sequence set forth in SEQ ID NO:80, or a sequence that exhibits at least 85%, 86%, 87%, 88%, 89%, 90%, 91%, 92%, 93%, 94%, 95%, 96%, 97%, 98%, 99% or more sequence identity to SEQ ID NO:80 or a partial sequence thereof. In some embodiments, the 5' homology arm comprises the sequence set forth in SEQ ID NO:80. In some embodiments, the 5' homology arm consists or consists essentially of the sequence set forth in SEQ ID NO:80.

In some embodiments, exemplary 3' homology arm for targeting integration at the endogenous CD247 locus comprises the sequence set forth in SEQ ID NO:81, or a sequence that exhibits at least 85%, 86%, 87%, 88%, 89%, 90%, 91%, 92%, 93%, 94%, 95%, 96%, 97%, 98%, 99% or more sequence identity to SEQ ID NO:81 or a partial sequence thereof. In some embodiments, the 3' homology arm comprises the sequence set forth in SEQ ID NO:81. In some embodiments, the 3' homology arm consists or consists essentially of the sequence set forth in SEQ ID NO:81.

In some aspects, the target site can determine the relative location and sequences of the homology arms. The homology arm can typically extend at least as far as the region in which end resection by the DNA repair mechanism can occur after the genetic disruption, e.g., DSB, is introduced, e.g., in order: to allow the resected single stranded overhang to find a complementary region within the template polynucleotide. The overall length could be limited by parameters such as plasmid size, viral packaging limits or construct size limit.

In some embodiments, the homology arm comprises at or about 500 to 1000, e.g., 600 to 900 or 700 to 800, base pairs of homology on either side of the target site at the endogenous gene. In some embodiments, the homology arm comprises at or about at least at or about or less than or about 200, 300, 400, 500, 600, 700, 800, 900 or 1000 base pairs homology 5' of the target site, 3' of the target site, or both 5' and 3' of the target site at a CD247 locus.

In some embodiments, the homology arm comprises at or about 10, 20, 30, 40, 50, 100, 200, 300, 400, 500, 600, 700, 800, 900, 1000, 1500, 2000, 3000, 4000, or 5000 base pairs homology 3' of the target site at a CD247 locus. In some embodiments, the homology arm comprises at or about 100 to 500, 200 to 400 or 250 to 350, base pairs homology 3' of the transgene and/or target site at a CD247 locus. In some embodiments, the homology arm comprises less than about 100, 90, 80, 70, 60, 50, 40, 30, 20, 15, or 10 base pairs homology 5' of the target site at a CD247 locus.

In some embodiments, the homology arm comprises at or about 10, 20, 30, 40, 50, 100, 200, 300, 400, 500, 600, 700, 800, 900, 1000, 1500, 2000, 3000, 4000, or 5000 base pairs homology 5' of the target site at a CD247 locus. In some embodiments, the homology arm comprises at or about 100 to 500, 200 to 400 or 250 to 350, base pairs homology 5' of the transgene and/or target site at a CD247 locus. In some embodiments, the homology arm comprises less than about 100, 90, 80, 70, 60, 50, 40, 30, 20, 15, or 10 base pairs homology 3' of the target site at a CD247 locus.

In some embodiments, the 3' end of the 5' homology arm is the position next to the 5' end of the transgene. In some embodiments, the 5' homology arm can extend at least at or about 10, 20, 30, 40, 50, 100, 200, 300, 400, 500, 600, 700, 800, 900, 1000, 1500, 2000, 3000, 4000, or 5000 nucleotides 5' from the 5' end of the transgene.

In some embodiments, the 5' end of the 3' homology arm is the position next to the 3' end of the transgene. In some embodiments, the 3' homology arm can extend at least at or about 10, 20, 30, 40, 50, 100, 200, 300, 400, 500, 600, 700, 800, 900, 1000, 1500, 2000, 3000, 4000, or 5000 nucleotides 3' from the 3' end of the transgene.

In some embodiments, for targeted insertion, the homology arms, e.g., the 5' and 3' the homology arms, may each comprise about 1000 base pairs (bp) of sequence flanking the most distal target sites (e.g., 1000 bp of sequence on either side of the mutation).

Exemplary homology arm lengths include at least at or about 50, 100, 200, 250, 300, 400, 500, 600, 700, 750, 800, 900, 1000, 2000, 3000, 4000, or 5000 nucleotides. In some embodiments, the homology arm length is at or about 50-100, 100-250, 250-500, 500-750, 750-1000, 1000-2000, 2000-3000, 3000-4000, or 4000-5000 nucleotides. Exemplary homology arm lengths include less than or less than about or is or is about 50, 100, 200, 250, 300, 400, 500, 600, 700, 750, 800, 900, 1000, 2000, 3000, 4000, or 5000 nucleotides. In some embodiments, the homology arm length is at or about 50-100, 100-250, 250-500, 500-750, 750-1000, 1000-2000, 2000-3000, 3000-4000, or 4000-5000 nucleotides. Exemplary homology arm lengths include from at or about 100 to at or about 1000 nucleotides, from at or about 100 to at or about 750 nucleotides, from at or about 100 to at or about 600 nucleotides, from at or about 100 to at or about 400 nucleotides, from at or about 100 to at or about 300 nucleotides, from at or about 100 to at or about 200 nucleotides, from at or about 200 to at or about 1000 nucleotides, from at or about 200 to at or about 750 nucleotides, from at or about 200 to at or about 600 nucleotides, from at or about 200 to at or about 400 nucleotides, from at or about 200 to at or about 300 nucleotides, from at or about 300 to at or about 1000 nucleotides, from at or about 300 to at or about 750 nucleotides, from at or about 300 to at or about 600 nucleotides, from at or about 300 to at or about 400 nucleotides, from at or about 400 to at or about 1000 nucleotides, from at or about 400 to at or about 750 nucleotides, from at or about 400 to at or about 600 nucleotides, from at or about 600 to at or about 1000 nucleotides, from at or about 600 to at or about 750 nucleotides or 750 to at or about 1000 nucleotides.

In some of any such embodiments, the transgene is integrated by a template polynucleotide introduced into each of a plurality of T cells. In particular embodiments, the template polynucleotide comprises the structure [5' homology arm]-[transgene]-[3' homology arm]. In certain embodiments, the 5' homology arm and the 3' homology arm comprises nucleic acid sequences homologous to nucleic acid sequences surrounding the at least at or about one target site. In some embodiments, the 5' homology arm comprises nucleic acid sequences that are homologous to nucleic acid sequences 5' of the target site. In particular embodiments, the 3' homology arm comprises nucleic acid sequences that are homologous to nucleic acid sequences 3' of the target site. In certain embodiments, the 5' homology arm and the 3' homology arm independently are at least at or about or at least at or about 10, 20, 30, 40, 50, 100, 200, 300, 400, 500, 600, 700, 800, 900, 1000, 1500, or 2000 nucleotides, or less than or less than about 10, 20, 30, 40, 50, 100, 200, 300, 400, 500, 600, 700, 800, 900, 1000, 1500, or 2000 nucleotides. In some embodiments, the 5' homology arm and the 3' homology arm independently are between at or about 50 and at or about 100, 100 and at or about 250, 250 and at or about 500, 500 and at or about 750, 750 and at or about 1000, 1000 and at or about 2000 nucleotides. In some of any such embodiments, the 5' homology arm and the 3' homology arm independently are between at or about 50 and at or about 100 nucleotides in length, at or about 100 and at or about 250 nucleotides in length, at or about 250 and at or about 500 nucleotides in length, at or about 500 and at or about 750 nucleotides in length, at or about 750 and at or about 1000 nucleotides in length, or at or about 1000 and at or about 2000 nucleotides in length.

In particular embodiments, the 5' homology arm and the 3' homology arm independently are from at or about 100 to at or about 1000 nucleotides, from at or about 100 to at or about 750 nucleotides, from at or about 100 to at or about 600 nucleotides, from at or about 100 to at or about 400 nucleotides, from at or about 100 to at or about 300 nucleotides, from at or about 100 to at or about 200 nucleotides, from at or about 200 to at or about 1000 nucleotides, from at or about 200 to at or about 750 nucleotides, from at or about 200 to at or about 600 nucleotides, from at or about 200 to at or about 400 nucleotides, from at or about 200 to at or about 300 nucleotides, from at or about 300 to at or about 1000 nucleotides, from at or about 300 to at or about 750 nucleotides, from at or about 300 to at or about 600 nucleotides, from at or about 300 to at or about 400 nucleotides, from at or about 400 to at or about 1000 nucleotides, from at or about 400 to at or about 750 nucleotides, from at or about 400 to at or about 600 nucleotides, from at or about 600 to at or about 1000 nucleotides, from at or about 600 to at or about 750 nucleotides or from at or about 750 to at or about 1000 nucleotides. In particular embodiments, the 5' homology arm and the 3' homology arm independently are from at or about 100 to at or about at or about 1000 nucleotides, from at or about 100 to at or about 750 nucleotides, from at or about 100 to at or about 600 nucleotides, from at or about 100 to at or about 400 nucleotides, from at or about 100 to at or about 300 nucleotides, from at or about 100 to at or about 200 nucleotides, from at or about 200 to at or about 1000 nucleotides, from at or about 200 to at or about 750 nucleotides, from at or about 200 to at or about 600 nucleotides, from at or about 200 to at or about 400 nucleotides, from at or about 200 to at or about 300 nucleotides, from at or about 300 to at or about 1000 nucleotides, from at or about 300 to at or about 750 nucleotides, from at or about 300 to at or about 600 nucleotides, from at or about 300 to at or about 400 nucleotides, from at or about 400 to at or about 1000 nucleotides, from at or about 400 to at or about 750 nucleotides, from at or about 400 to at or about 600 nucleotides, from at or about 600 to at or about 1000 nucleotides, from at or about 600 to at or about 750 nucleotides or from at or about 750 to at or about 1000 nucleotides in length. In some embodiments, the 5' homology arm and the 3' homology arm independently are at or about 200, 300, 400, 500, 600, 700 or 800 nucleotides in length, or any value between any of the foregoing. In some embodiments, the 5' homology arm and the 3' homology arm independently are greater than at or about 300 nucleotides in length, optionally wherein the 5' homology arm and the 3' homology arm independently are at or about 400, 500 or 600 nucleotides in length or any value between any of the foregoing. In some embodiments, the 5' homology arm and the 3' homology arm independently are greater than at or about 300 nucleotides in length.

In some embodiments, one or more of the homology arms contain a sequence of nucleotides are homologous to sequences that encode a CD3ζ chain or a fragment thereof. In some embodiments, one or more homology arms are connected or linked in frame with the transgene sequences encoding a chimeric receptor or a portion thereof. Thus, in some embodiments, one or more of the homology arms and the transgene together encode a CD3ζ chain or a fragment thereof that is larger than the portion of the CD3ζ chain encoded by the transgene alone. In some embodiments, the combination of one or more of the homology arms and the transgene together contains sequences that are homologous to a full exon of the endogenous gene, locus, or open reading frame that encodes the CD3ζ chain, CD247. In some embodiments, one or more homology arms contain a sequence of nucleotides that are homologous to all or a portion of an intron of the endogenous gene, locus, or open reading frame that encodes the CD3ζ chain, CD247.

In some embodiments, alternative HDR is employed. In some embodiments, alternative HDR proceeds more efficiently when the template polynucleotide has extended homology 5' to the target site (i.e., in the 5' direction of the target site strand). Accordingly, in some embodiments, the template polynucleotide has a longer homology arm and a shorter homology arm, wherein the longer homology arm can anneal 5' of the target site. In some embodiments, the arm that can anneal 5' to the target site is at least 25, 50, 75, 100, 125, 150, 175, or 200, 300, 400, 500, 600, 700, 800, 900, 1000, 1500, 2000, 3000, 4000, or 5000 nucleotides from the target site or the 5' or 3' end of the transgene. In some embodiments, the arm that can anneal 5' to the target site is at least 10%, 20%, 30%, 40%, or 50% longer than the arm that can anneal 3' to the target site. In some embodiments, the arm that can anneal 5' to the target site is at least 2×, 3×, 4×, or 5× longer than the arm that can anneal 3' to the target site. Depending on whether a ssDNA template can anneal to the intact strand or the targeted strand, the homology arm that anneals 5' to the target site may be at the 5' end of the ssDNA template or the 3' end of the ssDNA template, respectively.

Similarly, in some embodiments, the template polynucleotide has a 5' homology arm, a transgene, and a 3' homology arm, such that the template polynucleotide contains extended homology to the 5' of the target site. For example, the 5' homology arm and the 3' homology arm may be substantially the same length, but the transgene may extend farther 5' of the target site than 3' of the target site. In some embodiments, the homology arm extends at least 10%, 20%, 30%, 40%, 50%, 2×, 3×, 4×, or 5× further to the 5' end of the target site than the 3' end of the target site.

In some embodiments alternative HDR proceeds more efficiently when the template polynucleotide is centered on the target site. Accordingly, in some embodiments, the template polynucleotide has two homology arms that are essentially the same size. In some embodiments, the first homology arm (e.g., 5' homology arm) of a template polynucleotide may have a length that is within 10%, 9%, 8%, 7%, 6%, 5%, 4%, 3%, 2%, or 1% of the second homology arm (e.g., 3' homology arm) of the template polynucleotide.

Similarly, in some embodiments, the template polynucleotide has a 5' homology arm, a transgene, and a 3' homology arm, such that the template polynucleotide extends substantially the same distance on either side of the target site. For example, the homology arms may have different lengths, but the transgene may be selected to compensate for this. For example, the transgene may extend further 5' from the target site than it does 3' of the target site, but the homology arm 5' of the target site is shorter than the homology arm 3' of the target site, to compensate. The converse is also possible, e.g., that the transgene may extend further 3' from the target site than it does 5' of the target site, but the homology arm 3' of the target site is shorter than the homology arm 5' of the target site, to compensate.

In some embodiments, the length of the template polynucleotide, including the transgene sequence and the one or more homology arms, is between or between about 1000 to about 20,000 base pairs, such as about 1000, 1500, 2000, 2500, 3000, 3500, 4000, 4500, 5000, 6000, 7000, 8000, 9000, 10000, 11000, 12000, 13000, 14000, 15000, 16000, 17000, 18000, 19000 or 20000 base pairs. In some embodiments, the length of the template polynucleotide is limited by the maximum length of polynucleotide that can be prepared, synthesized or assembled and/or introduced into the cell or the capacity of the viral vector, and the type of polynucleotide or vector. In some aspects, the limited capacity of the template polynucleotide can determine the length of the transgene sequences and/or the one or more homology arms. In some aspects, the combined total length of the transgene sequences and the one or more homology arms must be within the maximum length or capacity of the polynucleotide or vector. For example, in some aspects, the transgene portion of the template polynucleotide is about 1000, 1500, 2000, 2500, 3000, 3500 or 4000 base pairs, and if the maximum length of the template polynucleotide is about 5000 base pairs, the remaining portion of the sequence can be divided among the one or more homology arms, e.g., such that the 3' or 5' homology arms can be approximately 500, 750, 1000, 1250, 1500, 1750 or 2000 base pairs.

In some aspects, the provided embodiments permit the use of a smaller or shorter nucleic acid sequence fragments for engineering compared to existing methods. For example, in some embodiments, the transgene sequences encodes a portion of or none of the CD3ζ or a portion thereof of the chimeric receptor. By utilizing a portion or all of the open reading frame sequences of the endogenous CD247 gene to encode the CD3ζ or a portion thereof of the chimeric receptor, the provided embodiments permit the use of smaller transgene sequences. In some embodiments, the transgene sequences that encode a portion of the chimeric receptor is fused in-frame with one or more of the exons of the endogenous CD247 open reading frame, and therefore can be placed under the control of the endogenous CD247 regulatory elements. Thus, in some cases, heterologous regulatory or control elements are not required, and compared to existing methods that require regulatory or control elements for expression, the transgene sequences may be smaller. In some aspects, the embodiments permit the use of smaller or shorter transgene sequences, e.g., transgene sequences that are approximately 100 to 1000 base pairs smaller, e.g., about 100, 200, 300, 400, 500, 600, 700, 800, 900 or 1000 base pairs smaller, than a transgene sequence used in existing methods, e.g., that includes the entire length of the primary signaling region, e.g., CD3ζ chain or a fragment thereof and/or containing heterologous regulatory elements. Thus, in cases where the maximum length of the polynucleotide is limited, the provided embodiments allow accommodation of larger homology arms and/or allow accommodation of nucleic acid sequences encoding additional molecules, as the length requirement for transgene sequences encoding a portion of the chimeric receptor is reduced. In some aspects, generation, delivery of the nucleic acid sequences, e.g., transgene sequences, and/or targeting efficiency by homology-directed repair (HDR), may be facilitated or improved compared to other methods.

3. Delivery of Template Polynucleotides

In some embodiments, the polynucleotide, such as a template polynucleotide containing transgene sequences encoding one or more chains of a chimeric receptor or a portion thereof (for example, described in Section I.B.2 herein), are introduced into the cells in nucleotide form, e.g., as a polynucleotide or a vector. In particular embodiments, the polynucleotide contains a transgene sequence that encodes a portion of a chimeric receptor and one or more homology arms, and can be introduced into the cell for homology-directed repair (HDR)-mediated integration of the transgene sequences.

In some aspects, the provided embodiments genetic engineering of cells, by the introduction of one or more agent(s) or components thereof capable of inducing a genetic disruption and a template polynucleotide, to induce HDR and targeted integration of the transgene sequences. In some aspects, the one or more agent(s) and the template polynucleotide are delivered simultaneously. In some aspects, the one or more agent(s) and the template polynucleotide are delivered sequentially. In some embodiments, the one or more agent(s) are delivered prior to the delivery of the polynucleotide.

In some embodiments, the template polynucleotide is introduced into the cell for engineering, in addition to the agent(s) capable of inducing a targeted genetic disruption, e.g., nuclease and/or gRNAs. In some embodiments, the template polynucleotide(s) may be delivered prior to, simultaneously or after one or more components of the agent(s) capable of inducing a targeted genetic disruption is introduced into a cell. In some embodiments, the template polynucleotide(s) are delivered simultaneously with the agents. In some embodiments, the template polynucleotides are delivered prior to the agents, for example, seconds to hours to days before the template polynucleotides, including, but not limited to, 1 to 60 minutes (or any time therebetween) before the agents, 1 to 24 hours (or any time therebetween) before the agents or more than 24 hours before the agents. In some embodiments, the template polynucleotides are delivered after the agents, seconds to hours to days after the template polynucleotides, including immediately after delivery of the agent, e.g., between 30 seconds to 4 hours, such as about 30 seconds, 1 minute, 2 minutes, 3 minutes, 4 minutes, 5 minutes, 6 minutes, 6 minutes, 8 minutes, 9 minutes, 10 minutes, 15 minutes, 20 minutes, 30 minutes, 40 minutes, 50 minutes, 60 minutes, 90 minutes, 2 hours, 3 hours or 4 hours after delivery of the agents and/or preferably within 4 hours of delivery of the agents. In some embodiments, the template polynucleotide is delivered more than 4 hours after delivery of the agents. In some embodiments, the template polynucleotide is introduced at or about 2 hours after the introduction of the one or more agents.

In some embodiments, the template polynucleotides may be delivered using the same delivery systems as the agent(s) capable of inducing a targeted genetic disruption, e.g., nuclease and/or gRNAs. In some embodiments, the template polynucleotides may be delivered using different same delivery systems as the agent(s) capable of inducing a targeted genetic disruption, e.g., nuclease and/or gRNAs. In some embodiments, the template polynucleotide is delivered simultaneously with the agent(s). In other embodiments, the template polynucleotide is delivered at a different time, before or after delivery of the agent(s). Any of the delivery method described herein in Section I.A.3 (e.g., in Tables 3 and 4) for delivery of nucleic acids in the agent(s) capable of inducing a targeted genetic disruption, e.g., nuclease and/or gRNAs, can be used to deliver the template polynucleotide.

In some embodiments, the one or more agent(s) and the template polynucleotide are delivered in the same format or method. For example, in some embodiments, the one or more agent(s) and the template polynucleotide are both comprised in a vector, e.g., viral vector. In some embodiments, the template polynucleotide is encoded on the same vector backbone, e.g. AAV genome, plasmid DNA, as the Cas9 and gRNA. In some aspects, the one or more agent(s) and the template polynucleotide are in different formats, e.g., ribonucleic acid-protein complex (RNP) for the Cas9-gRNA agent and a linear DNA for the template polynucleotide, but they are delivered using the same method.

In some embodiments, the template polynucleotide is a linear or circular nucleic acid molecule, such as a linear or circular DNA or linear RNA, and can be delivered using any of the methods described in Section I.A.3 herein (e.g., Tables 3 and 4 herein) for delivering nucleic acid molecules into the cell.

In particular embodiments, the polynucleotide, e.g., the template polynucleotide, are introduced into the cells in nucleotide form, e.g., as or within a non-viral vector. In some embodiments, the non-viral vector is or includes a polynucleotide, e.g., a DNA or RNA polynucleotide, that is suitable for transduction and/or transfection by any suitable and/or known non-viral method for gene delivery, such as but not limited to microinjection, electroporation, transient cell compression or squeezing (such as described in Lee, et al. (2012) *Nano Lett* 12: 6322-27), lipid-mediated transfection, peptide-mediated delivery, e.g., cell-penetrating peptides, or a combination thereof. In some embodiments, the non-viral polynucleotide is delivered into the cell by a non-viral method described herein, such as a non-viral method listed in Table 4 herein.

In some embodiments, the template polynucleotide sequence can be comprised in a vector molecule containing sequences that are not homologous to the region of interest in the genomic DNA. In some embodiments, the virus is a DNA virus (e.g., dsDNA or ssDNA virus). In some embodiments, the virus is an RNA virus (e.g., an ssRNA virus). Exemplary viral vectors/viruses include, e.g., retroviruses, lentiviruses, adenovirus, adeno-associated virus (AAV), vaccinia viruses, poxviruses, and herpes simplex viruses, or any of the viruses described elsewhere herein. A polynucleotide can be introduced into a cell as part of a vector molecule having additional sequences such as, for example, replication origins, promoters and genes encoding antibiotic resistance. Moreover, template polynucleotides can be introduced as naked nucleic acid, as nucleic acid complexed with materials such as a liposome, nanoparticle or poloxamer, or can be delivered by viruses (e.g., adenovirus, AAV, herpesvirus, retrovirus, lentivirus and integrase defective lentivirus (IDLV)).

In some embodiments, the template polynucleotide can be transferred into cells using recombinant infectious virus particles, such as, e.g., vectors derived from simian virus 40 (SV40), adenoviruses, adeno-associated virus (AAV). In some embodiments, the template polynucleotide is transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557 or HIV-1 derived lentiviral vectors.

In other aspects, the template polynucleotide is delivered by viral and/or non-viral gene transfer methods. In some embodiments, the template polynucleotide is delivered to the cell via an adeno associated virus (AAV). Any AAV vector can be used, including, but not limited to, AAV1, AAV2, AAV3, AAV4, AAV5, AAV6, AAV7, AAV8 and combinations thereof. In some instances, the AAV comprises LTRs that are of a heterologous serotype in comparison with the capsid serotype (e.g., AAV2 ITRs with AAV5, AAV6, or AAV8 capsids). The template polynucleotide may be delivered using the same gene transfer system as used to deliver the nuclease (including on the same vector) or may be delivered using a different delivery system that is used for the nuclease. In some embodiments, the template polynucleotide is delivered using a viral vector (e.g., AAV) and the nuclease(s) is(are) delivered in mRNA form. The cell may also be treated with one or more molecules that inhibit binding of the viral vector to a cell surface receptor as described herein prior to, simultaneously and/or after delivery of the viral vector (e.g., carrying the nuclease(s) and/or template polynucleotide).

In some embodiments, the retroviral vector has a long terminal repeat sequence (LTR), e.g., a recombinant retroviral vector derived from the Moloney murine leukemia virus (MoMLV), myeloproliferative sarcoma virus (MPSV), murine embryonic stem cell virus (MESV), murine stem cell virus (MSCV), or spleen focus forming virus (SFFV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109).

In some embodiments, the template polynucleotides are delivered using an AAV vector and the agent(s) capable of inducing a targeted genetic disruption, such as nuclease and/or gRNAs are delivered as a different form, such as mRNAs encoding the nucleases and/or gRNAs. In some embodiments, the template polynucleotides and nucleases are delivered using the same type of method, such as a viral vector, but on separate vectors. In some embodiments, the template polynucleotides are delivered in a different delivery system as the agents capable of inducing a genetic disruption, such as nucleases and/or gRNAs. Types or nucleic acids and vectors for delivery include any of those described in Section III herein.

In some embodiments, the template polynucleotides and nucleases may be on the same vector, for example an AAV vector (such as AAV6). In some embodiments, the template polynucleotides are delivered using an AAV vector and the agent(s) capable of inducing a targeted genetic disruption, such as nuclease and/or gRNAs are delivered as a different form, such as mRNAs encoding the nucleases and/or gRNAs. In some embodiments, the template polynucleotides and nucleases are delivered using the same type of method, such as a viral vector, but on separate vectors. In some embodiments, the template polynucleotides are delivered in a different delivery system as the agents capable of inducing a genetic disruption, such as nucleases and/or gRNAs. In some embodiments, the template polynucleotide is excised from a vector backbone in vivo, such as it is flanked by gRNA recognition sequences. In some embodiments, the template polynucleotide is on a separate polynucleotide molecule as the Cas9 and gRNA. In some embodiments, the Cas9 and the gRNA are introduced in the form of a ribonucleoprotein (RNP) complex, and the template polynucleotide is introduced as a polynucleotide molecule, such as in a vector or a linear nucleic acid molecule, such as linear DNA. Types or nucleic acids and vectors for delivery include any of those described in Section II herein.

In some embodiments, the template polynucleotide is an adenovirus vector, e.g., an AAV vector, e.g., a ssDNA molecule of a length and sequence that allows it to be packaged in an AAV capsid. The vector may be, e.g., less than 5 kb and may contain an ITR sequence that promotes packaging into the capsid. The vector may be integration-deficient. In some embodiments, the template polynucleotide comprises about 150 to 1000 nucleotides of homology on either side of the transgene and/or the target site. In some embodiments, the template polynucleotide comprises about 100, 150, 200, 300, 400, 500, 600, 700, 800, 900, 1000, 1500, or 2000 nucleotides 5' of the target site or transgene, 3' of the target site or transgene, or both 5' and 3' of the target site or transgene. In some embodiments, the template polynucleotide comprises at least 100, 150, 200, 300, 400, 500, 600, 700, 800, 900, 1000, 1500, or 2000 nucleotides 5' of the target site or transgene, 3' of the target site or transgene, or both 5' and 3' of the target site or transgene. In some embodiments, the template polynucleotide comprises at most 100, 150, 200, 300, 400, 500, 600, 700, 800, 900, 1000, 1500, or 2000 nucleotides 5' of the target site or transgene, 3' of the target site or transgene, or both 5' and 3' of the target site or transgene.

In some embodiments, the template polynucleotide is a lentiviral vector, e.g., an IDLV (integration deficiency lentivirus). In some embodiments, the template polynucleotide comprises about 500 to 1000 base pairs of homology on either side of the transgene and/or the target site. In some embodiments, the template polynucleotide comprises about 300, 400, 500, 600, 700, 800, 900, 1000, 1500, or 2000 base pairs of homology 5' of the target site or transgene, 3' of the target site or transgene, or both 5' and 3' of the target site or transgene. In some embodiments, the template polynucleotide comprises at least 300, 400, 500, 600, 700, 800, 900, 1000, 1500, or 2000 base pairs of homology 5' of the target site or transgene, 3' of the target site or transgene, or both 5' and 3' of the target site or transgene. In some embodiments, the template polynucleotide comprises no more than 300, 400, 500, 600, 700, 800, 900, 1000, 1500, or 2000 base pairs of homology 5' of the target site or transgene, 3' of the target site or transgene, or both 5' and 3' of the target site or transgene. In some embodiments, the template polynucleotide comprises one or more mutations, e.g., silent mutations, that prevent Cas9 from recognizing and cleaving the template polynucleotide. The template polynucleotide may comprise, e.g., at least 1, 2, 3, 4, 5, 10, 20, or 30 silent mutations relative to the corresponding sequence in the genome of the cell to be altered. In some embodiments, the template polynucleotide comprises at most 2, 3, 4, 5, 10, 20, 30, or 50 silent mutations relative to the corresponding sequence in the genome of the cell to be altered. In some embodiments, the cDNA comprises one or more mutations, e.g., silent mutations that prevent Cas9 from recognizing and cleaving the template polynucleotide. The template polynucleotide may comprise, e.g., at least 1, 2, 3, 4, 5, 10, 20, or 30 silent mutations relative to the corresponding sequence in the genome of the cell to be altered. In some embodiments, the template polynucleotide comprises at most 2, 3, 4, 5, 10, 20, 30, or 50 silent mutations relative to the corresponding sequence in the genome of the cell to be altered.

The double-stranded template polynucleotides described herein may include one or more non-natural bases and/or backbones. In particular, insertion of a template polynucleotide with methylated cytosines may be carried out using the methods described herein to achieve a state of transcriptional quiescence in a region of interest.

II. Nucleic Acids, Vectors and Delivery

In some embodiments, the polynucleotide, such as a polynucleotide such as a template polynucleotide encoding one or more chains of a chimeric receptor or a portion thereof, is introduced into the cells in nucleotide form, such as a polynucleotide or a vector. In particular embodiments, the polynucleotide contains a transgene that encodes the chimeric receptor or a portion thereof. In certain embodiments, the one or more agent(s) or components thereof for genetic disruption are introduced into the cells in nucleic acid form, such as polynucleotides and/or vectors. In some embodiments, the components for engineering can be delivered in various forms using various delivery methods, including any suitable methods used for delivery of agent(s) as described in Section I.A.3 and Tables 3 and 4 herein. Also provided are one or more polynucleotides (such as nucleic acid molecules) encoding one or more components of the one or more agent(s) capable of inducing a genetic disruption (for example, any described in Section I.A herein). Also provided are one or more template polynucleotides containing the transgene sequences (for example, any described in Section I.B.2 herein). Also provided are vectors, such as vectors for genetically engineering cells for targeted integration of the transgene, that include one or more such polynucleotides, such as a template polynucleotide or a polynucleotide encoding one or more components of the one or more agent(s) capable of inducing a genetic disruption.

In some embodiments, provided are polynucleotides, such as template polynucleotides for targeting transgene at a specific genomic target location, such as at the CD247 locus. In some embodiments, provided are any template polynucleotides described in Section I.B herein. In some embodiments, the template polynucleotide contains transgene that include nucleic acid sequences that encode a chimeric receptor or a portion thereof or other polypeptides and/or factors, and homology arms for targeted integration. In some embodiments, the template polynucleotide can be contained in a vector.

In some embodiments, agents capable of inducing a genetic disruption can be encoded in one or more polynucleotides. In some embodiments, the component of the agents, such as Cas9 molecule and/or a gRNA molecule, can be encoded in one or more polynucleotides, and introduced into the cells. In some embodiments, the polynucleotide encoding one or more component of the agents can be included in a vector.

In some embodiments, a vector may comprise a sequence that encodes a Cas9 molecule and/or a gRNA molecule and/or template polynucleotides. In some aspects, a vector may also comprise a sequence encoding a signal peptide (such as for nuclear localization, nucleolar localization, mitochondrial localization), fused, such as to a Cas9 molecule sequence. For example, a vector may comprise a nuclear localization sequence (such as from SV40) fused to the sequence encoding the Cas9 molecule. In some embodiments, provided are vectors for genetically engineering cells for targeted integration of the transgene sequences contained in the polynucleotides, such as the template polynucleotides described in Section I.B.2.

In particular embodiments, one or more regulatory/control elements, such as a promoter, an enhancer, an intron, a polyadenylation signal, a Kozak consensus sequence, internal ribosome entry sites (IRES), a 2A sequence, and splice acceptor or donor can be included in the vectors. In some embodiments, the promoter is selected from among an RNA pol I, pol II or pol III promoter. In some embodiments, the promoter is recognized by RNA polymerase II (such as a CMV, SV40 early region or adenovirus major late promoter). In another embodiment, the promoter is recognized by RNA polymerase III (such as a U6 or H1 promoter).

In certain embodiments, the promoter is a regulated promoter (such as inducible promoter). In some embodiments, the promoter is an inducible promoter or a repressible promoter. In some embodiments, the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof.

In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1α promoter (EF1α), mouse phosphoglycerate kinase 1 promoter (PGK), and chicken β-Actin promoter coupled with CMV early enhancer (CAGG). In some embodiments, the constitutive promoter is a synthetic or modified promoter. In some embodiments, the promoter is or comprises an MND promoter, a synthetic promoter that contains the U3 region of a modified MoMuLV LTR with myeloproliferative sarcoma virus enhancer (sequence set forth in SEQ ID NO:18 or 126; see Challita et al. (1995) J. Virol. 69(2):748-755). In some embodiments, the promoter is a tissue-specific promoter. In another embodiment, the promoter is a viral promoter. In another embodiment, the promoter is a non-viral promoter. In some embodiments, exemplary promoters can include, but are not limited to, human elongation factor 1 alpha (EF1α) promoter (such as set forth in SEQ ID NO:77 or 118) or a modified form thereof (EF1α promoter with HTLV1 enhancer; such as set forth in SEQ ID NO:119) or the MND promoter (such as set forth in SEQ ID NO:131). In some embodiments, the polynucleotide and/or vector does not include a regulatory element, e.g. promoter.

In particular embodiments, the polynucleotide, e.g., the polynucleotide encoding the chimeric receptor or a portion thereof, are introduced into the cells in nucleotide form, e.g., as or within a non-viral vector. In some embodiments, the polynucleotide is a DNA or an RNA polynucleotide. In some embodiments, the polynucleotide is a double-stranded or single-stranded polynucleotide. In some embodiments, the non-viral vector is or includes a polynucleotide, e.g., a DNA or RNA polynucleotide, that is suitable for transduction and/or transfection by any suitable and/or known non-viral method for gene delivery, such as but not limited to microinjection, electroporation, transient cell compression or squeezing (such as described in Lee, et al. (2012) *Nano Lett* 12: 6322-27), lipid-mediated transfection, peptide-mediated delivery, or a combination thereof. In some embodiments, the non-viral polynucleotide is delivered into the cell by a non-viral method described herein, such as a non-viral method listed in Table 4.

In some embodiments, the vector or delivery vehicle is a viral vector (e.g., for generation of recombinant viruses). In some embodiments, the virus is a DNA virus (e.g., dsDNA or ssDNA virus). In some embodiments, the virus is an RNA virus (e.g., an ssRNA virus). Exemplary viral vectors/viruses include, e.g., retroviruses, lentiviruses, adenovirus, adeno-associated virus (AAV), vaccinia viruses, poxviruses, and herpes simplex viruses, or any of the viruses described elsewhere herein.

In some embodiments, the virus infects dividing cells. In another embodiment, the virus infects non-dividing cells. In another embodiment, the virus infects both dividing and non-dividing cells. In another embodiment, the virus can integrate into the host genome. In another embodiment, the virus is engineered to have reduced immunity, e.g., in human. In another embodiment, the virus is replication-competent. In another embodiment, the virus is replication-defective, e.g., having one or more coding regions for the genes necessary for additional rounds of virion replication and/or packaging replaced with other genes or deleted. In another embodiment, the virus causes transient expression of the Cas9 molecule and/or the gRNA molecule for the purposes of transient induction of genetic disruption. In another embodiment, the virus causes long-lasting, e.g., at least 1 week, 2 weeks, 1 month, 2 months, 3 months, 6 months, 9 months, 1 year, 2 years, or permanent expression, of the Cas9 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In some embodiments, the polynucleotide containing the agent(s) and/or template polynucleotide is delivered by a recombinant retrovirus. In another embodiment, the retrovirus (e.g., Moloney murine leukemia virus) comprises a reverse transcriptase, e.g., that allows integration into the host genome. In some embodiments, the retrovirus is replication-competent. In another embodiment, the retrovirus is replication-defective, e.g., having one of more coding regions for the genes necessary for additional rounds of virion replication and packaging replaced with other genes, or deleted.

In some embodiments, the polynucleotide containing the agent(s) and/or template polynucleotide is delivered by a recombinant lentivirus. For example, the lentivirus is replication-defective, e.g., does not comprise one or more genes required for viral replication.

In some embodiments, the polynucleotide containing the agent(s) and/or template polynucleotide is delivered by a recombinant adenovirus. In another embodiment, the adenovirus is engineered to have reduced immunity in humans.

In some embodiments, the polynucleotide containing the agent(s) and/or template polynucleotide is delivered by a recombinant AAV. In some embodiments, the AAV can incorporate its genome into that of a host cell, e.g., a target cell as described herein. In another embodiment, the AAV is a self-complementary adeno-associated virus (scAAV), e.g., a scAAV that packages both strands which anneal together to form double stranded DNA. AAV serotypes that may be used in the disclosed methods, include AAV1, AAV2, modified AAV2 (e.g., modifications at Y444F, Y500F, Y730F and/or S662V), AAV3, modified AAV3 (e.g., modifications at Y705F, Y731F and/or T492V), AAV4, AAV5, AAV6, modified AAV6 (e.g., modifications at S663V and/or T492V), AAV7, AAV8, AAV 8.2, AAV9, AAV.rh10, modified AAV.rh10, AAV.rh32/33, modified AAV.rh32/33, AAV.rh43, modified AAV.rh43, AAV.rh64R1, modified AAV.rh64R1, and pseudotyped AAV, such as AAV2/8, AAV2/5 and AAV2/6 can also be used in the disclosed methods.

In some embodiments, the polynucleotide containing the agent(s) and/or template polynucleotide is delivered by a hybrid virus, e.g., a hybrid of one or more of the viruses described herein.

A packaging cell is used to form a virus particle that is capable of infecting a target cell. Such a cell includes a 293 cell, which can package adenovirus, and a ψ2 cell or a PA317 cell, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed, e.g., Cas9. For example, an AAV vector used in gene therapy typically only possesses inverted terminal repeat (ITR) sequences from the AAV genome which are required for packaging and gene expression in the host or target cell. The missing viral functions are supplied in trans by the packaging cell line. Henceforth, the viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In some embodiments, the viral vector has the ability of cell type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as a peptide ligand, a single chain antibody, a growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In some embodiments, the viral vector achieves cell type specific expression. For example, a tissue-specific promoter can be constructed to restrict expression of the agent capable of introducing a genetic disruption (e.g., Cas9 and gRNA) in only a specific target cell. The specificity of the vector can also be mediated by microRNA-dependent control of expression. In some embodiments, the viral vector has increased efficiency of fusion of the viral vector and a target cell membrane. For example, a fusion protein such as fusion-competent hemagglutinin (HA) can be incorporated to increase viral uptake into cells. In some embodiments, the viral vector has the ability of nuclear localization. For example, a virus that requires the breakdown of the nuclear membrane (during cell division) and therefore will not infect a non-diving cell can be altered to incorporate a nuclear localization peptide in the matrix protein of the virus thereby enabling the transduction of non-proliferating cells.

III. Engineered Cells Expressing Chimeric Receptors and Cell Compositions

Provided herein are genetically engineered cells comprising a modified CD247 locus that comprises nucleic acid sequences, such as a transgene encoding one or more chains of a chimeric receptor, such as a chimeric antigen receptor (CAR), or a portion thereof. In some aspects, the modified CD247 locus in the genetically engineered cell comprises exogenous nucleic acid sequences (e.g., transgene sequences) encoding one or more chains of a chimeric receptor or portion thereof, integrated into the endogenous CD247 locus. In some aspects, the provided engineered cells are produced using methods described herein, e.g., involving homology-dependent repair (HDR) by employing agent(s) for inducing a genetic disruption (for example, described in Section I.A) and template polynucleotides containing the transgene sequences for repair (for example, described in Section I.B). In some aspects, a part, e.g., a contiguous segment, of the provided polynucleotides, such as any template polynucleotides described in Section I.B, can be targeted for integration at the endogenous CD247 locus, to generate a cell containing a modified CD247 locus comprising a nucleic acid sequence encoding a chimeric receptor. In some aspects, the encoded chimeric receptor includes an intracellular region comprising a CD3zeta (CD3ζ) signaling domain. In some embodiments, the part of the template polynucleotide that is integrated by HDR into the endogenous CD247 locus includes the transgene sequence portion, such as any described herein, for example in Section I.B, of the template polynucleotide.

In some aspects, the cells are engineered to express a chimeric receptor, such as a chimeric antigen receptor (CAR). In some aspects, the chimeric receptor is encoded by the nucleic acid sequences present at the modified CD247 locus in the engineered cells. In some aspects, the cells are generated by integrating transgene sequences encoding all or a portion of the chimeric receptor, via HDR. In some embodiments, the chimeric receptor contains a binding domain that binds to or recognizes a ligand or an antigen, e.g., an antigen associated with a disease or disorder. In some aspects, the chimeric receptor contains an intracellular region containing a signaling region, e.g., a signaling region comprising CD3zeta (CD3ζ) chain or a fragment thereof, such as a signaling region or signaling domain of CD3ζ. In some embodiments, the chimeric receptor expressed by the cell typically contains a CD3ζ or a portion thereof at the C-terminus of the receptor. In some aspects, the nucleic acid sequences encoding the chimeric receptor or portion thereof present at the modified CD247 locus comprises exogenous nucleic acid sequences fused with an open reading frame or a partial sequence thereof of an endogenous CD247 locus. In some embodiments, at least a portion of the CD3ζ chain in the chimeric receptor is encoded by the sequences of the endogenous CD247 locus in the genome. In some aspects, the CD3ζ chain or portion thereof is a functional CD3ζ chain or portion. In some aspects, chimeric receptor is capable of signaling via the CD3ζ chain or a fragment thereof.

In some aspects, the engineered cells are immune cells, such as T cells. In some aspects, the immune cells are engineered to express a chimeric receptor, e.g., chimeric antigen receptor or modified chimeric receptors, such as any described herein.

In some embodiments, the methods, compositions, articles of manufacture, and/or kits provided herein are useful to generate, manufacture, or produce genetically engineered cells, e.g., genetically engineered immune cells and/or T cells, that have or contain a modified CD247 locus for expressing a chimeric receptor containing a CD3zeta (CD3ζ) signaling domain. In particular embodiments, the methods provided herein result in genetically engineered cells that have or contain a modified CD247 locus. In particular embodiments, the modified locus is or contains a fusion of a transgene, e.g., a transgene described in Section I.B, and an open reading frame of the endogenous CD247 gene. In certain embodiments, the transgene encodes a portion of a chimeric receptor that includes a CD3zeta (CD3ζ) chain or a fragment thereof, and is inserted in-frame into the open reading frame of the endogenous CD247 gene, resulting in a modified locus that encodes the full chimeric receptor. In some embodiments, the chimeric receptor is a chimeric antigen receptor (CAR).

In some cases, the cell is engineered to express one or more additional molecules, e.g., an additional factors and/or an accessory molecule, such as any additional molecules, including therapeutic molecules, described herein. In some embodiments, the additional molecules can include a marker, an additional chimeric receptor polypeptide chain, an antibody or an antigen-binding fragment thereof, an immunomodulatory molecule, a ligand, a cytokine or a chemokine. In some embodiments, the additional factors is a soluble molecule. In some embodiments, the additional factors is a membrane-bound molecule. In some aspects, the additional factors can be used to overcome or counteract the effect of an immunosuppressive environment, such as a tumor microenvironment (TME). In some aspects, exemplary additional molecule includes a cytokine, a cytokine receptor, a chimeric co-stimulatory receptor, a co-stimulatory ligand and other modulators of T cell function or activity. In some embodiments, the additional molecules expressed by the engineered cell include IL-7, IL-12, IL-15, CD40 ligand (CD40L), and 4-1BB ligand (4-1BBL). In some aspects, the additional molecule is an additional receptor, e.g., a membrane-bound receptor, that binds a different molecule. For example, in some embodiments, the additional molecule is a cytokine receptor or a chemokine receptor, e.g., IL-4 receptor or CCL2 receptor. In some cases, the engineered cells are called "armored CARs" or T cells redirected for universal cytokine killing (TRUCKs).

Also provided are compositions containing a plurality of the engineered cells. In some aspects, the compositions containing the engineered cells exhibit improved, uniform, homogeneous and/or stable expression and/or antigen binding by the chimeric receptor, compared to cells or cell compositions generated using other methods of engineering, such as methods in which the chimeric receptor is introduced randomly into the genome of a cell. In some embodiments, the engineered cells or the composition comprising the engineered cells can be used in therapy, e.g., adoptive cell therapy. In some embodiments, the provided cells or cell compositions can be used in any of the methods of treatment described herein or for therapeutic uses described herein.

A. Modified CD247 Locus

In some aspects, provided are genetically engineered cells comprising a modified CD247 locus. In some embodiments, the modified CD247 locus comprises a nucleic acid sequence encoding one or more chains of a chimeric receptor comprising an intracellular region comprising a CD3zeta (CD3ζ) signaling domain. In some embodiments, the nucleic acid sequence comprises a transgene sequence encoding a portion of the one or more chains of a chimeric receptor, the transgene sequence having been integrated at the endogenous CD247 locus, optionally via homology directed repair (HDR). In some embodiments, all (e.g., the entire or full CD3ζ signaling domain) or a fragment of the CD3zeta signaling domain is encoded by an open reading frame or a partial sequence thereof of the endogenous CD247 locus. In some embodiments, the nucleic acid sequence comprises a fusion of a transgene sequence encoding a portion of the chimeric receptor; and an open reading frame or a partial sequence thereof of the endogenous CD247 locus.

In some aspects, the modified CD247 locus s is generated as a result of genetic disruption and integration of transgene sequences (e.g. exogenous or heterologous nucleic acid sequences) that includes a sequence of nucleotides encoding a chimeric receptor or a portion thereof, such as via HDR methods. In some aspects, the nucleic acid sequence present at the modified CD247 locus includes the transgene sequence(s), such as an exogenous sequence, integrated at a region in the endogenous CD247 locus that normally would include an open reading frame encoding full length CD3ζ. In some aspects, upon targeted integration of the transgene by HDR, the genome of the cell contains a modified CD247 locus, comprising a nucleic acid sequence encoding a chimeric receptor or a portion thereof. In some embodiments, upon targeted integration, the modified CD247 locus contains the transgene integrated into a site within the open reading frame of the endogenous CD247 locus, such that a portion of the chimeric receptor is expressed from the engineered cell, and, also a portion of CD3ζ from the endogenous CD247 locus comprising an open reading frame encoding a CD3ζ chain.

In some aspects, upon targeted integration of the transgene by HDR, the genome of the cell contains modified CD247 locus, comprising a nucleic acid sequence encoding a chimeric receptor or a portion thereof. In some embodiments, upon targeted integration, the modified CD247 locus contains a fusion of the transgene and an open reading frame or a partial sequence thereof of an endogenous CD247 locus. In some embodiments, upon targeted integration, the modified CD247 locus contains the transgene integrated into a site within the open reading frame of the endogenous CD247 locus. In some embodiments, upon targeted integration, the modified CD247 locus contains nucleic acid sequences, e.g., a DNA sequence, encoding a complete, whole, and/or full length chimeric receptor, a portion of which is encoded the by the transgene, e.g., by the integrated transgenic or heterologous sequences, and the remaining portion of which is encoded by a portion of the open reading frame of the endogenous CD247 locus, e.g., one or more exons of the open reading frame of the endogenous CD247 locus. In some embodiments, upon targeted integration, the modified CD247 locus contains nucleic acid sequences, e.g., a DNA sequence, encoding a chimeric receptor that comprises a complete, whole, full length and/or entire CD3ζ signaling domain. For example, the CD3ζ signaling domain is functional and is capable of signal transduction. In such examples, a portion of the CD3ζ signaling domain is encoded by the transgene, e.g., by the integrated transgenic or heterologous sequences, and the remaining portion of which is encoded by a portion of the open reading frame of the endogenous CD247 locus, e.g., one or more exons of the open reading frame of the endogenous CD247 locus. Thus, together, the transgene sequence and CD247 locus encode the CD3ζ signaling domain of the chimeric receptor. In other examples, the entire CD3ζ signaling domain of the encoded chimeric receptor is encoded sequences present in the open reading frame of the endogenous CD247 locus, such as by one or more exons of the open reading frame of the endogenous CD247 locus.

In some embodiments, the encoded chimeric receptor is a receptor that contains an intracellular region that comprises all or a portion of the CD3ζ chain (e.g., an intracellular region of the CD3ζ chain, for example a CD3ζ signaling domain) In some of any embodiments, the intracellular region of the encoded chimeric receptor, e.g., encoded by the modified CD247 locus, comprises a CD3zeta (CD3ζ) signaling domain, such as the entire or full CD3ζ signaling domain (e.g., a full-length CD3ζ signaling domain, in some examples, comprising the sequence selected from any one of SEQ ID NOS:13-15). In some of any embodiments, the entire CD3ζ signaling domain is capable of signaling or signal transduction. In some aspects, the encoded chimeric receptor comprises the entire CD3ζ signaling domain (e.g., comprising the sequence selected from any one of SEQ ID NOS:13-15), which is partially or entirely encoded by an open reading frame or a partial sequence thereof of the endogenous CD247 locus. In some embodiments, the open reading frame or a partial sequence thereof of the endogenous CD247 locus encodes the CD3zeta signaling domain of the chimeric receptor. In some embodiments, the nucleic acid sequence comprises a transgene sequence encoding a portion of the chimeric receptor, said portion optionally encoding a fragment of the CD3zeta signaling domain, and wherein the open reading frame or a partial sequence thereof encodes the CD3zeta signaling domain or, optionally the further fragment of the CD3zeta signaling domain. In some embodiments, the transgene contains sequence of nucleotide encoding only a portion of a CD3ζ chain or a portion of the intracellular region of the CD3ζ chain. In some embodiments, the transgene does not comprise a full length CD3ζ chain. In some embodiments, the transgene does not include nucleic acid sequences encoding a CD3ζ chain. In some aspects, upon integration of the transgene, some or all of the nucleic acid sequences encoding the a CD3ζ chain or a fragment thereof of the chimeric receptor is derived from, or originates from, the open reading frame sequence of the endogenous CD247 locus or a partial sequence thereof. Thus, in some embodiments, the integration of the transgene generates a gene fusion of transgene and endogenous sequences of the CD247 locus, which together can encode a chimeric receptor that contains a CD3ζ chain or a fragment thereof.

In some embodiments, the transgene comprises a sequence of nucleotides encoding one or more of an extracellular region, a transmembrane domain and an intracellular region of a chimeric receptor, e.g., CAR. In some aspects, a portion of the intracellular region comprises a CD3ζ chain or a fragment thereof, and only a portion of the CD3ζ chain is encoded by the transgene. In some embodiments, the intracellular region encoded by the transgene does not comprise a sequence of nucleotides encoding a CD3ζ chain. In some embodiments, the open reading frame sequence of the endogenous CD247 locus or a partial sequence thereof encodes all or a portion of the CD3ζ chain present in the chimeric receptor. For example, in some embodiments, in the nucleic acid encoding a chimeric receptor present in the modified CD247 locus, some or all of the sequences encoding the CD3ζ chain or a fragment thereof is derived from or originated from the endogenous CD247 locus and/or the homology arm sequences, which contain sequences homologous to the endogenous CD247 locus.

In some embodiments, the integration of the transgene generates a gene fusion of transgene and endogenous sequences of the CD247 locus, which together encode a chimeric receptor containing a CD3ζ chain or a fragment thereof.

In some embodiments, upon targeted integration, the modified CD247 locus contains a nucleic acid sequence encoding a chimeric receptor or a portion thereof comprising at least one intron and at least one exon of the endogenous CD247 locus. In some embodiments, upon integration, the portion of the chimeric receptor is encoded by a partial sequence of the open reading frame of the endogenous CD247 locus that includes at least one intron and at least one exon of the endogenous CD247 locus. In some embodiments, upon integration, the portion of the chimeric receptor is encoded by a partial sequence of the open reading frame of the endogenous CD247 locus that includes at least one, at least two, at least three, at least four, at least five, at least six or at least seven introns of the endogenous CD247 locus. In some embodiments, the integrated transgene sequence does not comprise a sequence encoding a 3' UTR. In some embodiments, upon targeted integration, the modified CD247 locus contains a nucleic acid sequence encoding a chimeric receptor, and the nucleic acid sequence encodes a 3' UTR of the endogenous CD247 locus. In some embodiments, the open reading frame or a partial sequence thereof comprises a 3' UTR of the endogenous CD247 locus. In some embodiments, upon targeted integration, the modified CD247 locus contains a transgene that does not comprise an intron.

In certain embodiments, the transgene encodes a portion of a chimeric receptor, such as a CAR, and is inserted in-frame within an endogenous open reading frame of the CD247 locus encoding a CD3ζ chain. In some embodiments, the modified locus encodes the full length of the chimeric receptor. In particular embodiments, a portion of the encoded chimeric receptor is encoded by a nucleic acid sequence present in the transgene, and the remaining portion of the chimeric receptor is encoded by a nucleic acid sequence present in the open reading frame of the endogenous CD247 locus. In particular embodiments, the transcription of the modified locus results in an mRNA that encodes the chimeric receptor. In particular embodiments, a portion of the mRNA is transcribed from a nucleic acid sequence present in the transgene, and the remaining portion of the mRNA is transcribed from a nucleic acid sequence present in the open reading frame of the endogenous CD247 locus. In some embodiments, the transgene is integrated at a target site immediately upstream of and in frame with one or more exons of open reading frame of the endogenous CD247 locus that encodes the CD3ζ chain.

In some embodiments, the mRNA transcribed from the modified locus contains a 3'UTR that is encoded by the endogenous CD247 locus and/or is identical to a 3'UTR of an mRNA that is transcribed from the endogenous CD247 locus. In some embodiments, the transgene contains a ribosomal skipping element upstream, e.g., immediately upstream, of the sequence of nucleic acids encoding the portion of the CAR. In certain embodiments, the transcription of the modified locus results in an mRNA that encodes a full length of the CAR. In some embodiments, the mRNA encoding the CAR contains a 5'UTR that is encoded by the endogenous gene and/or is identical to a 5'UTR of an mRNA that is transcribed from the endogenous CD247 locus.

In certain embodiments, the modified locus contains a nucleic acid sequence encoding a chimeric receptor, and the nucleic acid sequence contains at least one, at least two, at least three, at least four, at least five, at least six or at least seven intron. In some embodiments, the open reading frame or a partial sequence thereof comprises at least one intron and at least one exon of the endogenous CD247 locus. In some embodiments, the introns are not located within the integrated transgene sequence. In some embodiments, the open reading frame or a partial sequence thereof encodes a 3' UTR of the endogenous CD247 locus. In some embodiments, the transgene sequence does not comprise an intron. In some embodiments, the transgene sequence is in-frame with one or more exons of the open reading frame or partial sequence thereof of the endogenous CD247 locus.

In some embodiments, the chimeric receptor, e.g., CAR, encoded by the modified CD247 locus is a functional CAR. In some embodiments, a CAR encoded by the modified locus binds to and/or is capable of binding to a target antigen. In some embodiments, the target antigen is associated with, specific to, and/or expressed on a cell or tissue that is associated with a disease, disorder, or condition. In some embodiments, the chimeric receptor, e.g., CAR, encoded by the modified CD247 locus is a functional CAR that is capable of stimulating and/or inducing a primary activation signal in a T cell, a signaling domain of a T cell receptor (TCR) component and/or a signaling domain comprising an immunoreceptor tyrosine-based activation motif (ITAM), such as via an intracellular signaling domain or region of a CD3-zeta (CD3ζ) chain or a functional variant or signaling portion thereof.

In some embodiments, upon targeted integration, the modified CD247 locus contains transgene sequences (e.g., encode a polypeptide, e.g., domain(s) or region(s) of a chimeric receptor), and the coding portion of the transgene (exogenous sequence is integrated in-frame with one or more exons of the open reading frame sequence at the endogenous CD247 locus. In some embodiments, the transgene sequences is integrated or inserted downstream of exon 1 and upstream of exon 8 of the open reading frame of the endogenous CD247 locus. In some embodiments, the transgene sequences is integrated or inserted downstream of exon 1 and upstream of exon 3 of the open reading frame of the endogenous CD247 locus.

In some embodiments, upon targeted integration, the modified CD247 locus contains nucleic acid sequences encoding a chimeric receptor comprising an intracellular region, wherein at least a portion of the intracellular region comprises the CD3zeta (CD3ζ) chain or a fragment thereof encoded by the open reading frame of the endogenous CD247 locus or a partial sequence thereof. In some embodiments, the sequence of nucleotides encoding the intracellular region comprises at least exons 3-8 of the open reading frame of the endogenous CD247 locus. In some embodiments, the sequence of nucleotides encoding the intracellular region comprises at least a portion of exon 2 and exons 3-8 of the open reading frame of the endogenous CD247 locus. In some embodiments, the sequence of nucleotides encoding the intracellular signaling region comprises less than the full length of exon 1 of the open reading frame of the endogenous CD247 locus. In some embodiments, the sequence of nucleotides encoding the intracellular region does not comprise exon 1 and/or comprises less than the full length of exon 2 of the open reading frame of the endogenous CD247 locus.

In some aspects, the encoded chimeric receptor is capable of signaling via the CD3zeta chain or a fragment thereof that is encoded by the fusion of transgene sequences and endogenous sequences of the CD247 locus. In some embodiments, the encoded CD3ζ chain or a fragment thereof comprises an 112 AA intracellular or cytoplasmic domain of isoform 3 of human CD3ζ (Accession No.: P20963.2) or a CD3 zeta signaling domain as described in U.S. Pat. Nos. 7,446,190 or 8,911,993. In some embodiments, the encoded CD3ζ chain or a fragment thereof comprises the sequence of amino acids set forth in SEQ ID NO: 13, 14 or 15 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 13, 14 or 15, or a partial sequence thereof.

In some embodiments, the transgene sequence is downstream of exon 1 and upstream of exon 8 of the open reading frame of the endogenous CD247 locus. In some embodiments, the transgene sequence is downstream of exon 1 and upstream of exon 3 of the open reading frame of the endogenous CD247 locus. In some embodiments, at least a fragment of the CD3ζ signaling domain, optionally the entire CD3ζ signaling domain, of the encoded chimeric receptor is encoded by the open reading frame of the endogenous CD247 locus or a partial sequence thereof. In some embodiments, the CD3ζ signaling domain is encoded by a sequence of nucleotides comprising at least exons 3-8 of the open reading frame of the endogenous CD247 locus. In some embodiments, the CD3ζ signaling domain is encoded by a sequence of nucleotides comprising at least a portion of exon 2 and exons 3-8 of the open reading frame of the endogenous CD247 locus. In some embodiments, the CD3ζ signaling domain is encoded by a sequence of nucleotides that does not comprise the full length of exon 1 of the open reading frame of the endogenous CD247 locus. In some embodiments, the CD3ζ signaling domain is encoded by a sequence of nucleotides that does not comprise exon 1 and/or does not comprise the full length of exon 2 of the open reading frame of the endogenous CD247 locus.

In some embodiments, the transgene sequence encoding a portion of the chimeric receptor comprises, in order: a sequence of nucleotides encoding an extracellular binding domain, optionally an scFv; a spacer, optionally comprising a sequence from a human immunoglobulin hinge, optionally from IgG1, IgG2 or IgG4 or a modified version thereof, optionally further comprising a $C_H2$ region and/or a $C_H3$ region; and a transmembrane domain, optionally from human CD28; an intracellular region comprising a costimulatory signaling domain, optionally from human 4-1BB; and/or the upon integration of the transgene sequence, the modified CD247 locus comprises, in order: a sequence of nucleotides encoding: an extracellular binding domain, optionally an scFv; a spacer, optionally comprising a sequence from a human immunoglobulin hinge, optionally from IgG1, IgG2 or IgG4 or a modified version thereof, optionally further comprising a $C_H2$ region and/or a $C_H3$ region; and a transmembrane domain, optionally from human CD28; an intracellular region comprising a costimulatory signaling domain, optionally from human 4-1BB; and the CD3zeta signaling domain. In some embodiments, the encoded intracellular region of the chimeric receptor comprises, from its N to C terminus in order: the one or more costimulatory signaling domain(s) and the CD3zeta chain or a fragment thereof.

B. Encoded Chimeric Receptors

In some embodiments, the chimeric receptor encoded by the engineered cells provided herein, or the engineered cells generated according to the methods provided herein, include chimeric receptors that contain an intracellular region comprising a CD3ζ chain or a fragment or a portion thereof (e.g., intracellular region of the CD3ζ chain, such as a CD3ζ signaling domain). In some aspects, at least a portion of the chimeric receptor is encoded by transgene sequences present in the polynucleotides provided herein, such as any template polynucleotides described in Section I.B.2 above. In some aspects, a transgene sequence encoding a portion of the chimeric receptor contained in the polynucleotides, is integrated at the endogenous CD247 locus of the engineered cell, to result in a modified CD247 locus that encodes a chimeric receptor, such as any chimeric receptor described herein. In some aspects, the encoded chimeric receptor contains a CD3ζ chain or a fragment or a portion thereof, such as a CD3ζ signaling domain, for example the entire or full CD3ζ signaling domain). In some embodiments, at least a portion of the CD3ζ chain, such as a portion of the CD3ζ signaling domain or the entire CD3ζ signaling domain, is encoded by the open reading frame sequences of the endogenous CD247 locus or a partial sequence thereof. In some embodiments, the engineered cells can also express one or more additional molecules, e.g., a marker, an additional chimeric receptor polypeptides, an antibody or an antigen-binding fragment thereof, an immunomodulatory molecule, a ligand, a cytokine or a chemokine. In some aspects, the transgene sequence encoding the chimeric receptor or a portion thereof contained in the polynucleotides, is integrated at the endogenous CD247 locus of the engineered cell, to result in a modified CD247 locus that encodes a chimeric receptor or a portion thereof, such as any chimeric receptor described herein, including one or more polypeptide chains of a multi-chain chimeric receptor.

In some embodiments, provided are engineered cells, such as immune cells, such as T cells, that express one or more chimeric receptor(s). Among the chimeric receptors are chimeric receptors or antigen receptors and receptors containing one or more component thereof. The chimeric receptors may include chimeric receptors, such as those containing ligand-binding domains or binding fragments thereof and intracellular signaling domains or regions, functional non-TCR antigen receptors, chimeric antigen receptors (CARs), chimeric autoantibody receptor (CAAR) and region(s), chain(s), domain(s) or component(s) of any of the foregoing.

The chimeric receptor, such as a CAR, encoded in the genetically engineered cells provided herein, generally contains various regions or domains such as one or more of extracellular region (e.g., containing one or more extracellular binding domain(s) and/or spacers), transmembrane domain and/or intracellular region (e.g., containing a CD3zeta (CD3ζ) chain or a fragment thereof and/or one or more costimulatory signaling domains). In some aspects, the encoded chimeric receptor further contains other domains, such as multimerization domains, linkers and/or regulatory elements. In some embodiments, the encoded chimeric receptor comprises, from its N to C terminus in order: an extracellular binding domain, a spacer, a transmembrane domain and an intracellular region.

In some embodiments, exemplary chimeric receptors expressed from the engineered cell comprises two or more receptor polypeptides, which, in some cases, contain different components, domains or regions. In some aspects, the chimeric receptor is a multi-chain receptor or a multi-chain chimeric receptor system, comprising two or more polypeptides that together comprise a functional chimeric receptor, or one or more of the polypeptides can regulate, modify or control the expression, activity or function of another receptor polypeptide. In some aspects, the chimeric receptor is a dual-chain receptor, comprising two polypeptides that together comprise a functional chimeric receptor. In some aspects, multi-chain receptors can allow spatial or temporal regulation or control of specificity, activity, antigen (or ligand) binding, function and/or expression of the receptor. In some of such embodiments, the chimeric receptor polypeptide chain encoded by the nucleic acid sequences at the modified CD247 locus is a chimeric receptor polypeptide chain that includes an intracellular region comprising a CD3zeta (CD3ζ) chain or a fragment thereof.

In some embodiments, the chimeric receptor, encoded in the genetically engineered cells provided herein, contains a transmembrane domain or a membrane association domain. In some aspects, the chimeric receptor also contains an extracellular region. In some aspects, the chimeric receptor also contains an intracellular region. In some embodiments, the chimeric receptor encoded in the genetically engineered cells provided herein, generally contains various regions or domains such as one or more of extracellular region (e.g., containing one or more extracellular binding domain(s) and/or spacers), transmembrane domain and intracellular region (e.g., containing an intracellular signaling region and/or one or more costimulatory signaling domains). In some cases, a spacer that separates or is positioned between the extracellular region, e.g. extracellular binding domain, and the transmembrane domain. In some aspects, the encoded chimeric receptor further contains other domains, such as multimerization domains, linkers and/or regulatory elements.

In some embodiments, exemplary chimeric receptors expressed from the engineered cell include multi-chain receptors that contain two or more receptor polypeptides, which, in some cases, contain different components, domains or regions. In some aspects, the chimeric receptor contains two or more polypeptides that together comprise a functional chimeric receptor. In some aspects, the multi-chain receptor is a dual-chain receptor, comprising two polypeptides that together comprise a functional chimeric receptor. In some embodiments, the chimeric receptor is a multi-chain receptor in which one or more of the polypeptides regulates, modifies or controls the expression, activity or function of another receptor polypeptide. In some aspects, multi-chain receptors allows spatial or temporal regulation or control of specificity, activity, antigen (or ligand) binding, function and/or expression of the receptor.

In some embodiments, the encoded chimeric receptor is a chimeric receptor, such as a CAR. An exemplary encoded CAR sequence comprises: an extracellular binding domain, a spacer, a transmembrane domain and an intracellular region comprising a primary signaling domain or region and one or more co-stimulatory signaling domain. In some embodiments, an exemplary encoded CAR sequence comprises: an extracellular binding domain, a spacer, a transmembrane domain and one or more costimulatory signaling domains and primary signaling domain or region.

In some embodiments, an exemplary encoded chimeric receptor comprises, in its N- to C-terminus order: a transmembrane domain (or a membrane association domain) and an intracellular region comprising a CD3ζ chain or a fragment thereof, wherein the nucleic acid sequence encoding the chimeric receptor is present in a modified CD247 locus. In some embodiments, at least a portion of the intracellular region comprises the CD3zeta (CD3ζ) chain or a fragment thereof encoded by the open reading frame of the endogenous CD247 locus or a partial sequence thereof. In some embodiments, an exemplary encoded chimeric receptor comprises, in its N- to C-terminus order: an extracellular region, a transmembrane domain and an intracellular region comprising a CD3ζ chain or a fragment thereof.

In some embodiments, an exemplary encoded chimeric receptor comprises, in its N- to C-terminus order: a signal peptide, an extracellular binding domain, a spacer, a transmembrane domain and an intracellular region comprising a CD3ζ chain or a fragment thereof, wherein the nucleic acid sequence encoding the chimeric receptor is present in a modified CD247 locus. In some embodiments, at least a portion of the intracellular region comprises the CD3zeta (CD3ζ) chain or a fragment thereof encoded by the open reading frame of the endogenous CD247 locus or a partial sequence thereof. In some embodiments, an exemplary encoded chimeric receptor comprises, in its N- to C-terminus order: a signal peptide, an extracellular binding domain, a spacer, a transmembrane domain and a costimulatory signaling domain and a CD3ζ chain or a fragment thereof. In some embodiments, an exemplary encoded chimeric receptor comprises, in its N- to C-terminus order: a signal peptide, an extracellular binding domain, a spacer, a transmembrane domain and two costimulatory signaling domains and a CD3ζ chain or a fragment thereof. In some embodiments, an exemplary encoded chimeric receptor comprises, in its N- to C-terminus order: a signal peptide, an extracellular binding domain, a spacer, a transmembrane domain and three costimulatory signaling domains and a CD3ζ chain or a fragment thereof.

In some embodiments, an exemplary encoded chimeric receptor comprises, in its N- to C-terminus order: a transmembrane domain (or a membrane association domain), an intracellular multimerization domain, optionally one or more costimulatory signaling domain(s), and a CD3ζ chain or a fragment thereof, wherein the nucleic acid sequence encoding the chimeric receptor is present in a modified CD247 locus. In some embodiments, at least a portion of the intracellular region comprises the CD3zeta (CD3ζ) chain or a fragment thereof encoded by the open reading frame of the endogenous CD247 locus or a partial sequence thereof. In some embodiments, an exemplary encoded chimeric receptor comprises, in its N- to C-terminus order: an extracellular multimerization domain, a transmembrane domain, optionally one or more costimulatory signaling domain(s), and a CD3ζ chain or a fragment thereof.

In some embodiments, an exemplary encoded CAR sequence comprises, in order: a sequence of nucleotides encoding an extracellular binding domain, optionally an scFv; a spacer, optionally comprising a sequence from a human immunoglobulin hinge, optionally from IgG1, IgG2 or IgG4 or a modified version thereof, optionally further comprising a $C_H2$ region and/or a $C_H3$ region; and a transmembrane domain, optionally from human CD28; an intracellular region comprising a costimulatory signaling domain, optionally from human 4-1BB; and a primary signaling domain or region, such as an intracellular signaling region of a CD3zeta chain. In some embodiments, the encoded intracellular region of the chimeric receptor comprises, from its N to C terminus in order: the one or more costimulatory signaling domain(s) and a primary signaling domain or region, such as containing a CD3zeta chain or a fragment thereof.

1. Chimeric Antigen Receptors (CARs)

In some embodiments, the chimeric receptor encoded by the modified CD247 locus is a chimeric antigen receptor (CAR). In some embodiments, the engineered cells, such as T cells, express a chimeric receptor such as a CAR, with specificity for a particular antigen (or marker or ligand), such as an antigen expressed on the surface of a particular cell type. In some aspects, at least a portion of any of the CARs described herein, including multi-chain or regulatable CAR, is encoded in the transgene sequences. In some aspects, the transgene sequences encoding the CARs described herein or a portion thereof, can be any described in Section I.B.2. In some aspects, upon integration of the transgene sequences via HDR, the resulting modified CD247 locus contains nucleic acid sequences encoding a CAR, such as any CAR described herein, including multi-chain or regulatable CAR.

In some embodiments, the chimeric receptor, e.g., CAR, encoded by the modified CD247 locus, contains one or more of extracellular region (e.g., containing one or more extracellular binding domain(s) and/or spacers), transmembrane domain and/or intracellular region (e.g., containing a primary signaling region or domain and/or one or more costimulatory signaling domains). In some aspects, the encoded chimeric receptor further contains other domains, such as multimerization domains. In some aspects, the modified CD247 locus contains sequences encoding linkers and/or regulatory elements. In some embodiments, the encoded chimeric receptor comprises, from its N to C terminus in order: an extracellular binding domain, a transmembrane domain and an intracellular region, e.g., comprising a primary signaling region or domain or a portion thereof and/or a costimulatory signaling domain. In some embodiments, the encoded chimeric receptor comprises, from its N to C terminus in order: an extracellular binding domain, a spacer, a transmembrane domain and an intracellular region, e.g., comprising a primary signaling region or domain or a portion thereof and/or a costimulatory signaling domain.

In some embodiments, the chimeric receptor, e.g., CAR, encoded by the modified CD247 locus, contains one or more of extracellular region (e.g., containing one or more extracellular binding domain(s) and/or spacers), transmembrane domain and/or intracellular region (e.g., containing a CD3zeta (CD3ζ) chain or a fragment thereof (such as intracellular region of the CD3ζ chain) and/or one or more costimulatory signaling domains). In some embodiments, the chimeric receptor includes an intracellular region comprising a CD3zeta (CD3ζ) chain or a fragment thereof, at the C-terminus of the chimeric receptor. In some aspects, the encoded chimeric receptor further contains other domains, such as multimerization domains. In some aspects, the modified CD247 locus contains sequences encoding linkers and/or regulatory elements. In some embodiments, the encoded chimeric receptor comprises, from its N to C terminus in order: an extracellular binding domain, a spacer, a transmembrane domain and an intracellular region, e.g., comprising a CD3zeta (CD3ζ) chain or a fragment thereof.

a. Binding Domain

In some embodiments, the extracellular region of the encoded chimeric receptor comprises a binding domain. In some embodiments, the binding domain is an extracellular binding domain. In some embodiments, the binding domain is or comprises a polypeptide, a ligand, a receptor, a ligand-binding domain, a receptor-binding domain, an antigen, an epitope, an antibody, an antigen-binding domain, an epitope-binding domain, an antibody-binding domain, a tag-binding domain or a fragment of any of the foregoing. In some embodiments, the binding domain is a ligand- or antigen-binding domain In some aspects, the extracellular binding domain, such as a ligand- (e.g., antigen-) binding region or domain(s) and the intracellular region or domain(s) are linked or connected via one or more linkers and/or transmembrane domain(s). In some embodiments, the chimeric antigen receptor includes a transmembrane domain disposed between the extracellular region and the intracellular region.

In some embodiments, the antigen, e.g., an antigen that binds the binding domain of the chimeric receptor, is a polypeptide. In some embodiments, the antigen is a carbohydrate or other molecule. In some embodiments, the antigen is selectively expressed or overexpressed on cells of the disease, disorder or condition, e.g., the tumor or pathogenic cells, as compared to normal or non-targeted cells or tissues, e.g., in healthy cells or tissues. In some embodiments, the disease, disorder or condition is an infectious disease or disorder, an autoimmune disease, an inflammatory disease, or a tumor or a cancer. In some embodiments, the antigen is expressed on normal cells and/or is expressed on the engineered cells. In some aspects, the chimeric receptor, e.g., a CAR, includes one or more regions or domains selected from an extracellular ligand- (e.g., antigen-) binding or region or domains, e.g., any of the antibody or fragment described herein, and an intracellular region. In some embodiments, the ligand- (e.g., antigen-) binding region or domain is or includes an scFv or a single-domain $V_H$ antibody and the intracellular region comprises an intracellular signaling region or domain comprising a CD3-zeta (CD3ζ) chain or a fragment thereof.

Exemplary encoded chimeric receptors, including CARs, include those described, for example, in International Pat. App. Pub. Nos. WO2000/14257, WO2013/126726, WO2012/129514, WO2014/031687, WO2013/166321, WO2013/071154, WO2013/123061, U.S. Pat. App. Pub. Nos. US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European Pat. App. No. EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; and Wu et al., Cancer, 2012 Mar. 18(2): 160-75. In some aspects, the antigen receptors include a CAR as described in U.S. Pat. No. 7,446,190, and those described in International Pat. App. Pub. No. Pub. No WO 2014/055668. Examples of the CARs include CARs as disclosed in any of the aforementioned references, such as WO2014/031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177).

In some embodiments, the encoded chimeric receptor, e.g., antigen receptor contains an extracellular binding domain, such as an antigen- or ligand-binding domain that binds, e.g., specifically binds, to an antigen, a ligand and/or a marker. Among the antigen receptors are functional non-TCR antigen receptors, such as chimeric antigen receptors (CARs),In some embodiments, the antigen receptor is a CAR that contains an extracellular antigen-recognition domain that specifically binds to an antigen. In some embodiments, the CAR is constructed with a specificity for a particular antigen, marker or ligand, such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more ligand- (e.g., antigen-) binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb), or a single domain antibody (sdAb), such as sdFv, nanobody, $V_H$H and $V_{NAR}$. In some embodiments, an antigen-binding fragment comprises antibody variable regions joined by a flexible linker.

In some embodiments, the encoded CAR contains an antibody or an antigen-binding fragment (e.g. scFv) that specifically recognizes an antigen or ligand, such as an intact antigen, expressed on the surface of a cell. In some embodiments, the antigen or ligand, is a protein expressed on the surface of cells. In some embodiments, the antigen or ligand is a polypeptide. In some embodiments, it is a carbohydrate or other molecule. In some embodiments, the antigen or ligand is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic malignancy, cancers of the immune system, such as lymphomas, leukemias, and/or myelomas, such as B, T, and myeloid leukemias, lymphomas, and multiple myelomas.

In some embodiments, the antigen or ligand is a tumor antigen or cancer marker. In some embodiments, the antigen associated with the disease or disorder is or includes $\alpha v\beta 6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the antibody or an antigen-binding fragment (e.g. scFv or $V_H$ domain) specifically recognizes an antigen, such as CD19. In some embodiments, the antibody or antigen-binding fragment is derived from, or is a variant of, antibodies or antigen-binding fragment that specifically binds to CD19.

In some embodiments, the antigen is CD19. In some embodiments, the scFv contains a $V_H$ and a $V_L$ derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

In some embodiments, the scFv is derived from FMC63. FMC63 generally refers to a mouse monoclonal IgG1 antibody raised against Nalm-1 and -16 cells expressing CD19 of human origin (Ling, N. R., et al. (1987). *Leucocyte typing III.* 302). In some embodiments, the FMC63 antibody comprises a CDR-H1 and a CDR-H2 set forth in SEQ ID NOS: 38 and 39, respectively, and a CDR-H3 set forth in SEQ ID NO: 40 or 54; and a CDR-L1 set forth in SEQ ID NO: 35 and a CDR-L2 set forth in SEQ ID NO: 36 or 55 and a CDR-L3 set forth in SEQ ID NO: 37 or 56. In some embodiments, the FMC63 antibody comprises a heavy chain variable region ($V_H$) comprising the amino acid sequence of SEQ ID NO: 41 and a light chain variable region ($V_L$) comprising the amino acid sequence of SEQ ID NO: 42.

In some embodiments, the scFv comprises a variable light chain containing a CDR-L1 sequence of SEQ ID NO:35, a CDR-L2 sequence of SEQ ID NO:36, and a CDR-L3 sequence of SEQ ID NO:37 and/or a variable heavy chain containing a CDR-H1 sequence of SEQ ID NO:38, a CDR-H2 sequence of SEQ ID NO:39, and a CDR-H3 sequence of SEQ ID NO:40. In some embodiments, the scFv comprises a variable heavy chain region set forth in SEQ ID NO:41 and a variable light chain region set forth in SEQ ID NO:42. In some embodiments, the variable heavy and variable light chains are connected by a linker. In some embodiments, the linker is set forth in SEQ ID NO:58. In some embodiments, the scFv comprises, in order, a $V_H$, a linker, and a $V_L$. In some embodiments, the scFv comprises, in order, a $V_L$, a linker, and a $V_H$. In some embodiments, the scFv is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO:57. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). In some embodiments, the SJ25C1 antibody comprises a CDR-H1, a CDR-H2 and a CDR-H3 sequence set forth in SEQ ID NOS: 47-49, respectively, and a CDR-L1, a CDR-L2 and a CDR-L3 sequence set forth in SEQ ID NOS: 44-46, respectively. In some embodiments, the SJ25C1 antibody comprises a heavy chain variable region ($V_H$) comprising the amino acid sequence of SEQ ID NO: 50 and a light chain variable region ($V_L$) comprising the amino acid sequence of SEQ ID NO: 51.

In some embodiments, the scFv comprises a variable light chain containing a CDR-L1 sequence of SEQ ID NO:44, a CDR-L2 sequence of SEQ ID NO: 45, and a CDR-L3 sequence of SEQ ID NO:46 and/or a variable heavy chain containing a CDR-H1 sequence of SEQ ID NO:47, a CDR-H2 sequence of SEQ ID NO:48, and a CDR-H3 sequence of SEQ ID NO:49. In some embodiments, the scFv comprises a variable heavy chain region set forth in SEQ ID NO:50 and a variable light chain region set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the antigen is CD20. In some embodiments, the scFv contains a $V_H$ and a $V_L$ derived from an antibody or an antibody fragment specific to CD20. In some embodiments, the antibody or antibody fragment that binds CD20 is an antibody that is or is derived from Rituximab, such as is Rituximab scFv.

In some embodiments, the antigen is CD22. In some embodiments, the scFv contains a $V_H$ and a $V_L$ derived from an antibody or an antibody fragment specific to CD22. In some embodiments, the antibody or antibody fragment that binds CD22 is an antibody that is or is derived from m971, such as is m971 scFv.

In some embodiments, the antigen is BCMA. In some embodiments, the scFv contains a $V_H$ and a $V_L$ derived from an antibody or an antibody fragment specific to BCMA. In some embodiments, the antibody or antibody fragment that binds BCMA is or contains a $V_H$ and a $V_L$ from an antibody or antibody fragment set forth in International Patent Applications, Publication Number WO 2016/090327 and WO 2016/090320.

In some embodiments, the antigen is GPRC5D. In some embodiments, the scFv contains a $V_H$ and a $V_L$ derived from an antibody or an antibody fragment specific to GPRC5D. In some embodiments, the antibody or antibody fragment that binds GPRC5D is or contains a $V_H$ and a $V_L$ from an antibody or antibody fragment set forth in International Patent Applications, Publication Number WO 2016/090329 and WO 2016/090312.

In some aspects, the encoded CAR contains a ligand- (e.g., antigen-) binding domain that binds or recognizes, e.g., specifically binds, a universal tag or a universal epitope. In some aspects, the binding domain can bind a molecule, a tag, a polypeptide and/or an epitope that can be linked to a different binding molecule (e.g., antibody or antigen-binding fragment) that recognizes an antigen associated with a disease or disorder. Exemplary tag or epitope includes a dye (e.g., fluorescein isothiocyanate) or a biotin. In some aspects, a binding molecule (e.g., antibody or antigen-binding fragment) linked to a tag, that recognizes the antigen associated with a disease or disorder, e.g., tumor antigen, with an engineered cell expressing a CAR specific for the tag, to effect cytotoxicity or other effector function of the engineered cell. In some aspects, the specificity of the CAR to the antigen associated with a disease or disorder is provided by the tagged binding molecule (e.g., antibody), and different tagged binding molecule can be used to target different antigens. Exemplary CARs specific for a universal tag or a universal epitope include those described, e.g., in U.S. Pat. No. 9,233,125, WO 2016/030414, Urbanska et al., (2012) Cancer Res 72: 1844-1852, and Tamada et al., (2012) Clin Cancer Res 18:6436-6445.

In some embodiments, the encoded CAR contains a TCR-like antibody, such as an antibody or an antigen-binding fragment (e.g. scFv) that specifically recognizes an intracellular antigen, such as a tumor-associated antigen, presented on the cell surface as a major histocompatibility complex (MHC)-peptide complex. In some embodiments, an antibody or antigen-binding portion thereof that recognizes an MHC-peptide complex can be expressed on cells as part of a chimeric receptor, such as an antigen receptor. Among the antigen receptors are functional non-T cell receptor (TCR) antigen receptors, such as chimeric antigen receptors (CARs). In some embodiments, a CAR containing an antibody or antigen-binding fragment that exhibits TCR-like specificity directed against peptide-MHC complexes also may be referred to as a TCR-like CAR. In some embodiments, the CAR is a TCR-like CAR and the antigen is a processed peptide antigen, such as a peptide antigen of an intracellular protein, which, like a TCR, is recognized on the cell surface in the context of an MHC molecule. In some embodiments, the extracellular antigen-binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, Major histocompatibility complex (MHC) includes a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning a chain, in some cases with three a domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases $CD4^+$ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by known methods (see e.g. US Pat. App. Pub. Nos. US 2002/0150914; US 2003/0223994; US 2004/0191260; US 2006/0034850; US 2007/00992530; US20090226474; US20090304679; and International App. Pub. No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described herein. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US Pat. App. Pub. No. US20020150914, US20140294841; and Cohen C J. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody, $V_H$H or $V_{NAR}$) or fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. In some aspects, the CAR is a bispecific CAR, e.g., containing two antigen-binding domains with different specificities.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In some embodiments, the antibody light chain constant region is chosen from, e.g., kappa or lambda, particularly kappa.

Among the binding domains of the encoded chimeric receptors are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies (sdAb) are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known. Exemplary single-domain antibodies include sdFv, nanobody, $V_H$H or $V_{NAR}$.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the encoded chimeric antigen receptor, including TCR-like CARs, includes an extracellular portion containing an antibody or antibody fragment. In some embodiments, the antibody or fragment includes an scFv. In some aspects, the antibody or antigen-binding fragment can be obtained by screening a plurality, such as a library, of antigen-binding fragments or molecules, such as by screening an scFv library for binding to a specific antigen or ligand.

In some embodiments, the encoded CAR is a multispecific CAR, e.g., contains a plurality of ligand- (e.g., antigen-) binding domains that can bind and/or recognize, e.g., specifically bind, a plurality of different antigens. In some aspects, the encoded CAR is a bispecific CAR, for example, targeting two antigens, such as by containing two antigen-binding domains with different specificities. In some embodiments, the CAR contains a bispecific binding domain, e.g., a bispecific antibody or fragment thereof, containing at least one antigen-binding domain binding to different surface antigens on a target cell, e.g., selected from any of the listed antigens as described herein, e.g. CD19 and CD22 or CD19 and CD20. In some embodiments, binding of the bispecific binding domain to each of its epitope or antigen can result in stimulation of function, activity and/or responses of the T cell, e.g., cytotoxic activity and subsequent lysis of the target cell. Among such exemplary bispecific binding domain can include tandem scFv molecules, in some cases fused to each other via, e.g. a flexible linker; diabodies and derivatives thereof, including tandem diabodies (Holliger et al, Prot Eng 9, 299-305 (1996); Kipriyanov et al, J Mol Biol 293, 41-66 (1999)); dual affinity retargeting (DART) molecules that can include the diabody format with a C-terminal disulfide bridge; bispecific T cell engager (BiTE) molecules, which contain tandem scFv molecules fused by a flexible linker (see e.g. Nagorsen and Bauerle, Exp Cell Res 317, 1255-1260 (2011); or triomabs that include whole hybrid mouse/rat IgG molecules (Seimetz et al, Cancer Treat Rev 36, 458-467 (2010). Any of such binding domains can be contained in any of the CARs described herein.

b. Spacer and Transmembrane Domain

In some aspects, the encoded chimeric receptor, e.g., a chimeric antigen receptor (CAR), includes an extracellular portion containing one or more ligand- (e.g., antigen-) binding domains, such as an antibody or fragment thereof, and one or more intracellular signaling region or domain (also interchangeably called a cytoplasmic signaling domain or region). In some aspects, the chimeric receptor, e.g., CAR, further includes a spacer and/or a transmembrane domain or portion. In some aspects, the spacer and/or transmembrane domain can link the extracellular portion containing the ligand- (e.g., antigen-) binding domain and the intracellular signaling region(s) or domain(s).

In some embodiments, the encoded chimeric receptor such as the CAR further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the chimeric receptor further comprises a spacer and/or a hinge region. In some embodiments, the constant region or portion is of a human IgG, such as IgG4, IgG2 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. In some embodiments, the spacer is less than 250 amino acids in length, less than 200 amino acids in length, less than 150 amino acids in length, less than 100 amino acids in length, less than 75 amino acids in length, less than 50 amino acids in length, less than 25 amino acids in length, less than 20 amino acids in length, less than 15 amino acids in length, less than 12 amino acids in length, or less than 10 amino acids in length. In some embodiments, the spacer is from or from about 10 to 250 amino acids in length, 10 to 150 amino acids in length, 10 to 100 amino acids in length, 10 to 50 amino acids in length, 10 to 25 amino acids in length, 10 to 15 amino acids in length, 15 to 250 amino acids in length, 15 to 150 amino acids in length, 15 to 100 amino acids in length, 15 to 50 amino acids in length, 15 to 25 amino acids in length, 25 to 250 amino acids in length, 25 to 100 amino acids in length, 25 to 50 amino acids in length, 50 to 250 amino acids in length, 50 to 150 amino acids in length, 50 to 100 amino acids in length, 100 to 250 amino acids in length, 100 to 150 amino acids in length, or 150 to 250 amino acids in length. Exemplary spacers include IgG4 hinge alone, IgG4 hinge linked to $C_H2$ and $C_H3$ domains, or IgG4 hinge linked to the $C_H3$ domain. Exemplary spacers include, but are not limited to, those described in Hudecek et al. (2013) *Clin. Cancer Res.*, 19:3153, Hudecek et al. (2015) *Cancer Immunol Res.* 3(2): 125-135 or International Pat. App. Pub. No. WO2014031687.

In some embodiments, the spacer can be derived all or in part from IgG4 and/or IgG2. In some embodiments, the spacer can be a chimeric polypeptide containing one or more of a hinge, $C_H2$ and/or $C_H3$ sequence(s) derived from IgG4, IgG2, and/or IgG2 and IgG4. In some embodiments, the spacer can contain mutations, such as one or more single amino acid mutations in one or more domains. In some examples, the amino acid modification is a substitution of a proline (P) for a serine (S) in the hinge region of an IgG4. In some embodiments, the amino acid modification is a substitution of a glutamine (Q) for an asparagine (N) to reduce glycosylation heterogeneity, such as an N to Q substitution at a position corresponding to position 177 in the $C_H2$ region of the IgG4 heavy chain constant region sequence set forth in SEQ ID NO: 128 (Uniprot Accession No. P01861; position corresponding to position 297 by EU numbering and position 79 of the hinge-$C_H2$-$C_H3$ spacer sequence set forth in SEQ ID NO:4) or an N to Q substitution at a position corresponding to position 176 in the $C_H2$ region of the IgG2 heavy chain constant region sequence set forth in SEQ ID NO: 127 (Uniprot Accession No. P01859; position corresponding to position 297 by EU numbering).

In some aspects, the spacer contains only a hinge region of an IgG, such as only a hinge of IgG4, IgG2 or IgG1, such as the hinge only spacer set forth in SEQ ID NO:1, and is encoded by the sequence set forth in SEQ ID NO: 2. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO:3. In some embodiments, the spacer is an Ig hinge, e.g., an IgG4 hinge, linked to a $C_H3$ domain only, such as set forth in SEQ ID NO:4. In some embodiments, the spacer is or comprises a glycine-serine rich sequence or other flexible linker such as known flexible linkers. In some embodiments, the constant region or portion is of IgD. In some embodiments, the spacer has the sequence set forth in SEQ ID NO: 5. In some embodiments, the spacer has a sequence of amino acids that exhibits at least or at least about 85%, 86%, 87%, 88%, 89%, 90%, 91%, 92%, 93%, 94%, 95%, 96%, 97%, 98%, 99% or more sequence identity to any of SEQ ID NOS: 1, 3, 4 and 5.

In some aspects, the spacer is a polypeptide spacer such as one or more selected from: (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) consists or comprises the sequence of amino acids set forth in SEQ ID NOS: 1, 3-5 or 27-34, or a variant of any of the foregoing having at least 85%, 86%, 87%, 88%, 89%, 90%, 91%, 92%, 93%, 94%, 95%, 96%, 97%, 98%, 99% or more sequence identity thereto, or (e) comprises or consists of the formula $X_1PPX_2P$, where $X_1$ is glycine, cysteine or arginine and $X_2$ is cysteine or threonine.

Exemplary spacers include those containing portion(s) of an immunoglobulin constant region such as those containing an Ig hinge, such as an IgG hinge domain. In some aspects, the spacer includes an IgG hinge alone, an IgG hinge linked to one or more of a $C_H2$ and $C_H3$ domain, or IgG hinge linked to the $C_H3$ domain. In some embodiments, the IgG hinge, $C_H2$ and/or $C_H3$ can be derived all or in part from IgG4 or IgG2. In some embodiments, the spacer can be a chimeric polypeptide containing one or more of a hinge, $C_H2$ and/or $C_H3$ sequence(s) derived from IgG4, IgG2, and/or IgG2 and IgG4. In some embodiments, the hinge region comprises all or a portion of an IgG4 hinge region and/or of an IgG2 hinge region, wherein the IgG4 hinge region is optionally a human IgG4 hinge region and the IgG2 hinge region is optionally a human IgG2 hinge region; the $C_H2$ region comprises all or a portion of an IgG4 $C_H2$ region and/or of an IgG2 $C_H2$ region, wherein the IgG4 $C_H2$ region is optionally a human IgG4 $C_H2$ region and the IgG2 $C_H2$ region is optionally a human IgG2 $C_H2$ region; and/or the $C_H3$ region comprises all or a portion of an IgG4 $C_H3$ region and/or of an IgG2 $C_H3$ region, wherein the IgG4 $C_H3$ region is optionally a human IgG4 $C_H3$ region and the IgG2 $C_H3$ region is optionally a human IgG2 $C_H3$ region. In some embodiments, the hinge, $C_H2$ and $C_H3$ comprises all or a portion of each of a hinge region, $C_H2$ and $C_H3$ from IgG4. In some embodiments, the hinge region is chimeric and comprises a hinge region from human IgG4 and human IgG2; the $C_H2$ region is chimeric and comprises a $C_H2$ region from human IgG4 and human IgG2; and/or the $C_H3$ region is chimeric and comprises a $C_H3$ region from human IgG4 and human IgG2. In some embodiments, the spacer comprises an IgG4/2 chimeric hinge or a modified IgG4 hinge comprising at least one amino acid replacement compared to human IgG4 hinge region; an human IgG2/4 chimeric $C_H2$ region; and a human IgG4 $C_H3$ region.

In some embodiments, the spacer can be derived all or in part from IgG4 and/or IgG2 and can contain mutations, such as one or more single amino acid mutations in one or more domains. In some examples, the amino acid modification is a substitution of a proline (P) for a serine (S) in the hinge region of an IgG4. In some embodiments, the amino acid modification is a substitution of a glutamine (Q) for an asparagine (N) to reduce glycosylation heterogeneity, such as an N177Q mutation at position 177, in the $C_H2$ region, of the full-length IgG4 Fc sequence set forth in SEQ ID NO: 128 or an N176Q. at position 176, in the $C_H2$ region, of the full-length IgG2 Fc sequence set forth in SEQ ID NO: 127. In some embodiments, the spacer is or comprises an IgG4/2 chimeric hinge or a modified IgG4 hinge; an IgG2/4 chimeric $C_H2$ region; and an IgG4 $C_H3$ region and optionally is about 228 amino acids in length; or a spacer set forth in SEQ ID NO: 129. In some embodiments, the ligand- (e.g., antigen-) binding or recognition domain of the CAR is linked to an intracellular region, e.g., containing one or more intracellular signaling components, such as an intracellular signaling region or domain, and/or signaling components that mimic activation through an antigen receptor complex, such as a TCR complex, and/or signal via another cell surface receptor. Thus, in some embodiments, the extracellular region, e.g., containing a binding domain such as an antigen binding component (e.g., antibody), is linked to one or more transmembrane and intracellular region(s) or domain(s). In some embodiments, the transmembrane domain is fused to the extracellular region. In some embodiments, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e., comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 (4-1BB), or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28 or a variant thereof. The extracellular region and transmembrane can be linked directly or indirectly. In some embodiments, the extracellular region and transmembrane are linked by a spacer, such as any described herein.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 8 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO:8; in some embodiments, the transmembrane-domain containing portion of the chimeric receptor comprises the sequence of amino acids set forth in SEQ ID NO: 9 or a sequence of amino acids having at least or at least about 85%, 86%, 87%, 88%, 89%, 90%, 91%, 92%, 93%, 94%, 95%, 96%, 97%, 98%, 99% or more sequence identity thereto.

c. Intracellular Region

In some aspects, the chimeric receptor, e.g., CAR, encoded in the modified CD247 locus, includes an intracellular region (also called cytoplasmic region) that comprises a signaling region or domain. In some embodiments, the intracellular region comprises an intracellular signaling region or domain. In some embodiments, the intracellular signaling region or domain is or comprises a primary signaling region, a signaling domain that is capable of stimulating and/or inducing a primary activation signal in a T cell, a signaling domain of a T cell receptor (TCR) component (e.g. an intracellular signaling domain or region of a CD3-zeta (CD3ζ) chain or a functional variant or signaling portion thereof), and/or a signaling domain comprising an immunoreceptor tyrosine-based activation motif (ITAM).

In some embodiments, the chimeric receptor, e.g., CAR, includes at least one intracellular signaling component or components, such as an intracellular signaling region or domain Among the intracellular signaling region are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

In some embodiments, upon ligation of the CAR, the cytoplasmic (or intracellular) domain or regions, e.g., intracellular signaling region, of the CAR stimulates and/or activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling region or domain of an antigen receptor component or costimulatory molecule is used in place of an intact immunostimulatory chain, for example, if it transduces the effector function signal. In some embodiments, the intracellular signaling regions, e.g., comprising intracellular domain or domains, include the cytoplasmic sequences of a T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability. In some embodiments, the intracellular signaling regions, e.g., comprising intracellular domain or domains, include the cytoplasmic sequences of a region or domain that is involved in providing costimulatory signal.

(i) Costimulatory Signaling Domain

In some embodiments, to promote full stimulation and/or activation, one or more components for generating secondary or costimulatory signal is included in the encoded CAR. In other embodiments, the encoded CAR does not include a component for generating a costimulatory signal. In some aspects, an additional receptor polypeptide or portion thereof is expressed in the same cell and provides the component for generating the secondary or costimulatory signal.

In some embodiments, the encoded CAR includes a signaling region and/or transmembrane portion of a costimulatory receptor, such as CD28, 4-1BB, OX40 (CD134), CD27, DAP10, DAP12, ICOS and/or other costimulatory receptors. In some aspects, the same CAR includes both the primary cytoplasmic signaling region and costimulatory signaling components.

In some embodiments, one or more different chimeric receptors can contain one or more different intracellular signaling region(s) or domain(s). In some embodiments, the primary cytoplasmic signaling region is included within one encoded CAR, whereas the costimulatory component is provided by another receptor, e.g., another CAR recognizing another antigen. In some embodiments, the encoded CARs include activating or stimulatory CARs, and costimulatory CARs, both expressed on the same cell (see WO2014/055668).

In certain embodiments, the intracellular signaling region comprises a CD28 transmembrane and signaling domain linked to a CD3 (e.g., CD3ζ) intracellular region or domain. In some embodiments, the intracellular region comprises a chimeric CD28 and CD137 (4-1BB, TNFRSF9) co-stimulatory domains, linked to a CD3ζ intracellular region or domain.

In some embodiments, the encoded CAR encompasses one or more, e.g., two or more, costimulatory domains and primary cytoplasmic signaling region, in the cytoplasmic portion. Exemplary CARs include intracellular components, such as intracellular signaling region(s) or domain(s), of CD3-zeta, CD28, CD137 (4-1BB), OX40 (CD134), CD27, DAP10, DAP12, NKG2D and/or ICOS. In some embodiments, the chimeric antigen receptor contains an intracellular signaling region or domain of a T cell costimulatory molecule, e.g., from CD28, CD137 (4-1BB), OX40 (CD134), CD27, DAP10, DAP12, NKG2D and/or ICOS, in some cases, between the transmembrane domain and intracellular signaling region or domain. In some aspects, the T cell costimulatory molecule is one or more of CD28, CD137 (4-1BB), OX40 (CD134), CD27, DAP10, DAP12, NKG2D and/or ICOS. In some embodiments, the costimulatory molecule is a human costimulatory molecule.

In some embodiments, the intracellular signaling region or domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular region comprises an intracellular costimulatory signaling domain or region of CD137(4-1BB) or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 12.

In some cases, the encoded CARs are referred to as first, second, third or fourth generation CARs. In some aspects, a first generation CAR is one that solely provides a primary stimulation or activation signal, e.g., via CD3-chain induced signal upon antigen binding; in some aspects, a second-generation CAR is one that provides such a signal and costimulatory signal, such as one including an intracellular signaling region(s) or domain(s) from one or more costimulatory receptor such as CD28, CD137 (4-1BB), OX40 (CD134), CD27, DAP10, DAP12, NKG2D, ICOS and/or other costimulatory receptors; in some aspects, a third generation CAR is one that includes multiple costimulatory domains of different costimulatory receptors, e.g., selected from CD28, CD137 (4-1BB), OX40 (CD134), CD27, DAP10, DAP12, NKG2D, ICOS and/or other costimulatory receptors; in some aspects, a fourth generation CAR is one that includes three or more costimulatory domains of different costimulatory receptors, e.g., selected from CD28, CD137 (4-1BB), OX40 (CD134), CD27, DAP10, DAP12, NKG2D, ICOS and/or other costimulatory receptors.

(ii) CD3ζ Chain

In some embodiments, the encoded chimeric receptor includes an intracellular component of a TCR complex, such as a TCR CD3ζ chain that mediates T-cell activation and cytotoxicity, e.g., CD3 zeta chain. Thus, in some aspects, the antigen-binding or antigen-recognition domain is linked to one or more cell signaling modules. In some embodiments, cell signaling modules include CD3 transmembrane domain, CD3 intracellular signaling domains, and/or other CD transmembrane domains. In some embodiments, the encoded chimeric receptor, e.g., CAR, further includes a portion of one or more additional molecules such as Fc receptor gamma (FcRγ), CD8 alpha, CD8 beta, CD4, CD25 or CD16. For example, in some aspects, the CAR includes a chimeric molecule between CD3 zeta (CD3ζ) and one or more of CD8 alpha, CD8 beta, CD4, CD25 or CD16.

In the context of a natural TCR, full stimulation generally requires not only signaling through the TCR, but also a costimulatory signal. T cell stimulation is in some aspects can be mediated by two classes of cytoplasmic signaling sequences: those that initiate antigen-dependent primary activation through the TCR (primary cytoplasmic signaling region(s) or domain(s)), and those that act in an antigen-independent manner to provide a secondary or co-stimulatory signal (secondary cytoplasmic signaling region(s) or domain(s)). In some aspects, the CAR includes one or both of such signaling components.

In some aspects, the encoded CAR includes an intracellular region comprising a primary cytoplasmic signaling region that regulates primary stimulation and/or activation of the TCR complex. In some embodiments, the encoded chimeric receptor includes an intracellular region that comprises a CD3ζ signaling domain, such as the entire or full CD3ζ signaling domain, for example, that is capable of signaling or signal transduction that mediates the T cell activation and/or cytotoxicity, upon engagement of the chimeric receptor. In some aspects, at least a fragment of the primary cytoplasmic signaling region, e.g., containing a CD3ζ chain or a fragment thereof, such as an intracellular signaling domain of CD3, or optionally the entire CD3ζ signaling domain, of the encoded chimeric receptor is encoded by the open reading frame of the endogenous CD247 locus or a partial sequence thereof. Primary cytoplasmic signaling region(s) that act in a stimulatory manner may contain signaling motifs which are known as immunoreceptor tyrosine-based activation motifs or ITAMs, e.g., derived from CD3 zeta (CD3ζ). In some embodiments, the CAR contain(s) a cytoplasmic signaling domain, fragment or portion thereof, or sequence derived from CD3. In some embodiments, the intracellular (or cytoplasmic) signaling region comprises a human CD3 zeta chain or a fragment or portion thereof, including the intracellular or cytoplasmic stimulatory signaling domain of CD3ζ or functional variant thereof, such as an 112 AA cytoplasmic domain of isoform 3 of human CD3ζ (Accession No.: P20963.2) or a CD3ζ signaling domain as described in U.S. Pat. Nos. 7,446,190 or 8,911,993. In some embodiments, the intracellular region of the encoded chimeric receptor comprises the sequence of amino acids set forth in SEQ ID NO: 13, 14 or 15 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 13, 14 or 15 or a partial sequence thereof. In some embodiments, exemplary CD3ζ chain or a fragment thereof encoded by the gene fusion of the transgene and endogenous sequences of the CD247 locus include the ITAM domains of the CD3ζ chain, e.g., amino acid residues 61-89, 100-128 or 131-159 of the human CD3ζ chain precursor sequence set forth in SEQ ID NO:73 or a sequence of amino acids that containing one or more ITAM domains from the CD3ζ chain and exhibits at least or at least about 85%, 86%, 87%, 88%, 89%, 90%, 91%, 92%, 93%, 94%, 95%, 96%, 97%, 98%, 99% or more sequence identity to SEQ ID NO: 73.

In some embodiments, the cell is engineered to express one or more additional molecules (e.g., polypeptides, such as an additional chimeric receptor polypeptides or portion thereof) are used to regulate, control, or modulate function and/or activity of the encoded CAR. Exemplary multi-chain chimeric receptors, such as multi-chain CARs, and are described herein, for example, in Section III.B.2.

In some embodiments, the encoded CAR contains an antibody, e.g., an antibody fragment, a transmembrane domain that is or contains a transmembrane portion of CD28 or a functional variant thereof, and an intracellular signaling region containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer. In some embodiments, the chimeric receptor comprises a CD3 zeta (CD3ζ) at the C-terminus of the receptor.

2. Multi-Chain CARs

In some embodiments, the chimeric receptor encoded by the nucleic acid sequences of the modified CD247 locus can be a multi-chain CAR. In some embodiments, if the multi-chain CAR comprising two or more polypeptide chains is expressed in the cell, at least one of the polypeptide chains include a CD3zeta (CD3ζ) chain or a fragment or portion thereof and encoded by the modified CD247 locus. In some aspects, the polynucleotide used to introduce nucleic acid sequences encoding one or more chains of the multi-chain CAR can include any described in Section I.B herein. In some aspects, a polynucleotide, e.g., template polynucleotide, contains transgene sequences encoding at least one chain of the multi-chain CAR or a portion thereof, such as at least a portion of at least one polypeptide of a multi-chain CAR that contains a CD3zeta (CD3ζ) chain or a fragment or portion thereof. In some aspects, the transgene sequence also includes sequences encoding a different or additional polypeptide, e.g., the other or additional chain of the multi-chain CAR, or additional molecules, such as those described in Section I.B.2.(vi) herein. In some aspects, an additional polynucleotide, e.g., an additional template polynucleotide, can be introduced, that encodes additional components of the multi-chain CAR. In some aspects, the additional polynucleotide can be any polynucleotide described herein, e.g., in Section I.B.2, or a modified form thereof, such as one comprising different homology arms for targeting the nucleic acid for integration at a distinct genomic locus.

In some embodiments, the provided engineered cells include cells that express multi-chain receptors, such as multi-chain CARs In some embodiments, exemplary multi-chain CARs can contain two or more genetically engineered receptors on the cell, which together can comprise a functional chimeric receptor. In some aspects, the various polypeptide chains in combination can perform functions or activities of a CAR, and/or regulate, control, or modulate function and/or activity of the CAR. In some aspects, a multi-chain CAR can contain two or more polypeptide chains, each recognizing the same of a different antigen and typically each including different regions or domains, such as a different intracellular signaling component. In some aspects, the intracellular signaling component of at least one of the genetically engineered receptor includes a CD3zeta (CD3ζ) chain or a fragment or portion thereof. In some aspects, the modified CD247 locus can include nucleic acid sequences encoding at least one chain of the multi-chain receptor, such as the receptor polypeptide that contains a CD3zeta (CD3ζ) chain or a fragment or portion thereof.

In some embodiments, the chimeric receptor is multi-chain CAR or a dual-chain CAR, that comprises two or more polypeptide chains. In some embodiments, the multi-chain receptor is a regulatable CAR, a conditionally active CAR or an inducible CAR. In some aspects, two or more polypeptides of the chimeric receptor, such as a dual-chain CAR, allows spatial or temporal regulation or control of specificity, activity, antigen (or ligand) binding, function and/or expression of the chimeric receptors. In some of such embodiments, the chimeric receptor encoded by the nucleic acid sequences at the modified CD247 locus can include one or more chains of the dual-chain or multi-chain receptors. In some aspects, in cases where only one of the dual-chain CAR is encoded by the modified CD247 locus, the other chain can be encoded by a separate nucleic acid molecule that is integrated at a different genomic location or is episomal.

In some embodiments, the multi-chain CARs can include combinations of activating and costimulatory CARs. For example, in some embodiments, the multi-chain CAR can include two polypeptides encoding CARs targeting two different antigens present individually on non-target cells, e.g., normal cells, but present together only on cells of the disease or condition to be treated. In some embodiments, the multi-chain CARs can include an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat. In some aspects, multi-chain CARs can include one or more polypeptides encoding CARs that are capable of being regulated, modulated or controlled.

In some embodiments, the multi-chain CAR includes one or more polypeptide chains encode one or more domains or regions of a CAR. In some aspects, various polypeptide chains in combination can comprise a CAR. In some embodiments, one or more additional domains or regions are present in the CAR. In some embodiments, various domains or regions present in one or more polypeptide chains of the multi-chain CAR are used to regulate, control, or modulate function and/or activity of the CAR. In some embodiments, the engineered cells express two or more polypeptide chains that contain different components, domains or regions. In some aspects, two or more polypeptide chains allows spatial or temporal regulation or control of specificity, activity, antigen (or ligand) binding, function and/or expression of the chimeric receptors. In some embodiments of the multi-chain CAR including more than one polypeptides, e.g., 2 or more polypeptides, the nucleic acid sequence encoding at least one polypeptide, such as the nucleic acid sequence encoding the polypeptide chain that contains a CD3 zeta (CD3ζ) in the intracellular region, e.g., at the C-terminus of the receptor, is targeted for integration at the endogenous CD247 locus. In some embodiments, the nucleic acid sequence encoding an additional molecule or polypeptide, e.g., additional polypeptide chain of the multi-chain CAR or an additional molecule, can be targeted at the same locus, e.g. by virtue of placement on the same polynucleotide used for targeting. In some nucleic acid sequence encoding an additional molecule or polypeptide is targeted at a different locus or is delivered by different methods.

In some aspects, one or more polypeptide chain encoding domains or regions of a CAR can target one or more antigens or molecules. Exemplary multi-chain CARs or other multi-targeting strategies include those described in, for example, in International Pat. App. Pub. No. WO 2014055668 or Fedorov et al., Sci. Transl. Medicine, Sci Transl Med. (2013) 5(215):215ra172; Sadelain, Curr Opin Immunol. (2016) 41: 68-76; Wang et al. (2017) Front. Immunol. 8:1934; Mirzaei et al. (2017) Front. Immunol. 8:1850; Marin-Acevedo et al. (2018) Journal of Hematology & Oncology 11:8; Fesnak et al. (2016) Nat Rev Cancer. 16(9): 566-581; and Abate-Daga and Davila, (2016) Molecular Therapy-Oncolytics 3, 16014.

In some embodiments, the engineered cells can express a first polypeptide chain of the chimeric receptor, e.g., CAR, which is capable of inducing an activating or stimulating signal to the cell, generally upon specific binding to the antigen recognized by the first polypeptide chain, e.g., the first antigen. In some embodiments, the cell can further express a second polypeptide chain of the chimeric receptor, e.g., CAR, in some cases called a chimeric costimulatory receptor, which is capable of inducing a costimulatory signal to the immune cell, generally upon specific binding to a second antigen recognized by the second polypeptide chain. In some embodiments, the first antigen and second antigen are the same. In some embodiments, the first antigen and second antigen are different.

In some embodiments, the first and/or second polypeptide chain is capable of inducing an activating or stimulating signal to the cell. In some embodiments, the receptor includes an intracellular signaling component containing ITAM or ITAM-like motifs. In some embodiments, the activation induced by the first polypeptide chain involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g., CD4 or CD8, etc.), activation of one or more transcription factors, such as NF-κB and/or AP-1, and/or induction of gene expression of factors such as cytokines, proliferation, and/or survival. In some embodiments, the activating domain is included within at least one of the multi-chain CAR, such as the polypeptide chain that is encoded by the modified CD247 locus, whereas the costimulatory component is provided by another polypeptide recognizing another antigen. In some embodiments, the engineered cells can include multi-chain CARs, including activating or stimulatory CARs, costimulatory CARs, both expressed on the same cell (see WO2014/055668). In some aspects, the cells express one or more stimulatory or activating CAR (such as those encoded by the modified CD247 locus as described herein, e.g., in Section III.A) and/or a costimulatory CAR.

In some embodiments, the first and/or second polypeptide chain, includes intracellular signaling regions or domains of costimulatory receptors such as CD28, CD137 (4-1BB), OX40 (CD134), CD27, DAP10, DAP12, NKG2D, ICOS and/or other costimulatory receptors. In some embodiments, the first and second polypeptide chains can contain intracellular signaling domain(s) of a costimulatory receptor that are different. In one embodiment, the first polypeptide chain contains a CD28 costimulatory signaling domain and the second polypeptide chain contain a 4-1BB co-stimulatory signaling region or vice versa.

In some embodiments, the first and/or second polypeptide chain includes both an intracellular signaling domain containing ITAM or ITAM-like motifs, such as those from a CD3zeta (CD3ζ) chain or a fragment or portion thereof, such as the CD3ζ intracellular signaling domain and an intracellular signaling domain of a costimulatory receptor. In some embodiments, the first polypeptide chain contains an intracellular signaling domain containing ITAM or ITAM-like motifs and the second polypeptide chain contains an intracellular signaling domain of a costimulatory receptor. The costimulatory signal in combination with the activating or stimulating signal induced in the same cell is one that results in an immune response, such as a robust and sustained immune response, such as increased gene expression, secretion of cytokines and other factors, and T cell mediated effector functions such as cell killing.

In some embodiments, neither ligation of the first polypeptide chain alone nor ligation of the second polypeptide chain alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the multiple polypeptide chains are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, one or more chain of the multi-chain CAR can include inhibitory CARs (iCARs, see Fedorov et al., *Sci. Transl. Medicine,* 5(215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects. In some embodiments, the inhibitory CAR can be encoded by the same polynucleotide as the stimulating or activating CAR (e.g., containing a CD3zeta (CD3ζ) chain or a fragment or portion thereof, such as the polynucleotide integrated at the CD247 locus), or by a different polynucleotide.

In some embodiments, the two polypeptide chains of the multi-chain CAR induce, respectively, an activating and an inhibitory signal to the cell, such that ligation of one polypeptide chain to its antigen activates the cell or induces a response, but ligation of the second polypeptide chain, e.g., an inhibitory receptor, to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, an additional receptor polypeptide expressed in the cell further includes an inhibitory CAR (e.g.

iCAR) and includes intracellular components that dampen or suppress an immune response, such as an ITAM- and/or co-stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In some embodiments, a multi-chain CAR can be employed where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific polypeptides, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

In some embodiments, one of the first and/or second polypeptide chains can regulate the expression, antigen binding and/or activity of the other polypeptide chain.

In some aspects, a two polypeptide chain system can be used to regulate the expression of at least one of the polypeptide chains. In some embodiments, the first polypeptide chain contains a first ligand- (e.g., antigen-) binding domain linked to a regulatory molecule, such as a transcription factor, linked via a regulatable cleavage element. In some aspects, the regulatable cleavage element is derived from a modified Notch receptor (e.g., synNotch), which is capable of cleaving and releasing an intracellular domain upon engagement of the first ligand- (e.g., antigen-) binding domain. In some aspects, the second polypeptide chain contains a second ligand- (e.g., antigen-) binding domain linked to an intracellular signaling component capable of inducing an activating or stimulating signal to the cell, such as an ITAM-containing intracellular signaling domain. In some aspects, the nucleic acid sequence encoding the second polypeptide chain is operably linked to transcriptional regulatory elements, e.g., promoter, that is capable of being regulated by a particular transcription factor, e.g., transcription factor encoded by the first polypeptide chain. In some aspects, engagement of a ligand or an antigen to the first ligand- (e.g., antigen-) binding domain leads to proteolytic release of the transcription factor, which in turn can induce the expression of the second polypeptide chain (see Roybal et al. (2016) Cell 164:770-779; Morsut et al. (2016) Cell 164:780-791). In some embodiments, the first antigen and second antigen are different.

In some instances, the chimeric receptor, e.g., CAR, is capable of being regulated, controlled, induced or inhibited, can be desirable to optimize the safety and efficacy of a therapy with the chimeric receptor. In some embodiments, the multi-chain CAR is a regulatable CAR. In some aspects, provided herein is an engineered cell comprising a CAR that is capable of being regulated. A chimeric receptor that is capable of being regulated, also referred to herein as a "regulatable chimeric receptor," or a "regulatable CAR" refers to multiple polypeptides, such as a set of at least two polypeptide chains, which when expressed in an engineered cell (e.g., engineered T cell), provides the engineered cell with the ability to generate an intracellular signal under the control of an inducer.

In some embodiments, the polypeptides of the regulatable CAR contain multimerization domains that are capable of multimerization with another multimerization domain. In some embodiments, the multimerization domain is capable of multimerization upon binding to an inducer. For example, the multimerization domain can bind an inducer, such as a chemical inducer, which results in multimerization of the polypeptides of the regulatable CAR by virtue of multimerization of the multimerization domain, thereby producing the regulatable CAR.

In some embodiments, one polypeptide of the regulatable CAR comprises a ligand- (e.g., antigen-) binding domain and a different polypeptide of the regulatable CAR comprises an intracellular signaling region, wherein multimerization of the two polypeptides by virtue of multimerization of the multimerization domain produces a regulatable CAR comprising a ligand-binding domain and an intracellular signaling region. In some embodiments, multimerization can induce, modulate, activate, mediate and/or promote signals in the engineered cell containing the regulatable CAR. In some embodiments, an inducer binds to a multimerization domain at least one polypeptide of a regulatable CAR and induces a conformational change of the regulatable CAR, wherein the conformational change activates signaling. In some embodiments, binding of a ligand to such chimeric receptors induces conformational changes in the polypeptide chain, including, in some cases, polypeptide chain oligomerization, which can render the receptors competent for intracellular signaling.

In some embodiments, an inducer functions to couple or multimerize (e.g., dimerize) a set of at least two polypeptide chains of a regulatable CAR expressed in an engineered cell in order: for the regulatable CAR to produce a desired intracellular signal such as during interaction of the regulatable CAR with a target antigen. Coupling or multimerization of at least two polypeptides of a regulatable CAR by an inducer is achieved upon binding of an inducer to a multimerization domain. For example, in some embodiments, a first polypeptide and a second polypeptide in an engineered cell may each comprise a multimerization domain capable of binding an inducer. Upon binding of the multimerization domain by the inducer, the first polypeptide and the second polypeptide are coupled together to produce the desired intracellular signal. In some embodiments, a multimerization domain is located on an intracellular portion of a polypeptide. In some embodiments, a multimerization domain is located on an extracellular portion of a polypeptide.

In some embodiments, a set of at least two polypeptides of a regulatable CAR comprises two, three, four, or five or more polypeptides. In some embodiments, the set of at least two polypeptides are the same polypeptides, for example, two, three, or more of the same polypeptides comprising an intracellular signaling region, and a multimerization domain. In some embodiments, the set of at least two polypeptides are different polypeptides, for example, a first polypeptide comprising an ligand- (e.g., antigen-) binding domain and a multimerization domain and a second polypeptide comprising an intracellular signaling region and a multimerization domain. In some embodiments, the intercellular signal is generated in the presence of an inducer. In some embodiments, the intracellular signal is generated in the absence of an inducer, e.g., an inducer interferes with multimerization of at least two polypeptides of a regulatable CAR thereby preventing intracellular signaling by the regulatable CAR.

In some embodiments, the multi-chain CAR, the nucleic acid sequence encoding at least one of the polypeptide chains, is integrated into the endogenous CD247 locus, e.g., by HDR. In some embodiments of the chimeric receptor, e.g., multi-chain CAR, the nucleic acid sequence encoding the chimeric receptor polypeptide chain that contains a CD3zeta (CD3ζ) chain or a fragment thereof, in some cases, at the C-terminus, is integrated into the endogenous CD247 locus, e.g., by HDR. In some embodiments, the nucleic acid sequences encoding the other of the two or more chimeric receptor polypeptide chains, e.g., ones that do not contain a CD3zeta (CD3ζ) chain or a fragment thereof, can be targeted within the same locus (e.g., within the same transgene sequence, typically placed 5' of the nucleic acid sequence encoding the chimeric receptor polypeptide chain that contains a CD3zeta (CD3ζ) chain or a fragment thereof), or at a different locus. In some aspects, the introduction of the nucleic acid sequences encoding the other of the two or more separate chimeric receptors, e.g., ones that do not contain a CD3zeta (CD3ζ) chain or a fragment thereof may be via different delivery methods, e.g., by transient delivery methods or as an episomal nucleic acid molecule.

In some embodiments, one or more of the polypeptide chains of a multi-chain CAR, can include a multimerization domain. In some embodiments, one or more of the receptor polypeptides, such as a portion of the chimeric receptor polypeptides provided, can include a multimerization domain. In some embodiments, the multimerization domain can multimerize (e.g., dimerize), upon binding of an inducer. An inducer contemplated herein includes, but is not limited to, a chemical inducer or a protein (e.g., a caspase). In some embodiments, the inducer is selected from an estrogen, a glucocorticoid, a vitamin D, a steroid, a tetracycline, a cyclosporine, Rapamycin, Coumermycin, Gibberellin, FK1012, FK506, FKCsA, rimiducid or HaXS, or analogs or derivatives thereof. In some embodiments, the inducer is AP20187 or an AP20187 analog, such as, AP1510.

In some embodiments, the multimerization domain can multimerize (e.g., dimerize), upon binding of an inducer such as an inducer provided herein. In some embodiments, the multimerization domain can be from an FKBP, a cyclophilin receptor, a steroid receptor, a tetracycline receptor, an estrogen receptor, a glucocorticoid receptor, a vitamin D receptor, Calcineurin A, CyP-Fas, FRB domain of mTOR, GyrB, GAI, GID1, Snap-tag and/or HaloTag, or portions or derivatives thereof. In some embodiments, the multimerization domain is an FK506 binding protein (FKBP) or derivative thereof, or fragment and/or multimer thereof, such as FKBP12v36. In some embodiments, FKBP comprises the amino acid sequence GVQVETISPGDGRTFPKRGQTCVVHYTGMLEDGKKMDSSRDRNKPFKFMLGKQEVIRGWEEG VAQMSVGQRAKLTISPDYAYGATGHPGIIPPHATLVFDVELLKLE (SEQ ID NO:82). In some embodiments, FKBP12v36 comprises the amino acid sequence GVQVETISPGDGRTFPKRGQTCVVHYTGMLEDGKKVDSSRDRNKPFKFMLGKQEVIRGWEEGV AQMSVGQRAKLTISPDYAYGATGHPGIIPPHATLVFDVELLKLE (SEQ ID NO:83).

Exemplary inducers and corresponding multimerization domains are known, e.g., as described in U.S. Pat. App. Pub. No. 2016/0046700, Clackson et al. (1998) Proc Natl Acad Sci USA. 95(18):10437-42; Spencer et al. (1993) Science 262(5136):1019-24; Farrar et al. (1996) Nature 383 (6596): 178-81; Miyamoto et al. (2012) Nature Chemical Biology 8(5): 465-70; Erhart et al. (2013) Chemistry and Biology 20(4): 549-57). In some embodiments, the inducer is rimiducid (also known as AP1903; CAS Index Name: 2-Piperidinecarboxylic acid, 1-[(2S)-1-oxo-2-(3,4,5-trimethoxyphenyl)butyl]-, 1,2-ethanediylbis [imino (2-oxo-2, 1-ethanediyl)oxy-3,1-phenylene[(1R)-3-(3,4-Dimethoxyphenyl)propylidene]]ester, [2S-[1(R*),2R*[S*[S*[1(R*), 2R]]]]]-(9Cl); CAS Registry Number: 195514-63-7; Molecular Formula: $C_{78}H_{98}N_4O_{20}$; Molecular Weight: 1411.65), and the multimerization domain is an FK506 binding protein (FKBP).

In some embodiments, the cell membrane of the engineered cell is impermeable to the inducer. In some embodiments, the cell membrane of the engineered cell is permeable to the inducer.

In some embodiments, the regulatable CAR are not part of a multimer or a dimer in the absence of the inducer. Upon the binding of the inducer, the multimerization domains can multimerize, e.g., dimerize. In some aspects, multimerization of the multimerization domain results in multimerization of a polypeptide of the regulatable CAR with another polypeptide of the regulatable CAR, e.g. multimeric complex of at least two polypeptides of the regulatable CARs. In some embodiments, multimerization of the multimerization domain can induce, modulate, activate, mediate and/or promote signal transduction by virtue of inducing physical proximity of signaling components or formation of the multimer or dimer. In some embodiments, upon the binding of an inducer, multimerization of the multimerization domain also induces multimerization of signaling domains linked, directly or indirectly, to the multimerization domain. In some embodiments, the multimerization induces, modulates, activates, mediates and/or promotes signaling through the signaling domain or region. In some embodiments, the signaling domain or region linked to the multimerization domain is an intracellular signaling region.

In some embodiments, the multimerization domain is intracellular or is associated with the cell membrane on the intracellular or cytoplasmic side of the engineered cell (e.g., engineered T cell). In some aspects, the intracellular multimerization domain is linked, directly or indirectly, to a membrane association domain (e.g., a lipid linking domain), such as a myristoylation domain, palmitoylation domain, prenylation domain, or a transmembrane domain. In some embodiments, the multimerization domain is intracellular, and is linked to the extracellular ligand- (e.g., antigen-) binding domain via a transmembrane domain. In some embodiments, the intracellular multimerization domain is linked, directly or indirectly, to the intracellular signaling region. In some aspects, induced multimerization of the multimerization domain also brings the intracellular signaling regions in proximity with one another, to allow multimerization, e.g., dimerization, and stimulate intracellular signaling. In some embodiments, a polypeptide of the regulatable CAR comprises a transmembrane domain, one or more intracellular signaling region(s), and one or more multimerization domain(s), each of which are linked directly or indirectly.

In some embodiments, the multimerization domain is extracellular or is associated with the cell membrane on the extracellular side of the engineered cell (e.g., engineered T cell). In some aspects, the extracellular multimerization domain is linked, directly or indirectly, to a membrane association domain (e.g., a lipid linking domain), such as a myristoylation domain, palmitoylation domain, prenylation domain, or a transmembrane domain. In some embodiments, the extracellular multimerization domain is linked, directly or indirectly, to a ligand-binding domain, e.g., an antigen-binding domain such as for binding to an antigen associated with a disease. In some embodiments, the multimerization domain is extracellular, and is linked to an intracellular signaling region via a transmembrane domain.

In some aspects, the membrane association domain is a transmembrane domain of an existing transmembrane protein. In some examples, the membrane association domain is any of the transmembrane domains described herein. In some aspects, the membrane association domain contains protein-protein interaction motifs or transmembrane sequences.

In some aspects, the membrane association domain is an acylation domain, such as a myristoylation domain, palmitoylation domain, prenylation domain (i.e., farnesylation, geranyl-geranylation, CAAX Box). For example, the membrane association domain can be an acylation sequence motif present in N-terminus or C-terminus of a protein. Such domains contain particular sequence motifs that can be recognized by acyltransferases that transfer acyl moieties to the polypeptide that contains the domain. For example, the acylation motifs can be modified with a single acyl moiety (in some cases, followed by several positively charged residues (e.g. human c-Src: MGSNKSKPKDASQRRR (SEQ ID NO:84) to improve association with anionic lipid head groups). In other aspects, the acetylation motif is capable of being modified with multiple acyl moieties. For example, dual acylation regions are located within the N-terminal regions of certain protein kinases, such as a subset of Src family members (e.g., Yes, Fyn, Lck) and G-protein alpha subunits. Exemplary dual acylation regions contain the sequence motif Met-Gly-Cys-Xaa-Cys, (SEQ ID NO:85) where the Met is cleaved, the Gly is N-acylated and one of the Cys residues is S-acylated. The Gly often is myristoylated and a Cys can be palmitoylated.

Other exemplary acylation regions include sequence motif Cys-Ala-Ala-Xaa (so called "CAAX boxes"; SEQ ID NO:86) that can modified with C15 or O10 isoprenyl moieties, and are known (see, e.g., Gauthier-Campbell et al. (2004) Molecular Biology of the Cell 15:2205-2217; Glabati et al. (1994) Biochem. J. 303: 697-700 and Zlakine et al. (1997) J. Cell Science 110:673-679; ten Klooster et al. (2007) Biology of the Cell 99:1-12; Vincent et al. (2003) Nature Biotechnology 21:936-40). In some embodiments, the acyl moiety is a C1-C20 alkyl, C2-C20 alkenyl, C2-C20 alkynyl, C3-C6 cycloalkyl, C1-C4 haloalkyl, C4-C12 cycloalkylalkyl, aryl, substituted aryl, or aryl (C1-C4) alkyl. In some embodiments, the acyl-containing moiety is a fatty acid, and examples of fatty acid moieties are propyl (C3), butyl (C4), pentyl (C5), hexyl (C6), heptyl (C7), octyl (C8), nonyl (C9), decyl (C10), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturated bonds (i.e., double bonds). In some examples, the acyl moiety is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphingosine, ceramide, ganglioside, cerebroside), or modified versions thereof. In certain embodiments, one, two, three, four or five or more acyl moieties are linked to a membrane association domain.

In some aspects, the membrane association domain is a domain that promotes an addition of a glycolipid (also known as glycosyl phosphatidylinositols or GPIs). In some aspects, a GPI molecule is post-translationally attached to a protein target by a transamidation reaction, which results in the cleavage of a carboxy-terminal GPI signal sequence (see, e.g., White et al. (2000) J. Cell Sci. 113:721) and the simultaneous transfer of the already synthesized GPI anchor molecule to the newly formed carboxy-terminal amino acid (See, e.g., Varki A, et al., editors. Essentials of Glycobiology. Cold Spring Harbor (N.Y.): Cold Spring Harbor Laboratory Press; 1999. Chapter 10, Glycophospholipid Anchors. Available from: ncbi nlm nih.gov/books/NBK20711/). In certain embodiments, the membrane association domain is a GPI signal sequence.

In some embodiments, a multimerization domain as provided herein is linked to an intracellular signaling regions, e.g., a primary signaling region and/or costimulatory signaling domains. In some embodiments, the multimerization domain is extracellular, and is linked to the intracellular signaling region via a transmembrane domain. In some embodiments, the multimerization domain is intracellular, and is linked to the ligand- (e.g., antigen-) binding domain via a transmembrane domain. The ligand-binding domain and transmembrane domain can be linked directly or indirectly. In some embodiments, the ligand-binding domain and transmembrane are linked by a spacer, such as any described herein. In some embodiments, the multimerization domain is an FK506 binding protein (FKBP) or derivative or fragment thereof, such as FKBP12v36. In some examples, upon the introduction of an inducer, such as a rimiducid, the polypeptides of the regulatable CAR multimerize, e.g., dimerize, thereby stimulating the signaling domains associated with the multimerization domain and forming a multimeric complex. Formation of the multimeric complex results in inducing, modulating, stimulating, activating, mediating and/or promoting signals through intracellular signaling region.

In some embodiments, signaling through the regulatable CAR can be modulated in a conditional manner through conditional multimerization. For example, the multimerization domain of the polypeptides of the regulatable CAR can bind an inducer to multimerize, and the inducer can be provided exogenously. In some aspects, upon binding of the inducer, the multimerization domain multimerizes and induces, modulates, activates, mediates and/or promotes signaling through the signaling domain. For example, the inducer can be exogenously administered, thereby controlling the location and duration of the signal provided to the engineered cell containing the regulatable CAR. In some embodiments, the multimerization domain of the polypeptides of the regulatable CAR can bind an inducer to multimerize, and the inducer can be provided endogenously. For example, the inducer can be produced endogenously by the engineered cell (e.g., engineered T cell) from a recombinant expression vector or from the genome of the engineered cell under the control of an inducible or conditional promoter, thereby controlling the location and duration of the signal provided to the engineered cell containing the regulatable CAR.

In some embodiments, the regulatable CAR is controlled using a suicide switch. Exemplary chimeric receptors utilize an inducible caspase-9 (iCasp9) system, comprising a fusion of human caspase-9 and a modified FKBP dimerization domain, allowing conditional dimerization upon binding with an inducer, e.g., AP1903. Upon dimerization by binding of the inducer, caspase-9 becomes activated and results in apoptosis and cell death of the cells expressing the chimeric receptor (see, e.g., Di Stasi et al. (2011) N. Engl. J. Med. 365:1673-1683).

In some embodiments, exemplary regulatable CAR includes: (1) a first polypeptide of a regulatable CAR comprising: (i) intracellular signaling region; and (ii) at least one multimerization domain capable of binding an inducer; and (2) a second polypeptide of a regulatable CAR comprising: (i) a ligand- (e.g., antigen-) binding domain; (ii) a transmembrane domain; and (iii) at least one multimerization domain capable of binding an inducer. In some embodiments, exemplary regulatable CAR includes: (1) a first polypeptide of a regulatable CAR comprising: (i) a transmembrane domain or an acylation domain; (ii) intracellular signaling region; and (iii) at least one multimerization domain capable of binding an inducer; and (2) a second polypeptide of a regulatable CAR comprising: (i) a ligand- (e.g., antigen-) binding domain; (ii) a transmembrane domain; and (iii) at least one multimerization domain capable of binding an inducer. In some embodiments, the intracellular signaling region further comprises a costimulatory signaling domain. In some embodiments, the second polypeptide further comprises a costimulatory signaling domain. In some embodiments, the at least one multimerization domain(s) on both polypeptides is intracellular. In some embodiments, the at least one multimerization domain(s) on both polypeptides is extracellular.

In some embodiments, exemplary regulatable CAR includes: (1) a first polypeptide of a regulatable CAR comprising: (i) at least one extracellular multimerization domain capable of binding an inducer; (ii) a transmembrane domain; and (iii) intracellular signaling region; and (2) a second polypeptide of a regulatable CAR comprising: (i) a ligand- (e.g., antigen-) binding domain; (ii) at least one extracellular multimerization domain capable of binding an inducer and (iii) a transmembrane domain, an acylation domain or a GPI signal sequence. In some embodiments, the intracellular signaling region further comprises a costimulatory signaling domain. In some embodiments, the second polypeptide further comprises a costimulatory signaling domain.

In some embodiments, exemplary regulatable CAR includes: (1) a first polypeptide of a regulatable CAR comprising: (i) a transmembrane domain or an acylation domain; (ii) at least one costimulatory domain; (iii) a multimerization domain capable of binding an inducer and (iv) intracellular signaling region; and (iii) at least one costimulatory domain; and (2) a second polypeptide of a regulatable CAR comprising: (i) a ligand- (e.g., antigen-) binding domain; (ii) a transmembrane domain; (iii) at least one costimulatory domain; and (iv) at least one extracellular multimerization domain capable of binding an inducer.

In some aspects, any of the regions and/or domains described in the exemplary regulatable CARs can be ordered in various different orders. In some aspects, the various polypeptides of the regulatable CAR(s) contain the multimerization domain on the same side of the cell membrane, e.g., the multimerization domain in the two or more polypeptides are all intracellular or all extracellular.

Variations of regulatable CARs are known, for example, described in U.S. Pat. App. Pub. No. 2014/0286987, U.S. Pat. App. Pub. No. 2015/0266973, International Pat. App. Pub. No. WO2014/127261, and International Pat. App. Pub. No. WO2015/142675.

3. Chimeric Auto-Antibody Receptor (CAAR)

In some embodiments, the chimeric receptor encoded by the modified CD247 locus is a chimeric autoantibody receptor (CAAR). In some aspects, the CAAR includes a CD3zeta (CD3ζ) chain or a fragment or a portion thereof, such as a CD3ζ signaling domain. In some aspects, all (e.g., the entire CD3ζ signaling domain) or a fragment of the CD3ζ signaling domain is encoded by an open reading frame or a partial sequence thereof of the endogenous CD247 locus. In some embodiments, the CAAR binds, e.g., specifically binds, or recognizes, an autoantibody. In some embodiments, a cell expressing the CAAR, such as a T cell engineered to express a CAAR, can be used to bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the chimeric receptor is a CAAR, such as any described in U.S. Patent Application Pub. No. US 2017/0051035.

In some embodiments, the CAAR comprises an autoantibody binding domain, a transmembrane domain, and one or more intracellular signaling region or domain (also interchangeably called a cytoplasmic signaling domain or region). In some embodiments, the intracellular signaling region comprises an intracellular signaling domain. In some embodiments, the intracellular signaling domain is or comprises a primary signaling region, a signaling domain that is capable of stimulating and/or inducing a primary activation signal in a T cell, a signaling domain of a T cell receptor (TCR) component (e.g. an intracellular signaling domain or region of a CD3-zeta (CD3ζ) chain or a functional variant or signaling portion thereof), and/or a signaling domain comprising an immunoreceptor tyrosine-based activation motif (ITAM).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

C. Cells and Preparation of Cells for Genetic Engineering

In some embodiments, provided are engineered cells, e.g., genetically engineered or modified cells, and methods of engineering cells, including genetically engineered cells comprising a modified CD247 locus that comprises a transgene sequence encoding a recombinant receptor or a portion thereof. In some embodiments, polynucleotides, e.g., template polynucleotides such as any of the template polynucleotides described herein, such as in Section I.B.2, containing nucleic acid sequences comprising transgene sequences encoding a portion of a chimeric receptor and/or additional molecule(s), are introduced into one a cell for engineering, e.g., according to the methods of engineering described herein. In some aspects, the cells are engineered using any of the methods provided herein. In some embodiments, the engineered cells contain a modified CD247 locus, said modified CD247 locus comprising a nucleic acid sequence encoding a chimeric receptor comprising an intracellular region comprising a CD3zeta (CD3ζ) signaling domain. In some aspects, the modified CD247 locus of the engineered cell include those described in Section III.A herein.

In some aspects, the transgene sequences (exogenous or heterologous nucleic acid sequences, such as any described in Section I.B.2 herein) in the polynucleotides (such as template polynucleotides, for example, described in Section I.B.2 herein) and/or portions thereof are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acid sequences are not naturally occurring, such as a nucleic acid sequences not found in nature or is modified from a nucleic acid sequence found in nature, including one comprising chimeric combinations of nucleic acids encoding various domains from multiple different cell types.

In some aspects, provided are method of producing a genetically engineered T cell, the method involving introducing any of the provided polynucleotides, e.g., described herein in Section I.B.2, into a T cell comprising a genetic disruption at a CD247 locus. In some aspects, the genetic disruption is introduced by any agents or methods for introducing a targeted genetic disruption, including any described herein, such as in Section I.A. In some aspects, the method produces a modified CD247 locus, said modified CD247 locus comprising a nucleic acid sequence encoding the chimeric receptor comprising an intracellular region comprising a CD3zeta (CD3ζ) signaling domain. In some aspects, provided are method of producing a genetically engineered T cell that involves introducing, into a T cell, one or more agent(s) capable of inducing a genetic disruption at a target site within an endogenous CD247 locus of the T cell; and introducing any of the provided polynucleotides, e.g., described herein in Section I.B.2, into a T cell comprising a genetic disruption at a CD247 locus, wherein the method produces a modified CD247 locus, said modified CD247 locus comprising a nucleic acid sequence encoding the chimeric receptor comprising an intracellular region comprising a CD3zeta (CD3ζ) signaling domain. In some embodiments, the nucleic acid sequence comprises a transgene sequence encoding a portion of the chimeric receptor, and the transgene sequence is targeted for integration within the endogenous CD247 locus via homology directed repair (HDR).

In some embodiments, provided are methods of producing a genetically engineered T cell that involves introducing, into a T cell, a polynucleotide comprising a nucleic acid sequence encoding a chimeric receptor or a portion thereof, said T cell having a genetic disruption within a CD247 locus of the T cell, wherein the nucleic acid sequence encoding the chimeric receptor or a portion thereof is targeted for integration within the endogenous CD247 locus via homology directed repair (HDR). In some embodiments, the method produces a modified CD247 locus, said modified CD247 locus comprising a nucleic acid sequence encoding a chimeric receptor comprising an intracellular region comprising a CD3zeta (CD3ζ) signaling domain. In some embodiments, the nucleic acid sequence comprises a transgene sequence encoding a portion of the chimeric receptor, such as any described herein, for example, in Section I.B.2. In some embodiments, upon performance of the methods, all (e.g., the entire or full CD3ζ signaling domain) or a fragment of the CD3ζ signaling domain in the genetically engineered T cell is encoded by an open reading frame or a partial sequence thereof of the endogenous CD247 locus. In some embodiments, the nucleic acid sequence comprises a transgene sequence encoding a portion of the chimeric receptor, said portion optionally encoding a fragment of the CD3zeta signaling domain (such as a portion of the entire CD3ζ; such as less than the entire CD3ζ signaling domain or the full length CD3ζ signaling domain), and wherein the open reading frame or a partial sequence thereof encodes the CD3zeta signaling domain (such as the entire or full CD3ζ signaling domain) or, optionally the further fragment of the CD3zeta signaling domain. In some embodiments, at least a fragment of the CD3zeta signaling domain, optionally the entire CD3zeta signaling domain, of the encoded chimeric receptor is encoded by the open reading frame of the endogenous CD247 locus or a partial sequence thereof.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as iPSCs. In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils. In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are CD45RO, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Pat. App. Pub. No. WO2009/072003 or US 20110003380.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of stimulating or activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/mL). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177, Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

Various methods for the introduction of genetically engineered components, e.g., agents for inducing a genetic disruption and/or nucleic acids encoding chimeric receptors, e.g., CARs, are known and may be used with the provided methods and compositions. Exemplary methods include those for transfer of nucleic acids encoding the polypeptides or receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell, or any delivery methods described in Section I.A herein. Other approaches and vectors for transfer of the nucleic acids encoding the recombinant products are those described, e.g., in WO2014055668 and U.S. Pat. No. 7,446,190.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (such as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, it may be desired to safeguard against the potential that overexpression of a stimulatory factor (for example, a lymphokine or a cytokine) could potentially result in an unwanted outcome or lower efficacy in a subject, such as a factor associated with toxicity in a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 11:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase (Mullen et al., Proc. Natl. Acad. Sci. USA. 89:33 (1992)).

In some embodiments, the cells, e.g., T cells, may be engineered either during or after expansion. This engineering for the introduction of the gene of the desired polypeptide or receptor can be carried out with any suitable retroviral vector, for example. The genetically modified cell population can then be liberated from the initial stimulus (the CD3/CD28 stimulus, for example) and subsequently be stimulated with a second type of stimulus (e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

As described herein, in some embodiments, the cells are incubated and/or cultured prior to or in connection with genetic engineering. The incubation steps can include culture, cultivation, stimulation, activation, propagation and/or freezing for preservation, e.g. cryopreservation.

D. Composition of Cells Expressing Chimeric Receptor

Also provided are plurality or populations of engineered cells, compositions containing such cells and/or enriched for such cells. In some aspects, the provided engineered cells and/or composition of engineered cells include any described herein, e.g., comprising a modified CD247 locus comprising a transgene sequence encoding a recombinant receptor or a portion thereof, and/or are produced by the methods described herein. In some aspects, the plurality or population of engineered cells contain any of the engineered cells described herein, e.g., in Section III.C herein. In some aspects, the provided cells and cell composition can be engineered using any of the methods described herein, e.g., using agent(s) or methods for introducing genetic disruption, for example, as described in Section I.A herein, and/or using polynucleotides, such as template polynucleotide descried herein, for example in Section I.B.2, via homology-directed repair (HDR). In some aspects, such cell population and/or compositions provided herein is or are comprised in a pharmaceutical composition or a composition for therapeutic uses or methods, for example, as described in Section V herein.

In some embodiments, the provided cell population and/or compositions containing engineered cells include a cell population that exhibits more improved, uniform, homogeneous and/or stable expression and/or antigen binding by the chimeric receptor, e.g., exhibit reduced coefficient of variation, compared to the expression and/or antigen binding of cell populations and/or compositions generated using other methods. In some embodiments, the cell population and/or compositions exhibit at least 100%, 95%, 90%, 80%, 70%, 60%, 50%, 40%, 30%, 20% or 10% lower coefficient of variation of expression of the chimeric receptor and/or antigen binding by the chimeric receptor compared to a respective population generated using other methods, e.g., random integration of sequences encoding the chimeric receptor. The coefficient of variation is defined as standard deviation of expression of the nucleic acid of interest (e.g., transgene sequences encoding a chimeric receptor or a portion thereof) within a population of cells, for example CD4+ and/or CD8+ T cells, divided by the mean of expression of the respective nucleic acid of interest in the respective population of cells. In some embodiments, the cell population and/or compositions exhibit a coefficient of variation that is lower than 0.70, 0.65, 0.60, 0.55, 0.50, 0.45, 0.40, 0.35 or 0.30 or less, when measured among CD4+ and/or CD8+ T cell populations that have been engineered using the methods provided herein.

In some embodiments, the provided cell population and/or compositions containing engineered cells include a cell population that exhibits minimal or reduced random integration of the transgene encoding a chimeric receptor or a portion thereof. In some aspects, random integration of transgene into the genome of the cell can result in adverse effects or cell death due to integration of the transgene into undesired location in the genome, e.g., into an essential gene or a gene critical in regulating the activity of the cell, and/or unregulated or uncontrolled expression of the receptor. In some aspects, random integration of the transgene is reduced by at least or greater than 50%, 60%, 70%, 80%, 90%, 91%, 92%, 93%, 94%, 95%, 96%, 97%, 98%, 99%, or more compared to cell populations generated using other methods.

In some embodiments, provided are cell population and/or compositions that include a plurality of engineered immune cells expressing a chimeric receptor, wherein the nucleic acid sequence encoding the chimeric receptor is present at the CD247 locus, e.g., by integration of a transgene encoding a portion of the chimeric receptor at the CD247 locus via homology directed repair (HDR). In some embodiments, at least or greater than 30%, 35%, 40%, 45%, 50%, 55%, 60%, 65%, 70%, 75%, 80%, or 90% of the cells in the composition and/or cells in the composition that contains a genetic disruption at the CD247 locus comprise integration of the transgene encoding a portion of the chimeric receptor at the CD247 locus.

In some embodiments, the provided compositions containing cells such as in which cells expressing the chimeric receptor make up at least 30%, 40%, 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. In some embodiments, the provided compositions containing cells such as in which cells expressing the chimeric receptor make up at least 30%, 40%, 50%, 60%, 70%, 80%, 90%, 91%, 92%, 93%, 94%, 95%, 96%, 97%, 98%, 99%, or more of the total cells in the composition that contains a genetic disruption at the CD247 locus.

IV. Methods of Treatment

Provided herein are methods of treatment, e.g., including administering any of the engineered cells or compositions containing the engineered cells described herein, for example, engineered cells comprising a modified CD247 locus comprising a transgene encoding a recombinant receptor or a portion thereof. In some aspects, also provided are methods of administering any of the engineered cells or compositions containing engineered cells described herein to a subject, such as a subject that has a disease or disorder. The engineered cells expressing a chimeric receptor, such as a chimeric antigen receptor (CAR), or compositions comprising the same, described herein are useful in a variety of therapeutic, diagnostic and prophylactic indications. For example, the engineered cells or compositions comprising the engineered cells are useful in treating a variety of diseases and disorders in a subject. Such methods and uses include therapeutic methods and uses, for example, involving administration of the engineered cells, or compositions containing the same, to a subject having a disease, condition, or disorder, such as a tumor or cancer. In some embodiments, the engineered cells or compositions comprising the same are administered in an effective amount to effect treatment of the disease or disorder. Uses include uses of the engineered cells or compositions in such methods and treatments, and in the preparation of a medicament in order: to carry out such therapeutic methods. In some embodiments, the methods are carried out by administering the engineered cells, or compositions comprising the same, to the subject having or suspected of having the disease or condition. In some embodiments, the methods thereby treat the disease or condition or disorder in the subject. Also provided are therapeutic methods for administering the cells and compositions to subjects, e.g., patients.

Methods for administration of cells for adoptive cell therapy are known and may be used in connection with the provided methods and compositions. For example, adoptive T cell therapy methods are described, e.g., in US Pat. App. Pub. No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described herein. In particular embodiments, the chimeric antigen receptor specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM). In some embodiments, disease or condition is a B cell malignancy selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

In some embodiments, the disease or disorder is a multiple myeloma (MM). In some embodiments, administration of the provided cells, e.g., engineered cells containing a modified CD247 locus encoding a chimeric receptor such as a CAR, can result in treatment of and/or amelioration of a disease or condition, such as a MM in the subject. In some embodiments, the subject has or is suspected of having a MM that is associated with expression of a tumor-associated antigen, such as a B cell maturation antigen (BCMA).

In some embodiments, the disease or disorder is a chronic lymphocytic leukemia (CLL). In some embodiments, administration of the provided cells, e.g., engineered cells containing a modified CD247 locus encoding a chimeric receptor such as a CAR, can result in treatment of and/or amelioration of a disease or condition, such as a CLL in the subject. In some embodiments, the subject has or is suspected of having a CLL that is associated with expression of a tumor-associated antigen, such as a Receptor Tyrosine Kinase Like Orphan Receptor 1 (ROR1).

In some embodiments, the disease or disorder is a solid tumor, or a cancer associated with a non-hematological tumor. In some embodiments, the disease or disorder is a solid tumor, or a cancer associated with a solid tumor. In some embodiments, the disease or disorder is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma. In some embodiments, the disease or disorder is a bladder, lung, brain, melanoma (e g small-cell lung, melanoma), breast, cervical, ovarian, colorectal, pancreatic, endometrial, esophageal, kidney, liver, prostate, skin, thyroid, or uterine cancers. In some embodiments, the disease or disorder is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.

In some embodiments, the disease or disorder is a non-small cell lung cancer (NSCLC). In some embodiments, administration of the provided cells, e.g., engineered cells containing a modified CD247 locus encoding a chimeric receptor such as a CAR, can result in treatment of and/or amelioration of a disease or condition, such as a NSCLC in the subject. In some embodiments, the subject has or is suspected of having a NSCLC that is associated with expression of a tumor-associated antigen, such as a Receptor Tyrosine Kinase Like Orphan Receptor 1 (ROR1).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is or includes $\alpha v\beta 6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22R$\alpha$), IL-13 receptor alpha 2 (IL-13R$\alpha$2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some aspects, the chimeric receptor, such as a CAR, specifically binds to an antigen associated with the disease or condition or expressed in cells of the environment of a lesion associated with the B cell malignancy. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30, or combinations thereof.

In some embodiments, the disease or condition is a myeloma, such as a multiple myeloma. In some aspects, the chimeric receptor, such as a CAR, specifically binds to an antigen associated with the disease or condition or expressed in cells of the environment of a lesion associated with the multiple myeloma. Antigens targeted by the receptors in some embodiments include antigens associated with multiple myeloma. In some aspects, the antigen, e.g., the second or additional antigen, such as the disease-specific antigen and/or related antigen, is expressed on multiple myeloma, such as B cell maturation antigen (BCMA), G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, β2-Microglobulin, HM1.24, IGF-1R, IL-6R, TRAIL-R1, and the activin receptor type IIA (ActRIIA). See Benson and Byrd, J. Clin. Oncol. (2012) 30(16): 2013-15; Tao and Anderson, Bone Marrow Research (2011): 924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603477, 8,008,450; U.S. Pub. No. U520120189622 or U520100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

In some embodiments, the disease or disorder is associated with expression of G protein-coupled receptor class C group 5 member D (GPRC5D) and/or expression of B cell maturation antigen (BCMA).

In some embodiments, the disease or disorder is a B cell-related disorder. In some of any of the provided embodiments of the provided methods, the disease or disorder associated with BCMA is an autoimmune disease or disorder. In some of any of the provided embodiments of the provided methods, the autoimmune disease or disorder is systemic lupus erythematosus (SLE), lupus nephritis, inflammatory bowel disease, rheumatoid arthritis, ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, poly-arteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis.

In some embodiments, the disease or disorder is a cancer. In some embodiments, the cancer is a GPRC5D-expressing cancer. In some embodiments, the cancer is a plasma cell malignancy and the plasma cell malignancy is multiple myeloma (MM) or plasmacytoma. In some embodiments, the cancer is multiple myeloma (MM). In some embodiments, the cancer is a relapsed/refractory multiple myeloma.

In some embodiments, the antigen is ROR1, and the disease or disorder is CLL. In some embodiments, the antigen is ROR1, and the disease or disorder is NSCLC.

In some embodiments, the antibody or an antigen-binding fragment (e.g. scFv or $V_H$ domain) specifically recognizes an antigen, such as CD19, BCMA, GPRC5D or ROR1. In some embodiments, the antibody or antigen-binding fragment is derived from, or is a variant of, antibodies or antigen-binding fragment that specifically binds to CD19, BCMA, GPRC5D or ROR1.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

For the prevention or treatment of disease, the appropriate dosage may depend on the type of disease to be treated, the type of cells or chimeric receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 $mg/m^2$ and 500 $mg/m^2$, such as between or between about 200 $mg/m^2$ and 400 $mg/m^2$, or 250 $mg/m^2$ and 350 $mg/m^2$, inclusive. In some instances, the subject is administered about 300 $mg/m^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 $mg/m^2$ of cyclophosphamide, daily for 3 days, prior to initiation of the cell therapy.

In some embodiments, where the lymphodepleting agent comprises fludarabine, the subject is administered fludarabine at a dose between or between about 1 $mg/m^2$ and 100 $mg/m^2$, such as between or between about 10 $mg/m^2$ and 75 $mg/m^2$, 15 $mg/m^2$ and 50 $mg/m^2$, 20 $mg/m^2$ and 40 $mg/m^2$, or 24 $mg/m^2$ and 35 $mg/m^2$, inclusive. In some instances, the subject is administered about 30 $mg/m^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 $mg/m^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described herein, and fludarabine at any dose or administration schedule, such as those described herein. For example, in some aspects, the subject is administered 60 mg/kg (~2 $g/m^2$) of cyclophosphamide and 3 to 5 doses of 25 $mg/m^2$ fludarabine prior to the first or subsequent dose.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR expressed by the population can be conjugated either directly or indirectly through a linker to a targeting moiety. The practice of conjugating compounds, e.g., the CAR, to targeting moieties is known. See, e.g., Wadwa et al., J. Drug Targeting 3: 1 1 1 (1995), and U.S. Pat. No. 5,087,616.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agent includes a cytokine, such as IL-2, for example, to enhance persistence.

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells comprises between at or about $2\times10^5$ of the cells/kg and at or about $2\times10^6$ of the cells/kg, such as between at or about $4\times10^5$ of the cells/kg and at or about $1\times10^6$ of the cells/kg or between at or about $6\times10^5$ of the cells/kg and at or about $8\times10^5$ of the cells/kg. In some embodiments, the dose of cells comprises no more than $2\times10^5$ of the cells (e.g. antigen-expressing, such as CAR-expressing cells) per kilogram body weight of the subject (cells/kg), such as no more than at or about $3\times10^5$ cells/kg, no more than at or about $4\times10^5$ cells/kg, no more than at or about $5\times10^5$ cells/kg, no more than at or about $6\times10^5$ cells/kg, no more than at or about $7\times10^5$ cells/kg, no more than at or about $8\times10^5$ cells/kg, no more than at or about $9\times10^5$ cells/kg, no more than at or about $1\times10^6$ cells/kg, or no more than at or about $2\times10^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about $1\times10^6$ cells/kg, or at least or at least about or at or about $2\times10^6$ cells/kg.

In certain embodiments, the cells, or individual populations of sub-types of cells, are administered to the subject at a range of at or about 0.1 million to at or about 100 billion cells and/or that amount of cells per kilogram of body weight of the subject, such as, e.g., at or about 0.1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), at or about 1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), such as at or about 10 million to at or about 100 billion cells (e.g., at or about 20 million cells, at or about 30 million cells, at or about 40 million cells, at or about 60 million cells, at or about 70 million cells, at or about 80 million cells, at or about 90 million cells, at or about 10 billion cells, at or about 25 billion cells, at or about 50 billion cells, at or about 75 billion cells, at or about 90 billion cells, or a range defined by any two of the foregoing values), and in some cases at or about 100 million cells to at or about 50 billion cells (e.g., at or about 120 million cells, at or about 250 million cells, at or about 350 million cells, at or about 650 million cells, at or about 800 million cells, at or about 900 million cells, at or about 3 billion cells, at or about 30 billion cells, at or about 45 billion cells) or any value in between these ranges and/or per kilogram of body weight of the subject. Dosages may vary depending on attributes particular to the disease or disorder and/or patient and/or other treatments. In some embodiments, such values refer to numbers of chimeric receptor-expressing cells; in other embodiments, they refer to number of T cells or PBMCs or total cells administered.

In some embodiments, for example, where the subject is a human, the dose includes fewer than about $5\times10^8$ total chimeric receptor (e.g., CAR)-expressing cells, T cells, or peripheral blood mononuclear cells (PBMCs), e.g., in the range of at or about $1\times10^6$ to at or about $5\times10^8$ such cells, such as at or about $2\times10^6$, $5\times10^6$, $1\times10^7$, $5\times10^7$, $1\times10^8$, $1.5\times10^8$, or $5\times10^8$ total such cells, or the range between any two of the foregoing values. In some embodiments, for example, where the subject is a human, the dose includes more than at or about $1\times10^6$ total chimeric receptor (e.g., CAR)-expressing cells, T cells, or peripheral blood mononuclear cells (PBMCs) and fewer than at or about $2\times10^9$ total chimeric receptor (e.g., CAR)-expressing cells, T cells, or peripheral blood mononuclear cells (PBMCs), e.g., in the range of at or about $2.5\times10^7$ to at or about $1.2\times10^9$ such cells, such as at or about $2.5\times10^7$, $5\times10^7$, $1\times10^8$, $1.5\times10^8$, $8\times10^8$, or $1.2\times10^9$ total such cells, or the range between any two of the foregoing values.

In some embodiments, the dose of genetically engineered cells comprises from at or about $1\times10^5$ to at or about $5\times10^8$ total CAR-expressing ($CAR^+$) T cells, from at or about $1\times10^5$ to at or about $2.5\times10^8$ total $CAR^+$ T cells, from at or about $1\times10^5$ to at or about $1\times10^8$ total $CAR^+$ T cells, from at or about $1\times10^5$ to at or about $5\times10^7$ total $CAR^+$ T cells, from at or about $1\times10^5$ to at or about $2.5\times10^7$ total $CAR^+$ T cells, from at or about $1\times10^5$ to at or about $1\times10^7$ total $CAR^+$ T cells, from at or about $1\times10^5$ to at or about $5\times10^6$ total CAR+ T cells, from at or about $1\times10^5$ to at or about $2.5\times10^6$ total $CAR^+$ T cells, from at or about $1\times10^5$ to at or about $1\times10^6$ total $CAR^+$ T cells, from at or about $1\times10^6$ to at or about $5\times10^8$ total CAR+ T cells, from at or about $1\times10^6$ to at or about $2.5\times10^8$ total $CAR^+$ T cells, from at or about $1\times10^6$ to at or about $1\times10^8$ total $CAR^+$ T cells, from at or about $1\times10^6$ to at or about $5\times10^7$ total $CAR^+$ T cells, from at or about $1\times10^6$ to at or about $2.5\times10^7$ total $CAR^+$ T cells, from at or about $1\times10^6$ to at or about $1\times10^7$ total $CAR^+$ T cells, from at or about $1\times10^6$ to at or about $5\times10^6$ total $CAR^+$ T cells, from at or about $1\times10^6$ to at or about $2.5\times10^6$ total $CAR^+$ T cells, from at or about $2.5\times10^6$ to at or about $5\times10^8$ total $CAR^+$ T cells, from at or about $2.5\times10^6$ to at or about $2.5\times10^8$ total $CAR^+$ T cells, from at or about $2.5\times10^6$ to at or about $1\times10^8$ total $CAR^+$ T cells, from at or about $2.5\times10^6$ to at or about $5\times10^7$ total $CAR^+$ T cells, from at or about $2.5\times10^6$ to at or about $2.5\times10^7$ total $CAR^+$ T cells, from at or about $2.5\times10^6$ to at or about $1\times10^7$ total $CAR^+$ T cells, from at or about $2.5\times10^6$ to at or about $5\times10^6$ total $CAR^+$ T cells, from at or about $5\times10^6$ to at or about $5\times10^8$ total $CAR^+$ T cells, from at or about $5\times10^6$ to at or about $2.5\times10^8$ total $CAR^+$ T cells, from at or about $5\times10^6$ to at or about $1\times10^8$ total $CAR^+$ T cells, from at or about $5\times10^6$ to at or about $5\times10^7$ total $CAR^+$ T cells, from at or about $5\times10^6$ to at or about $2.5\times10^7$ total $CAR^+$ T cells, from at or about $5\times10^6$ to at or about $1\times10^7$ total $CAR^+$ T cells, from at or about $1\times10^7$ to at or about $5\times10^8$ total $CAR^+$ T cells, from at or about $1\times10^7$ to at or about $2.5\times10^8$ total $CAR^+$ T cells, from at or about $1\times10^7$ to at or about $1\times10^8$ total $CAR^+$ T cells, from at or about $1\times10^7$ to at or about $5\times10^7$ total $CAR^+$ T cells, from at or about $1\times10^7$ to at or about $2.5\times10^7$ total $CAR^+$ T cells, from at or about $2.5\times10^7$ to at or about $5\times10^8$ total $CAR^+$ T cells, from at or about $2.5\times10^7$ to at or about $2.5\times10^8$ total $CAR^+$ T cells, from at or about $2.5\times10^7$ to at or about $1\times10^8$ total $CAR^+$ T cells, from at or about $2.5\times10^7$ to at or about $5\times10^7$ total $CAR^+$ T cells, from at or about $5\times10^7$ to at or about $5\times10^8$ total $CAR^+$ T cells, from at or about $5\times10^7$ to at or about $2.5\times10^8$ total $CAR^+$ T cells, from at or about $5\times10^7$ to at or about $1\times10^8$ total $CAR^+$ T cells, from at or about $1\times10^8$ to at or about $5\times10^8$ total $CAR^+$ T cells, from at or about $1\times10^8$ to at or about $2.5\times10^8$ total $CAR^+$ T cells, from at or about or $2.5\times10^8$ to at or about $5\times10^8$ total $CAR^+$ T cells. In some embodiments, the dose of genetically engineered cells comprises from or from about $2.5\times10^7$ to at or about $1.5\times10^8$ total $CAR^+$ T cells, such as from or from about $5\times10^7$ to or to about $1\times10^8$ total $CAR^+$ T cells.

In some embodiments, the dose of genetically engineered cells comprises at least at or about $1\times10^5$ $CAR^+$ cells, at least at or about $2.5\times10^5$ $CAR^+$ cells, at least at or about $5\times10^5$ $CAR^+$ cells, at least at or about $1\times10^6$ $CAR^+$ cells, at least at or about $2.5\times10^6$ $CAR^+$ cells, at least at or about $5\times10^6$ $CAR^+$ cells, at least at or about $1\times10^7$ $CAR^+$ cells, at least at or about $2.5\times10^7$ $CAR^+$ cells, at least at or about $5\times10^7$ CAR$^+$ cells, at least at or about 1x10$^8$ CAR$^+$ cells, at least at or about 1.5x10$^8$ CAR$^+$ cells, at least at or about 2.5x10$^8$ CAR$^+$ cells, or at least at or about 5x10$^8$ CAR$^+$ cells.

In some embodiments, the cell therapy comprises administration of a dose comprising a number of cell from or from about 1x10$^5$ to or to about 5x10$^8$ total chimeric receptor-expressing cells, total T cells, or total peripheral blood mononuclear cells (PBMCs), from or from about 5x10$^5$ to or to about 1x10$^7$ total chimeric receptor-expressing cells, total T cells, or total peripheral blood mononuclear cells (PBMCs) or from or from about 1x10$^6$ to or to about 1x10$^7$ total chimeric receptor-expressing cells, total T cells, or total peripheral blood mononuclear cells (PBMCs), each inclusive. In some embodiments, the cell therapy comprises administration of a dose of cells comprising a number of cells at least or at least about 1x10$^5$ total chimeric receptor-expressing cells, total T cells, or total peripheral blood mononuclear cells (PBMCs), such at least or at least 1x10$^6$, at least or at least about 1x10$^7$, at least or at least about 1x10$^8$ of such cells. In some embodiments, the number is with reference to the total number of CD3$^+$ or CD8$^+$, in some cases also chimeric receptor-expressing (e.g. CAR$^+$) cells. In some embodiments, the cell therapy comprises administration of a dose comprising a number of cell from or from about 1x10$^5$ to or to about 5x10$^8$ CD3$^+$ or CD8$^+$ total T cells or CD3$^+$ or CD8$^+$ chimeric receptor-expressing cells, from or from about 5x10$^5$ to or to about 1x10$^7$ CD3$^+$ or CD8$^+$ total T cells or CD3$^+$ or CD8$^+$ chimeric receptor-expressing cells, or from or from about 1x10$^6$ to or to about 1x10$^7$ CD3$^+$ or CD8$^+$ total T cells or CD3$^+$ or CD8$^+$ chimeric receptor-expressing cells, each inclusive. In some embodiments, the cell therapy comprises administration of a dose comprising a number of cell from or from about 1x10$^5$ to or to about 5x10$^8$ total CD3$^+$/CAR$^+$ or CD8$^+$/CAR$^+$ cells, from or from about 5x10$^5$ to or to about 1x10$^7$ total CD3$^+$/CAR$^+$ or CD8$^+$/CAR$^+$ cells, or from or from about 1x10$^6$ to or to about 1x10$^7$ total CD3$^+$/CAR$^+$ or CD8$^+$/CAR$^+$ cells, each inclusive.

In some embodiments, the T cells of the dose include CD4+ T cells, CD8+ T cells or CD4+ and CD8+ T cells.

In some embodiments, for example, where the subject is human, the CD8$^+$ T cells of the dose, including in a dose including CD4$^+$ and CD8$^+$ T cells, includes between at or about 1x10$^6$ and at or about 5x10$^8$ total chimeric receptor (e.g., CAR)-expressing CD8$^+$cells, e.g., in the range of from at or about 5x10$^6$ to at or about 1x10$^8$ such cells, such as 1x10$^7$, 2.5x10$^7$, 5x10$^7$, 7.5x10$^7$, 1x10$^8$, 1.5x10$^8$, or 5x10$^8$ total such cells, or the range between any two of the foregoing values. In some embodiments, the patient is administered multiple doses, and each of the doses or the total dose can be within any of the foregoing values. In some embodiments, the dose of cells comprises the administration of from or from about 1x10$^7$ to or to about 0.75x10$^8$ total chimeric receptor-expressing CD8$^+$ T cells, from or from about 1x10$^7$ to or to about 5x10$^7$ total chimeric receptor-expressing CD8$^+$ T cells, from or from about 1x10$^7$ to or to about 0.25x10$^8$ total chimeric receptor-expressing CD8$^+$ T cells, each inclusive. In some embodiments, the dose of cells comprises the administration of at or about 1x10$^7$, 2.5x10$^7$, 5x10$^7$, 7.5x10$^7$, 1x10$^8$, 1.5x10$^8$, 2.5x10$^8$, or 5x10$^8$ total chimeric receptor-expressing CD8$^+$ T cells.

In some embodiments, the dose of cells, e.g., chimeric receptor-expressing T cells, is administered to the subject as a single dose or is administered only one time within a period of two weeks, one month, three months, six months, 1 year or more. In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as over no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8$^+$ and CD4$^+$ T cells, respectively, and/or CD8+- and CD4+-enriched populations, respectively, e.g., CD4+ and/or CD8+ T cells each individually including cells genetically engineered to express the chimeric receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered from at or about 0 to at or about 12 hours apart, from at or about 0 to at or about 6 hours apart or from at or about 0 to at or about 2 hours apart. In some embodiments, the initiation of administration of the first composition and the initiation of administration of the second composition are carried out no more than at or about 2 hours, no more than at or about 1 hour, or no more than at or about 30 minutes apart, no more than at or about 15 minutes, no more than at or about 10 minutes or no more than at or about 5 minutes apart. In some embodiments, the initiation and/or completion of administration of the first composition and the completion and/or initiation of administration of the second composition are carried out no more than at or about 2 hours, no more than at or about 1 hour, or no more than at or about 30 minutes apart, no more than at or about 15 minutes, no more than at or about 10 minutes or no more than at or about 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a chimeric receptor to CD8+ cells expressing a chimeric receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+CD4+:CAR+CD8+ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or antitumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or chimeric receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., chimeric receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of chimeric receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or chimeric receptors being administered.

In some embodiments, the methods also include administering one or more additional doses of cells expressing a chimeric antigen receptor (CAR) and/or lymphodepleting therapy, and/or one or more steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., higher, such as 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells being administered.

V. Pharmaceutical Composition and Formulation

Also provided are compositions, such as pharmaceutical compositions and formulations for administration, such as for adoptive cell therapy. In some aspects, the pharmaceutical compositions contain any of the engineered cells or compositions containing the engineered cells described herein, e.g., comprising a modified CD247 locus comprising a transgene sequence encoding a portion of a chimeric receptor. In some embodiments, the dose of cells comprising cells engineered with a chimeric receptor, e.g. CAR, is provided as a composition or formulation, such as a pharmaceutical composition or formulation. Such compositions can be used in accord with the provided methods, and/or with the provided articles of manufacture or compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or chimeric receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. In some aspects, the cells are isolated from a subject, engineered, and administered to the same subject. In other aspects, they are isolated from one subject, engineered, and administered to another subject. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

VI. Kits And Articles of Manufacture

Also provided are articles of manufacture, systems, apparatuses, and kits useful in performing the provided embodiments. In some embodiments, the provided articles of manufacture or kits contain one or more components of the one or more agent(s) capable of inducing genetic disruption and/or template polynucleotide(s), e.g., template polynucleotides containing transgene sequences encoding a chimeric receptor or a portion thereof. In some embodiments, the articles of manufacture or kits can be used in methods for engineering T cells to express a chimeric receptor and/or other molecules, such as via integration of transgene sequences encoding a chimeric receptor or a portion thereof by homology-dependent repair (HDR), for example, to generate the engineered cells comprising a modified CD247 locus comprising a nucleic acid sequence encoding a chimeric receptor comprising an intracellular region comprising a CD3zeta (CD3ζ) signaling domain.

In some embodiments, the articles of manufacture or kits include polypeptides, nucleic acids, vectors and/or polynucleotides useful in performing the provided methods. In some embodiments, the articles of manufacture or kits include one or more agent(s) capable of inducing a genetic disruption, for example, at a CD247 locus (such as those described in Section I.A herein). In some embodiments, the articles of manufacture or kits include one or more nucleic acid molecules, e.g., a plasmid or a DNA fragment, that encodes one or more components of the one or more agent(s) capable of inducing genetic disruption and/or comprises template polynucleotide(s), e.g., for use in targeting transgene sequences into the cell via HDR, such as those described in Section I.B.2 herein. In some embodiments, the articles of manufacture or kits provided herein contain control vectors.

In some embodiments, the articles of manufacture or kits provided herein contain one or more agent(s), wherein each of the one or more agent is independently capable of inducing a genetic disruption of a target site within a CD247 locus; and a template polynucleotide comprising a transgene encoding a portion of a chimeric receptor, wherein the transgene is targeted for integration at or near the target site via homology directed repair (HDR). In some aspects, the one or more agent(s) capable of inducing a genetic disruption is any described herein. In some aspects, the one or more agent(s) is a ribonucleoprotein (RNP) complex comprising a Cas9/gRNA complex. In some aspects, the gRNA included in the RNP targets a target site in the CD247 locus, such as any target site described herein. In some aspects, the template polynucleotide is any of the template polynucleotide described herein.

In some embodiments, the articles of manufacture or kits include one or more containers, typically a plurality of containers, packaging material, and a label or package insert on or associated with the container or containers and/or packaging, generally including instructions for use, e.g., instructions for introducing the components into the cells for engineering.

The articles of manufacture provided herein contain packaging materials. Packaging materials for use in packaging the provided materials are well known. See, for example, U.S. Pat. Nos. 5,323,907, 5,052,558 and 5,033,252, each of which is incorporated herein in its entirety. Examples of packaging materials include, but are not limited to, blister packs, bottles, tubes, inhalers, pumps, bags, vials, containers, syringes, disposable laboratory supplies, e.g., pipette tips and/or plastic plates, or bottles. The articles of manufacture or kits can include a device so as to facilitate dispensing of the materials or to facilitate use in a high-throughput or large-scale manner, e.g., to facilitate use in robotic equipment. Typically, the packaging is non-reactive with the compositions contained therein.

In some embodiments, the one or more agent(s) capable of inducing genetic disruption and/or template polynucleotide(s) are packaged separately. In some embodiments, each container can have a single compartment. In some embodiments, other components of the articles of manufacture or kits are packaged separately, or together in a single compartment.

Also provided are articles of manufacture, systems, apparatuses, and kits useful in administering the provided cells and/or cell compositions, e.g., for use in therapy or treatment. In some embodiments, the articles of manufacture or kits provided herein contain T cells and/or T cell compositions, such as any T cells and/or T cell compositions described herein. In some aspects, the articles of manufacture or kits provided herein can be used for administration of the T cells or T cell compositions, and can include instructions for use.

In some embodiments, the articles of manufacture or kits provided herein contain T cells, and/or T cell compositions, such as any T cells, and/or T cell compositions described herein. In some embodiments, the T cells, and/or T cell compositions any of the modified T cells used the screening methods described herein. In some embodiments, the articles of manufacture or kits provided herein contain control or unmodified T cells and/or T cell compositions. In some embodiments, the article of manufacture or kits include one or more instructions for administration of the engineered cells and/or cell compositions for therapy.

The articles of manufacture and/or kits containing cells or cell compositions for therapy, may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition. The article of manufacture may include (a) a first container with a composition contained therein, wherein the composition includes engineered cells expressing a chimeric receptor; and (b) a second container with a composition contained therein, wherein the composition includes the second agent. In some embodiments, the article of manufacture may include (a) a first container with a first composition contained therein, wherein the composition includes a subtype of engineered cells expressing a chimeric receptor; and (b) a second container with a composition contained therein, wherein the composition includes a different subtype of engineered cells expressing a chimeric receptor. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

VII. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known. Reference to "about" a value or parameter herein includes (and describes) embodiments that are directed to that value or parameter per se. For example, description referring to "about X" includes description of "X". In some embodiments, "about" may refer to ±25%, ±20%, ±15%, ±10%, ±5%, or ±1%.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, corresponding residues can be identified, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A.M., and Griffin, H. G., eds., Humana Press, New. Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various known ways, in some embodiments, using publicly available computer software such as BLAST, BLAST-2, ALIGN or Megalign (DNASTAR) software. Appropriate parameters for aligning sequences can be determined, including any algorithms needed to achieve maximal alignment over the full length of the sequences being compared.

In some embodiments, "operably linked" may include the association of components, such as a DNA sequence, e.g. a heterologous nucleic acid) and a regulatory sequence(s), in such a way as to permit gene expression when the appropriate molecules (e.g. transcriptional activator proteins) are bound to the regulatory sequence. Hence, it means that the components described are in a relationship permitting them to function in their intended manner An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

VIII. Exemplary Embodiments

Among the provided embodiments are:

1. A genetically engineered T cell, comprising a modified CD247 locus, said modified CD247 locus comprising a nucleic acid sequence encoding a chimeric receptor comprising an intracellular region comprising a CD3zeta (CD3ζ) signaling domain.

2. The genetically engineered T cell of embodiment 1, wherein the nucleic acid sequence comprises a transgene sequence encoding a portion of the chimeric receptor, the transgene sequence having been integrated at the endogenous CD247 locus, optionally via homology directed repair (HDR).

3. The genetically engineered T cell of embodiment 1 or embodiment 2, wherein all or a fragment of the CD3ζ signaling domain is encoded by an open reading frame or a partial sequence thereof of the endogenous CD247 locus.

4. The genetically engineered T cell of any of embodiments 1-3, wherein the nucleic acid sequence comprises an in-frame fusion of (i) a transgene sequence encoding a portion of the chimeric receptor and (ii) an open reading frame or a partial sequence thereof of the endogenous CD247 locus.

5. A genetically engineered T cell, comprising a modified CD247 locus, said modified CD247 locus comprising a nucleic acid sequence encoding a chimeric receptor comprising an intracellular region comprising a CD3ζ (CD3ζ) signaling domain, wherein the nucleic acid sequence comprises an in-frame fusion of (i) a transgene sequence encoding a portion of the chimeric receptor and (ii) an open reading frame or a partial sequence thereof of an endogenous CD247 locus encoding the CD3ζ signaling domain.

6. The genetically engineered T cell of any of embodiments 2, 3, and 5, wherein the transgene sequence is in-frame with one or more exons of the open reading frame or partial sequence thereof of the endogenous CD247 locus.

7. The genetically engineered T cell of any of embodiments 2-6, wherein the transgene sequence does not comprise a sequence encoding a 3' UTR.

8. The genetically engineered T cell of any of embodiments 2-7, wherein the transgene sequence does not comprise an intron.

9. The genetically engineered T cell of any of embodiments 2-8, wherein the transgene sequence encodes a fragment of the CD3ζ signaling domain.

10. The genetically engineered T cell of any of embodiments 2-8, wherein the transgene sequence does not encode the CD3ζ signaling domain or a fragment thereof.

11. The genetically engineered T cell of any of embodiments 3-10, wherein the open reading frame or a partial sequence thereof comprises at least one intron and at least one exon of the endogenous CD247 locus.

12. The genetically engineered T cell of any of embodiments 3-11, wherein the open reading frame or a partial sequence thereof encodes a 3' UTR of the endogenous CD247 locus.

13. The genetically engineered T cell of any of embodiments 2-12, wherein the transgene sequence is downstream of exon 1 and upstream of exon 8 of the open reading frame of the endogenous CD247 locus.

14. The genetically engineered T cell of any of embodiments 2-13, wherein the transgene sequence is downstream of exon 1 and upstream of exon 3 of the open reading frame of the endogenous CD247 locus.

15. The genetically engineered T cell of any of embodiments 3-14, wherein at least a fragment of the CD3ζ signaling domain, optionally the entire CD3ζ signaling domain, of the encoded chimeric receptor is encoded by the open reading frame of the endogenous CD247 locus or a partial sequence thereof.

16. The genetically engineered T cell of any of embodiments 1-15, wherein the CD3ζ signaling domain is encoded by a sequence of nucleotides comprising at least a portion of exon 2 and exons 3-8 of the open reading frame of the endogenous CD247 locus.

17. The genetically engineered T cell of any of embodiments 1-16, wherein the CD3ζ signaling domain is encoded by a sequence of nucleotides that does not comprise exon 1, does not comprise the full length of exon 1 and/or does not comprise the full length of exon 2 of the open reading frame of the endogenous CD247 locus.

18. The genetically engineered T cell of any of embodiments 1-17, wherein the encoded chimeric receptor is capable of signaling via the CD3ζ signaling domain.

19. The genetically engineered T cell of any of embodiments 1-18, wherein the encoded CD3ζ signaling domain comprises the sequence selected from any one of SEQ ID NOS:13-15, or a sequence that exhibits at least 85%, 86%, 87%, 88%, 89%, 90%, 91%, 92%, 93%, 94%, 95%, 96%, 97%, 98%, 99% or more sequence identity to any one of SEQ ID NOS: 13-15, or a fragment thereof.

20. The genetically engineered T cell of any of embodiments 1-19, wherein the chimeric receptor is or comprises a functional non-T cell receptor (non-TCR) antigen receptor.

21. The genetically engineered T cell of any of embodiments 1-20, wherein the chimeric receptor is a chimeric antigen receptor (CAR).

22. The genetically engineered T cell of any of embodiments 1-21, wherein the chimeric receptor further comprises an extracellular region and/or a transmembrane domain.

23. The genetically engineered T cell of any of embodiments 2-22, wherein the transgene sequence comprises a sequence of nucleotides encoding one or more regions of the chimeric receptor, optionally wherein the transgene sequence comprises a sequence of nucleotides encoding one or more of an extracellular region, a transmembrane domain and/or a portion of the intracellular region.

24. The genetically engineered T cell of embodiment 23, wherein the extracellular region comprises a binding domain.

25. The genetically engineered T cell of embodiment 24, wherein the binding domain is or comprises an antibody or an antigen-binding fragment thereof.

26. The genetically engineered T cell of embodiment 24 or embodiment 25, wherein the binding domain is capable of binding to a target antigen that is associated with, specific to, and/or expressed on a cell or tissue of a disease, disorder or condition.

27. The genetically engineered T cell of embodiment 26, wherein the target antigen is a tumor antigen.

28. The genetically engineered T cell of embodiment 26 or embodiment 27, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

29. The genetically engineered T cell of any of embodiments 22-27, wherein the extracellular region comprises a spacer, optionally wherein the spacer is operably linked between the binding domain and the transmembrane domain 30. The genetically engineered T cell of embodiment 29, wherein the spacer comprises an immunoglobulin hinge region.

31. The genetically engineered T cell of embodiment 29 or embodiment 30, wherein the spacer comprises a $C_H2$ region and a $C_H3$ region.

32. The genetically engineered T cell of any of embodiments 23-31, wherein the portion of the intracellular region comprises one or more costimulatory signaling domain(s).

33. The genetically engineered T cell of embodiment 32, wherein the one or more costimulatory signaling domain comprises an intracellular signaling domain of a CD28, a 4-1BB or an ICOS or a signaling portion thereof.

34. The genetically engineered T cell of embodiment 32 or embodiment 33, wherein the one or more costimulatory signaling domain comprises an intracellular signaling domain of 4-1BB.

35. The genetically engineered T cell of any of embodiments 24-34, wherein the modified CD247 locus encodes a chimeric receptor that comprises, from its N to C terminus in order: the extracellular binding domain, the spacer, the transmembrane domain and an intracellular signaling region.

36. The genetically engineered T cell of any of embodiments 1-35, wherein:

the transgene sequence comprises in order: a sequence of nucleotides encoding an extracellular binding domain, optionally an scFv; a spacer, optionally comprising a sequence from a human immunoglobulin hinge, optionally from IgG1, IgG2 or IgG4 or a modified version thereof, optionally further comprising a $C_H2$ region and/or a $C_H3$ region; and a transmembrane domain, optionally from human CD28; a costimulatory signaling domain, optionally from human 4-1BB; and/or the modified CD247 locus comprises in order: a sequence of nucleotides encoding an extracellular binding domain, optionally an scFv; a spacer, optionally comprising a sequence from a human immunoglobulin hinge, optionally from IgG1, IgG2 or IgG4 or a modified version thereof, optionally further comprising a $C_H2$ region and/or a $C_H3$ region; and a transmembrane domain, optionally from human CD28; a costimulatory signaling domain, optionally from human 4-1BB; and the CD3ζ signaling domain.

37. The genetically engineered T cell of any of embodiments 21-36, wherein the CAR is a multi-chain CAR.

38. The genetically engineered T cell of any of embodiments 2-37, wherein the transgene sequence comprises a sequence of nucleotides encoding at least one further protein.

39. The genetically engineered T cell of any of embodiments 2-38, wherein the transgene sequence comprises one or more multicistronic element(s).

40. The genetically engineered T cell of embodiment 39, wherein the multicistronic element(s) is positioned between the sequence of nucleotides encoding the portion of the chimeric receptor and the sequence of nucleotides encoding the at least one further protein.

41. The genetically engineered T cell of any of embodiments 38-40, wherein the at least one further protein is a surrogate marker, optionally wherein the surrogate marker is a truncated receptor, optionally wherein the truncated receptor lacks an intracellular signaling domain and/or is not capable of mediating intracellular signaling when bound by its ligand.

42. The genetically engineered T cell of embodiment 39, wherein the chimeric receptor is a multi-chain CAR, and a multicistronic element is positioned between a sequence of nucleotides encoding one chain of the multi-chain CAR and a sequence of nucleotides encoding another chain of the multi-chain CAR.

43. The genetically engineered T cell of any of embodiments 39-42, wherein the one or more multicistronic element(s) are upstream of the sequence of nucleotides encoding the portion of the chimeric receptor.

44. The genetically engineered T cell of any of embodiments 39-43, wherein the one or more multicistronic element is or comprises a ribosome skip sequence, optionally wherein the ribosome skip sequence is a T2A, a P2A, an E2A, or an F2A element.

45. The genetically engineered T cell of any of embodiments 1-44, wherein the modified CD247 locus comprises the promoter and/or regulatory or control element of the endogenous CD247 locus operably linked to control expression the nucleic acid sequence encoding the chimeric receptor.

46. The genetically engineered T cell of any of embodiments 1-45, wherein the modified locus comprises one or more heterologous regulatory or control element(s) operably linked to control expression of the nucleic acid sequence encoding the chimeric receptor.

47. The genetically engineered T cell of embodiment 46, wherein the one or more heterologous regulatory or control element comprises a promoter, an enhancer, an intron, a polyadenylation signal, a Kozak consensus sequence, a splice acceptor sequence and/or a splice donor sequence.

48. The genetically engineered T cell of embodiment 47, wherein the heterologous promoter is or comprises a human elongation factor 1 alpha (EF1α) promoter or an MND promoter or a variant thereof.

49. The genetically engineered T cell of any of embodiments 1-48, wherein the T cell is a primary T cell derived from a subject, optionally wherein the subject is a human.

50. The genetically engineered T cell of any of embodiments 1-49, wherein the T cell is a CD8+ T cell or subtypes thereof.

51. The genetically engineered T cell of any of embodiments 1-49, wherein the T cell is a CD4+ T cell or subtypes thereof.

52. The genetically engineered T cell of any of embodiments 1-51, wherein the T cell is derived from a multipotent or pluripotent cell, which optionally is an iPSC.

53. A polynucleotide, comprising:
- (a) a nucleic acid sequence encoding a chimeric receptor or a portion thereof; and
- (b) one or more homology arm(s) linked to the nucleic acid sequence, wherein the one or more homology arm(s) comprise a sequence homologous to one or more region(s) of an open reading frame of a CD247 locus or a partial sequence thereof.

54. The polynucleotide of embodiment 53, wherein the chimeric receptor comprises an intracellular region and the nucleic acid sequence of (a) is a nucleic acid sequence encoding a portion of the chimeric receptor, said portion does not include the full intracellular region of the chimeric receptor.

55. A polynucleotide, comprising:
- (a) a nucleic acid sequence encoding a portion of a chimeric receptor, said chimeric receptor comprising an intracellular region, wherein the portion of the chimeric receptor includes less than the full intracellular region of the chimeric receptor; and
- (b) one or more homology arm(s) linked to the nucleic acid sequence, wherein the one or more homology arm(s) comprise a sequence homologous to one or more region(s) of an open reading frame of a CD247 locus or a partial sequence thereof.

56. The polynucleotide of embodiment 54 or embodiment 55, wherein the full intracellular region of the chimeric receptor comprises a CD3zeta (CD3ζ) signaling domain or a fragment thereof, wherein at least a portion of the intracellular region is encoded by the open reading frame of the endogenous CD247 locus or a partial sequence thereof when the chimeric receptor is expressed from a cell introduced with the polynucleotide.

57. The polynucleotide of any of embodiments 53-56, wherein the nucleic acid sequence encoding the portion of the chimeric receptor and the one or more homology arm(s) together comprise at least a fragment of a sequence of nucleotides encoding the intracellular region of the chimeric receptor, wherein at least a portion of the intracellular region comprises the CD3ζ signaling domain or a fragment thereof encoded by the open reading frame of the CD247 locus or a partial sequence thereof when the chimeric receptor is expressed from a cell introduced with the polynucleotide.

58. The polynucleotide of any of embodiments 53-57, wherein the nucleic acid sequence of (a) does not comprise a sequence encoding a 3' UTR.

59. The polynucleotide of any of embodiments 53-58, wherein the nucleic acid sequence of (a) does not comprise an intron.

60. The polynucleotide of any of embodiments 53-59, wherein the nucleic acid sequence of (a) encodes a fragment of the CD3ζ signaling domain, when the chimeric receptor is expressed from a cell introduced with the polynucleotide.

61. The polynucleotide of any of embodiments 53-59, wherein the nucleic acid sequence of (a) does not encode the CD3ζ signaling domain or a fragment thereof, when the chimeric receptor is expressed from a cell introduced with the polynucleotide.

62. The polynucleotide of any of embodiments 53-61, wherein the open reading frame or a partial sequence thereof comprises at least one intron and at least one exon of the endogenous CD247 locus.

63. The polynucleotide of any of embodiments 53-62, wherein the open reading frame or a partial sequence thereof encodes a 3' UTR of the endogenous CD247 locus.

64. The polynucleotide of any of embodiments 53-63, wherein at least a fragment of the CD3ζ signaling domain, optionally the entire CD3ζ signaling domain, of the encoded chimeric receptor is encoded by the open reading frame of the endogenous CD247 locus or a partial sequence thereof, when the chimeric receptor is expressed from a cell introduced with the polynucleotide.

65. The polynucleotide of any of embodiments 53-64, wherein the nucleic acid sequence of (a) is a sequence that is exogenous or heterologous to an open reading frame of the endogenous genomic CD247 locus a T cell, optionally a human T cell.

66. The polynucleotide of any of embodiments 53-65, wherein the nucleic acid sequence of (a) comprises a sequence of nucleotides that is in-frame with one or more exons of the open reading frame or a partial sequence thereof of the CD247 locus comprised in the one or more homology arm(s).

67. The polynucleotide of any of embodiments 53-66, wherein the one or more region(s) of the open reading frame is or comprises sequences that are upstream of exon 8 of the open reading frame of the CD247 locus.

68. The polynucleotide of any of embodiments 53-67, wherein the one or more region(s) of the open reading frame is or comprises sequences that are upstream of exon 3 of the open reading frame of the CD247 locus, optionally sequences that includes exon 3 of the open reading frame of the CD247 locus.

69. The polynucleotide of any of embodiments 53-68, wherein the one or more region(s) of the open reading frame is or comprises sequences that includes at least a portion of exon 2 of the open reading frame of the CD247 locus.

70. The polynucleotide of any of embodiments 53-69, wherein the one or more homology arm(s) does not comprise exon 1, does not comprise the full length of exon 1 and/or does not comprise the full length of exon 2 of the open reading frame of the endogenous CD247 locus.

71. The polynucleotide of any of embodiments 53-70, wherein, when expressed by a cell introduced with the polynucleotide, the chimeric receptor is capable of signaling via the CD3ζ signaling domain.

72. The polynucleotide of any of embodiments 53-71, wherein the CD3ζ signaling domain comprises the sequence selected from any one of SEQ ID NOS:13-15, or a sequence that exhibits at least 85%, 86%, 87%, 88%, 89%, 90%, 91%, 92%, 93%, 94%, 95%, 96%, 97%, 98%, 99% or more sequence identity to any one of SEQ ID NOS:13-15, or a fragment thereof.

73. The polynucleotide of any of embodiments 53-72, wherein the one or more homology arm comprises a 5' homology arm and a 3' homology arm.

74. The polynucleotide of any of embodiments 53-73, wherein the polynucleotide comprises the structure [5' homology arm]-[nucleic acid sequence of (a)]-[3' homology arm].

75. The polynucleotide of embodiment 73 or embodiment 74, wherein the 5' homology arm and the 3' homology arm independently are from at or about 50 to at or about 2000 nucleotides, from at or about 100 to at or about 1000 nucleotides, from at or about 100 to at or about 750 nucleotides, from at or about 100 to at or about 600 nucleotides, from at or about 100 to at or about 400 nucleotides, from at or about 100 to at or about 300 nucleotides, from at or about 100 to at or about 200 nucleotides, from at or about 200 to at or about 1000 nucleotides, from at or about 200 to at or about 750 nucleotides, from at or about 200 to at or about 600 nucleotides, from at or about 200 to at or about 400 nucleotides, from at or about 200 to at or about 300 nucleotides, from at or about 300 to at or about 1000 nucleotides, from at or about 300 to at or about 750 nucleotides, from at or about 300 to at or about 600 nucleotides, from at or about 300 to at or about 400 nucleotides, from at or about 400 to at or about 1000 nucleotides, from at or about 400 to at or about 750 nucleotides, from at or about 400 to at or about 600 nucleotides, from at or about 600 to at or about 1000 nucleotides, from at or about 600 to at or about 750 nucleotides or from at or about 750 to at or about 1000 nucleotides in length.

76. The polynucleotide of any of embodiments 73-75, wherein the 5' homology arm and the 3' homology arm independently are at or about 200, 300, 400, 500, 600, 700 or 800 nucleotides in length, or any value between any of the foregoing.

77. The polynucleotide of any of embodiments 73-76, wherein the 5' homology arm and the 3' homology arm independently are greater than at or about 300 nucleotides in length, optionally wherein the 5' homology arm and the 3' homology arm independently are at or about 400, 500 or 600 nucleotides in length, or any value between any of the foregoing.

78. The polynucleotide of any of embodiments 53-77, wherein the 5' homology arm comprises the sequence set forth in SEQ ID NO:80, or a sequence that exhibits at least 85%, 86%, 87%, 88%, 89%, 90%, 91%, 92%, 93%, 94%, 95%, 96%, 97%, 98%, 99% or more sequence identity to SEQ ID NO:80 or a partial sequence thereof.

79. The polynucleotide of any of embodiments 53-78, wherein the 3' homology arm comprises the sequence set forth in SEQ ID NO:81, or a sequence that exhibits at least 85%, 86%, 87%, 88%, 89%, 90%, 91%, 92%, 93%, 94%, 95%, 96%, 97%, 98%, 99% or more sequence identity to SEQ ID NO:81 or a partial sequence thereof.

80. The polynucleotide of any of embodiments 53-79, wherein the chimeric receptor is or comprises a functional non-T cell receptor (non-TCR) antigen receptor.

81. The polynucleotide of any of embodiments 53-80, wherein the chimeric receptor is a chimeric antigen receptor (CAR).

82. The polynucleotide of any of embodiments 53-81, wherein the nucleic acid sequence of (a) comprises a sequence of nucleotides encoding an extracellular region a sequence of nucleotides encoding a transmembrane domain and/or a portion of the intracellular region.

83. The polynucleotide of embodiment 82, wherein the extracellular region comprises a binding domain.

84. The polynucleotide of embodiment 83, wherein the binding domain is or comprises an antibody or an antigen-binding fragment thereof.

85. The polynucleotide of embodiment 83 or embodiment 84, wherein the binding domain is capable of binding to a target antigen that is associated with, specific to, and/or expressed on a cell or tissue of a disease, disorder or condition.

86. The polynucleotide of embodiment 85, wherein the target antigen is a tumor antigen.

87. The polynucleotide of embodiment 85 or embodiment 86, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

88. The polynucleotide of any of embodiments 82-87, wherein the extracellular region comprises a spacer, optionally wherein the spacer is operably linked between the binding domain and the transmembrane domain.

89. The polynucleotide of embodiment 88, wherein the spacer comprises an immunoglobulin hinge region.

90. The polynucleotide of embodiment 88 or embodiment 89, wherein the spacer comprises a $C_H2$ region and a $C_H3$ region.

91. The polynucleotide of any of embodiments 82-90, wherein the portion of the intracellular region comprises one or more costimulatory signaling domain(s).

92. The polynucleotide of embodiment 91, wherein the one or more costimulatory signaling domain comprises an intracellular signaling domain of a CD28, a 4-1BB or an ICOS or a signaling portion thereof.

93. The polynucleotide of embodiment 91 or embodiment 92, wherein the one or more costimulatory signaling domain comprises an intracellular signaling domain of 4-1BB.

94. The polynucleotide of any of embodiments 82-93, wherein the encoded chimeric receptor comprises, from its N to C terminus in order: the extracellular binding domain, the spacer, the transmembrane domain and an intracellular signaling region, when the chimeric receptor is expressed from a cell introduced with the polynucleotide.

95. The polynucleotide of any of embodiments 53-94, wherein:

- the nucleic acid sequence of (a) comprises in order: a sequence of nucleotides encoding an extracellular binding domain, optionally an scFv; a spacer, optionally comprising a sequence from a human immunoglobulin hinge, optionally from IgG1, IgG2 or IgG4 or a modified version thereof, optionally further comprising a $C_H2$ region and/or a $C_H3$ region; and a transmembrane domain, optionally from human CD28; a costimulatory signaling domain, optionally from human 4-1BB; and/or
- the modified CD247 locus comprises in order: a sequence of nucleotides encoding an extracellular binding domain, optionally an scFv; a spacer, optionally comprising a sequence from a human immunoglobulin hinge, optionally from IgG1, IgG2 or IgG4 or a modified version thereof, optionally further comprising a $C_H2$ region and/or a $C_H3$ region; and a transmembrane domain, optionally from human CD28; a costimulatory signaling domain, optionally from human 4-1BB; and the CD3 signaling domain.

96. The polynucleotide of any of embodiments 81-95, wherein the CAR is a multi-chain CAR.

97. The polynucleotide of any of embodiments 53-96, wherein the nucleic acid sequence of (a) comprises a sequence of nucleotides encoding at least one further protein.

98. The polynucleotide of any of embodiments 53-97, wherein the nucleic acid sequence of (a) comprises one or more multicistronic element(s).

99. The polynucleotide of embodiment 98, wherein the multicistronic element(s) is positioned between the sequence of nucleotides encoding the portion of the chimeric receptor and the sequence of nucleotides encoding the at least one further protein.

100. The polynucleotide of any of embodiments 97-99, wherein the at least one further protein is a surrogate marker, optionally wherein the surrogate marker is a truncated receptor, optionally wherein the truncated receptor lacks an intracellular signaling domain and/or is not capable of mediating intracellular signaling when bound by its ligand.

101. The polynucleotide of embodiment 100, wherein the chimeric receptor is a multi-chain CAR, and a multicistronic element is positioned between a sequence of nucleotides encoding one chain of the multi-chain CAR and a sequence of nucleotides encoding another chain of the multi-chain CAR.

102. The polynucleotide of any of embodiments 98-101, wherein the one or more multicistronic element(s) are upstream of the sequence of nucleotides encoding the portion of the chimeric receptor.

103. The polynucleotide of any of embodiments 98-102, wherein the one or more multicistronic element is or comprises a ribosome skip sequence, optionally wherein the ribosome skip sequence is a T2A, a P2A, an E2A, or an F2A element.

104. The polynucleotide of any of embodiments 53-103, wherein the modified CD247 locus comprises the promoter and/or regulatory or control element of the endogenous CD247 locus operably linked to control expression the nucleic acid sequence encoding the chimeric receptor.

105. The polynucleotide of any of embodiments 53-104, wherein the modified locus comprises one or more heterologous regulatory or control element(s) operably linked to control expression of the nucleic acid sequence encoding the chimeric receptor.

106. The polynucleotide of embodiment 105, wherein the one or more heterologous regulatory or control element comprises a promoter, an enhancer, an intron, a polyadenylation signal, a Kozak consensus sequence, a splice acceptor sequence and/or a splice donor sequence.

107. The polynucleotide of embodiment 106, wherein the heterologous promoter is or comprises a human elongation factor 1 alpha (EF1$\alpha$) promoter or an MND promoter or a variant thereof.

108. The polynucleotide of any of embodiments 53-107, wherein the polynucleotide is comprised in a viral vector.

109. The polynucleotide of embodiment 108, wherein the viral vector is an AAV vector.

110. The polynucleotide of embodiment 109, wherein the AAV vector is selected from among AAV1, AAV2, AAV3, AAV4, AAV5, AAV6, AAV7 or AAV8 vector.

111. The polynucleotide of embodiment 109 or embodiment 110, wherein the AAV vector is an AAV2 or AAV6 vector.

112. The polynucleotide of embodiment 108, wherein the viral vector is a retroviral vector, optionally a lentiviral vector.

113. The polynucleotide of any of embodiments 53-112, that is a linear polynucleotide, optionally a double-stranded polynucleotide or a single-stranded polynucleotide.

114. The polynucleotide of any of embodiments 52-113, wherein the polynucleotide is at least at or about 2500, 2750, 3000, 3250, 3500, 3750, 4000, 4250, 4500, 4760, 5000, 5250, 5500, 5750, 6000, 7000, 7500, 8000, 9000 or 10000 nucleotides in length, or any value between any of the foregoing.

115. The polynucleotide of any of embodiments 52-114, wherein the polynucleotide is between at or about 2500 and at or about 5000 nucleotides, at or about 3500 and at or about 4500 nucleotides, or at or about 3750 nucleotides and at or about 4250 nucleotides in length.

116. A method of producing a genetically engineered T cell, the method comprising introducing the polynucleotide of any of embodiments 53-115 into a T cell comprising a genetic disruption at a CD247 locus.

117. A method of producing a genetically engineered T cell, the method comprising:

(a) introducing, into a T cell, one or more agent(s) capable of inducing a genetic disruption at a target site within an endogenous CD247 locus of the T cell; and (b) introducing the polynucleotide of any of embodiments 53-115 into a T cell comprising a genetic disruption at a CD247 locus, wherein the method produces a modified CD247 locus, said modified CD247 locus comprising a nucleic acid sequence encoding the chimeric receptor comprising an intracellular region comprising a CD3ζ (CD3ζ) signaling domain 118. The method of embodiment 117, wherein the polynucleotide comprises a nucleic acid sequence encoding a chimeric receptor or a portion thereof, and the nucleic acid sequence encoding a chimeric receptor or a portion thereof is integrated within the endogenous CD247 locus via homology directed repair (HDR).

119. A method of producing a genetically engineered T cell, the method comprising introducing, into a T cell, a polynucleotide comprising a nucleic acid sequence encoding a chimeric receptor or a portion thereof, said T cell having a genetic disruption within a CD247 locus of the T cell, wherein the nucleic acid sequence encoding the chimeric receptor or a portion thereof is integrated within the endogenous CD247 locus via homology directed repair (HDR).

120. The method of embodiment 116 or embodiment 119, wherein the genetic disruption is carried out by introducing, into a T cell, one or more agent(s) capable of inducing a genetic disruption at a target site within an endogenous CD247 locus of the T cell.

121. The method of any of embodiments 116-120, wherein the method produces a modified CD247 locus, said modified CD247 locus comprising a nucleic acid sequence encoding a chimeric receptor comprising an intracellular region comprising a CD3 (CD3ζ) signaling domain 122. The method of any of embodiments 119-121, wherein the nucleic acid sequence comprises a nucleic acid sequence encoding a chimeric receptor or a portion thereof encoding a portion of the chimeric receptor.

123. The method of any of embodiments 119-122, wherein the polynucleotide further comprises one or more homology arm(s) linked to the nucleic acid sequence, wherein the one or more homology arm(s) comprise a sequence homologous to one or more region(s) of an open reading frame of a CD247 locus.

124. The method of any of embodiments 116-123, wherein the full intracellular region of the chimeric receptor comprises a CD3zeta (CD3ζ) signaling domain or a fragment thereof, wherein at least a portion of the intracellular region is encoded by the open reading frame of the endogenous CD247 locus or a partial sequence thereof in a cell generated by the method.

125. The method of any of embodiments 116-124, wherein the nucleic acid sequence encoding the portion of the chimeric receptor and the one or more homology arm(s) together comprise at least a fragment of a sequence of nucleotides encoding the intracellular region of the chimeric receptor, wherein at least a portion of the intracellular region comprises the CD3ζ signaling domain or a fragment thereof encoded by the open reading frame of the CD247 locus or a partial sequence thereof in a cell generated by the method.

126. The method of any of embodiments 119-125, wherein the nucleic acid sequence encoding a chimeric receptor or a portion thereof does not comprise a sequence encoding a 3' UTR.

127. The method of any of embodiments 119-126, wherein the nucleic acid sequence encoding a chimeric receptor or a portion thereof encodes a fragment of the CD3ζ signaling domain, in a cell generated by the method.

128. The method of any of embodiments 119-126, wherein the nucleic acid sequence encoding a chimeric receptor or a portion thereof does not encode the CD3ζ signaling domain or a fragment thereof, in a cell generated by the method.

129. The method of any of embodiments 119-128, wherein at least a fragment of the CD3ζ signaling domain, optionally the entire CD3ζ signaling domain, of the encoded chimeric receptor is encoded by the open reading frame of the endogenous CD247 locus or a partial sequence thereof, in a cell generated by the method.

130. The method of any of embodiments 119-129, wherein the nucleic acid sequence encoding a chimeric receptor or a portion thereof is a sequence that is exogenous or heterologous to an open reading frame of the endogenous genomic CD247 locus a T cell, optionally a human T cell.

131. The method of any of embodiments 119-130, wherein the nucleic acid sequence encoding a chimeric receptor or a portion thereof comprises a sequence of nucleotides that is in-frame with one or more exons of the open reading frame or a partial sequence thereof of the CD247 locus comprised in the one or more homology arm(s).

132. The method of any of embodiments 119-131, wherein, when expressed by a cell introduced with the polynucleotide, the chimeric receptor is capable of signaling via the CD3ζ signaling domain.

133. The method of any of embodiments 119-132, wherein the CD3ζ signaling domain comprises the sequence selected from any one of SEQ ID NOS:13-15, or a sequence that exhibits at least 85%, 86%, 87%, 88%, 89%, 90%, 91%, 92%, 93%, 94%, 95%, 96%, 97%, 98%, 99% or more sequence identity to any one of SEQ ID NOS:13-15, or a fragment thereof.

134. The method of any of embodiments 119-133, wherein the one or more homology arm comprises a 5' homology arm and a 3' homology arm.

135. The method of any of embodiments 119-134, wherein the polynucleotide comprises the structure [5' homology arm]-[nucleic acid sequence encoding a chimeric receptor or a portion thereof]-[3' homology arm].

136. The method of embodiment 134 or embodiment 135, wherein the 5' homology arm and the 3' homology arm independently are from at or about 50 to at or about 2000 nucleotides, from at or about 100 to at or about 1000 nucleotides, from at or about 100 to at or about 750 nucleotides, from at or about 100 to at or about 600 nucleotides, from at or about 100 to at or about 400 nucleotides, from at or about 100 to at or about 300 nucleotides, from at or about 100 to at or about 200 nucleotides, from at or about 200 to at or about 1000 nucleotides, from at or about 200 to at or about 750 nucleotides, from at or about 200 to at or about 600 nucleotides, from at or about 200 to at or about 400 nucleotides, from at or about 200 to at or about 300 nucleotides, from at or about 300 to at or about 1000 nucleotides, from at or about 300 to at or about 750 nucleotides, from at or about 300 to at or about 600 nucleotides, from at or about 300 to at or about 400 nucleotides, from at or about 400 to at or about 1000 nucleotides, from at or about 400 to at or about 750 nucleotides, from at or about 400 to at or about 600 nucleotides, from at or about 600 to at or about 1000 nucleotides, from at or about 600 to at or about 750 nucleotides or from at or about 750 to at or about 1000 nucleotides in length.

137. The method of any of embodiments 134-136, wherein the 5' homology arm and the 3' homology arm independently are at or about 200, 300, 400, 500, 600, 700 or 800 nucleotides in length, or any value between any of the foregoing.

138. The method of any of embodiments 134-137, wherein the 5' homology arm and the 3' homology arm independently are greater than at or about 300 nucleotides in length, optionally wherein the 5' homology arm and the 3' homology arm independently are at or about 400, 500 or 600 nucleotides in length, or any value between any of the foregoing.

139. The method of any of embodiments 134-138, wherein the 5' homology arm comprises the sequence set forth in SEQ ID NO:80, or a sequence that exhibits at least 85%, 86%, 87%, 88%, 89%, 90%, 91%, 92%, 93%, 94%, 95%, 96%, 97%, 98%, 99% or more sequence identity to SEQ ID NO:80 or a partial sequence thereof.

140. The method of any of embodiments 134-139, wherein the 3' homology arm comprises the sequence set forth in SEQ ID NO:81, or a sequence that exhibits at least 85%, 86%, 87%, 88%, 89%, 90%, 91%, 92%, 93%, 94%, 95%, 96%, 97%, 98%, 99% or more sequence identity to SEQ ID NO:81 or a partial sequence thereof.

141. The method of any of embodiments 117 and 120-140, wherein the one or more agent(s) capable of inducing a genetic disruption comprises a DNA binding protein or DNA-binding nucleic acid that specifically binds to or hybridizes to the target site, a fusion protein comprising a DNA-targeting protein and a nuclease, or an RNA-guided nuclease, optionally wherein the one or more agent(s) comprises a zinc finger nuclease (ZFN), a TAL-effector nuclease (TALEN), or and a CRISPR-Cas9 combination that specifically binds to, recognizes, or hybridizes to the target site.

142. The method of any of embodiments 117 and 120-141, wherein the each of the one or more agent(s) comprises a guide RNA (gRNA) having a targeting domain that is complementary to the at least one target site.

143. The method of any of embodiments 117 and 120-142, wherein the one or more agent(s) is introduced as a ribonucleoprotein (RNP) complex comprising the gRNA and a Cas9 protein.

144. The method of embodiment 143, wherein the RNP is introduced via electroporation, particle gun, calcium phosphate transfection, cell compression or squeezing, optionally via electroporation.

145. The method of embodiment 143 or embodiment 144, wherein the concentration of the RNP is at or about 1, 2, 2.5, 5, 10, 20, 25, 30, 40 or 50 μM, or a range defined by any two of the foregoing values, optionally wherein the concentration of the RNP is at or about 25 μM.

146. The method of any of embodiments 143-145, wherein the molar ratio of the gRNA and the Cas9 molecule in the RNP is at or about at or about 5:1, 4:1, 3:1, 2:1, 1:1, 1:2, 1:3, 1:4 or 1:5, or a range defined by any two of the foregoing values, optionally wherein the molar ratio of the gRNA and the Cas9 molecule in the RNP is at or about 2.6:1.

147. The method of any of embodiments 142-146, wherein the gRNA has a targeting domain sequence selected from CACCUUCACUCUCAGGAACA (SEQ ID NO:87); GAAUGACACCAUAGAUGAAG (SEQ ID NO:88); UGAAGAGGAUUCCAUCCAGC (SEQ ID NO:89); and UCCAGCAGGUAGCAGAGUUU (SEQ ID NO:90).

148. The method of any of embodiments 142-147, wherein the gRNA has a targeting domain sequence of CACCUUCACUCUCAGGAACA (SEQ ID NO:87).

149. The method of any of embodiments 142-147, wherein the gRNA has a targeting domain sequence of UGAAGAGGAUUCCAUCCAGC (SEQ ID NO:89)

150. The method of any of embodiments 116-149, wherein the T cell is a primary T cell derived from a subject, optionally wherein the subject is a human.

151. The method of any of embodiments 116-150, wherein the T cell is a CD8+ T cell or subtypes thereof.

152. The method of any of embodiments 116-150, wherein the T cell is a CD4+ T cell or subtypes thereof.

153. The method of any of embodiments 116-152, wherein the T cell is derived from a multipotent or pluripotent cell, which optionally is an iPSC.

154. The method of any of embodiments 119-153, wherein the polynucleotide is comprised in a viral vector.

155. The method of embodiment 154, wherein the viral vector is an AAV vector.

156. The method of embodiment 155, wherein the AAV vector is selected from among AAV1, AAV2, AAV3, AAV4, AAV5, AAV6, AAV7 or AAV8 vector.

157. The method of embodiment 155 or embodiment 156, wherein the AAV vector is an AAV2 or AAV6 vector.

158. The method of embodiment 154, wherein the viral vector is a retroviral vector, optionally a lentiviral vector.

159. The method of any of embodiments 119-153, wherein the polynucleotide is a linear polynucleotide, optionally a double-stranded polynucleotide or a single-stranded polynucleotide.

160. The method of any of embodiments 117 and 120-159, wherein the one or more agent(s) and the polynucleotide are introduced simultaneously or sequentially, in any order.

161. The method of any of embodiments 117 and 120-160, wherein the polynucleotide is introduced after the introduction of the one or more agent(s).

162. The method of embodiment 161, wherein the polynucleotide is introduced immediately after, or within about 30 seconds, 1 minute, 2 minutes, 3 minutes, 4 minutes, 5 minutes, 6 minutes, 6 minutes, 8 minutes, 9 minutes, 10 minutes, 15 minutes, 20 minutes, 30 minutes, 40 minutes, 50 minutes, 60 minutes, 90 minutes, 2 hours, 3 hours or 4 hours after the introduction of the agent.

163. The method of any of embodiments 117 and 120-162, wherein prior to the introducing of the one or more agent, the method comprises incubating the cells, in vitro with a stimulatory agent(s) under conditions to stimulate or activate the one or more immune cells.

164. The method of embodiment 163, wherein the stimulatory agent(s) comprises and anti-CD3 and/or anti-CD28 antibodies, optionally anti-CD3/anti-CD28 beads, optionally wherein the bead to cell ratio is or is about 1:1.

165. The method of embodiment 163 or embodiment 164, comprising removing the stimulatory agent(s) from the one or more immune cells prior to the introducing with the one or more agents.

166. The method of any of embodiments 117 and 120-165, wherein the method further comprises incubating the cells prior to, during or subsequent to the introducing of the one or more agents and/or the introducing of the polynucleotide with one or more recombinant cytokines, optionally wherein the one or more recombinant cytokines are selected from the group consisting of IL-2, IL-7, and IL-15.

167. The method of embodiment 166, wherein the one or more recombinant cytokine is added at a concentration selected from a concentration of IL-2 from at or about 10 U/mL to at or about 200 U/mL, optionally at or about 50 IU/mL to at or about 100 U/mL; IL-7 at a concentration of 0.5 ng/mL to 50 ng/mL, optionally at or about 5 ng/mL to at or about 10 ng/mL and/or IL-15 at a concentration of 0.1 ng/mL to 20 ng/mL, optionally at or about 0.5 ng/mL to at or about 5 ng/mL.

168. The method of embodiment 166 or embodiment 167, wherein the incubation is carried out subsequent to the introducing of the one or more agents and the introducing of the polynucleotide for up to or approximately 24 hours, 36 hours, 48 hours, 3, 4, 5, 6, 7, 8, 9, 10, 11, 12, 13, 14, 15, 16, 17, 18, 19, 20 or 21 days, optionally up to or about 7 days.

169. The method of any of embodiments 116-168, wherein at least or greater than 35%, 40%, 45%, 50%, 55%, 60%, 65%, 70%, 75%, 80%, or 90% of the cells in a plurality of engineered cells generated by the method comprise a genetic disruption of at least one target site within a CD247 locus.

170. The method of any of embodiments 116-169, wherein at least or greater than 35%, 40%, 45%, 50%, 55%, 60%, 65%, 70%, 75%, 80%, or 90% of the cells in a plurality of engineered cells generated by the method express the chimeric receptor or antigen-binding fragment thereof.

171. An engineered T cell or a plurality of engineered T cells generated using the method of any of embodiments 116-170.

172. A composition, comprising the engineered T cell any of embodiments 1-52 and 171.

173. A composition, comprising a plurality of the engineered T cell any of embodiments 1-52 and 171.

174. The composition of embodiment 172 or embodiment 173, wherein the composition comprises CD4+ and/or CD8+ T cells.

175. The composition of any of embodiments 172-174, wherein the composition comprises CD4+ and CD8+ T cells and the ratio of CD4+ to CD8+ T cells is from or from about 1:3 to 3:1, optionally 1:1.

176. The composition of any of embodiments 172-175, wherein cells expressing the chimeric receptor make up at least 30%, 40%, 50%, 60%, 70%, 80%, 90%, 91%, 92%, 93%, 94%, 95%, 96%, 97%, 98%, 99%, or more of the total cells in the composition or of the total CD4+ or CD8+ cells in the composition.

177. A method of treatment comprising administering the engineered cell, plurality of engineered cells or composition of any of embodiments 1-52 and 171-176 to a subject having a disease or disorder.

178. Use of the engineered cell, plurality of engineered cells or composition of any of embodiments 1-52 and 171-176 for the treatment of a disease or disorder.

179. Use of the engineered cell, plurality of engineered cells or composition of any of embodiments 1-52 and 171-176 in the manufacture of a medicament for treating a disease or disorder.

180. The engineered cell, plurality of engineered cells or composition of any of embodiments 1-52 and 171-176 for use in the treatment of a disease or disorder.

181. The method, use or the engineered cell, plurality of engineered cells or composition for use of any of embodiments 177-180, wherein the disease or disorder is a cancer or a tumor.

182. The method, use or the engineered cell, plurality of engineered cells or composition for use of embodiment 181, wherein the cancer or the tumor is a hematologic malignancy, optionally a lymphoma, a leukemia, or a plasma cell malignancy.

183. The method, use or the engineered cell, plurality of engineered cells or composition for use of embodiment 181 or embodiment 182, wherein the cancer is a lymphoma and the lymphoma is Burkitt's lymphoma, non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL).

184. The method, use or the engineered cell, plurality of engineered cells or composition for use of embodiment 181 or embodiment 182, wherein the cancer is a leukemia and the leukemia is chronic lymphocytic leukemia (CLL), plasma cell leukemia or acute lymphocytic leukemia (ALL).

185. The method, use or the engineered cell, plurality of engineered cells or composition for use of embodiment 181 or embodiment 182, wherein the cancer is a plasma cell malignancy and the plasma cell malignancy is multiple myeloma (MM).

186. The method, use or the engineered cell, plurality of engineered cells or composition for use of embodiment 181, wherein the tumor is a solid tumor.

187. The method, use or the engineered cell, plurality of engineered cells or composition for use of embodiment 186, wherein the solid tumor is a non-small cell lung cancer (NSCLC) or a head and neck squamous cell carcinoma (HNSCC).

188. A kit comprising:

one or more agent(s) capable of inducing a genetic disruption at a target site within a CD247 locus; and the polynucleotide of any of embodiments 53-115.

189. A kit, comprising:

one or more agent(s) capable of inducing a genetic disruption at a target site within a CD247 locus; and a polynucleotide comprising a nucleic acid sequence encoding chimeric receptor or a portion thereof, wherein the transgene encoding the chimeric receptor or antigen-binding fragment or chain thereof is targeted for integration at or near the target site via homology directed repair (HDR); and instructions for carrying out the method of any of embodiments 116-170.

IX. Examples

The following examples are included for illustrative purposes only and are not intended to limit the scope of the invention.

Example 1 Genetic Disruption at the Endogenous CD217Locus

Guide RNAs were assessed for genetic disruption within the endogenous CD247 locus (encoding CD3ζ) by CRISPR/Cas9-mediated gene editing.

Primary human CD4+ and CD8+ T cells were isolated by immunoaffinity-based selection from human peripheral blood mononuclear cells (PBMCs) obtained from healthy donors. The resulting CD4+ and CD8+ cells (at 1:1 ratio) were stimulated for 72 hours by culturing with an anti-CD3/anti-CD28 reagent. The anti-CD3/anti-CD28 reagent was removed, and the stimulated cells were electroporated with 2 μM ribonucleoprotein (RNP) complexes for introducing a genetic disruption at the endogenous CD247 locus by CRISPR/Cas9-mediated gene editing. The RNP complexes contained *Streptococcus pyogenes* Cas9 and one of the four (4) exemplary gRNAs with targeting domain sequences as follows: CACCUUCACUCUCAGGAACA (CD247 gRNA 1; SEQ ID NO:87); GAAUGACACCAUAGAUGAAG (CD247 gRNA 2; SEQ ID NO:88); UGAAGAGGAUUCCAUCCAGC (CD247 gRNA 3; SEQ ID NO:89); or UCCAGCAGGUAGCAGAGUUU (CD247 gRNA 4; SEQ ID NO:90), or mock treated (mock). The ratio of gRNA to Cas9 protein was about 2.0:1. The cells were cultured for 3 days and assessed by flow cytometry, staining with anti-CD3 antibody and an anti-T cell receptor (TCR) antibody.

As shown in FIG. 1, CD3 expression was knocked out in cells electroporated with RNP complexes containing CD247-targeted gRNAs, ranging from approximately 12.6% to 76.1% of the cells knocked out for CD3 expression. CD247 gRNA 3 (with targeting domain sequence set forth in SEQ ID NO:89) showed the highest knock-out efficiency.

Example 2 Targeted Integration of Transgene Sequences Encoding a Portion of a Chimeric Antigen Receptor (CAR) at the Endogenous CD247 Locus in a T Cell Human T cells were engineered to express a chimeric antigen receptor (CAR), where the nucleic acid sequences encoding the CAR or a portion thereof was targeted for integration at the endogenous CD247 locus (encoding CD3ζ), via homology-dependent repair (HDR).

A. Template Polynucleotides for HDR-Mediated Targeting

Exemplary template polynucleotides were generated for targeted integration of a transgene sequence that included nucleic acid sequences encoding a portion of a CAR including an scFv specific to the exemplary antigen BCMA, an immunoglobulin-derived spacer, a transmembrane domain derived from CD28 and a costimulatory region derived from 4-1BB.

The transgene sequences also included either a) the human elongation factor 1 alpha (EF1α) promoter to drive the expression of the CAR-encoding sequences under the control of a heterologous promoter; or b) a P2A ribosome skipping element upstream of the nucleic acid sequences encoding the portion of the anti-BCMA CAR, to drive expression of the CAR from the endogenous CD247 locus upon HDR-mediated targeted integration in-frame into the CD247 open reading frame. The transgene sequences also included either i) heterologous nucleic sequences encoding the intracellular portion of the CD3ζ chain and a heterologous polyadenylation signal (SV40 polyadenylation sequences; SV40pA), or ii) no heterologous sequences encoding a portion of the CD3ζ chain, such that upon targeted integration, the transcript encoding the CAR contained the endogenous 3' UTR of the CD3ζ chain.

The template polynucleotides also contained homology arms to direct targeted integration of the transgene sequence into the endogenous human CD247 locus of a T cell. The general structure of the exemplary template polynucleotides were as follows: [5' homology arm]-[transgene sequences]-[3' homology arm]. The 5' homology arm contained approximately 600 bp of sequence that was homologous to a portion of the first intron and the second exon of the endogenous human CD247 locus (5' homology arm sequence set forth in SEQ ID NO:80). The 3' homology arm contained approximately 600 bp sequence that was homologous to a portion of the second exon, including the sequence encoding the last 3 amino acids encoded by the second exon, and a portion of the second intron (3' homology arm sequence set forth in SEQ ID NO:81).

Table E1 sets forth the structure of the generated template polynucleotides.

TABLE E1

Exemplary Template Polynucleotides.

| Polynucleotide | Components of Exemplary Template Polynucleotide |
|---|---|
| A | [5' homology arm]-[P2A - anti-BCMA CAR (with heterologous CD3ζ) - SV40pA]-<br>[3' homology arm]<br>(endogenous CD3ζ promoter; heterologous 3' UTR) |
| B | [5' homology arm]-[P2A - anti-BCMA CAR (without heterologous CD3ζ)]-[3' homology arm]<br>(endogenous CD3ζ promoter; endogenous 3' UTR) |
| C | [5' homology arm]-[EF1α promoter - anti-BCMA CAR (with heterologous CD3ζ) -<br>SV40pA]-[3' homology arm]<br>(heterologous EF1α promoter; heterologous 3' UTR) |
| D | [5' homology arm]-[EF1α promoter - anti-BCMA CAR (without heterologous CD3ζ)]-[3' homology arm]<br>(heterologous EF1α promoter; endogenous 3' UTR) |

B. Generation of Engineered T Cells by HDR and Expression of CAR

For targeted integration by HDR, adeno-associated virus (AAV) vector constructs containing one of the four polynucleotides set forth in Table E1 were generated (Polynucleotides A, B, C, D). AAV stocks were produced by triple transfection of an AAV vector for introduction of the template polynucleotide, serotype helper plasmid and adenoviral helper plasmid into a 293T cell line. Transfected cells were collected, lysed and AAV stock was collected for transduction of cells.

Primary human CD4+ and CD8+ T cells were isolated from a human donor subject, stimulated and the stimulated cells were electroporated with 2 μM of the RNP complexes containing CD247-targeting gRNA 3 and *Streptococcus pyogenes* Cas9 at a gRNA to Cas9 protein of about 2.0:1, as described in Example 1 Immediately following electroporation, cells were transduced with AAV preparations containing one of Polynucleotides A, B, C, D at 5% v/v. As a control, nucleic acid sequences encoding the anti-BCMA CAR was introduced by lentiviral transduction or mock treated.

The cells were cultured for 3 days and assessed by flow cytometry, staining with an anti-CD3 epsilon (anti-CD3ε) antibody and a BCMA-Fc (soluble human BCMA fused at its C-terminus to an Fc region of IgG) fusion polypeptide, to detect expression of the anti-BCMA CAR.

Figure 2A:
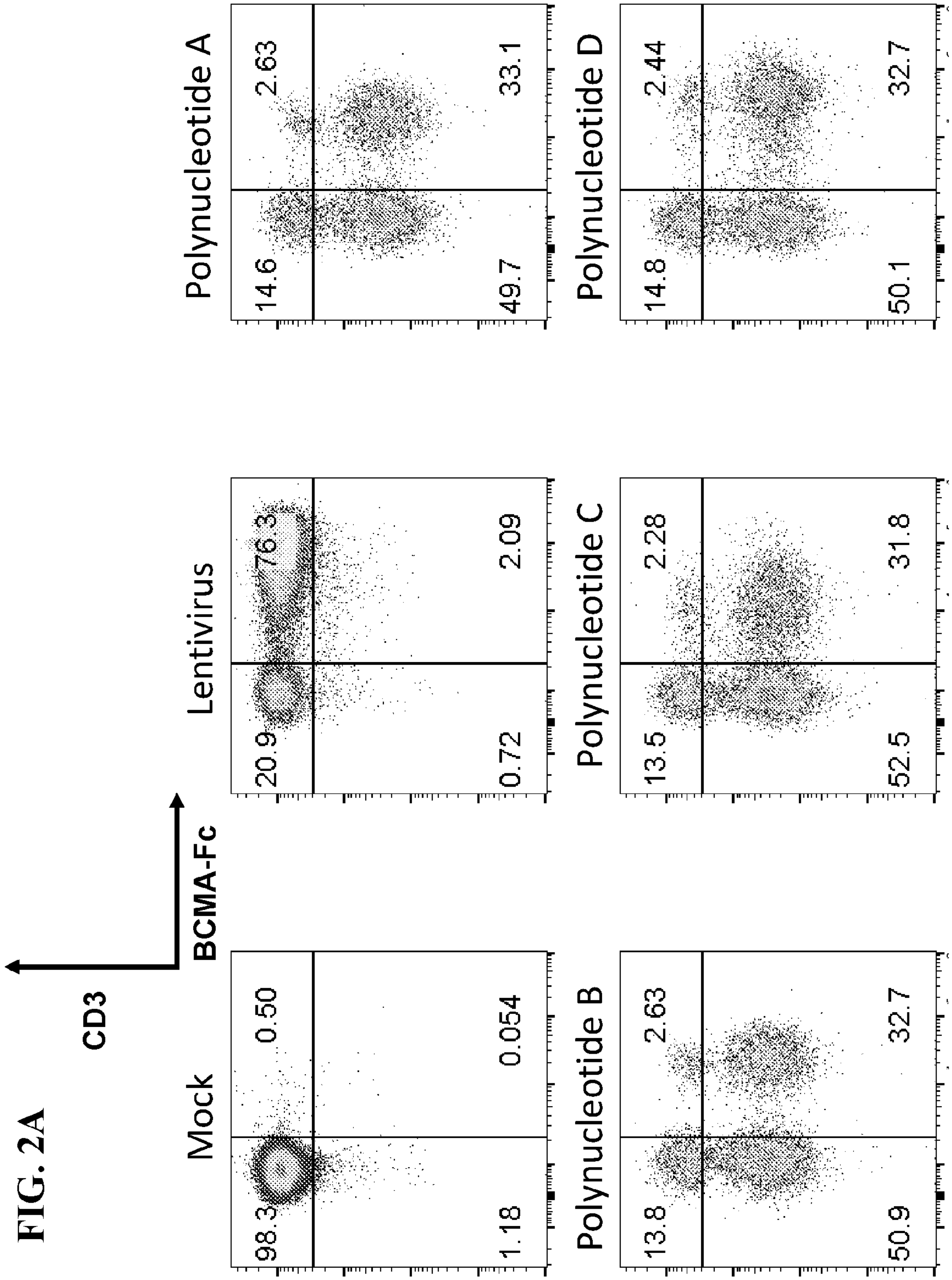
FIG. 2A depicts the surface expression of CD3 (detected using an anti-CD3ε antibody) and an anti-BCMA chimeric antigen receptor (CAR) (detected using BCMA-Fc; soluble human BCMA fused at its C-terminus to an Fc region of IgG), as assessed by flow cytometry, in T cells that were electroporated with an RNP complex containing CD247-targeting gRNA 3 and incubated adeno-associated virus (AAV) constructs that contained one of four polynucleotides (Polynucleotides A, B, C, D; described in Table E1) containing transgene sequences encoding an anti-BCMA CAR or a portion thereof and regulatory and/or multicistronic elements; or T cells subject to a mock electroporation and transduction (mock) as controls.
Figure 2B:
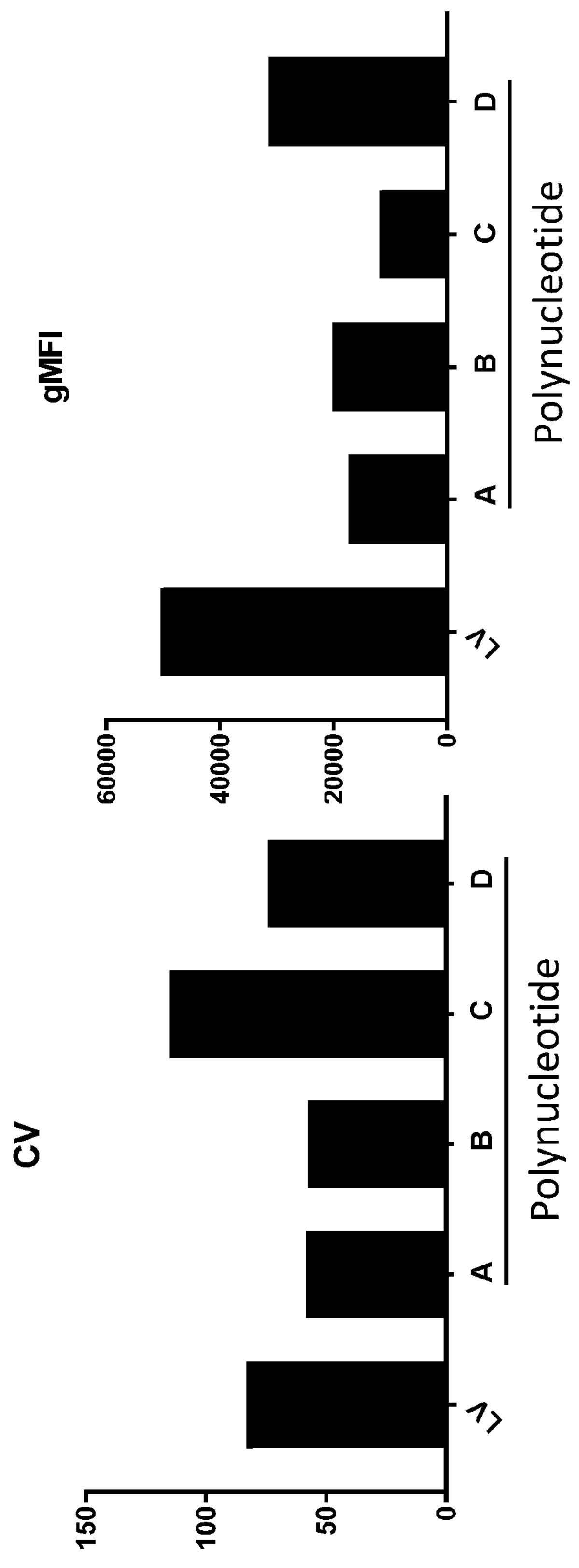
FIG. 2B depicts the coefficient of variation (CV) (the standard deviation of signal within a population of cells divided by the mean of the signal in the respective population) and the geometric mean fluorescence (gMFI) of expression of the exemplary anti-BCMA CAR engineered as described in Example 2.B.

As shown in FIG. 2A, introduction of each of the 4 template polynucleotides (Polynucleotides A, B, C, D) resulted in targeted integration of the anti-BCMA CAR into the CD247 locus as evidenced by expression of the anti-BCMA CAR on the surface of the cell, and less than 20% of the cells expressing CD3. FIG. 2B depicts the coefficient of variation (CV) (the standard deviation of signal within a population of cells divided by the mean of the signal in the respective population) and the geometric mean fluorescence (gMFI) of expression of the exemplary anti-BCMA CAR under each condition. As shown, targeted integration of the nucleic acids at the endogenous CD247 locus via HDR resulted in a lower coefficient of variation for certain of the tested polynucleotides.

Example 3 Assessment of Functional Activity of CAR-Expressing Cells Engineered by Targeted Integration of Transgene Sequences Encoding a Portion of a Chimeric Antigen Receptor (CAR) at the Endogenous CD247 Locus in a T Cell Engineered cells generated as described in Example 2 were assessed for cytolytic activity and cytokine production following antigen-dependent stimulation.

To assess cytolytic activity, engineered CAR-expressing T cells were cultured in a 96-well plate with RPMI 8226 multiple myeloma cells (ATCC® CCL-155™; expressing low level of BCMA) or BCMA-transduced K562 chronic myelogenous leukemia (CML) cells (ATCC® CCL-243™; K562-BCMA, expressing high levels of BCMA), and were incubated at an E:T ratio of 2:1, 1:1 or 1:2. Mock electroporated and transduced cells (mock) and target cells cultured without CAR+ cells (target only) were assessed as controls. The loss of NucLight Red (NLR)-labeled viable target cells was measured over 49 hours, as determined by red fluorescent signal (using the IncuCyte® Live Cell Analysis System, Essen Bioscience). Percent lysis was determined normalized to CAR+ population.

Cytokine production was also assessed following co-culture of the engineered anti-BCMA CAR-expressing cells with target cells. Supernatants from the co-cultured cells were collected for measurement of interferon-gamma (IFN-γ), tumor necrosis factor alpha (TNF-α) and interleukin-2 (IL-2), using a multiplex cytokine immunoassay.

Figure 3A:
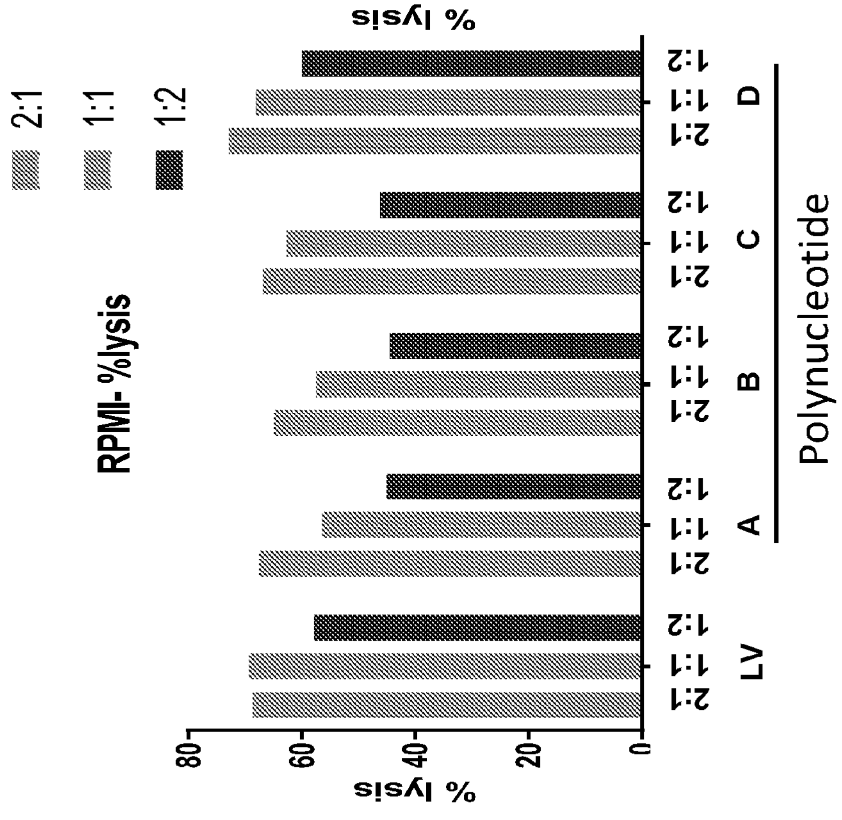
FIG. 3A shows the percent total lysis from a cytolytic activity assay after a co-culture of CAR-expressing T cells engineered using AAV constructs containing one of four polynucleotides (Polynucleotides A, B, C, D; described in Table E1) containing transgene sequences encoding an anti-BCMA CAR or a portion thereof and regulatory and/or multicistronic elements, and RPMI 8226 multiple myeloma cells (ATCC® CCL-155™; expressing low level of BCMA), at E:T ratio of 2:1, 1:1 or 1:2. The loss of NucLight Red (NLR)-labeled viable target cells was measured over 49 hours, as determined by red fluorescent signal (using the IncuCyte® Live Cell Analysis System, Essen Bioscience). Mock electroporated and transduced cells (mock) and target cells cultured without CAR+ cells (target only) were assessed as controls. Percent lysis was determined normalized to CAR+ population.

The percent total lysis during the experiment at each of the assessed E:T ratios for each group of engineered cells against RPMI 8226 cells is shown in FIG. 3A. The lysis of RPMI 8226 cells at the 2:1, 1:1 and 1:2 E:T ratios observed over time is shown in FIGS. 3C, 3D and 3E, respectively. As shown, cells engineered to express the exemplary anti-BCMA CAR by targeted integration at the CD247 locus via HDR exhibited activity that was comparable to cells engineered with CARs by lentiviral delivery, against the exemplary RPMI 8226 cells.

Figure 3B:
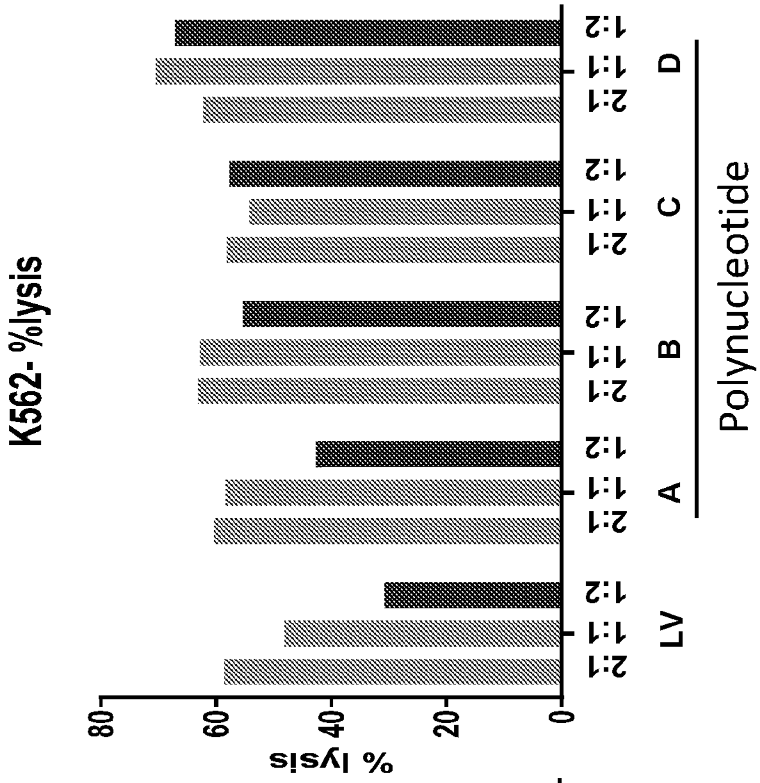
FIG. 3B shows the percent total lysis from a cytolytic activity assay after a co-culture of engineered CAR-expressing T cells and K562 chronic myelogenous leukemia (CML) cells (ATCC® CCL-243™; K562-BCMA, expressing high levels of BCMA), at E:T ratio of 2:1, 1:1 or 1:2.
Figure 3C:
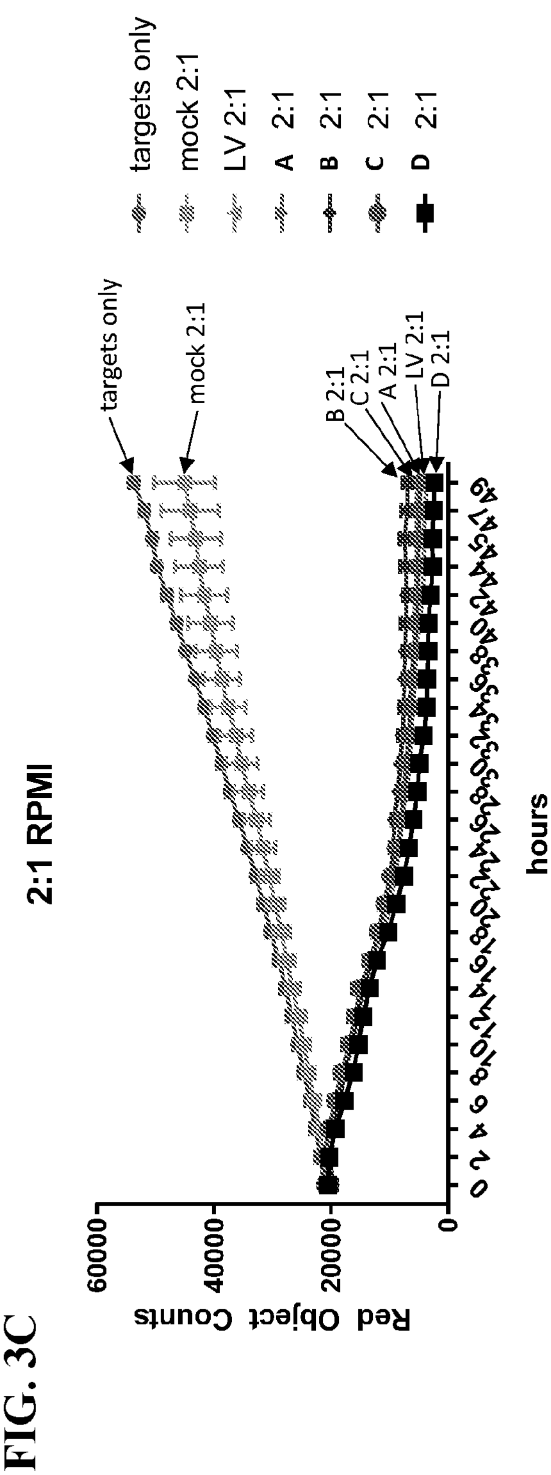
FIGS. 3C-3E show the lysis of RPMI 8226 cells over time at the 2:1 (FIG. 3C), 1:1 (FIG. 3D) and 1:2 (FIG. 3E) E:T ratios, as determined by red fluorescent signal.
Figure 3D:
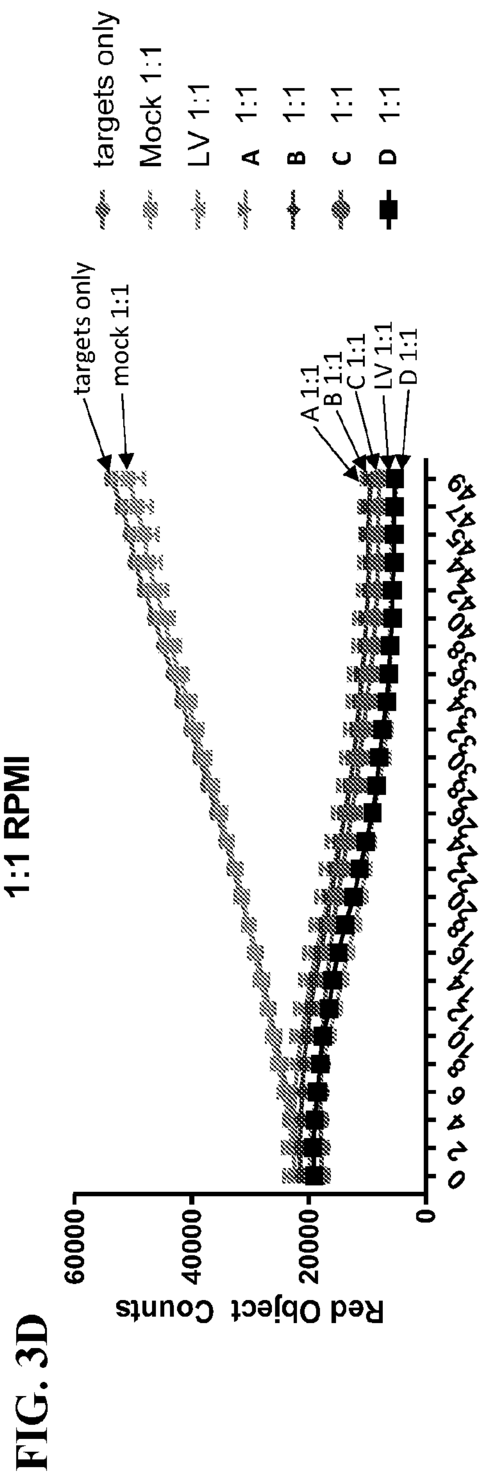
Figure 3E:
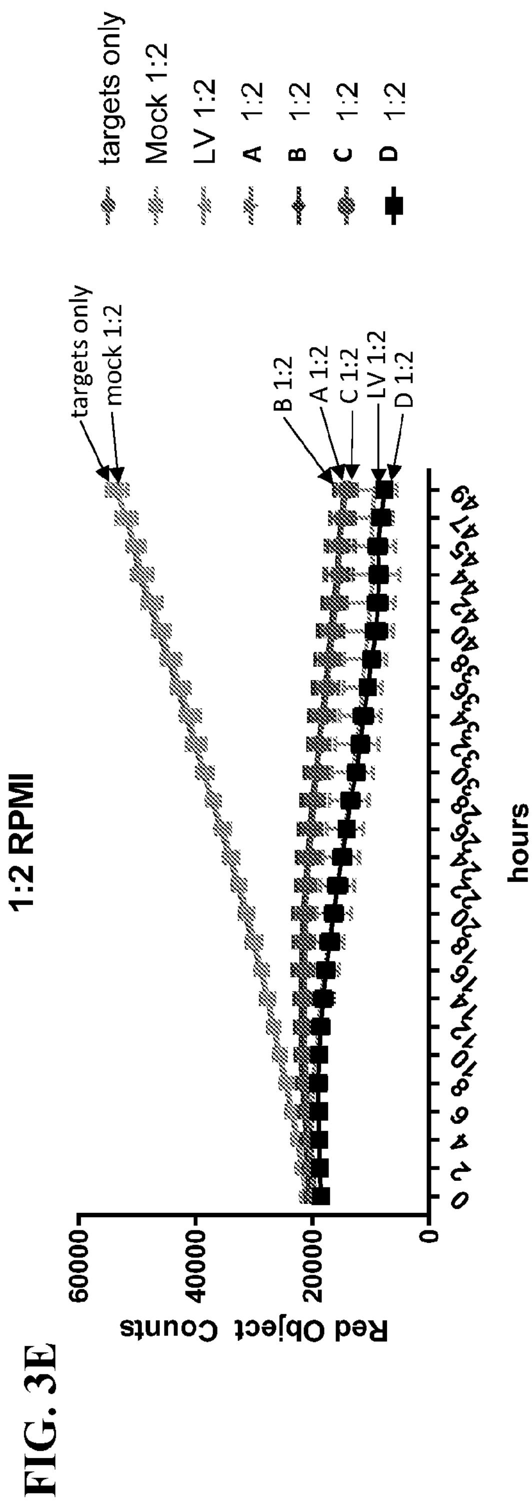
Figure 3F:
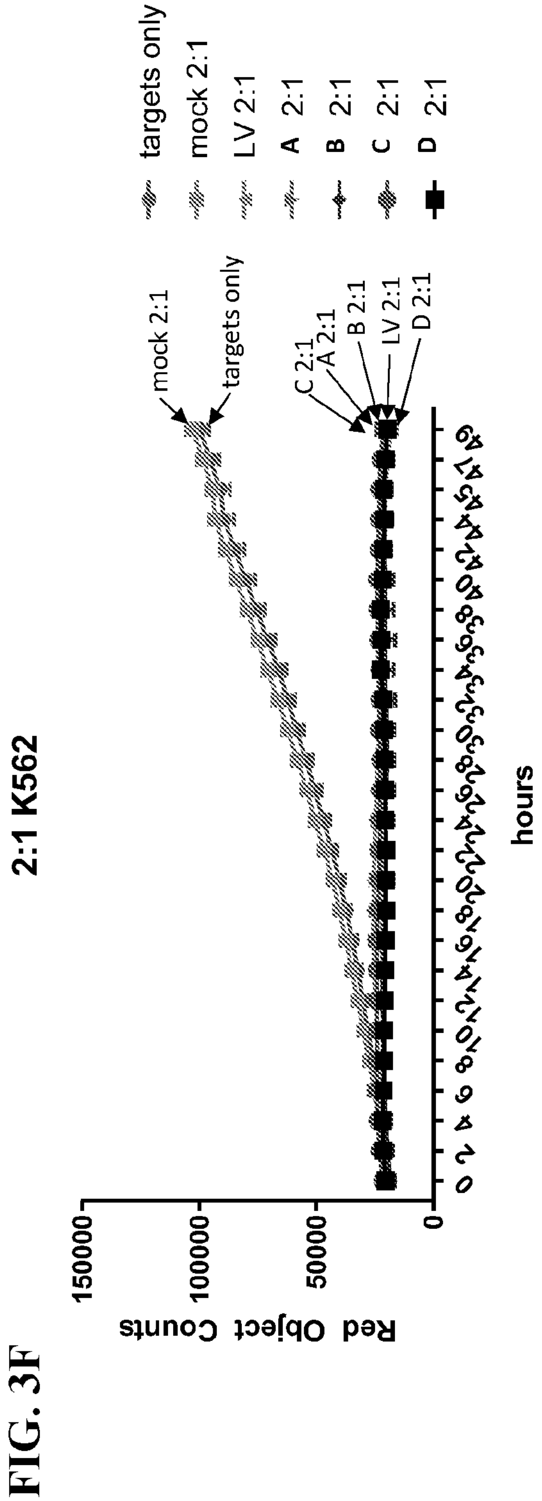
FIGS. 3F-3H show the lysis of K562 cells over time at the 2:1 (FIG. 3F), 1:1 (FIG. 3G) and 1:2 (FIG. 3H) E:T ratios.
Figure 3G:
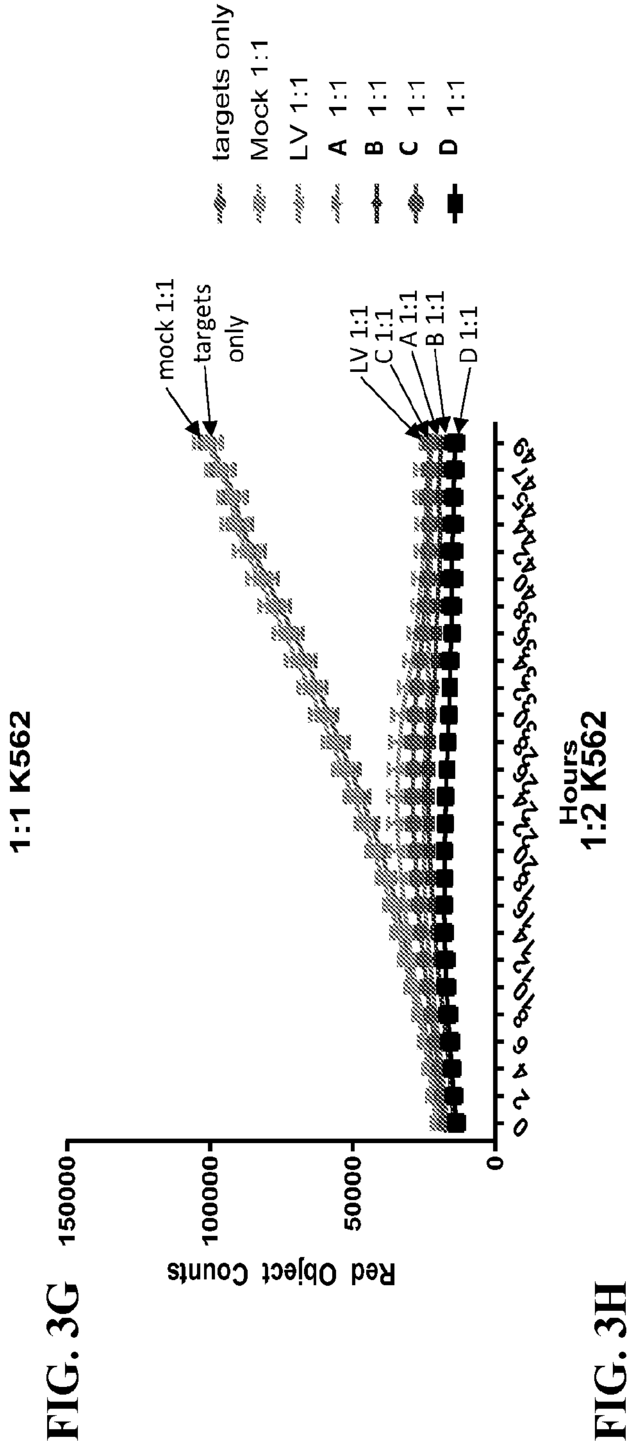
Figure 3H:
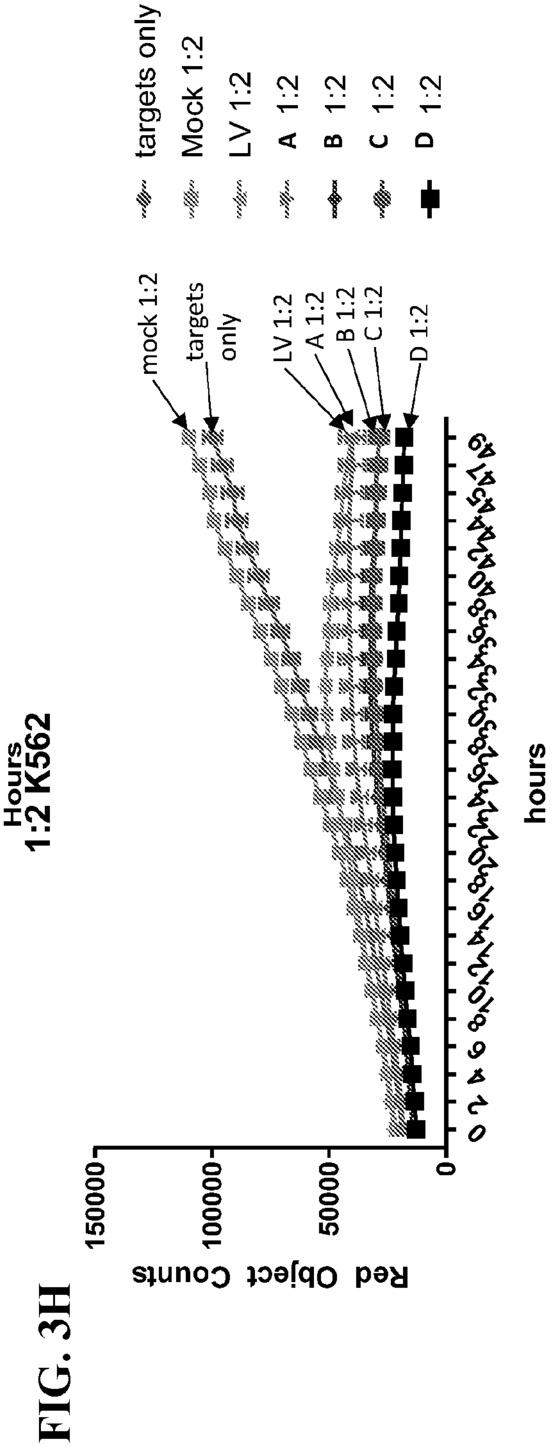

Results against the alternative K562-BCMA target cells that express relatively higher BCMA are shown in FIGS. 3B and 3F-3H. The percent total lysis during the experiment at each of the assessed E:T ratios for each group of engineered cells is shown in FIG. 3B, and the lysis of K562 target cells observed over time at the 2:1, 1:1 and 1:2 E:T ratios is shown in FIGS. 3F, 3G and 3H, respectively. In this experiment, cells engineered to express the exemplary anti-BCMA CAR by targeted integration at the CD247 locus via HDR exhibited comparable or greater cytolytic activity against the K562-BMCA target cells at the various E:T ratios, compared to cells engineered using lentiviral transduction. In particular, the greatest cytolytic activity was observed in cells engineered by targeted integration of the CAR using Polynucleotide D (expressed using the EF1α promoter and containing the endogenous CD3ζ 3' UTR), particularly at the lower E:T ratio, indicating its superior activity when used as a construct for HDR-mediated targeted integration.

Figure 4A:
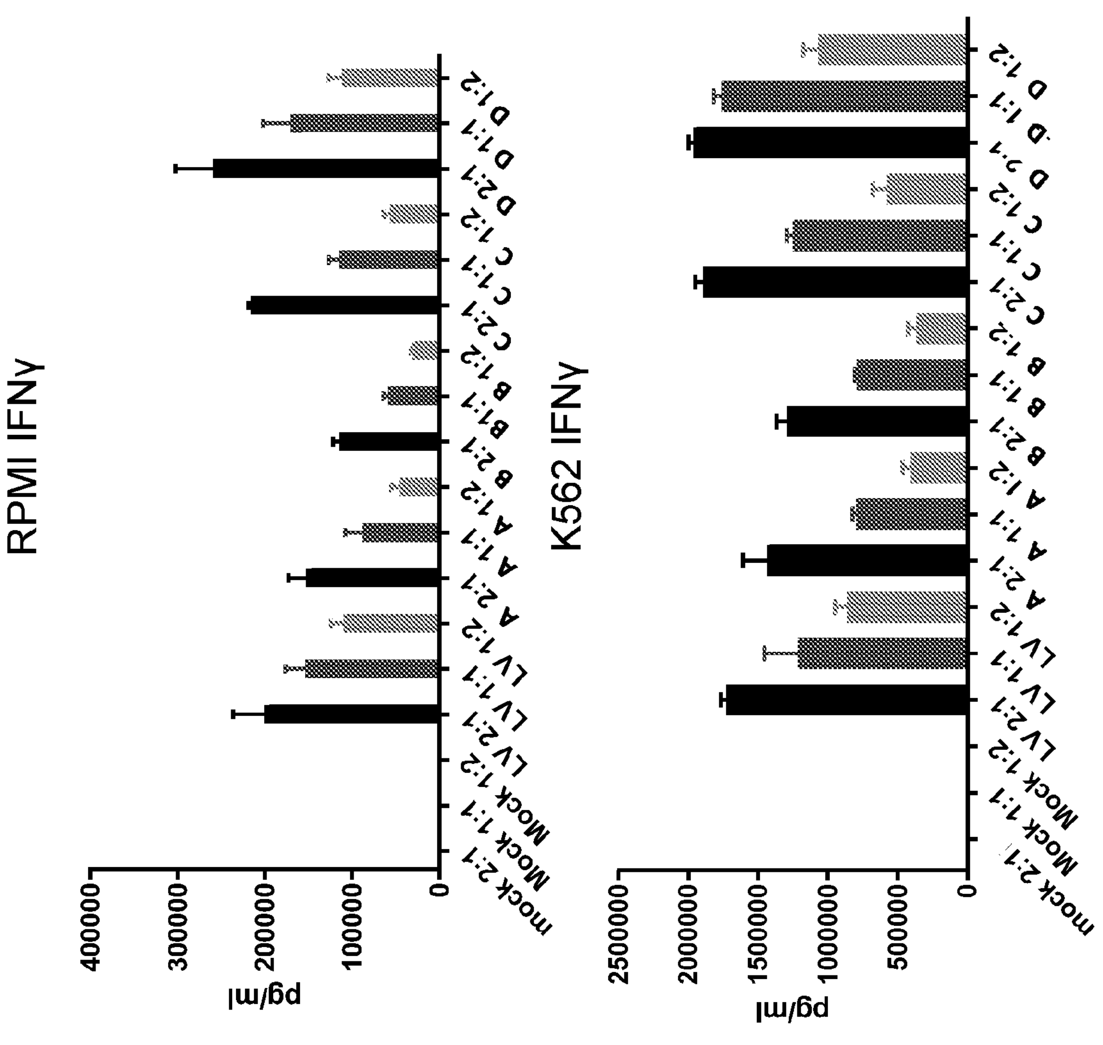
FIGS. 4A-4C depict the level of interferon-gamma (IFN-γ.
Figure 4B:
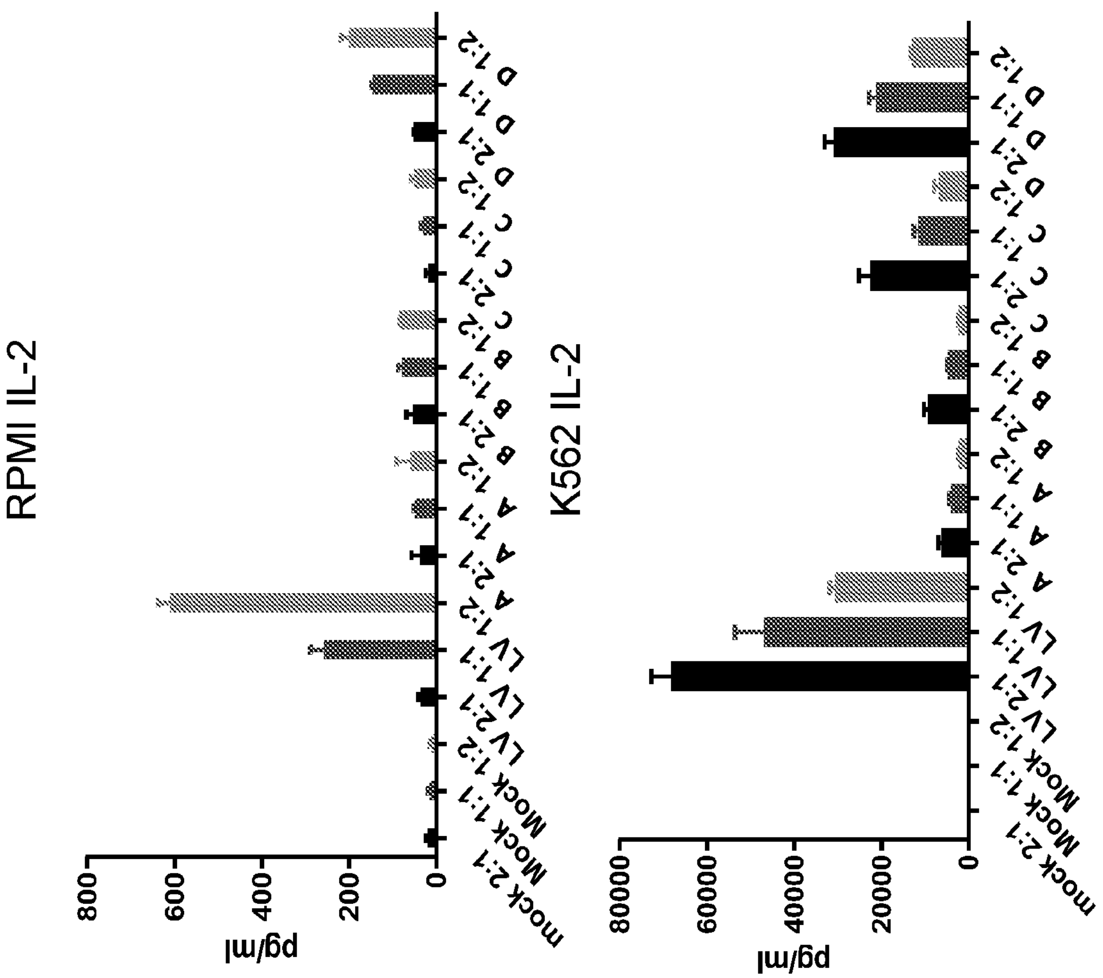
Figure 4C:
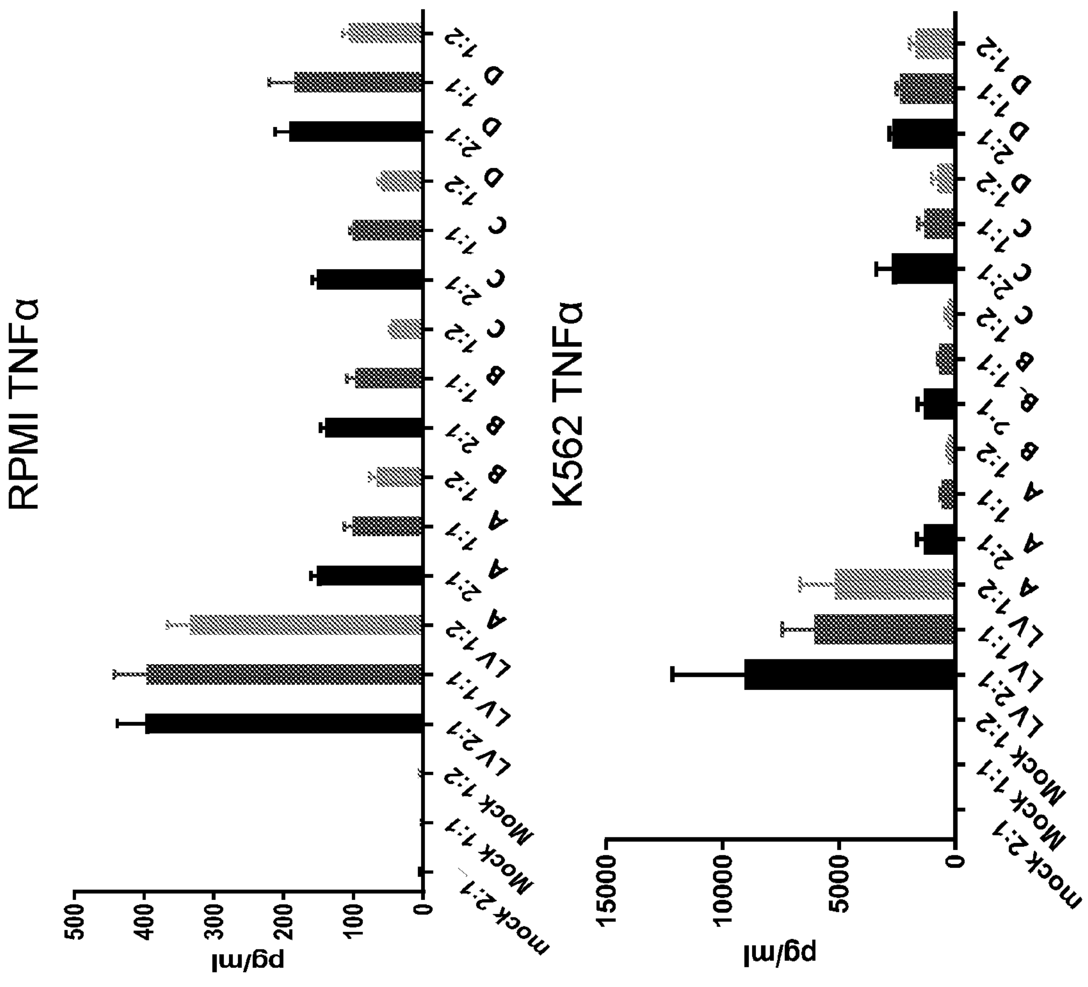

As shown in FIG. 4A, cells engineered using HDR produced comparable or higher IFN-γ compared to cells engineered using lentiviral transduction, against both BCMA-expressing cell line. In this study, cells engineered by targeted integration of the CAR using Polynucleotide D exhibited the highest general production of IFN-γ. As shown in FIGS. 4B-4C, IL-2 and TNF-α production was lower in cells engineered by targeted integration of the CAR into the CD247 locus using HDR.

The results were consistent with comparable or improved activity of primary T cells engineered to express an exemplary CAR by HDR-mediated integration of the nucleic acid sequences encoding the CAR or a portion thereof at the endogenous CD247 locus, compared to cells engineered using lentiviral transduction.

Example 4 Comparison of Expression of CAR in T Cell by HDR-Mediated Integration Using Various Template Polynucleotide Constructs or by Lentiviral Delivery T cells were engineered to express an exemplary CAR by targeting the nucleic acid sequences encoding all or a portion the CAR for integration at the endogenous CD247 locus (encoding CD3ζ), via HDR using various constructs as described above, or by lentiviral delivery, and expression and activity of the CAR was assessed.

Figure 5:
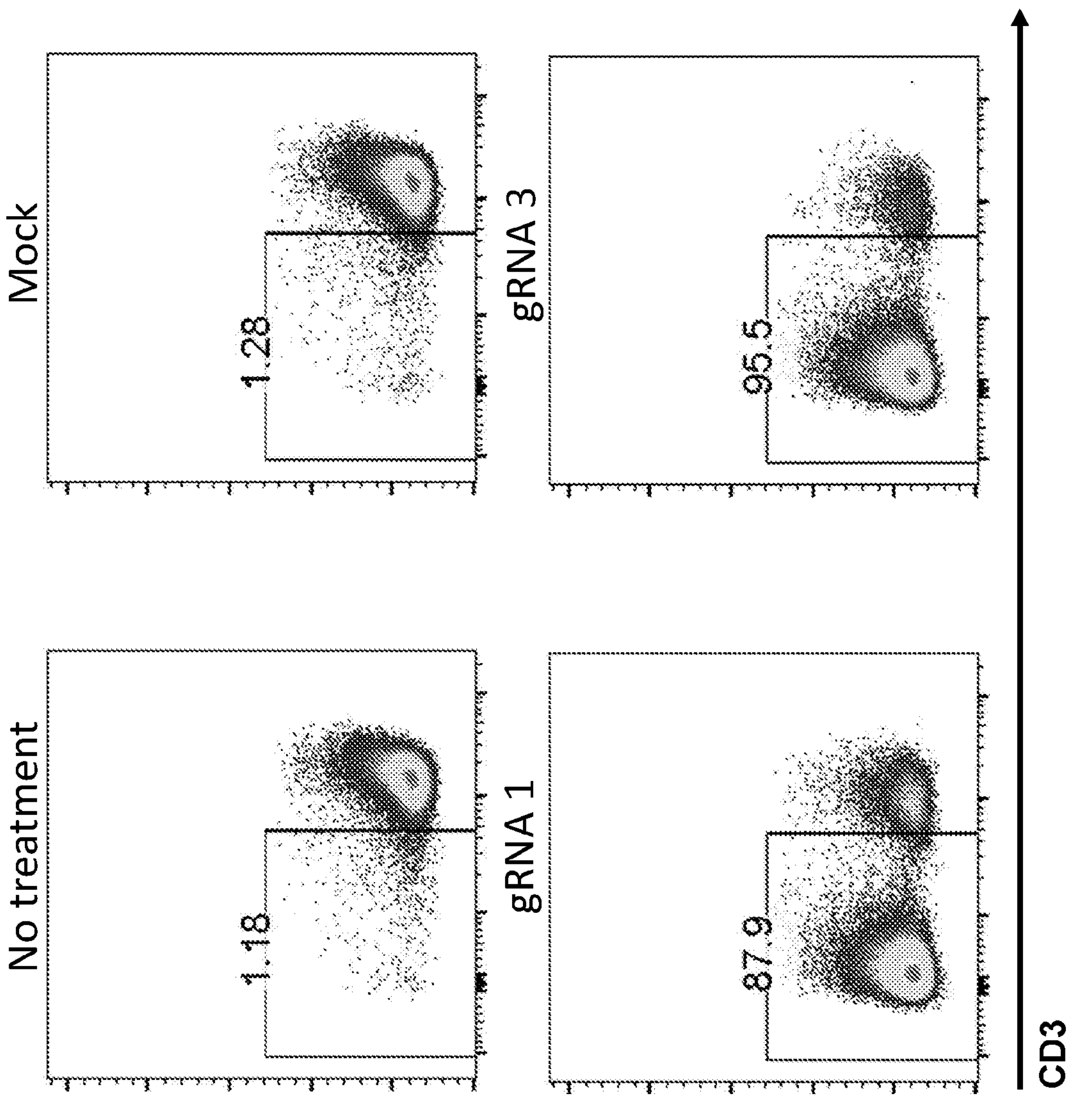
FIG. 5 depicts surface expression of CD3, as assessed by flow cytometry, in T cells that were electroporated with ribonucleoprotein (RNP) complexes containing CD247-targeting gRNA 1 or gRNA 3, each with Alt-R modifications (IDT Technologies; Coralville, IA),at a gRNA to Cas9 protein at a ratio of about 2.6:1 and a concentration of 25 μM.

Primary human T cells were stimulated as described in Example 1 above, and the stimulated cells were electroporated with RNP complexes containing synthesized gRNA 1 or gRNA 3, each with Alt-R modifications (IDT Technologies; Coralville, IA). The RNP complexes contained gRNA to Cas9 protein at a ratio of about 2.6:1 and the cells were electroporated with RNP at a concentration of 25 μM. As shown in FIG. 5, approximately 87.9% and 95.5% of the cells were knocked out for CD3 expression using gRNA 1 and gRNA 3, respectively. These results support that modification of the gRNA, ratio of the gRNA to Cas9 protein and/or higher concentration of RNPs resulted in higher efficiency of knock-out of the CD247 locus.

For generation of CAR-expressing cells by HDR, primary human CD4+ and CD8+ T cells were isolated from three human donor subjects (Donors 1-3), stimulated and electroporated with 25 μM of RNP complexes containing CD247-targeting modified gRNA 1 (Donor 1) or gRNA 3 (Donors 2 and 3) as described above Immediately following electroporation, the cells were incubated with AAV preparations containing Polynucleotides A, B, C, D (as set forth in Table E1 above). As a control, cells were engineered by introducing nucleic acid sequences encoding the anti-BCMA CAR via lentiviral transduction, or electroporated with CD247-targeting RNP but not contacted with AAV preparations, or mock treated (mock). Four days after electroporation and/or transduction, cells were stained with CD3 epsilon (anti-CD3ε) antibody and a BCMA-Fc (soluble human BCMA fused at its C-terminus to an Fc region of IgG) fusion polypeptide, to detect expression of the anti-BCMA CAR.

The cells were incubated with labeled MM.1S (ATCC® CRL-2974™) human B lymphoblast target cells, at an effector:target (E:T) ratio of 2:1 or 1:2, and the loss of NucLight Red (NLR)-labeled viable target cells was measured over three days, as determined by red fluorescent signal (using the IncuCyte® Live Cell Analysis System, Essen Bioscience). The percent of lysed cells (% lysis) was determined, normalized across three donors and averaged from triplicate samples. Cytokine production by collecting supernatants from the co-cultured cells at 24 hours, and measuring IFN-γ, TNF-α and IL-2, using a multiplex cytokine immunoassay.

Figure 6A:
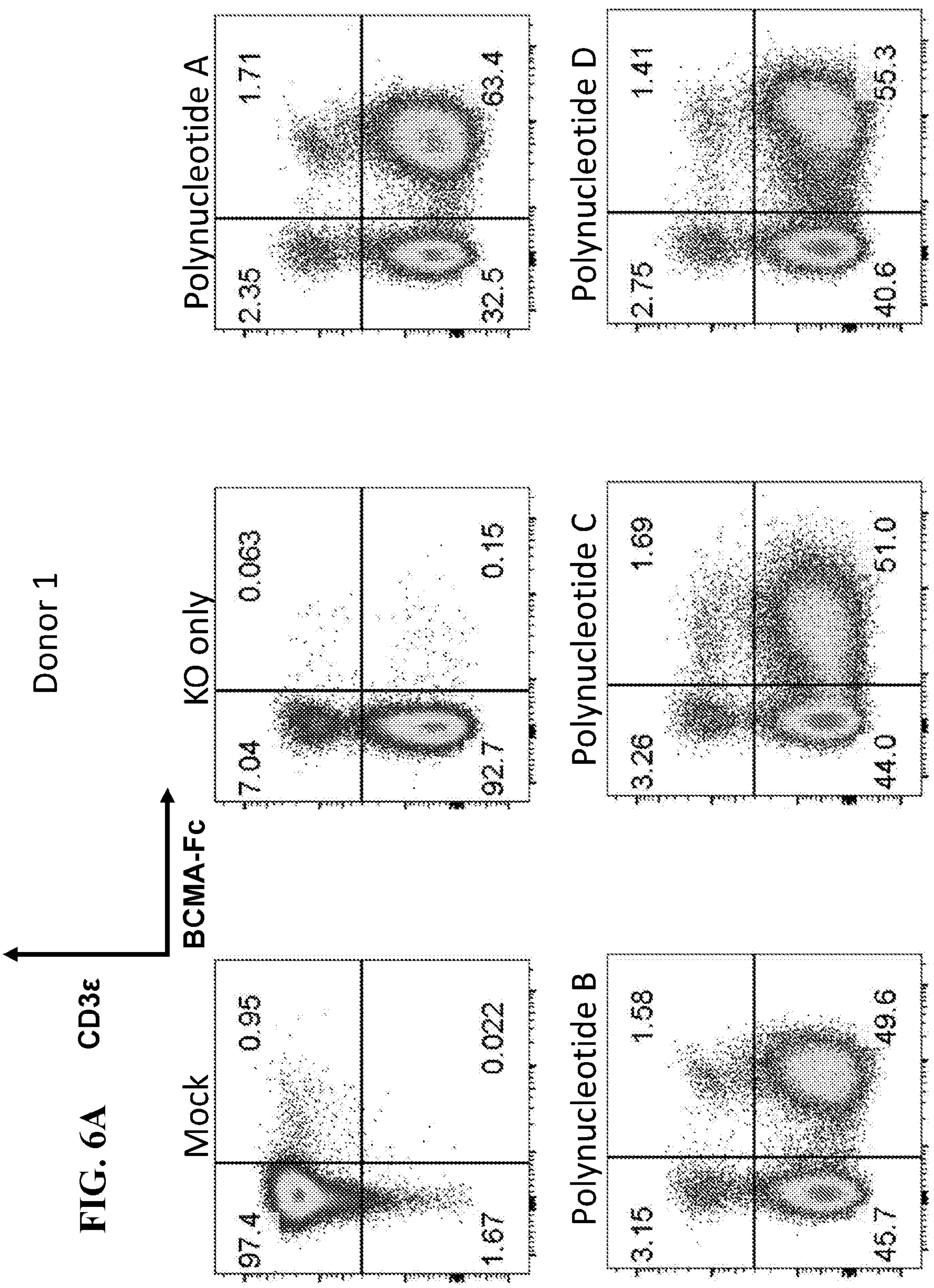
FIGS. 6A-6B depicts the surface expression of CD3 (detected using an anti-CD3ε antibody) and an anti-BCMA chimeric antigen receptor (CAR) (detected using BCMA-Fc; soluble human BCMA fused at its C-terminus to an Fc region of IgG), as assessed by flow cytometry, in T cells from a representative donor (Donor 1) that were electroporated with an RNP complex containing CD247-targeting gRNA 3 and incubated adeno-associated virus (AAV) constructs that contained one of four polynucleotides (Polynucleotides A, B, C, D; described in Table E1); or T cells engineered to express the anti-BCMA CAR by lentiviral delivery (lentivirus; see FIG. 6B); T cells subject to a mock electroporation and transduction (mock) or T cells subject to mock transduction and electroporation with CD247-targeting RNP only (KO only) as controls.
Figure 6B:
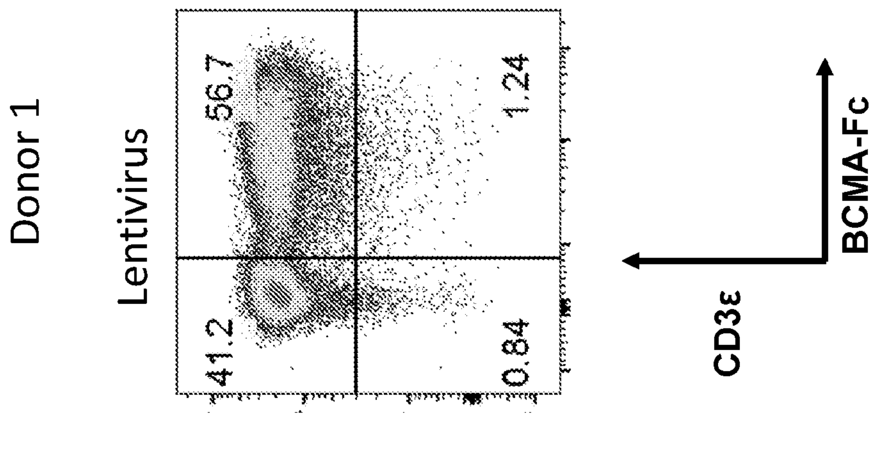
Figure 6C:
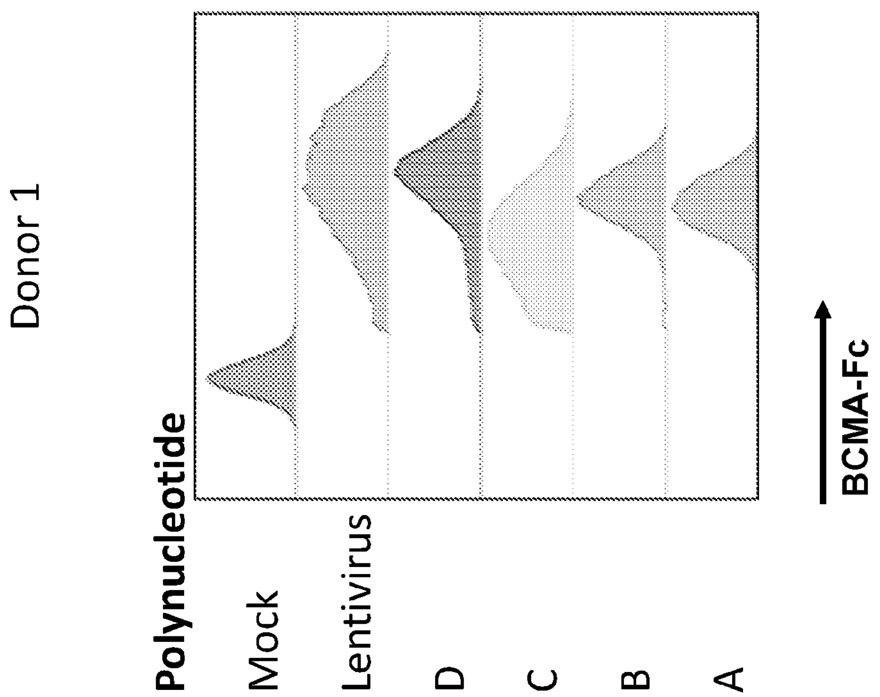
FIG. 6C shows a histogram of anti-BCMA CAR expression in each group.

Representative results from an exemplary donor are shown in FIGS. 6A-6C. CD3 knockout efficiency as shown by the CD3ε population in the gRNA 3 in this experiment was approximately 90%. Introduction of each of the 4 template polynucleotides for targeted integration by HDR at the CD247 locus (Polynucleotides A, B, C, D), resulted in approximately 49% to 65% of the cells expressing the anti-BCMA CAR on the surface of the cell. In cells targeted for integration into the CD247 locus by HDR (see Polynucleotide A, B, C and D panels of FIG. 6A), there was a loss of CD3 surface expression in cells expressing anti-BCMA CAR consistent with knock out of CD247 in some cells. As shown in FIG. 6B, lentiviral delivery resulted in approximately 58% of the cells expressing the anti-BCMA CAR on the surface of the cell. The percentage of cells in the quadrants in flow cytometry plots, gated similarly as in FIGS. 6A-6B, in results from two additional donors (Donors 2 and 3, CD3 knockout using gRNA 3) are shown in Tables E2 and E3 below.

TABLE E2

Percentage of cells present in each indicated quadrant in Flow Cytometry Plots for Donor 2 Engineered Cells

| Cells | CD3+/BCMA− quadrant | CD3+/BCMA+ quadrant | CD3−/BCMA+ quadrant | CD3−/BCMA− quadrant |
|---|---|---|---|---|
| Mock | 98.6 | 0.45 | 8.32E−3 | 0.95 |
| KO only | 16.3 | 0.045 | 0.096 | 83.6 |
| Polynucleotide A | 7.76 | 1.89 | 42.5 | 48.1 |
| Polynucleotide B | 8.75 | 1.46 | 31.0 | 58.8 |
| Polynucleotide C | 8.55 | 1.44 | 29.1 | 60.9 |
| Polynucleotide D | 8.46 | 1.66 | 36.1 | 53.7 |
| Lentivirus | 38.2 | 60.6 | 0.65 | 0.52 |

TABLE E3

Percentage of cells present in each indicated quadrant in Flow Cytometry Plots for Donor 3 Engineered Cells

| Cells | CD3+/BCMA− quadrant | CD3+/BCMA+ quadrant | CD3−/BCMA+ quadrant | CD3−/BCMA− quadrant |
|---|---|---|---|---|
| Mock | 95.8 | 0.72 | 0.021 | 3.44 |
| KO only | 7.57 | 0.043 | 0.19 | 92.2 |
| Polynucleotide A | 1.41 | 1.33 | 66.7 | 30.6 |
| Polynucleotide B | 11.0 | 2.13 | 47.0 | 39.9 |
| Polynucleotide C | 2.46 | 1.59 | 54.7 | 41.2 |
| Polynucleotide D | 3.35 | 1.84 | 55.6 | 39.3 |
| Lentivirus | 51.4 | 44.7 | 2.14 | 1.79 |

As shown in FIG. 6C, the distribution of level of CAR expression was more narrow and uniform, among cells engineered by HDR-mediated targeted integration using strategies in which the CAR was engineered to be expressed under the control of the heterologous EF1α promoter and contain the endogenous CD3ζ 3' UTR, compared to strategies in which the HDR template integrated the heterologous EF1α promoter and a full exogenous CAR into the CD247 locus (i.e., compare Polynucleotide D (endogenous CD3ζ 3' UTR) to Polynucleotide C (heterologous 3' UTR). The level of CAR expression was also tighter than in cells engineered to express the CAR by lentiviral delivery. This result was consistent with a lower coefficient of variation and tighter ranges in the level of expression of the CAR in cells engineered by HDR.

Figure 7B:
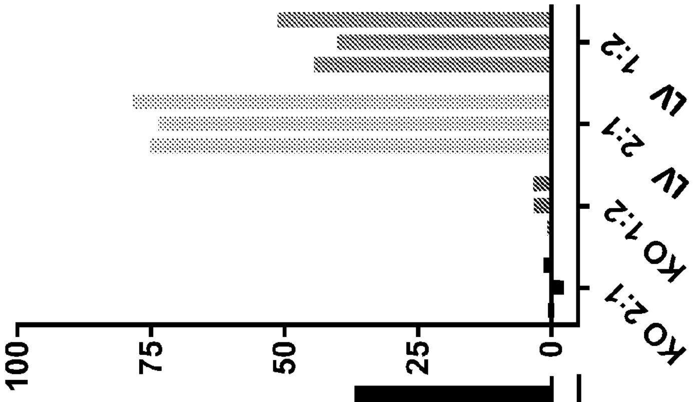
FIGS. 7A-7B shows the percent total lysis from a cytolytic activity assay after a co-culture of CAR-expressing T cells engineered using AAV constructs containing one of four polynucleotides (Polynucleotides A, B, C, D; described in Table E1 see FIG. 7A) containing transgene sequences encoding an anti-BCMA CAR and MM.1S (ATCC® CRL-2974™) human B lymphoblast target cells, at E:T ratio of 2:1 or 1:2. T cells engineered to express the anti-BCMA CAR by lentiviral delivery (lentivirus; see FIG. 7B) and T cells subject to mock transduction and electroporation with CD247-targeting RNP only (KO) were also assessed as controls. The % lysis values were averaged from triplicate samples and normalized across three donors.
Figure 7A:
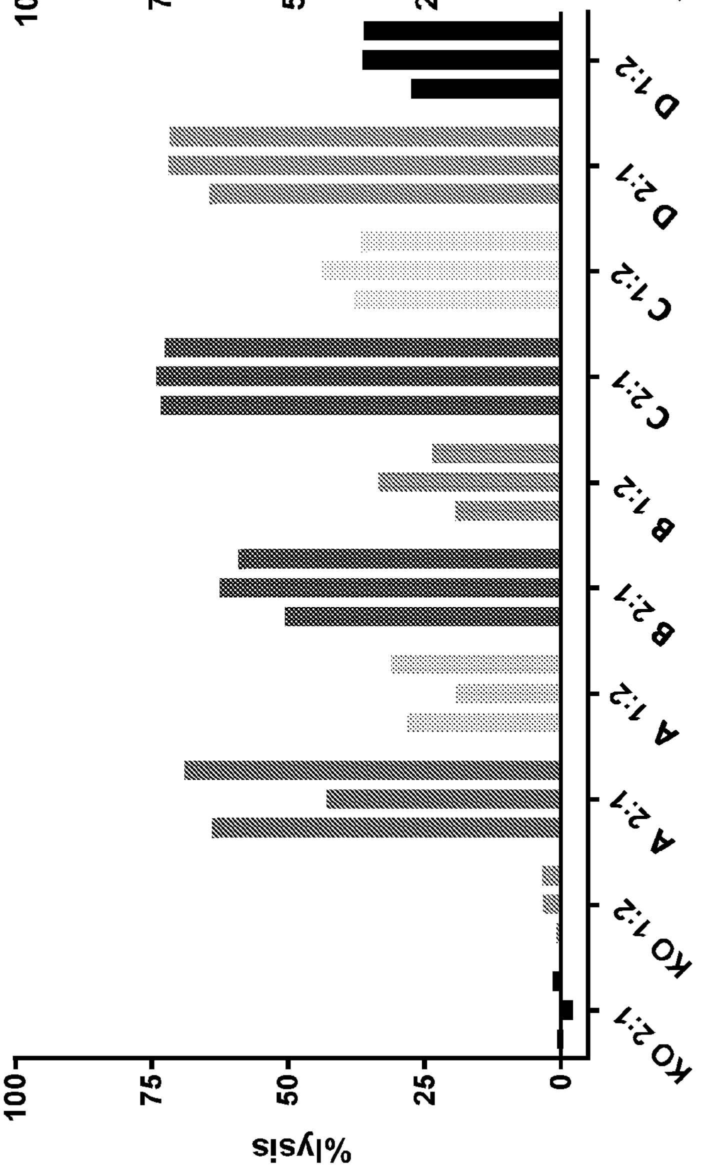

As shown in FIG. 7A, among cells engineered by HDR using different polynucleotides, cytolytic activity as represented by % lysis was generally higher in cells engineered by HDR with CAR expressed under the control of the heterologous EF1α promoter (Polynucleotides C and D), compared to cells engineered by HDR with CAR expressed under the control of the endogenous CD247 promoter (Polynucleotides A and B). As shown in FIG. 7B, cytolytic activity as represented by % lysis was similar to that observed in cells engineered by lentiviral delivery.

Figure 8B:
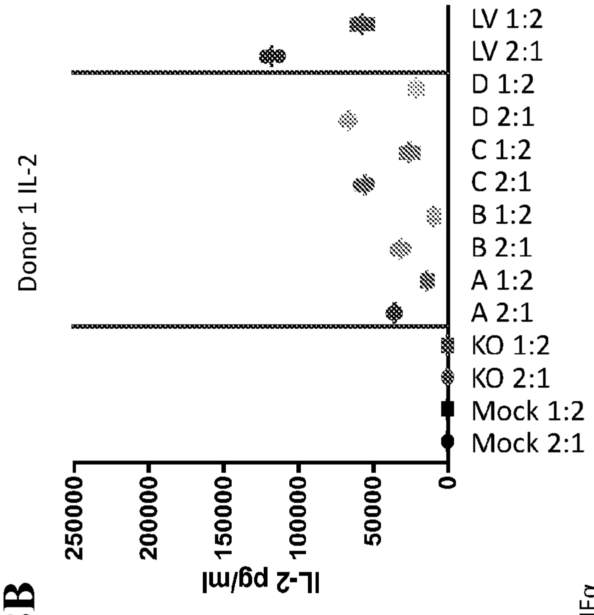
FIGS. 8A-8C depict the level of interferon-gamma (IFN-γ.
Figure 8A:
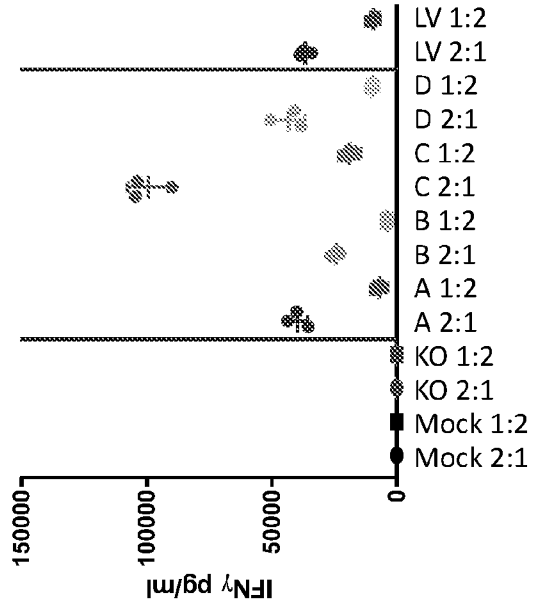
Figure 8C:
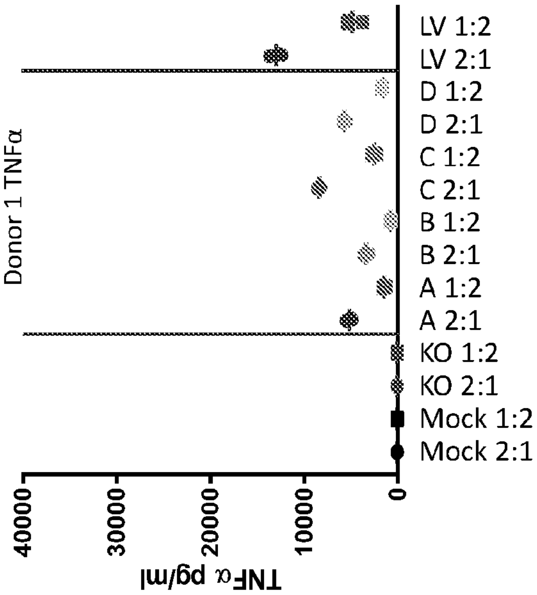

As shown in FIGS. 8A-8C, the level of IFN-γ (FIG. 8A), TNF-α (FIG. 8B) and IL-2 (FIG. 8C) production by cells engineered by HDR was generally similar or lower compared to cells engineered using lentiviral delivery. Among cells engineered by HDR, cells with CAR expressed using the EF1α promoter and containing the endogenous CD3ζ 3' UTR (Polynucleotide D) produced the highest IL-2, and cells with CAR expressed using the EF1α promoter and SV40pA (Polynucleotide C) exhibited the highest IFN-γ production in one donor.

The results were consistent with primary T cells engineered to express an exemplary CAR by HDR-mediated integration of the nucleic acid sequences encoding the CAR or a portion thereof, for example, using a construct that contains the heterologous EF1α promoter and containing the endogenous CD3ζ 3' UTR, at the endogenous CD247 locus, resulting in cells expressing functional CARs with comparable or improved cytolytic activity and cytokine production compared to cells engineered by lentiviral delivery. The results support the use of HDR-mediated integration of the nucleic acid sequences encoding the CAR or a portion thereof at the CD247 locus (encoding CD3ζ) for expression of the CAR with the 3' UTR of the endogenous CD247 locus for engineering T cells that exhibit high and uniform CAR expression with consistent functional activity.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|---|---|
| 1 | ESKYGPPCPPCP | spacer (IgG4hinge) (aa) |
| 2 | GAATCTAAGTACGGACCGCCCTGCCCCCCTTGCCCT | spacer (IgG4hinge) (nt) |
| 3 | ESKYGPPCPPCPGQPREPQVYTLPPSQEEMTKNQVSLTCLVKGFYPSDIAVEWESNG<br>QPENNYKTTPPVLDSDGSFFLYSRLTVDKSRWQEGNVFSCSVMHEALHNHYTQKSLS<br>LSLGK | Hinge-$C_H3$ spacer |
| 4 | ESKYGPPCPPCPAPEFLGGPSVFLFPPKPKDTLMISRTPEVTCVVVDVSQEDPEVQF<br>NWYVDGVEVHNAKTKPREEQFNSTYRVVSVLTVLHQDWLNGKEYKCKVSNKGLPSSI<br>EKTISKAKGQPREPQVYTLPPSQEEMTKNQVSLTCLVKGFYPSDIAVEWESNGQPEN<br>NYKTTPPVLDSDGSFFLYSRLTVDKSRWQEGNVFSCSVMHEALHNHYTQKSLSLSLG<br>K | Hinge-CH2-$C_H3$ spacer |
| 5 | RWPESPKAQASSVPTAQPQAEGSLAKATTAPATTRNTGRGGEEKKKEKEKEEQEERE<br>TKTPECPSHTQPLGVYLLTPAVQDLWLRDKATFTCFVVGSDLKDAHLTWEVAGKVPT<br>GGVEEGLLERHSNGSQSQHSRLTLPRSLWNAGTSVTCTLNHPSLPPQRLMALREPAA<br>QAPVKLSLNLLASSDPPEAASWLLCEVSGFSPPNILLMWLEDQREVNTSGFAPARPP<br>PQPGSTTFWAWSVLRVPAPPSPQPATYTCVVSHEDSRTLLNASRSLEVSYVTDH | IgD-hinge-Fc |
| 6 | LEGGGEGRGSLLTCGDVEENPGPR | T2A |
| 7 | MLLLVTSLLLCELPHPAFLLIPRKVCNGIGIGEFKDSLSINATNIKHFKNCTSISGD<br>LHILPVAFRGDSFTHTPPLDPQELDILKTVKEITGFLLIQAWPENRTDLHAFENLEI<br>IRGRTKQHGQFSLAVVSLNITSLGLRSLKEISDGDVIISGNKNLCYANTINWKKLFG<br>TSGQKTKIISNRGENSCKATGQVCHALCSPEGCWGPEPRDCVSCRNVSRGRECVDKC<br>NLLEGEPREFVENSECIQCHPECLPQAMNITCTGRGPDNCIQCAHYIDGPHCVKTCP<br>AGVMGENNTLVWKYADAGHVCHLCHPNCTYGCTGPGLEGCPTNGPKIPSIATGMVGA<br>LLLLLVVALGIGLFM | tEGFR |
| 8 | FWVLVVVGGVLACYSLLVTVAFIIFWV | CD28 (aa 153-179 of Uniprot P10747) |
| 9 | IEVMYPPPYLDNEKSNGTIIHVKGKHLCPSPLFPGPSKP<br>FWVLVVVGGVLACYSLLVTVAFIIFWV | CD28 (aa 114-179 of Uniprot P10747) |
| 10 | RSKRSRLLHSDYMNMTPRRPGPTRKHYQPYAPPRDFAAYRS | CD28 (aa 180-220 of Uniprot P10747) |
| 11 | RSKRSRGGHSDYMNMTPRRPGPTRKHYQPYAPPRDFAAYRS | CD28 (LL to GG) |
| 12 | KRGRKKLLYIFKQPFMRPVQTTQEEDGCSCRFPEEEEGGCEL | 4-1BB (aa 214-255 of Q07011.1) |

-continued

| Sequences | | |
|---|---|---|
| # | SEQUENCE | ANNOTATION |
| 13 | RVKFSRSADAPAYQQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPR | CD3 zeta |
| 14 | RVKFSRSAEPPAYQQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPR | CD3 zeta |
| 15 | RVKFSRSADAPAYKQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPR | CD3 zeta |
| 16 | RKVCNGIGIGEFKDSLSINATNIKHFKNCTSISGDLHILPVAFRGDSFTHTPPLDPQ ELDILKTVKEITGFLLIQAWPENRTDLHAFENLEIIRGRTKQHGQFSLAVVSLNITS LGLRSLKEISDGDVIISGNKNLCYANTINWKKLFGTSGQKTKIISNRGENSCKATGQ VCHALCSPEGCWGPEPRDCVSCRNVSRGRECVDKCNLLEGEPREFVENSECIQCHPE CLPQAMNITCTGRGPDNCIQCAHYIDGPHCVKTCPAGVMGENNTLVWKYADAGHVCH LCHPNCTYGCTGPGLEGCPTNGPKIPSIATGMVGALLLLLVVALGIGLFM | tEGFR |
| 17 | EGRGSLLTCGDVEENPGP | T2A |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | -PGGG-(SGGGG)5-P- wherein P is proline, G is glycine and S is serine | Linker |
| 23 | GSADDAKKDAAKKDGKS | Linker |
| 24 | atgcttctcctggtgacaagccttctgctctgtgagttaccacacccagcattcctc ctgatccca | GMCSFR alpha chain signal sequence |
| 25 | MLLLVTSLLLCELPHPAFLLIP | GMCSFR alpha chain signal sequence |
| 26 | MALPVTALLLPLALLLHA | CD8 alpha signal peptide |
| 27 | EPKSCDKTHTCPPCP | Hinge |
| 28 | ERKCCVECPPCP | Hinge |
| 29 | ELKTPLGDTHTCPRCPEPKSCDTPPPCPRCPEPKSCDTPPPCPRCPEPKSCDTPPPC PRCP | Hinge |
| 30 | ESKYGPPCPSCP | Hinge |
| 31 | $X_1PPX_2P$<br>$X_1$ is glycine, cysteine or arginine<br>$X_2$ is cysteine or threonine | Hinge |
| 32 | Tyr Gly Pro Pro Cys Pro Pro Cys Pro | Hinge |
| 33 | Lys Tyr Gly Pro Pro Cys Pro Pro Cys Pro | Hinge |
| 34 | Glu Val Val Val Lys Tyr Gly Pro Pro Cys Pro Pro Cys Pro | Hinge |
| 35 | RASQDISKYLN | CDR L1 |
| 36 | SRLHSGV | CDR L2 |
| 37 | GNTLPYTFG | CDR L3 |
| 38 | DYGVS | CDR H1 |
| 39 | VIWGSETTYYNSALKS | CDR H2 |
| 40 | YAMDYWG | CDR H3 |

-continued

| Sequences | | |
|---|---|---|
| # | SEQUENCE | ANNOTATION |
| 41 | EVKLQESGPGLVAPSQSLSVTCTVSGVSLPDYGVSWIRQPPRKGLEWLGVIWGSETT YYNSALKSRLTIIKDNSKSQVFLKMNSLQTDDTAIYYCAKHYYYGGSYAMDYWGQGT SVTVSS | VH |
| 42 | DIQMTQTTSSLSASLGDRVTISCRASQDISKYLNWYQQKPDGTVKLLIYHTSRLHSG VPSRFSGSGSGTDYSLTISNLEQEDIATYFCQQGNTLPYTFGGGTKLEIT | VL |
| 43 | DIQMTQTTSSLSASLGDRVTISCRASQDIsKYLNWYQQKPDGTVKLLIYHTSRLHSG VPSRFSGSGSGTDYSLTISNLEQEDIATYFCQQGNTLPYTFGGGTKLEITGSTSGSG KPGSGEGSTKGEVKLQESGPGLVAPSQSLSVTCTVSGVSLPDYGVSWIRQPPRKGLE WLGVIWGSETTYYNSALKSRLTIIKDNSKSQVFLKMNSLQTDDTAIYYCAKHYYYGG SYAMDYWGQGTSVTVSS | scFv |
| 44 | KASQNVGTNVA | CDR L1 |
| 45 | SATYRNS | CDR L2 |
| 46 | QQYNRYPYT | CDR L3 |
| 47 | SYWMN | CDR H1 |
| 48 | QIYPGDGDTNYNGKFKG | CDR H2 |
| 49 | KTISSVVDFYFDY | CDR H3 |
| 50 | EVKLQQSGAELVRPGSSVKISCKASGYAFSSYWMNWVKQRPGQGLEWIGQIYPGDGD TNYNGKFKGQATLTADKSSSTAYMQLSGLTSEDSAVYFCARKTISSVVDFYFDYWGQ GTTVTVSS | VH |
| 51 | DIELTQSPKFMSTSVGDRVSVTCKASQNVGTNVAWYQQKPGQSPKPLIYSATYRNSG VPDRFTGSGSGTDFTLTITNVQSKDLADYFCQQYNRYPYTSGGGTKLEIKR | VL |
| 52 | GGGGSGGGGSGGGGS | Linker |
| 53 | EVKLQQSGAELVRPGSSVKISCKASGYAFSSYWMNWVKQRPGQGLEWIGQIYPGDGD TNYNGKFKGQATLTADKSSSTAYMQLSGLTSEDSAVYFCARKTISSVVDFYFDYWGQ GTTVTVSSGGGGSGGGGSGGGGSDIELTQSPKFMSTSVGDRVSVTCKASQNVGTNVA WYQQKPGQSPKPLIYSATYRNSGVPDRFTGSGSGTDFTLTITNVQSKDLADYFCQQY NRYPYTSGGGTKLEIKR | scFv |
| 54 | HYYYGGSYAMDY | HC-CDR3 |
| 55 | HTSRLHS | LC-CDR2 |
| 56 | QQGNTLPYT | LC-CDR3 |
| 57 | gacatccagatgacccagaccacctccagcctgagcgccagcctgggcgaccgggtg accatcagctgccgggccagccaggacatcagcaagtacctgaactggtatcagcag aagcccgacggcaccgtcaagctgctgatctaccacaccagccggctgcacagcggc gtgcccagccggtttagcggcagcggctccggcaccgactacagcctgaccatctcc aacctggaacaggaagatatcgccacctacttttgccagcagggcaacacactgccc tacacctttggcggcggaacaaagctggaaatcaccggcagcacctccggcagcggc aagcctggcagcggcgagggcagcaccaagggcgaggtgaagctgcaggaaagcggc cctggcctggtggccccccagccagagcctgagcgtgacctgcaccgtgagcggcgtg agcctgcccgactacggcgtgagctggatccggcagcccccccaggaagggcctggaa tggctgggcgtgatctggggcagcgagaccacctactacaacagcgccctgaagagc cggctgaccatcatcaaggacaacagcaagagccaggtgttcctgaagatgaacagc ctgcagaccgacgacaccgccatctactactgcgccaagcactactactacggcggc agctacgccatggactactggggccagggcaccagcgtgaccgtgagcagc | Sequence encoding scFv |
| 58 | GSTSGSGKPGSGEGSTKG | Linker |
| 59 | CACCTTCACTCTCAGGAACA | CD247 (CD3z) target sequence 1 |
| 60 | GAATGACACCATAGATGAAG | CD247 (CD3z) target sequence 2 |
| 61 | TGAAGAGGATTCCATCCAGC | CD247 (CD3z) target sequence 3 |
| 62 | TCCAGCAGGTAGCAGAGTTT | CD247 (CD3z) target sequence 4 |

Sequences

| # | SEQUENCE | ANNOTATION |
|---|---|---|
| 63 | CACCTTCACTCTCAGGAACAGG | CD247 (CD3z) target sequence + PAM 1 |
| 64 | GAATGACACCATAGATGAAGAGG | CD247 (CD3z) target sequence + PAM 2 |
| 65 | TGAAGAGGATTCCATCCAGCAGG | CD247 (CD3z) target sequence + PAM 3 |
| 66 | TCCAGCAGGTAGCAGAGTTTGGG | CD247 (CD3z) target sequence + PAM 4 |
| 67 | AGACGCCCCCGCGTACCAGC | CD247 (CD3z) target sequence 5 |
| 68 | GCTGACTTACGTTATAGAGC | CD247 (CD3z) target sequence 6 |
| 69 | TTTCACCGCGGCCATCCTGC | CD247 (CD3z) target sequence 7 |
| 70 | TAATCGGCAACTGTGCCTGC | CD247 (CD3z) target sequence 8 |
| 71 | CGGAGGCCTACAGTGAGATT | CD247 (CD3z) target sequence 9 |
| 72 | TGGTACCCACCTTCACTCTC | CD247 (CD3z) target sequence 10 |
| 73 | MKWKALFTAAILQAQLPITEAQSFGLLDPKLCYLLDGILFIYGVILTALFLRVKFSR SADAPAYQQGQNQLYNELNLGRREEYDVLDKRRGRDPEMGGKPQRRKNPQEGLYNEL QKDKMAEAYSEIGMKGERRRGKGHDGLYQGLSTATKDTYDALHMQALPPR | CD247 isoform 1 precursor protein sequence (NCBI Reference Sequence: NP_932170.1) |
| 74 | tgctttctcaaaggccccacagtcctccacttcctggggaggtagctgcagaataaa accagcagagactccttttctcctaaccgtcccggccaccgctgcctcagcctctgc ctcccagcctctttctgagggaaaggacaagatgaagtggaaggcgcttttcaccgc ggccatcctgcaggcacagttgccgattacagaggcacagagctttggcctgctgga tcccaaactctgctacctgctggatggaatcctcttcatctatggtgtcattctcac tgccttgttcctgagagtgaagttcagcaggagcgcagacgcccccgcgtaccagca gggccagaaccagctctataacgagctcaatctaggacgaagagaggagtacgatgt tttggacaagagacgtggccgggaccctgagatggggggaaagccgcagagaaggaa gaaccctcaggaaggcctgtacaatgaactgcagaaagataagatggcggaggccta cagtgagattgggatgaaaggcgagcgccggaggggcaaggggcacgatggcctta ccagggtctcagtacagccaccaaggacacctacgacgcccttcacatgcaggccct gccccctcgctaacagccaggggatttcaccactcaaaggccagacctgcagacgcc cagattatgagacacaggatgaagcatttacaacccggttcactcttctcagccact gaagtattcccctttatgtacaggatgctttggttatatttagctccaaaccttcac acacagactgttgtccctgcactctttaagggagtgtactcccagggcttacggccc tggccttgggccctctggtttgccggtggtgcaggtagacctgtctcctggcggttc ctcgttctccctgggaggcgggcgcactgcctctcacagctgagttgttgagtctgt tttgtaaagtccccagagaaagcgcagatgctagcacatgccctaatgtctgtatca ctctgtgtctgagtggcttcactcctgctgtaaatttggcttctgttgtcaccttca cctcctttcaaggtaactgtactgggccatgttgtgcctccctggtgagagggccgg gcagaggggcagatggaaaggagcctaggccaggtgcaaccagggagctgcaggggc atgggaaggtgggcgggcaggggagggtcagccagggcctgcgagggcagcgggagc ctccctgcctcaggcctctgtgccgcaccattgaactgtaccatgtgctacaggggc cagaagatgaacagactgaccttgatgagctgtgcacaaagtggcataaaaaacatg tggttacacagtgtgaataaagtgctgcggagcaagaggaggccgttgattcacttc acgctttcagcgaatgacaaaatcatctttgtgaaggcctcgcaggaagacccaaca catgggacctataactgcccagcggacagtggcaggacaggaaaaacccgtcaatgt actaggatactgctgcgtcattacagggcacaggccatggatggaaaacgctctctg ctctgctttttttctactgttttaatttatactggcatgctaaagccttcctatttt gcataataaatgcttcagtgaaaatgcaaaaaaaaaa | CD247 isoform 1 precursor mRNA sequence (NCBI Reference Sequence: NM_198053.2) |

-continued

| # | SEQUENCE | ANNOTATION |
|---|---|---|
| 75 | MKWKALFTAAILQAQLPITEAQSFGLLDPKLCYLLDGILFIYGVILTALFLRVKFSR SADAPAYQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR | CD247 isoform 2 precursor protein sequence (NCBI Reference Sequence: NP_000725.1) |
| 76 | tgctttctcaaaggccccacagtcctccacttcctggggaggtagctgcagaataaa accagcagagactccttttctcctaaccgtcccggccaccgctgcctcagcctctgc ctcccagcctctttctgagggaaaggacaagatgaagtggaaggcgcttttcaccgc ggccatcctgcaggcacagttgccgattacagaggcacagagctttggcctgctgga tcccaaactctgctacctgctggatggaatcctcttcatctatggtgtcattctcac tgccttgttcctgagagtgaagttcagcaggagcgcagacgcccccgcgtaccagca gggccagaaccagctctataacgagctcaatctaggacgaagagaggagtacgatgt tttggacaagagacgtggccgggaccctgagatggggggaaagccgagaaggaagaa ccctcaggaaggcctgtacaatgaactgcagaaagataagatggcggaggcctacag tgagattgggatgaaaggcgagcgccggaggggcaaggggcacgatggcctttacca gggtctcagtacagccaccaaggacacctacgacgcccttcacatgcaggccctgcc ccctcgctaacagccaggggatttcaccactcaaaggccagacctgcagacgcccag attatgagacacaggatgaagcatttacaacccggttcactcttctcagccactgaa gtattcccctttatgtacaggatgctttggttatatttagctccaaaccttcacaca cagactgttgtccctgcactctttaagggagtgtactcccagggcttacggccctgg ccttgggccctctggtttgccggtggtgcaggtagacctgtctcctggcggttcctc gttctccctgggaggcgggcgcactgcctctcacagctgagttgttgagtctgtttt gtaaagtccccagagaaagcgcagatgctagcacatgccctaatgtctgtatcactc tgtgtctgagtggcttcactcctgctgtaaatttggcttctgttgtcaccttcacct cctttcaaggtaactgtactgggccatgttgtgcctccctggtgagagggccgggca gaggggcagatggaaaggagcctaggccaggtgcaaccagggagctgcaggggcatg ggaaggtgggcgggcaggggagggtcagccagggcctgcgagggcagcgggagcctc cctgcctcaggcctctgtgccgcaccattgaactgtaccatgtgctacaggggccag aagatgaacagactgaccttgatgagctgtgcacaaagtggcataaaaaacatgtgg ttacacagtgtgaataaagtgctgcggagcaagaggaggccgttgattcacttcacg ctttcagcgaatgacaaaatcatctttgtgaaggcctcgcaggaagacccaacacat gggacctataactgcccagcggacagtggcaggacaggaaaaacccgtcaatgtact aggatactgctgcgtcattacagggcacaggccatggatggaaaacgctctctgctc tgcttttttttctactgttttaatttatactggcatgctaaagccttcctattttgca taataaatgcttcagtgaaaatgcaaaaaaaaaa | CD247 isoform 2 precursor mRNA sequence (NCBI Reference Sequence: NM_000734.3) |
| 77 | cgtgaggctccggtgcccgtcagtgggcagagcgcacatcgcccacagtccccgaga agttggggggaggggtcggcaattgaaccggtgcctagagaaggtggcgcggggtaa actgggaaagtgatgtcgtgtactggctccgcctttttcccgagggtgggggagaac cgtatataagtgcagtagtcgccgtgaacgttctttttcgcaacgggtttgccgcca gaacacaggtaagtgccgtgtgtggttcccgcgggcctggcctctttacgggttatg gcccttgcgtgccttgaattacttccacgcccctggctgcagtacgtgattcttgat cccgagcttcgggttggaagtgggtgggagagttcgaggccttgcgcttaaggagcc ccttcgcctcgtgcttgagttgaggcctggcctgggcgctggggccgccgcgtgcga atctggtggcaccttcgcgcctgtctcgctgctttcgataagtctctagccatttaa aatttttgatgacctgctgcgacgctttttttctggcaagatagtcttgtaaatgcg ggccaagatctgcacactggtatttcggtttttggggccgcgggcggcgacggggcc cgtgcgtcccagcgcacatgttcggcgaggcggggcctgcgagcgcggccaccgaga atcggacgggggtagtctcaagctggccggcctgctctggtgcctggcctcgcgccg ccgtgtatcgccccgccctgggcggcaaggctggcccggtcggcaccagttgcgtga gcggaaagatggccgcttcccggccctgctgcagggagctcaaaatggaggacgcgg cgctcgggagagcgggcgggtgagtcacccacacaaaggaaaagggcctttccgtcc tcagccgtcgcttcatgtgactccacggagtaccgggcgccgtccaggcacctcgat tagttctcgagcttttggagtacgtcgtctttaggttggggggaggggttttatgcg atggagtttccccacactgagtgggtggagactgaagttaggccagcttggcacttg atgtaattctccttggaatttgccctttttgagtttggatcttggttcattctcaag cctcagacagtggttcaaagtttttttcttccatttcaggtgtcgtgaa | EF1alpha promoter (GenBank: J04617.1) |
| 78 | CTGACCTCTTCTCTTCCTCCCACAG | human HBB splice acceptor site |
| 79 | TTTCTCTCCACAG | Human IgG splice acceptor site |
| 80 | AGATCCCACTGTCCTAGGCGGGAGAGTGCTTGGCACTGAGGAGGCAGGGAGTTGGGG GAGAGTTAACCCAGATTCTCCCTGTCCTAGTTAACTGTCAGATATTGAAATGATCTC ATTTGACCATCATTTGACCTATTGTCTCCCTGTGGGTAGGCCTCAGAGCCACACACC TCAGGCCAGGAGTACCATTCATCCAGACGTGAACATCTTCCCGAGGCTTCCAGAGTT CTTGGTTCACACCGGGGCTAACATGGCTGGGCTTCTGCTGCAGTGGCAGGAGCTCTG TGCACAGAGAACAGCCTCATCTGCTCGCCTTGTTTCCACCTCCCCTCCCATTGCCCC AGGTTCTTTGGCCCCACAGCGGCCACATCTGCCGTTGGTGCCAATAGGTTTTCCAGG AGCTGGTTGAGGTGGGAGGGAGGGAGAGGGTTGTGATCAGGCTGAGGCATGGGGATT | 5' homology arm |

-continued

Sequences

| # | SEQUENCE | ANNOTATION |
|---|---|---|
| | GGATATAGTCTCCGTGTCATGATTTATTTGGTCAGTCAGTCCTAGTGCCACCCTGGG<br>GTAATGGGGATGTGTTCTCGTCACCTTGGGCCTGGCTGACCAGCTTTATCTCTTGGC<br>ACAGAGGCACAGAGCTTTGGCCTGCTGGAT | |
| 81 | AGAGTGAAGGTGGGTACCACTGGGCTTTGGGAGGAGGGCACGGGGTCCCCCACTTGA<br>TGGATGTTCAGAGGGGCCTTGGTCTTGGAAGGTCTCAAGCTCGGGTGGTGCCTGGGG<br>CTTGGTATCCAGGAGCAAAGCAAGGACCAGCCAAGTGTGTGCCTTGAGTGGGCTGAG<br>GAGGAGGTGGCAGTGTCTGGCTGAGATGGACAGGGTAGGAGGGAGAGCCTGGTGCTA<br>GGCACCTCCATGACAAGCCGTACAAATGTGTGCACATCAGAGTGTCCCAGGGAAGGC<br>GATGCTACTGGTGACAAAGGGGCTTACACTCAGGCAGAGGTCCTTCTTTCCAAGTGT<br>GAATGAAGGCCATGTTAGCCTTTCTCTTGAAAAGGCCCTTTCCTCATCTGTAACTGG<br>GGAGCTGACCAGAGCGTGGGTTTTTCACTTGGTGCCTTGCAGACCCTGGATTTCTTC<br>GTGGGGCTGGTCATGGTGTGGGCAGAGATTGGAAGAATTTAGGAGTAAAGGGGAGAA<br>TCCAGTCCCAGTCATCACTTCAGTGCTTCTCAACCCATTTCTTGTTTGAATTTTGGA<br>CTTTGGCATAATATTTTATTTGAAAAACCA | 3' homology arm |
| 82 | GVQVETISPGDGRTFPKRGQTCVVHYTGMLEDGKKMDSSRDRNKPFKFMLGKQEVIR<br>GWEEGVAQMSVGQRAKLTISPDYAYGATGHPGIIPPHATLVFDVELLKLE | FKBP |
| 83 | GVQVETISPGDGRTFPKRGQTCVVHYTGMLEDGKKVDSSRDRNKPFKFMLGKQEVIR<br>GWEEGVAQMSVGQRAKLTISPDYAYGATGHPGIIPPHATLVFDVELLKLE | FKBP12v36 |
| 84 | MGSNKSKPKDASQRRR | human C-Src<br>acylation motif |
| 85 | MGCXC | dual acylation motif |
| 86 | CAAX | CAAX motif |
| 87 | CACCUUCACUCUCAGGAACA | CD247 (CD3z)<br>targeting domain 1 |
| 88 | GAAUGACACCAUAGAUGAAG | CD247 (CD3z)<br>targeting domain 2 |
| 89 | UGAAGAGGAUUCCAUCCAGC | CD247 (CD3z)<br>targeting domain 3 |
| 90 | UCCAGCAGGUAGCAGAGUUU | CD247 (CD3z)<br>targeting domain 4 |
| 91 | AGACGCCCCCGCGUACCAGC | CD247 (CD3z)<br>targeting domain 5 |
| 92 | GCUGACUUACGUUAUAGAGC | CD247 (CD3z)<br>targeting domain 6 |
| 93 | UUUCACCGCGGCCAUCCUGC | CD247 (CD3z)<br>targeting domain 7 |
| 94 | UAAUCGGCAACUGUGCCUGC | CD247 (CD3z)<br>targeting domain 8 |
| 95 | CGGAGGCCUACAGUGAGAUU | CD247 (CD3z)<br>targeting domain 9 |
| 96 | UGGUACCCACCUUCACUCUC | CD247 (CD3z)<br>targeting domain 10 |
| 97 | NNNNNNNNNNNNNNNNNNNNGUUUUAGAGCUAGAAAUAGCAAGUUAAAAUAAGGCUA<br>GUCCGUUAUCAACUUGAAAAAGUGGCACCGAGUCGGUGC | exemplary gRNA<br>complementary<br>domain |
| 98 | NNNNNNNNNNNNNNNNNNNNGUUUUAGAGCUAUGCUGAAA**AGCAUAGC**AAG**UUAAAA**<br>UAAGGCUAGUCCGUUAUCAACUUGAAAAAGUGGCACCGAGUCGGUGC | exemplary gRNA<br>complementary<br>domain |
| 99 | NNNNNNNNNNNNNNNNNNNNGUUUUAGAGCUAUGCUGGAAA**CAGCAUAGC**AAG**UUAA**<br>**AAU**AAGGCUAGUCCGUUAUCAACUUGAAAAAGUGGCACCGAGUCGGUGC | exemplary gRNA<br>complementary<br>domain |
| 100 | NNNNNNNNNNNNNNNNNNNNGUUUUAGAGCUAUGCUGUUUUGGAAA**CAAAACAGCAU**<br>**AGC**AAG**UUAAAAU**AAGGCUAGUCCGUUAUCAACUUGAAAAAGUGGCACCGAGUCGGU<br>GC | exemplary gRNA<br>complementary<br>domain |

-continued

Sequences

| # | SEQUENCE | ANNOTATION |
|---|---|---|
| 101 | NNNNNNNNNNNNNNNNNNNNGUAUUAGAGCUAGAAAUAGCAAGUUAAUAUAAGGCUA<br>GUCCGUUAUCAACUUGAAAAAGUGGCACCGAGUCGGUGC | exemplary gRNA |
| 102 | NNNNNNNNNNNNNNNNNNNNGUUUAAGAGCUAGAAAUAGCAAGUUUAAAUAAGGCUA<br>GUCCGUUAUCAACUUGAAAAAGUGGCACCGAGUCGGUGC | exemplary gRNA |
| 103 | NNNNNNNNNNNNNNNNNNNNGUAUUAGAGCUAUGCUGUAUUGGAAACAAUACAGCAU<br>AGCAAGUUAAUAUAAGGCUAGUCCGUUAUCAACUUGAAAAAGUGGCACCGAGUCGGU<br>GC | exemplary gRNA |
| 104 | AAGGCUAGUCCGUUAUCAACUUGAAAAAGUGGCACCGAGUCGGUGCU | exemplary proximal<br>and tail domain |
| 105 | AAGGCUAGUCCGUUAUCAACUUGAAAAAGUGGCACCGAGUCGGUGGUGC | exemplary proximal<br>and tail domain |
| 106 | AAGGCUAGUCCGUUAUCAACUUGAAAAAGUGGCACCGAGUCGGUGCGGAUC | exemplary proximal<br>and tail domain |
| 107 | AAGGCUAGUCCGUUAUCAACUUGAAAAAGUG | exemplary proximal<br>and tail domain |
| 108 | AAGGCUAGUCCGUUAUCA | exemplary proximal<br>and tail domain |
| 109 | AAGGCUAGUCCG | exemplary proximal<br>and tail domain |
| 110 | NNNNNNNNNNNNNNNNNNNNGUUUUAGAGCUAGAAAUAGCAAGUUAAAAUAAGGCUA<br>GUCCGUUAUCAACUUGAAAAAGUGGCACCGAGUCGGUGCUUUUUU | exemplary chimeric<br>gRNA |
| 111 | NNNNNNNNNNNNNNNNNNNNGUUUUAGUACUCUGGAAACAGAAUCUACUAAAACAAG<br>GCAAAAUGCCGUGUUUAUCUCGUCAACUUGUUGGCGAGAUUUUUU | exemplary chimeric<br>gRNA |
| 112 | KKPYSIGLDIGTNSVGWAVVTDDYKVPAKKMKVLGNTDKSHIEKNLLGALLFDSGNT<br>AEDRRLKRTARRRYTRRRNRILYLQEIFSEEMGKVDDSFFHRLEDSFLVTEDKRGER<br>HPIFGNLEEEVKYHENFPTIYHLRQYLADNPEKVDLRLVYLALAHIIKFRGHFLIEG<br>KFDTRNNDVQRLFQEFLAVYDNTFENSSLQEQNVQVEEILTDKISKSAKKDRVLKLF<br>PNEKSNGRFAEFLKLIVGNQADFKKHFELEEKAPLQFSKDTYEEELEVLLAQIGDNY<br>AELFLSAKKLYDSILLSGILTVTDVGTKAPLSASMIQRYNEHQMDLAQLKQFIRQKL<br>SDKYNEVFSDVSKDGYAGYIDGKTNQEAFYKYLKGLLNKIEGSGYFLDKIEREDFLR<br>KQRTFDNGSIPHQIHLQEMRAIIRRQAEFYPFLADNQDRIEKLLTFRIPYYVGPLAR<br>GKSDFAWLSRKSADKITPWNFDEIVDKESSAEAFINRMTNYDLYLPNQKVLPKHSLL<br>YEKFTVYNELTKVKYKTEQGKTAFFDANMKQEIFDGVFKVYRKVTKDKLMDFLEKEF<br>DEFRIVDLTGLDKENKVFNASYGTYHDLCKILDKDFLDNSKNEKILEDIVLTLTLFE<br>DREMIRKRLENYSDLLTKEQVKKLERRHYTGWGRLSAELIHGIRNKESRKTILDYLI<br>DDGNSNRNFMQLINDDALSFKEEIAKAQVIGETDNLNQVVSDIAGSPAIKKGILQSL<br>KIVDELVKIMGHQPENIVVEMARENQFTNQGRRNSQQRLKGLTDSIKEFGSQILKEH<br>PVENSQLQNDRLFLYYLQNGRDMYTGEELDIDYLSQYDIDHIIPQAFIKDNSIDNRV<br>LTSSKENRGKSDDVPSKDVVRKMKSYWSKLLSAKLITQRKFDNLTKAERGGLTDDDK<br>AGFIKRQLVETRQITKHVARILDERFNTETDENNKKIRQVKIVTLKSNLVSNFRKEF<br>ELYKVREINDYHHAHDAYLNAVIGKALLGVYPQLEPEFVYGDYPHFHGHKENKATAK<br>KFFYSNIMNFFKKDDVRTDKNGEIIWKKDEHISNIKKVLSYPQVNIVKKVEEQTGGF<br>SKESILPKGNSDKLIPRKTKKFYWDTKKYGGFDSPIVAYSILVIADIEKGKSKKLKT<br>VKALVGVTIMEKMTFERDPVAFLERKGYRNVQEENIIKLPKYSLFKLENGRKRLLAS<br>ARELQKGNEIVLPNHLGTLLYHAKNIHKVDEPKHLDYVDKHKDEFKELLDVVSNFSK<br>KYTLAEGNLEKIKELYAQNNGEDLKELASSFINLLTFTAIGAPATFKFFDKNIDRKR<br>YTSTTEILNATLIHQSITGLYETRIDLNKLGGD | *Streptococcus<br>mutans* Cas9 |
| 113 | DKKYSIGLDIGTNSVGWAVITDEYKVPSKKFKVLGNTDRHSIKKNLIGALLFDSGET<br>AEATRLKRTARRRYTRRKNRICYLQEIFSNEMAKVDDSFFHRLEESFLVEEDKKHER<br>HPIFGNIVDEVAYHEKYPTIYHLRKKLVDSTDKADLRLIYLALAHMIKFRGHFLIEG<br>DLNPDNSDVDKLFIQLVQTYNQLFEENPINASGVDAKAILSARLSKSRRLENLIAQL<br>PGEKKNGLFGNLIALSLGLTPNFKSNFDLAEDAKLQLSKDTYDDDLDNLLAQIGDQY<br>ADLFLAAKNLSDAILLSDILRVNTEITKAPLSASMIKRYDEHHQDLTLLKALVRQQL<br>PEKYKEIFFDQSKNGYAGYIDGGASQEEFYKFIKPILEKMDGTEELLVKLNREDLLR<br>KQRTFDNGSIPHQIHLGELHAILRRQEDFYPFLKDNREKIEKILTFRIPYYVGPLAR<br>GNSRFAWMTRKSEETITPWNFEEVVDKGASAQSFIERMTNFDKNLPNEKVLPKHSLL<br>YEYFTVYNELTKVKYVTEGMRKPAFLSGEQKKAIVDLLFKTNRKVTVKQLKEDYFKK<br>IECFDSVEISGVEDRFNASLGTYHDLLKIIKDKDFLDNEENEDILEDIVLTLTLFED<br>REMIEERLKTYAHLFDDKVMKQLKRRRYTGWGRLSRKLINGIRDKQSGKTILDFLKS<br>DGFANRNFMQLIHDDSLTFKEDIQKAQVSGQGDSLHEHIANLAGSPAIKKGILQTVK<br>VVDELVKVMGRHKPENIVIEMARENQTTQKGQKNSRERMKRIEEGIKELGSQILKEH<br>PVENTQLQNEKLYLYYLQNGRDMYVDQELDINRLSDYDVDHIVPQSFLKDDSIDNKV<br>LTRSDKNRGKSDNVPSEEVVKKMKNYWRQLLNAKLITQRKFDNLTKAERGGLSELDK | *Streptococcus<br>pyogenes* Cas9 |

-continued

Sequences

| # | SEQUENCE | ANNOTATION |
|---|---|---|
| | AGFIKRQLVETRQITKHVAQILDSRMNTKYDENDKLIREVKVITLKSKLVSDFRKDF QFYKVREINNYHHAHDAYLNAVVGTALIKKYPKLESEFVYGDYKVYDVRKMIAKSEQ EIGKATAKYFFYSNIMNFFKTEITLANGEIRKRPLIETNGETGEIVWDKGRDFATVR KVLSMPQVNIVKKTEVQTGGFSKESILPKRNSDKLIARKKDWDPKKYGGFDSPTVAY SVLVVAKVEKGKSKKLKSVKELLGITIMERSSFEKNPIDFLEAKGYKEVKKDLIIKL PKYSLFELENGRKRMLASAGELQKGNELALPSKYVNFLYLASHYEKLKGSPEDNEQK QLFVEQHKHYLDEIIEQISEFSKRVILADANLDKVLSAYNKHRDKPIREQAENIIHL FTLTNLGAPAAFKYFDTTIDRKRYTSTKEVLDATLIHQSITGLYETRIDLSQLGGD | |
| 114 | TKPYSIGLDIGTNSVGWAVTTDNYKVPSKKMKVLGNTSKKYIKKNLLGVLLFDSGIT AEGRRLKRTARRRYTRRRNRILYLQEIFSTEMATLDDAFFQRLDDSFLVPDDKRDSK YPIFGNLVEEKAYHDEFPTIYHLRKYLADSTKKADLRLVYLALAHMIKYRGHFLIEG EFNSKNNDIQKNFQDFLDTYNAIFESDLSLENSKQLEEIVKDKISKLEKKDRILKLF PGEKNSGIFSEFLKLIVGNQADFRKCFNLDEKASLHFSKESYDEDLETLLGYIGDDY SDVFLKAKKLYDAILLSGFLTVTDNETEAPLSSAMIKRYNEHKEDLALLKEYIRNIS LKTYNEVFKDDTKNGYAGYIDGKTNQEDFYVYLKKLLAEFEGADYFLEKIDREDFLR KQRTFDNGSIPYQIHLQEMRAILDKQAKFYPFLAKNKERIEKILTFRIPYYVGPLAR GNSDFAWSIRKRNEKITPWNFEDVIDKESSAEAFINRMTSFDLYLPEEKVLPKHSLL YETFNVYNELTKVRFIAESMRDYQFLDSKQKKDIVRLYFKDKRKVTDKDIIEYLHAI YGYDGIELKGIEKQFNSSLSTYHDLLNIINDKEFLDDSSNEAIIEEIIHTLTIFEDR EMIKQRLSKFENIFDKSVLKKLSRRHYTGWGKLSAKLINGIRDEKSGNTILDYLIDD GISNRNFMQLIHDDALSFKKKIQKAQIIGDEDKGNIKEVVKSLPGSPAIKKGILQSI KIVDELVKVMGGRKPESIVVEMARENQYTNQGKSNSQQRLKRLEKSLKELGSKILKE NIPAKLSKIDNNALQNDRLYLYYLQNGKDMYTGDDLDIDRLSNYDIDHIIPQAFLKD NSIDNKVLVSSASNRGKSDDVPSLEVVKKRKTFWYQLLKSKLISQRKFDNLTKAERG GLSPEDKAGFIQRQLVETRQITKHVARLLDEKFNNKKDENNRAVRTVKIITLKSTLV SQFRKDFELYKVREINDFHHAHDAYLNAVVASALLKKYPKLEPEFVYGDYPKYNSFR ERKSATEKVYFYSNIMNIFKKSISLADGRVIERPLIEVNEETGESVWNKESDLATVR RVLSYPQVNVVKKVEEQNHGLDRGKPKGLFNANLSSKPKPNSNENLVGAKEYLDPKK YGGYAGISNSFTVLVKGTIEKGAKKKITNVLEFQGISILDRINYRKDKLNFLLEKGY KDIELIIELPKYSLFELSDGSRRMLASILSTNNKRGEIHKGNQIFLSQKFVKLLYHA KRISNTINENHRKYVENHKKEFEELFYYILEFNENYVGAKKNGKLLNSAFQSWQNHS IDELCSSFIGPTGSERKGLFELTSRGSAADFEFLGVKIPRYRDYTPSSLLKDATLIH QSVTGLYETRIDLAKLGEG | *Streptococcus thermophilus* Cas9 |
| 115 | KKPYTIGLDIGTNSVGWAVLTDQYDLVKRKMKIAGDSEKKQIKKNFWGVRLFDEGQT AADRRMARTARRRIERRRNRISYLQGIFAEEMSKTDANFFCRLSDSFYVDNEKRNSR HPFFATIEEEVEYHKNYPTIYHLREELVNSSEKADLRLVYLALAHIIKYRGNFLIEG ALDTQNTSVDGIYKQFIQTYNQVFASGIEDGSLKKLEDNKDVAKILVEKVTRKEKLE RILKLYPGEKSAGMFAQFISLIVGSKGNFQKPFDLIEKSDIECAKDSYEEDLESLLA LIGDEYAELFVAAKNAYSAVVLSSIITVAETETNAKLSASMIERFDTHEEDLGELKA FIKLHLPKHYEEIFSNTEKHGYAGYIDGKTKQADFYKYMKMTLENIEGADYFIAKIE KENFLRKQRTFDNGAIPHQLHLEELEAILHQQAKYYPFLKENYDKIKSLVTFRIPYF VGPLANGQSEFAWLTRKADGEIRPWNIEEKVDFGKSAVDFIEKMTNKDTYLPKENVL PKHSLCYQKYLVYNELTKVRYINDQGKTSYFSGQEKEQIFNDLFKQKRKVKKKDLEL FLRNMSHVESPTIEGLEDSFNSSYSTYHDLLKVGIKQEILDNPVNTEMLENIVKILT VFEDKRMIKEQLQQFSDVLDGVVLKKLERRHYTGWGRLSAKLLMGIRDKQSHLTILD YLMNDDGLNRNLMQLINDSNLSFKSIIEKEQVTTADKDIQSIVADLAGSPAIKKGIL QSLKIVDELVSVMGYPPQTIVVEMARENQTTGKGKNNSRPRYKSLEKAIKEFGSQIL KEHPTDNQELRNNRLYLYYLQNGKDMYTGQDLDIHNLSNYDIDHIVPQSFITDNSID NLVLTSSAGNREKGDDVPPLEIVRKRKVFWEKLYQGNLMSKRKFDYLTKAERGGLTE ADKARFIHRQLVETRQITKNVANILHQRFNYEKDDHGNTMKQVRIVTLKSALVSQFR KQFQLYKVRDVNDYHHAHDAYLNGVVANTLLKVYPQLEPEFVYGDYHQFDWFKANKA TAKKQFYTNIMLFFAQKDRIIDENGEILWDKKYLDTVKKVMSYRQMNIVKKTEIQKG EFSKATIKPKGNSSKLIPRKTNWDPMKYGGLDSPNMAYAVVIEYAKGKNKLVFEKKI IRVTIMERKAFEKDEKAFLEEQGYRQPKVLAKLPKYTLYECEEGRRRMLASANEAQK GNQQVLPNHLVTLLHHAANCEVSDGKSLDYIESNREMFAELLAHVSEFAKRYTLAEA NLNKINQLFEQNKEGDIKAIAQSFVDLMAFNAMGAPASFKFFETTIERKRYNNLKEL LNSTIIYQSITGLYESRKRLDD | *Listeria innocua* Cas9 |
| 116 | MAAFKPNSINYILGLDIGIASVGWAMVEIDEEENPIRLIDLGVRVFERAEVPKTGDS LAMARRLARSVRRLTRRRAHRLLRTRRLLKREGVLQAANFDENGLIKSLPNTPWQLR AAALDRKLTPLEWSAVLLHLIKHRGYLSQRKNEGETADKELGALLKGVAGNAHALQT GDFRTPAELALNKFEKESGHIRNQRSDYSHTFSRKDLQAELILLFEKQKEFGNPHVS GGLKEGIETLLMTQRPALSGDAVQKMLGHCTFEPAEPKAAKNTYTAERFIWLTKLNN LRILEQGSERPLTDTERATLMDEPYRKSKLTYAQARKLLGLEDTAFFKGLRYGKDNA EASTLMEMKAYHAISRALEKEGLKDKKSPLNLSPELQDEIGTAFSLFKTDEDITGRL KDRIQPEILEALLKHISFDKFVQISLKALRRIVPLMEQGKRYDEACAEIYGDHYGKK NTEEKIYLPPIPADEIRNPVVLRALSQARKVINGVVRRYGSPARIHIETAREVGKSF KDRKEIEKRQEENRKDREKAAAKFREYFPNFVGEPKSKDILKLRLYEQQHGKCLYSG KEINLGRLNEKGYVEIDHALPFSRTWDDSFNNKVLVLGSENQNKGNQTPYEYFNGKD NSREWQEFKARVETSRFPRSKKQRILLQKFDEDGFKERNLNDTRYVNRFLCQFVADR MRLTGKGKKRVFASNGQITNLLRGFWGLRKVRAENDRHHALDAVVVACSTVAMQQKI TRFVRYKEMNAFDGKTIDKETGEVLHQKTHFPQPWEFFAQEVMIRVFGKPDGKPEFE EADTLEKLRTLLAEKLSSRPEAVHEYVTPLFVSRAPNRKMSGQGHMETVKSAKRLDE | *Neisseria meningitidis* Cas9 |

-continued

Sequences

| # | SEQUENCE | ANNOTATION |
|---|---|---|
| | GVSVLRVPLTQLKLKDLEKMVNREREPKLYEALKARLEAHKDDPAKAFAEPFYKYDK AGNRTQQVKAVRVEVQVQKTGVWVRNHNGIADNATMVRVDVFEKGDKYYLVPIYSWQV AKGILPDRAVVQGKDEEDWQLIDDSFNFKFSLHPNDLVEVITKKARMFGYFASCHRG TGNINIRIHDLDHKIGKNGILEGIGVKTALSFQKYQIDELGKEIRPCRLKKRPPVR | |
| 117 | MDKKYSIGLDIGTNSVGWAVITDEYKVPSKKFKVLGNTDRHSIKKNLIGALLFDSGE TAEATRLKRTARRRYTRRKNRICYLQEIFSNEMAKVDDSFFHRLEESFLVEEDKKHE RHPIFGNIVDEVAYHEKYPTIYHLRKKLVDSTDKADLRLIYLALAHMIKFRGHFLIE GDLNPDNSDVDKLFIQLVQTYNQLFEENPINASGVDAKAILSARLSKSRRLENLIAQ LPGEKKNGLFGNLIALSLGLTPNFKSNFDLAEDAKLQLSKDTYDDDLDNLLAQIGDQ YADLFLAAKNLSDAILLSDILRVNTEITKAPLSASMIKRYDEHHQDLTLLKALVRQQ LPEKYKEIFFDQSKNGYAGYIDGGASQEEFYKFIKPILEKMDGTEELLVKLNREDLL RKQRTFDNGSIPHQIHLGELHAILRRQEDFYPFLKDNREKIEKILTFRIPYYVGPLA RGNSRFAWMTRKSEETITPWNFEEVVDKGASAQSFIERMTNFDKNLPNEKVLPKHSL LYEYFTVYNELTKVKYVTEGMRKPAFLSGEQKKAIVDLLFKTNRKVTVKQLKEDYFK KIECFDSVEISGVEDRFNASLGTYHDLLKIIKDKDFLDNEENEDILEDIVLTLTLFE DREMIEERLKTYAHLFDDKVMKQLKRRRYTGWGRLSRKLINGIRDKQSGKTILDFLK SDGFANRNFMQLIHDDSLTFKEDIQKAQVSGQGDSLHEHIANLAGSPAIKKGILQTV KVVDELVKVMGRHKPENIVIEMARENQTTQKGQKNSRERMKRIEEGIKELGSQILKE HPVENTQLQNEKLYLYYLQNGRDMYVDQELDINRLSDYDVDHIVPQSFLKDDSIDNK VLTRSDKNRGKSDNVPSEEVVKKMKNYWRQLLNAKLITQRKFDNLTKAERGGLSELD KAGFIKRQLVETRQITKHVAQILDSRMNTKYDENDKLIREVKVITLKSKLVSDFRKD FQFYKVREINNYHHAHDAYLNAVVGTALIKKYPKLESEFVYGDYKVYDVRKMIAKSE QEIGKATAKYFFYSNIMNFFKTEITLANGEIRKRPLIETNGETGEIVWDKGRDFATV RKVLSMPQVNIVKKTEVQTGGFSKESILPKRNSDKLIARKKDWDPKKYGGFDSPTVA YSVLVVAKVEKGKSKKLKSVKELLGITIMERSSFEKNPIDFLEAKGYKEVKKDLIIK LPKYSLFELENGRKRMLASAGELQKGNELALPSKYVNFLYLASHYEKLKGSPEDNEQ KQLFVEQHKHYLDEIIEQISEFSKRVILADANLDKVLSAYNKHRDKPIREQAENIIH LFTLTNLGAPAAFKYFDTTIDRKRYTSTKEVLDATLIHQSITGLYETRIDLSQLGGD | *Streptococcus pyogenes* Cas9 |
| 118 | CGTGAGGCTCCGGTGCCCGTCAGTGGGCAGAGCGCACATCGCCCACAGTCCCCGAGA AGTTGGGGGGAGGGGTCGGCAATTGAACCGGTGCCTAGAGAAGGTGGCGCGGGGTAA ACTGGGAAAGTGATGTCGTGTACTGGCTCCGCCTTTTTCCCGAGGGTGGGGGAGAAC CGTATATAAGTGCACTAGTCGCCGTGAACGTTCTTTTTCGCAACGGGTTTGCCGCCA GAACACAGGTAAGTGCCGTGTGTGGTTCCCGCGGGCCTGGCCTCTTTACGGGTTATG GCCCTTGCGTGCCTTGAATTACTTCCACCTGGCTGCAGTACGTGATTCTTGATCCCG AGCTTCGGGTTGGAAGTGGGTGGGAGAGTTCGTGGCCTTGCGCTTAAGGAGCCCCTT CGCCTCGTGCTTGAGTTGTGGCCTGGCCTGGGCGCTGGGGCCGCCGCGTGCGAATCT GGTGGCACCTTCGCGCCTGTCTCGCTGCTTTCGATAAGTCTCTAGCCATTTAAAATT TTTGATGACCTGCTGCGACGCTTTTTTTCTGGCAAGATAGTCTTGTAAATGCGGGCC AAGATCAGCACACTGGTATTTCGGTTTTTGGGGCCGCGGGCGGCGACGGGGCCCGTG CGTCCCAGCGCACATGTTCGGCGAGGCGGGGCCTGCGAGCGCGGCCACCGAGAATCG GACGGGGGTAGTCTCAAGCTGCCCGGCCTGCTCTGGTGCCTGGCCTCGCGCCGCCGT GTATCGCCCCGCCCTGGGCGGCAAGGCTGGCCCGGTCGGCACCAGTTGCGTGAGCGG AAAGATGGCCGCTTCCCGGCCCTGCTGCAGGGAGCACAAAATGGAGGACGCGGCGCT CGGGAGAGCGGGCGGGTGAGTCACCCACACAAAGGAAAAGGGCCTTTCCGTCCTCAG CCGTCGCTTCATGTGACTCCACGGAGTACCGGGCGCCGTCCAGGCACCTCGATTAGT TCTCCAGCTTTTGGAGTACGTCGTCTTTAGGTTGGGGGGAGGGGTTTTATGCGATGG AGTTTCCCCACACTGAGTGGGTGGAGACTGAAGTTAGGCCAGCTTGGCACTTGATGT AATTCTCCTTGGAATTTGCCCTTTTTGAGTTTGGATCTTGGTTCATTCTCAAGCCTC AGACAGTGGTTCAAAGTTTTTTTCTTCCATTTCAGGTGTCGTGAAAACTACCCCTAA AAGCCAAA | EF1alpha promoter |
| 119 | GGATCTGCGATCGCTCCGGTGCCCGTCAGTGGGCAGAGCGCACATCGCCCACAGTCC CCGAGAAGTTGGGGGGAGGGGTCGGCAATTGAACCGGTGCCTAGAGAAGGTGGCGCG GGGTAAACTGGGAAAGTGATGTCGTGTACTGGCTCCGCCTTTTTCCCGAGGGTGGGG GAGAACCGTATATAAGTGCAGTAGTCGCCGTGAACGTTCTTTTTCGCAACGGGTTTG CCGCCAGAACACAGCTGAAGCTTCGAGGGGCTCGCATCTCTCCTTCACGCGCCCGCC GCCCTACCTGAGGCCGCCATCCACGCCGGTTGAGTCGCGTTCTGCCGCCTCCCGCCT GTGGTGCCTCCTGAACTGCGTCCGCCGTCTAGGTAAGTTTAAAGCTCAGGTCGAGAC CGGGCCTTTGTCCGGCGCTCCCTTGGAGCCTACCTAGACTCAGCCGGCTCTCCACGC TTTGCCTGACCCTGCTTGCTCAACTCTACGTCTTTGTTTCGTTTTCTGTTCTGCGCC GTTACAGATCCAAGCTGTGACCGGCGCCTAC | Ef1alpha promoter with HTLV1 enhancer |
| 120 | GGATCTGGAGCGACGAATTTTAGTCTACTGAAACAAGCGGGAGACGTGGAGGAAAAC CCTGGACCT | P2A nucleotide sequence |
| 121 | atggataaaaagtacagcatcgggctggacatcggtacaaactcagtggggtgggcc gtgattacggacgagtacaaggtaccctccaaaaaatttaaagtgctgggtaacacg gacagacactctataaagaaaaatcttattggagccttgctgttcgactcaggcgag acagccgaagccacaaggttgaagcggaccgccaggaggcggtataccaggagaaag aaccgcatatgctacctgcaagaaatcttcagtaacgagatggcaaaggttgacgat agctttttccatcgcctggaagaatcctttcttgttgaggaagacaagaagcacgaa cggcaccccatctttggcaatattgtcgacgaagtggcatatcacgaaaagtacccg actatctaccacctcaggaagaagctggtggactctaccgataaggcggacctcaga | *S. pyogenes* Cas9 codon optimized nucleic acid sequence |

-continued

Sequences

| # | SEQUENCE | ANNOTATION |
|---|---|---|
| | cttatttatttggcactcgcccacatgattaaatttagaggacatttcttgatcgag<br>ggcgacctgaacccggacaacagtgacgtcgataagctgttcatccaacttgtgcag<br>acctacaatcaactgttcgaagaaaaccctataaatgcttcaggagtcgacgctaaa<br>gcaatcctgtccgcgcgcctctcaaaatctagaagacttgagaatctgattgctcag<br>ttgcccggggaaaagaaaaatggattgtttggcaacctgatcgccctcagtctcgga<br>ctgaccccaaatttcaaaagtaacttcgacctggccgaagacgctaagctccagctg<br>tccaaggacacatacgatgacgacctcgacaatctgctggcccagattggggatcag<br>tacgccgatctctttttggcagcaaagaacctgtccgacgccatcctgttgagcgat<br>atcttgagagtgaacaccgaaattactaaagcaccccttagcgcatctatgatcaag<br>cggtacgacgagcatcatcaggatctgaccctgctgaaggctcttgtgaggcaacag<br>ctccccgaaaaatacaaggaaatcttctttgaccagagcaaaaacggctacgctggc<br>tatatagatggtggggccagtcaggaggaattctataaattcatcaagcccattctc<br>gagaaaatggacggcacagaggagttgctggtcaaacttaacagggaggacctgctg<br>cggaagcagcggacctttgacaacgggtctatcccccaccagattcatctgggcgaa<br>ctgcacgcaatcctgaggaggcaggaggattttatccttttcttaaagataaccgc<br>gagaaaatagaaaagattcttacattcaggatcccgtactacgtgggacctctcgcc<br>cggggcaattcacggtttgcctggatgacaaggaagtcagaggagactattacacct<br>tggaacttcgaagaagtggtggacaagggtgcatctgcccagtctttcatcgagcgg<br>atgacaaattttgacaagaacctccctaatgagaaggtgctgcccaaacattctctg<br>ctctacgagtactttaccgtctacaatgaactgactaaagtcaagtacgtcaccgag<br>ggaatgaggaagccggcattccttagtggagaacagaagaaggcgattgtagacctg<br>ttgttcaagaccaacaggaaggtgactgtgaagcaacttaaagaagactactttaag<br>aagatcgaatgttttgacagtgtggaaatttcaggggttgaagaccgcttcaatgcg<br>tcattggggacttaccatgatcttctcaagatcataaaggacaaagacttcctggac<br>aacgaagaaaatgaggatattctcgaagacatcgtcctcaccctgaccctgttcgaa<br>gacagggaaatgatagaagagcgcttgaaaacctatgcccacctcttcgacgataaa<br>gttatgaagcagctgaagcgcaggagatacacaggatggggaagattgtcaaggaag<br>ctgatcaatggaattagggataaacagagtggcaagaccatactggatttcctcaaa<br>tctgatggcttcgccaataggaacttcatgcaactgattcacgatgactctcttacc<br>ttcaaggaggacattcaaaaggctcaggtgagcgggcagggagactcccttcatgaa<br>cacatcgcgaatttggcaggttcccccgctattaaaaagggcatccttcaaactgtc<br>aaggtggtggatgaattggtcaaggtaatgggcagacataagccagaaaatattgtg<br>atcgagatggcccgcgaaaaccagaccacacagaagggccagaaaaatagtagagag<br>cggatgaagaggatcgaggagggcatcaaagagctgggatctcagattctcaaagaa<br>caccccgtagaaaacacacagctgcagaacgaaaaattgtacttgtactatctgcag<br>aacggcagagacatgtacgtcgaccaagaacttgatattaatagactgtccgactat<br>gacgtagaccatatcgtgccccagtccttcctgaaggacgactccattgataacaaa<br>gtcttgacaagaagcgacaagaacaggggtaaaagtgataatgtgcctagcgaggag<br>gtggtgaaaaaaatgaagaactactggcgacagctgcttaatgcaaagctcattaca<br>caacggaagttcgataatctgacgaaagcagagagaggtggcttgtctgagttggac<br>aaggcagggtttattaagcggcagctggtggaaactaggcagatcacaaagcacgtg<br>gcgcagattttggacagccggatgaacacaaaatacgacgaaaatgataaactgata<br>cgagaggtcaaagttatcacgctgaaaagcaagctggtgtccgattttcggaaagac<br>ttccagttctacaaagttcgcgagattaataactaccatcatgctcacgatgcgtac<br>ctgaacgctgttgtcgggaccgccttgataaagaagtacccaaagctggaatccgag<br>ttcgtatacggggattacaaagtgtacgatgtgaggaaaatgatagccaagtccgag<br>caggagattggaaaggccacagctaagtacttcttttattctaacatcatgaatttt<br>tttaagacggaaattaccctggccaacggagagatcagaaagcggccccttatagag<br>acaaatggtgaaacaggtgaaatcgtctgggataagggcagggatttcgctactgtg<br>aggaaggtgctgagtatgccacaggtaaatatcgtgaaaaaaaccgaagtacagacc<br>ggaggattttccaaggaaagcattttgcctaaaagaaactcagacaagctcatcgcc<br>cgcaagaaagattgggaccctaagaaatacgggggatttgactcacccaccgtagcc<br>tattctgtgctggtggtagctaaggtggaaaaaggaaagtctaagaagctgaagtcc<br>gtgaaggaactcttgggaatcactatcatggaaagatcatcctttgaaaagaaccct<br>atcgatttcctggaggctaagggttacaaggaggtcaagaaagacctcatcattaaa<br>ctgccaaaatactctctcttcgagctggaaaatggcaggaagagaatgttggccagc<br>gccggagagctgcaaaagggaaacgagcttgctctgccctccaaatatgttaatttt<br>ctctatctcgcttcccactatgaaaagctgaaagggtctcccgaagataacgagcag<br>aagcagctgttcgtcgaacagcacaagcactatctggatgaaataatcgaacaaata<br>agcgagttcagcaaaagggttatcctggcggatgctaatttggacaaagtactgtct<br>gcttataacaagcaccgggataagcctattagggaacaagccgagaatataattcac<br>ctctttacactcacgaatctcggagcccccgccgccttcaaatactttgatacgact<br>atcgaccggaaacggtataccagtaccaaagaggtcctcgatgccaccctcatccac<br>cagtcaattactggcctgtacgaaacacggatcgacctctctcaactgggcggcgac<br>tag | |
| 122 | MDKKYSIGLDIGTNSVGWAVITDEYKVPSKKFKVLGNTDRHSIKKNLIGALLEDSGE<br>TAEATRLKRTARRRYTRRKNRICYLQEIFSNEMAKVDDSFEHRLEESELVEEDKKHE<br>RHPIFGNIVDEVAYHEKYPTIYHLRKKLVDSTDKADLRLIYLALAHMIKFRGHFLIE<br>GDLNPDNSDVDKLFIQLVQTYNQLFEENPINASGVDAKAILSARLSKSRRLENLIAQ<br>LPGEKKNGLFGNLIALSLGLTPNEKSNEDLAEDAKLQLSKDTYDDDLDNLLAQIGDQ<br>YADLFLAAKNLSDAILLSDILRVNTEITKAPLSASMIKRYDEHHQDLTLLKALVRQQ<br>LPEKYKEIFFDQSKNGYAGYIDGGASQEEFYKFIKPILEKMDGTEELLVKLNREDLL<br>RKQRTFDNGSIPHQIHLGELHAILRRQEDFYPFLKDNREKIEKILTFRIPYYVGPLA<br>RGNSRFAWMTRKSEETITPWNFEEVVDKGASAQSFIERMTNFDKNLPNEKVLPKHSL | *S. pyogenes* Cas9 |

-continued

Sequences

| # | SEQUENCE | ANNOTATION |
|---|---|---|
| | LYEYFTVYNELTKVKYVTEGMRKPAELSGEQKKAIVDLLEKTNRKVTVKQLKEDYFK<br>KIECFDSVEISGVEDRFNASLGTYHDLLKIIKDKDFLDNEENEDILEDIVLTLTLFE<br>DREMIEERLKTYAHLFDDKVMKQLKRRRYTGWGRLSRKLINGIRDKQSGKTILDFLK<br>SDGFANRNFMQLIHDDSLTFKEDIQKAQVSGQGDSLHEHIANLAGSPAIKKGILQTV<br>KVVDELVKVMGRHKPENIVIEMARENQTTQKGQKNSRERMKRIEEGIKELGSQILKE<br>HPVENTQLQNEKLYLYYLQNGRDMYVDQELDINRLSDYDVDHIVPQSFLKDDSIDNK<br>VLTRSDKNRGKSDNVPSEEVVKKMKNYWRQLLNAKLITQRKFDNLTKAERGGLSELD<br>KAGFIKRQLVETRQITKHVAQILDSRMNTKYDENDKLIREVKVITLKSKLVSDFRKD<br>FQFYKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDFATV<br>RKVLSMPQVNIVKKTEVQTGGFSKESILPKRNSDKLIARKKDWDPKKYGGFDSPTVA<br>YSVLVVAKVEKGKSKKLKSVKELLGITIMERSSFEKNPIDFLEAKGYKEVKKDLIIK<br>LPKYSLFELENGRKRMLASAGELQKGNELALPSKYVNFLYLASHYEKLKGSPEDNEQ<br>KQLFVEQHKHYLDEIIEQISEFSKRVILADANLDKVLSAYNKHRDKPIREQAENIIH<br>LFTLTNLGAPAAFKYFDTTIDRKRYTSTKEVLDATLIHQSITGLYETRIDLSQLGGD | |
| 123 | atggccgccttcaagcccaaccccatcaactacatcctgggcctggacatcggcatc<br>gccagcgtgggctgggccatggtggagatcgacgaggacgagaaccccatctgcctg<br>atcgacctgggtgtgcgcgtgttcgagcgcgctgaggtgcccaagactggtgacagt<br>ctggctatggctcgccggcttgctcgctctgttcggcgccttactcgccggcgcgct<br>caccgccttctgcgcgctcgccgcctgctgaagcgcgagggtgtgctgcaggctgcc<br>gacttcgacgagaacggcctgatcaagagcctgcccaacactccttggcagctgcgc<br>gctgccgctctggaccgcaagctgactcctctggagtggagcgccgtgctgctgcac<br>ctgatcaagcaccgcggctacctgagccagcgcaagaacgagggcgagaccgccgac<br>aaggagctgggtgctctgctgaagggcgtggccgacaacgcccacgccctgcagact<br>ggtgacttccgcactcctgctgagctggccctgaacaagttcgagaaggagagcggc<br>cacatccgcaaccagcgcggcgactacagccacaccttcagccgcaaggacctgcag<br>gccgagctgatcctgctgttcgagaagcagaaggagttcggcaaccccacgtgagc<br>ggcggcctgaaggagggcatcgagaccctgctgatgacccagcgccccgccctgagc<br>ggcgacgccgtgcagaagatgctgggccactgcaccttcgagccagccgagcccaag<br>gccgccaagaacacctacaccgccgagcgcttcatctggctgaccaagctgaacaac<br>ctgcgcatcctggagcagggcagcgagcgccccctgaccgacaccgagcgcgccacc<br>ctgatggacgagccctaccgcaagagcaagctgacctacgcccaggcccgcaagctg<br>ctgggtctggaggacaccgccttcttcaagggcctgcgctacggcaaggacaacgcc<br>gaggccagcaccctgatggagatgaaggcctaccacgccatcagccgcgccctggag<br>aaggagggcctgaaggacaagaagagtcctctgaacctgagccccgagctgcaggac<br>gagatcggcaccgccttcagcctgttcaagaccgacgaggacatcaccggccgcctg<br>aaggaccgcatccagcccgagatcctggaggccctgctgaagcacatcagcttcgac<br>aagttcgtgcagatcagcctgaaggccctgcgccgcatcgtgcccctgatggagcag<br>ggcaagcgctacgacgaggcctgcgccgagatctacggcgaccactacggcaagaag<br>aacaccgaggagaagatctacctgcctcctatccccgccgacgagatccgcaacccc<br>gtggtgctgcgcgccctgagccaggcccgcaaggtgatcaacggcgtggtgcgccgc<br>tacggcagccccgcccgcatccacatcgagaccgcccgcgaggtgggcaagagcttc<br>aaggaccgcaaggagatcgagaagcgccaggaggagaaccgcaaggaccgcgagaag<br>gccgccgccaagttccgcgagtacttccccaacttcgtgggcgagcccaagagcaag<br>gacatcctgaagctgcgcctgtacgagcagcagcacggcaagtgcctgtacagcggc<br>aaggagatcaacctgggccgcctgaacgagaagggctacgtggagatcgaccacgcc<br>ctgcccttcagccgcacctgggacgacagcttcaacaacaaggtgctggtgctgggc<br>agcgagaaccagaacaagggcaaccagacccccctacgagtacttcaacggcaaggac<br>aacagccgcgagtggcaggagttcaaggcccgcgtggagaccagccgcttcccccgc<br>agcaagaagcagcgcatcctgctgcagaagttcgacgaggacggcttcaaggagcgc<br>aacctgaacgacacccgctacgtgaaccgcttcctgtgccagttcgtggccgaccgc<br>atgcgcctgaccggcaagggcaagaagcgcgtgttcgccagcaacggccagatcacc<br>aacctgctgcgcggcttctggggcctgcgcaaggtgcgcgccgagaacgaccgccac<br>cacgccctggacgccgtggtggtggcctgcagcaccgtggccatgcagcagaagatc<br>acccgcttcgtgcgctacaaggagatgaacgccttcgacggtaaaaccatcgacaag<br>gagaccggcgaggtgctgcaccagaagacccacttcccccagccctgggagttcttc<br>gcccaggaggtgatgatccgcgtgttcggcaagcccgacggcaagcccgagttcgag<br>gaggccgacacccccgagaagctgcgcaccctgctggccgagaagctgagcagccgc<br>cctgaggccgtgcacgagtacgtgactcctctgttcgtgagccgcgcccccaaccgc<br>aagatgagcggtcagggtcacatggagaccgtgaagagcgccaagcgcctggacgag<br>ggcgtgagcgtgctgcgcgtgcccctgacccagctgaagctgaaggacctggagaag<br>atggtgaaccgcgagcgcgagcccaagctgtacgaggccctgaaggcccgcctggag<br>gcccacaaggacgaccccgccaaggccttcgccgagcccttctacaagtacgacaag<br>gccggcaaccgcacccagcaggtgaaggccgtgcgcgtggagcaggtgcagaagacc<br>ggcgtgtgggtgcgcaaccacaacggcatcgccgacaacgccaccatggtgcgcgtg<br>gacgtgttcgagaagggcgacaagtactacctggtgcccatctacagctggcaggtg<br>gccaagggcatcctgcccgaccgcgccgtggtgcagggcaaggacgaggaggactgg<br>cagctgatcgacgacagcttcaacttcaagttcagcctgcaccccaacgacctggtg<br>gaggtgatcaccaagaaggcccgcatgttcggctacttcgccagctgccaccgcggc<br>accggcaacatcaacatccgcatccacgacctggaccacaagatcggcaagaacggc<br>atcctggagggcatcggcgtgaagaccgccctgagcttccagaagtaccagatcgac<br>gagctgggcaaggagatccgcccctgccgcctgaagaagcgccctcctgtgcgctaa | *N. meningitidis*<br>Cas9 codon<br>optimized nucleic<br>acid sequence |

-continued

Sequences

| # | SEQUENCE | ANNOTATION |
|---|---|---|
| 124 | MAAFKPNPINYILGLDIGIASVGWAMVEIDEDENPICLIDLGVRVFERAEVPKTGDS<br>LAMARRLARSVRRLTRRRAHRLLRARRLLKREGVLQAADFDENGLIKSLPNTPWQLR<br>AAALDRKLTPLEWSAVLLHLIKHRGYLSQRKNEGETADKELGALLKGVADNAHALQT<br>GDFRTPAELALNKFEKESGHIRNQRGDYSHTFSRKDLQAELILLFEKQKEFGNPHVS<br>GGLKEGIETLLMTQRPALSGDAVQKMLGHCTFEPAEPKAAKNTYTAERFIWLTKLNN<br>LRILEQGSERPLTDTERATLMDEPYRKSKLTYAQARKLLGLEDTAFFKGLRYGKDNA<br>EASTLMEMKAYHAISRALEKEGLKDKKSPLNLSPELQDEIGTAFSLFKTDEDITGRL<br>KDRIQPEILEALLKHISEDKEVQISLKALRRIVPLMEQGKRYDEACAEIYGDHYGKK<br>NTEEKIYLPPIFADEIRNPVVLRALSQARKVINGVVRRYGSPARIHIETAREVGKSF<br>KDRKEIEKRQEENRKDREKAAAKFREYFPNFVGEPKSKDILKLRLYEQQHGKCLYSG<br>KEINLGRLNEKGYVEIDHALPFSRTWDDSFNNKVLVLGSENQNKGNQTPYEYFNGKD<br>NSREWQEFKARVETSRFPRSKKQRILLQKFDEDGEKERNLNDTRYVNRELCQFVADR<br>MRLTGKGKKRVFASNGQITNLLRGFWGLRKVRAENDRHHALDAVVVACSTVAMQQKI<br>TREVRYKEMNAFDGKTIDKETGEVLHQKTHFPQPWEFFAQEVMIRVFGKPDGKPEFE<br>EADTPEKLRTLLAEKLSSRPEAVHEYVTPLFVSRAPNRKMSGQGHMETVKSAKRLDE<br>GVSVLRVPLTQLKLKDLEKMVNREREPKLYEALKARLEAHKDDPAKAFAEPFYKYDK<br>AGNRTQQVKAVRVEQVQKTGVWVRNHNGIADNATMVRVDVFEKGDKYYLVPIYSWQV<br>AKGILPDRAVVQGKDEEDWQLIDDSENFKFSLHPNDLVEVITKKARMFGYFASCHRG<br>TGNINIRIHDLDHKIGKNGILEGIGVKTALSFQKYQIDELGKEIRPCRLKKRPPVR | *N. meningitidis*<br>Cas9 |
| 125 | atgaaaaggaactacattctggggctggacatcgggattacaagcgtggggtatggg<br>attattgactatgaaacaagggacgtgatcgacgcaggcgtcagactgttcaaggag<br>gccaacgtggaaaacaatgagggacggagaagcaagaggggagccaggcgcctgaaa<br>cgacggagaaggcacagaatccagagggtgaagaaactgctgttcgattacaacctg<br>ctgaccgaccattctgagctgagtggaattaatccttatgaagccagggtgaaaggc<br>ctgagtcagaagctgtcagaggaagagttttccgcagctctgctgcacctggctaag<br>cgccgaggagtgcataacgtcaatgaggtggaagaggacaccggcaacgagctgtct<br>acaaaggaacagatctcacgcaatagcaaagctctggaagagaagtatgtcgcagag<br>ctgcagctggaacggctgaagaaagatggcgaggtgagagggtcaattaataggttc<br>aagacaagcgactacgtcaaagaagccaagcagctgctgaaagtgcagaaggcttac<br>caccagctggatcagagcttcatcgatacttatatcgacctgctggagactcggaga<br>acctactatgagggaccaggagaagggagccccttcggatggaaagacatcaaggaa<br>tggtacgagatgctgatgggacattgcacctattttccagaagagctgagaagcgtc<br>aagtacgcttataacgcagatctgtacaacgccctgaatgacctgaacaacctggtc<br>atcaccagggatgaaaacgagaaactggaatactatgagaagttccagatcatcgaa<br>aacgtgtttaagcagaagaaaaagcctacactgaaacagattgctaaggagatcctg<br>gtcaacgaagaggacatcaagggctaccgggtgacaagcactggaaaaccagagttc<br>accaatctgaaagtgtatcacgatattaaggacatcacagcacggaaagaaatcatt<br>gagaacgccgaactgctggatcagattgctaagatcctgactatctaccagagctcc<br>gaggacatccaggaagagctgactaacctgaacagcgagctgacccaggaagagatc<br>gaacagattagtaatctgaaggggtacaccggaacacacaacctgtccctgaaagct<br>atcaatctgattctggatgagctgtggcatacaaacgacaatcagattgcaatcttt<br>aaccggctgaagctggtcccaaaaaaggtggacctgagtcagcagaaagagatccca<br>accacactggtggacgatttcattctgtcacccgtggtcaagcggagcttcatccag<br>agcatcaaagtgatcaacgccatcatcaagaagtacggcctgcccaatgatatcatt<br>atcgagctggctagggagaagaacagcaaggacgcacagaagatgatcaatgagatg<br>cagaaacgaaaccggcagaccaatgaacgcattgaagagattatccgaactaccggg<br>aaagagaacgcaaagtacctgattgaaaaaatcaagctgcacgatatgcaggaggga<br>aagtgtctgtattctctggaggccatcccccctggaggacctgctgaacaatccattc<br>aactacgaggtcgatcatattatccccagaagcgtgtccttcgacaattcctttaac<br>aacaaggtgctggtcaagcaggaagagaactctaaaaagggcaataggactcctttc<br>cagtacctgtctagttcagattccaagatctcttacgaaacctttaaaaagcacatt<br>ctgaatctggccaaaggaaagggccgcatcagcaagaccaaaaaggagtacctgctg<br>gaagagcgggacatcaacagattctccgtccagaaggattttattaaccggaatctg<br>gtggacacaagatacgctactcgcggcctgatgaatctgctgcgatcctatttccgg<br>gtgaacaatctggatgtgaaagtcaagtccatcaacggcgggttcacatcttttctg<br>aggcgcaaatggaagtttaaaaaggagcgcaacaaagggtacaagcaccatgccgaa<br>gatgctctgattatcgcaaatgccgacttcatctttaaggagtggaaaaagctggac<br>aaagccaagaaagtgatggagaaccagatgttcgaagagaagcaggccgaatctatg<br>cccgaaatcgagacagaacaggagtacaaggagattttcatcactcctcaccagatc<br>aagcatatcaaggatttcaaggactacaagtactctcaccgggtggataaaaagccc<br>aacagagagctgatcaatgacaccctgtatagtacaagaaaagacgataaggggaat<br>accctgattgtgaacaatctgaacggactgtacgacaaagataatgacaagctgaaa<br>aagctgatcaacaaaagtcccgagaagctgctgatgtaccaccatgatcctcagaca<br>tatcagaaactgaagctgattatggagcagtacggcgacgagaagaacccactgtat<br>aagtactatgaagagactgggaactacctgaccaagtatagcaaaaaggataatggc<br>cccgtgatcaagaagatcaagtactatgggaacaagctgaatgcccatctggacatc<br>acagacgattaccctaacagtcgcaacaaggtggtcaagctgtcactgaagccatac<br>agattcgatgtctatctggacaacggcgtgtataaatttgtgactgtcaagaatctg<br>gatgtcatcaaaaaggagaactactatgaagtgaatagcaagtgctacgaagaggct<br>aaaaagctgaaaaagattagcaaccaggcagagttcatcgcctccttttacaacaac<br>gacctgattaagatcaatggcgaactgtatagggtcatcggggtgaacaatgatctg<br>ctgaaccgcattgaagtgaatatgattgacatcacttaccgagagtatctggaaaac | *S. aureus* Cas9<br>codon optimized<br>nucleic acid<br>sequence |

-continued

Sequences

| # | SEQUENCE | ANNOTATION |
|---|---|---|
| | atgaatgataagcgccccctcgaattatcaaaacaattgcctctaagactcagagt<br>atcaaaaagtactcaaccgacattctgggaaacctgtatgaggtgaagagcaaaaag<br>caccctcagattatcaaaaagggc | |
| 126 | MKRNYILGLDIGITSVGYGIIDYETRDVIDAGVRLFKEANVENNEGRRSKRGARRLK<br>RRRRHRIQRVKKLLFDYNLLTDHSELSGINPYEARVKGLSQKLSEEEFSAALLHLAK<br>RRGVHNVNEVEEDTGNELSTKEQISRNSKALEEKYVAELQLERLKKDGEVRGSINRF<br>KTSDYVKEAKQLLKVQKAYHQLDQSFIDTYIDLLETRRTYYEGPGEGSPFGWKDIKE<br>WYEMLMGHCTYFPEELRSVKYAYNADLYNALNDLNNLVITRDENEKLEYYEKFQIIE<br>NVFKQKKKPTLKQIAKEILVNEEDIKGYRVTSTGKPEFTNLKVYHDIKDITARKEII<br>ENAELLDQIAKILTIYQSSEDIQEELTNLNSELTQEEIEQISNLKGYTGTHNLSLKA<br>INLILDELWHTNDNQIAIFNRLKLVPKKVDLSQQKEIPTTLVDDFILSPVVKRSFIQ<br>SIKVINAIIKKYGLPNDIIIELAREKNSKDAQKMINEMQKRNRQTNERIEEIIRTTG<br>KENAKYLIEKIKLHDMQEGKCLYSLEAIPLEDLLNNPFNYEVDHIIPRSVSFDNSFN<br>NKVLVKQEENSKKGNRTPFQYLSSSDSKISYETFKKHILNLAKGKGRISKTKKEYLL<br>EERDINRFSVQKDFINRNLVDTRYATRGLMNLLRSYFRVNNLDVKVKSINGGFTSFL<br>RRKWKFKKERNKGYKHHAEDALIIANADFIFKEWKKLDKAKKVMENQMFEEKQAESM<br>PEIETEQEYKEIFITPHQIKHIKDFKDYKYSHRVDKKPNRELINDTLYSTRKDDKGN<br>TLIVNNLNGLYDKDNDKLKKLINKSPEKLLMYHHDPQTYQKLKLIMEQYGDEKNPLY<br>KYYEETGNYLTKYSKKDNGPVIKKIKYYGNKLNAHLDITDDYPNSRNKVVKLSLKPY<br>RFDVYLDNGVYKFVTVKNLDVIKKENYYEVNSKCYEEAKKLKKISNQAEFIASFYNN<br>DLIKINGELYRVIGVNNDLLNRIEVNMIDITYREYLENMNDKRPPRIIKTIASKTQS<br>IKKYSTDILGNLYEVKSKKHPQIIKKG | *S. aureus* Cas9 |
| 127 | ASTKGPSVFPLAPCSRSTSESTAALGCLVKDYFPEPVTVSWNSGALTSGVHTFPAVL<br>QSSGLYSLSSVVTVPSSNFGTQTYTCNVDHKPSNTKVDKTVERKCCVECPPCPAPPV<br>AGPSVFLFPPKPKDTLMISRTPEVTCVVVDVSHEDPEVQFNWYVDGVEVHNAKTKPR<br>EEQFNSTFRVVSVLTVVHQDWLNGKEYKCKVSNKGLPAPIEKTISKTKGQPREPQVY<br>TLPPSREEMTKNQVSLTCLVKGFYPSDISVEWESNGQPENNYKTTPPMLDSDGSFFL<br>YSKLTVDKSRWQQGNVFSCSVMHEALHNHYTQKSLSLSPGK | Human IgG2 Fc<br>(Uniprot P01859) |
| 128 | ASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPSCPAPEF<br>LGGPSVFLFPPKPKDTLMISRTPEVTCVVVDVSQEDPEVQFNWYVDGVEVHNAKTKP<br>REEQFNSTYRVVSVLTVLHQDWLNGKEYKCKVSNKGLPSSIEKTISKAKGQPREPQV<br>YTLPPSQEEMTKNQVSLTCLVKGFYPSDIAVEWESNGQPENNYKTTPPVLDSDGSFF<br>LYSRLTVDKSRWQEGNVFSCSVMHEALHNHYTQKSLSLSLGK | Human IgG4 Fc<br>(Uniprot P01861) |
| 129 | ESKYGPPCPPCPAPPVAGPSVFLFPPKPKDTLMISRTPEVTCVVVDVSQEDPEVQFN<br>WYVDGVEVHNAKTKPREEQFQSTYRVVSVLTVLHQDWLNGKEYKCKVSNKGLPSSIE<br>KTISKAKGQPREPQVYTLPPSQEEMTKNQVSLTCLVKGFYPSDIAVEWESNGQPENN<br>YKTTPPVLDSDGSFFLYSRLTVDKSRWQEGNVFSCSVMHEALHNHYTQKSLSLSLGK | Spacer |
| 130 | tgctttatttgtgaaatttgtgatgctattgctttatttgtaaccattataagctgc<br>aataaacaagttaacaacaacaattgcattcattttatgtttcaggttcagggggag<br>gtgtgggaggttttttaaa | SV40 poly A signal |
| 131 | gaacagagaaacaggagaatatgggccaaacaggatatctgtggtaagcagttcctg<br>ccccggctcagggccaagaacagttggaacagcagaatatgggccaaacaggatatc<br>tgtggtaagcagttcctgccccggctcagggccaagaacagatggtccccagatgcg<br>gtcccgccctcagcagtttctagagaaccatcagatgtttccagggtgccccaagga<br>cctgaaatgaccctgtgccttatttgaactaaccaatcagttcgcttctcgcttctg<br>ttcgcgcgcttctgctccccgagctctatataagcagagctcgtttagtgaaccgtc<br>agatc | MND promoter |

The invention claimed is:

1. A genetically engineered T cell, comprising a modified endogenous CD247 locus, said modified endogenous CD247 locus comprising a nucleic acid sequence encoding a chimeric receptor comprising an intracellular region comprising a CD3zeta (CD3z) signaling domain, wherein the nucleic acid sequence comprises a transgene sequence encoding a portion of the chimeric receptor, wherein the transgene sequence is integrated at the endogenous CD247 locus to result in the modified endogenous CD247 locus, and wherein the CD3z signaling domain or a fragment of the CD3z signaling domain is encoded by an open reading frame or a partial sequence thereof of the endogenous CD247 locus.

2. The genetically engineered T cell of claim 1, wherein the nucleic acid sequence encoding the chimeric receptor comprises an in-frame fusion of (i) the transgene sequence encoding the portion of the chimeric receptor and (ii) the open reading frame or partial sequence thereof of the endogenous CD247 locus.

3. The genetically engineered T cell of claim 1, wherein the transgene sequence does not comprise a sequence encoding a 3' UTR and/or does not comprise an intron.

4. The genetically engineered T cell of claim 1, wherein the transgene sequence encodes a heterologous fragment of the CD3z signaling domain or does not encode the CD3z signaling domain or fragment thereof.

5. The genetically engineered T cell of claim 1, wherein the open reading frame or partial sequence thereof comprises at least one intron and at least one exon of the endogenous CD247 locus, and/or encodes a 3' UTR of the endogenous CD247 locus.

6. The genetically engineered T cell of claim 1, wherein the transgene sequence is downstream of exon 1 and upstream of exon 8 of the open reading frame of the endogenous CD247 locus.

7. The genetically engineered T cell of claim 1, wherein the CD3z signaling domain or fragment thereof is encoded by the open reading frame or partial sequence thereof of the endogenous CD247 locus.

8. The genetically engineered T cell of claim 1, wherein the chimeric receptor is capable of signaling via the CD3z signaling domain when expressed in the T cell.

9. The genetically engineered T cell of claim 1, wherein the chimeric receptor is a chimeric antigen receptor (CAR).

10. The genetically engineered T cell of claim 1, wherein the chimeric receptor comprises (i) an extracellular region comprising a binding domain, (ii) a transmembrane domain, and (iii) the intracellular region.

11. The genetically engineered T cell of claim 10, wherein the binding domain comprises an antibody or an antigen-binding fragment thereof.

12. The genetically engineered T cell of claim 10, wherein the binding domain is capable of binding to a target antigen that is associated with, specific to, and/or expressed on a cell or tissue of a disease, disorder or condition.

13. The genetically engineered T cell of claim 1, wherein the intracellular region comprises one or more costimulatory signaling domains.

14. The genetically engineered T cell of claim 13, wherein the one or more costimulatory signaling domains comprise an intracellular signaling domain of CD28, 4-1BB or ICOS, or a signaling portion thereof.

15. The genetically engineered T cell of claim 1, wherein the T cell is a primary T cell derived from a human subject.

16. A composition comprising the genetically engineered T cell of claim 1.

* * * * *

SEQUENCE LISTING

<160> NUMBER OF SEQ ID NOS: 131

<210> SEQ ID NO 1
<211> LENGTH: 12
<212> TYPE: PRT
<213> ORGANISM: Homo sapiens
<220> FEATURE:
<223> OTHER INFORMATION: spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 2
gaatctaagt acggaccgcc ctgccccct tgccct 36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

```
Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115
```

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125
```

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 5
<211> LENGTH: 282
<212> TYPE: PRT
<213> ORGANISM: Artificial Sequence
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

```
Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
            20


<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
```

```
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355


<210> SEQ ID NO 8
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: Uniprot P10747
<309> DATABASE ENTRY DATE: 1989-07-01

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 9
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: Uniprot P10747
<309> DATABASE ENTRY DATE: 1989-07-01

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65


<210> SEQ ID NO 10
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: Uniprot P10747
```

<309> DATABASE ENTRY DATE: 1989-07-01

<400> SEQUENCE: 10

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 11
<211> LENGTH: 41
<212> TYPE: PRT
<213> ORGANISM: Homo sapiens
<220> FEATURE:
<223> OTHER INFORMATION: CD28 (LL to GG)

<400> SEQUENCE: 11

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 12
<211> LENGTH: 42
<212> TYPE: PRT
<213> ORGANISM: Homo sapiens
<220> FEATURE:
<223> OTHER INFORMATION: 4-1BB
<300> PUBLICATION INFORMATION:
<308> DATABASE ACCESSION NUMBER: Uniprot Q07011.1
<309> DATABASE ENTRY DATE: 1995-02-01

<400> SEQUENCE: 12

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 14
<211> LENGTH: 112
<212> TYPE: PRT
<213> ORGANISM: hmo sapiens
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu

```
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335


<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15

Gly Pro


<210> SEQ ID NO 18
```

```
<211> LENGTH: 22
<212> TYPE: PRT
<213> ORGANISM: Artificial Sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15

Pro Gly Pro


<210> SEQ ID NO 20
<211> LENGTH: 20
<212> TYPE: PRT
<213> ORGANISM: Artificial Sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1               5                   10                  15

Asn Pro Gly Pro
            20


<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15

Glu Ser Asn Pro Gly Pro
            20


<210> SEQ ID NO 22
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly Pro
1               5                   10
```

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1               5                   10                  15

Ser

<210> SEQ ID NO 24
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 24
atgcttctcc tggtgacaag ccttctgctc tgtgagttac cacacccagc attcctcctg     60
atccca                                                                66

<210> SEQ ID NO 25
<211> LENGTH: 22
<212> TYPE: PRT
<213> ORGANISM: Artificial Sequence
<220> FEATURE:
<223> OTHER INFORMATION: GMCSFR alpha chain signal sequence

<400> SEQUENCE: 25

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1               5                   10                  15

His Ala

<210> SEQ ID NO 27
<211> LENGTH: 15
<212> TYPE: PRT
<213> ORGANISM: Artificial Sequence
<220> FEATURE:
<223> OTHER INFORMATION: Hinge

<400> SEQUENCE: 27

Glu Pro Lys Ser Cys Asp Lys Thr His Thr Cys Pro Pro Cys Pro
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Hinge

<400> SEQUENCE: 28

Glu Arg Lys Cys Cys Val Glu Cys Pro Pro Cys Pro
1               5                   10

<210> SEQ ID NO 29
<211> LENGTH: 61
<212> TYPE: PRT
<213> ORGANISM: Artificial Sequence
<220> FEATURE:
<223> OTHER INFORMATION: Hinge

<400> SEQUENCE: 29

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Pro Cys Pro Arg Cys Pro
    50                  55                  60

<210> SEQ ID NO 30
<211> LENGTH: 12
<212> TYPE: PRT
<213> ORGANISM: Artificial Sequence
<220> FEATURE:
<223> OTHER INFORMATION: Hinge

<400> SEQUENCE: 30

Glu Ser Lys Tyr Gly Pro Pro Cys Pro Ser Cys Pro
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Hinge
<220> FEATURE:
<221> NAME/KEY: VARIANT
<222> LOCATION: (1)...(1)
<223> OTHER INFORMATION: Xaa is glycine, cysteine or arginine
<220> FEATURE:
<221> NAME/KEY: VARIANT
<222> LOCATION: (4)...(4)
<223> OTHER INFORMATION: Xaa is cysteine or threonine

<400> SEQUENCE: 31

Xaa Pro Pro Xaa Pro
1               5

<210> SEQ ID NO 32
<211> LENGTH: 9
<212> TYPE: PRT
<213> ORGANISM: Artificial Sequence
<220> FEATURE:
<223> OTHER INFORMATION: Hinge

<400> SEQUENCE: 32

Tyr Gly Pro Pro Cys Pro Pro Cys Pro
1               5

<210> SEQ ID NO 33
<211> LENGTH: 10
<212> TYPE: PRT

<213> ORGANISM: Artificial Sequence
<220> FEATURE:
<223> OTHER INFORMATION: Hinge

<400> SEQUENCE: 33

Lys Tyr Gly Pro Pro Cys Pro Pro Cys Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Hinge

<400> SEQUENCE: 34

Glu Val Val Val Lys Tyr Gly Pro Pro Cys Pro Pro Cys Pro
1               5                   10

<210> SEQ ID NO 35
<211> LENGTH: 11
<212> TYPE: PRT
<213> ORGANISM: Artificial Sequence
<220> FEATURE:
<223> OTHER INFORMATION: CDR L1

<400> SEQUENCE: 35

Arg Ala Ser Gln Asp Ile Ser Lys Tyr Leu Asn
1               5                   10

<210> SEQ ID NO 36
<211> LENGTH: 7
<212> TYPE: PRT
<213> ORGANISM: Artificial Sequence
<220> FEATURE:
<223> OTHER INFORMATION: CDR L2

<400> SEQUENCE: 36

Ser Arg Leu His Ser Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: CDR L3

<400> SEQUENCE: 37

Gly Asn Thr Leu Pro Tyr Thr Phe Gly
1               5

<210> SEQ ID NO 38
<211> LENGTH: 5
<212> TYPE: PRT
<213> ORGANISM: Artificial Sequence
<220> FEATURE:
<223> OTHER INFORMATION: CDR H1

<400> SEQUENCE: 38

Asp Tyr Gly Val Ser
1               5

<210> SEQ ID NO 39
<211> LENGTH: 16
<212> TYPE: PRT
<213> ORGANISM: Artificial Sequence

<220> FEATURE:
<223> OTHER INFORMATION: CDR H2

<400> SEQUENCE: 39

Val Ile Trp Gly Ser Glu Thr Thr Tyr Tyr Asn Ser Ala Leu Lys Ser
1 5 10 15

<210> SEQ ID NO 40
<211> LENGTH: 7
<212> TYPE: PRT
<213> ORGANISM: Artificial Sequence
<220> FEATURE:
<223> OTHER INFORMATION: CDR H3

<400> SEQUENCE: 40

Tyr Ala Met Asp Tyr Trp Gly
1 5

<210> SEQ ID NO 41
<211> LENGTH: 120
<212> TYPE: PRT
<213> ORGANISM: Artificial Sequence
<220> FEATURE:
<223> OTHER INFORMATION: VH

<400> SEQUENCE: 41

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser
115 120

<210> SEQ ID NO 42
<211> LENGTH: 107
<212> TYPE: PRT
<213> ORGANISM: Artificial Sequence
<220> FEATURE:
<223> OTHER INFORMATION: VL

<400> SEQUENCE: 42

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

```
Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105


<210> SEQ ID NO 43
<211> LENGTH: 245
<212> TYPE: PRT
<213> ORGANISM: Artificial Sequence
<220> FEATURE:
<223> OTHER INFORMATION: scFv

<400> SEQUENCE: 43

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 44
<211> LENGTH: 11
<212> TYPE: PRT
<213> ORGANISM: Artificial Sequence
<220> FEATURE:
<223> OTHER INFORMATION: CDR L1

<400> SEQUENCE: 44

Lys Ala Ser Gln Asn Val Gly Thr Asn Val Ala
1               5                   10
```

<210> SEQ ID NO 45
<211> LENGTH: 7
<212> TYPE: PRT
<213> ORGANISM: Artificial Sequence
<220> FEATURE:
<223> OTHER INFORMATION: CDR L2

<400> SEQUENCE: 45

Ser Ala Thr Tyr Arg Asn Ser
1               5

<210> SEQ ID NO 46
<211> LENGTH: 9
<212> TYPE: PRT
<213> ORGANISM: Artificial Sequence
<220> FEATURE:
<223> OTHER INFORMATION: CDR L3

<400> SEQUENCE: 46

Gln Gln Tyr Asn Arg Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: CDR H1

<400> SEQUENCE: 47

Ser Tyr Trp Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: CDR H2

<400> SEQUENCE: 48

Gln Ile Tyr Pro Gly Asp Gly Asp Thr Asn Tyr Asn Gly Lys Phe Lys
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: CDR H3

<400> SEQUENCE: 49

Lys Thr Ile Ser Ser Val Val Asp Phe Tyr Phe Asp Tyr
1               5                   10

<210> SEQ ID NO 50
<211> LENGTH: 122
<212> TYPE: PRT
<213> ORGANISM: Artificial Sequence
<220> FEATURE:
<223> OTHER INFORMATION: VH

<400> SEQUENCE: 50

Glu Val Lys Leu Gln Gln Ser Gly Ala Glu Leu Val Arg Pro Gly Ser
1               5                   10                  15

```
Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120


<210> SEQ ID NO 51
<211> LENGTH: 108
<212> TYPE: PRT
<213> ORGANISM: Artificial Sequence
<220> FEATURE:
<223> OTHER INFORMATION: VL

<400> SEQUENCE: 51

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105


<210> SEQ ID NO 52
<211> LENGTH: 15
<212> TYPE: PRT
<213> ORGANISM: Artificial Sequence
<220> FEATURE:
<223> OTHER INFORMATION: linker

<400> SEQUENCE: 52

Gly Gly Gly Gly Ser Gly Gly Gly Gly Ser Gly Gly Gly Gly Ser
1               5                   10                  15


<210> SEQ ID NO 53
<211> LENGTH: 245
<212> TYPE: PRT
<213> ORGANISM: Artificial Sequence
<220> FEATURE:
<223> OTHER INFORMATION: scFv

<400> SEQUENCE: 53

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
```

```
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245


<210> SEQ ID NO 54
<211> LENGTH: 12
<212> TYPE: PRT
<213> ORGANISM: Artificial Sequence
<220> FEATURE:
<223> OTHER INFORMATION: HC-CDR3

<400> SEQUENCE: 54

His Tyr Tyr Tyr Gly Gly Ser Tyr Ala Met Asp Tyr
1               5                   10


<210> SEQ ID NO 55
<211> LENGTH: 7
<212> TYPE: PRT
<213> ORGANISM: Artificial Sequence
<220> FEATURE:
<223> OTHER INFORMATION: LC-CDR2

<400> SEQUENCE: 55

His Thr Ser Arg Leu His Ser
1               5


<210> SEQ ID NO 56
<211> LENGTH: 9
<212> TYPE: PRT
<213> ORGANISM: Artificial Sequence
<220> FEATURE:
<223> OTHER INFORMATION: LC-CDR3

<400> SEQUENCE: 56
```

Gln Gln Gly Asn Thr Leu Pro Tyr Thr
1 5

<210> SEQ ID NO 57
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 57
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggaacag 240
gaagatatcg ccacctactt ttgccagcag ggcaacacac tgccctacac ctttggcggc 300
ggaacaaagc tggaaatcac cggcagcacc tccggcagcg gcaagcctgg cagcggcgag 360
ggcagcacca agggcgaggt gaagctgcag gaaagcggcc ctggcctggt ggcccccagc 420
cagagcctga gcgtgacctg caccgtgagc ggcgtgagcc tgcccgacta cggcgtgagc 480
tggatccggc agcccccag gaagggcctg gaatggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgc 660
gccaagcact actactacgg cggcagctac gccatggact actggggcca gggcaccagc 720
gtgaccgtga gcagc 735

<210> SEQ ID NO 58
<211> LENGTH: 18
<212> TYPE: PRT
<213> ORGANISM: Artificial Sequence
<220> FEATURE:
<223> OTHER INFORMATION: linker

<400> SEQUENCE: 58

Gly Ser Thr Ser Gly Ser Gly Lys Pro Gly Ser Gly Glu Gly Ser Thr
1 5 10 15

Lys Gly

<210> SEQ ID NO 59
<211> LENGTH: 20
<212> TYPE: DNA
<213> ORGANISM: Artificial Sequence
<220> FEATURE:
<223> OTHER INFORMATION: CD247 (CD3z) target sequence 1

<400> SEQUENCE: 59
caccttcact ctcaggaaca 20

<210> SEQ ID NO 60
<211> LENGTH: 20
<212> TYPE: DNA
<213> ORGANISM: Artificial Sequence
<220> FEATURE:
<223> OTHER INFORMATION: CD247 (CD3z) target sequence 2

<400> SEQUENCE: 60
gaatgacacc atagatgaag 20

<210> SEQ ID NO 61
<211> LENGTH: 20
<212> TYPE: DNA
<213> ORGANISM: Artificial Sequence
<220> FEATURE:
<223> OTHER INFORMATION: CD247 (CD3z) target sequence 3

<400> SEQUENCE: 61
tgaagaggat tccatccagc 20

<210> SEQ ID NO 62
<211> LENGTH: 20
<212> TYPE: DNA
<213> ORGANISM: Artificial Sequence
<220> FEATURE:
<223> OTHER INFORMATION: CD247 (CD3z) target sequence 4

<400> SEQUENCE: 62
tccagcaggt agcagagttt 20

<210> SEQ ID NO 63
<211> LENGTH: 22
<212> TYPE: DNA
<213> ORGANISM: Artificial Sequence
<220> FEATURE:
<223> OTHER INFORMATION: CD247 (CD3z) target sequence + PAM 1

<400> SEQUENCE: 63
caccttcact ctcaggaaca gg 22

<210> SEQ ID NO 64
<211> LENGTH: 23
<212> TYPE: DNA
<213> ORGANISM: Artificial Sequence
<220> FEATURE:
<223> OTHER INFORMATION: CD247 (CD3z) target sequence + PAM 2

<400> SEQUENCE: 64
gaatgacacc atagatgaag agg 23

<210> SEQ ID NO 65
<211> LENGTH: 23
<212> TYPE: DNA
<213> ORGANISM: Artificial Sequence
<220> FEATURE:
<223> OTHER INFORMATION: CD247 (CD3z) target sequence + PAM 3

<400> SEQUENCE: 65
tgaagaggat tccatccagc agg 23

<210> SEQ ID NO 66
<211> LENGTH: 23
<212> TYPE: DNA
<213> ORGANISM: Artificial Sequence
<220> FEATURE:
<223> OTHER INFORMATION: CD247 (CD3z) target sequence + PAM 4

<400> SEQUENCE: 66
tccagcaggt agcagagttt ggg 23

<210> SEQ ID NO 67
<211> LENGTH: 20
<212> TYPE: DNA
<213> ORGANISM: Artificial Sequence
<220> FEATURE:
<223> OTHER INFORMATION: CD247 (CD3z) target sequence 5

<400> SEQUENCE: 67
agacgccccc gcgtaccagc 20

<210> SEQ ID NO 68
<211> LENGTH: 20
<212> TYPE: DNA
<213> ORGANISM: Artificial Sequence
<220> FEATURE:
<223> OTHER INFORMATION: CD247 (CD3z) target sequence 6

<400> SEQUENCE: 68
gctgacttac gttatagagc 20

<210> SEQ ID NO 69
<211> LENGTH: 20
<212> TYPE: DNA
<213> ORGANISM: Artificial Sequence
<220> FEATURE:
<223> OTHER INFORMATION: CD247 (CD3z) target sequence 7

<400> SEQUENCE: 69
tttcaccgcg gccatcctgc 20

<210> SEQ ID NO 70
<211> LENGTH: 20
<212> TYPE: DNA
<213> ORGANISM: Artificial Sequence
<220> FEATURE:
<223> OTHER INFORMATION: CD247 (CD3z) target sequence 8

<400> SEQUENCE: 70
taatcggcaa ctgtgcctgc 20

<210> SEQ ID NO 71
<211> LENGTH: 20
<212> TYPE: DNA
<213> ORGANISM: Artificial Sequence
<220> FEATURE:
<223> OTHER INFORMATION: CD247 (CD3z) target sequence 9

<400> SEQUENCE: 71
cggaggccta cagtgagatt 20

<210> SEQ ID NO 72
<211> LENGTH: 20
<212> TYPE: DNA
<213> ORGANISM: Artificial Sequence
<220> FEATURE:
<223> OTHER INFORMATION: CD247 (CD3z) target sequence 10

<400> SEQUENCE: 72
tggtacccac cttcactctc 20

<210> SEQ ID NO 73
<211> LENGTH: 164
<212> TYPE: PRT
<213> ORGANISM: Homo sapiens
<220> FEATURE:
<223> OTHER INFORMATION: CD247 isoform 1 precursor protein sequence
<300> PUBLICATION INFORMATION:
<308> DATABASE ACCESSION NUMBER: NP_932170.1
<309> DATABASE ENTRY DATE: 2020-03-28

<400> SEQUENCE: 73

Met Lys Trp Lys Ala Leu Phe Thr Ala Ala Ile Leu Gln Ala Gln Leu

```
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 74
<211> LENGTH: 1690
<212> TYPE: DNA
<213> ORGANISM: Homo sapiens
<220> FEATURE:
<223> OTHER INFORMATION: CD247 isoform 1 precursor mRNA sequence
<300> PUBLICATION INFORMATION:
<308> DATABASE ACCESSION NUMBER: NM_198053.2
<309> DATABASE ENTRY DATE: 2020-01-13

<400> SEQUENCE: 74

tgctttctca aaggccccac agtcctccac ttcctgggga ggtagctgca gaataaaacc     60

agcagagact ccttttctcc taaccgtccc ggccaccgct gcctcagcct ctgcctccca    120

gcctctttct gagggaaagg acaagatgaa gtggaaggcg cttttcaccg cggccatcct    180

gcaggcacag ttgccgatta cagaggcaca gagctttggc ctgctggatc ccaaactctg    240

ctacctgctg gatggaatcc tcttcatcta tggtgtcatt ctcactgcct tgttcctgag    300

agtgaagttc agcaggagcg cagacgcccc cgcgtaccag cagggccaga accagctcta    360

taacgagctc aatctaggac gaagagagga gtacgatgtt ttggacaaga gacgtggccg    420

ggaccctgag atggggggaa agccgcagag aaggaagaac cctcaggaag gcctgtacaa    480

tgaactgcag aaagataaga tggcggaggc ctacagtgag attgggatga aaggcgagcg    540

ccggaggggc aaggggcacg atggccttta ccagggtctc agtacagcca ccaaggacac    600

ctacgacgcc cttcacatgc aggccctgcc ccctcgctaa cagccagggg atttcaccac    660

tcaaaggcca gacctgcaga cgcccagatt atgagacaca ggatgaagca tttacaaccc    720

ggttcactct tctcagccac tgaagtattc ccctttatgt acaggatgct ttggttatat    780

ttagctccaa accttcacac acagactgtt gtccctgcac tctttaaggg agtgtactcc    840

cagggcttac ggccctggcc ttgggccctc tggtttgccg gtggtgcagg tagacctgtc    900

tcctggcggt tcctcgttct ccctgggagg cgggcgcact gcctctcaca gctgagttgt    960

tgagtctgtt ttgtaaagtc cccagagaaa gcgcagatgc tagcacatgc cctaatgtct   1020

gtatcactct gtgtctgagt ggcttcactc ctgctgtaaa tttggcttct gttgtcacct   1080
```

tcacctcctt tcaaggtaac tgtactgggc catgttgtgc ctccctggtg agagggccgg 1140
gcagaggggc agatggaaag gagcctaggc caggtgcaac cagggagctg caggggcatg 1200
ggaaggtggg cgggcagggg agggtcagcc agggcctgcg agggcagcgg gagcctccct 1260
gcctcaggcc tctgtgccgc accattgaac tgtaccatgt gctacagggg ccagaagatg 1320
aacagactga ccttgatgag ctgtgcacaa agtggcataa aaaacatgtg gttacacagt 1380
gtgaataaag tgctgcggag caagaggagg ccgttgattc acttcacgct ttcagcgaat 1440
gacaaaatca tctttgtgaa ggcctcgcag gaagacccaa cacatgggac ctataactgc 1500
ccagcggaca gtggcaggac aggaaaaacc cgtcaatgta ctaggatact gctgcgtcat 1560
tacagggcac aggccatgga tggaaaacgc tctctgctct gctttttttc tactgtttta 1620
atttatactg gcatgctaaa gccttcctat tttgcataat aaatgcttca gtgaaaatgc 1680
aaaaaaaaaa 1690

<210> SEQ ID NO 75
<211> LENGTH: 163
<212> TYPE: PRT
<213> ORGANISM: Homo sapiens
<220> FEATURE:
<223> OTHER INFORMATION: CD247 isoform 2 precursor protein sequence
<300> PUBLICATION INFORMATION:
<308> DATABASE ACCESSION NUMBER: NO_000725.1
<309> DATABASE ENTRY DATE: 2020-02-20

<400> SEQUENCE: 75

Met Lys Trp Lys Ala Leu Phe Thr Ala Ala Ile Leu Gln Ala Gln Leu
1 5 10 15

Pro Ile Thr Glu Ala Gln Ser Phe Gly Leu Leu Asp Pro Lys Leu Cys
20 25 30

Tyr Leu Leu Asp Gly Ile Leu Phe Ile Tyr Gly Val Ile Leu Thr Ala
35 40 45

Leu Phe Leu Arg Val Lys Phe Ser Arg Ser Ala Asp Ala Pro Ala Tyr
50 55 60

Gln Gln Gly Gln Asn Gln Leu Tyr Asn Glu Leu Asn Leu Gly Arg Arg
65 70 75 80

Glu Glu Tyr Asp Val Leu Asp Lys Arg Arg Gly Arg Asp Pro Glu Met
85 90 95

Gly Gly Lys Pro Arg Arg Lys Asn Pro Gln Glu Gly Leu Tyr Asn Glu
100 105 110

Leu Gln Lys Asp Lys Met Ala Glu Ala Tyr Ser Glu Ile Gly Met Lys
115 120 125

Gly Glu Arg Arg Arg Gly Lys Gly His Asp Gly Leu Tyr Gln Gly Leu
130 135 140

Ser Thr Ala Thr Lys Asp Thr Tyr Asp Ala Leu His Met Gln Ala Leu
145 150 155 160

Pro Pro Arg

<210> SEQ ID NO 76
<211> LENGTH: 1687
<212> TYPE: DNA
<213> ORGANISM: Homo sapiens
<220> FEATURE:
<223> OTHER INFORMATION: CD247 isoform 2 precursor mRNA sequence

<400> SEQUENCE: 76
tgctttctca aaggccccac agtcctccac ttcctgggga ggtagctgca gaataaaacc 60
agcagagact ccttttctcc taaccgtccc ggccaccgct gcctcagcct ctgcctccca 120
gcctctttct gagggaaagg acaagatgaa gtggaaggcg cttttcaccg cggccatcct 180
gcaggcacag ttgccgatta cagaggcaca gagctttggc ctgctggatc ccaaactctg 240
ctacctgctg gatggaatcc tcttcatcta tggtgtcatt ctcactgcct tgttcctgag 300
agtgaagttc agcaggagcg cagacgcccc cgcgtaccag cagggccaga accagctcta 360
taacgagctc aatctaggac gaagagagga gtacgatgtt ttggacaaga gacgtggccg 420
ggaccctgag atggggggaa agccgagaag gaagaaccct caggaaggcc tgtacaatga 480
actgcagaaa gataagatgg cggaggccta cagtgagatt gggatgaaag gcgagcgccg 540
gaggggcaag gggcacgatg gcctttacca gggtctcagt acagccacca aggacaccta 600
cgacgccctt cacatgcagg ccctgccccc tcgctaacag ccaggggatt tcaccactca 660
aaggccagac ctgcagacgc ccagattatg agacacagga tgaagcattt acaacccggt 720
tcactcttct cagccactga agtattcccc tttatgtaca ggatgctttg gttatattta 780
gctccaaacc ttcacacaca gactgttgtc cctgcactct ttaagggagt gtactcccag 840
ggcttacggc cctggccttg ggccctctgg tttgccggtg gtgcaggtag acctgtctcc 900
tggcggttcc tcgttctccc tgggaggcgg gcgcactgcc tctcacagct gagttgttga 960
gtctgttttg taaagtcccc agagaaagcg cagatgctag cacatgccct aatgtctgta 1020
tcactctgtg tctgagtggc ttcactcctg ctgtaaattt ggcttctgtt gtcaccttca 1080
cctcctttca aggtaactgt actgggccat gttgtgcctc cctggtgaga gggccgggca 1140
gaggggcaga tggaaaggag cctaggccag gtgcaaccag ggagctgcag gggcatggga 1200
aggtgggcgg gcaggggagg gtcagccagg gcctgcgagg gcagcgggag cctccctgcc 1260
tcaggcctct gtgccgcacc attgaactgt accatgtgct acaggggcca gaagatgaac 1320
agactgacct tgatgagctg tgcacaaagt ggcataaaaa acatgtggtt acacagtgtg 1380
aataaagtgc tgcggagcaa gaggaggccg ttgattcact tcacgctttc agcgaatgac 1440
aaaatcatct ttgtgaaggc ctcgcaggaa gacccaacac atgggaccta taactgccca 1500
gcggacagtg gcaggacagg aaaaacccgt caatgtacta ggatactgct gcgtcattac 1560
agggcacagg ccatggatgg aaaacgctct ctgctctgct ttttttctac tgttttaatt 1620
tatactggca tgctaaagcc ttcctatttt gcataataaa tgcttcagtg aaaatgcaaa 1680
aaaaaaa 1687

<210> SEQ ID NO 77
<211> LENGTH: 1189
<212> TYPE: DNA
<213> ORGANISM: Homo sapiens
<220> FEATURE:
<223> OTHER INFORMATION: EF1alpha promoter
<300> PUBLICATION INFORMATION:
<308> DATABASE ACCESSION NUMBER: J04617.1
<309> DATABASE ENTRY DATE: 1994-11-07

<400> SEQUENCE: 77
cgtgaggctc cggtgcccgt cagtgggcag agcgcacatc gcccacagtc cccgagaagt 60
tggggggagg ggtcggcaat tgaaccggtg cctagagaag gtggcgcggg gtaaactggg 120
aaagtgatgt cgtgtactgg ctccgccttt ttcccgaggg tgggggagaa ccgtatataa 180
gtgcagtagt cgccgtgaac gttctttttc gcaacgggtt tgccgccaga acacaggtaa 240
gtgccgtgtg tggttcccgc gggcctggcc tctttacggg ttatggccct tgcgtgcctt 300
gaattacttc cacgcccctg gctgcagtac gtgattcttg atcccgagct tcgggttgga 360
agtgggtggg agagttcgag gccttgcgct taaggagccc cttcgcctcg tgcttgagtt 420
gaggcctggc ctgggcgctg gggccgccgc gtgcgaatct ggtggcacct tcgcgcctgt 480
ctcgctgctt tcgataagtc tctagccatt taaaattttt gatgacctgc tgcgacgctt 540
tttttctggc aagatagtct tgtaaatgcg ggccaagatc tgcacactgg tatttcggtt 600
tttggggccg cgggcggcga cggggcccgt gcgtcccagc gcacatgttc ggcgaggcgg 660
ggcctgcgag cgcggccacc gagaatcgga cgggggtagt ctcaagctgg ccggcctgct 720
ctggtgcctg gcctcgcgcc gccgtgtatc gccccgccct gggcggcaag gctggcccgg 780
tcggcaccag ttgcgtgagc ggaaagatgg ccgcttcccg gccctgctgc agggagctca 840
aaatggagga cgcggcgctc gggagagcgg gcgggtgagt cacccacaca aaggaaaagg 900
gcctttccgt cctcagccgt cgcttcatgt gactccacgg agtaccgggc gccgtccagg 960
cacctcgatt agttctcgag cttttggagt acgtcgtctt taggttgggg ggaggggttt 1020
tatgcgatgg agtttcccca cactgagtgg gtggagactg aagttaggcc agcttggcac 1080
ttgatgtaat tctccttgga atttgccctt tttgagtttg gatcttggtt cattctcaag 1140
cctcagacag tggttcaaag tttttttctt ccatttcagg tgtcgtgaa 1189

<210> SEQ ID NO 78
<211> LENGTH: 25
<212> TYPE: DNA
<213> ORGANISM: Artificial Sequence
<220> FEATURE:
<223> OTHER INFORMATION: human HBB splice acceptor site

<400> SEQUENCE: 78
ctgacctctt ctcttcctcc cacag 25

<210> SEQ ID NO 79
<211> LENGTH: 13
<212> TYPE: DNA
<213> ORGANISM: Artificial Sequence
<220> FEATURE:
<223> OTHER INFORMATION: Human IgG splice acceptor site

<400> SEQUENCE: 79
tttctctcca cag 13

<210> SEQ ID NO 80
<211> LENGTH: 600
<212> TYPE: DNA
<213> ORGANISM: Artificial Sequence
<220> FEATURE:
<223> OTHER INFORMATION: 5' homology arm

<400> SEQUENCE: 80
agatcccact gtcctaggcg ggagagtgct tggcactgag gaggcaggga gttgggggag 60
agttaaccca gattctccct gtcctagtta actgtcagat attgaaatga tctcatttga 120
ccatcatttg acctattgtc tccctgtggg taggcctcag agccacacac ctcaggccag 180
gagtaccatt catccagacg tgaacatctt cccgaggctt ccagagttct tggttcacac 240
cggggctaac atggctgggc ttctgctgca gtggcaggag ctctgtgcac agagaacagc 300
ctcatctgct cgccttgttt ccacctcccc tcccattgcc ccaggttctt tggccccaca 360
gcggccacat ctgccgttgg tgccaatagg ttttccagga gctggttgag gtgggaggga 420

```
gggagagggt tgtgatcagg ctgaggcatg gggattggat atagtctccg tgtcatgatt    480

tatttggtca gtcagtccta gtgccaccct ggggtaatgg ggatgtgttc tcgtcacctt    540

gggcctggct gaccagcttt atctcttggc acagaggcac agagctttgg cctgctggat    600


<210> SEQ ID NO 81
<211> LENGTH: 600
<212> TYPE: DNA
<213> ORGANISM: Artificial Sequence
<220> FEATURE:
<223> OTHER INFORMATION: 3' homology arm

<400> SEQUENCE: 81

agagtgaagg tgggtaccac tgggctttgg gaggagggca cggggtcccc cacttgatgg     60

atgttcagag gggccttggt cttggaaggt ctcaagctcg ggtggtgcct ggggcttggt    120

atccaggagc aaagcaagga ccagccaagt gtgtgccttg agtgggctga ggaggaggtg    180

gcagtgtctg gctgagatgg acagggtagg agggagagcc tggtgctagg cacctccatg    240

acaagccgta caaatgtgtg cacatcagag tgtcccaggg aaggcgatgc tactggtgac    300

aaaggggctt acactcaggc agaggtcctt ctttccaagt gtgaatgaag gccatgttag    360

cctttctctt gaaaaggccc tttcctcatc tgtaactggg gagctgacca gagcgtgggt    420

ttttcacttg gtgccttgca gaccctggat ttcttcgtgg ggctggtcat ggtgtgggca    480

gagattggaa gaatttagga gtaaagggga gaatccagtc ccagtcatca cttcagtgct    540

tctcaaccca tttcttgttt gaattttgga ctttggcata atattttatt tgaaaaacca    600


<210> SEQ ID NO 82
<211> LENGTH: 107
<212> TYPE: PRT
<213> ORGANISM: Artificial Sequence
<220> FEATURE:
<223> OTHER INFORMATION: FKBP

<400> SEQUENCE: 82

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Met Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105


<210> SEQ ID NO 83
<211> LENGTH: 107
<212> TYPE: PRT
<213> ORGANISM: Artificial Sequence
<220> FEATURE:
<223> OTHER INFORMATION: FKBP12v36

<400> SEQUENCE: 83

Gly Val Gln Val Glu Thr Ile Ser Pro Gly Asp Gly Arg Thr Phe Pro
1               5                   10                  15
```

```
Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 84
<211> LENGTH: 16
<212> TYPE: PRT
<213> ORGANISM: Artificial Sequence
<220> FEATURE:
<223> OTHER INFORMATION: human C-Src acylation motif

<400> SEQUENCE: 84

```
Met Gly Ser Asn Lys Ser Lys Pro Lys Asp Ala Ser Gln Arg Arg Arg
1               5                   10                  15
```

<210> SEQ ID NO 85
<211> LENGTH: 5
<212> TYPE: PRT
<213> ORGANISM: Artificial Sequence
<220> FEATURE:
<223> OTHER INFORMATION: dual acylation motif
<220> FEATURE:
<221> NAME/KEY: VARIANT
<222> LOCATION: (4)...(4)
<223> OTHER INFORMATION: Xaa is any amino acid

<400> SEQUENCE: 85

```
Met Gly Cys Xaa Cys
1               5
```

<210> SEQ ID NO 86
<211> LENGTH: 4
<212> TYPE: PRT
<213> ORGANISM: Artificial Sequence
<220> FEATURE:
<223> OTHER INFORMATION: CAAX motif
<220> FEATURE:
<221> NAME/KEY: VARIANT
<222> LOCATION: (4)...(4)
<223> OTHER INFORMATION: Xaa is any amino acid

<400> SEQUENCE: 86

```
Cys Ala Ala Xaa
1
```

<210> SEQ ID NO 87
<211> LENGTH: 20
<212> TYPE: RNA
<213> ORGANISM: Artificial Sequence
<220> FEATURE:
<223> OTHER INFORMATION: CD247 (CD3z) targeting domain 1

<400> SEQUENCE: 87

```
caccuucacu cucaggaaca                                            20
```

<210> SEQ ID NO 88
<211> LENGTH: 20
<212> TYPE: RNA
<213> ORGANISM: Artificial Sequence
<220> FEATURE:
<223> OTHER INFORMATION: CD247 (CD3z) targeting domain 2

<400> SEQUENCE: 88
gaaugacacc auagaugaag 20

<210> SEQ ID NO 89
<211> LENGTH: 20
<212> TYPE: RNA
<213> ORGANISM: Artificial Sequence
<220> FEATURE:
<223> OTHER INFORMATION: CD247 (CD3z) targeting domain 3

<400> SEQUENCE: 89
ugaagaggau uccauccagc 20

<210> SEQ ID NO 90
<211> LENGTH: 20
<212> TYPE: RNA
<213> ORGANISM: Artificial Sequence
<220> FEATURE:
<223> OTHER INFORMATION: CD247 (CD3z) targeting domain 4

<400> SEQUENCE: 90
uccagcaggu agcagaguuu 20

<210> SEQ ID NO 91
<211> LENGTH: 20
<212> TYPE: RNA
<213> ORGANISM: Artificial Sequence
<220> FEATURE:
<223> OTHER INFORMATION: CD247 (CD3z) targeting domain 5

<400> SEQUENCE: 91
agacgccccc gcguaccagc 20

<210> SEQ ID NO 92
<211> LENGTH: 20
<212> TYPE: RNA
<213> ORGANISM: Artificial Sequence
<220> FEATURE:
<223> OTHER INFORMATION: CD247 (CD3z) targeting domain 6

<400> SEQUENCE: 92
gcugacuuac guuauagagc 20

<210> SEQ ID NO 93
<211> LENGTH: 20
<212> TYPE: RNA
<213> ORGANISM: Artificial Sequence
<220> FEATURE:
<223> OTHER INFORMATION: CD247 (CD3z) targeting domain 7

<400> SEQUENCE: 93
uuucaccgcg gccauccugc 20

<210> SEQ ID NO 94
<211> LENGTH: 20
<212> TYPE: RNA
<213> ORGANISM: Artificial Sequence
<220> FEATURE:
<223> OTHER INFORMATION: CD247 (CD3z) targeting domain 8

<400> SEQUENCE: 94
uaaucggcaa cugugccugc 20

<210> SEQ ID NO 95
<211> LENGTH: 20
<212> TYPE: RNA
<213> ORGANISM: Artificial Sequence
<220> FEATURE:
<223> OTHER INFORMATION: CD247 (CD3z) targeting domain 9

<400> SEQUENCE: 95
cggaggccua cagugagauu 20

<210> SEQ ID NO 96
<211> LENGTH: 20
<212> TYPE: RNA
<213> ORGANISM: Artificial Sequence
<220> FEATURE:
<223> OTHER INFORMATION: CD247 (CD3z) targeting domain 10

<400> SEQUENCE: 96
ugguacccac cuucacucuc 20

<210> SEQ ID NO 97
<211> LENGTH: 96
<212> TYPE: RNA
<213> ORGANISM: Artificial Sequence
<220> FEATURE:
<223> OTHER INFORMATION: exemplary gRNA complementary domain
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 97
nnnnnnnnnn nnnnnnnnnn guuuuagagc uagaaauagc aaguuaaaau aaggcuaguc 60
cguuaucaac uugaaaaagu ggcaccgagu cggugc 96

<210> SEQ ID NO 98
<211> LENGTH: 104
<212> TYPE: RNA
<213> ORGANISM: Artificial Sequence
<220> FEATURE:
<223> OTHER INFORMATION: exemplary gRNA complementary domain
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 98
nnnnnnnnnn nnnnnnnnnn guuuuagagc uaugcugaaa agcauagcaa guuaaaauaa 60
ggcuaguccg uuaucaacuu gaaaaagugg caccgagucg gugc 104

<210> SEQ ID NO 99
<211> LENGTH: 106
<212> TYPE: RNA
<213> ORGANISM: Artificial Sequence
<220> FEATURE:
<223> OTHER INFORMATION: exemplary gRNA complementary domain
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 99
nnnnnnnnnn nnnnnnnnnn guuuuagagc uaugcuggaa acagcauagc aaguuaaaau 60
aaggcuaguc cguuaucaac uugaaaaagu ggcaccgagu cggugc 106

<210> SEQ ID NO 100
<211> LENGTH: 116
<212> TYPE: RNA
<213> ORGANISM: Artificial Sequence
<220> FEATURE:
<223> OTHER INFORMATION: exemplary gRNA complementary domain
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 100
nnnnnnnnnn nnnnnnnnnn guuuuagagc uaugcuguuu uggaaacaaa acagcauagc 60
aaguuaaaau aaggcuaguc cguuaucaac uugaaaaagu ggcaccgagu cggugc 116

<210> SEQ ID NO 101
<211> LENGTH: 96
<212> TYPE: RNA
<213> ORGANISM: Artificial Sequence
<220> FEATURE:
<223> OTHER INFORMATION: exemplary gRNA
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 101
nnnnnnnnnn nnnnnnnnnn guauuagagc uagaaauagc aaguuaauau aaggcuaguc 60
cguuaucaac uugaaaaagu ggcaccgagu cggugc 96

<210> SEQ ID NO 102
<211> LENGTH: 96
<212> TYPE: RNA
<213> ORGANISM: Artificial Sequence
<220> FEATURE:
<223> OTHER INFORMATION: exemplary gRNA
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 102
nnnnnnnnnn nnnnnnnnnn guuuaagagc uagaaauagc aaguuuaaau aaggcuaguc 60
cgguaucaac uugaaaaagu ggcaccgagu cggugc 96

<210> SEQ ID NO 103
<211> LENGTH: 116
<212> TYPE: RNA
<213> ORGANISM: Artificial Sequence
<220> FEATURE:
<223> OTHER INFORMATION: exemplary gRNA
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 103
nnnnnnnnnn nnnnnnnnnn guauuagagc uaugcuguau uggaaacaau acagcauagc 60
aaguuaauau aaggcuaguc cguuaucaac uugaaaaagu ggcaccgagu cggugc 116

<210> SEQ ID NO 104
<211> LENGTH: 47
<212> TYPE: RNA
<213> ORGANISM: Artificial Sequence
<220> FEATURE:
<223> OTHER INFORMATION: exemplary proximal and tail domain

<400> SEQUENCE: 104
aaggcuaguc cguuaucaac uugaaaaagu ggcaccgagu cggugcu 47

<210> SEQ ID NO 105
<211> LENGTH: 49
<212> TYPE: RNA
<213> ORGANISM: Artificial Sequence
<220> FEATURE:
<223> OTHER INFORMATION: exemplary proximal and tail domain

<400> SEQUENCE: 105
aaggcuaguc cguuaucaac uugaaaaagu ggcaccgagu cgguggugc 49

<210> SEQ ID NO 106
<211> LENGTH: 51
<212> TYPE: RNA
<213> ORGANISM: Artificial Sequence
<220> FEATURE:
<223> OTHER INFORMATION: exemplary proximal and tail domain

<400> SEQUENCE: 106
aaggcuaguc cguuaucaac uugaaaaagu ggcaccgagu cggugcggau c 51

<210> SEQ ID NO 107
<211> LENGTH: 31
<212> TYPE: RNA
<213> ORGANISM: Artificial Sequence
<220> FEATURE:
<223> OTHER INFORMATION: exemplary proximal and tail domain

<400> SEQUENCE: 107
aaggcuaguc cguuaucaac uugaaaaagu g 31

<210> SEQ ID NO 108
<211> LENGTH: 18
<212> TYPE: RNA
<213> ORGANISM: Artificial Sequence
<220> FEATURE:
<223> OTHER INFORMATION: exemplary proximal and tail domain

<400> SEQUENCE: 108
aaggcuaguc cguuauca 18

<210> SEQ ID NO 109
<211> LENGTH: 12
<212> TYPE: RNA
<213> ORGANISM: Artificial Sequence
<220> FEATURE:
<223> OTHER INFORMATION: exemplary proximal and tail domain

<400> SEQUENCE: 109
aaggcuaguc cg 12

<210> SEQ ID NO 110
<211> LENGTH: 102
<212> TYPE: RNA
<213> ORGANISM: Artificial Sequence
<220> FEATURE:
<223> OTHER INFORMATION: exemplary chimeric gRNA
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 110
nnnnnnnnnn nnnnnnnnnn guuuuagagc uagaaauagc aaguuaaaau aaggcuaguc 60
cguuaucaac uugaaaaagu ggcaccgagu cggugcuuuu uu 102

<210> SEQ ID NO 111
<211> LENGTH: 102
<212> TYPE: RNA
<213> ORGANISM: Artificial Sequence
<220> FEATURE:
<223> OTHER INFORMATION: exemplary chimeric gRNA
<220> FEATURE:
<221> NAME/KEY: modified_base
<222> LOCATION: (1)...(20)
<223> OTHER INFORMATION: a, c, u, g, unknown or other
<220> FEATURE:
<221> NAME/KEY: modified_base
<222> LOCATION: (1)...(20)
<223> OTHER INFORMATION: n is a, c, g, or u

<400> SEQUENCE: 111
nnnnnnnnnn nnnnnnnnnn guuuuaguac ucuggaaaca gaaucuacua aaacaaggca 60
aaaugccgug uuuaucucgu caacuuguug gcgagauuuu uu 102

<210> SEQ ID NO 112
<211> LENGTH: 1344
<212> TYPE: PRT
<213> ORGANISM: Streptococcus mutans
<220> FEATURE:
<223> OTHER INFORMATION: Cas9

<400> SEQUENCE: 112

Lys Lys Pro Tyr Ser Ile Gly Leu Asp Ile Gly Thr Asn Ser Val Gly
1 5 10 15

Trp Ala Val Val Thr Asp Asp Tyr Lys Val Pro Ala Lys Lys Met Lys
20 25 30

Val Leu Gly Asn Thr Asp Lys Ser His Ile Glu Lys Asn Leu Leu Gly
35 40 45

```
Ala Leu Leu Phe Asp Ser Gly Asn Thr Ala Glu Asp Arg Arg Leu Lys
    50                  55                  60

Arg Thr Ala Arg Arg Arg Tyr Thr Arg Arg Arg Asn Arg Ile Leu Tyr
65                  70                  75                  80

Leu Gln Glu Ile Phe Ser Glu Glu Met Gly Lys Val Asp Asp Ser Phe
                85                  90                  95

Phe His Arg Leu Glu Asp Ser Phe Leu Val Thr Glu Asp Lys Arg Gly
            100                 105                 110

Glu Arg His Pro Ile Phe Gly Asn Leu Glu Glu Glu Val Lys Tyr His
        115                 120                 125

Glu Asn Phe Pro Thr Ile Tyr His Leu Arg Gln Tyr Leu Ala Asp Asn
    130                 135                 140

Pro Glu Lys Val Asp Leu Arg Leu Val Tyr Leu Ala Leu Ala His Ile
145                 150                 155                 160

Ile Lys Phe Arg Gly His Phe Leu Ile Glu Gly Lys Phe Asp Thr Arg
                165                 170                 175

Asn Asn Asp Val Gln Arg Leu Phe Gln Glu Phe Leu Ala Val Tyr Asp
            180                 185                 190

Asn Thr Phe Glu Asn Ser Ser Leu Gln Glu Gln Asn Val Gln Val Glu
        195                 200                 205

Glu Ile Leu Thr Asp Lys Ile Ser Lys Ser Ala Lys Lys Asp Arg Val
    210                 215                 220

Leu Lys Leu Phe Pro Asn Glu Lys Ser Asn Gly Arg Phe Ala Glu Phe
225                 230                 235                 240

Leu Lys Leu Ile Val Gly Asn Gln Ala Asp Phe Lys Lys His Phe Glu
                245                 250                 255

Leu Glu Glu Lys Ala Pro Leu Gln Phe Ser Lys Asp Thr Tyr Glu Glu
            260                 265                 270

Glu Leu Glu Val Leu Leu Ala Gln Ile Gly Asp Asn Tyr Ala Glu Leu
        275                 280                 285

Phe Leu Ser Ala Lys Lys Leu Tyr Asp Ser Ile Leu Leu Ser Gly Ile
    290                 295                 300

Leu Thr Val Thr Asp Val Gly Thr Lys Ala Pro Leu Ser Ala Ser Met
305                 310                 315                 320

Ile Gln Arg Tyr Asn Glu His Gln Met Asp Leu Ala Gln Leu Lys Gln
                325                 330                 335

Phe Ile Arg Gln Lys Leu Ser Asp Lys Tyr Asn Glu Val Phe Ser Asp
            340                 345                 350

Val Ser Lys Asp Gly Tyr Ala Gly Tyr Ile Asp Gly Lys Thr Asn Gln
        355                 360                 365

Glu Ala Phe Tyr Lys Tyr Leu Lys Gly Leu Leu Asn Lys Ile Glu Gly
    370                 375                 380

Ser Gly Tyr Phe Leu Asp Lys Ile Glu Arg Glu Asp Phe Leu Arg Lys
385                 390                 395                 400

Gln Arg Thr Phe Asp Asn Gly Ser Ile Pro His Gln Ile His Leu Gln
                405                 410                 415

Glu Met Arg Ala Ile Ile Arg Arg Gln Ala Glu Phe Tyr Pro Phe Leu
            420                 425                 430

Ala Asp Asn Gln Asp Arg Ile Glu Lys Leu Leu Thr Phe Arg Ile Pro
        435                 440                 445

Tyr Tyr Val Gly Pro Leu Ala Arg Gly Lys Ser Asp Phe Ala Trp Leu
    450                 455                 460
```

```
Ser Arg Lys Ser Ala Asp Lys Ile Thr Pro Trp Asn Phe Asp Glu Ile
465                 470                 475                 480

Val Asp Lys Glu Ser Ser Ala Glu Ala Phe Ile Asn Arg Met Thr Asn
                485                 490                 495

Tyr Asp Leu Tyr Leu Pro Asn Gln Lys Val Leu Pro Lys His Ser Leu
            500                 505                 510

Leu Tyr Glu Lys Phe Thr Val Tyr Asn Glu Leu Thr Lys Val Lys Tyr
        515                 520                 525

Lys Thr Glu Gln Gly Lys Thr Ala Phe Phe Asp Ala Asn Met Lys Gln
    530                 535                 540

Glu Ile Phe Asp Gly Val Phe Lys Val Tyr Arg Lys Val Thr Lys Asp
545                 550                 555                 560

Lys Leu Met Asp Phe Leu Glu Lys Glu Phe Asp Glu Phe Arg Ile Val
                565                 570                 575

Asp Leu Thr Gly Leu Asp Lys Glu Asn Lys Val Phe Asn Ala Ser Tyr
            580                 585                 590

Gly Thr Tyr His Asp Leu Cys Lys Ile Leu Asp Lys Asp Phe Leu Asp
        595                 600                 605

Asn Ser Lys Asn Glu Lys Ile Leu Glu Asp Ile Val Leu Thr Leu Thr
    610                 615                 620

Leu Phe Glu Asp Arg Glu Met Ile Arg Lys Arg Leu Glu Asn Tyr Ser
625                 630                 635                 640

Asp Leu Leu Thr Lys Glu Gln Val Lys Lys Leu Glu Arg Arg His Tyr
                645                 650                 655

Thr Gly Trp Gly Arg Leu Ser Ala Glu Leu Ile His Gly Ile Arg Asn
            660                 665                 670

Lys Glu Ser Arg Lys Thr Ile Leu Asp Tyr Leu Ile Asp Asp Gly Asn
        675                 680                 685

Ser Asn Arg Asn Phe Met Gln Leu Ile Asn Asp Asp Ala Leu Ser Phe
    690                 695                 700

Lys Glu Glu Ile Ala Lys Ala Gln Val Ile Gly Glu Thr Asp Asn Leu
705                 710                 715                 720

Asn Gln Val Val Ser Asp Ile Ala Gly Ser Pro Ala Ile Lys Lys Gly
                725                 730                 735

Ile Leu Gln Ser Leu Lys Ile Val Asp Glu Leu Val Lys Ile Met Gly
            740                 745                 750

His Gln Pro Glu Asn Ile Val Val Glu Met Ala Arg Glu Asn Gln Phe
        755                 760                 765

Thr Asn Gln Gly Arg Arg Asn Ser Gln Gln Arg Leu Lys Gly Leu Thr
    770                 775                 780

Asp Ser Ile Lys Glu Phe Gly Ser Gln Ile Leu Lys Glu His Pro Val
785                 790                 795                 800

Glu Asn Ser Gln Leu Gln Asn Asp Arg Leu Phe Leu Tyr Tyr Leu Gln
                805                 810                 815

Asn Gly Arg Asp Met Tyr Thr Gly Glu Glu Leu Asp Ile Asp Tyr Leu
            820                 825                 830

Ser Gln Tyr Asp Ile Asp His Ile Ile Pro Gln Ala Phe Ile Lys Asp
        835                 840                 845

Asn Ser Ile Asp Asn Arg Val Leu Thr Ser Ser Lys Glu Asn Arg Gly
    850                 855                 860

Lys Ser Asp Asp Val Pro Ser Lys Asp Val Val Arg Lys Met Lys Ser
865                 870                 875                 880

Tyr Trp Ser Lys Leu Leu Ser Ala Lys Leu Ile Thr Gln Arg Lys Phe
```

```
                885                 890                 895

Asp Asn Leu Thr Lys Ala Glu Arg Gly Gly Leu Thr Asp Asp Lys
            900                 905                 910

Ala Gly Phe Ile Lys Arg Gln Leu Val Glu Thr Arg Gln Ile Thr Lys
        915                 920                 925

His Val Ala Arg Ile Leu Asp Glu Arg Phe Asn Thr Glu Thr Asp Glu
    930                 935                 940

Asn Asn Lys Lys Ile Arg Gln Val Lys Ile Val Thr Leu Lys Ser Asn
945                 950                 955                 960

Leu Val Ser Asn Phe Arg Lys Glu Phe Glu Leu Tyr Lys Val Arg Glu
                965                 970                 975

Ile Asn Asp Tyr His His Ala His Asp Ala Tyr Leu Asn Ala Val Ile
            980                 985                 990

Gly Lys Ala Leu Leu Gly Val Tyr Pro Gln Leu Glu Pro Glu Phe Val
        995                 1000                1005

Tyr Gly Asp Tyr Pro His Phe His Gly His Lys Glu Asn Lys Ala Thr
    1010                1015                1020

Ala Lys Lys Phe Phe Tyr Ser Asn Ile Met Asn Phe Phe Lys Lys Asp
1025                1030                1035                1040

Asp Val Arg Thr Asp Lys Asn Gly Glu Ile Ile Trp Lys Lys Asp Glu
                1045                1050                1055

His Ile Ser Asn Ile Lys Lys Val Leu Ser Tyr Pro Gln Val Asn Ile
            1060                1065                1070

Val Lys Lys Val Glu Glu Gln Thr Gly Gly Phe Ser Lys Glu Ser Ile
        1075                1080                1085

Leu Pro Lys Gly Asn Ser Asp Lys Leu Ile Pro Arg Lys Thr Lys Lys
    1090                1095                1100

Phe Tyr Trp Asp Thr Lys Lys Tyr Gly Gly Phe Asp Ser Pro Ile Val
1105                1110                1115                1120

Ala Tyr Ser Ile Leu Val Ile Ala Asp Ile Glu Lys Gly Lys Ser Lys
                1125                1130                1135

Lys Leu Lys Thr Val Lys Ala Leu Val Gly Val Thr Ile Met Glu Lys
            1140                1145                1150

Met Thr Phe Glu Arg Asp Pro Val Ala Phe Leu Glu Arg Lys Gly Tyr
        1155                1160                1165

Arg Asn Val Gln Glu Glu Asn Ile Ile Lys Leu Pro Lys Tyr Ser Leu
    1170                1175                1180

Phe Lys Leu Glu Asn Gly Arg Lys Arg Leu Leu Ala Ser Ala Arg Glu
1185                1190                1195                1200

Leu Gln Lys Gly Asn Glu Ile Val Leu Pro Asn His Leu Gly Thr Leu
                1205                1210                1215

Leu Tyr His Ala Lys Asn Ile His Lys Val Asp Glu Pro Lys His Leu
            1220                1225                1230

Asp Tyr Val Asp Lys His Lys Asp Glu Phe Lys Glu Leu Leu Asp Val
        1235                1240                1245

Val Ser Asn Phe Ser Lys Lys Tyr Thr Leu Ala Glu Gly Asn Leu Glu
    1250                1255                1260

Lys Ile Lys Glu Leu Tyr Ala Gln Asn Asn Gly Glu Asp Leu Lys Glu
1265                1270                1275                1280

Leu Ala Ser Ser Phe Ile Asn Leu Leu Thr Phe Thr Ala Ile Gly Ala
                1285                1290                1295

Pro Ala Thr Phe Lys Phe Phe Asp Lys Asn Ile Asp Arg Lys Arg Tyr
            1300                1305                1310
```

```
Thr Ser Thr Thr Glu Ile Leu Asn Ala Thr Leu Ile His Gln Ser Ile
        1315                1320                1325

Thr Gly Leu Tyr Glu Thr Arg Ile Asp Leu Asn Lys Leu Gly Gly Asp
    1330                1335                1340


<210> SEQ ID NO 113
<211> LENGTH: 1367
<212> TYPE: PRT
<213> ORGANISM: Streptococcus pyogenes
<220> FEATURE:
<223> OTHER INFORMATION: Cas9

<400> SEQUENCE: 113

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335
```

```
Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750
```

His Lys Pro Glu Asn Ile Val Ile Glu Met Ala Arg Glu Asn Gln Thr
755 760 765

Thr Gln Lys Gly Gln Lys Asn Ser Arg Glu Arg Met Lys Arg Ile Glu
770 775 780

Glu Gly Ile Lys Glu Leu Gly Ser Gln Ile Leu Lys Glu His Pro Val
785 790 795 800

Glu Asn Thr Gln Leu Gln Asn Glu Lys Leu Tyr Leu Tyr Tyr Leu Gln
805 810 815

Asn Gly Arg Asp Met Tyr Val Asp Gln Glu Leu Asp Ile Asn Arg Leu
820 825 830

Ser Asp Tyr Asp Val Asp His Ile Val Pro Gln Ser Phe Leu Lys Asp
835 840 845

Asp Ser Ile Asp Asn Lys Val Leu Thr Arg Ser Asp Lys Asn Arg Gly
850 855 860

Lys Ser Asp Asn Val Pro Ser Glu Glu Val Val Lys Lys Met Lys Asn
865 870 875 880

Tyr Trp Arg Gln Leu Leu Asn Ala Lys Leu Ile Thr Gln Arg Lys Phe
885 890 895

Asp Asn Leu Thr Lys Ala Glu Arg Gly Gly Leu Ser Glu Leu Asp Lys
900 905 910

Ala Gly Phe Ile Lys Arg Gln Leu Val Glu Thr Arg Gln Ile Thr Lys
915 920 925

His Val Ala Gln Ile Leu Asp Ser Arg Met Asn Thr Lys Tyr Asp Glu
930 935 940

Asn Asp Lys Leu Ile Arg Glu Val Lys Val Ile Thr Leu Lys Ser Lys
945 950 955 960

Leu Val Ser Asp Phe Arg Lys Asp Phe Gln Phe Tyr Lys Val Arg Glu
965 970 975

Ile Asn Asn Tyr His His Ala His Asp Ala Tyr Leu Asn Ala Val Val
980 985 990

Gly Thr Ala Leu Ile Lys Lys Tyr Pro Lys Leu Glu Ser Glu Phe Val
995 1000 1005

Tyr Gly Asp Tyr Lys Val Tyr Asp Val Arg Lys Met Ile Ala Lys Ser
1010 1015 1020

Glu Gln Glu Ile Gly Lys Ala Thr Ala Lys Tyr Phe Phe Tyr Ser Asn
1025 1030 1035 1040

Ile Met Asn Phe Phe Lys Thr Glu Ile Thr Leu Ala Asn Gly Glu Ile
1045 1050 1055

Arg Lys Arg Pro Leu Ile Glu Thr Asn Gly Glu Thr Gly Glu Ile Val
1060 1065 1070

Trp Asp Lys Gly Arg Asp Phe Ala Thr Val Arg Lys Val Leu Ser Met
1075 1080 1085

Pro Gln Val Asn Ile Val Lys Lys Thr Glu Val Gln Thr Gly Gly Phe
1090 1095 1100

Ser Lys Glu Ser Ile Leu Pro Lys Arg Asn Ser Asp Lys Leu Ile Ala
1105 1110 1115 1120

Arg Lys Lys Asp Trp Asp Pro Lys Lys Tyr Gly Gly Phe Asp Ser Pro
1125 1130 1135

Thr Val Ala Tyr Ser Val Leu Val Val Ala Lys Val Glu Lys Gly Lys
1140 1145 1150

Ser Lys Lys Leu Lys Ser Val Lys Glu Leu Leu Gly Ile Thr Ile Met
1155 1160 1165

Glu Arg Ser Ser Phe Glu Lys Asn Pro Ile Asp Phe Leu Glu Ala Lys

```
    1170                1175                1180

Gly Tyr Lys Glu Val Lys Lys Asp Leu Ile Ile Lys Leu Pro Lys Tyr
1185                1190                1195                1200

Ser Leu Phe Glu Leu Glu Asn Gly Arg Lys Arg Met Leu Ala Ser Ala
                1205                1210                1215

Gly Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser Pro
        1235                1240                1245

Glu Asp Asn Glu Gln Lys Gln Leu Phe Val Glu Gln His Lys His Tyr
    1250                1255                1260

Leu Asp Glu Ile Ile Glu Gln Ile Ser Glu Phe Ser Lys Arg Val Ile
1265                1270                1275                1280

Leu Ala Asp Ala Asn Leu Asp Lys Val Leu Ser Ala Tyr Asn Lys His
                1285                1290                1295

Arg Asp Lys Pro Ile Arg Glu Gln Ala Glu Asn Ile Ile His Leu Phe
            1300                1305                1310

Thr Leu Thr Asn Leu Gly Ala Pro Ala Ala Phe Lys Tyr Phe Asp Thr
        1315                1320                1325

Thr Ile Asp Arg Lys Arg Tyr Thr Ser Thr Lys Glu Val Leu Asp Ala
    1330                1335                1340

Thr Leu Ile His Gln Ser Ile Thr Gly Leu Tyr Glu Thr Arg Ile Asp
1345                1350                1355                1360

Leu Ser Gln Leu Gly Gly Asp
                1365


<210> SEQ ID NO 114
<211> LENGTH: 1387
<212> TYPE: PRT
<213> ORGANISM: Streptococcus thermophilus
<220> FEATURE:
<223> OTHER INFORMATION: Cas9

<400> SEQUENCE: 114

Thr Lys Pro Tyr Ser Ile Gly Leu Asp Ile Gly Thr Asn Ser Val Gly
1               5                   10                  15

Trp Ala Val Thr Thr Asp Asn Tyr Lys Val Pro Ser Lys Lys Met Lys
            20                  25                  30

Val Leu Gly Asn Thr Ser Lys Lys Tyr Ile Lys Lys Asn Leu Leu Gly
        35                  40                  45

Val Leu Leu Phe Asp Ser Gly Ile Thr Ala Glu Gly Arg Arg Leu Lys
    50                  55                  60

Arg Thr Ala Arg Arg Arg Tyr Thr Arg Arg Arg Asn Arg Ile Leu Tyr
65                  70                  75                  80

Leu Gln Glu Ile Phe Ser Thr Glu Met Ala Thr Leu Asp Asp Ala Phe
                85                  90                  95

Phe Gln Arg Leu Asp Asp Ser Phe Leu Val Pro Asp Asp Lys Arg Asp
            100                 105                 110

Ser Lys Tyr Pro Ile Phe Gly Asn Leu Val Glu Glu Lys Ala Tyr His
        115                 120                 125

Asp Glu Phe Pro Thr Ile Tyr His Leu Arg Lys Tyr Leu Ala Asp Ser
    130                 135                 140

Thr Lys Lys Ala Asp Leu Arg Leu Val Tyr Leu Ala Leu Ala His Met
145                 150                 155                 160

Ile Lys Tyr Arg Gly His Phe Leu Ile Glu Gly Glu Phe Asn Ser Lys
```

```
                165                 170                 175

Asn Asn Asp Ile Gln Lys Asn Phe Gln Asp Phe Leu Asp Thr Tyr Asn
            180                 185                 190

Ala Ile Phe Glu Ser Asp Leu Ser Leu Glu Asn Ser Lys Gln Leu Glu
        195                 200                 205

Glu Ile Val Lys Asp Lys Ile Ser Lys Leu Glu Lys Lys Asp Arg Ile
    210                 215                 220

Leu Lys Leu Phe Pro Gly Glu Lys Asn Ser Gly Ile Phe Ser Glu Phe
225                 230                 235                 240

Leu Lys Leu Ile Val Gly Asn Gln Ala Asp Phe Arg Lys Cys Phe Asn
                245                 250                 255

Leu Asp Glu Lys Ala Ser Leu His Phe Ser Lys Glu Ser Tyr Asp Glu
            260                 265                 270

Asp Leu Glu Thr Leu Leu Gly Tyr Ile Gly Asp Asp Tyr Ser Asp Val
        275                 280                 285

Phe Leu Lys Ala Lys Lys Leu Tyr Asp Ala Ile Leu Leu Ser Gly Phe
    290                 295                 300

Leu Thr Val Thr Asp Asn Glu Thr Glu Ala Pro Leu Ser Ser Ala Met
305                 310                 315                 320

Ile Lys Arg Tyr Asn Glu His Lys Glu Asp Leu Ala Leu Leu Lys Glu
                325                 330                 335

Tyr Ile Arg Asn Ile Ser Leu Lys Thr Tyr Asn Glu Val Phe Lys Asp
            340                 345                 350

Asp Thr Lys Asn Gly Tyr Ala Gly Tyr Ile Asp Gly Lys Thr Asn Gln
        355                 360                 365

Glu Asp Phe Tyr Val Tyr Leu Lys Lys Leu Leu Ala Glu Phe Glu Gly
    370                 375                 380

Ala Asp Tyr Phe Leu Glu Lys Ile Asp Arg Glu Asp Phe Leu Arg Lys
385                 390                 395                 400

Gln Arg Thr Phe Asp Asn Gly Ser Ile Pro Tyr Gln Ile His Leu Gln
                405                 410                 415

Glu Met Arg Ala Ile Leu Asp Lys Gln Ala Lys Phe Tyr Pro Phe Leu
            420                 425                 430

Ala Lys Asn Lys Glu Arg Ile Glu Lys Ile Leu Thr Phe Arg Ile Pro
        435                 440                 445

Tyr Tyr Val Gly Pro Leu Ala Arg Gly Asn Ser Asp Phe Ala Trp Ser
    450                 455                 460

Ile Arg Lys Arg Asn Glu Lys Ile Thr Pro Trp Asn Phe Glu Asp Val
465                 470                 475                 480

Ile Asp Lys Glu Ser Ser Ala Glu Ala Phe Ile Asn Arg Met Thr Ser
                485                 490                 495

Phe Asp Leu Tyr Leu Pro Glu Glu Lys Val Leu Pro Lys His Ser Leu
            500                 505                 510

Leu Tyr Glu Thr Phe Asn Val Tyr Asn Glu Leu Thr Lys Val Arg Phe
        515                 520                 525

Ile Ala Glu Ser Met Arg Asp Tyr Gln Phe Leu Asp Ser Lys Gln Lys
    530                 535                 540

Lys Asp Ile Val Arg Leu Tyr Phe Lys Asp Lys Arg Lys Val Thr Asp
545                 550                 555                 560

Lys Asp Ile Ile Glu Tyr Leu His Ala Ile Tyr Gly Tyr Asp Gly Ile
                565                 570                 575

Glu Leu Lys Gly Ile Glu Lys Gln Phe Asn Ser Ser Leu Ser Thr Tyr
            580                 585                 590
```

```
His Asp Leu Leu Asn Ile Ile Asn Asp Lys Glu Phe Leu Asp Asp Ser
        595                 600                 605

Ser Asn Glu Ala Ile Ile Glu Glu Ile Ile His Thr Leu Thr Ile Phe
    610                 615                 620

Glu Asp Arg Glu Met Ile Lys Gln Arg Leu Ser Lys Phe Glu Asn Ile
625                 630                 635                 640

Phe Asp Lys Ser Val Leu Lys Lys Leu Ser Arg Arg His Tyr Thr Gly
                645                 650                 655

Trp Gly Lys Leu Ser Ala Lys Leu Ile Asn Gly Ile Arg Asp Glu Lys
            660                 665                 670

Ser Gly Asn Thr Ile Leu Asp Tyr Leu Ile Asp Asp Gly Ile Ser Asn
        675                 680                 685

Arg Asn Phe Met Gln Leu Ile His Asp Asp Ala Leu Ser Phe Lys Lys
    690                 695                 700

Lys Ile Gln Lys Ala Gln Ile Ile Gly Asp Glu Asp Lys Gly Asn Ile
705                 710                 715                 720

Lys Glu Val Val Lys Ser Leu Pro Gly Ser Pro Ala Ile Lys Lys Gly
                725                 730                 735

Ile Leu Gln Ser Ile Lys Ile Val Asp Glu Leu Val Lys Val Met Gly
            740                 745                 750

Gly Arg Lys Pro Glu Ser Ile Val Val Glu Met Ala Arg Glu Asn Gln
        755                 760                 765

Tyr Thr Asn Gln Gly Lys Ser Asn Ser Gln Gln Arg Leu Lys Arg Leu
    770                 775                 780

Glu Lys Ser Leu Lys Glu Leu Gly Ser Lys Ile Leu Lys Glu Asn Ile
785                 790                 795                 800

Pro Ala Lys Leu Ser Lys Ile Asp Asn Asn Ala Leu Gln Asn Asp Arg
                805                 810                 815

Leu Tyr Leu Tyr Tyr Leu Gln Asn Gly Lys Asp Met Tyr Thr Gly Asp
            820                 825                 830

Asp Leu Asp Ile Asp Arg Leu Ser Asn Tyr Asp Ile Asp His Ile Ile
        835                 840                 845

Pro Gln Ala Phe Leu Lys Asp Asn Ser Ile Asp Asn Lys Val Leu Val
    850                 855                 860

Ser Ser Ala Ser Asn Arg Gly Lys Ser Asp Asp Val Pro Ser Leu Glu
865                 870                 875                 880

Val Val Lys Lys Arg Lys Thr Phe Trp Tyr Gln Leu Leu Lys Ser Lys
                885                 890                 895

Leu Ile Ser Gln Arg Lys Phe Asp Asn Leu Thr Lys Ala Glu Arg Gly
            900                 905                 910

Gly Leu Ser Pro Glu Asp Lys Ala Gly Phe Ile Gln Arg Gln Leu Val
        915                 920                 925

Glu Thr Arg Gln Ile Thr Lys His Val Ala Arg Leu Leu Asp Glu Lys
    930                 935                 940

Phe Asn Asn Lys Lys Asp Glu Asn Asn Arg Ala Val Arg Thr Val Lys
945                 950                 955                 960

Ile Ile Thr Leu Lys Ser Thr Leu Val Ser Gln Phe Arg Lys Asp Phe
                965                 970                 975

Glu Leu Tyr Lys Val Arg Glu Ile Asn Asp Phe His His Ala His Asp
            980                 985                 990

Ala Tyr Leu Asn Ala Val Val Ala Ser Ala Leu Leu Lys Lys Tyr Pro
        995                 1000                1005
```

Lys Leu Glu Pro Glu Phe Val Tyr Gly Asp Tyr Pro Lys Tyr Asn Ser
1010 1015 1020

Phe Arg Glu Arg Lys Ser Ala Thr Glu Lys Val Tyr Phe Tyr Ser Asn
1025 1030 1035 1040

Ile Met Asn Ile Phe Lys Lys Ser Ile Ser Leu Ala Asp Gly Arg Val
1045 1050 1055

Ile Glu Arg Pro Leu Ile Glu Val Asn Glu Glu Thr Gly Glu Ser Val
1060 1065 1070

Trp Asn Lys Glu Ser Asp Leu Ala Thr Val Arg Arg Val Leu Ser Tyr
1075 1080 1085

Pro Gln Val Asn Val Val Lys Lys Val Glu Glu Gln Asn His Gly Leu
1090 1095 1100

Asp Arg Gly Lys Pro Lys Gly Leu Phe Asn Ala Asn Leu Ser Ser Lys
1105 1110 1115 1120

Pro Lys Pro Asn Ser Asn Glu Asn Leu Val Gly Ala Lys Glu Tyr Leu
1125 1130 1135

Asp Pro Lys Lys Tyr Gly Gly Tyr Ala Gly Ile Ser Asn Ser Phe Thr
1140 1145 1150

Val Leu Val Lys Gly Thr Ile Glu Lys Gly Ala Lys Lys Lys Ile Thr
1155 1160 1165

Asn Val Leu Glu Phe Gln Gly Ile Ser Ile Leu Asp Arg Ile Asn Tyr
1170 1175 1180

Arg Lys Asp Lys Leu Asn Phe Leu Leu Glu Lys Gly Tyr Lys Asp Ile
1185 1190 1195 1200

Glu Leu Ile Ile Glu Leu Pro Lys Tyr Ser Leu Phe Glu Leu Ser Asp
1205 1210 1215

Gly Ser Arg Arg Met Leu Ala Ser Ile Leu Ser Thr Asn Asn Lys Arg
1220 1225 1230

Gly Glu Ile His Lys Gly Asn Gln Ile Phe Leu Ser Gln Lys Phe Val
1235 1240 1245

Lys Leu Leu Tyr His Ala Lys Arg Ile Ser Asn Thr Ile Asn Glu Asn
1250 1255 1260

His Arg Lys Tyr Val Glu Asn His Lys Lys Glu Phe Glu Glu Leu Phe
1265 1270 1275 1280

Tyr Tyr Ile Leu Glu Phe Asn Glu Asn Tyr Val Gly Ala Lys Lys Asn
1285 1290 1295

Gly Lys Leu Leu Asn Ser Ala Phe Gln Ser Trp Gln Asn His Ser Ile
1300 1305 1310

Asp Glu Leu Cys Ser Ser Phe Ile Gly Pro Thr Gly Ser Glu Arg Lys
1315 1320 1325

Gly Leu Phe Glu Leu Thr Ser Arg Gly Ser Ala Ala Asp Phe Glu Phe
1330 1335 1340

Leu Gly Val Lys Ile Pro Arg Tyr Arg Asp Tyr Thr Pro Ser Ser Leu
1345 1350 1355 1360

Leu Lys Asp Ala Thr Leu Ile His Gln Ser Val Thr Gly Leu Tyr Glu
1365 1370 1375

Thr Arg Ile Asp Leu Ala Lys Leu Gly Glu Gly
1380 1385

<210> SEQ ID NO 115
<211> LENGTH: 1333
<212> TYPE: PRT
<213> ORGANISM: Listeria innocua
<220> FEATURE:
<223> OTHER INFORMATION: Cas9

<400> SEQUENCE: 115

Lys Lys Pro Tyr Thr Ile Gly Leu Asp Ile Gly Thr Asn Ser Val Gly
1               5                   10                  15

Trp Ala Val Leu Thr Asp Gln Tyr Asp Leu Val Lys Arg Lys Met Lys
            20                  25                  30

Ile Ala Gly Asp Ser Glu Lys Lys Gln Ile Lys Lys Asn Phe Trp Gly
        35                  40                  45

Val Arg Leu Phe Asp Glu Gly Gln Thr Ala Ala Asp Arg Arg Met Ala
    50                  55                  60

Arg Thr Ala Arg Arg Arg Ile Glu Arg Arg Arg Asn Arg Ile Ser Tyr
65                  70                  75                  80

Leu Gln Gly Ile Phe Ala Glu Glu Met Ser Lys Thr Asp Ala Asn Phe
                85                  90                  95

Phe Cys Arg Leu Ser Asp Ser Phe Tyr Val Asp Asn Glu Lys Arg Asn
            100                 105                 110

Ser Arg His Pro Phe Phe Ala Thr Ile Glu Glu Glu Val Glu Tyr His
        115                 120                 125

Lys Asn Tyr Pro Thr Ile Tyr His Leu Arg Glu Glu Leu Val Asn Ser
    130                 135                 140

Ser Glu Lys Ala Asp Leu Arg Leu Val Tyr Leu Ala Leu Ala His Ile
145                 150                 155                 160

Ile Lys Tyr Arg Gly Asn Phe Leu Ile Glu Gly Ala Leu Asp Thr Gln
                165                 170                 175

Asn Thr Ser Val Asp Gly Ile Tyr Lys Gln Phe Ile Gln Thr Tyr Asn
            180                 185                 190

Gln Val Phe Ala Ser Gly Ile Glu Asp Gly Ser Leu Lys Lys Leu Glu
        195                 200                 205

Asp Asn Lys Asp Val Ala Lys Ile Leu Val Glu Lys Val Thr Arg Lys
    210                 215                 220

Glu Lys Leu Glu Arg Ile Leu Lys Leu Tyr Pro Gly Glu Lys Ser Ala
225                 230                 235                 240

Gly Met Phe Ala Gln Phe Ile Ser Leu Ile Val Gly Ser Lys Gly Asn
                245                 250                 255

Phe Gln Lys Pro Phe Asp Leu Ile Glu Lys Ser Asp Ile Glu Cys Ala
            260                 265                 270

Lys Asp Ser Tyr Glu Glu Asp Leu Glu Ser Leu Leu Ala Leu Ile Gly
        275                 280                 285

Asp Glu Tyr Ala Glu Leu Phe Val Ala Ala Lys Asn Ala Tyr Ser Ala
    290                 295                 300

Val Val Leu Ser Ser Ile Ile Thr Val Ala Glu Thr Glu Thr Asn Ala
305                 310                 315                 320

Lys Leu Ser Ala Ser Met Ile Glu Arg Phe Asp Thr His Glu Glu Asp
                325                 330                 335

Leu Gly Glu Leu Lys Ala Phe Ile Lys Leu His Leu Pro Lys His Tyr
            340                 345                 350

Glu Glu Ile Phe Ser Asn Thr Glu Lys His Gly Tyr Ala Gly Tyr Ile
        355                 360                 365

Asp Gly Lys Thr Lys Gln Ala Asp Phe Tyr Lys Tyr Met Lys Met Thr
    370                 375                 380

Leu Glu Asn Ile Glu Gly Ala Asp Tyr Phe Ile Ala Lys Ile Glu Lys
385                 390                 395                 400

Glu Asn Phe Leu Arg Lys Gln Arg Thr Phe Asp Asn Gly Ala Ile Pro

```
                405                 410                 415

His Gln Leu His Leu Glu Glu Leu Glu Ala Ile Leu His Gln Gln Ala
            420                 425                 430

Lys Tyr Tyr Pro Phe Leu Lys Glu Asn Tyr Asp Lys Ile Lys Ser Leu
        435                 440                 445

Val Thr Phe Arg Ile Pro Tyr Phe Val Gly Pro Leu Ala Asn Gly Gln
    450                 455                 460

Ser Glu Phe Ala Trp Leu Thr Arg Lys Ala Asp Gly Glu Ile Arg Pro
465                 470                 475                 480

Trp Asn Ile Glu Glu Lys Val Asp Phe Gly Lys Ser Ala Val Asp Phe
                485                 490                 495

Ile Glu Lys Met Thr Asn Lys Asp Thr Tyr Leu Pro Lys Glu Asn Val
            500                 505                 510

Leu Pro Lys His Ser Leu Cys Tyr Gln Lys Tyr Leu Val Tyr Asn Glu
        515                 520                 525

Leu Thr Lys Val Arg Tyr Ile Asn Asp Gln Gly Lys Thr Ser Tyr Phe
    530                 535                 540

Ser Gly Gln Glu Lys Glu Gln Ile Phe Asn Asp Leu Phe Lys Gln Lys
545                 550                 555                 560

Arg Lys Val Lys Lys Lys Asp Leu Glu Leu Phe Leu Arg Asn Met Ser
                565                 570                 575

His Val Glu Ser Pro Thr Ile Glu Gly Leu Glu Asp Ser Phe Asn Ser
            580                 585                 590

Ser Tyr Ser Thr Tyr His Asp Leu Leu Lys Val Gly Ile Lys Gln Glu
        595                 600                 605

Ile Leu Asp Asn Pro Val Asn Thr Glu Met Leu Glu Asn Ile Val Lys
    610                 615                 620

Ile Leu Thr Val Phe Glu Asp Lys Arg Met Ile Lys Glu Gln Leu Gln
625                 630                 635                 640

Gln Phe Ser Asp Val Leu Asp Gly Val Val Leu Lys Lys Leu Glu Arg
                645                 650                 655

Arg His Tyr Thr Gly Trp Gly Arg Leu Ser Ala Lys Leu Leu Met Gly
            660                 665                 670

Ile Arg Asp Lys Gln Ser His Leu Thr Ile Leu Asp Tyr Leu Met Asn
        675                 680                 685

Asp Asp Gly Leu Asn Arg Asn Leu Met Gln Leu Ile Asn Asp Ser Asn
    690                 695                 700

Leu Ser Phe Lys Ser Ile Ile Glu Lys Glu Gln Val Thr Thr Ala Asp
705                 710                 715                 720

Lys Asp Ile Gln Ser Ile Val Ala Asp Leu Ala Gly Ser Pro Ala Ile
                725                 730                 735

Lys Lys Gly Ile Leu Gln Ser Leu Lys Ile Val Asp Glu Leu Val Ser
            740                 745                 750

Val Met Gly Tyr Pro Pro Gln Thr Ile Val Val Glu Met Ala Arg Glu
        755                 760                 765

Asn Gln Thr Thr Gly Lys Gly Lys Asn Asn Ser Arg Pro Arg Tyr Lys
    770                 775                 780

Ser Leu Glu Lys Ala Ile Lys Glu Phe Gly Ser Gln Ile Leu Lys Glu
785                 790                 795                 800

His Pro Thr Asp Asn Gln Glu Leu Arg Asn Asn Arg Leu Tyr Leu Tyr
                805                 810                 815

Tyr Leu Gln Asn Gly Lys Asp Met Tyr Thr Gly Gln Asp Leu Asp Ile
            820                 825                 830
```

```
His Asn Leu Ser Asn Tyr Asp Ile Asp His Ile Val Pro Gln Ser Phe
        835                 840                 845

Ile Thr Asp Asn Ser Ile Asp Asn Leu Val Leu Thr Ser Ser Ala Gly
    850                 855                 860

Asn Arg Glu Lys Gly Asp Asp Val Pro Pro Leu Glu Ile Val Arg Lys
865                 870                 875                 880

Arg Lys Val Phe Trp Glu Lys Leu Tyr Gln Gly Asn Leu Met Ser Lys
                885                 890                 895

Arg Lys Phe Asp Tyr Leu Thr Lys Ala Glu Arg Gly Gly Leu Thr Glu
            900                 905                 910

Ala Asp Lys Ala Arg Phe Ile His Arg Gln Leu Val Glu Thr Arg Gln
        915                 920                 925

Ile Thr Lys Asn Val Ala Asn Ile Leu His Gln Arg Phe Asn Tyr Glu
    930                 935                 940

Lys Asp Asp His Gly Asn Thr Met Lys Gln Val Arg Ile Val Thr Leu
945                 950                 955                 960

Lys Ser Ala Leu Val Ser Gln Phe Arg Lys Gln Phe Gln Leu Tyr Lys
                965                 970                 975

Val Arg Asp Val Asn Asp Tyr His His Ala His Asp Ala Tyr Leu Asn
            980                 985                 990

Gly Val Val Ala Asn Thr Leu Leu Lys Val Tyr Pro Gln Leu Glu Pro
        995                 1000                1005

Glu Phe Val Tyr Gly Asp Tyr His Gln Phe Asp Trp Phe Lys Ala Asn
    1010                1015                1020

Lys Ala Thr Ala Lys Lys Gln Phe Tyr Thr Asn Ile Met Leu Phe Phe
1025                1030                1035                1040

Ala Gln Lys Asp Arg Ile Ile Asp Glu Asn Gly Glu Ile Leu Trp Asp
                1045                1050                1055

Lys Lys Tyr Leu Asp Thr Val Lys Lys Val Met Ser Tyr Arg Gln Met
            1060                1065                1070

Asn Ile Val Lys Lys Thr Glu Ile Gln Lys Gly Glu Phe Ser Lys Ala
        1075                1080                1085

Thr Ile Lys Pro Lys Gly Asn Ser Ser Lys Leu Ile Pro Arg Lys Thr
    1090                1095                1100

Asn Trp Asp Pro Met Lys Tyr Gly Gly Leu Asp Ser Pro Asn Met Ala
1105                1110                1115                1120

Tyr Ala Val Val Ile Glu Tyr Ala Lys Gly Lys Asn Lys Leu Val Phe
                1125                1130                1135

Glu Lys Lys Ile Ile Arg Val Thr Ile Met Glu Arg Lys Ala Phe Glu
            1140                1145                1150

Lys Asp Glu Lys Ala Phe Leu Glu Glu Gln Gly Tyr Arg Gln Pro Lys
        1155                1160                1165

Val Leu Ala Lys Leu Pro Lys Tyr Thr Leu Tyr Glu Cys Glu Glu Gly
    1170                1175                1180

Arg Arg Arg Met Leu Ala Ser Ala Asn Glu Ala Gln Lys Gly Asn Gln
1185                1190                1195                1200

Gln Val Leu Pro Asn His Leu Val Thr Leu Leu His His Ala Ala Asn
                1205                1210                1215

Cys Glu Val Ser Asp Gly Lys Ser Leu Asp Tyr Ile Glu Ser Asn Arg
            1220                1225                1230

Glu Met Phe Ala Glu Leu Leu Ala His Val Ser Glu Phe Ala Lys Arg
        1235                1240                1245
```

```
Tyr Thr Leu Ala Glu Ala Asn Leu Asn Lys Ile Asn Gln Leu Phe Glu
    1250                1255                1260

Gln Asn Lys Glu Gly Asp Ile Lys Ala Ile Ala Gln Ser Phe Val Asp
1265                1270                1275                1280

Leu Met Ala Phe Asn Ala Met Gly Ala Pro Ala Ser Phe Lys Phe Phe
                1285                1290                1295

Glu Thr Thr Ile Glu Arg Lys Arg Tyr Asn Asn Leu Lys Glu Leu Leu
            1300                1305                1310

Asn Ser Thr Ile Ile Tyr Gln Ser Ile Thr Gly Leu Tyr Glu Ser Arg
        1315                1320                1325

Lys Arg Leu Asp Asp
    1330


<210> SEQ ID NO 116
<211> LENGTH: 1082
<212> TYPE: PRT
<213> ORGANISM: Neisseria meningitidis
<220> FEATURE:
<223> OTHER INFORMATION: Cas9

<400> SEQUENCE: 116

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Thr Arg Arg Leu Leu Lys Arg Glu Gly Val Leu Gln Ala Ala Asn
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Gly Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Ser Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270
```

```
Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
        675                 680                 685

Gly Lys Gly Lys Lys Arg Val Phe Ala Ser Asn Gly Gln Ile Thr Asn
```

```
    690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765

Lys Thr His Phe Pro Gln Pro Trp Glu Phe Phe Ala Gln Glu Val Met
    770                 775                 780

Ile Arg Val Phe Gly Lys Pro Asp Gly Lys Pro Glu Phe Glu Glu Ala
785                 790                 795                 800

Asp Thr Leu Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
        835                 840                 845

Ser Ala Lys Arg Leu Asp Glu Gly Val Ser Val Leu Arg Val Pro Leu
    850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys His
    1010                1015                1020

Arg Gly Thr Gly Asn Ile Asn Ile Arg Ile His Asp Leu Asp His Lys
1025                1030                1035                1040

Ile Gly Lys Asn Gly Ile Leu Glu Gly Ile Gly Val Lys Thr Ala Leu
                1045                1050                1055

Ser Phe Gln Lys Tyr Gln Ile Asp Glu Leu Gly Lys Glu Ile Arg Pro
            1060                1065                1070

Cys Arg Leu Lys Lys Arg Pro Pro Val Arg
        1075                1080
```

<210> SEQ ID NO 117
<211> LENGTH: 1368
<212> TYPE: PRT
<213> ORGANISM: Streptococcus pyogenes

```
<220> FEATURE:
<223> OTHER INFORMATION: Cas9

<400> SEQUENCE: 117

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400
```

```
Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815
```

```
Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
                1045                1050                1055

Ile Arg Lys Arg Pro Leu Ile Glu Thr Asn Gly Glu Thr Gly Glu Ile
            1060                1065                1070

Val Trp Asp Lys Gly Arg Asp Phe Ala Thr Val Arg Lys Val Leu Ser
        1075                1080                1085

Met Pro Gln Val Asn Ile Val Lys Lys Thr Glu Val Gln Thr Gly Gly
    1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
                1125                1130                1135

Pro Thr Val Ala Tyr Ser Val Leu Val Val Ala Lys Val Glu Lys Gly
            1140                1145                1150

Lys Ser Lys Lys Leu Lys Ser Val Lys Glu Leu Leu Gly Ile Thr Ile
        1155                1160                1165

Met Glu Arg Ser Ser Phe Glu Lys Asn Pro Ile Asp Phe Leu Glu Ala
    1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
                1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
```

```
        1235                1240                1245

Pro Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
                1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
        1315                1320                1325

Thr Thr Ile Asp Arg Lys Arg Tyr Thr Ser Thr Lys Glu Val Leu Asp
    1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp
                1365
```

<210> SEQ ID NO 118
<211> LENGTH: 1205
<212> TYPE: DNA
<213> ORGANISM: Artificial Sequence
<220> FEATURE:
<223> OTHER INFORMATION: EF1alpha promoter

<400> SEQUENCE: 118

```
cgtgaggctc cggtgcccgt cagtgggcag agcgcacatc gcccacagtc cccgagaagt     60

tgggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcactagt cgccgtgaac gttcttttc gcaacgggtt tgccgccaga acacaggtaa    240

gtgccgtgtg tggttcccgc gggcctggcc tctttacggg ttatggccct tgcgtgcctt    300

gaattacttc cacctggctg cagtacgtga ttcttgatcc cgagcttcgg gttggaagtg    360

ggtgggagag ttcgtggcct tgcgcttaag gagccccttc gcctcgtgct tgagttgtgg    420

cctggcctgg gcgctggggc cgccgcgtgc gaatctggtg gcaccttcgc gcctgtctcg    480

ctgctttcga taagtctcta gccatttaaa atttttgatg acctgctgcg acgctttttt    540

tctggcaaga tagtcttgta aatgcgggcc aagatcagca cactggtatt tcggtttttg    600

gggccgcggg cggcgacggg gcccgtgcgt cccagcgcac atgttcggcg aggcggggcc    660

tgcgagcgcg gccaccgaga atcggacggg ggtagtctca agctgcccgg cctgctctgg    720

tgcctggcct cgcgccgccg tgtatcgccc cgccctgggc ggcaaggctg gcccggtcgg    780

caccagttgc gtgagcggaa agatggccgc ttcccggccc tgctgcaggg agcacaaaat    840

ggaggacgcg gcgctcggga gagcgggcgg gtgagtcacc cacacaaagg aaaagggcct    900

ttccgtcctc agccgtcgct tcatgtgact ccacggagta ccgggcgccg tccaggcacc    960

tcgattagtt ctccagcttt tggagtacgt cgtctttagg ttggggggag gggttttatg   1020

cgatggagtt tccccacact gagtgggtgg agactgaagt taggccagct tggcacttga   1080

tgtaattctc cttggaattt gcccttttg agtttggatc ttggttcatt ctcaagcctc   1140

agacagtggt tcaaagtttt tttcttccat ttcaggtgtc gtgaaaacta cccctaaaag   1200

ccaaa                                                                 1205
```

```
<210> SEQ ID NO 119
<211> LENGTH: 544
<212> TYPE: DNA
<213> ORGANISM: Artificial Sequence
<220> FEATURE:
<223> OTHER INFORMATION: Ef1alpha promoter with HTLV1 enhancer

<400> SEQUENCE: 119

ggatctgcga tcgctccggt gcccgtcagt gggcagagcg cacatcgccc acagtccccg     60

agaagttggg gggaggggtc ggcaattgaa ccggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctac                                                                 544


<210> SEQ ID NO 120
<211> LENGTH: 66
<212> TYPE: DNA
<213> ORGANISM: Artificial Sequence
<220> FEATURE:
<223> OTHER INFORMATION: P2A nucleotide sequence

<400> SEQUENCE: 120

ggatctggag cgacgaattt tagtctactg aaacaagcgg gagacgtgga ggaaaaccct     60

ggacct                                                                66


<210> SEQ ID NO 121
<211> LENGTH: 4107
<212> TYPE: DNA
<213> ORGANISM: streptococcus pyogenes
<220> FEATURE:
<223> OTHER INFORMATION: Cas9 codon optimized nucleic acid sequence

<400> SEQUENCE: 121

atggataaaa agtacagcat cgggctggac atcggtacaa actcagtggg gtgggccgtg     60

attacggacg agtacaaggt accctccaaa aaatttaaag tgctgggtaa cacggacaga    120

cactctataa agaaaaatct tattggagcc ttgctgttcg actcaggcga gacagccgaa    180

gccacaaggt tgaagcggac cgccaggagg cggtatacca ggagaaagaa ccgcatatgc    240

tacctgcaag aaatcttcag taacgagatg gcaaaggttg acgatagctt tttccatcgc    300

ctggaagaat cctttcttgt tgaggaagac aagaagcacg aacggcaccc catctttggc    360

aatattgtcg acgaagtggc atatcacgaa aagtacccga ctatctacca cctcaggaag    420

aagctggtgg actctaccga taaggcggac ctcagactta tttatttggc actcgcccac    480

atgattaaat ttagaggaca tttcttgatc gagggcgacc tgaacccgga caacagtgac    540

gtcgataagc tgttcatcca acttgtgcag acctacaatc aactgttcga agaaaaccct    600

ataaatgctt caggagtcga cgctaaagca atcctgtccg cgcgcctctc aaaatctaga    660

agacttgaga atctgattgc tcagttgccc ggggaaaaga aaaatggatt gtttggcaac    720

ctgatcgccc tcagtctcgg actgacccca aatttcaaaa gtaacttcga cctggccgaa    780
```

```
gacgctaagc tccagctgtc caaggacaca tacgatgacg acctcgacaa tctgctggcc    840
cagattgggg atcagtacgc cgatctcttt ttggcagcaa agaacctgtc cgacgccatc    900
ctgttgagcg atatcttgag agtgaacacc gaaattacta aagcacccct tagcgcatct    960
atgatcaagc ggtacgacga gcatcatcag gatctgaccc tgctgaaggc tcttgtgagg   1020
caacagctcc ccgaaaaata caaggaaatc ttctttgacc agagcaaaaa cggctacgct   1080
ggctatatag atggtggggc cagtcaggag gaattctata aattcatcaa gcccattctc   1140
gagaaaatgg acggcacaga ggagttgctg gtcaaactta acagggagga cctgctgcgg   1200
aagcagcgga cctttgacaa cgggtctatc ccccaccaga ttcatctggg cgaactgcac   1260
gcaatcctga ggaggcagga ggatttttat ccttttctta aagataaccg cgagaaaata   1320
gaaaagattc ttacattcag gatcccgtac tacgtgggac ctctcgcccg gggcaattca   1380
cggtttgcct ggatgacaag gaagtcagag gagactatta caccttggaa cttcgaagaa   1440
gtggtggaca agggtgcatc tgcccagtct ttcatcgagc ggatgacaaa ttttgacaag   1500
aacctcccta atgagaaggt gctgcccaaa cattctctgc tctacgagta ctttaccgtc   1560
tacaatgaac tgactaaagt caagtacgtc accgagggaa tgaggaagcc ggcattcctt   1620
agtggagaac agaagaaggc gattgtagac ctgttgttca agaccaacag gaaggtgact   1680
gtgaagcaac ttaaagaaga ctactttaag aagatcgaat gttttgacag tgtggaaatt   1740
tcaggggttg aagaccgctt caatgcgtca ttggggactt accatgatct tctcaagatc   1800
ataaaggaca aagacttcct ggacaacgaa gaaaatgagg atattctcga agacatcgtc   1860
ctcaccctga ccctgttcga agacagggaa atgatagaag agcgcttgaa aacctatgcc   1920
cacctcttcg acgataaagt tatgaagcag ctgaagcgca ggagatacac aggatgggga   1980
agattgtcaa ggaagctgat caatggaatt agggataaac agagtggcaa gaccatactg   2040
gatttcctca aatctgatgg cttcgccaat aggaacttca tgcaactgat tcacgatgac   2100
tctcttacct tcaaggagga cattcaaaag gctcaggtga gcgggcaggg agactccctt   2160
catgaacaca tcgcgaattt ggcaggttcc cccgctatta aaaagggcat ccttcaaact   2220
gtcaaggtgg tggatgaatt ggtcaaggta atgggcagac ataagccaga aaatattgtg   2280
atcgagatgg cccgcgaaaa ccagaccaca cagaagggcc agaaaaatag tagagagcgg   2340
atgaagagga tcgaggaggg catcaaagag ctgggatctc agattctcaa agaacacccc   2400
gtagaaaaca cacagctgca gaacgaaaaa ttgtacttgt actatctgca gaacggcaga   2460
gacatgtacg tcgaccaaga acttgatatt aatagactgt ccgactatga cgtagaccat   2520
atcgtgcccc agtccttcct gaaggacgac tccattgata acaaagtctt gacaagaagc   2580
gacaagaaca ggggtaaaag tgataatgtg cctagcgagg aggtggtgaa aaaaatgaag   2640
aactactggc gacagctgct taatgcaaag ctcattacac aacggaagtt cgataatctg   2700
acgaaagcag agagaggtgg cttgtctgag ttggacaagg cagggtttat taagcggcag   2760
ctggtggaaa ctaggcagat cacaaagcac gtggcgcaga ttttggacag ccggatgaac   2820
acaaaatacg acgaaaatga taaactgata cgagaggtca aagttatcac gctgaaaagc   2880
aagctggtgt ccgattttcg gaaagacttc cagttctaca aagttcgcga gattaataac   2940
taccatcatg ctcacgatgc gtacctgaac gctgttgtcg ggaccgcctt gataaagaag   3000
tacccaaagc tggaatccga gttcgtatac ggggattaca aagtgtacga tgtgaggaaa   3060
atgatagcca agtccgagca ggagattgga aaggccacag ctaagtactt cttttattct   3120
aacatcatga atttttttaa gacggaaatt accctggcca acggagagat cagaaagcgg   3180
```

```
ccccttatag agacaaatgg tgaaacaggt gaaatcgtct gggataaggg cagggatttc   3240

gctactgtga ggaaggtgct gagtatgcca caggtaaata tcgtgaaaaa aaccgaagta   3300

cagaccggag gattttccaa ggaaagcatt ttgcctaaaa gaaactcaga caagctcatc   3360

gcccgcaaga aagattggga ccctaagaaa tacgggggat ttgactcacc caccgtagcc   3420

tattctgtgc tggtggtagc taaggtggaa aaaggaaagt ctaagaagct gaagtccgtg   3480

aaggaactct tgggaatcac tatcatggaa agatcatcct ttgaaaagaa ccctatcgat   3540

ttcctggagg ctaagggtta caaggaggtc aagaaagacc tcatcattaa actgccaaaa   3600

tactctctct tcgagctgga aaatggcagg aagagaatgt tggccagcgc cggagagctg   3660

caaaagggaa acgagcttgc tctgccctcc aaatatgtta attttctcta tctcgcttcc   3720

cactatgaaa agctgaaagg gtctcccgaa gataacgagc agaagcagct gttcgtcgaa   3780

cagcacaagc actatctgga tgaaataatc gaacaaataa gcgagttcag caaaagggtt   3840

atcctggcgg atgctaattt ggacaaagta ctgtctgctt ataacaagca ccgggataag   3900

cctattaggg aacaagccga gaatataatt cacctcttta cactcacgaa tctcggagcc   3960

cccgccgcct tcaaatactt tgatacgact atcgaccgga aacggtatac cagtaccaaa   4020

gaggtcctcg atgccaccct catccaccag tcaattactg gcctgtacga aacacggatc   4080

gacctctctc aactgggcgg cgactag                                      4107
```

<210> SEQ ID NO 122
<211> LENGTH: 1368
<212> TYPE: PRT
<213> ORGANISM: streptococus pyogenes
<220> FEATURE:
<223> OTHER INFORMATION: Cas9

<400> SEQUENCE: 122

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

```
Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
```

```
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr Ser
1025                1030                1035                1040
```

Asn Ile Met Asn Phe Phe Lys Thr Glu Ile Thr Leu Ala Asn Gly Glu
                1045                1050                1055

Ile Arg Lys Arg Pro Leu Ile Glu Thr Asn Gly Glu Thr Gly Glu Ile
            1060                1065                1070

Val Trp Asp Lys Gly Arg Asp Phe Ala Thr Val Arg Lys Val Leu Ser
        1075                1080                1085

Met Pro Gln Val Asn Ile Val Lys Lys Thr Glu Val Gln Thr Gly Gly
    1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
                1125                1130                1135

Pro Thr Val Ala Tyr Ser Val Leu Val Val Ala Lys Val Glu Lys Gly
            1140                1145                1150

Lys Ser Lys Lys Leu Lys Ser Val Lys Glu Leu Leu Gly Ile Thr Ile
        1155                1160                1165

Met Glu Arg Ser Ser Phe Glu Lys Asn Pro Ile Asp Phe Leu Glu Ala
    1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
                1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
                1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
        1315                1320                1325

Thr Thr Ile Asp Arg Lys Arg Tyr Thr Ser Thr Lys Glu Val Leu Asp
    1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp
                1365

<210> SEQ ID NO 123
<211> LENGTH: 3249
<212> TYPE: DNA
<213> ORGANISM: Neisseria meningitidis
<220> FEATURE:
<223> OTHER INFORMATION: Cas9 codon optimized nucleic acid sequence

<400> SEQUENCE: 123
atggccgcct tcaagcccaa ccccatcaac tacatcctgg gcctggacat cggcatcgcc 60
agcgtgggct gggccatggt ggagatcgac gaggacgaga accccatctg cctgatcgac 120
ctgggtgtgc gcgtgttcga gcgcgctgag gtgcccaaga ctggtgacag tctggctatg 180

-continued

```
gctcgccggc ttgctcgctc tgttcggcgc cttactcgcc ggcgcgctca ccgccttctg    240
cgcgctcgcc gcctgctgaa gcgcgagggt gtgctgcagg ctgccgactt cgacgagaac    300
ggcctgatca agagcctgcc caacactcct tggcagctgc gcgctgccgc tctggaccgc    360
aagctgactc ctctggagtg gagcgccgtg ctgctgcacc tgatcaagca ccgcggctac    420
ctgagccagc gcaagaacga gggcgagacc gccgacaagg agctgggtgc tctgctgaag    480
ggcgtggccg acaacgccca cgccctgcag actggtgact tccgcactcc tgctgagctg    540
gccctgaaca agttcgagaa ggagagcggc cacatccgca accagcgcgg cgactacagc    600
cacaccttca gccgcaagga cctgcaggcc gagctgatcc tgctgttcga gaagcagaag    660
gagttcggca acccccacgt gagcggcggc ctgaaggagg gcatcgagac cctgctgatg    720
acccagcgcc ccgccctgag cggcgacgcc gtgcagaaga tgctgggcca ctgcaccttc    780
gagccagccg agcccaaggc cgccaagaac acctacaccg ccgagcgctt catctggctg    840
accaagctga acaacctgcg catcctggag cagggcagcg agcgcccccct gaccgacacc    900
gagcgcgcca ccctgatgga cgagccctac cgcaagagca agctgaccta cgcccaggcc    960
cgcaagctgc tgggtctgga ggacaccgcc ttcttcaagg gcctgcgcta cggcaaggac   1020
aacgccgagg ccagcaccct gatggagatg aaggcctacc acgccatcag ccgcgccctg   1080
gagaaggagg gcctgaagga caagaagagt cctctgaacc tgagccccga gctgcaggac   1140
gagatcggca ccgccttcag cctgttcaag accgacgagg acatcaccgg ccgcctgaag   1200
gaccgcatcc agcccgagat cctggaggcc ctgctgaagc acatcagctt cgacaagttc   1260
gtgcagatca gcctgaaggc cctgcgccgc atcgtgcccc tgatggagca gggcaagcgc   1320
tacgacgagg cctgcgccga gatctacggc gaccactacg gcaagaagaa caccgaggag   1380
aagatctacc tgcctcctat ccccgccgac gagatccgca accccgtggt gctgcgcgcc   1440
ctgagccagg cccgcaaggt gatcaacggc gtggtgcgcc gctacggcag ccccgcccgc   1500
atccacatcg agaccgcccg cgaggtgggc aagagcttca aggaccgcaa ggagatcgag   1560
aagcgccagg aggagaaccg caaggaccgc gagaaggccg ccgccaagtt ccgcgagtac   1620
ttccccaact tcgtgggcga gcccaagagc aaggacatcc tgaagctgcg cctgtacgag   1680
cagcagcacg gcaagtgcct gtacagcggc aaggagatca acctgggccg cctgaacgag   1740
aagggctacg tggagatcga ccacgccctg cccttcagcc gcacctggga cgacagcttc   1800
aacaacaagg tgctggtgct gggcagcgag aaccagaaca agggcaacca gaccccctac   1860
gagtacttca acggcaagga caacagccgc gagtggcagg agttcaaggc ccgcgtggag   1920
accagccgct tcccccgcag caagaagcag cgcatcctgc tgcagaagtt cgacgaggac   1980
ggcttcaagg agcgcaacct gaacgacacc cgctacgtga accgcttcct gtgccagttc   2040
gtggccgacc gcatgcgcct gaccggcaag ggcaagaagc gcgtgttcgc cagcaacggc   2100
cagatcacca acctgctgcg cggcttctgg ggcctgcgca aggtgcgcgc cgagaacgac   2160
cgccaccacg ccctggacgc cgtggtggtg gcctgcagca ccgtggccat gcagcagaag   2220
atcacccgct tcgtgcgcta caaggagatg aacgccttcg acggtaaaac catcgacaag   2280
gagaccggcg aggtgctgca ccagaagacc cacttccccc agccctggga gttcttcgcc   2340
caggaggtga tgatccgcgt gttcggcaag cccgacggca agcccgagtt cgaggaggcc   2400
gacacccccg agaagctgcg caccctgctg gccgagaagc tgagcagccg ccctgaggcc   2460
gtgcacgagt acgtgactcc tctgttcgtg agccgcgccc ccaaccgcaa gatgagcggt   2520
```

```
cagggtcaca tggagaccgt gaagagcgcc aagcgcctgg acgagggcgt gagcgtgctg   2580

cgcgtgcccc tgacccagct gaagctgaag gacctggaga agatggtgaa ccgcgagcgc   2640

gagcccaagc tgtacgaggc cctgaaggcc cgcctggagg cccacaagga cgaccccgcc   2700

aaggccttcg ccgagccctt ctacaagtac gacaaggccg gcaaccgcac ccagcaggtg   2760

aaggccgtgc gcgtggagca ggtgcagaag accggcgtgt gggtgcgcaa ccacaacggc   2820

atcgccgaca acgccaccat ggtgcgcgtg gacgtgttcg agaagggcga caagtactac   2880

ctggtgccca tctacagctg gcaggtggcc aagggcatcc tgcccgaccg cgccgtggtg   2940

cagggcaagg acgaggagga ctggcagctg atcgacgaca gcttcaactt caagttcagc   3000

ctgcacccca acgacctggt ggaggtgatc accaagaagg cccgcatgtt cggctacttc   3060

gccagctgcc accgcggcac cggcaacatc aacatccgca tccacgacct ggaccacaag   3120

atcggcaaga acggcatcct ggagggcatc ggcgtgaaga ccgccctgag cttccagaag   3180

taccagatcg acgagctggg caaggagatc cgcccctgcc gcctgaagaa gcgccctcct   3240

gtgcgctaa                                                           3249
```

<210> SEQ ID NO 124
<211> LENGTH: 1082
<212> TYPE: PRT
<213> ORGANISM: Neisseria meningitidis
<220> FEATURE:
<223> OTHER INFORMATION: Cas9

<400> SEQUENCE: 124

```
Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
```

```
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655
```

```
Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
        675                 680                 685

Gly Lys Gly Lys Lys Arg Val Phe Ala Ser Asn Gly Gln Ile Thr Asn
    690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765

Lys Thr His Phe Pro Gln Pro Trp Glu Phe Phe Ala Gln Glu Val Met
    770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
        835                 840                 845

Ser Ala Lys Arg Leu Asp Glu Gly Val Ser Val Leu Arg Val Pro Leu
    850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys His
    1010                1015                1020

Arg Gly Thr Gly Asn Ile Asn Ile Arg Ile His Asp Leu Asp His Lys
1025                1030                1035                1040

Ile Gly Lys Asn Gly Ile Leu Glu Gly Ile Gly Val Lys Thr Ala Leu
                1045                1050                1055

Ser Phe Gln Lys Tyr Gln Ile Asp Glu Leu Gly Lys Glu Ile Arg Pro
            1060                1065                1070
```

Cys Arg Leu Lys Lys Arg Pro Pro Val Arg
1075 1080

<210> SEQ ID NO 125
<211> LENGTH: 3159
<212> TYPE: DNA
<213> ORGANISM: staphylococcus aureus
<220> FEATURE:
<223> OTHER INFORMATION: Cas9 codon optimized nucleic acid sequence

<400> SEQUENCE: 125
atgaaaagga actacattct ggggctggac atcgggatta caagcgtggg gtatgggatt 60
attgactatg aaacaaggga cgtgatcgac gcaggcgtca gactgttcaa ggaggccaac 120
gtggaaaaca atgagggacg gagaagcaag aggggagcca ggcgcctgaa acgacggaga 180
aggcacagaa tccagagggt gaagaaactg ctgttcgatt acaacctgct gaccgaccat 240
tctgagctga gtggaattaa tccttatgaa gccagggtga aaggcctgag tcagaagctg 300
tcagaggaag agttttccgc agctctgctg cacctggcta agcgccgagg agtgcataac 360
gtcaatgagg tggaagagga caccggcaac gagctgtcta caaaggaaca gatctcacgc 420
aatagcaaag ctctggaaga gaagtatgtc gcagagctgc agctggaacg gctgaagaaa 480
gatggcgagg tgagagggtc aattaatagg ttcaagacaa gcgactacgt caaagaagcc 540
aagcagctgc tgaaagtgca gaaggcttac caccagctgg atcagagctt catcgatact 600
tatatcgacc tgctggagac tcggagaacc tactatgagg gaccaggaga agggagcccc 660
ttcggatgga aagacatcaa ggaatggtac gagatgctga tgggacattg cacctatttt 720
ccagaagagc tgagaagcgt caagtacgct tataacgcag atctgtacaa cgccctgaat 780
gacctgaaca acctggtcat caccagggat gaaaacgaga aactggaata ctatgagaag 840
ttccagatca tcgaaaacgt gtttaagcag aagaaaaagc ctacactgaa acagattgct 900
aaggagatcc tggtcaacga agaggacatc aagggctacc gggtgacaag cactggaaaa 960
ccagagttca ccaatctgaa agtgtatcac gatattaagg acatcacagc acggaaagaa 1020
atcattgaga acgccgaact gctggatcag attgctaaga tcctgactat ctaccagagc 1080
tccgaggaca tccaggaaga gctgactaac ctgaacagcg agctgaccca ggaagagatc 1140
gaacagatta gtaatctgaa ggggtacacc ggaacacaca acctgtccct gaaagctatc 1200
aatctgattc tggatgagct gtggcataca aacgacaatc agattgcaat ctttaaccgg 1260
ctgaagctgg tcccaaaaaa ggtggacctg agtcagcaga aagagatccc aaccacactg 1320
gtggacgatt tcattctgtc acccgtggtc aagcggagct tcatccagag catcaaagtg 1380
atcaacgcca tcatcaagaa gtacggcctg cccaatgata tcattatcga gctggctagg 1440
gagaagaaca gcaaggacgc acagaagatg atcaatgaga tgcagaaacg aaaccggcag 1500
accaatgaac gcattgaaga gattatccga actaccggga aagagaacgc aaagtacctg 1560
attgaaaaaa tcaagctgca cgatatgcag gagggaaagt gtctgtattc tctggaggcc 1620 atcccccctgg aggacctgct gaacaatcca ttcaactacg aggtcgatca tattatcccc 1680
agaagcgtgt ccttcgacaa ttcctttaac aacaaggtgc tggtcaagca ggaagagaac 1740
tctaaaaagg gcaataggac tcctttccag tacctgtcta gttcagattc caagatctct 1800
tacgaaacct ttaaaaagca cattctgaat ctggccaaag gaaagggccg catcagcaag 1860
accaaaaagg agtacctgct ggaagagcgg gacatcaaca gattctccgt ccagaaggat 1920
tttattaacc ggaatctggt ggacacaaga tacgctactc gcggcctgat gaatctgctg 1980

```
cgatcctatt tccgggtgaa caatctggat gtgaaagtca agtccatcaa cggcgggttc   2040

acatcttttc tgaggcgcaa atggaagttt aaaaaggagc gcaacaaagg gtacaagcac   2100

catgccgaag atgctctgat tatcgcaaat gccgacttca tctttaagga gtggaaaaag   2160

ctggacaaag ccaagaaagt gatggagaac cagatgttcg aagagaagca ggccgaatct   2220

atgcccgaaa tcgagacaga acaggagtac aaggagattt tcatcactcc tcaccagatc   2280

aagcatatca aggatttcaa ggactacaag tactctcacc gggtggataa aaagcccaac   2340

agagagctga tcaatgacac cctgtatagt acaagaaaag acgataaggg gaataccctg   2400

attgtgaaca atctgaacgg actgtacgac aaagataatg acaagctgaa aaagctgatc   2460

aacaaaagtc ccgagaagct gctgatgtac caccatgatc ctcagacata tcagaaactg   2520

aagctgatta tggagcagta cggcgacgag aagaacccac tgtataagta ctatgaagag   2580

actgggaact acctgaccaa gtatagcaaa aaggataatg gccccgtgat caagaagatc   2640

aagtactatg ggaacaagct gaatgcccat ctggacatca cagacgatta ccctaacagt   2700

cgcaacaagg tggtcaagct gtcactgaag ccatacagat tcgatgtcta tctggacaac   2760

ggcgtgtata aatttgtgac tgtcaagaat ctggatgtca tcaaaaagga gaactactat   2820

gaagtgaata gcaagtgcta cgaagaggct aaaaagctga aaaagattag caaccaggca   2880

gagttcatcg cctcctttta caacaacgac ctgattaaga tcaatggcga actgtatagg   2940

gtcatcgggg tgaacaatga tctgctgaac cgcattgaag tgaatatgat tgacatcact   3000

taccgagagt atctggaaaa catgaatgat aagcgccccc ctcgaattat caaaacaatt   3060

gcctctaaga ctcagagtat caaaaagtac tcaaccgaca ttctgggaaa cctgtatgag   3120

gtgaagagca aaaagcaccc tcagattatc aaaaagggc                          3159
```

<210> SEQ ID NO 126
<211> LENGTH: 1053
<212> TYPE: PRT
<213> ORGANISM: staphylococcus aureus
<220> FEATURE:
<223> OTHER INFORMATION: Cas9

<400> SEQUENCE: 126

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160
```

```
Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575
```

```
Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
```

```
        995                 1000                1005

Asn Asp Lys Arg Pro Pro Arg Ile Ile Lys Thr Ile Ala Ser Lys Thr
    1010                1015                1020

Gln Ser Ile Lys Lys Tyr Ser Thr Asp Ile Leu Gly Asn Leu Tyr Glu
1025                1030                1035                1040

Val Lys Ser Lys Lys His Pro Gln Ile Ile Lys Lys Gly
                1045                1050


<210> SEQ ID NO 127
<211> LENGTH: 326
<212> TYPE: PRT
<213> ORGANISM: Homo sapiens
<220> FEATURE:
<223> OTHER INFORMATION: Human IgG2 Fc
<300> PUBLICATION INFORMATION:
<308> DATABASE ACCESSION NUMBER: Uniprot P01859
<309> DATABASE ENTRY DATE: 2008-12-16

<400> SEQUENCE: 127

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
```

```
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 128
<211> LENGTH: 327
<212> TYPE: PRT
<213> ORGANISM: Homo sapiens
<220> FEATURE:
<223> OTHER INFORMATION: Human IgG4 Fc
<300> PUBLICATION INFORMATION:
<308> DATABASE ACCESSION NUMBER: Uniprot P01861
<309> DATABASE ENTRY DATE: 1986-07-21

<400> SEQUENCE: 128

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
```

305 310 315 320

Leu Ser Leu Ser Leu Gly Lys
325

<210> SEQ ID NO 129
<211> LENGTH: 228
<212> TYPE: PRT
<213> ORGANISM: Artificial Sequence
<220> FEATURE:
<223> OTHER INFORMATION: Spacer

<400> SEQUENCE: 129

Glu Ser Lys Tyr Gly Pro Pro Cys Pro Pro Cys Pro Ala Pro Pro Val
1 5 10 15

Ala Gly Pro Ser Val Phe Leu Phe Pro Pro Lys Pro Lys Asp Thr Leu
20 25 30

Met Ile Ser Arg Thr Pro Glu Val Thr Cys Val Val Val Asp Val Ser
35 40 45

Gln Glu Asp Pro Glu Val Gln Phe Asn Trp Tyr Val Asp Gly Val Glu
50 55 60

Val His Asn Ala Lys Thr Lys Pro Arg Glu Glu Gln Phe Gln Ser Thr
65 70 75 80

Tyr Arg Val Val Ser Val Leu Thr Val Leu His Gln Asp Trp Leu Asn
85 90 95

Gly Lys Glu Tyr Lys Cys Lys Val Ser Asn Lys Gly Leu Pro Ser Ser
100 105 110

Ile Glu Lys Thr Ile Ser Lys Ala Lys Gly Gln Pro Arg Glu Pro Gln
115 120 125

Val Tyr Thr Leu Pro Pro Ser Gln Glu Glu Met Thr Lys Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Arg Leu Thr
180 185 190

Val Asp Lys Ser Arg Trp Gln Glu Gly Asn Val Phe Ser Cys Ser Val
195 200 205

Met His Glu Ala Leu His Asn His Tyr Thr Gln Lys Ser Leu Ser Leu
210 215 220

Ser Leu Gly Lys
225

<210> SEQ ID NO 130
<211> LENGTH: 133
<212> TYPE: DNA
<213> ORGANISM: Artificial Sequence
<220> FEATURE:
<223> OTHER INFORMATION: SV40 poly A signal

<400> SEQUENCE: 130
tgctttattt gtgaaatttg tgatgctatt gctttatttg taaccattat aagctgcaat 60
aaacaagtta acaacaacaa ttgcattcat tttatgtttc aggttcaggg ggaggtgtgg 120
gaggtttttt aaa 133

<210> SEQ ID NO 131
<211> LENGTH: 347

```
<212> TYPE: DNA
<213> ORGANISM: Artificial Sequence
<220> FEATURE:
<223> OTHER INFORMATION: MND promoter

<400> SEQUENCE: 131

gaacagagaa acaggagaat atgggccaaa caggatatct gtggtaagca gttcctgccc     60

cggctcaggg ccaagaacag ttggaacagc agaatatggg ccaaacagga tatctgtggt    120

aagcagttcc tgccccggct cagggccaag aacagatggt ccccagatgc ggtcccgccc    180

tcagcagttt ctagagaacc atcagatgtt tccagggtgc cccaaggacc tgaaatgacc    240

ctgtgcctta tttgaactaa ccaatcagtt cgcttctcgc ttctgttcgc gcgcttctgc    300

tccccgagct ctatataagc agagctcgtt tagtgaaccg tcagatc                  347
```